US012611401B2

(12) United States Patent
Aspnes et al.

(10) Patent No.: US 12,611,401 B2
(45) **Date of Patent: *Apr. 28, 2026**

(54) COMBINATIONS COMPRISING BENZODIOXOL AS GLP-1R AGONISTS FOR USE IN THE TREATMENT OF NASH/NAFLD AND RELATED DISEASES

(71) Applicant: Pfizer Inc., New York, NY (US)

(72) Inventors: Gary E. Aspnes, Biberach an der Riss (DE); Scott W. Bagley, Mystic, CT (US); John M. Curto, Mystic, CT (US); Matthew Dowling, Old Lyme, CT (US); David James Edmonds, Riehen (CH); Dilinie Fernando, Jamaica Plain, MA (US); Mark E. Flanagan, Gales Ferry, CT (US); Kentaro Futatsugi, Sharon, MA (US); David Andrew Griffith, Sudbury, MA (US); Kim Huard, Berkeley, CA (US); Gajendra Ingle, New Haven, CT (US); Wenhua Jiao, Salem, CT (US); Shawn M. LaCasse, Griswold, CT (US); Yajing Lian, Waterford, CT (US); Chris Limberakis, Pawcatuck, CT (US); Allyn T. Londregan, Barrington, RI (US); Alan M. Mathiowetz, Waltham, MA (US); David Walter Piotrowski, Waterford, CT (US); Roger B. Ruggeri, Waterford, CT (US); Kristin Wiglesworth, Germantown, MD (US)

(73) Assignee: Pfizer Inc., New York, NY (US)

( * ) Notice: Subject to any disclaimer, the term of this patent is extended or adjusted under 35 U.S.C. 154(b) by 1047 days.

This patent is subject to a terminal disclaimer.

(21) Appl. No.: 17/612,672

(22) PCT Filed: May 15, 2020

(86) PCT No.: PCT/IB2020/054637

§ 371 (c)(1),
(2) Date: Nov. 19, 2021

(87) PCT Pub. No.: WO2020/234726

PCT Pub. Date: Nov. 26, 2020

(65) Prior Publication Data

US 2022/0387402 A1 Dec. 8, 2022

Related U.S. Application Data

(60) Provisional application No. 62/850,133, filed on May 20, 2019.

(51) Int. Cl.

| | |
|---|---|
| *A61K 31/438* | (2006.01) |
| *A61K 31/454* | (2006.01) |
| *A61K 31/4545* | (2006.01) |
| *A61K 31/46* | (2006.01) |
| *A61K 31/496* | (2006.01) |

(Continued)

(52) U.S. Cl.

CPC .......... *A61K 31/438* (2013.01); *A61K 31/454* (2013.01); *A61K 31/4545* (2013.01); *A61K 31/46* (2013.01); *A61K 31/496* (2013.01); *A61K 31/506* (2013.01); *A61K 31/5377* (2013.01); *A61K 38/1709* (2013.01); *A61K 38/1796* (2013.01); *A61K 38/26* (2013.01); *A61K 38/28* (2013.01); *A61K 45/06* (2013.01); *A61P 1/16* (2018.01)

(58) Field of Classification Search

CPC ................ A61K 31/438; A61K 31/454; A61K 31/4545; A61K 31/46; A61K 31/496; A61K 31/506; A61K 31/5377; A61P 1/16

See application file for complete search history.

(56) References Cited

U.S. PATENT DOCUMENTS

| | | | |
|---|---|---|---|
| 4,465,850 | A | 8/1984 | Cragoe et al. |
| 8,859,577 | B2 | 10/2014 | Didiuk et al. |

(Continued)

FOREIGN PATENT DOCUMENTS

| | | | |
|---|---|---|---|
| CA | 3038479 | A1 | 3/2018 |
| JP | 2012-522060 | A | 9/2012 |

(Continued)

OTHER PUBLICATIONS

Haque et al., "Identification of potent 11mer Glucagon-Like Peptide-1 Receptor agonist peptides with novel C-terminal amino acids: Homohomophenylalanine analogs", Peptides, vol. 31(5), pp. 950-955 (2010).

(Continued)

*Primary Examiner* — Rebecca L Anderson
(74) *Attorney, Agent, or Firm* — Hamilton, Brook, Smith & Reynolds, P.C.

(57) ABSTRACT

In part, the invention provides a new combination comprising (1) a GLP-1R agonist and (2) an ACC inhibitor or a DGAT2 inhibitor, or a KHK inhibitor or FXR agonist. The invention further provides new methods for treating diseases and disorders, for example, fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, obesity, and type 2 diabetes, for example, using the new combination described herein.

11 Claims, 25 Drawing Sheets

(51) Int. Cl.

| | |
|---|---|
| ***A61K 31/506*** | (2006.01) |
| ***A61K 31/5377*** | (2006.01) |
| ***A61K 38/17*** | (2006.01) |
| ***A61K 38/26*** | (2006.01) |
| ***A61K 38/28*** | (2006.01) |
| ***A61K 45/06*** | (2006.01) |
| ***A61P 1/16*** | (2006.01) |

(56) References Cited

U.S. PATENT DOCUMENTS

| | | | | |
|---|---|---|---|---|
| 8,957,073 | B2 | 2/2015 | Allen et al. | |
| 9,150,568 | B2 | 10/2015 | Tully et al. | |
| 9,809,579 | B2 | 11/2017 | Dowling et al. | |
| 10,071,992 | B2 | 9/2018 | Boehm et al. | |
| 10,208,019 | B2 | 2/2019 | Aspnes et al. | |
| 10,669,259 | B2 | 6/2020 | Aspnes et al. | |
| 10,676,465 | B2 | 6/2020 | Aspnes et al. | |
| 10,683,281 | B2 | 6/2020 | Aspnes et al. | |
| 10,851,081 | B2 | 12/2020 | Aspnes et al. | |
| 10,934,279 | B2 | 3/2021 | Aspnes et al. | |
| 12,378,230 | B2 * | 8/2025 | Aspnes ................ | C07D 413/14 |
| 2004/0127504 | A1 | 7/2004 | Cowart et al. | |
| 2013/0331349 | A1 | 12/2013 | Tully et al. | |
| 2017/0183328 | A1 | 6/2017 | Dowling et al. | |
| 2018/0051012 | A1 | 2/2018 | Boehm et al. | |
| 2018/0170908 | A1 | 6/2018 | Aspnes et al. | |

FOREIGN PATENT DOCUMENTS

| | | | |
|---|---|---|---|
| JP | 2013-526536 | A | 6/2013 |
| JP | 2013-540119 | A | 10/2013 |
| WO | 2010/114824 | A1 | 10/2010 |
| WO | 2012/042433 | A1 | 4/2012 |
| WO | 2012/087519 | A1 | 6/2012 |
| WO | 2018/033832 | A1 | 2/2018 |
| WO | 2018/109607 | | 6/2018 |
| WO | 2019/102311 | | 5/2019 |
| WO | 2019/239319 | | 12/2019 |
| WO | 2020/234726 | A1 | 11/2020 |

OTHER PUBLICATIONS

Sanyal et al., "Challenges and Opportunities in Drug and Biomarker Development for Nonalcoholic Steatohepatitis: Findings and Recommendations From an American Association for the Study of Liver Diseases—U.S. Food and Drug Administration Joint Workshop", Hepatology, vol. 61(4), pp. 1392-1405 (2015).

EASL-EASD-EASO Clinical Practical Guidelines for the management of non-alcoholic fatty liver disease, Journal of Hepatology, vol. 64(4), pp. 1388-1402 (2016).

Day et al., "Hepatic steatosis: Innocent Bystander or Guilty Party?", Hepatology, vol. 27(6), pp. 1463-1466 (1998).

Sorensen et al., "Prospective evaluation of alcohol abuse and alcoholic liver injury in men as predictors of development of cirrhosis", Lancet, vol. 2(8397), pp. 241-244 (1984).

Wanless et al., "Fatty Liver Hepatitis (Steatohepatitis) and Obesity: An Autopsy Study with Analysis of Risk Factors", Hepatology, vol. 12(5), pp. 1106-1110 (1990).

Reeves et al., "Hepatic stellate cell activation occurs in the absence of hepatitis in alcoholic liver disease and correlates with the severity of steatosis", Journal of Hepatology, vol. 25(5), pp. 677-683 (1996).

Cohen et al., "Human Fatty Liver Disease: Old Questions and New Insights", Science, vol. 332(6037), pp. 1519-1523 (2011).

Savage et al., "Reversal of diet-induced hepatic steatosis and hepatic insulin resistance by antisense oligonucleotide inhibitors of acetyl-CoA carboxylases 1 and 2", J. Clin. Invest., vol. 116(3), pp. 817-824 (2006).

Oh, et al., "Glucose and fat metabolism in adipose tisue of acetyl-CoA carboxylase 2 knockout mice", PNAS, vol. 102(5); pp. 1384-1389 (2005).

Saggerson, "Malonyl-CoA, a Key Signaling Molecule in Mammalian Cells", Annu. Rev. Nutr., vol. 28, pp. 253-272 (2008).

Waite et al., "Studies on the Mechanism of Fatty Acid Synthesis", J. Biol. Chem., vol. 237(9); pp. 2750-2757 (1962).

Berod et al., "De novo fatty acid synthesis controls the fate between regulatory T and T helper 17 cells", Nat. Med, vol. 20(11), pp. 1327-1333 (2014).

Ross et al., "The acetyl-CoA carboxylase inhibitor PF-05221304 exerts direct effects on hepatic inflammation and fibrosis independent of benefits on steatosis", Abstract PS-132, Journal of Hepatology, vol. 70, p. e86 (2019).

Griffith et al., "Decreasing the Rate of Metabolic Ketone Reduction in the Discovery of a Clinical Acetyl-CoA Carboxylase Inhibitor for the Treatment of Diabetes", vol. 57(24), pp. 10512-10526 (2014).

Kim et al., "Acetyl CoA Carboxylase Inhibition Reduces Hepatic Steatosis but Elevates Plasma Triglycerides in Mice and Humans: A Bedside to Bench Investigation", Cell Metab., vol. 26(2), pp. 394-406 (2017).

Stiede et al., "Acetyl-Coenzyme A Carboxylase Inhibition Reduces De Nove Lipogenesis in Overweight Male Subjects: A Randomized, Double-Blind, Crossover Study", Hepatology, vol. 66(2), pp. 324-334 (2017).

Lawitz et al., "Acetyl-CoA Carboxylase Inhibitor GS-0976 for 12 Weeks Reduces Hepatic De Novo Lipogenesis and Steatosis in Patients With Nonalcoholic Steatophetatis", Clinical Gastroenterology aand Hepatology, vol. 16, pp. 1983-1991 (2018).

Rau et al., "Progression from Nonalcoholic Fatty Liver to Nonalcoholic Steatohepatitis is Marked by a Higher Frequency of Th17 Cells in the Liver and an Increased Th17/Resting Regulatory T Cell Ration in Peripheral Blood and in the Liver", J. Immunol., vol. 196(1), pp. 97-105 (2016).

Coleman et al., "Mammalian Triacylglycerol Matabolism: Synthesis, Lipolysis, and Signaling", Chem. Rev., vol. 111(10), pp. 6359-6386 (2011).

Erion et al., "Diacylglycerol-mediated insulin resistance", Nat. Med, vol. 16(4), pp. 400-402 (2010).

Choi et al., "Increased very low density lipoprotein (VLDL) secretion, hepatic steatosis, and insulin resistance", Trends Endocrinol. Metab, vol. 22(9), pp. 353-363 (2011).

St-Pierre et al., "Low-Density Lipoprotein Subfractions and the Long-Term Risk of Ischemic Heart Disease in Men", Arterioscler. Throm. Vasc. Biol., vol. 25(3), pp. 553-559 (2005).

Smith et al., "Obesity resistance and multiple mechanisms of triglyceride synthesis in mice lacking Dgat", Nat. Genet. vol. 25. pp. 87-90 (2000).

Buhman et al., "DGAT1 Is Not Essential for Intestinal Triacylglycerol Absorption or Chylomicron Synthesis", J. Biol. Chem., vol. 277(28), pp. 25474-25479 (2002).

Lee et al., "Intestine-specific expression of acyl CoA:diacylglycerol acyltransferase 1 reverses resistance to diet-induced hepatic steatosis and obesity in Dgat1-/-mice", J. Lipid Res., vol. 51, pp. 1770-1780 (2010).

Yen et al., "DGAT enzymes and triacylglycerol biosynthesis", J. Lipid Res., vol. 49, pp. 2283-2301 (2008).

Stone et al., "Lipopenia and Skin Barrier Abnormalities in DGAT2-deficient Mice", J. Biol. Chem., vol. 279(12), pp. 11767-11776 (2004).

Liu, et al., "Knockdown of Acyl-CoA:diacylglycerol acyltransferase 2 2ith antisense oligonucleotide reduces VLDL TG and ApoB secretion in mice", Biochimica et Biophysica Acta, vol. 1781, pp. 97-104 (2008).

Choi et al., "Suppression of Diacylglycerol Acyltransferase-2 (DGAT2), but not DGAT1, with Antisense Oligonucleotides Reverses Diet-induced Hepatic Steatosis and Insulin Resistance", J. Biol. Chem, vol. 282(31), pp. 22678-22688 (2007).

Yu, et al., "Antisense Oligonucleotide Reduction of DGAT2 Expression Improves Hepatic Steatosis and Hyperlipidemia in Obese Mice", Hepatology, vol. 42(2), pp. 362-371 (2005).

Ishimoto et al., "Opposing effects of fructokinase C and A isoforms on fructose-induced metabolic syndrome in mice", PNAS, vol. 109(11), pp. 4320-4325 (2012.

(56) References Cited

OTHER PUBLICATIONS

Diggle et al., "Ketohexokinase: Expression and Localization of the Principal Fructose-metabolizing Enzyme", J. Histochem Cytochem, vol. 57(8), pp. 763-774 (2009).
Bouteldja et al., "The biochemical basis of hereditary fructose intolerance", J. Inherit Metab Dis., vol. 33(2), pp. 105-112 (2010).
Tolan, "Molecular Basis of Hereditary Fructose Intolerane: Mutations and Polymorphisms in the Human Aldolase B Gene", Human Mutation, vol. 6(3), pp. 210-218 1995).
Ali et al., "Hereditary fructose intolerance", J. Med. Genet., vol. 35(5), pp. 353-365 (1998).
Lanaspa et al., "Endogenous fructose production and metabolism in the liver contributes to the development of metabolic syndrome", Nature Comm., vol. 4:2434 (2013).
Hampp et al., "Use of Antidiabetic Drugs in the U.S., 2003-2012", Diabetes Care, vol. 37, pp. 1367-1374 (2014).
Meier et al., "Glucagon-like Peptide 1 and Gastric Inhibitory Polypeptide", Biodrugs, vol. 17(2), pp. 93-102 (2003).
Vilsboll et al., "Reduced Postprandial Concentrations of Intact Biologically Active Glucagon-Like Peptide 1 in Type 2 Diabetic Patients", Diabetes, vol. 50, pp. 609-613 (2001).
Holst, "The Physiology of Glucagon-Like Peptide 1", Physiol Rev., vol. 87(4), pp. 1409-1439 (2007).
Meier, "GLP-1 receptor agonists for individualized treatment of type 2 diabetes mellitus", Nat. Rev. Endocrinol., vol. 8(12), pp. 728-742 (2012).
Seol et al., "Isolation of Proteins That Interact Specifically with the Retinoid X Receptor: Two Novel Orphan Receptors", Mol. Endocrinol., vol. 9(1), pp. 72-85 (1995).
Forman et al., Identification of a Nuclear Receptor That is Activated by Farnesol Metabolites, Cell, vol. 81(5), pp. 687-693 (1995).
Makishima et al., "Identification of Nuclear Receptor for Bile Acids", Science, vol. 284(5418), pp. 1362-1364 (1999).
Parks et al., "Bile Acids: Natural Ligands for an Orphan Nuclear Receptor", Science, vol. 284(5418), pp. 1365-1368 (1999).
Wang et al., "Endogenous Bile Acids Are Ligands for the Nuclear Receptor FXR/BAR", Molecular Cell, vol. 3(5), pp. 643-553 (1999).
Urizar et al., "The Farnesoid X-activated Receptor Mediates Bile Acid Activation of Phospholipid Transfer Protein Gene Expression", J. Biol. Chem., vol. 275(50), pp. 39313-39317 (2000).
Crawley, "Farnesoid X receptor modulators: a patent review", Exp. Opin, Ther. Patents, vol. 20(8); pp. 1047-1057 (2010).
Haque, T., et al., "Identification of potent Ilmer Glucagon-Like Peptide-1 Receptor agonist peptides with novel C-terminal amino acids: Homohomophenylalanine analogs," Peptides, 2010, 31(5):950-955.
International Preliminary Report on Patentability issued in PCT/IB2020/054637; mailed on Dec. 2, 2021; 13 pp.
International Search Report issued in PCT/IB2020/054637; mailed on Jul. 24, 2020; 4 pp.
Written Opinion issued in PCT/IB2020/054637; mailed on Jul. 24, 2020; 11 pp.

* cited by examiner

PXRD pattern of crystalline Form 1 of Example DGAT2i Compound

PXRD pattern of crystalline Form 2 of Example DGAT2i Compound

COMBINATIONS COMPRISING BENZODIOXOL AS GLP-1R AGONISTS FOR USE IN THE TREATMENT OF NASH/NAFLD AND RELATED DISEASES

This application is a national phase filing under 35 U.S.C. § 371 of international patent application number PCT/IB2020/054637 filed May 15, 2020, which in turn claims the benefit of priority to U.S. Provisional Patent Application Ser. No. 62/850,133 filed May 20, 2019.

The invention relates to combinations and methods for treating fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease. In part, the invention provides a new combination comprising a GLP-1R agonist and in the same or a separate composition comprising an ACC inhibitor. The invention also provides a new pharmaceutical composition comprising a GLP-1R agonist and in the same or a separate composition comprising a DGAT2 inhibitor. The invention also provides a new combination comprising a GLP-1R agonist and in the same or a separate composition comprising a KHK inhibitor. The invention also provides a new combination comprising a GLP-1R agonist and in the same or a separate composition comprising a FXR agonist. The invention further provides new methods for treating fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, for example, using the new combination described herein.

BACKGROUND OF THE INVENTION

Nonalcoholic steatohepatitis (NASH) is a clinical and histological subset of non-alcoholic fatty liver disease (NAFLD, defined as presence of >5% hepatic steatosis) that is associated with increased all cause mortality, cirrhosis and end stage liver disease, increased cardiovascular mortality, and increased incidence of both liver related and non liver related cancers (Sanyal et al, *Hepatology* 2015; 61 (4):1392-1405). NAFLD is the most common cause of chronic liver disease in the Western world. It is the hepatic manifestation of metabolic syndrome, and is a spectrum of hepatic conditions encompassing steatosis, NASH, fibrosis, cirrhosis, end stage liver disease, and ultimately hepatocellular carcinoma. NAFLD and NASH are considered the primary fatty liver diseases as they account for the greatest proportion of individuals with elevated hepatic lipids. The severity of NAFLD/NASH is based on the presence of lipid, inflammatory cell infiltrate, hepatocyte ballooning, and the degree of fibrosis. Although not all individuals with steatosis progress to NASH, a substantial portion do. At the present time, treatment options are limited to lifestyle modification including exercise and diet (EASL-EASD-EASO Clinical Practice Guidelines, *J. Hepatol.* 2016; 64(6):1388-1402).

Alterations in lipid metabolism have been hypothesized to contribute to the molecular pathogenesis of NAFLD and NASH. Steatosis is a necessary but not sufficient component of the pathogenesis of NASH (Day C, and James O., Hepatology. 1998; 27(6):1463-6). Consistent with this, multiple studies have demonstrated that the severity of steatosis predicts the risk of concomitant steatohepatitis as well as the risk of progression to cirrhosis (Sorensen et al, *Lancet.* 1984; 2(8397): 241-4; Wanless I and Lentz J, *Hepatology* 1990; 12(5):1106-10; Reeves H, et al, *J. Hepatol.* 1996; 25(5): 677-83). Hepatic steatosis is a consequence of an imbalance in TG production/uptake into the liver and clearance/removal (Cohen J C, et al, *Science.* 2011; 332(6037):1519-1523). It is hypothesized that reducing steatosis, the metabolic driver underpinning the development of NAFLD/NASH, will result in subsequent improvements in hepatic inflammation and fibrosis.

Savage, et al., demonstrated that ACC1 and ACC2 are both involved in regulating fat oxidation in hepatocytes while ACC1, the dominant isoform in rat liver, is the sole regulator of fatty acid synthesis. Furthermore, in their model, combined reduction of both isoforms is required to significantly lower hepatic malonyl-CoA levels, increase fat oxidation in the fed state, reduce lipid accumulation, and improve insulin action in vivo. Thus, hepatic ACC1 and ACC2 inhibitors may be useful in the treatment of NAFLD and hepatic insulin resistance. See, Savage, D. B., et al., "Reversal of diet-induced hepatic steatosis and hepatic insulin resistance by antisense oligonucleotide inhibitors of acetyl-CoA carboxylases 1 and 2" *J. Clin. Invest.* 2006; 116(3):817-24. See also, Oh, W., et al., "Glucose and fat metabolism in adipose tissue of acetyl-CoA carboxylase 2 knockout mice" *PNAS,* 102(5) 1384-1389 (2005).

Acetyl-CoA Carboxylase (ACC) play a key role in regulating lipid metabolism. ACC catalyzes an essential and rate limiting step in the process of de novo lipogenesis (DNL) (Saggerson D, *Annu. Rev. Nutr.* 2008; 28:253-72.). Further, ACC also regulates mitochondrial beta-oxidation of fatty acids through allosteric regulation of the enzyme carnitine palmitoyltransferase 1 (CPT1) (Saggerson, 2008; Waite M, and Wakil S J. *J. Biol. Chem.* 1962; 237:2750-2757.). Emerging data also suggest that suppression of DNL through ACC inhibition may directly reduce inflammation by restraining the formation of the inflammatory interleukin-17 (IL-17) secreting T-cells of the T helper 17 lineage (Th17 cells) and favoring the development of anti-inflammatory FoxP3(+) regulatory T (Treg) cells (Berod L, et al. *Nat. Med.* 2014; 20(11): 1327-33). Recently, ACC inhibition has also been shown to suppress primary human hepatic stellate cell activation in-vitro and reduce hepatic fibrosis in rat models (Ross et al, Abstract PS-132 Journal of Hepatology 2019 vol. 70 page e86).

Inhibition of ACC activity is hypothesized to be beneficial to patients with NASH by at least three independent mechanisms. As summarized above, humans with NAFLD show marked elevations in hepatic DNL and normalization of this increased flux through pharmacologic hepatic ACC inhibition is hypothesized to reduce steatosis. Consistent with this, ACC inhibitors have been shown to inhibit DNL. In addition, the effect of ACC inhibitions to increase fatty acid oxidation may also contribute to reduce liver fat content. See Griffith D A, et al. *J. Med. Chem.* 2014; 57(24):10512-10526; Kim C W, et al. *Cell Metab.* 2017; 26, 394-406; Stiede K et al. *Hepatology.* 2017; 66(2):324-334; Lawitz E J, et al. *Clin Gastroenterol Hepatol.* 2018 (https://doi.org/10.1016/j.cgh.2018.04.042). In addition, inhibition of DNL in IL-17 secreting T-cells is expected to suppress hepatic inflammation by restraining the formation of the inflammatory Th17 cells (Berod et al., 2014), a pathway that may be important in NASH pathogenesis (Rau M, et al. *J. Immunol.* 2016; 196(1):97-105), and favoring the development of anti-inflammatory Treg cells. Further, ACC inhibition may reduce stellate cell activation and fibrosis (Ross et al., 2019)

4-(4-(1-Isopropyl-7-oxo-1,4,6,7-tetrahydrospiro[indazole-5,4'-piperidine]-1'-carbonyl)-6-methoxypyridin-2-yl)

benzoic acid is a selective ACC inhibitor and was prepared as the free acid in Example 9 of U.S. Pat. No. 8,859,577, which is the U.S. national phase of International Application No. PCT/162011/054119, the disclosures of which are hereby incorporated herein by reference in their entireties for all purposes. Crystal forms of 4-(4-(1-Isopropyl-7-oxo-1,4,6,7-tetrahydrospiro[indazole-5,4'-piperidine]-1'-carbonyl)-6-methoxypyridin-2-yl)benzoic acid, including an anhydrous mono-tris form (Form 1) and a trihydrate of the mono-tris salt (Form 2), are described in International PCT Application No. PCT/162018/058966, the disclosure of which is hereby incorporated by reference herein in its entirety for all purposes.

Triglycerides or triacylglycerols (TG) represent a major form of energy storage in mammals. TG's are formed by the sequential esterification of glycerol with three fatty acids of varying chain lengths and degrees of saturation (Coleman, R. A., and Mashek, D. G. 2011. *Chem. Rev.* 111: 6359-6386). TG synthesized in the intestine or liver are packaged into chylomicrons or very low-density lipoprotein (VLDL), respectively, and exported to peripheral tissues where they are hydrolysed to their constituent fatty acids and glycerol by lipoprotein lipase (LPL). The resultant non-esterified fatty acids (NEFA) can either be metabolised further to produce energy or reesterified and stored.

Under normal physiological conditions, the energy-dense TG remains sequestered in various adipose depots until there is a demand for its release, whereupon, it is hydrolyzed to glycerol and free fatty acids which are then released into the blood stream. This process is tightly regulated by the opposing actions of insulin and hormones such as catecholamines which promote the deposition and mobilization of TG stores under various physiological conditions. In the post-prandial setting, insulin acts to inhibit lipolysis, thereby, restraining the release of energy in the form of NEFA and ensuring the appropriate storage of dietary lipids in adipose depots. However, in patients with type 2 diabetes, the ability of insulin to suppress lipolysis is impaired and NEFA flux from adipocytes is inappropriately elevated. This, in turn, results in increased delivery of lipid to tissues such as muscle and liver. In the absence of energetic demand the TG and other lipid metabolites, such as diacylglycerol (DAG) can accumulate and cause a loss of insulin sensitivity (Erion, D. M., and Shulman, G. I. 2010. Nat Med 16: 400-402). Insulin resistance in muscle is characterized by reduced glucose uptake and glycogen storage, whilst in the liver, loss of insulin signaling gives rise to dysregulated glucose output and over-production of TG-rich VLDL, a hallmark of type 2 diabetes (Choi, S. H., and Ginsberg, H. N. 2011. *Trends Endocrinol. Metab.* 22: 353-363). Elevated secretion of TG-enriched VLDL, so called VLDL1 particles, is thought to stimulate the production of small, dense low-density lipoprotein (sdLDL), a proatherogenic subfraction of LDL that is associated with elevated risk of coronary heart disease (St-Pierre, A. C. et. al. 2005. *Arterioscler. Thromb. Vasc. Biol.* 25: 553-559).

In mammals, two diacylglycerol acyltransferases (DGAT) enzymes (DGAT1 and DGAT2) have been characterized. Although these enzymes catalyze the same enzymatic reaction, their respective amino acid sequences are unrelated and they occupy distinct gene families. Mice harboring a disruption in the gene encoding DGAT1 are resistant to diet-induced obesity and have elevated energy expenditure and activity (Smith, S. J. et. al., 2000. *Nat Genet* 25: 87-90). Dgat1−/− mice exhibit dysregulated postaborpative release of chylomicrons and accumulate lipid in the enterocytes (Buhman, K. K. et. al. 2002. *J. Biol. Chem.* 277: 25474-25479). The metabolically favorable phenotype observed in these mice is suggested to be driven by loss of DGAT1 expression in the intestine (Lee, B., et. al. 2010. *J. Lipid Res.* 51: 1770-1780). Importantly, despite a defect in lactation in female Dgat1−/− mice, these animals retain the capacity to synthesize TG suggesting the existence of additional DGAT enzymes. This observation and the isolation of a second DGAT from the fungus *Mortierella ramanniana* led to the identification and characterization of DGAT2 (Yen, C. L. et. al. 2008. *J. Lipid Res.* 49: 2283-2301).

DGAT2 is highly expressed in liver and adipose, and unlike DGAT1, exhibits exquisite substrate specificity for DAG (Yen, C. L., 2008). Deletion of the DGAT2 gene in rodents results in defective intrauterine growth, severe lipemia, impaired skin barrier function, and early post-natal death (Stone, S. J. et. al. 2004. *J. Biol. Chem.* 279: 11767-11776). Due to the lethality caused by loss of DGAT2, much of our understanding of the physiological role of DGAT2 derives from studies performed with antisense oligonucleotides (ASO) in rodent models of metabolic disease. In this setting, inhibition of hepatic DGAT2 resulted in improvements in plasma lipoprotein profile (decrease in total cholesterol and TG) and a reduction of hepatic lipid burden which was accompanied by improved insulin sensitivity and whole-body glucose control (Liu, Y. et. al. 2008. *Biochim. Biophys. Acta* 1781: 97-104; Choi, C. S. et. al. 2007. *J. Biol. Chem.* 282: 22678-22688; Yu, X. X. et. al. 2005. *Hepatology* 42: 362-371). Although the molecular mechanisms underlying these observations are not fully elucidated, it is clear that suppression of DGAT2 results in a down-regulation of the expression of multiple genes encoding proteins involved in lipogenesis, including sterol regulatory element-binding proteins 1c (SREBP1c) and stearoyl CoA-desaturase 1 (SCD1) (Choi, 2007; Yu, 2005). In parallel, oxidative pathways are induced as evidenced by increased expression of genes such as carnitine palmitoyl transferase 1 (CPT1) (Choi, 2007). The net result of these changes is to decrease the levels of hepatic DAG and TG lipid which, in turn, leads to improved insulin responsiveness in the liver. Furthermore, DGAT2 inhibition suppresses hepatic VLDL TG secretion and reduction in circulating cholesterol levels. Finally, plasma apolipoprotein B (APOB) levels were suppressed, possibly due to decreased supply of TG for lipidation of the newly synthesized APOB protein (Liu, 2008; Yu, 2005). The beneficial effects of DGAT2 inhibition on both glycemic control and plasma cholesterol profile suggest that this target might be valuable in the treatment of metabolic disease (Choi, 2007). In addition, the observation that suppression of DGAT2 activity results in reduced hepatic lipid accumulation suggests that inhibitors of this enzyme might have utility in the treatment of NASH.

(S)-2-(5-((3-Ethoxypyridin-2-yl)oxy)pyridin-3-yl)-N-(tetrahydrofuran-3-yl)pyrimidine-5-carboxamide [including its crystalline solid forms (Form 1 and Form 2)] is a DGAT2 inhibitor described in Example 1 of U.S. Pat. No. 10,071,992, the disclosure of which is hereby incorporated herein by reference in its entirety for all purposes.

Ketohexokinase (KHK) is the principal enzyme in fructose metabolism and catalyzes the conversion of fructose to fructose-1-phosphate (F1P). KHK is expressed as two alternative mRNA splice variants, denoted KHKa and KHKc, resulting from alternative splicing of the third exon. The affinity and capacity of KHKc for fructose phosphorylation is much greater than KHKa as evidenced by a much lower Km (Ishimoto, Lanaspa et al., *PNAS* 109, 4320-4325, 2012). While KHKa is ubiquitously expressed, the expression of KHKc is highest in the liver, kidney and intestines, the primary sites of fructose metabolism in the body (Diggle C P, et al. (2009) *J Histochem Cytochem* 57:763-774; Ishimoto, Lanaspa, et al., *PNAS* 109, 4320-4325, 2012). Additionally, loss of function mutations have been reported in humans and termed Essential Fructosuria (OMIM #229800), with no adverse effects except the appearance of fructose in the urine after ingestion of the sugar.

A more severe condition involved in fructose metabolism is Hereditary Fructose Intolerance (HFI, OMIM #229600) which is caused by defects in aldolase B (GENE: ALDOB) which is the enzyme responsible for breaking down F1P and is immediately downstream of the KHK step in the pathway (Bouteldja N, et. al, *J. Inherit. Metab. Dis.* 2010 April; 33(2):105-12; Tolan, D R, *Hum Mutat.* 1995; 6(3):210-8; http://www.omim.org/entry/229600). It is a rare disorder which affects an estimated 1 in 20,000 people, and mutations result in accumulation of F1P, depletion of ATP, and increase in uric acid, the combination of which causes hypoglycemia, hyperuricemia, and lactic acidosis, among other metabolic derangements. HFI impairs the body's ability to metabolize dietary fructose resulting in acute symptoms such as vomiting, severe hypoglycemia, diarrhea, and abdominal distress, leading to long term growth defects, liver and kidney damage and potentially death (Ali M et al, *J. Med. Genet.* 1998 May: 35(5):353-65). Patients generally suffer through the first years of life prior to diagnosis, and the only course of treatment is avoiding fructose in the diet. This is made challenging by the presence of this macronutrient in a majority of food items. In addition to physical symptoms, many patients experience emotional and social isolation as a consequence of their unusual diet, and constantly struggle to adhere to strict dietary limitations (HFI-INFO Discussion Board, http://hfiinfo.proboards.com. Accessed 14 Dec. 2015). Even when they appear non-symptomatic, some patients develop NAFLD and kidney disease, which underscores the inadequacy of self-imposed dietary restriction as the only treatment option, and the high unmet medical need for this condition.

In hyperglycemic conditions, endogenous fructose production occurs through the polyol pathway, a pathway by which glucose is converted to fructose with sorbitol as an intermediate. The activity of this pathway increases with hyperglycemia. In these studies, the authors demonstrated that the KHK null mice were protected from glucose induced weight gain, insulin resistance and hepatic steatosis suggesting that under hyperglycemic conditions, endogenously produced fructose may contribute to insulin resistance and hepatic steatosis (Lanaspa, M. A., et al., *Nature Comm.* 4, 2434, 2013). Therefore, the inhibition of KHK is anticipated to benefit many diseases where alterations of either or both of endogenous or ingested fructose are involved.

[(1R,5S,6R)-3-{2-[(2S)-2-methylazetidin-1-yl]-6-(trifluoromethyl)pyrimidin-4-yl}-3-azabicyclo[3.1.0]hex-6-yl] acetic acid (including a crystalline free acid form thereof) is a ketohexokinase inhibitor and is described in Example 4 of U.S. Pat. No. 9,809,579, the disclosure of which is hereby incorporated herein by reference in its entirety for all purposes.

Currently, various pharmacological approaches are available for treating hyperglycemia and subsequently, Type 2 diabetes mellitus, also known as, T2DM (Hampp, C. et al. *Use of Antidiabetic Drugs in the U.S.,* 2003-2012, Diabetes Care 2014, 37, 1367-1374). These may be grouped into six major classes, each acting through a different primary mechanism: (A) Insulin secretogogues, including sulphonyl-ureas (e.g., glipizide, glimepiride, glyburide), meglitinides (e.g., nateglinide, repaglinide), dipeptidyl peptidase IV (DPP-IV) inhibitors (e.g., sitagliptin, vildagliptin, alogliptin, dutogliptin, linagliptin, saxagliptin), and glucagon-like peptide-1 receptor (GLP-1R) agonists (e.g., liraglutide, albiglutide, exenatide, lixisenatide, dulaglutide, semaglutide), which enhance secretion of insulin by acting on the pancreatic beta-cells. Sulphonyl-ureas and meglitinides have limited efficacy and tolerability, cause weight gain and often induce hypoglycemia. DPP-IV inhibitors have limited efficacy. Marketed GLP-1R agonists are peptides administered by subcutaneous injection. Liraglutide is additionally approved for the treatment of obesity. (B) Biguanides (e.g., metformin) are thought to act primarily by decreasing hepatic glucose production. Biguanides often cause gastrointestinal disturbances and lactic acidosis, further limiting their use. (C) Inhibitors of alpha-glucosidase (e.g., acarbose) decrease intestinal glucose absorption. These agents often cause gastrointestinal disturbances. (D) Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia. (E) Insulin is used in more severe cases, either alone or in combination with the above agents, and frequent use may also lead to weight gain and carries a risk of hypoglycemia. (F) sodium-glucose linked transporter cotransporter 2 (SGLT2) inhibitors (e.g., dapagliflozin, empagliflozin, canagliflozin, ertugliflozin) inhibit reabsorption of glucose in the kidneys and thereby lower glucose levels in the blood. This emerging class of drugs may be associated with ketoacidosis and urinary tract infections.

However, with the exception of GLP-1R agonists and SGLT2 inhibitors, the drugs for T2DM have limited efficacy and do not address the most important problems, the declining β-cell function and the associated obesity.

Obesity is a chronic disease that is highly prevalent in modern society and is associated with numerous medical problems including hypertension, hypercholesterolemia, and coronary heart disease. It is further highly correlated with T2DM and insulin resistance, the latter of which is generally accompanied by hyperinsulinemia or hyperglycemia, or both. In addition, T2DM is associated with a two to fourfold increased risk of coronary artery disease. Presently, the only treatment that eliminates obesity with high efficacy is bariatric surgery, but this treatment is costly and risky. Pharmacological intervention is generally less efficacious and associated with side effects. There is therefore an obvious need for more efficacious pharmacological intervention with fewer side effects and convenient administration.

Although T2DM is most commonly associated with hyperglycemia and insulin resistance, other diseases associated with T2DM include hepatic insulin resistance, impaired glucose tolerance, diabetic neuropathy, diabetic nephropathy, diabetic retinopathy, obesity, dyslipidemia, hypertension, hyperinsulinemia and nonalcoholic fatty liver disease (NAFLD).

NAFLD is the hepatic manifestation of metabolic syndrome, and is a spectrum of hepatic conditions encompassing steatosis, non-alcoholic steatohepatitis (NASH), fibrosis, cirrhosis and ultimately hepatocellular carcinoma. NAFLD and NASH are considered the primary fatty liver diseases as they account for the greatest proportion of individuals with elevated hepatic lipids. The severity of NAFLD/NASH is based on the presence of lipid, inflammatory cell infiltrate, hepatocyte ballooning, and the degree of fibrosis. Although not all individuals with steatosis progress to NASH, a substantial portion does.

GLP-1 is a 30 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of beta-cells. In non-clinical experiments GLP-1 promotes continued beta-cell competence by stimulating transcription of genes important for glucose-dependent insulin secretion and by promoting beta-cell neogenesis (Meier, et al. *Biodrugs.* 2003; 17 (2): 93-102).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption. In people with T2DM, the normal post-prandial rise in GLP-1 is absent or reduced (Vilsboll T, et al. *Diabetes.* 2001. 50; 609-613).

Holst (*Physiol. Rev.* 2007, 87, 1409) and Meier (*Nat. Rev. Endocrinol.* 2012, 8, 728) describe that GLP-1 receptor agonists, such as GLP-1, liraglutide and exendin-4, have 3 major pharmacological activities to improve glycemic control in patients such as those with T2DM by reducing fasting and postprandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically salt thereof [such as its 2-amino-2-(hydroxymethyl)propane-1,3-diol salt, also known as its tris salt] is a GLP-1R agonist described in U.S. Pat. No. 10,208,019 (see Example 4A-01 of the patent), the disclosure of which is hereby incorporated by reference herein in its entirety for all purposes.

Additional GLP-1R agonists that are useful for the present invention are described in U.S. Provisional Patent Application No. 62/684,696 filed Jun. 13, 2018, and U.S. Provisional Patent Application No. 62/846,944 filed May 13, 2019, the disclosure of each of which is hereby incorporated by reference herein in its entirety for all purposes.

The farnesoid X receptor (FXR) is a member of the nuclear hormone receptor superfamily and is primarily expressed in the liver, kidney and intestine (see, e.g., Seol et al. (1995) Mol. Endocrinol. 9:72-85 and Forman et al. (1995) Cell 81:687-693). It functions as a heterodimer with the retinoid X receptor (RXR) and binds to response elements in the promoters of target genes to regulate gene transcription. The FXR-RXR heterodimer binds with highest affinity to an inverted repeat-1 (IR-1) response element, in which consensus receptor-binding hexamers are separated by one nucleotide. FXR is part of an interrelated process, in that FXR is activated by bile acids (the end product of cholesterol metabolism) (see, e.g., Makishima et al. (1999) Science 284: 1362-1365, Parks et al. (1999) Science 284: 1365-1368, Wang et al. (1999) Mol. Cell. 3:543-553), which serve to inhibit cholesterol catabolism. See also, Urizar et al. (2000) J. Biol. Chem. 275:39313-39317.

FXR is a key regulator of cholesterol homeostasis, triglyceride synthesis and lipogenesis. (Crawley, Expert Opinion Ther. Patents (2010), 20(8): 1047-1057). In addition to the treatment of dyslipidemia, multiple indications for FXR have been described, including treatment of liver disease, diabetes, vitamin D-related diseases, drug-induced side effects and hepatitis. (Crawley, supra). While advances have been made in the development of novel FXR agonists, significant room for improvement remains.

The FXR agonist Tropifexor or a pharmaceutically acceptable salt thereof is described in, e.g., Example 1-1B of U.S. Pat. No. 9,150,568, the disclosure of which is hereby incorporated herein by reference in its entirety for all purposes. The chemical name of Tropifexor is 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid.

In view of the above, there exists a need for medicaments, for example, oral medicaments, containing combination of GLP-1R agonist and ACC1 and/or ACC2 inhibitors; combination of GLP-1R agonist and DGAT2 inhibitor; combination of GLP-1R agonist and KHK inhibitor; and/or combination of GLP-1R agonist and FXR agonist to treat diseases or disorders including NAFLD, and NASH. The specific combinations described herein satisfy the existing need.

SUMMARY OF THE INVENTION

The invention relates to combinations and methods for treating fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease. In part, the invention provides a new combination comprising a GLP-1R agonist in a pharmaceutical composition and in the same or a separate composition comprising an ACC inhibitor. The invention also provides a new combination comprising a GLP-1R agonist in a pharmaceutical composition and in the same or a separate composition comprising a DGAT2 inhibitor. The invention also provides a new combination comprising a GLP-1R agonist in a pharmaceutical composition and in the same or a separate composition comprising a KHK inhibitor. The invention also provides a new combination comprising a GLP-1R agonist in a pharmaceutical composition and in the same or a separate composition comprising a FXR agonist. The invention further provides new methods for treating fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, for example, using the new combination described herein.

In one embodiment, the present invention provides a combination comprising a therapeutically effective amount of a composition comprising (1) GLP-1R agonist (e.g. one of the compounds of Examples 1 to 103, or pharmaceutically acceptable salt thereof) and in the same or a separate composition (2) 4-(4-(1-isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof.

One embodiment (Embodiment A) of the present invention provides a combination comprising (1) GLP-1R agonist and (2) 4-(4-(1-isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2; and 2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid, or pharmaceutically acceptable salt thereof.

In one embodiment, the present invention provides a method for treating a disease or condition in a patient in need thereof, which method comprises administering to the patient a therapeutically effective amount of a combination comprising (1) GLP-1R agonist (e.g. one of the compounds of Examples 1 to 103, or pharmaceutically acceptable salt thereof) and (2) 4-(4-(1-isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof.

One embodiment (Embodiment B) of the present invention provides a method for treating a disease or condition in a patient in need thereof, which method comprises administering to the patient a therapeutically effective amount of a combination comprising (1) GLP-1R agonist and (2) 4-(4-(1-isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, wherein:

the disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, obesity, and type 2 diabetes; and the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2; and 2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid, or pharmaceutically acceptable salt thereof.

In one embodiment, the present invention provides a method for reducing at least one point in severity of nonalcoholic fatty liver disease or nonalcoholic steatohepatitis grading scoring systems, reducing the level of serum markers of nonalcoholic steatohepatitis activity, reducing nonalcoholic steatohepatitis disease activity or reducing the medical consequences of nonalcoholic steatohepatitis in a patient, which method comprises administering to the patient a therapeutically effective amount of a combination comprising (1) GLP-1R agonist (e.g. one of the compounds of Examples 1 to 103, or pharmaceutically acceptable salt thereof) and (2) 4-(4-(1-isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof.

One embodiment (Embodiment C) of the present invention provides a method for reducing at least one point in severity of nonalcoholic fatty liver disease or nonalcoholic steatohepatitis grading scoring systems, reducing the level of serum markers of nonalcoholic steatohepatitis activity, reducing nonalcoholic steatohepatitis disease activity or reducing the medical consequences of nonalcoholic steatohepatitis in a patient, which method comprises administering to the patient a therapeutically effective amount of a combination comprising (1) GLP-1R agonist and (2) 4-(4-(1-isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2; and 2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid, or pharmaceutically acceptable salt thereof.

In one embodiment, the present invention provides a combination comprising (1) GLP-1R agonist (e.g. one of the compounds of Examples 1 to 103, or pharmaceutically acceptable salt thereof) in a pharmaceutical composition and (2) in the same or a separate composition [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid or a pharmaceutically acceptable salt thereof.

One embodiment (Embodiment D) of the present invention provides a combination comprising (1) GLP-1R agonist and (2) [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid or a pharmaceutically acceptable salt thereof, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;
2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;
2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;
2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2; and
2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid, or pharmaceutically acceptable salt thereof.

In one embodiment, the present invention provides a method for treating a disease or condition a patient in need thereof, which method comprises administering to the patient a therapeutically effective amount of a combination comprising (1) GLP-1R agonist (e.g. one of the compounds of Examples 1 to 103, or pharmaceutically acceptable salt thereof) and (2) [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid or a pharmaceutically acceptable salt thereof.

One embodiment (Embodiment E) of the present invention provides a method for treating a disease or condition in a patient in need thereof, which method comprises administering to the patient a therapeutically effective amount of a combination comprising (1) GLP-1R agonist and (2) [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid or a pharmaceutically acceptable salt thereof or a pharmaceutically acceptable salt thereof, wherein:

the disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, obesity, and type 2 diabetes; and the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;
2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;
2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;
2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;
2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;
2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;
2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;
2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;
2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;
2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;
2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;
2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;
2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;
2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2; and
2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid, or pharmaceutically acceptable salt thereof.

In one embodiment, the present invention provides a method for reducing at least one point in severity of nonalcoholic fatty liver disease or nonalcoholic steatohepatitis grading scoring systems, reducing the level of serum markers of nonalcoholic steatohepatitis activity, reducing nonalcoholic steatohepatitis disease activity or reducing the medical consequences of nonalcoholic steatohepatitis in a patient, which method comprises administering to the patient a therapeutically effective amount of a combination comprising (1) GLP-1R agonist (e.g. one of the compounds of Examples 1 to 103, or pharmaceutically acceptable salt thereof) and (2) [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid or a pharmaceutically acceptable salt thereof.

One embodiment (Embodiment F) of the present invention provides a method for reducing at least one point in severity of nonalcoholic fatty liver disease or nonalcoholic steatohepatitis grading scoring systems, reducing the level of serum markers of nonalcoholic steatohepatitis activity, reducing nonalcoholic steatohepatitis disease activity or reducing the medical consequences of nonalcoholic steatohepatitis in a patient, which method comprises administering to the patient a therapeutically effective amount of a combination comprising (1) GLP-1R agonist and (2) [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid or a pharmaceutically acceptable salt thereof, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;
2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;
2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;
2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;
2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;
2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;
2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;
2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;
2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;
2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;
2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;
2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2; and 2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid, or pharmaceutically acceptable salt thereof.

In one embodiment, the present invention provides a combination comprising a therapeutically effective amount of (1) GLP-1R agonist (e.g. one of the compounds of Examples 1 to 103, or pharmaceutically acceptable salt thereof) in a pharmaceutical composition and (2) in the same or a separate composition (S)-2-(5-((3-Ethoxypyridin-2-yl)oxy)pyridin-3-yl)-N-(tetrahydrofuran-3-yl)pyrimidine-5-carboxamide or a pharmaceutically acceptable salt thereof.

One embodiment (Embodiment G), the present invention provides a combination comprising (1) GLP-1R agonist and (2) (S)-2-(5-((3-Ethoxypyridin-2-yl)oxy)pyridin-3-yl)-N-(tetrahydrofuran-3-yl)pyrimidine-5-carboxamide or a pharmaceutically acceptable salt thereof, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2; and 2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid, or pharmaceutically acceptable salt thereof.

In one embodiment, the present invention provides a method for treating a disease or condition a patient in need thereof, which method comprises administering to the patient a therapeutically effective amount of a combination comprising (1) GLP-1R agonist (e.g. one of the compounds of Examples 1 to 103, or pharmaceutically acceptable salt thereof) and (2) (S)-2-(5-((3-Ethoxypyridin-2-yl)oxy)pyridin-3-yl)-N-(tetrahydrofuran-3-yl)pyrimidine-5-carboxamide or a pharmaceutically acceptable salt thereof.

One embodiment (Embodiment H) of the present invention provides a method for treating a disease or condition in a patient in need thereof, which method comprises administering to the patient a therapeutically effective amount of a combination comprising (1) GLP-1R agonist and (2) (S)-2-(5-((3-Ethoxypyridin-2-yl)oxy)pyridin-3-yl)-N-(tetrahydrofuran-3-yl)pyrimidine-5-carboxamide or a pharmaceutically acceptable salt thereof, wherein:

the disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, obesity, and type 2 diabetes; and the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2; and 2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid, or pharmaceutically acceptable salt thereof.

In one embodiment, the present invention provides a method for reducing at least one point in severity of nonalcoholic fatty liver disease or nonalcoholic steatohepatitis grading scoring systems, reducing the level of serum markers of nonalcoholic steatohepatitis activity, reducing nonalcoholic steatohepatitis disease activity or reducing the medical consequences of nonalcoholic steatohepatitis in a patient, which method comprises administering to the patient a therapeutically effective amount of a combination comprising (1) GLP-1R agonist (e.g. one of the compounds of Examples 1 to 103, or pharmaceutically acceptable salt thereof) and (2) (S)-2-(5-((3-Ethoxypyridin-2-yl)oxy)pyridin-3-yl)-N-(tetrahydrofuran-3-yl)pyrimidine-5-carboxamide or a pharmaceutically acceptable salt thereof.

One embodiment (Embodiment I) of the present invention provides a method for reducing at least one point in severity of nonalcoholic fatty liver disease or nonalcoholic steatohepatitis grading scoring systems, reducing the level of serum markers of nonalcoholic steatohepatitis activity, reducing nonalcoholic steatohepatitis disease activity or reducing the medical consequences of nonalcoholic steatohepatitis in a patient, which method comprises administering to the patient a therapeutically effective amount of a combination comprising (1) GLP-1R agonist and (2) (S)-2-(5-((3-Ethoxypyridin-2-yl)oxy)pyridin-3-yl)-N-(tetrahydrofuran-3-yl)pyrimidine-5-carboxamide or a pharmaceutically acceptable salt thereof, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2; and 2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid, or pharmaceutically acceptable salt thereof.

In one embodiment, the present invention provides a combination comprising a therapeutically effective amount of (1) GLP-1R agonist (e.g. one of the compounds of Examples 1 to 103, or pharmaceutically acceptable salt thereof) in a pharmaceutical composition and (2) in the same or a separate composition 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid or a pharmaceutically acceptable salt thereof.

One embodiment (Embodiment J) of the present invention provides a combination comprising (1) GLP-1R agonist and (2) 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid or a pharmaceutically acceptable salt thereof, wherein the GLP-1R agonist selected from:

2-({4-[2-(4-chloro-2-fluorophenyl)-1,3-benzodioxol-4-yl] piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl] piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2; and 2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid, or pharmaceutically acceptable salt thereof.

In one embodiment, the present invention provides a method for treating a disease or condition a patient in need thereof, which method comprises administering to the patient a therapeutically effective amount of a combination comprising (1) GLP-1R agonist (e.g. one of the compounds of Examples 1 to 103, or pharmaceutically acceptable salt thereof) and (2) (2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid or a pharmaceutically acceptable salt thereof.

One embodiment (Embodiment K) of the present invention provides a method for treating a disease or condition in a patient in need thereof, which method comprises administering to the patient a therapeutically effective amount of a combination comprising (1) GLP-1R agonist and (2) 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid or a pharmaceutically acceptable salt thereof, wherein:

the disease or condition selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, obesity, and type 2 diabetes; and the GLP-1R agonist selected from:

2-({4-[2-(4-chloro-2-fluorophenyl)-1,3-benzodioxol-4-yl] piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl] piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2; and 2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid, or pharmaceutically acceptable salt thereof.

In one embodiment, the present invention provides a method for reducing at least one point in severity of nonalcoholic fatty liver disease or nonalcoholic steatohepatitis grading scoring systems, reducing the level of serum markers of nonalcoholic steatohepatitis activity, reducing nonalcoholic steatohepatitis disease activity or reducing the medical consequences of nonalcoholic steatohepatitis in a patient, which method comprises administering to the patient a therapeutically effective amount of a combination comprising (1) GLP-1R agonist (e.g. one of the compounds of Examples 1 to 103, or pharmaceutically acceptable salt thereof) and (2) 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid or a pharmaceutically acceptable salt thereof.

One embodiment (Embodiment L) of the present invention provides a method for reducing at least one point in severity of nonalcoholic fatty liver disease or nonalcoholic steatohepatitis grading scoring systems, reducing the level of serum markers of nonalcoholic steatohepatitis activity, reducing nonalcoholic steatohepatitis disease activity or reducing the medical consequences of nonalcoholic steatohepatitis in a patient, which method comprises administering to the patient a therapeutically effective amount of a combination comprising (1) GLP-1R agonist and (2) 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid or a pharmaceutically acceptable salt thereof, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2; and 2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid, or pharmaceutically acceptable salt thereof.

Any one of the combinations of the invention described here may further optionally comprise at least one other pharmaceutical agent.

Any one of the methods of use/treatment of the invention described here may further optionally comprise administration of at least one other pharmaceutical agent.

In some embodiments, the at least one other pharmaceutical agent (in the combination of the presentation, including both the pharmaceutical compositions of the invention and method of use of the invention) is selected from the group consisting of an acetyl-CoA carboxylase- (ACC) inhibitor, a diacylglycerol O-acyltransferase 1 (DGAT-1) inhibitor, monoacylglycerol O-acyltransferase inhibitors, a phosphodiesterase (PDE)-10 inhibitor, an AMPK activator, a sulfonylurea, a meglitinide, an α-amylase inhibitor, an α-glucoside hydrolase inhibitor, an α-glucosidase inhibitor, a PPARγ agonist, a PPAR α/γ agonist, a biguanide, a glucagon-like peptide 1 (GLP-1) modulator, liraglutide, albiglutide, exenatide, albiglutide, lixisenatide, dulaglutide, semaglutide, a protein tyrosine phosphatase-1B (PTP-1B) inhibitor, SIRT-1 activator, a dipeptidyl peptidase IV (DPP-IV) inhibitor, an insulin secretagogue, a fatty acid oxidation inhibitor, an A2 antagonist, a c-jun amino-terminal kinase (JNK) inhibitor, glucokinase activators (GKa), insulin, an insulin mimetic, a glycogen phosphorylase inhibitor, a VPAC2 receptor agonist, SGLT2 inhibitors, a glucagon receptor modulator, GPR119 modulators, FGF21 derivatives or analogs, TGR5 receptor modulators, GPBAR1 receptor modulators, GPR40 agonists, GPR120 modulators, high affinity nicotinic acid receptor (HM74A) activators, SGLT1 inhibitors, inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors, inhibitors or modulators of PDHK2 or PDHK4, inhibitors of MAP4K4, modulators of IL1 family including IL1 beta, HMG-CoA reductase inhibitors, squalene synthetase inhibitors, fibrates, bile acid sequestrants, ACAT inhibitors, MTP inhibitors, lipoxygenase inhibitors, cholesterol absorption inhibitors, PCSK9 modulators, cholesteryl ester transfer protein inhibitors and modulators of RXRalpha.

In some embodiments, the at least one other pharmaceutical agent (in the combination of the presentation, including both the pharmaceutical compositions of the invention and method of use of the invention) is selected from the group consisting of cysteamine or a pharmaceutically acceptable salt thereof, cystamine or a pharmaceutically acceptable salt thereof, an anti-oxidant compound, lecithin, vitamin B complex, a bile salt preparations, an antagonists of Cannabinoid-1 (CB1) receptor, an inverse agonists of Cannabinoid-1 (CB1) receptor, a peroxisome proliferator-activated receptor) activity regulators, a benzothiazepine or benzothiepine compound, an RNA antisense construct to inhibit protein tyrosine phosphatase PTPRU, a heteroatom-linked substituted piperidine and derivatives thereof, an azacyclopentane derivative capable of inhibiting stearoyl-coenzyme alpha delta-9 desaturase, acylamide compound having secretagogue or inducer activity of adiponectin, a quaternary ammonium compound, Glatiramer acetate, pentraxin proteins, a HMG-CoA reductase inhibitor, n-acetyl cysteine, isoflavone compound, a macrolide antibiotic, a galectin inhibitor, an antibody, or any combination of thereof.

The invention also includes:

any one of the combinations of the invention, for use as a medicament;

any one of the combinations of the invention, for treating fatty liver, nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and with hepatocellular carcinoma or with a metabolic-related disease;

use of any one of the combinations of the invention for treating fatty liver, nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and with hepatocellular carcinoma or with a metabolic-related disease; and use of any one of the combinations of the invention for the manufacture of a medicament for treating fatty liver, nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and with hepatocellular carcinoma or with a metabolic-related disease.

It is to be understood that both the foregoing general description and the following detailed description are exemplary and explanatory only and are not restrictive of the invention, as claimed.

BRIEF DESCRIPTION OF THE DRAWINGS

FIG. 15 summarizes the effect of administration of 4-(4-(1-Isopropyl-7-oxo-1,4,6,7-tetrahydrospiro[indazole-5,4'- piperidine]-1'-carbonyl)-6-methoxypyridin-2-yl)benzoic acid and (S)-2-(5-((3-ethoxypyridin-2-yl)oxy)pyridin-3-yl)-N-(tetrahydrofuran-3-yl)pyrimidine-5-carboxamide as monotherapy and in combination on hepatic lipogenic gene expression in Western diet fed rats, specifically sterol-CoA desaturase (SCD1).

Figure 16:
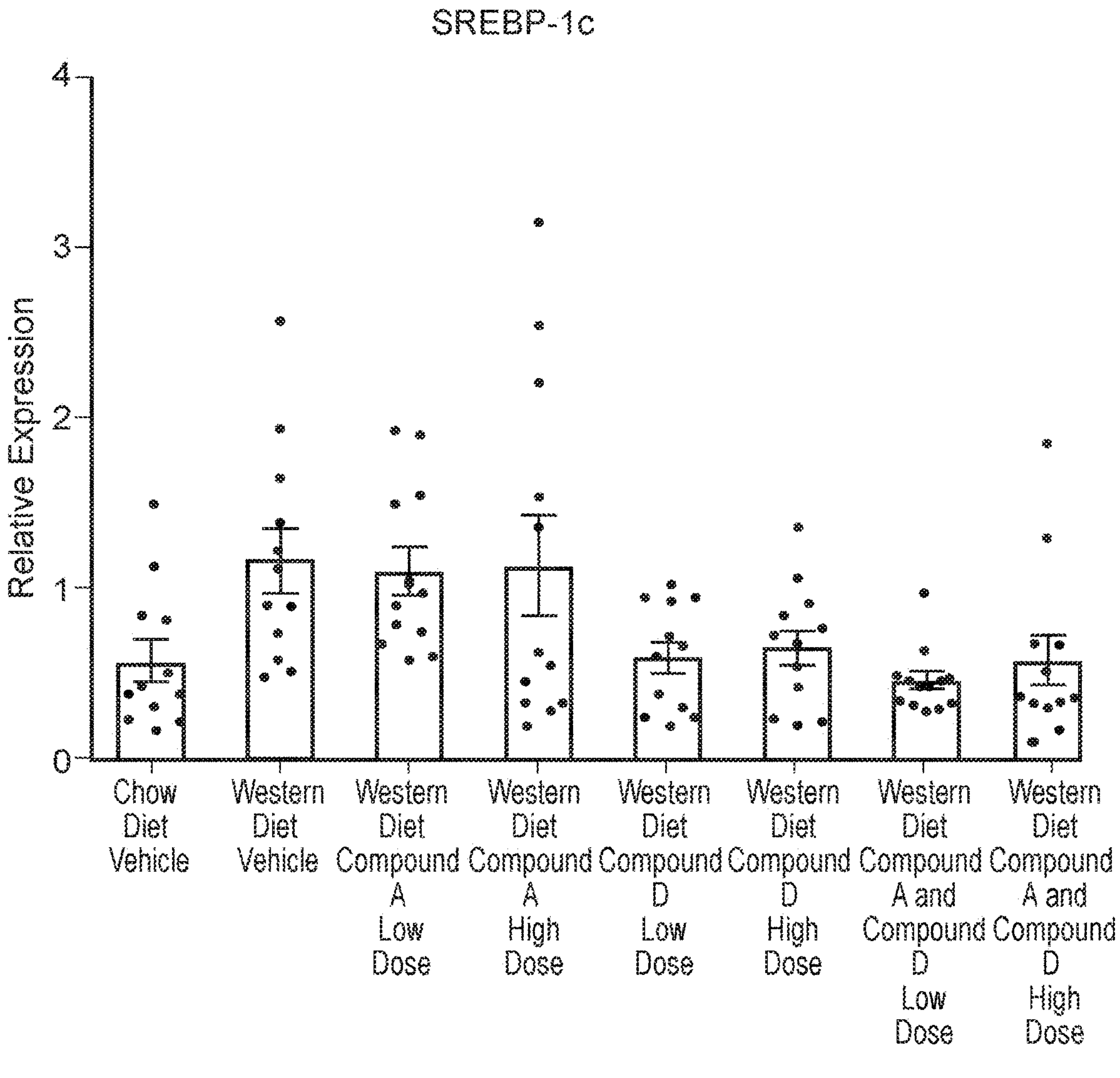

FIG. 16 summarizes the effect of administration of 4-(4-(1-Isopropyl-7-oxo-1,4,6,7-tetrahydrospiro[indazole-5,4'-piperidine]-1'-carbonyl)-6-methoxypyridin-2-yl)benzoic acid and (S)-2-(5-((3-ethoxypyridin-2-yl)oxy)pyridin-3-yl)-N-(tetrahydrofuran-3-yl)pyrimidine-5-carboxamide as monotherapy and in combination on hepatic lipogenic gene expression in Western diet fed rats, specifically sterol regulatory element-binding protein 1c (SREBP-1c).

Figure 17:
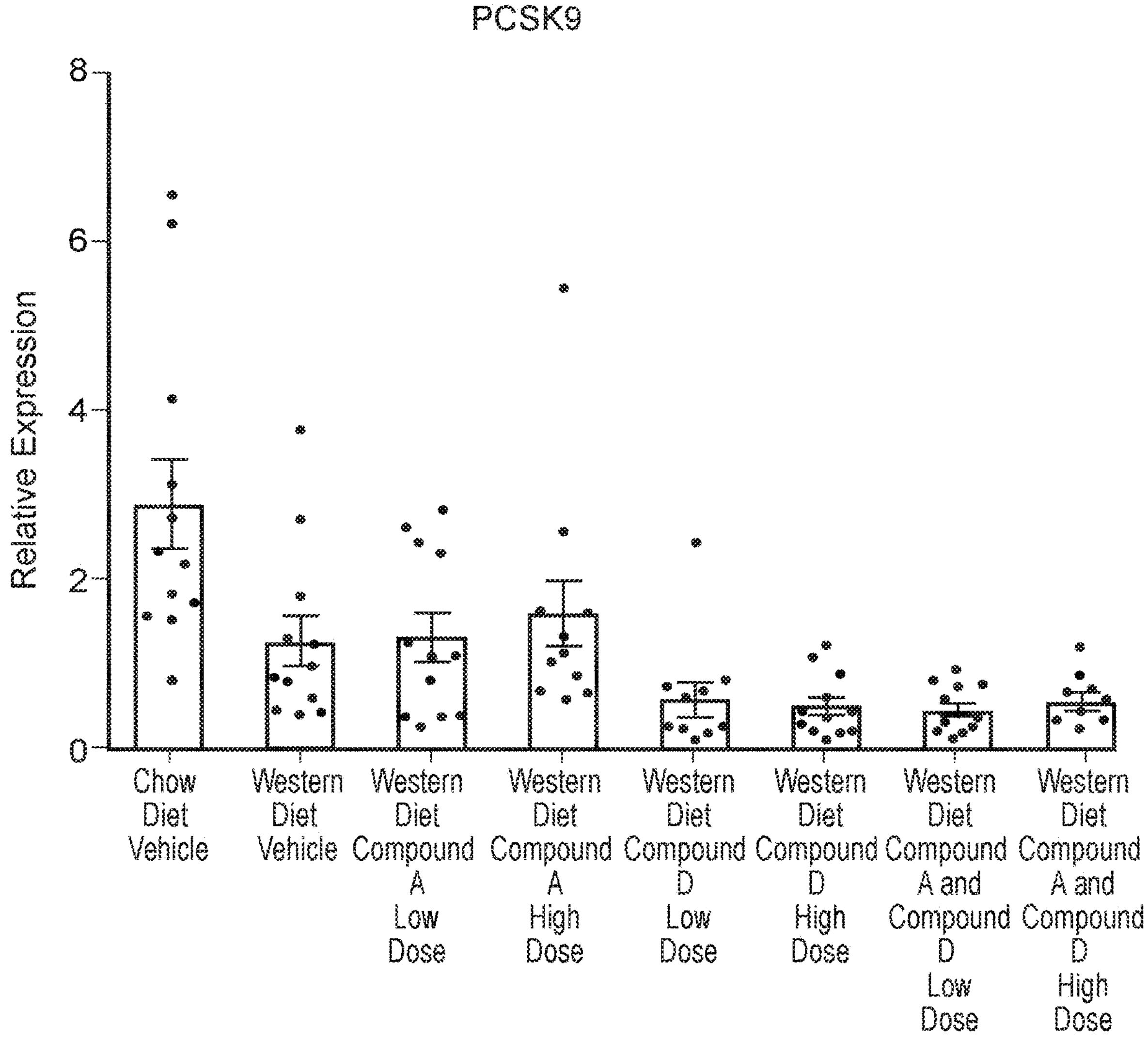

FIG. 17 summarizes the effect of administration of 4-(4-(1-Isopropyl-7-oxo-1,4,6,7-tetrahydrospiro[indazole-5,4'-piperidine]-1'-carbonyl)-6-methoxypyridin-2-yl)benzoic acid and (S)-2-(5-((3-ethoxypyridin-2-yl)oxy)pyridin-3-yl)-N-(tetrahydrofuran-3-yl)pyrimidine-5-carboxamide as monotherapy and in combination on hepatic lipogenic gene expression in Western diet fed rats, specifically proprotein convertase subtilisin/kexin type 9 (PCSK9).

Figure 18:
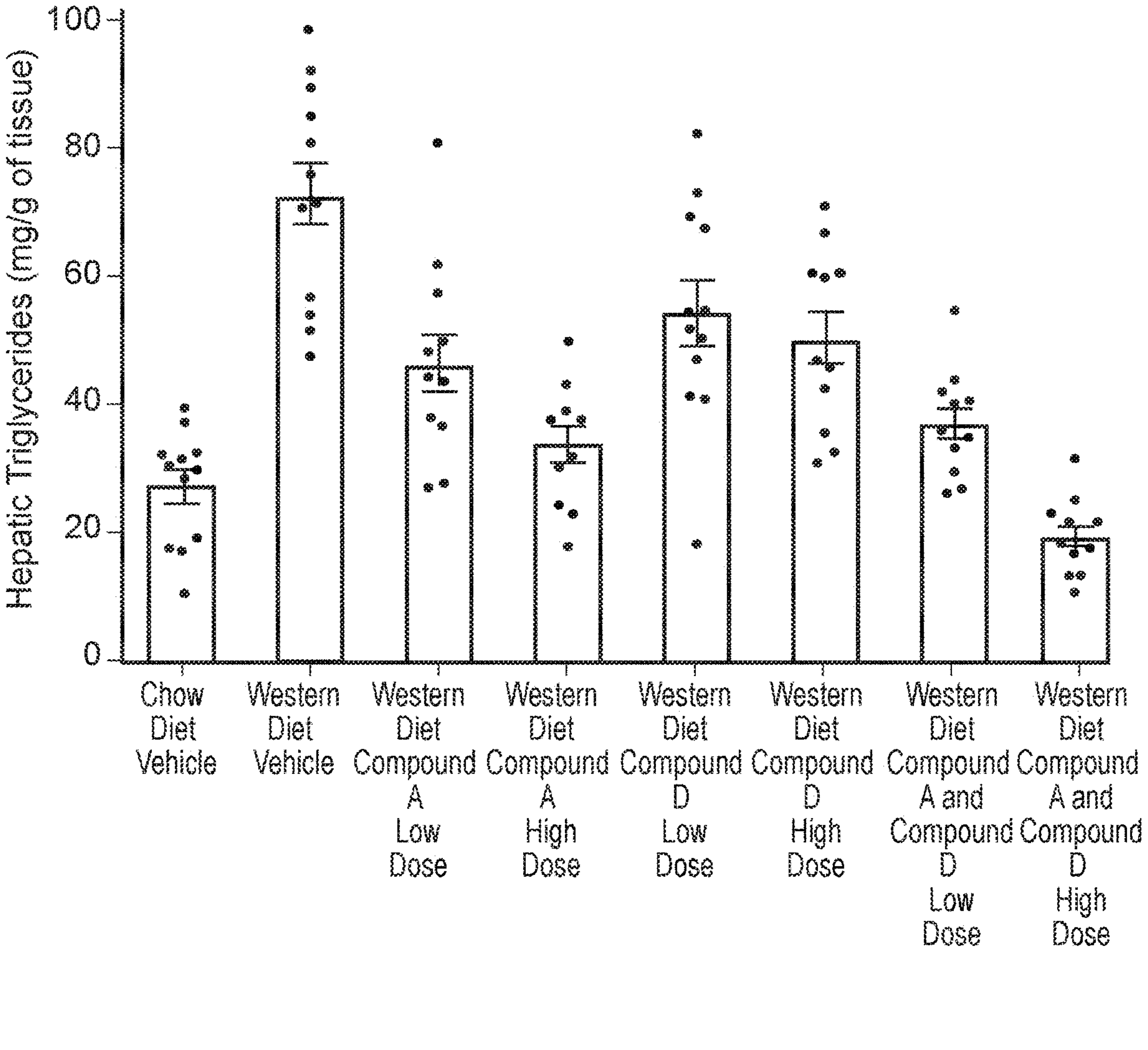

FIG. 18 summarizes the effects of oral administration as monotherapy and in combination of 4-(4-(1-Isopropyl-7-oxo-1,4,6,7-tetrahydrospiro[indazole-5,4'-piperidine]-1'-carbonyl)-6-methoxypyridin-2-yl)benzoic acid and (S)-2-(5-((3-ethoxypyridin-2-yl)oxy)pyridin-3-yl)-N-(tetrahydrofuran-3-yl)pyrimidine-5-carboxamide on hepatic triglyceride levels in Western diet fed Sprague Dawley rats.

Figure 19:
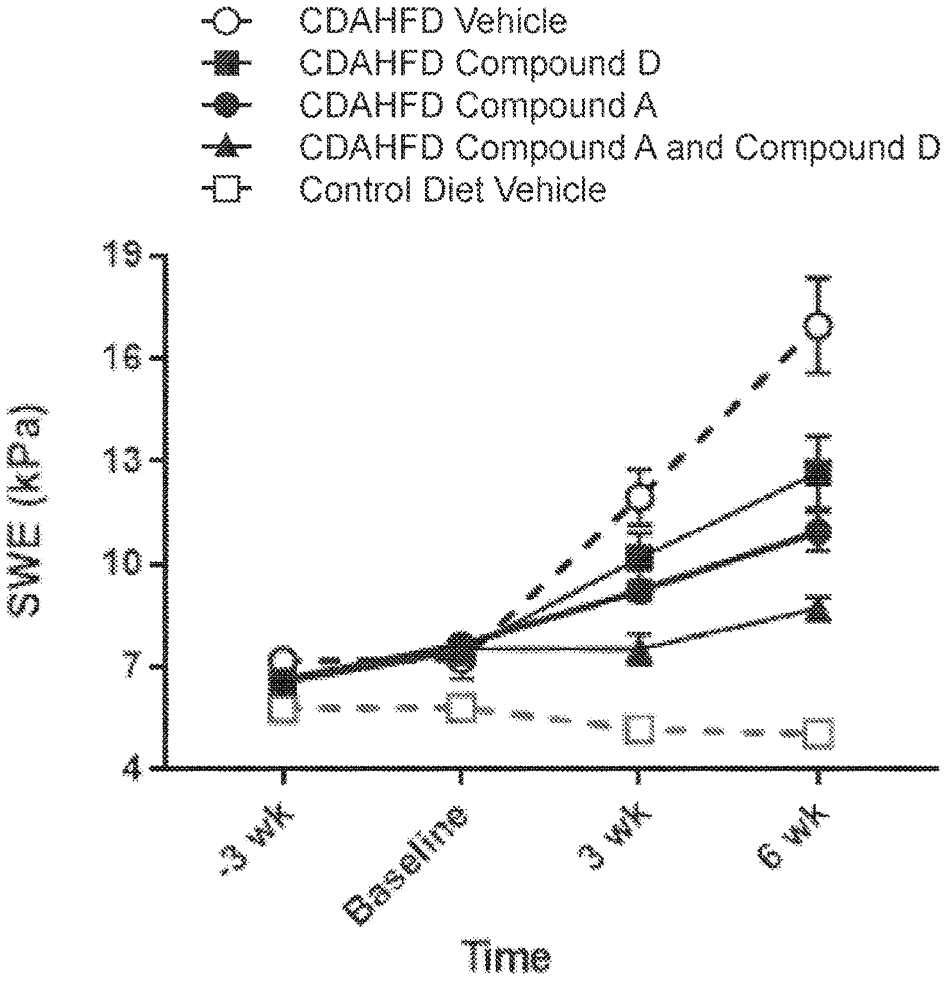

FIG. 19 summarizes the effects of oral administration as monotherapy and in combination of 4-(4-(1-Isopropyl-7-oxo-1,4,6,7-tetrahydrospiro[indazole-5,4'-piperidine]-1'-carbonyl)-6-methoxypyridin-2-yl)benzoic acid and (S)-2-(5-((3-ethoxypyridin-2-yl)oxy)pyridin-3-yl)-N-(tetrahydrofuran-3-yl)pyrimidine-5-carboxamide on elasticity of the liver, a marker of hepatic inflammation and fibrosis, in choline deficient and high fat diet (CDAHFD) fed Male Wistar Hann rats.

Figure 20:
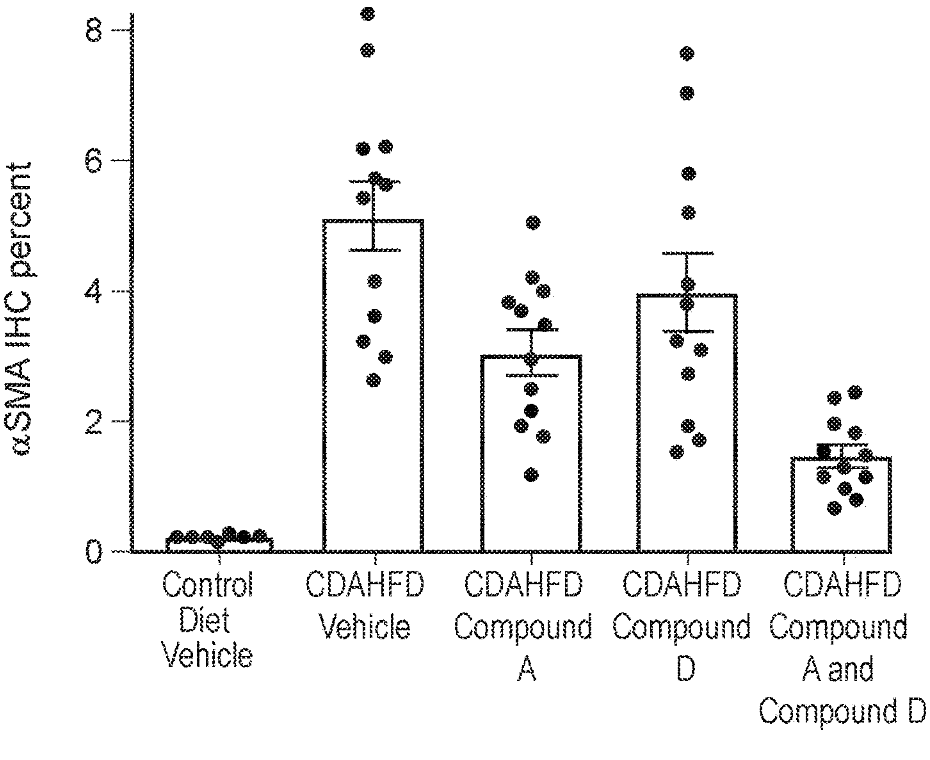

FIG. 20 summarizes the effects of oral administration as monotherapy and in combination of 4-(4-(1-Isopropyl-7-oxo-1,4,6,7-tetrahydrospiro[indazole-5,4'-piperidine]-1'-carbonyl)-6-methoxypyridin-2-yl)benzoic acid and (S)-2-(5-((3-ethoxypyridin-2-yl)oxy)pyridin-3-yl)-N-(tetrahydrofuran-3-yl)pyrimidine-5-carboxamide on hepatic alpha smooth actin (αSMA) immunohistochemistry, a marker of myofibroblast activation and fibrogenesis, in CDAHFD fed Male Wistar Hann rats.

Figure 21:
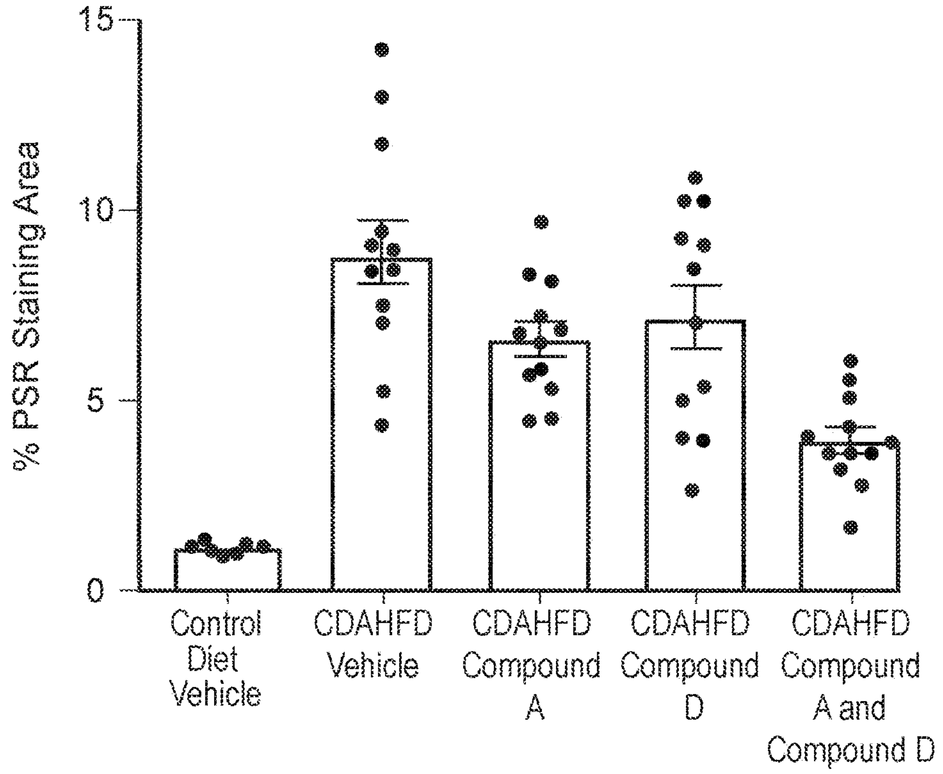

FIG. 21 summarizes the effects of oral administration as monotherapy and in combination of 4-(4-(1-Isopropyl-7-oxo-1,4,6,7-tetrahydrospiro[indazole-5,4'-piperidine]-1'-carbonyl)-6-methoxypyridin-2-yl)benzoic acid and (S)-2-(5-((3-ethoxypyridin-2-yl)oxy)pyridin-3-yl)-N-(tetrahydrofuran-3-yl)pyrimidine-5-carboxamide on hepatic Picosirius red staining in CDAHFD fed Male Wistar Hann rats.

Figure 22:
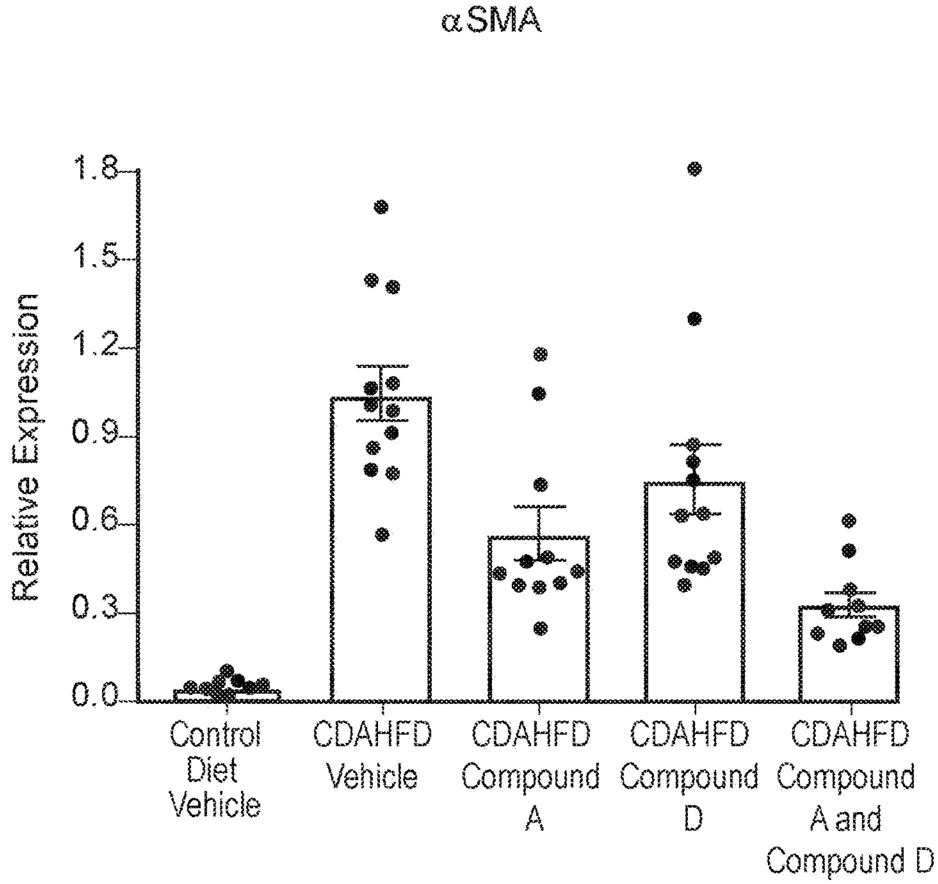

FIG. 22 summarizes the effects of oral administration as monotherapy and in combination of 4-(4-(1-Isopropyl-7-oxo-1,4,6,7-tetrahydrospiro[indazole-5,4'-piperidine]-1'-carbonyl)-6-methoxypyridin-2-yl)benzoic acid and (S)-2-(5-((3-ethoxypyridin-2-yl)oxy)pyridin-3-yl)-N-(tetrahydrofuran-3-yl)pyrimidine-5-carboxamide on hepatic alpha smooth actin (αSMA) gene expression in CDAHFD fed Male Wistar Hann rats.

Figure 23:
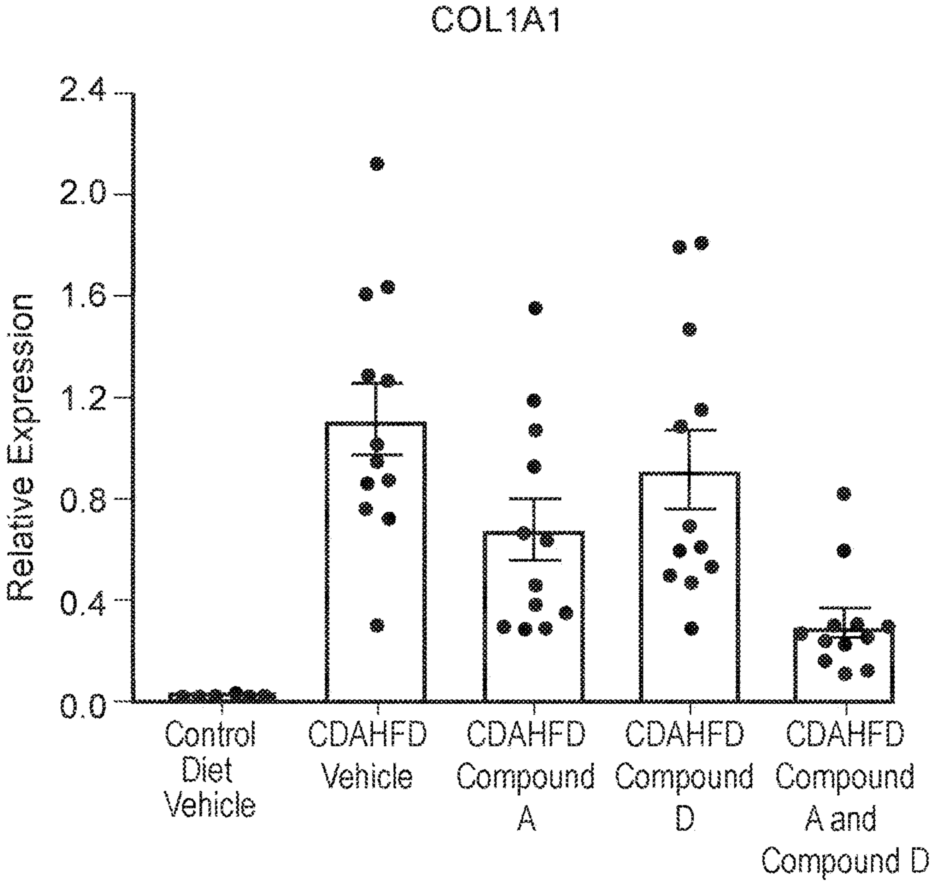

FIG. 23 summarizes the effects of oral administration as monotherapy and in combination of 4-(4-(1-Isopropyl-7-oxo-1,4,6,7-tetrahydrospiro[indazole-5,4'-piperidine]-1'-carbonyl)-6-methoxypyridin-2-yl)benzoic acid and (S)-2-(5-((3-ethoxypyridin-2-yl)oxy)pyridin-3-yl)-N-(tetrahydrofuran-3-yl)pyrimidine-5-carboxamide on hepatic collagen 1A1 gene expression in CDAHFD fed Male Wistar Hann rats.

Figure 24:
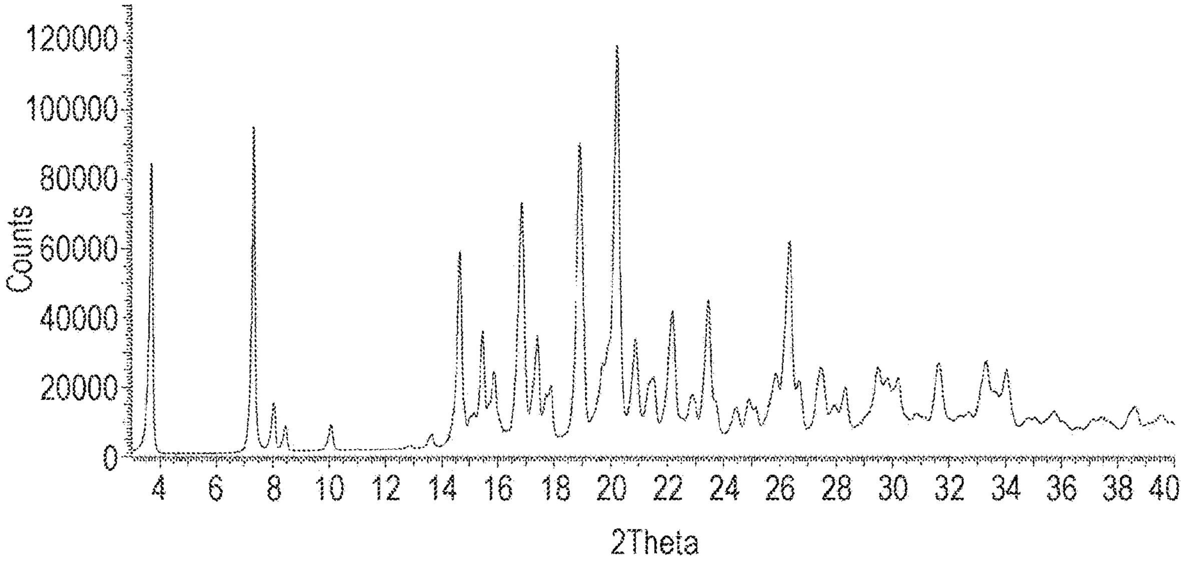

FIG. 24 represents an observed powder X-ray diffraction pattern for an anhydrous (anhydrate) crystal form (Form 1) of tris salt of compound Example 7.

Figure 25:
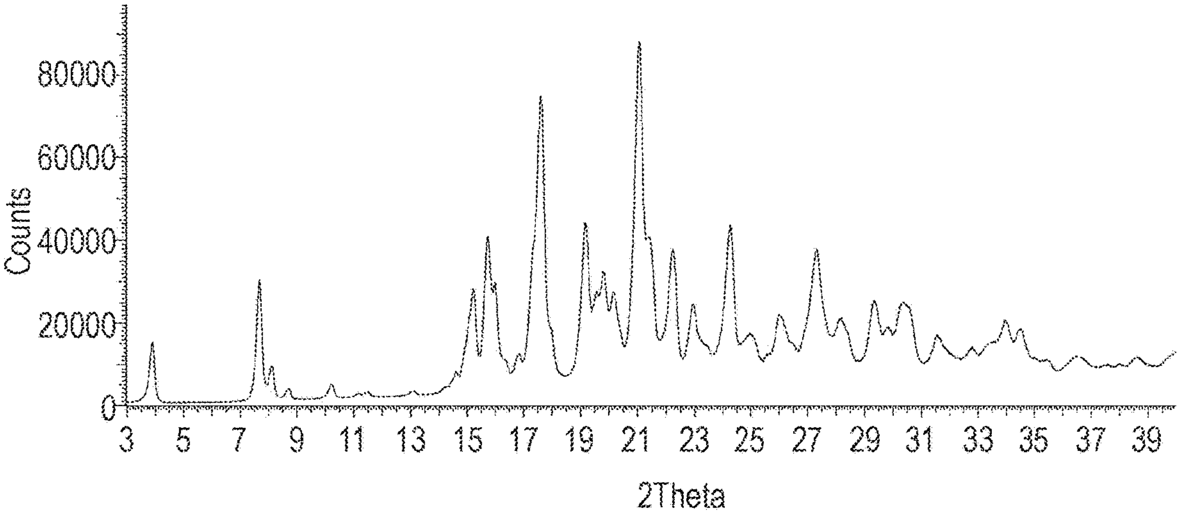

FIG. 25 represents an observed powder X-ray diffraction pattern for an anhydrous (anhydrate) crystal form (Form A) of tris salt of compound Example 10.

DETAILED DESCRIPTION OF THE INVENTION

The invention may be understood more readily by reference to the following detailed description of exemplary embodiments of the invention and the examples included therein.

It is to be understood that this invention is not limited to specific synthetic methods of making that may of course vary. It is also to be understood that the terminology used herein is for the purpose of describing particular embodiments only and is not intended to be limiting. In this specification and in the claims that follow, reference will be made to a number of terms that shall be defined to have the following meanings:

As used herein in the specification, "a" or "an" may mean one or more. As used herein in the claim(s), when used in conjunction with the word "comprising", the words "a" or "an" may mean one or more than one. As used herein "another" may mean at least a second or more.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated to require a tighter range.

"Compounds" when used herein includes any pharmaceutically acceptable derivative or variation, including conformational isomers (e.g., cis and trans isomers) and all optical isomers (e.g., enantiomers and diastereomers), racemic, diastereomeric and other mixtures of such isomers, as well as solvates, hydrates, isomorphs, polymorphs, tautomers, esters, salt forms, and prodrugs. The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the compounds of the invention include but are not limited to those having a carboxyl moiety wherein the free hydrogen is replaced by $(C_1-C_4)$alkyl, $(C_2-C_7)$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

As used herein, an arrowhead, "/" or wavy line, "~" denotes a point of attachment of a substituent to another group.

"Patient" refers to warm blooded animals such as, for example, guinea pigs, mice, rats, gerbils, cats, rabbits, dogs, cattle, goats, sheep, horses, monkeys, chimpanzees, and humans. A "mammal" is a patient.

By "pharmaceutically acceptable" is meant that the substance or composition must be compatible chemically and/or toxicologically, with the other ingredients comprising a formulation, and/or the mammal being treated therewith.

As used herein, the following terms have the general meaning for administration of pharmaceutical agents: QD means once daily and BID means twice daily.

As used herein, the expressions "reaction-inert solvent" and "inert solvent" refer to a solvent or a mixture thereof which does not interact with starting materials, reagents, intermediates or products in a manner which adversely affects the yield of the desired product.

As used herein, the term "selectivity" or "selective" refers to a greater effect of a compound in a first assay, compared to the effect of the same compound in a second assay. For example, in "gut selective" compounds, the first assay is for the half life of the compound in the intestine and the second assay is for the half life of the compound in the liver.

"Therapeutically effective amount" means an amount of all pharmacological agents in the combination therapy described herein that treats the particular disease, condition, or disorder described herein.

The term "treating", "treat" or "treatment" as used herein embraces preventative, i.e., prophylactic; palliative treatment, i.e., relieve, alleviate, or slow the progression of the patient's disease (or condition) or any tissue damage associated with the disease (or condition); and reversal where the patient's disease (or condition) is not only alleviated but any tissue damage associated with the disease (or condition) is placed in a better state then when treatment was initiated. This latter could occur, for example and not limitation, from any one or more of the following: demonstration of NASH resolution and/or from an improvement in the fibrosis score based on liver biopsy; lower incidence of progression to cirrhosis, hepatocellular carcinoma, and/or other liver related outcomes; a reduction or improvement of the level of serum or imaging based markers of nonalcoholic steatohepatitis activity; reduction or improvement of nonalcoholic steatohepatitis disease activity; or reduction in the medical consequences of nonalcoholic steatohepatitis.

It appears that the administration of an ACC inhibitor may have positive effects to lower hepatic TGs and potentially other beneficial effects on treatment of NASH. Increases in circulating TG levels has been reported to be a mechanistic consequence of hepatic ACC inhibition (Kim et al, 2017), though doses of ACC inhibitors that only partially inhibit DNL may not produce elevations in circulating TGs (Bergman et al., (2018) *J. of Hepatology*, Volume 68, S582). It has been discovered that administration of 4-(4-(1-isopropyl-7-oxo-1,4,6,7-tetrahydrospiro[indazole-5,4'-piperidine]-1'-carbonyl)-6-methoxypyridin-2-yl)benzoic acid, optionally administered as a pharmaceutically acceptable salt, has a potential to result in elevations in circulating TGs (generally measured from plasma) in Western diet fed Sprague Dawley rats as was observed in human subjects.

The compounds of the invention may contain asymmetric or chiral centers, and, therefore, exist in different stereoisomeric forms. Unless specified otherwise, it is intended that all stereoisomeric forms of the compounds of the invention as well as mixtures thereof, including racemic mixtures, form part of the invention. In addition, the invention embraces all geometric and positional isomers. For example, if a compound of the invention incorporates a double bond or a fused ring, both the cis- and trans-forms, as well as mixtures, are embraced within the scope of the invention.

Chiral compounds of the invention (and chiral precursors thereof) may be obtained in enantiomerically-enriched form using chromatography, typically high pressure liquid chromatography (HPLC) or supercritical fluid chromatography (SFC), on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine (DEA) or isopropylamine. Concentration of the eluent affords the enriched mixture.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereoisomers and converting (e.g. hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

Where the compounds of the invention possess two or more stereogenic centers and the absolute or relative stereochemistry is given in the name, the designations R and S refer respectively to each stereogenic center in ascending numerical order (1, 2, 3, etc.) according to the conventional IUPAC number schemes for each molecule. Where the compounds of the invention possess one or more stereogenic centers and no stereochemistry is given in the name or structure, it is understood that the name or structure is intended to encompass all forms of the compound, including the racemic form.

It is also possible that the intermediates and compounds of the invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations.

Valence tautomers include interconversions by reorganization of some of the bonding electrons.

Included within the scope of the claimed compounds invention are all stereoisomers, geometric isomers and tautomeric forms of the compounds of the invention, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

The invention includes all pharmaceutically acceptable isotopically-labelled compounds of the invention wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$, $^{124}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the invention, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Tomography (PET) studies for examining substrate receptor occupancy.

Isotopically-labelled compounds of the invention can generally be prepared by conventional techniques known to those skilled in the art or by processes analogous to those described in the accompanying Examples and Preparations using an appropriate isotopically-labelled reagent in place of the non-labelled reagent previously employed.

The compounds of the invention may be isolated and used per se, or when possible, in the form of its pharmaceutically acceptable salt. The term "salts" refers to inorganic and organic salts of a compound of the invention. These salts can be prepared in situ during the final isolation and purification of a compound, or by separately treating the compound with a suitable organic or inorganic acid or base and isolating the salt thus formed. The acids which are used to prepare the pharmaceutically acceptable acid addition salts of the aforementioned base compounds of this invention are those which form non-toxic acid addition salts, (i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, naphthylate, mesylate, glucoheptonate, lactobionate, laurylsulphonate, hexafluorophosphate, benzene sulfonate, tosylate, formate, trifluoroacetate, oxalate, besylate, palmitinate, pamoate, malonate, stearate, laurate, malate, borate, p-toluenesulfonate and pamoate (i.e., 1,1'-methylene-bis-(2-hydroxy-3-naphthoate)) salts.

The invention also relates to base addition salts of the compounds of the invention. The chemical bases that may be used as reagents to prepare pharmaceutically acceptable base salts of those compounds of the invention that are acidic in nature are those that form non-toxic base salts with such compounds. Such non-toxic base salts include, but are not limited to those derived from such pharmacologically acceptable cations such as alkali metal cations (e.g., lithium, potassium and sodium) and alkaline earth metal cations (e.g., calcium and magnesium), ammonium or water-soluble amine addition salts such as N-methylglucamine-(meglumine), tetramethylammonium, tetraethylammonium, methylamine, dimethylamine, trimethylamine, triethylamine, ethylamine, and the lower alkanolammonium and other base salts of pharmaceutically acceptable organic amines. See e.g. Berge, et al. *J. Pharm. Sci.* 66, 1-19 (1977).

Certain compounds of the invention may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound of the invention followed by gradual or fast cooling. The presence of polymorphs may be determined by solid probe NMR spectroscopy, IR spectroscopy, differential scanning calorimetry, powder X-ray diffraction or such other techniques.

In a further embodiment, the composition further includes at least one additional pharmaceutical agent selected from the group consisting of an anti-inflammation agent, an anti-diabetic agent, an anti-fibrotic agent, an anti-steatiotic agent, and a cholesterol/lipid modulating agent.

In another embodiment, the method for treating a condition selected from the group consisting of hyperlipidemia, Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertriglyceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), non-alcoholic fatty liver disease (NAFLD), includes the administration of a therapeutically effective amount of a combination described herein.

In a further embodiment, the method for treating a metabolic or metabolic-related disease, condition or disorder includes the step of administering to a patient in need of such treatment a combination comprising at least two separate pharmaceutical compositions (i) a first composition that includes (S)-2-(5-((3-ethoxypyridin-2-yl)oxy)pyridin-3-yl)-N-(tetrahydrofuran-3-yl)pyrimidine-5-carboxamide, or a pharmaceutically acceptable salt thereof, present in a therapeutically effective amount, in admixture with at least one pharmaceutically acceptable excipient;

(ii) a second composition that includes 4-(4-(1-Isopropyl-7-oxo-1,4,6,7-tetrahydrospiro[indazole-5,4'-piperidine]-1'-carbonyl)-6-methoxypyridin-2-yl)benzoic acid, or a pharmaceutically acceptable salt thereof, present in a therapeutically effective amount, in admixture with at least one pharmaceutically acceptable excipient; and optionally (iii) a third composition comprising at least one additional pharmaceutical agent selected from the group consisting of an anti-inflammatory agent, an anti-diabetic agent, an anti-fibrotic agent, an anti-steatiotic agent, and a cholesterol/lipid modulating agent and an anti-diabetic agent, and at least one pharmaceutically acceptable excipient.

In yet a further embodiment, the method of the invention is performed when said first composition, said second composition, and said third composition are administered simultaneously.

In yet another embodiment, the method of the invention is performed when first composition, said second composition, and said third composition are administered separately or sequentially and in any order.

In one embodiment, when three compositions are administered, the first composition and the second composition are administered simultaneously and the third composition is administered sequentially. In another embodiment, the three separate compositions are administered sequentially and in any order.

Compounds of the invention may be synthesized by synthetic routes that include processes analogous to those well-known in the chemical arts, particularly in light of the description contained herein. The starting materials are generally available from commercial sources such as Aldrich Chemicals (Milwaukee, WI) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)). A preparation of (S)-2-(5-((3-ethoxypyridin-2-yl)oxy)pyridin-3-yl)-N-(tetrahydrofuran-3-yl)pyrimidine-5-carboxamide is presented in Example 1 of US 2018-0051012A1, hereby incorporated herein by reference in its entireties for all purposes. A preparation of 4-(4-(1-Isopropyl-7-oxo-1,4,6,7-tetrahydrospiro[indazole-5,4'-piperidine]-t-carbonyl)-6-methoxypyridin-2-yl)benzoic acid is in Example 9 of U.S. Pat. No. 8,859,577, hereby incorporated herein by reference in its entireties for all purposes.

GLP-1R Agonist/ACCi Combination

Embodiments A, B, and C relate to combinations of a GLP-1R agonist (including those described herein) and the ACC inhibitor 4-(4-(1-isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof.

Embodiment A1 is a further embodiment of Embodiment A, wherein the GLP-1R agonist is 2-[(4-{6-[(4-cyano-2-fluorobenzyl)oxy]pyridin-2-yl}piperid in-1-yl)methyl]-1-[(2S)-oxetan-2-ylmethyl]-1H-benzimidazole-6-carboxylic acid, or a pharmaceutically acceptable salt thereof.

Embodiment A2 is a further embodiment of Embodiment A or A1, the GLP-1R agonist is a pharmaceutically acceptable salt of 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid.

Embodiment A3 is a further embodiment of Embodiment A2, wherein the pharmaceutically acceptable salt is a tris salt.

Embodiment A4 is a further embodiment of Embodiment A, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof. In a further embodiment, the GLP-1R agonist is a pharmaceutically acceptable salt.

Embodiment A5 is a further embodiment of Embodiment A4, wherein the GLP-1R agonist is selected from:

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof. In a further embodiment, the GLP-1R agonist is a pharmaceutically acceptable salt.

Embodiment A6 is a further embodiment of Embodiment A5, wherein the pharmaceutically acceptable salt is a tris salt.

Embodiment A7 is a further embodiment of any one of Embodiment A or Embodiments A1 to A5, wherein the 4-(4-(1-isopropyl-7-oxo-1,4,6,7-tetrahydrospiro[indazole-5,4'-piperidine]-1'-carbonyl)-6-methoxypyridin-2-yl)benzoic acid or pharmaceutically acceptable salt thereof is 2-amino-2-(hydroxymethyl)propane-1,3-diol salt of 4-(4-(1-Isopropyl-7-oxo-1,4,6,7-tetrahydrospiro[indazole-5,4'-piperidine]-1'-carbonyl)-6-methoxypyridin-2-yl)benzoic acid.

Embodiment A8 is a further embodiment of Embodiment A7, wherein the 2-amino-2-(hydroxymethyl)propane-1,3-diol salt of 4-(4-(1-Isopropyl-7-oxo-1,4,6,7-tetrahydrospiro[indazole-5,4'-piperidine]-t-carbonyl)-6-methoxypyridin-2-yl)benzoic acid is a crystal form.

Embodiment A9 is a further embodiment of Embodiment A8, wherein the ratio of 4-(4-(1-isopropyl-7-oxo-1,4,6,7-tetrahydrospiro[indazole-5,4'-piperidine]-1'-carbonyl)-6-methoxypyridin-2-yl)benzoic acid and 2-amino-2-(hydroxymethyl)propane-1,3-diol in the crystal form is 1:1.

Embodiment A10 is a further embodiment of Embodiment A8 or A9, wherein the crystal form is an anhydrous crystal form.

Embodiment A11 is a further embodiment of Embodiment A10, wherein the anhydrous crystal form has a PXRD pattern comprising peaks at diffraction angles of 9.6, 10.7, and 11.3 2Θ, ±0.2° 2Θ.

Embodiment A12 is a further embodiment of Embodiment A10 or A11, wherein the anhydrous crystal form has a Raman spectrum comprising peak shifts at 1511, 1561, and 1615 $cm^{-1}$, ±2 $cm^{-1}$.

Embodiment A13 is a further embodiment of any one of Embodiments A10 to A12, wherein the anhydrous crystal form has a $^{13}C$ ssNMR spectrum comprising chemical shifts at 22.9, 146.2, and 161.9 ppm, ±0.2 ppm.

Embodiment A14 is a further embodiment of Embodiment A13, wherein the anhydrous crystal form has an analytical parameter selected from the group consisting of a Raman spectrum comprising peak shifts at 1511 and 1615 $cm^{-1}$, ±2 $cm^{-1}$, and a $^{13}C$ ssNMR spectrum comprising at least one chemical shift at 22.9, 146.2, or 161.9 ppm, ±0.2 ppm.

Embodiment A15 is a further embodiment of Embodiment A8 or A9, wherein the crystal form is a trihydrate crystal form.

Embodiment A16 is a further embodiment of Embodiment A15, wherein the trihydrate crystal form has a PXRD pattern comprising peaks at diffraction angles of 8.4, 9.0, and 10.5 2Θ, ±0.2° 2Θ.

Embodiment A17 is a further embodiment of Embodiment A15 or A16, wherein the trihydrate crystal form has a Raman spectrum comprising peak shifts at 1507, 1557, and 1610 $cm^{-1}$, ±2 $cm^{-1}$.

Embodiment A18 is a further embodiment of any one of Embodiment A15 to A17, wherein the trihydrate crystal form has a $^{13}C$ ssNMR spectrum comprising chemical shifts at 19.2, 149.5, and 163.8 ppm, ±0.2 ppm.

Embodiment A19 is a further embodiment of Embodiment A18, wherein the trihydrate crystal form has an analytical parameter selected from the group consisting of a PXRD pattern comprising peaks at diffraction angles of 8.4 and 9.0 2Θ, ±0.2° 2Θ, a Raman spectrum comprising peak shifts at 1557 and 1610 $cm^{-1}$, ±2 $cm^{-1}$, and a $^{13}C$ ssNMR spectrum comprising at least one chemical shift at 19.2, 149.5, or 163.8 ppm, ±0.2 ppm.

Embodiment A20 is a further embodiment of Embodiment A18, wherein the trihydrate crystal form has an analytical parameter selected from the group consisting of a PXRD pattern comprising peaks at diffraction angles of 8.4 and 9.0 2Θ, ±0.2° 2Θ, and a Raman spectrum comprising at least one peak shift at 1507, 1557, or 1610 $cm^{-1}$, +2 $cm^{-1}$.

Embodiment A21 is a further embodiment of Embodiment A18, wherein the trihydrate crystal form has an analytical parameter selected from the group consisting of a PXRD pattern comprising peaks at diffraction angles of 8.4 and 9.0 2Θ, ±0.2° 2Θ, and a $^{13}C$ ssNMR spectrum comprising at least one chemical shift at 19.2, 149.5, or 163.8 ppm, ±0.2 ppm.

Embodiment A22 is a further embodiment of Embodiment A or any one of Embodiments A1 to A12, the composition further comprises at least one other pharmaceutical agent.

Embodiment A23 is a further embodiment of Embodiment A22, wherein the at least one other pharmaceutical agent is selected from the group consisting of an acetyl-CoA carboxylase-(ACC) inhibitor, a diacylglycerol O-acyltransferase 1 (DGAT-1) inhibitor, monoacylglycerol O-acyltransferase inhibitors, a phosphodiesterase (PDE)-10 inhibitor, an AMPK activator, a sulfonylurea, a meglitinide, an α-amylase inhibitor, an α-glucoside hydrolase inhibitor, an α-glucosidase inhibitor, a PPARγ agonist, a PPAR α/γ agonist, a biguanide, a glucagon-like peptide 1 (GLP-1) modulator, liraglutide, albiglutide, exenatide, albiglutide, lixisenatide, dulaglutide, semaglutide, a protein tyrosine phosphatase-1B (PTP-1B) inhibitor, SIRT-1 activator, a dipeptidyl peptidase IV (DPP-IV) inhibitor, an insulin secretagogue, a fatty acid oxidation inhibitor, an A2 antagonist, a c-jun amino-terminal kinase (JNK) inhibitor, glucokinase activators (GKa), insulin, an insulin mimetic, a glycogen phosphorylase inhibitor, a VPAC2 receptor agonist, SGLT2 inhibitors, a glucagon receptor modulator, GPR119 modulators, FGF21 derivatives or analogs, TGR5 receptor modulators, GPBAR1 receptor modulators, GPR40 agonists, GPR120 modulators, high affinity nicotinic acid receptor (HM74A) activators, SGLT1 inhibitors, inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors, inhibitors or modulators of PDHK2 or PDHK4, inhibitors of MAP4K4, modulators of IL1 family including IL1 beta, HMG-CoA reductase inhibitors, squalene synthetase inhibitors, fibrates, bile acid sequestrants, ACAT inhibitors, MTP inhibitors, lipoxygenase inhibitors, cholesterol absorption inhibitors, PCSK9 modulators, cholesteryl ester transfer protein inhibitors and modulators of RXRalpha.

Embodiment B1 is a further embodiment of Embodiment B, wherein the disease or condition is fatty liver.

Embodiment B2 is a further embodiment of Embodiment B, wherein the disease or condition is nonalcoholic fatty liver disease.

Embodiment B3 is a further embodiment of Embodiment B, wherein the disease or condition is nonalcoholic steatohepatitis.

Embodiment B4 is a further embodiment of Embodiment B, wherein the disease or condition is nonalcoholic steatohepatitis with liver fibrosis.

Embodiment B5 is a further embodiment of Embodiment B wherein the disease or condition is nonalcoholic steatohepatitis with cirrhosis.

Embodiment B6 is a further embodiment of Embodiment B, wherein the disease or condition is nonalcoholic steatohepatitis with cirrhosis and with hepatocellular carcinoma.

Embodiment B7 is a further embodiment of Embodiment B, wherein the disease or condition is nonalcoholic steatohepatitis with cirrhosis and with a metabolic-related disease.

Embodiment B8 is a further embodiment of Embodiment B or any one of Embodiments B1 to B7, wherein the GLP-1R agonist is 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

Embodiment B9 is a further embodiment of Embodiment B8, wherein the GLP-1R agonist is a pharmaceutically acceptable salt of 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid.

Embodiment B10 is a further embodiment of Embodiment B9, wherein the pharmaceutically acceptable salt is a tris salt.

Embodiment B11 is a further embodiment of Embodiment B or any one of Embodiments B1 to B7, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;
2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;
2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;
2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;
2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;
2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and
2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof.

Embodiment B12 is a further embodiment of Embodiment B11, wherein the GLP-1R agonist is selected from:

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;
2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;
2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and
2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof. In a further embodiment, the GLP-1R agonist a pharmaceutically acceptable salt.

Embodiment B13 is a further embodiment of Embodiment B12, wherein the pharmaceutically acceptable salt is a tris salt.

Embodiment B14 is a further embodiment of any one of Embodiment B or Embodiment B1 to B13, wherein the 4-(4-(1-isopropyl-7-oxo-1,4,6,7-tetrahydrospiro[indazole-5,4'-piperidine]-1'-carbonyl)-6-methoxypyridin-2-yl)benzoic acid or pharmaceutically acceptable salt thereof is 2-amino-2-(hydroxymethyl)propane-1,3-diol salt of 4-(4-(1-Isopropyl-7-oxo-1,4,6,7-tetrahydrospiro[indazole-5,4'-piperidine]-1'-carbonyl)-6-methoxypyridin-2-yl)benzoic acid.

Embodiment B15 is a further embodiment of Embodiment B14, wherein the 2-amino-2-(hydroxymethyl)propane-1,3-diol salt of 4-(4-(1-Isopropyl-7-oxo-1,4,6,7-tetrahydrospiro[indazole-5,4'-piperidine]-t-carbonyl)-6-methoxypyridin-2-yl)benzoic acid is a crystal form.

Embodiment B16 is a further embodiment of Embodiment B15, wherein the ratio of 4-(4-(1-isopropyl-7-oxo-1,4,6,7-tetrahydrospiro[indazole-5,4'-piperidine]-1'-carbonyl)-6-methoxypyridin-2-yl)benzoic acid and 2-amino-2-(hydroxymethyl)propane-1,3-diol in the crystal form is 1:1.

Embodiment B17 is a further embodiment of Embodiment B15 or B16, wherein the crystal form is an anhydrous crystal form.

Embodiment B18 is a further embodiment of Embodiment B17, wherein the anhydrous crystal form has a PXRD pattern comprising peaks at diffraction angles of 9.6, 10.7, and 11.3 2Θ, ±0.2° 2Θ.

Embodiment B19 is a further embodiment of Embodiment B17 or B18, wherein the anhydrous crystal form has a Raman spectrum comprising peak shifts at 1511, 1561, and 1615 $cm^{-1}$, ±2 $cm^{-1}$.

Embodiment B20 is a further embodiment of any one of Embodiments B17 to B19, wherein the anhydrous crystal form has a $^{13}C$ ssNMR spectrum comprising chemical shifts at 22.9, 146.2, and 161.9 ppm, +0.2 ppm.

Embodiment B21 is a further embodiment of Embodiment B20, wherein the anhydrous crystal form has an analytical parameter selected from the group consisting of a Raman spectrum comprising peak shifts at 1511 and 1615

$cm^{-1}$, +2 $cm^{-1}$, and a $^{13}C$ ssNMR spectrum comprising at least one chemical shift at 22.9, 146.2, or 161.9 ppm, ±0.2 ppm.

Embodiment B22 is a further embodiment of Embodiment B15 or B16, wherein the crystal form is a trihydrate crystal form.

Embodiment B23 is a further embodiment of Embodiment B22, wherein the trihydrate crystal form has a PXRD pattern comprising peaks at diffraction angles of 8.4, 9.0, and 10.5 2Θ, ±0.2° 2Θ.

Embodiment B24 is a further embodiment of Embodiment B22 or B23, wherein the trihydrate crystal form has a Raman spectrum comprising peak shifts at 1507, 1557, and 1610 $cm^{-1}$, ±2 $cm^{-1}$.

Embodiment B25 is a further embodiment of any one of Embodiment B22 to B24, wherein the trihydrate crystal form has a $^{13}C$ ssNMR spectrum comprising chemical shifts at 19.2, 149.5, and 163.8 ppm, ±0.2 ppm.

Embodiment B26 is a further embodiment of Embodiment B25, wherein the trihydrate crystal form has an analytical parameter selected from the group consisting of a PXRD pattern comprising peaks at diffraction angles of 8.4 and 9.0 2Θ, ±0.2° 2Θ, a Raman spectrum comprising peak shifts at 1557 and 1610 $cm^{-1}$, ±2 $cm^{-1}$, and a $^{13}C$ ssNMR spectrum comprising at least one chemical shift at 19.2, 149.5, or 163.8 ppm, ±0.2 ppm.

Embodiment B27 is a further embodiment of Embodiment B25, wherein the trihydrate crystal form has an analytical parameter selected from the group consisting of a PXRD pattern comprising peaks at diffraction angles of 8.4 and 9.0 2Θ, ±0.2° 2Θ, and a Raman spectrum comprising at least one peak shift at 1507, 1557, or 1610 $cm^{-1}$, ±2 $cm^{-1}$.

Embodiment B28 is a further embodiment of Embodiment B25, wherein the trihydrate crystal form has an analytical parameter selected from the group consisting of a PXRD pattern comprising peaks at diffraction angles of 8.4 and 9.0 2Θ, ±0.2° 2Θ, and a $^{13}C$ ssNMR spectrum comprising at least one chemical shift at 19.2, 149.5, or 163.8 ppm, +0.2 ppm.

Embodiment B29 is a further embodiment of Embodiment B or any one of Embodiments B1 to B28, the method further comprises administration of at least one other pharmaceutical agent.

Embodiment C1 is a further embodiment of Embodiment C, wherein the GLP-1R agonist is 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

Embodiment C2 is a further embodiment of Embodiment C1, wherein the GLP-1R agonist is a pharmaceutically acceptable salt of 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid.

Embodiment C3 is a further embodiment of Embodiment C2, wherein the pharmaceutically acceptable salt is a tris salt.

Embodiment C4 is a further embodiment of Embodiment C, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof.

Embodiment C5 is a further embodiment of Embodiment C4, wherein the GLP-1R agonist is selected from:

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof. In a further embodiment, the GLP-1R agonist a pharmaceutically acceptable salt.

Embodiment C6 is a further embodiment of Embodiment C5, wherein the pharmaceutically acceptable salt is a tris salt.

Embodiment C7 is a further embodiment of any one of Embodiment C or Embodiment C1 to B6, wherein the 4-(4-(1-isopropyl-7-oxo-1,4,6,7-tetrahydrospiro[indazole-5,4'-piperidine]-1'-carbonyl)-6-methoxypyridin-2-yl)benzoic acid or pharmaceutically acceptable salt thereof is 2-amino-2-(hydroxymethyl)propane-1,3-diol salt of 4-(4-(1-Isopropyl-7-oxo-1,4,6,7-tetrahydrospiro[indazole-5,4'-piperidine]-1'-carbonyl)-6-methoxypyridin-2-yl)benzoic acid.

Embodiment C8 is a further embodiment of Embodiment C7, wherein the 2-amino-2-(hydroxymethyl)propane-1,3-diol salt of 4-(4-(1-Isopropyl-7-oxo-1,4,6,7-tetrahydrospiro[indazole-5,4'-piperidine]-t-carbonyl)-6-methoxypyridin-2-yl)benzoic acid is a crystal form.

Embodiment C9 is a further embodiment of Embodiment C8, wherein the ratio of 4-(4-(1-isopropyl-7-oxo-1,4,6,7-tetrahydrospiro[indazole-5,4'-piperidine]-1'-carbonyl)-6-methoxypyridin-2-yl)benzoic acid and 2-amino-2-(hydroxymethyl)propane-1,3-diol in the crystal form is 1:1.

Embodiment C10 is a further embodiment of Embodiment C8 or C9, wherein the crystal form is an anhydrous crystal form.

Embodiment C11 is a further embodiment of Embodiment C10, wherein the anhydrous crystal form has a PXRD pattern comprising peaks at diffraction angles of 9.6, 10.7, and 11.3 2Θ, ±0.2° 2Θ.

Embodiment C12 is a further embodiment of Embodiment C10 or C11, wherein the anhydrous crystal form has a Raman spectrum comprising peak shifts at 1511, 1561, and 1615 $cm^{-1}$, ±2 $cm^{-1}$.

Embodiment C13 is a further embodiment of any one of Embodiments C10 to C12, wherein the anhydrous crystal form has a $^{13}C$ ssNMR spectrum comprising chemical shifts at 22.9, 146.2, and 161.9 ppm, +0.2 ppm.

Embodiment 14 is a further embodiment of Embodiment C13, wherein the anhydrous crystal form has an analytical parameter selected from the group consisting of a Raman spectrum comprising peak shifts at 1511 and 1615 $cm^{-1}$, ±2 $cm^{-1}$, and a $^{13}C$ ssNMR spectrum comprising at least one chemical shift at 22.9, 146.2, or 161.9 ppm, ±0.2 ppm.

Embodiment C15 is a further embodiment of Embodiment C8 or BC9, wherein the crystal form is a trihydrate crystal form.

Embodiment C16 is a further embodiment of Embodiment C15, wherein the trihydrate crystal form has a PXRD pattern comprising peaks at diffraction angles of 8.4, 9.0, and 10.5 2Θ, ±0.2° 2Θ.

Embodiment C17 is a further embodiment of Embodiment C15 or C16, wherein the trihydrate crystal form has a Raman spectrum comprising peak shifts at 1507, 1557, and 1610 $cm^{-1}$, ±2 $cm^{-1}$.

Embodiment C18 is a further embodiment of any one of Embodiment C15 to C16, wherein the trihydrate crystal form has a $^{13}C$ ssNMR spectrum comprising chemical shifts at 19.2, 149.5, and 163.8 ppm, ±0.2 ppm.

Embodiment C19 is a further embodiment of Embodiment C18, wherein the trihydrate crystal form has an analytical parameter selected from the group consisting of a PXRD pattern comprising peaks at diffraction angles of 8.4 and 9.0 2Θ, ±0.2° 2Θ, a Raman spectrum comprising peak shifts at 1557 and 1610 $cm^{-1}$, ±2 $cm^{-1}$, and a $^{13}C$ ssNMR spectrum comprising at least one chemical shift at 19.2, 149.5, or 163.8 ppm, ±0.2 ppm.

Embodiment C20 is a further embodiment of Embodiment C18, wherein the trihydrate crystal form has an analytical parameter selected from the group consisting of a PXRD pattern comprising peaks at diffraction angles of 8.4 and 9.0 2Θ, ±0.2° 2Θ, and a Raman spectrum comprising at least one peak shift at 1507, 1557, or 1610 $cm^{-1}$, ±2 $cm^{-1}$.

Embodiment C21 is a further embodiment of Embodiment C18, wherein the trihydrate crystal form has an analytical parameter selected from the group consisting of a PXRD pattern comprising peaks at diffraction angles of 8.4 and 9.0 2Θ, ±0.2° 2Θ, and a $^{13}C$ ssNMR spectrum comprising at least one chemical shift at 19.2, 149.5, or 163.8 ppm, +0.2 ppm.

Embodiment C22 is a further embodiment of Embodiment C or any one of Embodiments C1 to C21, the method further comprises administration of at least one other pharmaceutical agent.

In each of embodiments of the methods of treatment of the invention (including Embodiment B, Embodiments B1 to B29, Embodiment C, and Embodiments C1 to C29), each of the GLP-1R agonist and the ACC inhibitor be can present in a same composition or in separate compositions. The combined amount of the GLP-1R agonist and the ACC inhibitor is therapeutically effective for the methods described herein. Even when the GLP-1R agonist and the ACC inhibitor are present in separate compositions, they can be administered simultaneously or sequentially; and when they are administered sequentially, they can be administered in any order.

GLP-1R Agonist/KHKi Combination

Embodiments D, E, and F relate to combination of GLP-1R agonist (including those described herein) and the KHKi inhibitor [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid or a pharmaceutically acceptable salt thereof.

Embodiment D1 is a further embodiment of Embodiment D, wherein the GLP-1R agonist is 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

Embodiment D2 is a further embodiment of Embodiment D or D1, the GLP-1R agonist is a pharmaceutically acceptable salt of 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid.

Embodiment D3 is a further embodiment of Embodiment D2, wherein the pharmaceutically acceptable salt is a tris salt.

Embodiment D4 is a further embodiment of Embodiment D, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof.

Embodiment D5 is a further embodiment of Embodiment D4, wherein the GLP-1R agonist is selected from:

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof. In a further embodiment, the GLP-1R agonist a pharmaceutically acceptable salt.

Embodiment D6 is a further embodiment of Embodiment D5, wherein the pharmaceutically acceptable salt is a tris salt. In some further embodiments, the tris salt is a crystal form, for example, as one described herein.

Embodiment D7 is a further embodiment of any one of Embodiment D or Embodiments D1 to D6, wherein the [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid or a pharmaceutically acceptable salt thereof is [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid.

Embodiment D8 is a further embodiment of Embodiment D7, wherein the [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid is a crystal form.

Embodiment D9 is a further embodiment of Embodiment D8, wherein the crystal form has a PXRD pattern comprising peaks at diffraction angles of 9.0, 10.4, 15.0, and 21.4 2Θ, ±0.2° 2Θ.

Embodiment D10 is a further embodiment of Embodiment D8, wherein the crystal form has a PXRD pattern comprising peaks at diffraction angles of 9.0, 15.0 19.6, 21.4, and 26.5 2Θ, ±0.2° 2Θ.

Embodiment D11 is a further embodiment of Embodiment D8, wherein the crystal form has a PXRD pattern comprising peaks at diffraction angles of 10.4, 11.5, 15.0, 19.6, and 26.5 2Θ, ±0.2° 2Θ.

Embodiment D12 is a further embodiment of any one of Embodiment D or Embodiments D1 to D11, wherein the composition further comprises at least one other pharmaceutical agent.

Embodiment E1 is a further embodiment of Embodiment E, wherein the disease or condition is fatty liver.

Embodiment E2 is a further embodiment of Embodiment E, wherein the disease or condition is nonalcoholic fatty liver disease.

Embodiment E3 is a further embodiment of Embodiment E, wherein the disease or condition is nonalcoholic steatohepatitis.

Embodiment E4 is a further embodiment of Embodiment E, wherein the disease or condition is nonalcoholic steatohepatitis with liver fibrosis.

Embodiment E5 is a further embodiment of Embodiment E, wherein the disease or condition is nonalcoholic steatohepatitis with cirrhosis.

Embodiment E6 is a further embodiment of Embodiment E, wherein the disease or condition is nonalcoholic steatohepatitis with cirrhosis and with hepatocellular carcinoma.

Embodiment E7 is a further embodiment of Embodiment E, wherein the disease or condition is nonalcoholic steatohepatitis with cirrhosis and with a metabolic-related disease.

Embodiment E8 is a further embodiment of Embodiment E or any one of Embodiments E1 to E7, wherein the GLP-1R agonist is 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

Embodiment E9 is a further embodiment of Embodiment E8, wherein the GLP-1R agonist is a pharmaceutically acceptable salt of 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid.

Embodiment E10 is a further embodiment of Embodiment E9, wherein the pharmaceutically acceptable salt is a tris salt.

Embodiment E11 is a further embodiment of Embodiment E or any one of Embodiments E1 to E7, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof.

Embodiment E12 is a further embodiment of Embodiment E11, wherein the GLP-1R agonist is selected from:

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof. In a further embodiment, the GLP-1R agonist a pharmaceutically acceptable salt.

Embodiment E13 is a further embodiment of Embodiment E12, wherein the pharmaceutically acceptable salt is a tris salt. In some further embodiments, the tris salt is a crystal form, for example, as one described herein.

Embodiment E14 is a further embodiment of any one of Embodiment E or Embodiments E1 to E13, wherein the [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid or a pharmaceutically acceptable salt thereof is [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid (free acid).

Embodiment E15 is a further embodiment of Embodiment E14, wherein the [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid is a crystal form.

Embodiment E16 is a further embodiment of Embodiment E15, wherein the crystal form has a PXRD pattern comprising peaks at diffraction angles of 9.0, 10.4, 15.0, and 21.4 2Θ, ±0.2° 2Θ.

Embodiment E17 is a further embodiment of Embodiment E15, wherein the crystal form has a PXRD pattern comprising peaks at diffraction angles of 9.0, 15.0 19.6, 21.4, and 26.5 2Θ, ±0.2° 2Θ.

Embodiment E18 is a further embodiment of Embodiment E15, wherein the crystal form has a PXRD pattern comprising peaks at diffraction angles of 10.4, 11.5, 15.0, 19.6, and 26.5 2Θ, ±0.2° 2Θ.

Embodiment E19 is a further embodiment of Embodiment E or any one of Embodiments E1 to E18, the method further comprises administration of at least one other pharmaceutical agent.

Embodiment F1 is a further embodiment of Embodiment F, wherein the GLP-1R agonist is 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

Embodiment F2 is a further embodiment of Embodiment F1, wherein the GLP-1R agonist is a pharmaceutically acceptable salt of 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid.

Embodiment F3 is a further embodiment of Embodiment F2, wherein the pharmaceutically acceptable salt is a tris salt.

Embodiment F4 is a further embodiment of Embodiment F, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyrid in-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof.

Embodiment F5 is a further embodiment of Embodiment F4, wherein the GLP-1R agonist is selected from:

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof. In a further embodiment, the GLP-1R agonist a pharmaceutically acceptable salt.

Embodiment F6 is a further embodiment of Embodiment F5, wherein the pharmaceutically acceptable salt is a tris salt. In some further embodiments, the tris salt is a crystal form, for example, as one described herein.

Embodiment F7 is a further embodiment of any one of Embodiment F or Embodiments F1 to F6, wherein the [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid or a pharmaceutically acceptable salt thereof is [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid.

Embodiment F8 is a further embodiment of Embodiment F7, wherein the [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid is a crystal form.

Embodiment F9 is a further embodiment of Embodiment F8, wherein the crystal form has a PXRD pattern comprising peaks at diffraction angles of 9.0, 10.4, 15.0, and 21.4 2Θ, ±0.2° 2Θ.

Embodiment F10 is a further embodiment of Embodiment F8, wherein the crystal form has a PXRD pattern comprising peaks at diffraction angles of 9.0, 15.0 19.6, 21.4, and 26.5 2Θ, ±0.2° 2Θ.

Embodiment F11 is a further embodiment of Embodiment F8, wherein the crystal form has a PXRD pattern comprising peaks at diffraction angles of 10.4, 11.5, 15.0, 19.6, and 26.5 2Θ, ±0.2° 2Θ.

Embodiment F12 is a further embodiment of Embodiment F or any one of Embodiments F1 to F11, wherein the method further comprises administration of at least one other pharmaceutical agent.

In each of embodiments of the methods of treatment of the invention (including Embodiment E, Embodiments E1 to E19, Embodiment F, and Embodiments F1 to F12), each of the GLP-1R agonist and the KHK inhibitor be can present in a same composition or in separate compositions. The combined amount of the GLP-1R agonist and the KHK inhibitor is therapeutically effective for the methods described herein. Even when the GLP-1R agonist and the KHK inhibitor are present in separate compositions, they can be administered simultaneously or sequentially; and when they are administered sequentially, they can be administered in any order.

GLP-1R Agonist/DGAT2 Inhibitor Combination

Embodiments G, H, and I relate to combination of GLP-1R agonist (including those described herein) and the DGAT2 inhibitor (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof.

Embodiment G1 is a further embodiment of Embodiment G, wherein the GLP-1R agonist is 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

Embodiment G2 is a further embodiment of Embodiment G or G1, the GLP-1R agonist is a pharmaceutically acceptable salt of 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid.

Embodiment G3 is a further embodiment of Embodiment G2, wherein the pharmaceutically acceptable salt is a tris salt.

Embodiment G4 is a further embodiment of Embodiment G, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof.

Embodiment G5 is a further embodiment of Embodiment G4, wherein the GLP-1R agonist is selected from:

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof. In a further embodiment, the GLP-1R agonist a pharmaceutically acceptable salt.

Embodiment G6 is a further embodiment of Embodiment G5, wherein the pharmaceutically acceptable salt is a tris salt. In some further embodiments, the tris salt is a crystal form, for example, as one described herein.

Embodiment G7 is a further embodiment of any one of Embodiment G or Embodiments G1 to G6, wherein the (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof is (S)-2-(5-((3-ethoxypyridin-2-yl)oxy)pyridin-3-yl)-N-(tetrahydrofuran-3-yl) pyrimidine-5-carboxamide.

Embodiment G8 is a further embodiment of Embodiment G7, wherein the (S)-2-(5-((3-ethoxypyridin-2-yl)oxy)pyridin-3-yl)-N-(tetrahydrofuran-3-yl)pyrimidine-5-carboxamide is a crystal form.

Embodiment G9 is a further embodiment of Embodiment G8, wherein the crystal form has a PXRD pattern comprising peaks at diffraction angles of 5.3, 7.7, 15.4 2Θ, ±0.2° 2Θ (Form 1).

Embodiment G10 is a further embodiment of Embodiment G8, wherein the crystal form has a PXRD pattern comprising peaks at diffraction angles of 6.5, 9.3, 13.6 2Θ, ±0.2° 2Θ (Form 2).

Embodiment G11 is a further embodiment of any one of Embodiment G or Embodiments G1 to G10, wherein the composition further comprises at least one other pharmaceutical agent.

Embodiment H1 is a further embodiment of Embodiment H, wherein the disease or condition is fatty liver.

Embodiment H2 is a further embodiment of Embodiment H, wherein the disease or condition is nonalcoholic fatty liver disease.

Embodiment H3 is a further embodiment of Embodiment H, wherein the disease or condition is nonalcoholic steatohepatitis.

Embodiment H4 is a further embodiment of Embodiment H, wherein the disease or condition is nonalcoholic steatohepatitis with liver fibrosis.

Embodiment H5 is a further embodiment of Embodiment H, wherein the disease or condition is nonalcoholic steatohepatitis with cirrhosis.

Embodiment H6 is a further embodiment of Embodiment H, wherein the disease or condition is nonalcoholic steatohepatitis with cirrhosis and with hepatocellular carcinoma.

Embodiment H7 is a further embodiment of Embodiment H, wherein the disease or condition is nonalcoholic steatohepatitis with cirrhosis and with a metabolic-related disease.

Embodiment H8 is a further embodiment of Embodiment H or any one of Embodiments H1 to H7, wherein the GLP-1R agonist is 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

Embodiment H9 is a further embodiment of Embodiment H8, wherein the GLP-1R agonist is a pharmaceutically acceptable salt of 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid.

Embodiment H10 is a further embodiment of Embodiment H9, wherein the pharmaceutically acceptable salt is a tris salt.

Embodiment H11 is a further embodiment of Embodiment H or any one of Embodiments H1 to H7, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof.

Embodiment H12 is a further embodiment of Embodiment H11, wherein the GLP-1R agonist is selected from:

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof. In a further embodiment, the GLP-1R agonist a pharmaceutically acceptable salt.

Embodiment H13 is a further embodiment of Embodiment H12, wherein the pharmaceutically acceptable salt is a tris salt. In some further embodiments, the tris salt is a crystal form, for example, as one described herein.

Embodiment H14 is a further embodiment of any one of Embodiment H or Embodiments H1 to H13, wherein the (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof is (S)-2-(5-((3-ethoxypyridin-2-yl)oxy)pyridin-3-yl)-N-(tetrahydrofuran-3-yl) pyrimidine-5-carboxamide.

Embodiment H15 is a further embodiment of Embodiment H14, wherein the (S)-2-(5-((3-ethoxypyridin-2-yl)oxy) pyridin-3-yl)-N-(tetrahydrofuran-3-yl)pyrimidine-5-carboxamide is a crystal form.

Embodiment H16 is a further embodiment of Embodiment H15, wherein the crystal form has a PXRD pattern comprising peaks at diffraction angles of 5.3, 7.7, 15.4 2⊖, ±0.2° 2⊖ (Form 1).

Embodiment H17 is a further embodiment of Embodiment H15, wherein the crystal form has a PXRD pattern comprising peaks at diffraction angles of 6.5, 9.3, 13.6 2⊖, ±0.2° 2⊖ (Form 2).

Embodiment H18 is a further embodiment of Embodiment H or any one of Embodiments H1 to E17, the method further comprises administration of at least one other pharmaceutical agent.

Embodiment I1 is a further embodiment of Embodiment I, wherein the GLP-1R agonist is 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

Embodiment I2 is a further embodiment of Embodiment I1, wherein the GLP-1R agonist is a pharmaceutically acceptable salt of 2-[(4-{6-[(4-cyano-2-fluorobenzyl)oxy] pyridin-2-yl}piperidin-1-yl)methyl]-1-[(2S)-oxetan-2-ylmethyl]-1H-benzimidazole-6-carboxylic acid.

Embodiment I3 is a further embodiment of Embodiment I2, wherein the pharmaceutically acceptable salt is a tris salt.

Embodiment I4 is a further embodiment of Embodiment I, wherein the GLP-1R agonist selected from:

2-({4-[2-(4-chloro-2-fluorophenyl)-1,3-benzodioxol-4-yl] piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl] piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof.

Embodiment I5 is a further embodiment of Embodiment I4, wherein the GLP-1R agonist is selected from:

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof. In a further embodiment, the GLP-1R agonist a pharmaceutically acceptable salt.

Embodiment I6 is a further embodiment of Embodiment I5, wherein the pharmaceutically acceptable salt is a tris salt. In some further embodiments, the tris salt is a crystal form, for example, as one described herein.

Embodiment I7 is a further embodiment of any one of Embodiment I or Embodiments I1 to I6, wherein the (S)-2-(5-((3-ethoxypyridin-2-yl)oxy)pyridin-3-yl)-N-(tetrahydrofuran-3-yl)pyrimidine-5-carboxamide or a pharmaceutically acceptable salt thereof is (S)-2-(5-((3-ethoxypyridin-2-yl)oxy)pyridin-3-yl)-N-(tetrahydrofuran-3-yl)pyrimidine-5-carboxamide.

Embodiment I8 is a further embodiment of Embodiment I7, wherein the (S)-2-(5-((3-ethoxypyridin-2-yl)oxy)pyridin-3-yl)-N-(tetrahydrofuran-3-yl)pyrimidine-5-carboxamide is a crystal form.

Embodiment I9 is a further embodiment of Embodiment I8, wherein the crystal form has a PXRD pattern comprising peaks at diffraction angles of 5.3, 7.7, 15.4 2Θ, ±0.2° 2Θ (Form 1).

Embodiment I10 is a further embodiment of Embodiment I8, wherein the crystal form has a PXRD pattern comprising peaks at diffraction angles of 6.5, 9.3, 13.6 2Θ, ±0.2° 2Θ (Form 2).

Embodiment I11 is a further embodiment of any one of Embodiment I or Embodiments I1 to I10, wherein the composition further comprises at least one other pharmaceutical agent.

In each of embodiments of the methods of treatment of the invention (including Embodiment E, Embodiments H1 to H18, Embodiment F, and Embodiments I1 to I11), each of the GLP-1R agonist and the DGAT2 inhibitor be can present in a same composition or in separate compositions. The combined amount of the GLP-1R agonist and the DGAT2 inhibitor is therapeutically effective for the methods described herein. Even when the GLP-1R agonist and the DGT2 inhibitor are present in separate compositions, they can be administered simultaneously or sequentially; and when they are administered sequentially, they can be administered in any order.

GLP-1R Agonist/FXR Agonist Combination

Embodiments J, K, and L relate to combination of GLP-1R agonist (including those described herein) and the FXR agonist 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid (also known as Tropifexor) or a pharmaceutically acceptable salt thereof.

Embodiment J1 is a further embodiment of Embodiment J, wherein the GLP-1R agonist is 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

Embodiment J2 is a further embodiment of Embodiment J or J1, the GLP-1R agonist is a pharmaceutically acceptable salt of 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid.

Embodiment J3 is a further embodiment of Embodiment J2, wherein the pharmaceutically acceptable salt is a tris salt.

Embodiment J4 is a further embodiment of Embodiment J, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyrid in-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof.

Embodiment J5 is a further embodiment of Embodiment J4, wherein the GLP-1R agonist is selected from:

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof. In a further embodiment, the GLP-1R agonist a pharmaceutically acceptable salt.

Embodiment J6 is a further embodiment of Embodiment J5, wherein the pharmaceutically acceptable salt is a tris salt. In some further embodiments, the tris salt is a crystal form, for example, as one described herein.

Embodiment J7 is a further embodiment of any one of Embodiment J or Embodiments J1 to J6, wherein the 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid or a pharmaceutically acceptable salt thereof is 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid.

Embodiment J8 is a further embodiment of any one of Embodiment J or Embodiments J1 to J7, wherein the composition further comprises at least one other pharmaceutical agent.

Embodiment K1 is a further embodiment of Embodiment K, wherein the disease or condition is fatty liver.

Embodiment K2 is a further embodiment of Embodiment K, wherein the disease or condition is nonalcoholic fatty liver disease.

Embodiment K3 is a further embodiment of Embodiment K, wherein the disease or condition is nonalcoholic steatohepatitis.

Embodiment K4 is a further embodiment of Embodiment K, wherein the disease or condition is nonalcoholic steatohepatitis with liver fibrosis.

Embodiment K5 is a further embodiment of Embodiment K, wherein the disease or condition is nonalcoholic steatohepatitis with cirrhosis.

Embodiment K6 is a further embodiment of Embodiment K, wherein the disease or condition is nonalcoholic steatohepatitis with cirrhosis and with hepatocellular carcinoma.

Embodiment K7 is a further embodiment of Embodiment K, wherein the disease or condition is nonalcoholic steatohepatitis with cirrhosis and with a metabolic-related disease.

Embodiment K8 is a further embodiment of Embodiment K or any one of Embodiments K1 to K7, wherein the GLP-1R agonist is 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

Embodiment K9 is a further embodiment of Embodiment K8, wherein the GLP-1R agonist is a pharmaceutically acceptable salt of 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid.

Embodiment K10 is a further embodiment of Embodiment K9, wherein the pharmaceutically acceptable salt is a tris salt.

Embodiment K11 is a further embodiment of Embodiment K or any one of Embodiments K1 to K7, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof.

Embodiment K12 is a further embodiment of Embodiment K11, wherein the GLP-1R agonist is selected from:

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof. In a further embodiment, the GLP-1R agonist a pharmaceutically acceptable salt.

Embodiment K13 is a further embodiment of Embodiment K12, wherein the pharmaceutically acceptable salt is a tris salt. In some further embodiments, the tris salt is a crystal form, for example, as one described herein.

Embodiment K14 is a further embodiment of any one of Embodiment K or Embodiments K1 to K13, wherein the 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid or a pharmaceutically acceptable salt thereof is 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid.

Embodiment K15 is a further embodiment of Embodiment K or any one of Embodiments K1 to K14, the method further comprises administration of at least one other pharmaceutical agent.

Embodiment L1 is a further embodiment of Embodiment L, wherein the GLP-1R agonist is 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

Embodiment L2 is a further embodiment of Embodiment L1, wherein the GLP-1R agonist is a pharmaceutically acceptable salt of 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid.

Embodiment L3 is a further embodiment of Embodiment L2, wherein the pharmaceutically acceptable salt is a tris salt.

Embodiment L4 is a further embodiment of Embodiment L, wherein the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridin-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyrid in-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof.

Embodiment L5 is a further embodiment of Embodiment L4, wherein the GLP-1R agonist is selected from:

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof. In a further embodiment, the GLP-1R agonist a pharmaceutically acceptable salt.

Embodiment L6 is a further embodiment of Embodiment L5, wherein the pharmaceutically acceptable salt is a tris salt. In some further embodiments, the tris salt is a crystal form, for example, as one described herein.

Embodiment L7 is a further embodiment of any one of Embodiment L or Embodiments L1 to L6, wherein the 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid or a pharmaceutically acceptable salt thereof is 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid.

Embodiment L8 is a further embodiment of any one of Embodiment L or Embodiments L1 to L7, wherein the composition further comprises at least one other pharmaceutical agent.

In each of embodiments of the methods of treatment of the invention (including Embodiment K, Embodiments K1 to K15, Embodiment L, and Embodiments L1 to L8), each of the GLP-1R agonist and the FXR agonist be can present in a same composition or in separate compositions. The combined amount of the GLP-1R agonist and the FXR agonist is therapeutically effective for the methods described herein. Even when the GLP-1R agonist and the FXR agonist are present in separate compositions, they can be administered simultaneously or sequentially; and when they are administered sequentially, they can be administered in any order.

Combination Agents

The compounds in the combination of the invention (either in composition or method) can be administered separately or together as separate agents or in a fixed-dose combination or in combination with one or more additional therapeutic agents. When administered in combination, each component may be administered at the same time (i.e. simultaneously) or sequentially in any order at different points in time. Thus, each component may be administered separately but sufficiently closely in time so as to provide the desired therapeutic effect. Thus, the methods of treatment described herein include use of combination agents to administer two or more agents in combination.

The combination agents are administered to a patient or mammal in a therapeutically effective amount. By "therapeutically effective amount" it is meant an amount of the compounds of the invention that, when administered alone or in combination with an additional therapeutic agent to a mammal, is effective to treat the desired disease/condition e.g., NASH.

Examples of suitable anti-diabetic agents include (e.g. insulins, metformin, DPPIV inhibitors, GLP-1 agonists, analogues and mimetics, SGLT1 and SGLT2 inhibitors). Suitable anti-diabetic agents include an acetyl-CoA carboxylase- (ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S., et al., Drug Discovery Today, 12(9/10), 373-381 (2007)), SIRT-1 activator (e.g., resveratrol, GSK2245840 or GSK184072), a dipeptidyl peptidase IV (DPP-IV) inhibitor (e.g., those in WO2005116014, sitagliptin, vildagliptin, alogliptin, dutogliptin, linagliptin and saxagliptin), an insulin secretagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), Ertugliflozin, ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4) 359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKC-γ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors (e.g. SSTR1, SSTR2, SSTR3 and SSTR5), inhibitors or modulators of PDHK2 or PDHK4, inhibitors of MAP4K4, modulators of IL1 family including IL1 beta, modulators of RXRalpha. In addition suitable anti-diabetic agents include mechanisms listed by Carpino, P. A., Goodwin, B. Expert Opin. Ther. Pat, 2010, 20(12), 1627-51.

Suitable anti-obesity agents include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $\beta_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, NY and Procter & Gamble Company, Cincinnati, OH), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, the combination of naltrexone with buproprion and the like.

Preferred anti-obesity agents for use in the combination aspects of the invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as pegylated $PYY_{3-36}$ e.g., those described in US Publication 2006/0178501), opioid antagonists (e.g., naltrexone), the combination of naltrexone with buproprion, oleoyl-estrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3), phentermine and topiramate (trade name: Qsymia), and sibutramine. Preferably, compounds of the invention and combination therapies are administered in conjunction with exercise and a sensible diet.

The compounds of the invention may be used in combination with cholesterol modulating agents (including cholesterol lowering agents) such as a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, an ion-exchange resin, an antioxidant, an ACAT inhibitor or a bile acid sequestrant or an agent such as mipomersen.

Examples of suitable cholesterol/lipid lowering agents and lipid profile therapies include: HMG-CoA reductase inhibitors (e.g., pravastatin, lovastatin, atorvastatin, simvastatin, fluvastatin, NK-104 (a.k.a. itavastatin, or nisvastatin or nisvastatin) and ZD-4522 (a.k.a. rosuvastatin, or itavastatin or visastatin); squalene synthetase inhibitors; fibrates; bile acid sequestrants (such as questran); ACAT inhibitors; MTP inhibitors; lipoxygenase inhibitors; cholesterol absorption inhibitors; and cholesteryl ester transfer protein inhibitors. Other atherosclerotic agents include PCSK9 modulators.

In another embodiment, the compounds of the invention may be co-administered with agents for the treatment of non-alcoholic steatohepatitis (NASH) and/or non-alcoholic fatty liver disease (NAFLD), such as Orlistat, TZDs and other insulin sensitizing agents, FGF21 analogs, Metformin, Omega-3-acid ethyl esters (e.g. Lovaza), Fibrates, HMG CoA-reductase Inhibitors, Ezitimbe, Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buproprion, SGLT2 Inhibitors, Phentermine, Topiramate, Incretin (GLP and GIP) analogs and Angiotensin-receptor blockers.

In another embodiment, the additional pharmaceutical agent is selected from the group consisting of cysteamine or a pharmaceutically acceptable salt thereof, cystamine or a pharmaceutically acceptable salt thereof, an anti-oxidant compound, lecithin, vitamin B complex, a bile salt preparations, an antagonists of Cannabinoid-1 (CB1) receptor, an inverse agonists of Cannabinoid-1 (CB1) receptor, a peroxisome proliferator-activated receptor) activity regulators, a benzothiazepine or benzothiepine compound, an RNA antisense construct to inhibit protein tyrosine phosphatase PTPRU, a heteroatom-linked substituted piperidine and derivatives thereof, an azacyclopentane derivative capable of inhibiting stearoyl-coenzyme alpha delta-9 desaturase, acylamide compound having secretagogue or inducer activity of adiponectin, a quaternary ammonium compound, Glatiramer acetate, pentraxin proteins, a HMG-CoA reductase inhibitor, n-acetyl cysteine, isoflavone compound, a macrolide antibiotic, a galectin inhibitor, an antibody, or any combination of thereof.

Additional therapeutic agents include anti-coagulant or coagulation inhibitory agents, anti-platelet or platelet inhibitory agents, thrombin inhibitors, thrombolytic or fibrinolytic agents, anti-arrhythmic agents, anti-hypertensive agents, calcium channel blockers (L-type and T-type), cardiac glycosides, diuretics, mineralocorticoid receptor antagonists, NO donating agents such as organonitrates, NO promoting agents such as phosphodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid hormone receptor antagonist), anti-infective agents, anti-viral agents, anti-bacterial agents, and anti-fungal agents.

Agents used in an ICU setting are included, for example, dobutamine, dopamine, epinephrine, nitroglycerin, nitroprusside etc.

Combination agents useful for treating vasculitis are included, for example, azathioprine, cyclophosphamide, mycophenolate, mofetil, rituximab etc.

In another embodiment, the invention provides a combination wherein an additional agent (the third agent) is at least one agent selected from a factor Xa inhibitor, an anti-coagulant agent, an anti-platelet agent, a thrombin inhibiting agent, a thrombolytic agent, and a fibrinolytic agent. Exemplary factor Xa inhibitors include apixaban and rivaroxaban. Examples of suitable anti-coagulants for use in combination with the compounds of the invention include heparins (e.g., unfractioned and low molecular weight heparins such as enoxaparin and dalteparin).

In another preferred embodiment the additional (the third agent) is at least one agent selected from warfarin, dabigatran, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

A preferred third agent is at least one anti-platelet agent. Especially preferred anti-platelet agents are aspirin and clopidogrel.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and COX-2 inhibitors such as CELEBREX or piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., Pletal, dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticagrelor, prasugrel, ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, dabigatran, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrhythmic agents include: Class I agents (such as propafenone); Class II agents (such as metoprolol, atenolol, carvadiol and propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

The compounds of the invention may be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid ticrynafen, chlorthalidone, torsemide, furosemide, musolimine, bumetanide, triamterene, amiloride, spironolactone); renin inhibitors; ACE inhibitors (e.g., captopril, zofenopril, fosinopril, enalapril, ceranopril, cilazapril, delapril, pentopril, quinapril, ramipril, lisinopril); AT-1 receptor antagonists (e.g., losartan, irbesartan, valsartan); ET receptor antagonists (e.g., sitaxsentan, atrasentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary anti-anginal agent is ivabradine.

Examples of suitable calcium channel blockers (L-type or T-type) include diltiazem, verapamil, nifedipine and amlodipine and mybefradil.

Examples of suitable cardiac glycosides include digitalis and ouabain.

In one embodiment, the compounds of the invention may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™), hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™).

In another embodiment, the compounds of the invention may be co-administered with a loop diuretic. In still another embodiment, the loop diuretic is selected from furosemide and torsemide. In still another embodiment, the compounds of the invention may be co-administered with furosemide. In still another embodiment, the compounds of the invention may be co-administered with torsemide which may optionally be a controlled or modified release form of torsemide.

In another embodiment, the compounds of the invention may be co-administered with a thiazide-type diuretic. In still another embodiment, the thiazide-type diuretic is selected from the group consisting of chlorothiazide and hydrochlorothiazide. In still another embodiment, the compounds of the invention may be co-administered with chlorothiazide. In still another embodiment, the compounds of the invention may be co-administered with hydrochlorothiazide.

In another embodiment, the compounds of the invention may be co-administered with a phthalimidine-type diuretic. In still another embodiment, the phthalimidine-type diuretic is chlorthalidone. Examples of suitable mineralocorticoid receptor antagonists include sprionolactone and eplerenone. Examples of suitable phosphodiesterase inhibitors include: PDE III inhibitors (such as cilostazol); and PDE V inhibitors (such as sildenafil).

Those skilled in the art will recognize that the compounds of this invention may also be used in conjunction with other cardiovascular or cerebrovascular treatments including PCI, stenting, drug eluting stents, stem cell therapy and medical devices such as implanted pacemakers, defibrillators, or cardiac resynchronization therapy.

The dosage of each therapeutic agent, e.g., the GLP-1R agonist described herein, and any additional therapeutic agent, is generally dependent upon a number of factors including the health of the subject being treated, the extent of treatment desired, the nature and kind of concurrent therapy, if any, and the frequency of treatment and the nature of the effect desired. In general, the dosage range of each therapeutic agent is in the range of from about 0.001 mg to about 100 mg per kilogram body weight of the individual per day, preferably from about 0.1 mg to about 10 mg per kilogram body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of treatment of the invention, a compound of the invention or a combination of a compound of the invention and at least one additional pharmaceutical agent (referred to herein as a "combination") is administered to a subject in need of such treatment, preferably in the form of a pharmaceutical composition. In the combination aspect of the invention, the compound of the invention and at least one other pharmaceutical agent (e.g., another anti-obesity agent,) may be administered either separately or in a pharmaceutical composition comprising both. It is generally preferred that such administration be oral.

When a combination of a compound of the invention and at least one other pharmaceutical agent are administered together, such administration may be sequential in time or simultaneous. Simultaneous administration of drug combinations is generally preferred. For sequential administration, a compound of the invention and the additional pharmaceutical agent may be administered in any order. It is generally preferred that such administration be oral. It is especially preferred that such administration be oral and simultaneous. When a compound of the invention and the additional pharmaceutical agent are administered sequentially, the administration of each may be by the same or by different methods.

According to the methods of the invention, a compound of the invention or a combination is preferably administered in the form of a pharmaceutical composition. Accordingly, a compound of the invention or a combination can be administered to a patient separately or together in any conventional oral, rectal, transdermal, parenteral (e.g., intravenous, intramuscular or subcutaneous), intracisternal, intravaginal, intraperitoneal, topical (e.g., powder, ointment, cream, spray or lotion), buccal or nasal dosage form (e.g., spray, drops or inhalant).

The compounds of the invention or combinations can be administered alone but will generally be administered in an admixture with one or more suitable pharmaceutical excipients, adjuvants, diluents or carriers known in the art and selected with regard to the intended route of administration and standard pharmaceutical practice. The compound of the invention or combination may be formulated to provide immediate-, delayed-, modified-, sustained-, pulsed- or controlled-release dosage forms depending on the desired route of administration and the specificity of release profile, commensurate with therapeutic needs.

The pharmaceutical composition comprises a compound of the invention or a combination in an amount generally in the range of from about 1% to about 75%, 80%, 85%, 90% or even 95% (by weight) of the composition, usually in the range of about 1%, 2% or 3% to about 50%, 60% or 70%, more frequently in the range of about 1%, 2% or 3% to less than 50% such as about 25%, 30% or 35%.

Methods of preparing various pharmaceutical compositions with a specific amount of active compound are known to those skilled in this art. For examples, see Remington: The Practice of Pharmacy, Lippincott Williams and Wilkins, Baltimore Md. 20.sup.th ed. 2000.

Compositions suitable for parenteral injection generally include pharmaceutically acceptable sterile aqueous or nonaqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, triglycerides including vegetable oils such as olive oil, and injectable organic esters such as ethyl oleate. A preferred carrier is Miglyol® brand caprylic/capric acid ester with glycerine or propylene glycol (e.g., Miglyol® 812, Miglyol® 829, Miglyol® 840) available from Condea Vista Co., Cranford, N.J. Proper fluidity can be maintained, for example, by the use of a coating such as lecithin, by the maintenance of the required particle size in the case of dispersions, and by the use of surfactants.

These compositions for parenteral injection may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, chews, lozenges, pills, powders, and multiparticulate preparations (granules). In such solid dosage forms, a compound of the invention or a combination is admixed with at least one inert excipient, diluent or carrier. Suitable excipients, diluents or carriers include materials such as sodium citrate or dicalcium phosphate and/or (a) one or more fillers or extenders (e.g., microcrystalline cellulose (available as Avicel™ from FMC Corp.) starches, lactose, sucrose, mannitol, silicic acid, xylitol, sorbitol, dextrose, calcium hydrogen phosphate, dextrin, alpha-cyclodextrin, beta-cyclodextrin, polyethylene glycol, medium chain fatty acids, titanium oxide, magnesium oxide, aluminum oxide and the like); (b) one or more binders (e.g., carboxymethylcellulose, methylcellulose, hydroxypropylcellulose, hydroxypropylmethylcellulose, gelatin, gum arabic, ethyl cellulose, polyvinyl alcohol, pullulan, pregelatinized starch, agar, tragacanth, alginates, gelatin, polyvinylpyrrolidone, sucrose, acacia and the like); (c) one or more humectants (e.g., glycerol and the like); (d) one or more disintegrating agents (e.g., agar-agar, calcium carbonate, potato or tapioca starch, alginic acid, certain complex silicates, sodium carbonate, sodium lauryl sulphate, sodium starch glycolate (available as Explotab™ from Edward Mendell Co.), cross-linked polyvinyl pyrrolidone, croscarmellose sodium A-type (available as Ac-Si-Sol™), polacrilin potassium (an ion exchange resin) and the like); (e) one or more solution retarders (e.g., paraffin and the like); (f) one or more absorption accelerators (e.g., quaternary ammonium compounds and the like); (g) one or more wetting agents (e.g., cetyl alcohol, glycerol monostearate and the like); (h) one or more adsorbents (e.g., kaolin, bentonite and the like); and/or (i) one or more lubricants (e.g., talc, calcium stearate, magnesium stearate, stearic acid, polyoxyl stearate, cetanol, talc, hydrogenated caster oil, sucrose esters of fatty acid, dimethylpolysiloxane, microcrystalline wax, yellow beeswax, white beeswax, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules may be prepared with coatings and shells, such as enteric coatings and others well known in the art. They may also contain opacifying agents, and can also be of such composition that they release the compound of the invention and/or the additional pharmaceutical agent in a delayed manner. Examples of embedding compositions that can be used are polymeric substances and waxes. The drug may also be in micro-encapsulated form, if appropriate, with one or more of the above-mentioned excipients.

For tablets, the active agent will typically comprise less than 50% (by weight) of the formulation, for example less than about 10% such as 5% or 2.5% by weight. The predominant portion of the formulation comprises fillers, diluents, disintegrants, lubricants and optionally, flavors. The composition of these excipients is well known in the art. Frequently, the fillers/diluents will comprise mixtures of two or more of the following components: microcrystalline cellulose, mannitol, lactose (all types), starch, and di-calcium phosphate. The filler/diluent mixtures typically comprise less than 98% of the formulation and preferably less than 95%, for example 93.5%. Preferred disintegrants include Ac-Di-Sol™, Explotab™, starch and sodium lauryl sulphate. When present a disintegrant will usually comprise less than 10% of the formulation or less than 5%, for example about 3%. A preferred lubricant is magnesium stearate. When present a lubricant will usually comprise less than 5% of the formulation or less than 3%, for example about 1%.

Tablets may be manufactured by standard tabletting processes, for example, direct compression or a wet, dry or melt granulation, melt congealing process and extrusion. The tablet cores may be mono or multi-layer(s) and can be coated with appropriate overcoats known in the art.

Liquid dosage forms for oral administration include pharmaceutically acceptable emulsions, solutions, suspensions, syrups, and elixirs. In addition to the compound of the invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), Miglyol® (available from CONDEA Vista Co., Cranford, N.J.), glycerol, tetrahydrofurfuryl alcohol, polyethylene glycols and fatty acid esters of sorbitan, or mixtures of these substances, and the like.

Besides such inert diluents, the composition may also include excipients, such as wetting agents, emulsifying and suspending agents, sweetening, flavoring, and perfuming agents.

Oral liquid forms of the compounds of the invention or combinations include solutions, wherein the active compound is fully dissolved. Examples of solvents include all pharmaceutically precedented solvents suitable for oral administration, particularly those in which the compounds of the invention show good solubility, e.g., polyethylene glycol, polypropylene glycol, edible oils and glyceryl- and glyceride-based systems. Glyceryl- and glyceride-based systems may include, for example, the following branded products (and corresponding generic products): Captex™ 355 EP (glyceryl tricaprylate/caprate, from Abitec, Columbus Ohio), Crodamol™ GTC/C (medium chain triglyceride, from Croda, Cowick Hall, UK) or Labrafac™ CC (medium chain triglyides, from Gattefosse), Captex™ 500P (glyceryl triacetate i.e. triacetin, from Abitec), Capmul™ MCM (medium chain mono- and diglycerides, from Abitec), Miglyol™ 812 (caprylic/capric triglyceride, from Condea, Cranford N.J.), Miglyol™ 829 (caprylic/capric/succinic triglyceride, from Condea), Miglyol™ 840 (propylene glycol dicaprylate/dicaprate, from Condea), Labrafil™ M1944CS (oleoyl macrogol-6 glycerides, from Gattefosse), Peceol™ (glyceryl monooleate, from Gattefosse) and Maisine™ 35-1 (glyceryl monooleate, from Gattefosse). Of particular interest are the medium chain (about C.sub.8 to C.sub.10) triglyceride oils. These solvents frequently make up the predominant portion of the composition, i.e., greater than about 50%, usually greater than about 80%, for example about 95% or 99%. Adjuvants and additives may also be included with the solvents principally as taste-mask agents, palatability and flavoring agents, antioxidants, stabilizers, texture and viscosity modifiers and solubilizers.

Suspensions, in addition to the compound of the invention or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the invention or a combination with suitable non-irritating excipients or carriers, such as cocoa butter, polyethylene glycol or a suppository wax which are solid at ordinary room temperature, but liquid at body temperature, and therefore, melt in the rectum or vaginal cavity thereby releasing the active component(s).

Dosage forms for topical administration of the compounds of the invention or combinations include ointments, creams, lotions, powders and sprays. The drugs are admixed with a pharmaceutically acceptable excipient, diluent or carrier, and any preservatives, buffers, or propellants that may be required.

When compounds are poorly soluble in water, e.g., less than about 1.mu.g/mL, liquid compositions in solubilizing, non-aqueous solvents such as the medium chain triglyceride oils discussed above are a preferred dosage form for these compounds.

Solid amorphous dispersions, including dispersions formed by a spray-drying process, are also a preferred dosage form for the poorly soluble compounds of the invention. By "solid amorphous dispersion" is meant a solid material in which at least a portion of the poorly soluble compound is in the amorphous form and dispersed in a water-soluble polymer. By "amorphous" is meant that the poorly soluble compound is not crystalline. By "crystalline" is meant that the compound exhibits long-range order in three dimensions of at least 100 repeat units in each dimension. Thus, the term amorphous is intended to include not only material which has essentially no order, but also material which may have some small degree of order, but the order is in less than three dimensions and/or is only over short distances. Amorphous material may be characterized by techniques known in the art such as powder x-ray diffraction (PXRD) crystallography, solid state NMR, or thermal techniques such as differential scanning calorimetry (DSC).

Preferably, at least a major portion (i.e., at least about 60 wt %) of the poorly soluble compound in the solid amorphous dispersion is amorphous. The compound can exist within the solid amorphous dispersion in relatively pure amorphous domains or regions, as a solid solution of the compound homogeneously distributed throughout the polymer or any combination of these states or those states that lie intermediate between them. Preferably, the solid amorphous dispersion is substantially homogeneous so that the amorphous compound is dispersed as homogeneously as possible throughout the polymer. As used herein, "substantially homogeneous" means that the fraction of the compound that is present in relatively pure amorphous domains or regions within the solid amorphous dispersion is relatively small, on the order of less than 20 wt %, and preferably less than 10 wt % of the total amount of drug.

Water-soluble polymers suitable for use in the solid amorphous dispersions should be inert, in the sense that they do not chemically react with the poorly soluble compound in an adverse manner, are pharmaceutically acceptable, and have at least some solubility in aqueous solution at physiologically relevant pHs (e.g. 1-8). The polymer can be neutral or ionizable, and should have an aqueous-solubility of at least 0.1 mg/mL over at least a portion of the pH range of 1-8.

Water-soluble polymers suitable for use with the invention may be cellulosic or non-cellulosic. The polymers may be neutral or ionizable in aqueous solution. Of these, ionizable and cellulosic polymers are preferred, with ionizable cellulosic polymers being more preferred.

Exemplary water-soluble polymers include hydroxypropyl methyl cellulose acetate succinate (HPMCAS), hydroxypropyl methyl cellulose (HPMC), hydroxypropyl methyl cellulose phthalate (HPMCP), carboxy methyl ethyl cellulose (CMEC), cellulose acetate phthalate (CAP), cellulose acetate trimellitate (CAT), polyvinylpyrrolidone (PVP), hydroxypropyl cellulose (HPC), methyl cellulose (MC), block copolymers of ethylene oxide and propylene oxide (PEO/PPO, also known as poloxamers), and mixtures thereof. Especially preferred polymers include HPMCAS, HPMC, HPMCP, CMEC, CAP, CAT, PVP, poloxamers, and mixtures thereof. Most preferred is HPMCAS. See European Patent Application Publication No. 0 901 786 A2, the disclosure of which is incorporated herein by reference.

The solid amorphous dispersions may be prepared according to any process for forming solid amorphous dispersions that results in at least a major portion (at least 60%) of the poorly soluble compound being in the amorphous state. Such processes include mechanical, thermal and solvent processes. Exemplary mechanical processes include milling and extrusion; melt processes including high temperature fusion, solvent-modified fusion and melt-congeal processes; and solvent processes including non-solvent precipitation, spray coating and spray drying. See, for example, the following U.S. patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes. In a preferred process, the solid amorphous dispersion is formed by spray drying, as disclosed in European Patent Application Publication No. 0 901 786 A2. In this process, the compound and polymer are dissolved in a solvent, such as acetone or methanol, and the solvent is then rapidly removed from the solution by spray drying to form the solid amorphous dispersion. The solid amorphous dispersions may be prepared to contain up to about 99 wt % of the compound, e.g., 1 wt %, 5 wt %, 10 wt %, 25 wt %, 50 wt %, 75 wt %, 95 wt %, or 98 wt % as desired.

The solid dispersion may be used as the dosage form itself or it may serve as a manufacturing-use-product (MUP) in the preparation of other dosage forms such as capsules, tablets, solutions or suspensions. An example of an aqueous suspension is an aqueous suspension of a 1:1 (w/w) compound/HPMCAS-HF spray-dried dispersion containing 2.5 mg/mL of compound in 2% polysorbate-80. Solid dispersions for use in a tablet or capsule will generally be mixed with other excipients or adjuvants typically found in such dosage forms. For example, an exemplary filler for capsules contains a 2:1 (w/w) compound/HPMCAS-MF spray-dried dispersion (60%), lactose (fast flow) (15%), microcrystalline cellulose (e.g., Avicel.sup.(R0-102) (15.8%), sodium starch (7%), sodium lauryl sulfate (2%) and magnesium stearate (1%).

The HPMCAS polymers are available in low, medium and high grades as Aqoat.sup.®—LF, Aqoat.sup.®—MF and Aqoat.sup.®—HF respectively from Shin-Etsu Chemical Co., LTD, Tokyo, Japan. The higher MF and HF grades are generally preferred.

The following paragraphs describe exemplary formulations, dosages, etc. useful for non-human animals. The administration of a combination described herein can be effected orally or non-orally.

An amount of each of the components in a combination described herein, together or in combination with an another agent is administered such that an effective dose is received. Generally, a daily dose that is administered orally to an animal is between about 0.01 and about 1,000 mg/kg of body weight, e.g., between about 0.01 and about 300 mg/kg or between about 0.01 and about 100 mg/kg or between about 0.01 and about 50 mg/kg of body weight, or between about 0.01 and about 25 mg/kg, or about 0.01 and about 10 mg/kg or about 0.01 and about 5 mg/kg.

Conveniently, a compound of the invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the invention (or combination) can also be added directly to the feed, as such, or in the form of an animal feed supplement, also referred to as a premix or concentrate. A premix or concentrate of the compound in an excipient, diluent or carrier is more commonly employed for the inclusion of the agent in the feed. Suitable excipients, diluents or carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective excipient, diluent or carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the invention with a sufficient amount of animal feed to provide from about $10^{-3}$ to about 500 ppm of the compound in the feed or water.

The preferred medicated swine, cattle, sheep and goat feed generally contain from about 1 to about 400 grams of a compound of the invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the invention (or combination) per ton of feed.

For parenteral administration in animals, the compounds of the invention (or combination) may be prepared in the form of a paste or a pellet and administered as an implant, usually under the skin of the head or ear of the animal in which increase in lean meat deposition and improvement in lean meat to fat ratio is sought.

Paste Formulations may be prepared by dispersing the drug in a pharmaceutically acceptable oil such as peanut oil, sesame oil, corn oil or the like.

Pellets containing a therapeutically effective amount of each of the components in a combination described herein, with a diluent such as carbowax, carnuba wax, and the like, and a lubricant, such as magnesium or calcium stearate, may be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The invention has several advantageous veterinary features. For the pet owner or veterinarian who wishes to increase leanness and/or trim unwanted fat from pet animals, the instant invention provides the means by which this may be accomplished. For poultry, beef and swine breeders, utilization of the method of the invention yields leaner animals that command higher sale prices from the meat industry.

EXAMPLES

Unless specified otherwise, starting materials are generally available from commercial sources such as Aldrich Chemicals Co. (Milwaukee, WI), Lancaster Synthesis, Inc. (Windham, NH), Acros Organics (Fairlawn, NJ), Maybridge Chemical Company, Ltd. (Cornwall, England) and Tyger Scientific (Princeton, NJ). Certain common abbreviations and acronyms have been employed which may include: AcOH (acetic acid), DBU (1,8-diazabicyclo[5.4.0]undec-7-ene), CDI (1,1'-carbonyldiimidazole), DCM (dichloromethane), DEA (diethylamine), DIPEA (N,N-diisopropylethylamine), DMAP (4-dimethylaminopyridine), DMF (N,N'-dimethylformamide), DMSO (dimethylsulfoxide), EDCI (N-(3-dimethylaminopropyl)-N'-ethylcarbodiimide), $Et_2O$ (diethyl ether), EtOAc (ethyl acetate), EtOH (ethanol), G or g (gram), HATU (2-(1H-7-azabenzotriazol-1-yl)-1,1,3,3-tetramethyl uronium hexafluorophosphate methanaminium), HBTU (0-benzotriazol-1-yl-N,N,N',N'-tetramethyluronium hexafluoro phosphate), HOBT (1-hydroxybenzotriazole), H or h (hour), IPA (isopropyl alcohol), KHMDS (potassium hexamethyldisilazane), MeOH (methanol), L or l (liter), mL (milliliter) MTBE (tert-butyl methyl ether), mg (milligram), $NaBH(OAc)_3$ (sodium triacetoxyborohydride), NaHMDS (sodium hexamethyldisilazane), NMP (N-methylpyrrolidone), RH (relative humidity), RT or rt (room temperature which is the same as ambient temperature (about 20 to 25° C.)), SEM ([2-(Trimethylsilyl)ethoxy]methyl), TEA (triethylamine), TFA (trifluoroacetic acid), THF (tetrahydrofuran), and $T_3P$ (propane phosphonic acid anhydride).

$^1H$ Nuclear magnetic resonance (NMR) spectra were in all cases consistent with the proposed structures. Characteristic chemical shifts (δ) are given in parts-per-million (ppm) relative to the residual proton signal in the deuterated solvent ($CHCl_3$ at 7.27 ppm; $CD_2HOD$ at 3.31 ppm) and are reported using conventional abbreviations for designation of major peaks: e.g. s, singlet; d, doublet; t, triplet; q, quartet; m, multiplet; br, broad.

ssNMR means solid-state NMR.

PXRD means Powder X-ray Diffraction.

The term "substantially the same" when used to describe X-ray powder diffraction patterns is mean to include patterns in which peaks are within a standard deviation of +/−0.2° 2Θ.

As used herein, the term "substantially pure" with reference to a particular crystalline form means that the crystalline form includes less than 10%, preferably less than 5%, preferably less than 3%, preferably less than 1% by weight of any other physical form of the same compound.

Reactions were performed in air or, when oxygen- or moisture-sensitive reagents or intermediates were employed, under an inert atmosphere (nitrogen or argon). When appropriate, reaction apparatuses were dried under dynamic vacuum using a heat gun, and anhydrous solvents (Sure-Seal™ products from Aldrich Chemical Company, Milwaukee, Wisconsin or DriSolv™ products from EMD Chemicals, Gibbstown, NJ) were employed. Commercial solvents and reagents were used without further purification. When indicated, reactions were heated by microwave irradiation using Biotage Initiator or Personal Chemistry Emrys Optimizer microwaves. Reaction progress was monitored using thin layer chromatography (TLC), liquid chromatography-mass spectrometry (LCMS), high performance liquid chromatography (HPLC), and/or gas chromatography-mass spectrometry (GCMS) analyses. TLC was performed on pre-coated silica gel plates with a fluorescence indicator (254 nm excitation wavelength) and visualized under UV light and/or with $I_2$, $KMnO_4$, $CoCl_2$, phosphomolybdic acid, and/or ceric ammonium molybdate stains. LCMS data were acquired on an Agilent 1100 Series instrument with a Leap Technologies autosampler, Gemini C18 columns, MeCN/water gradients, and either TFA, formic acid, or ammonium hydroxide modifiers. The column eluent was analyzed using Waters ZQ mass spectrometer scanning in both positive and negative ion modes from 100 to 1200 Da. Other similar instruments were also used. HPLC data were acquired on an Agilent 1100 Series instrument using Gemini or XBridge C18 columns, MeCN/water gradients, and either TFA or ammonium hydroxide modifiers. GCMS data were acquired using a Hewlett Packard 6890 oven with an HP 6890 injector, HP-1 column (12 m×0.2 mm×0.33 μm), and helium carrier gas. The sample was analyzed on an HP 5973 mass selective detector scanning from 50 to 550 Da using electron ionization. Purifications were performed by medium performance liquid chromatography (MPLC) using Isco CombiFlash Companion, AnaLogix IntelliFlash 280, Biotage SP1, or Biotage Isolera One instruments and pre-packed Isco RediSep or Biotage Snap silica cartridges. Chiral purifications were performed by chiral supercritical fluid chromatography (SFC) using Berger or Thar instruments; ChiralPAK-AD, -AS, -IC, Chiralcel-OD, or -OJ columns; and $CO_2$ mixtures with MeOH, EtOH, iPrOH, or MeCN, alone or modified using TFA or $iPrNH_2$. UV detection was used to trigger fraction collection.

Mass spectrometry data are reported from LCMS analyses. Mass spectrometry (MS) was performed via atmospheric pressure chemical ionization (APCI), electrospray Ionization (ESI), electron impact ionization (EI) or electron scatter (ES) ionization sources. Mass spectrometry data is reported from either liquid chromatography-mass spectrometry (LCMS), atmospheric pressure chemical ionization (APCI) or gas chromatography-mass spectrometry (GCMS)

instrumentation. The symbol ♦ denotes that the chlorine isotope pattern was observed in the mass spectrum. Proton nuclear magnetic spectroscopy ($^{1}H$ NMR) chemical shifts are given in parts per million downfield from tetramethylsilane and were recorded on 300, 400, 500, or 600 MHz Varian spectrometers. Chemical shifts are expressed in parts per million (ppm, δ) referenced to the deuterated solvent residual peaks. The peak shapes are described as follows: s, singlet; d, doublet; t, triplet; q, quartet; quin, quintet; m, multiplet; br s, broad singlet; app, apparent. Analytical SFC data were acquired on a Berger analytical instrument as described above. Optical rotation data were acquired on a PerkinElmer model 343 polarimeter using a 1 dm cell. Silica gel chromatography was performed primarily using a medium pressure Biotage or ISCO systems using columns pre-packaged by various commercial vendors including Biotage and ISCO. Microanalyses were performed by Quantitative Technologies Inc. and were within 0.4% of the calculated values.

Unless otherwise noted, chemical reactions were performed at room/ambient temperature (about 23 degrees Celsius).

The compounds and intermediates described below generally were named using the naming convention provided with ChemBioDraw Ultra, Version 12.0 (CambridgeSoft Corp., Cambridge, Massachusetts). The naming convention provided with ChemBioDraw Ultra, Version 12.0 are well known by those skilled in the art and it is believed that the naming convention provided with ChemBioDraw Ultra, Version 12.0 generally comports with the IUPAC (International Union for Pure and Applied Chemistry) recommendations on Nomenclature of Organic Chemistry and the CAS Index rules. Unless noted otherwise, all reactants were obtained commercially without further purifications or were prepared using methods known in the literature.

Chiral separations were used to separate enantiomers or diastereomers of some intermediates during the preparation of the compounds of the invention. When chiral separation was done, the separated enantiomers were designated as ENT-1 or ENT-2 (or DIAST-1 or DIAST-2), according to their order of elution. In some embodiments, enantiomers designated as ENT-1 or ENT-2 can be used as starting materials to prepare other enantiomers or diastereomers. In such situations, the resulting enantiomers prepared are designated as ENT-X1 and ENT-X2, respectively, according to their starting materials; similarly, the diastereomers prepared are designated as DIAST-X1 and DIAST-X2, respectively, (or DIAST-according to their starting materials. DIAST-Y and DIAST-Z nomenclature is used similarly, in syntheses employing multiple intermediates.

For compounds with two chiral centers, the stereoisomers at each stereocenter were separated at different times. The designation of ENT-1 or ENT-2 (or DIAST-1 or DIAST-2) of an intermediate or an example refers to the order of elution for the separation done at that step. It is recognized that when stereoisomers at a chiral center are separated in a compound with two or more centers, the separated enantiomers are diastereomers of each other. By way of example, but not limitation, Examples 15 and 16 have two chiral centers. The chiral center of the cyclopropyl moiety was separated when intermediate C36 was separated into ENT-1, giving intermediate P17, and ENT-2, giving intermediate P18. P18 was then used in preparing C70, which had one stereoisomer enriched at the cyclopropyl chiral carbon and a mixture of stereoisomers at the dioxolane carbon. C70 was then separated into DIAST-Y1 at the dioxolane carbon, giving intermediate C71, and DIAST-Y2 at the dioxolane carbon, giving intermediate C72, where these intermediates are enriched in a single stereoisomer. C71 was then used to prepare Example 15, which is identified by name as 2-{6-[2-(4-chloro-2-fluorophenyl)-2-methyl-1,3-benzodioxol-4-yl]-6-azaspiro[2.5]oct-1-yl}-1-(2-methoxyethyl)-1H-benzimidazole-6-carboxylic acid, DIAST-X1, trifluoroacetate salt [from P18 via C71]. In these preparations, after a mixture is subjected to separation procedures, the chiral center is identified with "abs" near that center, with the understanding that the separated enantiomers may not be enantiomerically pure. Typically, the enriched enantiomer at each chiral center is >90% of the isolated material. Preferably, the enriched enantiomer at each center is >98% of the mixture.

In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated either by the absence of drawn or described stereochemistry, or by the presence of (+/−) adjacent to the structure; in this latter case, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times. All starting materials in these Preparations and Examples are either commercially available or can be prepared by methods known in the art or as described herein.

The terms "concentrated", "evaporated", and "concentrated in vacuo" refer to the removal of solvent at reduced pressure on a rotary evaporator with a bath temperature less than 60° C. The abbreviation "min" and "h" stand for "minutes" and "hours" respectively. The term "TLC" refers to thin layer chromatography, "room temperature or ambient temperature" means a temperature between 18 to 25° C., "GCMS" refers to gas chromatography-mass spectrometry, "LCMS" refers to liquid chromatography-mass spectrometry, "UPLC" refers to ultra performance liquid chromatography and "HPLC" refers to high pressure liquid chromatography, "SFC" refers to supercritical fluid chromatography.

Hydrogenation may be performed in a Parr Shaker under pressurized hydrogen gas, or in Thales-nano H-Cube flow hydrogenation apparatus at full hydrogen and a flow rate between 1-2 mL/min at specified temperature.

HPLC, UPLC, LCMS, GCMS, and SFC retention times were measured using the methods noted in the procedures.

PREPARATION OF INTERMEDIATES AND EXAMPLES

Preparation P1 tert-Butyl 4-[2-(4-chloro-2-fluorophenyl)-1,3-benzodioxol-4-yl]piperidine-1-carboxylate (P1)

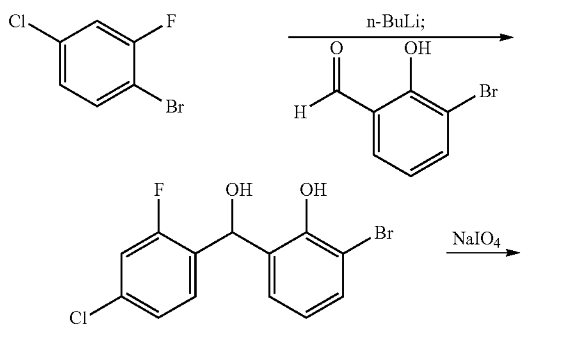

C1

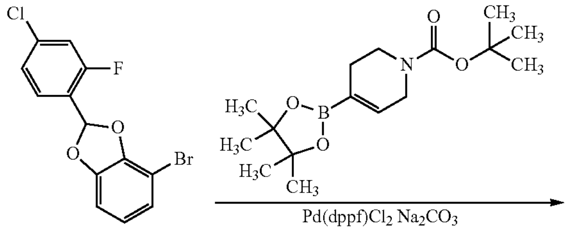

C2

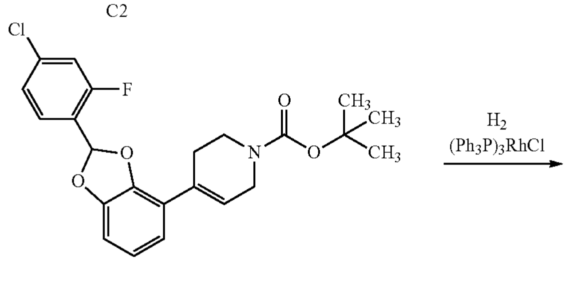

C3

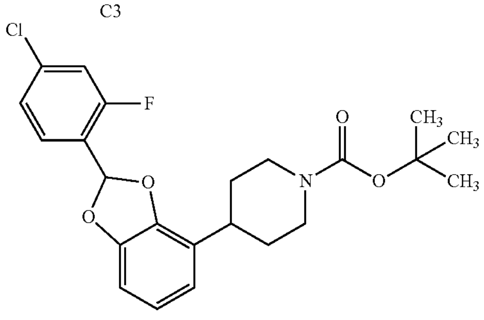

P1

Step 1. Synthesis of 2-bromo-6-[(4-chloro-2-fluorophenyl)(hydroxy)methyl]phenol (C1)

This experiment was carried out in two batches of the same scale. n-Butyllithium (2.5 M solution in hexanes; 32.8 mL, 82.0 mmol) was slowly added to a −70° C. solution of 1-bromo-4-chloro-2-fluorobenzene (17.2 g, 82.1 mmol) in diethyl ether (100 mL), while the temperature of the reaction mixture was maintained below −60° C. After the reaction mixture had been stirred at −70° C. for 20 minutes, a solution of 3-bromo-2-hydroxybenzaldehyde (5.5 g, 27 mmol) in diethyl ether (100 mL) was slowly added, while the reaction temperature was maintained below −60° C. After a further 1 hour of stirring at −70° C., the reaction was quenched by addition of aqueous ammonium chloride solution (50 mL) at −70° C., and the resulting mixture was diluted with water (100 mL). The two batches were combined at this point and extracted with ethyl acetate (400 mL); the organic layer was washed with saturated aqueous sodium chloride solution (200 mL), dried over sodium sulfate, filtered, and concentrated in vacuo. Silica gel chromatography (Gradient: 0% to 7% ethyl acetate in petroleum ether) afforded C1 as a white solid. Combined yield: 15.7 g, 47.4 mmol, 88%. $^1$H NMR (400 MHz, chloroform-d) δ 7.44 (dd, J=8.0, 1.5 Hz, 1H), 7.37 (dd, J=8.1, 8.1 Hz, 1H), 7.15 (br dd, J=8.5, 2.1 Hz, 1H), 7.12-7.05 (m, 2H), 6.80 (dd, J=7.8, 7.8 Hz, 1H), 6.78 (s, 1H), 6.31 (d, J=4.8 Hz, 1H), 3.02 (br d, J=4.9 Hz, 1H).

Step 2. Synthesis of 4-bromo-2-(4-chloro-2-fluorophenyl)-1,3-benzodioxole (C2)

To a solution of C1 (15.7 g, 47.4 mmol) in methanol (450 mL) was added a solution of sodium periodate (25.4 g, 119 mmol) in water (105 mL), and the reaction mixture was stirred at 30° C. for 16 hours, whereupon it was concentrated in vacuo. After the residue had been diluted with dichloromethane (500 mL), it was washed with water (500 mL). The dichloromethane solution was then dried over sodium sulfate, filtered, and concentrated in vacuo. Purification via silica gel chromatography (Eluent: petroleum ether) provided C2 as a white solid. Yield: 10.0 g, 30.3 mmol, 64%. The following $^1$H NMR data was obtained from an experiment carried out in the same manner but on smaller scale. $^1$H NMR (400 MHz, DMSO-$d_6$) δ 7.67-7.61 (m, 2H), 7.50 (s, 1H), 7.43 (br dd, J=8, 2 Hz, 1H), 7.09 (dd, J=8.3, 1.1 Hz, 1H), 7.01 (dd, J=7.9, 1.1 Hz, 1H), 6.86 (dd, J=8.1, 8.1 Hz, 1H).

Step 3. Synthesis of tert-butyl 4-[2-(4-chloro-2-fluorophenyl)-1,3-benzodioxol-4-yl]-3,6-dihydropyridine-1(2H)-carboxylate (C3)

A reaction flask containing a suspension of C2 (8.00 g, 24.3 mmol), tert-butyl 4-(4,4,5,5-tetramethyl-1,3,2-dioxaborolan-2-yl)-3,6-dihydropyridine-1(2H)-carboxylate (9.01 g, 29.1 mmol), sodium carbonate (5.15 g, 48.6 mmol), and [1,1'-bis(diphenylphosphino)ferrocene]dichloro-palladium (II) [Pd(dppf)$Cl_2$; 888 mg, 1.21 mmol] in 1,4-dioxane (80 mL) and water (32 mL) was evacuated and charged with nitrogen. This evacuation cycle was repeated twice, and then the reaction mixture was stirred at 90° C. for 16 hours. After removal of solvent in vacuo, the residue was partitioned between ethyl acetate (200 mL) and water (200 mL). The organic layer was washed with saturated aqueous sodium chloride solution (100 mL), dried over sodium sulfate, filtered, and concentrated under reduced pressure. Chromatography on silica gel (Gradient: 0% to 4.3% ethyl acetate in petroleum ether) provided the product, which was combined with material from a similar reaction carried out using C2 (2.00 g, 6.07 mmol) to afford C3 as a light-yellow gum. Combined yield: 10.3 g, 23.8 mmol, 78%. $^1$H NMR (400 MHz, chloroform-d) δ 7.53 (dd, J=8.3, 7.8 Hz, 1H), 7.23-7.16 (m, 3H), 6.88-6.83 (m, 2H), 6.81-6.76 (m, 1H), 6.34-

6.28 (br m, 1H), 4.10-4.05 (m, 2H), 3.61 (br dd, J=6, 5 Hz, 2H), 2.59-2.50 (br m, 2H), 1.48 (s, 9H).

Step 4. Synthesis of tert-butyl 4-[2-(4-chloro-2-fluorophenyl)-1,3-benzodioxol-4-yl]piperidine-1-carboxylate (P1)

A solution of C3 (10.3 g, 23.8 mmol) and tris(triphenylphosphine)rhodium(I) chloride (Wilkinson's catalyst; 1.54 g, 1.66 mmol) in methanol (100 mL) was stirred at 50° C. under hydrogen (45 psi) for 18 hours. The reaction mixture was then filtered through a pad of diatomaceous earth, and the filtrate was concentrated under reduced pressure and subjected to silica gel chromatography (Gradient: 0% to 9% ethyl acetate in petroleum ether). The resulting material was combined with that from a similar reaction carried out using C3 (1.67 g, 3.87 mmol) to afford P1 as a colorless gum. Combined yield: 10.3 g, 23.7 mmol, 86%. LCMS m/z 456.1♦ [M+Na$^+$]. $^1$H NMR (400 MHz, chloroform-d) δ 7.52 (dd, J=8.5, 7.6 Hz, 1H), 7.23-7.17 (m, 2H), 7.16 (s, 1H), 6.83 (dd, J=7.8, 7.8 Hz, 1H), 6.78-6.69 (m, 2H), 4.35-4.10 (br m, 2H), 2.89-2.71 (m, 3H), 1.89-1.77 (m, 2H), 1.77-1.63 (m, 2H), 1.47 (s, 9H).

Preparation P2 tert-Butyl 4-[2-(4-chloro-2-fluorophenyl)-2-methyl-1,3-benzodioxol-4-yl]piperidine-1-carboxylate (P2)

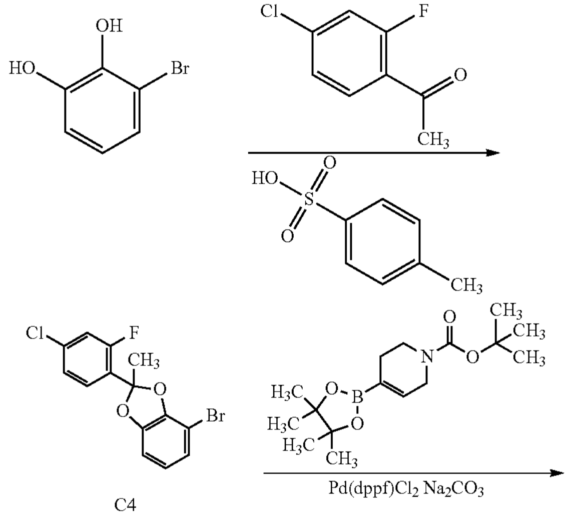

C4

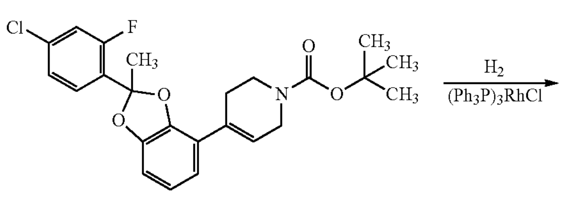

C5

-continued

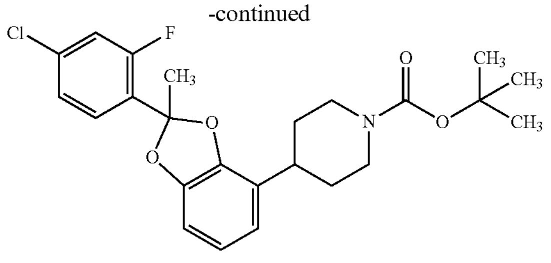

P2

Step 1. Synthesis of 4-bromo-2-(4-chloro-2-fluorophenyl)-2-methyl-1,3-benzodioxole (C4)

To a solution of 3-bromobenzene-1,2-diol (330 g, 1.75 mol) in toluene (1.5 L) were added 1-(4-chloro-2-fluorophenyl)ethanone (316 g, 1.83 mol) and p-toluenesulfonic acid (6.02 g, 35.0 mmol). The reaction apparatus was fitted with a Dean-Stark trap, and the reaction mixture was heated at 140° C. for 60 hours, whereupon the solution was concentrated in vacuo and purified using silica gel chromatography (Eluent: petroleum ether); C4 was obtained as a mixture of yellow oil and solid. Yield: 158 g, 460 mmol, 26%. $^1$H NMR (400 MHz, chloroform-d): δ 7.54 (dd, J=8.4, 8.4 Hz, 1H), 7.17-7.10 (m, 2H), 6.95 (dd, J=7.9, 1.4 Hz, 1H), 6.75 (dd, component of ABX pattern, J=7.8, 1.4 Hz, 1H), 6.70 (dd, component of ABX pattern, J=7.9, 7.9 Hz, 1H), 2.11 (d, J=1.1 Hz, 3H).

Step 2. Synthesis of tert-butyl 4-[2-(4-chloro-2-fluorophenyl)-2-methyl-1,3-benzodioxol-4-yl]-3,6-dihydropyridine-1(2H)-carboxylate (C5)

tert-Butyl 4-(4,4,5,5-tetramethyl-1,3,2-dioxaborolan-2-yl)-3,6-dihydropyridine-1(2H)-carboxylate (62 g, 200 mmol) and sodium carbonate (100 g, 940 mmol) were added to a solution of C4 (58.0 g, 169 mmol) in 1,4-dioxane (600 mL). After addition of [1,1'-bis(diphenylphosphino)ferrocene]dichloropalladium(II) (6.0 g, 8.2 mmol), the reaction mixture was heated to 90° C. and stirred for 16 hours. Water (500 mL) was then added, and the resulting mixture was extracted with ethyl acetate (2×500 mL). The combined organic layers were washed with saturated aqueous sodium chloride solution (2×500 mL), dried over sodium sulfate, filtered, and concentrated in vacuo. Silica gel chromatography (Gradient: 0% to 9% ethyl acetate in petroleum ether) provided C5 as a yellow oil. Yield: 56.0 g, 126 mmol, 75%. $^1$H NMR (400 MHz, chloroform-d) δ 7.50 (dd, J=8.2, 8.2 Hz, 1H), 7.17-7.09 (m, 2H), 6.83-6.77 (m, 2H), 6.74 (dd, component of ABX pattern, J=5.4, 3.6 Hz, 1H), 6.39-6.33 (br m, 1H), 4.14-4.08 (m, 2H), 3.70-3.56 (m, 2H), 2.66-2.45 (m, 2H), 2.07 (d, J=1.1 Hz, 3H), 1.50 (s, 9H).

Step 3. Synthesis of tert-butyl 4-[2-(4-chloro-2-fluorophenyl)-2-methyl-1,3-benzodioxol-4-yl]piperidine-1-carboxylate (P2)

To a solution of C5 (56.0 g, 126 mmol) in methanol (200 mL) was added tris(triphenylphosphine)rhodium(I) chloride (Wilkinson's catalyst; 8.10 g, 8.75 mmol), and the reaction mixture was heated to 50° C. for 18 hours under hydrogen (45 psi). It was then cooled to 25° C. and filtered through diatomaceous earth. The filtrate was concentrated in vacuo, and purified twice using silica gel chromatography (First column—Gradient: 0% to 9% ethyl acetate in petroleum ether; Second column—Gradient: 0% to 2% ethyl acetate in petroleum ether), affording P2 as a yellow solid. Yield: 37.0 g, 82.6 mmol, 66%. LCMS m/z 392.1♦ [(M−2-methylprop-1-ene)+H]$^+$. $^1$H NMR (400 MHz, chloroform-d) δ 7.51 (dd, J=8.3, 8.0 Hz, 1H), 7.17-7.09 (m, 2H), 6.77 (dd, component of ABC pattern, J=7.8, 7.8 Hz, 1H), 6.70 (dd, component of ABC pattern, J=7.7, 1.3 Hz, 1H), 6.66 (dd, component of ABC pattern, J=7.8, 1.3 Hz, 1H), 4.37-4.13 (br m, 2H), 2.92-2.73 (m, 3H), 2.05 (d, J=1.1 Hz, 3H), 1.90-1.63 (m, 4H), 1.49 (s, 9H).

Preparation P3

4-[(2S)-2-(4-Chloro-2-fluorophenyl)-2-methyl-1,3-benzodioxol-4-yl]piperidine, p-toluenesulfonate Salt (P3)

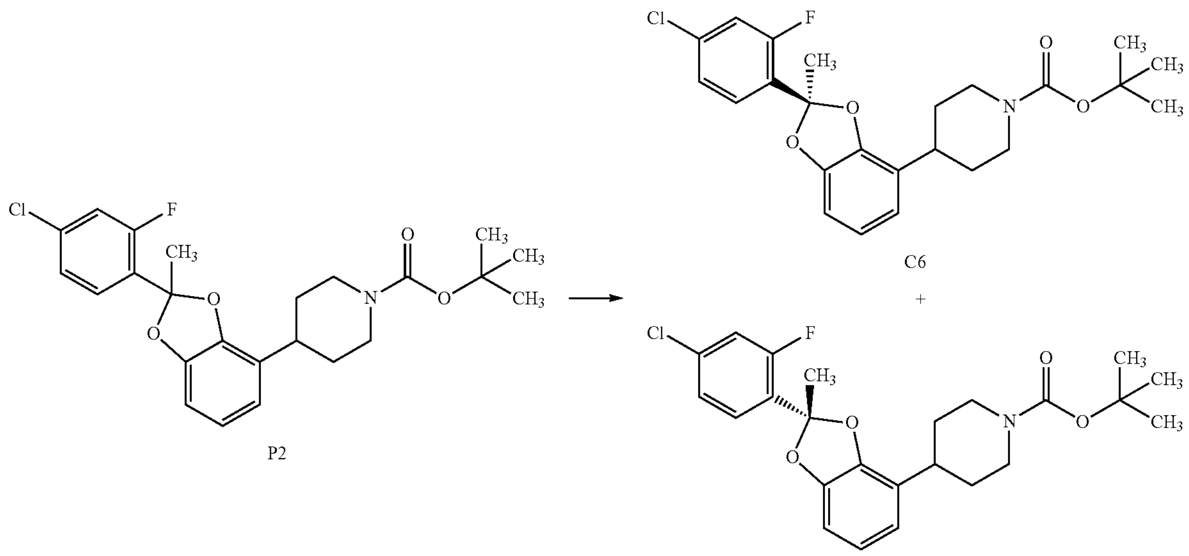

P2

C6

+

C7

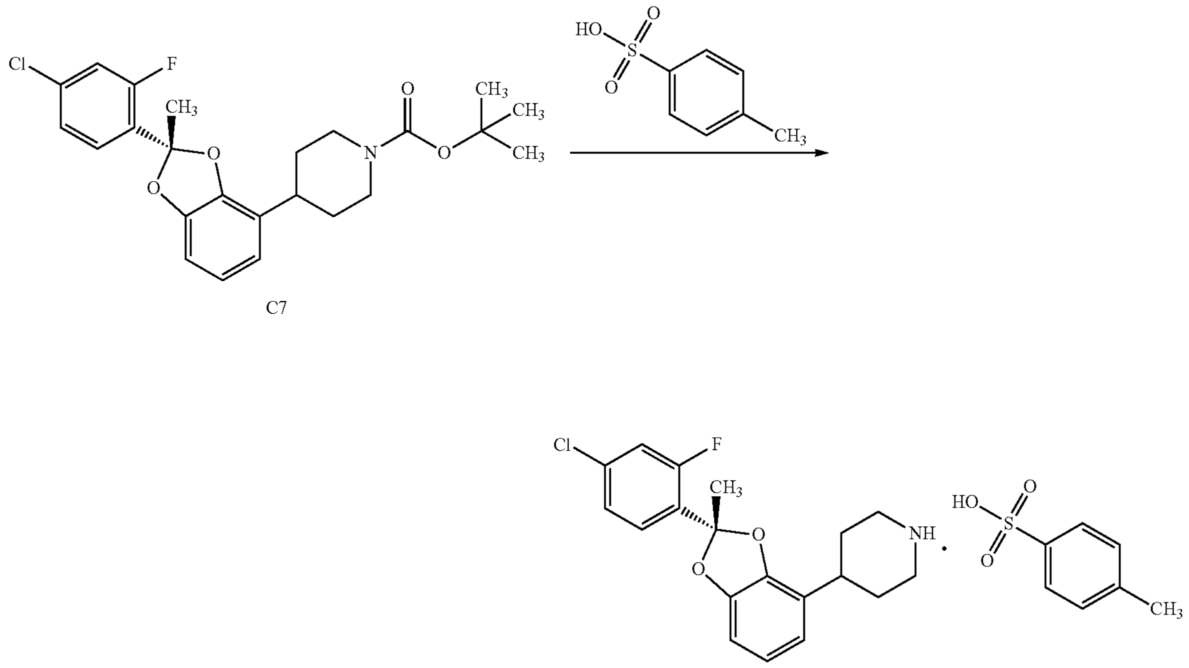

C7

P3

Step 1. Isolation of tert-butyl 4-[(2R)-2-(4-chloro-2-fluorophenyl)-2-methyl-1,3-benzodioxol-4-yl]piperidine-1-carboxylate (C6) and tert-butyl 4-[(2S)-2-(4-chloro-2-fluorophenyl)-2-methyl-1,3-benzodioxol-4-yl]piperidine-1-carboxylate (C7)

Separation of P2 (75.2 g, 168 mmol) into its component enantiomers was carried out via SFC (supercritical fluid chromatography) [Column: Chiral Technologies Chiralpak AD-H, 5 μm; Mobile phase: 4:1 carbon dioxide/(2-propanol containing 0.2% 1-aminopropan-2-ol)]. The first-eluting compound was designated as C6, and the second-eluting enantiomer as C7. The indicated absolute configurations were assigned on the basis of a single-crystal X-ray structure determination carried out on C8, which was derived from C6 (see below).

C6—Yield: 38.0 g, 84.8 mmol, 50%. Retention time 3.64 minutes [Column: Chiral Technologies Chiralpak AD-H, 4.6×250 mm, 5 μm; Mobile phase A: carbon dioxide; Mobile phase B: 2-propanol containing 0.2% 1-aminopropan-2-ol; Gradient: 5% B for 1.00 minute, then 5% to 60% B over 8.00 minutes; Flow rate: 3.0 mL/minute; Back pressure: 120 bar]. C7—Yield: 36.8 g, 82.2 mmol, 49%. Retention time 4.19 minutes (Analytical SFC conditions identical to those used for C6).

Step 2. Synthesis of 4-[(2S)-2-(4-chloro-2-fluorophenyl)-2-methyl-1,3-benzodioxol-4-yl]piperidine, p-toluenesulfonate Salt (P3)

A solution of C7 (1.62 g, 3.62 mmol) in ethyl acetate (36 mL) was treated with p-toluenesulfonic acid monohydrate (791 mg, 4.16 mmol) and heated at 45° C. After 23 hours, the reaction mixture was allowed to cool to room temperature and the solid was collected via filtration. It was rinsed with a mixture of ethyl acetate and heptane (1:1, 2×15 mL) to afford P3 as a white solid. Yield: 1.37 g, 2.63 mmol, 73%. LCMS m/z 348.1♦ $[M+H]^+$. $^1$H NMR (400 MHz, DMSO-$d_6$) δ 8.53 (v br s, 1H), 8.29 (v br s, 1H), 7.65-7.55 (m, 2H), 7.47 (d, J=8.1 Hz, 2H), 7.35 (dd, J=8.4, 2.0 Hz, 1H), 7.11 (d, J=7.8 Hz, 2H), 6.88-6.81 (m, 2H), 6.75-6.68 (m, 1H), 3.42-3.33 (m, 2H), 3.11-2.93 (m, 3H), 2.29 (s, 3H), 2.03 (s, 3H), 1.98-1.82 (m, 4H).

Conversion of C6 to 4-[(2R)-2-(4-chloro-2-fluorophenyl)-2-methyl-1,3-benzodioxol-4-yl]piperidine, methanesulfonate Salt (C8) for Determination of Absolute Stereochemistry

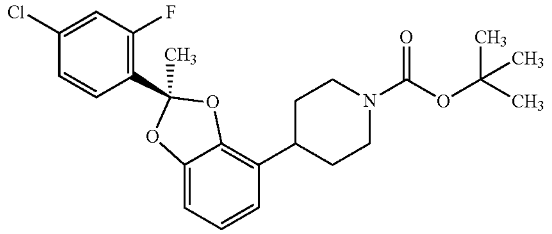

C6

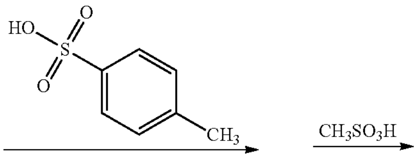

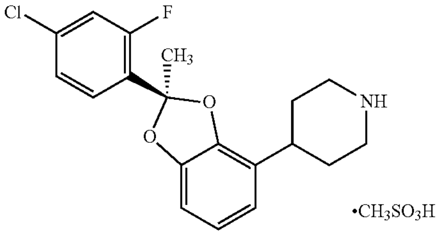

C8 p-Toluenesulfonic acid (377 mg, 2.19 mmol) was added to a solution of C6 (490 mg, 1.09 mmol) in ethyl acetate (5.5 mL), and the reaction mixture was stirred at room temperature overnight. After dilution with additional ethyl acetate, the reaction mixture was washed sequentially with aqueous sodium bicarbonate solution, water, and saturated aqueous sodium chloride solution, dried over sodium sulfate, filtered, and concentrated in vacuo. Yield: 375 mg, 1.08 mmol, 99%. $^1$H NMR (400 MHz, methanol-$d_4$) δ 7.59 (dd, J=8.3. 8.3 Hz, 1H), 7.27 (dd, J=10.9, 2.0 Hz, 1H), 7.20 (br dd, J=8.4, 2.1 Hz, 1H), 6.81-6.75 (m, 1H), 6.74-6.67 (m, 2H), 3.18-3.09 (m, 2H), 2.88-2.77 (m, 1H), 2.77-2.67 (m, 2H), 2.02 (d, J=0.7 Hz, 3H), 1.85-1.73 (m, 4H).

A 0.1 M solution of this free base (4-[(2R)-2-(4-chloro-2-fluorophenyl)-2-methyl-1,3-benzodioxol-4-yl]piperidine) in ethyl acetate was prepared and subjected to a salt screen. Only the methanesulfonate salt formation is described here. A mixture of methanesulfonic acid (25 μL, 39 μmol) and the solution of substrate (0.1 M; 0.25 mL, 25 μmol) was stirred overnight. Sufficient methanol was then added to dissolve the solid present, and ethyl acetate (3 mL) was added. The resulting solution was allowed to evaporate slowly, without stirring, to afford crystals of C8; one of these was used for the single crystal X-ray structure determination described below.

Single-Crystal X-Ray Structural Determination of C8

Single Crystal X-Ray Analysis

Data collection was performed on a Bruker D8 Quest diffractometer at room temperature. Data collection consisted of omega and phi scans.

The structure was solved by intrinsic phasing using SHELX software suite in the orthorhombic class space group $P2_12_12_1$. The structure was subsequently refined by the full-matrix least squares method. All non-hydrogen atoms were found and refined using anisotropic displacement parameters.

Formation of the methanesulfonate salt was confirmed via N1_H1X_O4 proton transfer. The hydrogen atoms located on nitrogen and oxygen were found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek). The results indicate that the absolute structure has been correctly assigned; the method calculates that the probability that the structure is correct is 100%. The Hooft parameter is reported as 0.02 with an esd of 0.0012 and the Parson's parameter is reported as 0.07 with an esd of 0.009. The absolute configuration at C7 was confirmed as (R).

The asymmetric unit is comprised of one molecule of the protonated free base of C8 and one molecule of deprotonated methanesulfonic acid. The final R-index was 4.6%. A final difference Fourier revealed no missing or misplaced electron density.

Pertinent crystal, data collection, and refinement information is summarized in Table A. Atomic coordinates, bond lengths, bond angles, and displacement parameters are listed in Tables B-D.

SOFTWARE AND REFERENCES

SHELXTL, Version 5.1, Bruker AXS, 1997.

PLATON, A. L. Spek, *J. Appl. Cryst* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Strayer, and A. L. Spek, *J. Appl. Cryst.* 2008, 41, 96-103.

H. D. Flack, *Acta Cryst.* 1983, A39, 867-881.

TABLE A

Crystal data and structure refinement for C8.

| | |
|---|---|
| Empirical formula | $C_{20}H_{23}ClFNO_5S$ |
| Formula weight | 443.90 |
| Temperature | 296(2) K |
| Wavelength | 1.54178 Å |
| Crystal system | Orthorhombic |
| Space group | $P2_12_12_1$ |
| Unit cell dimensions | a = 6.5348(5) Å α = 90° |
| | b = 9.3688(7) Å β = 90° |
| | c = 35.214(3) Å γ = 90° |
| Volume | 2155.9(3) $Å^3$ |
| Z | 4 |
| Density (calculated) | 1.368 $Mg/m^3$ |
| Absorption coefficient | 2.823 $mm^{-1}$ |
| F(000) | 928 |
| Crystal size | 0.480 × 0.100 × 0.040 $mm^3$ |
| Theta range for data collection | 2.509 to 70.483° |
| Index ranges | −7 <= h <= 7, |
| | −11 <= k <= 8, |
| | −42<=/<=42 |
| Reflections collected | 16311 |
| Independent reflections | 4035 [$R_{int}$ = 0.0638] |
| Completeness to theta = 67.679° | 99.0% |
| Absorption correction | Empirical |
| Refinement method | Full-matrix least-squares on $F^2$ |
| Data/restraints/parameters | 4035/2/271 |
| Goodness-of-fit on $F^2$ | 0.832 |
| Final R indices [I > 2σ(I)] | R1 = 0.0463, wR2 = 0.1227 |
| R indices (all data) | R1 = 0.0507, wR2 = 0.1294 |
| Absolute structure parameter | −0.003(18) |
| Extinction coefficient | 0.0051(6) |
| Largest diff. peak and hole | 0.256 and −0.305 e · $Å^{-3}$ |

TABLE B

Atomic coordinates (×$10^4$) and equivalent isotropic displacement parameters ($Å^2$ × $10^3$) for C8. U(eq) is defined as one-third of the trace of the orthogonalized $U^{ij}$ tensor.

| | x | y | z | U(eq) |
|---|---|---|---|---|
| S(1) | 3842(2) | 9910(1) | 5317(1) | 57(1) |
| Cl(1) | −1625(2) | −718(1) | 6588(1) | 80(1) |
| O(1) | 6138(4) | 3727(3) | 6876(1) | 53(1) |
| F(1) | 639(5) | 3071(4) | 7503(1) | 89(1) |
| O(2) | 3445(4) | 5043(3) | 7117(1) | 57(1) |
| O(4) | 2909(6) | 11013(4) | 5082(1) | 78(1) |
| O(3) | 3708(7) | 10299(4) | 5708(1) | 83(1) |
| N(1) | 10461(5) | 2909(4) | 5493(1) | 56(1) |
| C(9) | 5652(6) | 4826(4) | 6629(1) | 44(1) |
| C(1) | 3361(7) | 1662(4) | 6697(1) | 53(1) |
| C(6) | 2957(6) | 2523(4) | 7012(1) | 49(1) |
| C(10) | 4075(6) | 5613(4) | 6776(1) | 47(1) |
| C(14) | 6628(6) | 5138(4) | 6294(1) | 47(1) |
| O(5) | 5833(7) | 9578(4) | 5179(1) | 96(1) |
| C(15) | 8265(6) | 4182(4) | 6130(1) | 49(1) |
| C(5) | 1105(7) | 2270(5) | 7190(1) | 59(1) |
| C(16) | 7309(6) | 3048(5) | 5874(1) | 54(1) |
| C(2) | 1971(7) | 670(4) | 6567(1) | 55(1) |
| C(4) | −286(7) | 1288(5) | 7080(1) | 64(1) |
| C(7) | 4448(6) | 3667(4) | 7142(1) | 52(1) |
| C(13) | 5876(8) | 6374(5) | 6113(1) | 60(1) |
| C(11) | 3359(7) | 6819(4) | 6602(1) | 57(1) |
| C(8) | 5296(8) | 3485(6) | 7537(1) | 64(1) |
| C(19) | 9905(7) | 4976(6) | 5902(1) | 67(1) |
| C(17) | 8902(7) | 2063(5) | 5702(1) | 59(1) |

TABLE B-continued

| Atomic coordinates (×10^4) and equivalent isotropic displacement parameters (Å^2 × 10^3) for C8. U(eq) is defined as one-third of the trace of the orthogonalized $U^{ij}$ tensor. | | | | |
|---|---|---|---|---|
| | x | y | z | U(eq) |
| C(12) | 4316(8) | 7178(5) | 6263(1) | 65(1) |
| C(3) | 150(7) | 497(4) | 6756(1) | 56(1) |
| C(18) | 11476(7) | 3977(6) | 5738(1) | 73(1) |
| C(20) | 2328(14) | 8399(7) | 5260(2) | 117(3) |

TABLE C

| Bond lengths [Å] and angles [°] for C8. | | | |
|---|---|---|---|
| S(1)—O(5) | 1.423(4) | C(4)—C(3) | 1.389(6) |
| S(1)—O(3) | 1.428(3) | C(4)—H(4) | 0.9300 |
| S(1)—O(4) | 1.458(3) | C(7)—C(8) | 1.506(6) |
| S(1)—C(20) | 1.738(6) | C(13)—C(12) | 1.373(7) |
| Cl(1)—C(3) | 1.729(5) | C(13)—H(13) | 0.9300 |
| O(1)—C(9) | 1.385(4) | C(11)—C(12) | 1.388(7) |
| O(1)—C(7) | 1.449(4) | C(11)—H(11) | 0.9300 |
| F(1)—C(5) | 1.367(4) | C(8)—H(8A) | 0.9600 |
| O(2)—C(10) | 1.376(4) | C(8)—H(8B) | 0.9600 |
| O(2)—C(7) | 1.449(4) | C(8)—H(8C) | 0.9600 |
| N(1)—C(18) | 1.478(6) | C(19)—C(18) | 1.505(7) |
| N(1)—C(17) | 1.486(5) | C(19)—H(19A) | 0.9700 |
| N(1)—H(1X) | 0.99(2) | C(19)—H(19B) | 0.9700 |
| N(1)—H(1Y) | 0.97(2) | C(17)—H(17A) | 0.9700 |
| C(9)—C(10) | 1.369(5) | C(17)—H(17B) | 0.9700 |
| C(9)—C(14) | 1.375(5) | C(12)—H(12) | 0.9300 |
| C(1)—C(2) | 1.378(6) | C(18)—H(18A) | 0.9700 |
| C(1)—C(6) | 1.395(5) | C(18)—H(18B) | 0.9700 |
| C(1)—H(1) | 0.9300 | C(20)—H(20A) | 0.9600 |
| C(6)—C(5) | 1.384(6) | C(20)—H(20B) | 0.9600 |
| C(6)—C(7) | 1.519(6) | C(20)—H(20C) | 0.9600 |
| C(10)—C(11) | 1.369(5) | | |
| C(14)—C(13) | 1.409(6) | O(5)—S(1)—O(3) | 116.2(3) |
| C(14)—C(15) | 1.509(5) | O(5)—S(1)—O(4) | 110.1(2) |
| C(15)—C(16) | 1.527(5) | O(3)—S(1)—O(4) | 109.9(2) |
| C(15)—C(19) | 1.531(6) | O(5)—S(1)—C(20) | 107.6(4) |
| C(15)—H(15) | 0.9800 | O(3)—S(1)—C(20) | 106.6(3) |
| C(5)—C(4) | 1.351(7) | O(4)—S(1)—C(20) | 105.9(4) |
| C(16)—C(17) | 1.518(6) | C(9)—O(1)—C(7) | 105.0(3) |
| C(16)—H(16A) | 0.9700 | C(10)—O(2)—C(7) | 105.2(3) |
| C(16)—H(16B) | 0.9700 | C(18)—N(1)—C(17) | 112.3(3) |
| C(2)—C(3) | 1.372(6) | C(18)—N(1)—H(1X) | 107(3) |
| C(2)—H(2) | 0.9300 | C(17)—N(1)—H(1X) | 113(3) |
| C(18)—N(1)—H(1Y) | 113(3) | C(1)—C(2)—H(2) | 120.3 |
| C(17)—N(1)—H(1Y) | 103(3) | C(5)—C(4)—C(3) | 117.5(4) |
| H(1X)—N(1)—H(1Y) | 108(4) | C(5)—C(4)—H(4) | 121.2 |
| C(10)—C(9)—C(14) | 124.1(3) | C(3)—C(4)—H(4) | 121.2 |
| C(10)—C(9)—O(1) | 109.6(3) | O(1)—C(7)—O(2) | 105.7(3) |
| C(14)—C(9)—O(1) | 126.3(3) | O(1)—C(7)—C(8) | 108.7(3) |
| C(2)—C(1)—C(6) | 121.9(4) | O(2)—C(7)—C(8) | 108.8(3) |
| C(2)—C(1)—H(1) | 119.0 | O(1)—C(7)—C(6) | 108.7(3) |
| C(6)—C(1)—H(1) | 119.0 | O(2)—C(7)—C(6) | 108.6(3) |
| C(5)—C(6)—C(1) | 115.3(4) | C(8)—C(7)—C(6) | 115.8(3) |
| C(5)—C(6)—C(7) | 123.0(3) | C(12)—C(13)—C(14) | 122.4(4) |
| C(1)—C(6)—C(7) | 121.7(4) | C(12)—C(13)—H(13) | 118.8 |
| C(9)—C(10)—C(11) | 122.1(4) | C(14)—C(13)—H(13) | 118.8 |
| C(9)—C(10)—O(2) | 110.3(3) | C(10)—C(11)—C(12) | 115.6(4) |
| C(11)—C(10)—O(2) | 127.5(4) | C(10)—C(11)—H(11) | 122.2 |
| C(9)—C(14)—C(13) | 113.6(4) | C(12)—C(11)—H(11) | 122.2 |
| C(9)—C(14)—C(15) | 122.1(3) | C(7)—C(8)—H(8A) | 109.5 |
| C(13)—C(14)—C(15) | 124.2(3) | C(7)—C(8)—H(8B) | 109.5 |
| C(14)—C(15)—C(16) | 110.4(3) | H(8A)—C(8)—H(8B) | 109.5 |
| C(14)—C(15)—C(19) | 114.1(3) | C(7)—C(8)—H(8C) | 109.5 |
| C(16)—C(15)—C(19) | 108.4(3) | H(8A)—C(8)—H(8C) | 109.5 |
| C(14)—C(15)—H(15) | 107.9 | H(8B)—C(8)—H(8C) | 109.5 |
| C(16)—C(15)—H(15) | 107.9 | C(18)—C(19)—C(15) | 112.2(4) |
| C(19)—C(15)—H(15) | 107.9 | C(18)—C(19)—H(19A) | 109.2 |
| C(4)—C(5)—F(1) | 117.2(4) | C(15)—C(19)—H(19A) | 109.2 |
| C(4)—C(5)—C(6) | 125.0(4) | C(18)—C(19)—H(19B) | 109.2 |
| F(1)—C(5)—C(6) | 117.9(4) | C(15)—C(19)—H(19B) | 109.2 |
| C(17)—C(16)—C(15) | 112.2(3) | H(19A)—C(19)—H(19B) | 107.9 |
| C(17)—C(16)—H(16A) | 109.2 | N(1)—C(17)—C(16) | 110.1(3) |
| C(15)—C(16)—H(16A) | 109.2 | N(1)—C(17)—H(17A) | 109.6 |

TABLE C-continued

| Bond lengths [Å] and angles [°] for C8. | | | |
|---|---|---|---|
| C(17)—C(16)—H(16B) | 109.2 | C(16)—C(17)—H(17A) | 109.6 |
| C(15)—C(16)—H(16B) | 109.2 | N(1)—C(17)—H(17B) | 109.6 |
| H(16A)—C(16)—H(16B) | 107.9 | C(16)—C(17)—H(17B) | 109.6 |
| C(3)—C(2)—C(1) | 119.4(4) | H(17A)—C(17)—H(17B) | 108.2 |
| C(3)—C(2)—H(2) | 120.3 | C(13)—C(12)—C(11) | 122.1(4) |
| C(1)—C(2)—H(2) | 120.3 | C(13)—C(12)—H(12) | 118.9 |
| | | C(11)—C(12)—H(12) | 118.9 |
| C(2)—C(3)—C(4) | 120.8(4) | H(18A)—C(18)—H(18B) | 108.2 |
| C(2)—C(3)—Cl(1) | 119.6(3) | S(1)—C(20)—H(20A) | 109.5 |
| C(4)—C(3)—Cl(1) | 119.6(3) | S(1)—C(20)—H(20B) | 109.5 |
| N(1)—C(18)—C(19) | 109.9(3) | H(20A)—C(20)—H(20B) | 109.5 |
| N(1)—C(18)—H(18A) | 109.7 | S(1)—C(20)—H(20C) | 109.5 |
| C(19)—C(18)—H(18A) | 109.7 | H(20A)—C(20)—H(20C) | 109.5 |
| N(1)—C(18)—H(18B) | 109.7 | H(20B)—C(20)—H(20C) | 109.5 |
| C(19)—C(18)—H(18B) | 109.7 | | |

Symmetry Transformations Used to Generate Equivalent Atoms.

TABLE D

Anisotropic displacement parameters ($Å^2 \times 10^3$) for C8. The anisotropic displacement factor exponent takes the form: $-2\pi^2[h^2 a^{*2}U^{11} + \ldots + 2\ h\ k\ a^*\ b^*\ U^{12}]$.

| | $U^{11}$ | $U^{22}$ | $U^{33}$ | $U^{23}$ | $U^{13}$ | $U^{12}$ |
|---|---|---|---|---|---|---|
| S(1) | 73(1) | 48(1) | 48(1) | -2(1) | 7(1) | -1(1) |
| Cl(1) | 81(1) | 78(1) | 81(1) | -8(1) | 1(1) | -8(1) |
| O(1) | 54(1) | 50(1) | 56(1) | 14(1) | 10(1) | 17(1) |
| F(1) | 83(2) | 103(2) | 79(2) | -40(2) | 38(2) | -6(2) |
| O(2) | 66(2) | 49(1) | 54(1) | 2(1) | 11(1) | 18(1) |
| O(4) | 87(2) | 84(2) | 64(2) | 19(2) | 17(2) | 21(2) |
| O(3) | 122(3) | 80(2) | 47(1) | -3(1) | 7(2) | -13(2) |
| N(1) | 47(2) | 73(2) | 48(2) | 7(2) | 3(1) | 11(2) |
| C(9) | 51(2) | 38(2) | 44(2) | 2(1) | -7(1) | 2(2) |
| C(1) | 63(2) | 46(2) | 50(2) | 5(2) | 21(2) | 13(2) |
| C(6) | 55(2) | 47(2) | 45(2) | 5(1) | 11(2) | 19(2) |
| C(10) | 55(2) | 39(2) | 46(2) | -5(1) | -4(2) | 6(2) |
| C(14) | 54(2) | 46(2) | 42(2) | 0(1) | -9(2) | -5(2) |
| O(5) | 88(2) | 88(3) | 113(3) | -24(2) | 13(2) | 21(2) |
| C(15) | 47(2) | 61(2) | 40(2) | 3(2) | -3(1) | -2(2) |
| C(5) | 60(2) | 62(2) | 54(2) | -6(2) | 19(2) | 13(2) |
| C(16) | 43(2) | 53(2) | 65(2) | -4(2) | 8(2) | -6(2) |

TABLE D-continued

Anisotropic displacement parameters ($Å^2 \times 10^3$) for C8. The anisotropic displacement factor exponent takes the form: $-2\pi^2[h^2 a^{*2}U^{11} + \ldots + 2\ h\ k\ a^*\ b^*\ U^{12}]$.

| | $U^{11}$ | $U^{22}$ | $U^{33}$ | $U^{23}$ | $U^{13}$ | $U^{12}$ |
|---|---|---|---|---|---|---|
| C(2) | 72(3) | 49(2) | 45(2) | 2(2) | 16(2) | 14(2) |
| C(4) | 57(2) | 68(3) | 65(2) | -3(2) | 23(2) | 6(2) |
| C(7) | 54(2) | 50(2) | 51(2) | 7(2) | 12(2) | 16(2) |
| C(13) | 81(3) | 54(2) | 46(2) | 9(2) | -4(2) | 4(2) |
| C(11) | 70(3) | 46(2) | 54(2) | -8(2) | -14(2) | 17(2) |
| C(8) | 69(3) | 71(3) | 51(2) | 4(2) | 4(2) | 15(2) |
| C(19) | 54(2) | 78(3) | 70(3) | -13(2) | 2(2) | -25(2) |
| C(17) | 54(2) | 57(2) | 67(2) | -3(2) | 8(2) | 3(2) |
| C(12) | 96(3) | 43(2) | 56(2) | 5(2) | -14(2) | 13(2) |
| C(3) | 64(2) | 52(2) | 52(2) | 4(2) | 2(2) | 14(2) |
| C(18) | 43(2) | 103(4) | 73(3) | 7(3) | 3(2) | -18(2) |
| C(20) | 153(7) | 87(4) | 110(5) | -14(4) | -6(5) | -57(5) |

Preparation of P3, di-p-toluoyl-L-tartrate salt

4-[(2S)-2-(4-Chloro-2-fluorophenyl)-2-methyl-1,3-benzodioxol-4-yl]piperidine, di-p-toluoyl-L-tartrate Salt (P3, di-p-toluoyl-L-tartrate Salt)

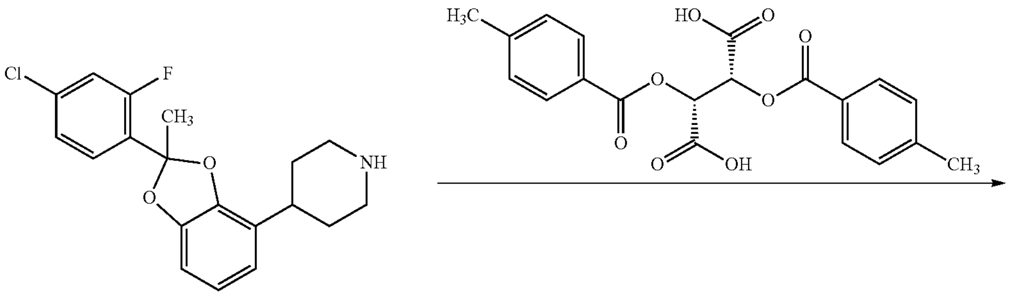

C13, free base

-continued

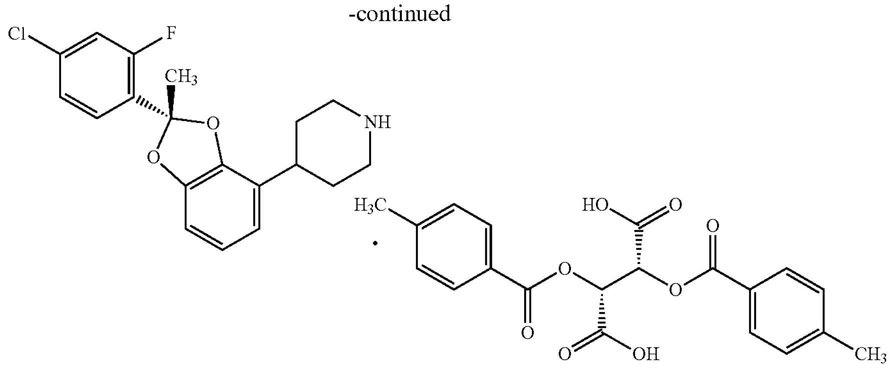

P3, di-p-toluoyl-L-tartrate salt

A solution of C13, free base (519 mg, 1.49 mmol) and di-p-toluoyl-L-tartaric acid (278 mg, 0.719 mmol) in acetonitrile (7.5 mL) was stirred at 50° C. for 1.5 hours. The mixture was allowed to cool to room temperature at 0.2° C./minute. After 15 hours at room temperature, the mixture was heated to 65° C. and charged with acetonitrile (15 mL). The mixture was allowed to cool to room temperature at 0.2° C./minute. After 15 hours at room temperature, the mixture was heated to 54° C. After 3 hours, the solid was collected by filtration, and dried in a vacuum oven at 35° C. under nitrogen, providing P3, di-p-toluoyl-L-tartrate salt as a white solid (217 mg, 0.296 mmol, 20%, 82% ee).

A solution of P3, di-p-toluoyl-L-tartrate salt (217 mg, 0.296 mmol, 82% ee) in acetonitrile (8.0 mL) at 50° C. was allowed to cool to room temperature at 0.2° C./minute. After 15 hours, the solid was collected by filtration, and dried in a vacuum oven at 35° C. under nitrogen, providing P3, di-p-toluoyl-L-tartrate salt as a white solid (190 mg, 0.259 mmol, 88%, 88% ee). LCMS m/z 348.1♦ $[M+H]^+$. $^1H$ NMR (400 MHz, DMSO-$d_6$) δ 8.9-8.5 (br s, 2H), 7.79 (d, J=8.1 Hz, 4H), 7.64-7.54 (m, 2H), 7.34 (dd, J=8.4, 2.1 Hz, 1H), 7.26 (d, J=8.0 Hz, 4H), 6.87-6.78 (m, 2H), 6.69 (dd, J=6.7, 2.5 Hz, 1H), 5.58 (s, 2H), 3.37-3.28 (m, 2H, assumed; partially obscured by water peak), 3.05-2.89 (m, 3H), 2.33 (s, 6H), 2.02 (s, 3H), 1.92-1.80 (m, 4H). Retention time: Peak 1 (4.97 minutes, minor) and Peak 2 (5.31 minutes, Major) {Column: Chiralpak IC-U 3.0×50 mm, 1.6 μm; Mobile phase A: carbon dioxide; Mobile phase B: 0.1% isopropylamine in methanol; Gradient: 10% B for 5.00 minutes, then 45% B for 0.6 minutes; Flow rate: 1.7 mL/minute; Back pressure: 130 bar}.

Preparation P4 tert-Butyl 4-[2-(4-cyano-2-fluorophenyl)-2-methyl-1,3-benzodioxol-4-yl]piperidine-1-carboxylate (P4)

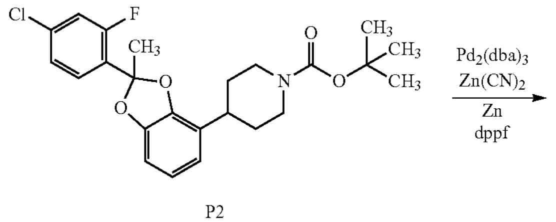

P2

-continued

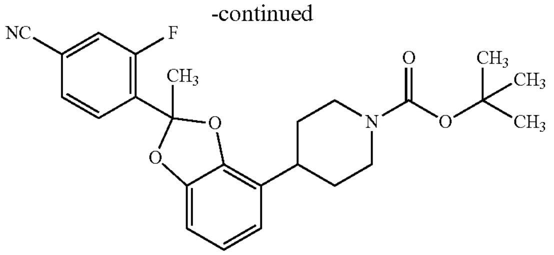

P4

A suspension of P2 (2.00 g, 4.46 mmol), zinc cyanide (734 mg, 6.25 mol), zinc (70.1 mg, 1.07 mmol), 1,1'-bis (diphenylphosphino)ferrocene (dppf; 198 mg, 0.357 mmol) and tris(dibenzylideneacetone)dipalladium(0) (164 mg, 0.179 mmol) in N,N-dimethylacetamide (20 mL) was stirred at 120° C. for 16 hours, whereupon it was filtered. The filtrate was mixed with water (50 mL) and extracted with ethyl acetate (3×50 mL); the combined organic layers were then washed sequentially with water (30 mL) and with saturated aqueous sodium chloride solution (20 mL), and concentrated in vacuo. Silica gel chromatography (Gradient: 0% to 30% ethyl acetate in petroleum ether) afforded a solid, which was treated with acetonitrile (15 mL) and water (15 mL) and subjected to lyophilization. This provided P4 as a light yellow solid. Yield: 1.17 g, 2.67 mmol, 60%. LCMS m/z 461.3 $[M+Na^+]$. $^1H$ NMR (400 MHz, chloroform-d) 7.71 (dd, J=7.7, 7.6 Hz, 1H), 7.45 (dd, J=8.0, 1.6 Hz, 1H), 7.42 (dd, J=10.0, 1.5 Hz, 1H), 6.79 (dd, component of ABC pattern, J=7.7, 7.6 Hz, 1H), 6.72 (dd, component of ABC pattern, J=7.8, 1.3 Hz, 1H), 6.68 (dd, component of ABC pattern, J=7.8, 1.3 Hz, 1H), 4.37-4.14 (br m, 2H), 2.91-2.73 (m, 3H), 2.07 (d, J=1.1 Hz, 3H), 1.89-1.62 (m, 4H), 1.49 (s, 9H).

Preparations P5 and P6

4-Bromo-2-phenyl-1,3-benzodioxole, ENT-1 (P5) and 4-Bromo-2-phenyl-1,3-benzodioxole, ENT-2 (P6)

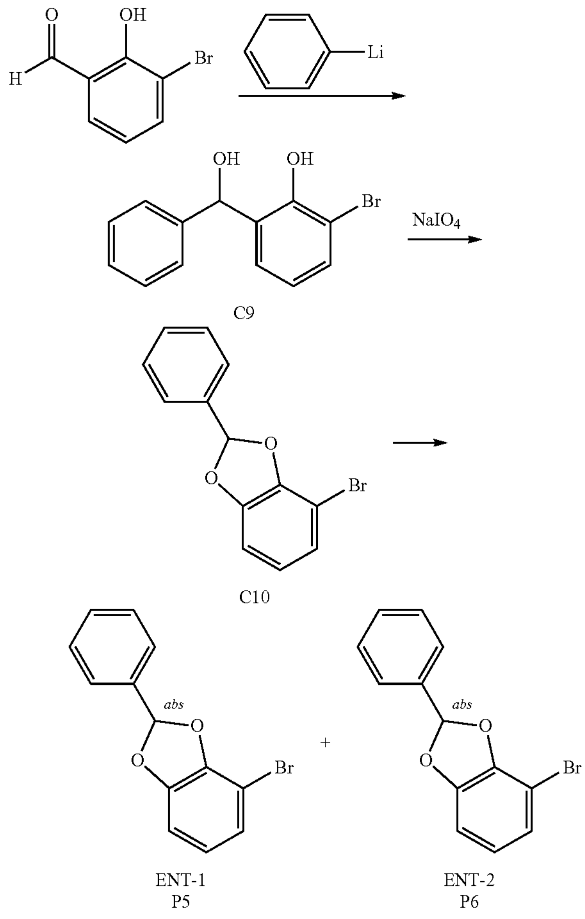

C9

C10

ENT-1
P5

ENT-2
P6

Step 1. Synthesis of 2-bromo-6-[hydroxy(phenyl)methyl]phenol (C9)

Phenyllithium (1.9 M solution in 1-butoxybutane; 78.5 mL, 149 mmol) was slowly added to a −70° C. solution of 3-bromo-2-hydroxybenzaldehyde (10.0 g, 49.7 mmol) in tetrahydrofuran (70 mL), at a rate that maintained the reaction temperature below −60° C. The resulting suspension was stirred at −70° C. for 1 hour, and then allowed to warm to room temperature overnight, whereupon it was poured into a 0° C. aqueous ammonium chloride solution (30 mL). This mixture was extracted with ethyl acetate (3×30 mL), and the combined organic layers were washed with saturated aqueous sodium chloride solution (30 mL), dried over sodium sulfate, filtered, and concentrated in vacuo. Silica gel chromatography (Gradient: 0% to 5% ethyl acetate in petroleum ether) provided C9 as a yellow solid. Yield: 6.11 g, 21.9 mmol, 44%. $^1$H NMR (400 MHz, chloroform-d) δ 7.45-7.28 (m, 6H), 7.22-7.18 (m, 1H), 7.06 (br d, J=7.7 Hz, 1H), 6.77 (dd, J=7.9, 7.8 Hz, 1H), 6.06 (br s, 1H), 2.89 (br s, 1H).

Step 2. Synthesis of 4-bromo-2-phenyl-1,3-benzodioxole (C10)

To a solution of C9 (6.11 g, 21.9 mmol) in methanol (370 mL) was added a solution of sodium periodate (11.7 g, 54.7 mmol) in water (175 mL). The reaction mixture was stirred at 30° C. for 40 hours, whereupon most of the methanol was removed via concentration in vacuo. The resulting mixture was extracted with dichloromethane (5×100 mL), and the combined organic layers were washed sequentially with aqueous sodium sulfite solution (100 mL) and saturated aqueous sodium chloride solution (100 mL), dried over sodium sulfate, filtered, and concentrated under reduced pressure. Chromatography on silica gel (Eluent: petroleum ether) provided C10 as a colorless oil. Yield: 4.50 g, 16.2 mmol, 74%. LCMS m/z 278.5 (bromine isotope pattern observed) [M+H]$^+$. $^1$H NMR (400 MHz, chloroform-d) δ 7.62-7.57 (m, 2H), 7.49-7.43 (m, 3H), 7.04 (s, 1H), 7.00 (dd, J=8.0, 1.4 Hz, 1H), 6.79 (dd, component of ABX pattern, J=7.8, 1.4 Hz, 1H), 6.75 (dd, component of ABX pattern, J=7.9, 7.8 Hz, 1H).

Step 3. Isolation of 4-bromo-2-phenyl-1,3-benzodioxole, ENT-1 (P5) and 4-bromo-2-phenyl-1,3-benzodioxole, ENT-2 (P6)

The enantiomers comprising C10 (5.00 g, 18.0 mmol) were separated using SFC [Column: Chiral Technologies ChiralCel OD, 10 μm; Mobile phase: 3:1 carbon dioxide/(methanol containing 0.1% ammonium hydroxide)]. The first-eluting enantiomer was designated as ENT-1 (P5), and the second-eluting enantiomer as ENT-2 (P6); both were obtained as yellow oils.

P5 Yield: 2.20 g, 7.94 mmol, 44%. LCMS m/z 277.0 (bromine isotope pattern observed) [M+H]$^+$. $^1$H NMR (400 MHz, chloroform-d) δ 7.63-7.55 (m, 2H), 7.51-7.42 (m, 3H), 7.04 (s, 1H), 7.00 (dd, J=8.0, 1.3 Hz, 1H), 6.80 (dd, component of ABX pattern, J=7.8, 1.4 Hz, 1H), 6.75 (dd, component of ABX pattern, J=7.9, 7.8 Hz, 1H). Retention time 3.28 minutes (Column: Chiral Technologies ChiralCel OD-H, 4.6×150 mm, 5 μm; Mobile phase A: carbon dioxide; Mobile phase B: methanol containing 0.05% diethylamine; Gradient: 5% to 40% B over 5.5 minutes; Flow rate: 2.5 mL/minute).

P6 Yield: 2.00 g, 7.22 mmol, 40%. LCMS m/z 276.9 (bromine isotope pattern observed) [M+H]$^+$. $^1$H NMR (400 MHz, chloroform-d) δ 7.63-7.55 (m, 2H), 7.50-7.42 (m, 3H), 7.04 (s, 1H), 7.00 (dd, J=8.0, 1.4 Hz, 1H), 6.80 (dd, component of ABX pattern, J=7.8, 1.4 Hz, 1H), 6.75 (dd, component of ABX pattern, J=7.9, 7.9 Hz, 1H). Retention time 3.73 minutes (Analytical conditions identical to those used for P5).

Preparation P7 tert-Butyl 4-[2-(5-chloropyridin-2-yl)-2-methyl-1,3-benzodioxol-4-yl]piperidine-1-carboxylate (P7)

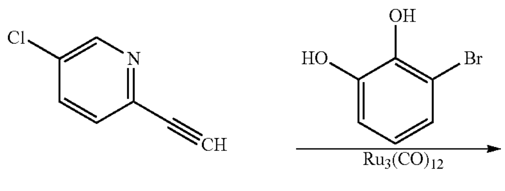

-continued

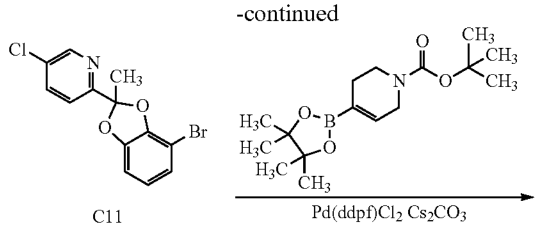

C11

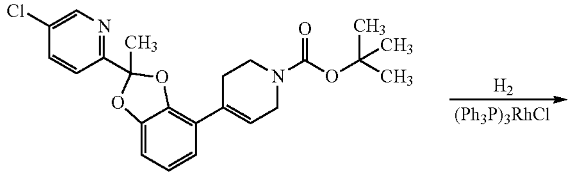

C12

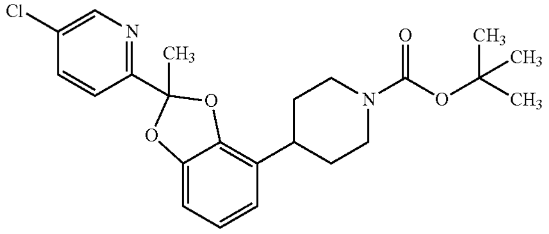

P7

Step 1. Synthesis of 2-(4-bromo-2-methyl-1,3-benzodioxol-2-yl)-5-chloropyridine (C11)

A mixture of 5-chloro-2-ethynylpyridine (1.80 g, 13.1 mmol), 3-bromobenzene-1,2-diol (2.47 g, 13.1 mmol), and triruthenium dodecacarbonyl (167 mg, 0.261 mmol) in toluene (25 mL) was degassed for 1 minute and then heated at 100° C. for 16 hours. The reaction mixture was diluted with ethyl acetate (30 mL) and filtered through a pad of diatomaceous earth; the filtrate was concentrated in vacuo and purified using silica gel chromatography (Gradient: 0% to 1% ethyl acetate in petroleum ether) to provide C11 as a yellow oil. Yield: 1.73 g, 5.30 mmol, 40%. LCMS m/z 325.6 (bromine-chlorine isotope pattern observed) $[M+H]^+$. $^1H$ NMR (400 MHz, chloroform-d) δ 8.63 (dd, J=2.4, 0.7 Hz, 1H), 7.71 (dd, component of ABX pattern, J=8.4, 2.4 Hz, 1H), 7.60 (dd, component of ABX pattern, J=8.4, 0.7 Hz, 1H), 6.97 (dd, J=8.0, 1.4 Hz, 1H), 6.76 (dd, component of ABX pattern, J=7.8, 1.4 Hz, 1H), 6.72 (dd, component of ABX pattern, J=8.0, 7.8 Hz, 1H), 2.10 (s, 3H).

Step 2. Synthesis of tert-butyl 4-[2-(5-chloropyridin-2-yl)-2-methyl-1,3-benzodioxol-4-yl]-3,6-dihydropyridine-1(2H)-carboxylate (C12)

[1,1'-Bis(diphenylphosphino)ferrocene]dichloropalladium(II) (388 mg, 0.530 mmol) was added to a suspension of C11 (1.73 g, 5.30 mmol), tert-butyl 4-(4,4,5,5-tetramethyl-1,3,2-dioxaborolan-2-yl)-3,6-dihydropyridine-1(2H)-carboxylate (1.64 g, 5.30 mmol), and cesium carbonate (5.18 g, 15.9 mmol) in 1,4-dioxane (35 mL) and water (6 mL). The reaction mixture was stirred at 90° C. for 4 hours, whereupon it was diluted with ethyl acetate (30 mL) and water (5 mL). The organic layer was concentrated in vacuo and the residue was subjected to silica gel chromatography (Gradient: 0% to 5% ethyl acetate in petroleum ether), affording C12 as a yellow gum. Yield: 1.85 g, 4.31 mmol, 81%. LCMS m/z 451.0♦ $[M+Na^+]$. $^1H$ NMR (400 MHz, chloroform-d) δ 8.62 (dd, J=2.5, 0.8 Hz, 1H), 7.69 (dd, component of ABX pattern, J=8.4, 2.4 Hz, 1H), 7.57 (dd, component of ABX pattern, J=8.4, 0.8 Hz, 1H), 6.84-6.79 (m, 2H), 6.78-6.73 (m, 1H), 6.39-6.33 (br m, 1H), 4.13-4.07 (m, 2H), 3.68-3.58 (m, 2H), 2.60-2.51 (br m, 2H), 2.07 (s, 3H), 1.49 (s, 9H).

Step 3. Synthesis of tert-butyl 4-[2-(5-chloropyridin-2-yl)-2-methyl-1,3-benzodioxol-4-yl]piperidine-1-carboxylate (P7)

A solution of C12 (2.61 g, 6.08 mmol) and tris(triphenylphosphine)rhodium(I) chloride (Wilkinson's catalyst; 563 mg, 0.608 mmol) in methanol (100 mL) was degassed under vacuum and then purged with hydrogen; this evacuation-purge cycle was carried out a total of three times. The reaction mixture was then stirred at 60° C. under hydrogen (50 psi) for 16 hours, whereupon it was filtered. The filtrate was concentrated in vacuo, and the residue was purified using silica gel chromatography (Gradient: 0% to 10% ethyl acetate in petroleum ether); the resulting material was combined with material from a similar hydrogenation carried out on C12 (110 mg, 0.256 mmol) to provide P7 as a light-yellow gum. Combined yield: 2.05 g, 4.76 mmol, 75%. LCMS m/z 431.3♦ $[M+H]^+$. $^1H$ NMR (400 MHz, chloroform-d) δ 8.62 (d, J=2.3 Hz, 1H), 7.69 (dd, component of ABX pattern, J=8.4, 2.4 Hz, 1H), 7.57 (d, half of AB quartet, J=8.4 Hz, 1H), 6.79 (dd, component of ABC pattern, J=7.8, 7.7 Hz, 1H), 6.72 (dd, component of ABC pattern, J=7.8, 1.3 Hz, 1H), 6.68 (br d, component of ABC pattern, J=7.9 Hz, 1H), 4.32-4.12 (br m, 2H), 2.91-2.73 (m, 3H), 2.05 (s, 3H), 1.90-1.62 (m, 4H), 1.48 (s, 9H).

Preparations P8 and P9 tert-Butyl 4-[2-(5-chloropyridin-2-yl)-2-methyl-1,3-benzodioxol-4-yl]piperidine-1-carboxylate, ENT-1 (P8) and tert-Butyl 4-[2-(5-chloropyridin-2-yl)-2-methyl-1,3-benzodioxol-4-yl]piperidine-1-carboxylate, ENT-2 (P9)

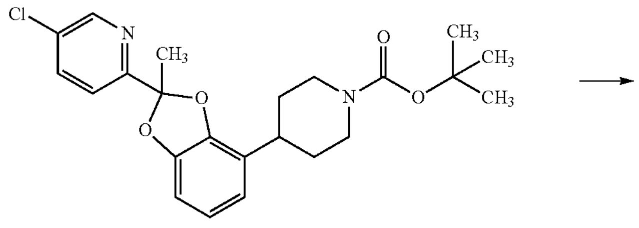

P7

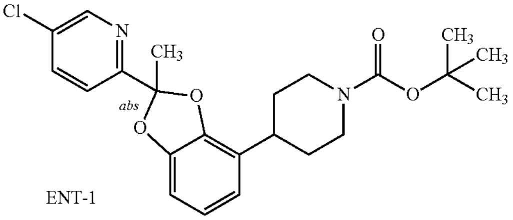

ENT-1

P8

+

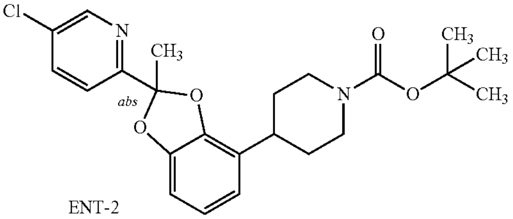

ENT-2

P9

Separation of P7 (500 mg, 1.16 mmol) into its component enantiomers was effected using SFC {Column: Phenomenex Lux Amylose-1, 5 μm; Mobile phase: 9:1 carbon dioxide/[2-propanol containing 0.2% (7 M ammonia in methanol)]}. The first-eluting enantiomer was designated as ENT-1 (P8), and the second-eluting enantiomer as ENT-2 (P9).

P8 Yield: 228 mg, 0.529 mmol, 46%. Retention time 4.00 minutes {Column: Phenomenex Lux Amylose-1, 4.6×250 mm, 5 μm; Mobile phase A: carbon dioxide; Mobile phase B: [2-propanol containing 0.2% (7 M ammonia in methanol)]; Gradient: 5% B for 1.00 minute, then 5% to 60% B over 8.00 minutes; Flow rate: 3.0 mL/minute; Back pressure: 120 bar}.

P9 Yield: 229 mg, 0.531 mmol, 46%. Retention time 4.50 minutes (Analytical conditions identical to those used for P8).

Preparation P10

{4-[2-(4-Chloro-2-fluorophenyl)-2-methyl-1,3-benzodioxol-4-yl]piperidin-1-yl}acetic acid (P10)

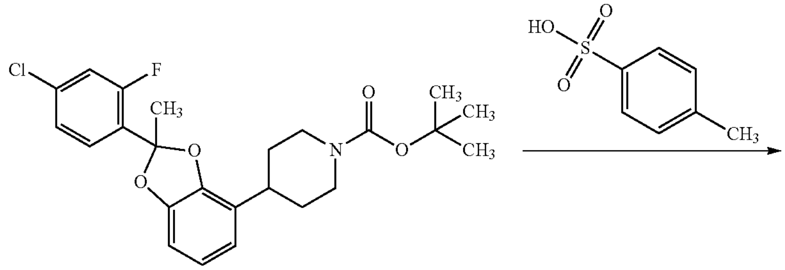

P2

-continued

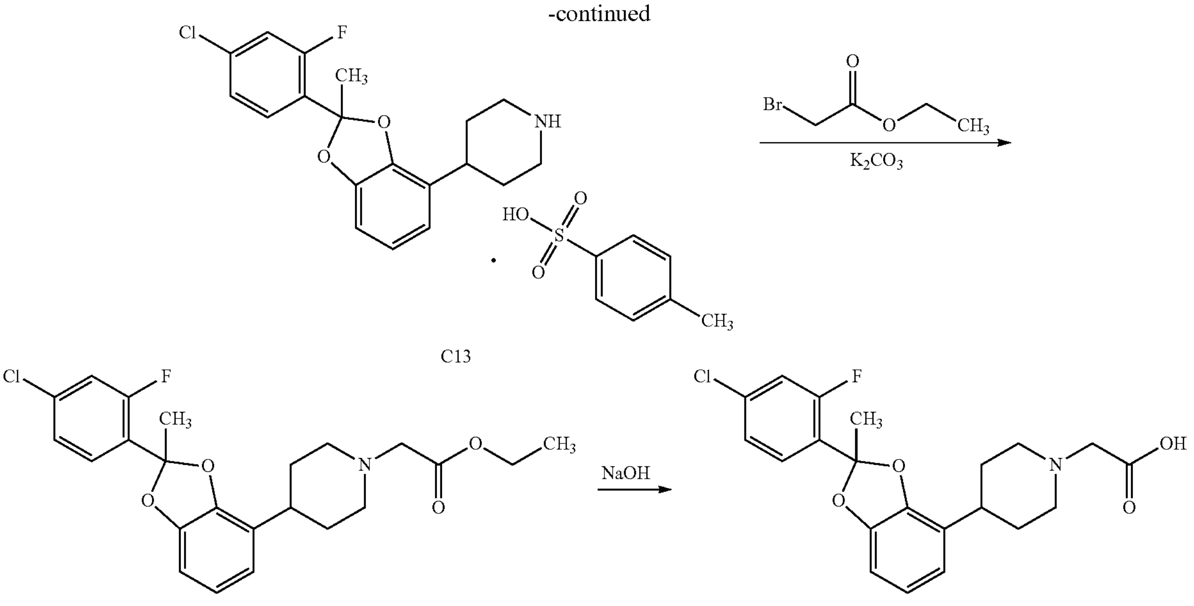

C13

C14

P10

Step 1. Synthesis of 4-[2-(4-chloro-2-fluorophenyl)-2-methyl-1,3-benzodioxol-4-yl]piperidine, p-toluenesulfonate Salt (C13)

A solution of P2 (5.0 g, 11 mmol) and p-toluenesulfonic acid (4.81 g, 27.9 mmol) in ethyl acetate (100 mL) was stirred at 60° C. for 2 hours, whereupon it was concentrated in vacuo to afford C13 as a yellow gum. This material was taken directly into the following step. LCMS m/z 347.9♦ $[M+H]^+$.

Step 2. Synthesis of ethyl {4-[2-(4-chloro-2-fluorophenyl)-2-methyl-1,3-benzodioxol-4-yl]piperidin-1-yl}acetate (C14)

Potassium carbonate (7.71 g, 55.8 mmol) and ethyl bromoacetate (1.86 g, 11.2 mmol) were added to a solution of C13 (from the previous step; 1 mmol) in acetonitrile (150 mL), and the reaction mixture was stirred at 55° C. for 16 hours. It was then filtered, and the filtrate was concentrated in vacuo and purified using silica gel chromatography (Gradient: 0% to 30% ethyl acetate in petroleum ether) to afford C14 as a yellow gum. By $^1H$ NMR analysis, this material was not entirely pure. Yield: 3.57 g, 8.23 mmol, 75% over 2 steps. $^1H$ NMR (400 MHz, chloroform-d), C14 peaks only: δ 7.52 (dd, J=8.4, 8.0 Hz, 1H), 7.17-7.07 (m, 2H), 6.77 (dd, component of ABC pattern, J=7.8, 7.8 Hz, 1H), 6.72-6.67 (m, 2H), 4.21 (q, J=7.1 Hz, 2H), 3.27 (s, 2H), 3.07 (m, 2H), 2.70 (tt, J=12.1, 3.8 Hz, 1H), 2.35 (ddd, J=11.5, 11.5, 2.7 Hz, 2H), 2.04 (d, J=1.1 Hz, 3H), 2.02-1.76 (m, 4H), 1.29 (t, J=7.1 Hz, 3H).

Step 3. Synthesis of {4-[2-(4-chloro-2-fluorophenyl)-2-methyl-1,3-benzodioxol-4-yl]piperidin-1-yl}acetic acid (P10)

A solution of C14 (3.57 g, 8.23 mmol) and aqueous sodium hydroxide solution (3 M; 13.7 mL, 41.1 mmol) in a mixture of methanol (80 mL) and tetrahydrofuran (40 mL) was stirred at 25° C. for 16 hours. After removal of solvents in vacuo, the aqueous residue was acidified to pH 7 by addition of 1 M hydrochloric acid, and then extracted with a mixture of dichloromethane and methanol (10:1, 2×100 mL). The combined organic layers were dried over sodium sulfate, filtered, and concentrated under reduced pressure to provide P10 as a yellow solid. Yield: 2.95 g, 7.27 mmol, 88%. LCMS m/z 406.2♦ $[M+H]^+$. $^1H$ NMR (400 MHz, methanol-$d_4$) δ 7.61 (dd, J=8.3, 8.3 Hz, 1H), 7.29 (dd, J=10.9, 2.0 Hz, 1H), 7.22 (ddd, J=8.4, 2.0, 0.8 Hz, 1H), 6.82 (dd, component of ABC pattern, J=8.3, 7.1 Hz, 1H), 6.78-6.72 (m, 2H), 3.65-3.54 (br m, 2H), 3.51 (s, 2H), 3.04-2.88 (m, 3H), 2.23-2.07 (m, 2H), 2.07-1.93 (m, 2H), 2.04 (d, J=1.1 Hz, 3H).

Preparation P11

Methyl 2-(chloromethyl)-1-(2-methoxyethyl)-1H-benzimidazole-6-carboxylate (P11)

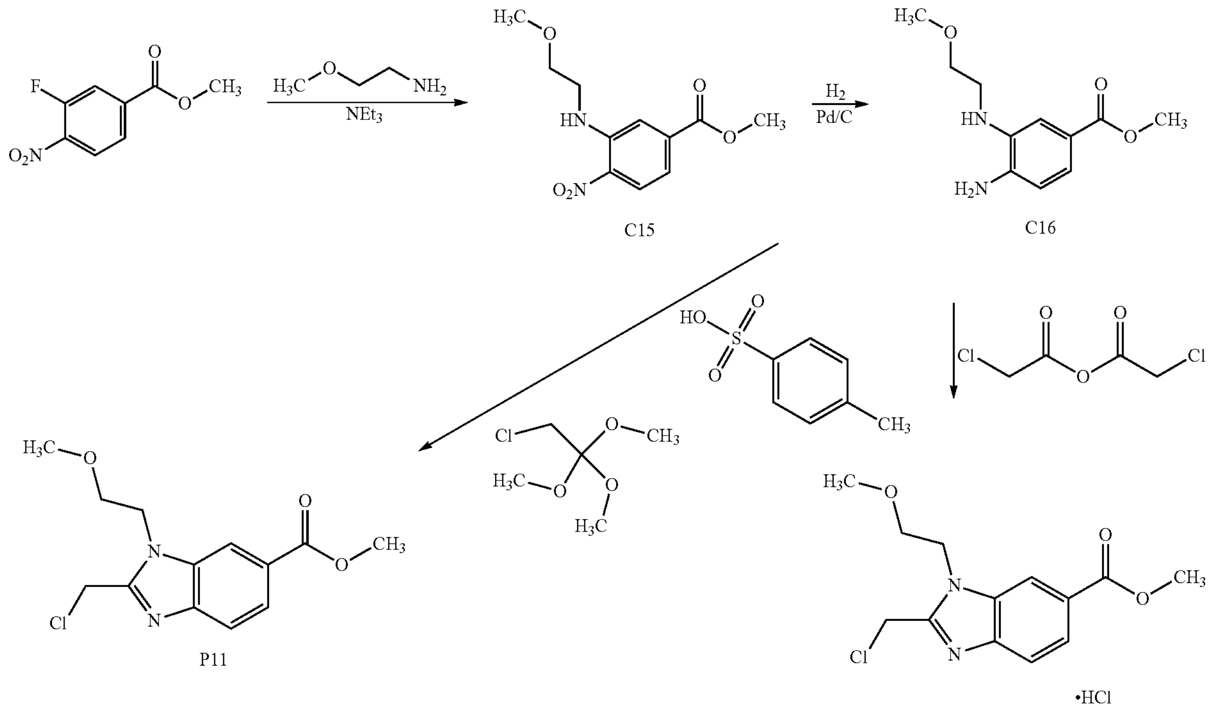

C15

C16

P11

•HCl

P11, HCl salt

Step 1. Synthesis of methyl 3-[(2-methoxyethyl) amino]-4-nitrobenzoate (C15)

To a colorless solution of methyl 3-fluoro-4-nitrobenzoate (50 g, 250 mmol) in tetrahydrofuran (400 mL) was added triethylamine (40.7 g, 402 mmol, 55.8 mL) followed by addition of 2-methoxyethanamine (30.2 g, 402 mmol) in tetrahydrofuran (100 mL), drop-wise, at room temperature. The resultant yellow solution was stirred at 55° C. for 18 hours. The solution was cooled to room temperature and concentrated under reduced pressure to remove tetrahydrofuran. The resultant yellow solid was dissolved in ethyl acetate (800 mL) and washed with saturated aqueous ammonium chloride solution (250 mL). The aqueous phase was separated and extracted with ethyl acetate (200 mL). The combined organic layers were washed with saturated aqueous sodium chloride solution (3×250 mL), dried over sodium sulfate, filtered, and concentrated under reduced pressure to yield C15 (60.2 g, 94%) as a yellow solid. $^1$H NMR (600 MHz, chloroform-d) δ 8.23 (d, 1H), 8.17 (br s, 1H), 7.58 (d, 1H), 7.25 (dd, 1H), 3.95 (s, 3H), 3.69-3.73 (m, 2H), 3.56 (m, 2H), 3.45 (s, 3H); LCMS m/z 255.4 $[M+H]^+$.

Step 2. Synthesis of methyl 4-amino-3-[(2-methoxyethyl)amino]benzoate (C16)

To solution of C15 (30 g, 118 mmol) in methanol (500 mL) was added Pd/C (10 g, 94 mmol). This reaction was stirred at room temperature under 15 psi hydrogen for 18 hours. The black suspension was filtered through diatomaceous earth and the filter cake was washed with methanol (500 mL). The combined filtrates were concentrated in vacuo to give C16 (26.5 g, quantitative) as a brown oil, which solidified on standing. $^1$H NMR (400 MHz, chloroform-d) δ 7.48 (dd, 1H), 7.36 (d, 1H), 6.69 (d, 1H), 3.87 (s, 3H), 3.77 (br s, 2H), 3.68 (t, 2H), 3.41 (s, 3H), 3.32 (t, 2H); LCMS m/z 224.7 $[M+H]^+$.

Step 3. Synthesis of methyl 2-(chloromethyl)-1-(2-methoxyethyl)-1H-benzimidazole-6-carboxylate (P11)

To a solution of C16 (5.00 g, 22.3 mmol) in tetrahydrofuran (100 mL) was added 2-chloro-1,1,1-trimethoxyethane (3.31 mL, 24.6 mmol), followed by p-toluenesulfonic acid monohydrate (84.8 mg, 0.446 mmol). The reaction mixture was heated at 45° C. for 5 hours, whereupon it was concentrated in vacuo; the residual oil was dissolved in ethyl acetate (10 mL) and heated until a solution formed. This was slowly stirred while cooling to room temperature overnight. The precipitate was collected via filtration and washed with heptane to afford P11 as a gray solid. Yield: 5.73 g, 20.3 mmol, 91%. $^1$H NMR (600 MHz, chloroform-d) δ 8.12 (br s, 1H), 8.01 (br d, J=8.6 Hz, 1H), 7.79 (d, J=8.4 Hz, 1H), 4.96 (s, 2H), 4.52 (t, J=5.1 Hz, 2H), 3.96 (s, 3H), 3.74 (t, J=5.1 Hz, 2H), 3.28 (s, 3H).

Step 4. Synthesis of methyl 2-(chloromethyl)-1-(2-methoxyethyl)-1H-benzimidazole-6-carboxylate, Hydrochloride Salt (P11, HCl Salt)

A solution of C16 (5.0 g, 24 mmol) in 1,4-dioxane (100 mL) was heated to 100° C., a solution of chloroacetic anhydride (4.1 g, 24.5 mmol) in 1,4-dioxane (60 mL) was added via addition funnel over a period of 10 hours, and the reaction mixture was stirred for another 12 hours at 100° C. The following day, the reaction was cooled to room temperature and the 1,4-dioxane was removed under reduced pressure. The crude reaction mixture was dissolved in ethyl acetate and washed with saturated aqueous sodium bicarbonate solution. The ethyl acetate layer was separated, dried over sodium sulfate, and filtered. A solution of 4 M hydrogen chloride in 1,4-dioxane (1.1 equiv.) was added to the ethyl acetate solution with constant stirring. The hydrochloride salt of P11 precipitated out as a pale yellow solid. The suspension was stirred for 1 hour and the hydrochloride salt of P11 was then collected by filtration to give a yellow solid (6.1 g, 86%). $^1$H NMR (600 MHz, $CD_3OD$) δ 8.64 (s, 1H), 8.30 (d, 1H), 7.92 (d, 1H), 5.32 (s, 2H), 4.84 (m, 2H), 3.99 (s, 3H), 3.83 (t, 2H), 3.31 (s, 3H). LCMS m/z 283.2 $[M+H]^+$.

Preparation P12

Methyl 1-(2-methoxyethyl)-2-(piperazin-1-ylmethyl)-1H-benzimidazole-6-carboxylate (P12)

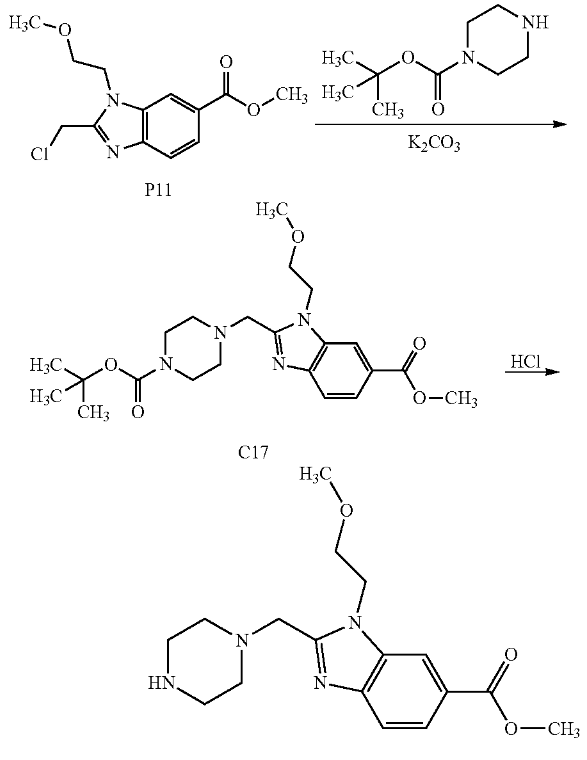

P11

C17

P12

Step 1. Synthesis of methyl 2-{[4-(tert-butoxycarbonyl)piperazin-1-yl]methyl}-1-(2-methoxyethyl)-1H-benzimidazole-6-carboxylate (C17)

Compound P11 (1.59 g, 5.62 mmol) was added to a 15° C. mixture of tert-butyl piperazine-1-carboxylate (1.00 g, 5.37 mmol) and potassium carbonate (2.97 g, 21.5 mmol) in acetonitrile (15 mL), and the reaction mixture was stirred at 55° C. for 12 hours. It was then combined with a similar reaction carried out using P11 and tert-butyl piperazine-1-carboxylate (200 mg, 1.07 mmol), and the mixture was filtered. After the filtrate had been concentrated in vacuo, the residue was purified via chromatography on silica gel (Gradient: 0% to 60% ethyl acetate in petroleum ether) to provide C17 as a pale yellow solid. Combined yield: 2.30 g, 5.32 mmol, 83%. LCMS m/z 433.0 $[M+H]^+$. $^1$H NMR (400 MHz, chloroform-d) δ 8.12 (d, J=1.5 Hz, 1H), 7.96 (dd, J=8.4, 1.5 Hz, 1H), 7.73 (d, J=8.5 Hz, 1H), 4.58 (t, J=5.4 Hz, 2H), 3.95 (s, 3H), 3.89 (s, 2H), 3.73 (t, J=5.4 Hz, 2H), 3.46-3.37 (br m, 4H), 3.28 (s, 3H), 2.54-2.44 (br m, 4H), 1.45 (s, 9H).

Step 2. Synthesis of methyl 1-(2-methoxyethyl)-2-(piperazin-1-ylmethyl)-1H-benzimidazole-6-carboxylate (P12)

To a solution of C17 (2.30 g, 5.32 mmol) in dichloromethane (80 mL) was added a solution of hydrogen chloride in ethyl acetate (20 mL). The reaction mixture was stirred at 20° C. for 2 hours, whereupon it was concentrated in vacuo. The residue was diluted with water (20 mL), adjusted to a pH of 9 to 10 by addition of saturated aqueous sodium bicarbonate solution, and extracted with a mixture of ethyl acetate and methanol (10:1, 15×50 mL). The combined organic layers were dried over sodium sulfate, filtered, and concentrated in vacuo to afford P12 as a pale yellow solid. Yield: 1.68 g, 5.05 mmol, 95%. LCMS m/z 332.8 $[M+H]^+$. $^1$H NMR (400 MHz, chloroform-d) δ 8.13 (br s, 1H), 7.96 (br d, J=8.5 Hz, 1H), 7.72 (d, J=8.5 Hz, 1H), 4.59 (t, J=5.5 Hz, 2H), 3.95 (s, 3H), 3.86 (s, 2H), 3.75 (t, J=5.5 Hz, 2H), 3.29 (s, 3H), 2.87 (t, J=4.8 Hz, 4H), 2.50 (br m, 4H).

Preparation P13

6-Bromo-2-(chloromethyl)-1-(2-methoxyethyl)-1H-imidazo[4,5-b]pyridine (P13)

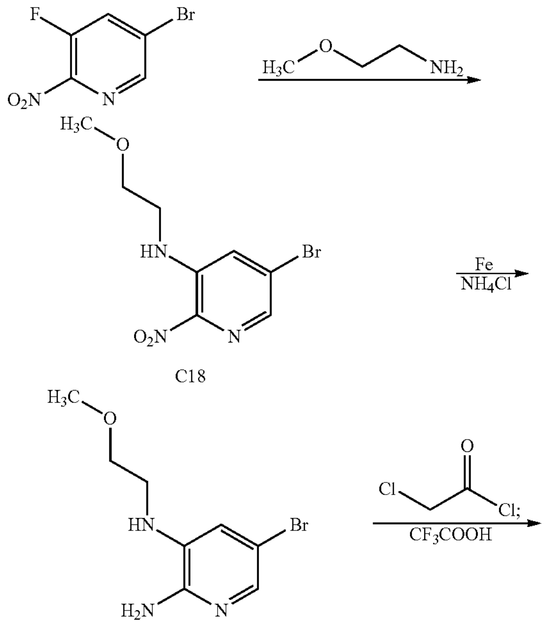

C18

C19

-continued

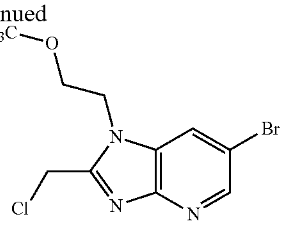

P13

Step 1. Synthesis of 5-bromo-N-(2-methoxyethyl)-2-nitropyridin-3-amine (C18)

A solution of 5-bromo-3-fluoro-2-nitropyridine (400 mg, 1.81 mmol) and 2-methoxyethanamine (408 mg, 5.43 mmol) in tetrahydrofuran (10 mL) was stirred at 25° C. for 2 hours, whereupon it was diluted with ethyl acetate (100 mL) and washed with water (50 mL). The organic layer was washed with saturated aqueous sodium chloride solution (50 mL), dried over magnesium sulfate, filtered, and concentrated to afford C18 as a yellow solid. Yield: 430 mg, 1.56 mmol, 86%.

Step 2. Synthesis of 5-bromo-$N^3$-(2-methoxyethyl)pyridine-2,3-diamine (C19)

A solution of C18 (430 mg, 1.56 mmol), ammonium chloride (833 mg, 15.6 mmol), and iron powder (870 mg, 15.6 mmol) in a mixture of methanol (10 mL) and water (2 mL) was stirred at 80° C. for 30 minutes. The resulting suspension was poured into water (50 mL) and extracted with ethyl acetate (2×50 mL); the combined organic layers were dried over magnesium sulfate, filtered, and concentrated to provide C19 as a brown solid. Yield: 350 mg, 1.42 mmol, 91%. $^1$H NMR (400 MHz, chloroform-d) δ 7.63 (d, J=2.1 Hz, 1H), 6.88 (d, J=2.0 Hz, 1H), 4.33-4.19 (br s, 2H), 3.65 (dd, J=5.6, 4.6 Hz, 2H), 3.40 (s, 3H), 3.22 (br t, J=5 Hz, 2H).

Step 3. Synthesis of 6-bromo-2-(chloromethyl)-1-(2-methoxyethyl)-1H-imidazo[4,5-b]pyridine (P13)

A solution of C19 (400 mg, 1.63 mmol) in 1,4-dioxane (8 mL) was treated with chloroacetyl chloride (0.284 mL, 3.57 mmol) and stirred at room temperature until LCMS analysis indicated complete conversion of C19 to the intermediate amide. After removal of the 1,4-dioxane in vacuo, the residue was dissolved in trifluoroacetic acid (8 mL) and heated at 80° C. for 18 hours, whereupon the reaction mixture was cooled to room temperature and concentrated under reduced pressure. The resulting oil was dissolved in ethyl acetate (50 mL) and neutralized by addition of saturated aqueous sodium bicarbonate solution. The aqueous layer was extracted with ethyl acetate (20 mL), and the combined organic layers were dried over sodium sulfate, filtered, and concentrated in vacuo. Silica gel chromatography (Gradient: 0% to 80% ethyl acetate in heptane) afforded P13 as a solid. Yield: 176 mg, 0.578 mmol, 35%. LCMS m/z 306.1 (bromine-chlorine isotope pattern observed) $[M+H]^+$. $^1$H NMR (600 MHz, chloroform-d) δ 8.58 (br s, 1H), 7.89 (br s, 1H), 4.92 (s, 2H), 4.44 (t, J=5.0 Hz, 2H), 3.71 (t, J=5.0 Hz, 2H), 3.28 (s, 3H).

Preparation P14

Methyl 2-{[4-(2,3-dihydroxyphenyl)piperidin-1-yl]methyl}-1-(2-methoxyethyl)-1H-benzimidazole-6-carboxylate (P14)

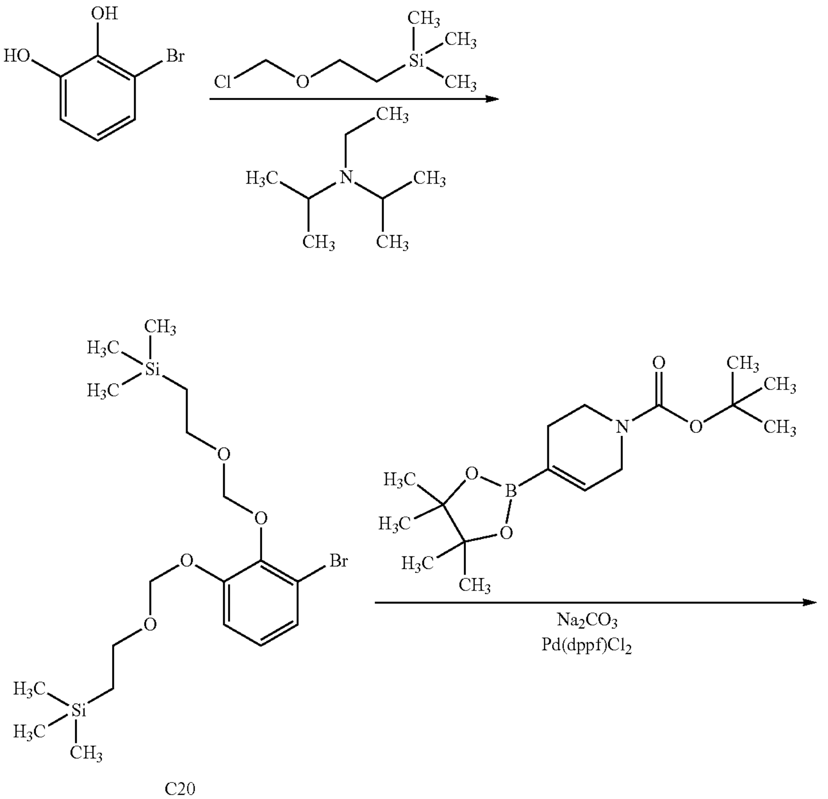

C20

-continued
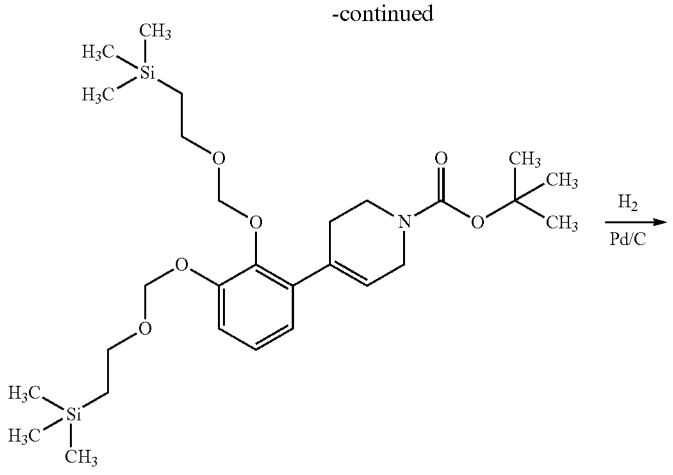
C21
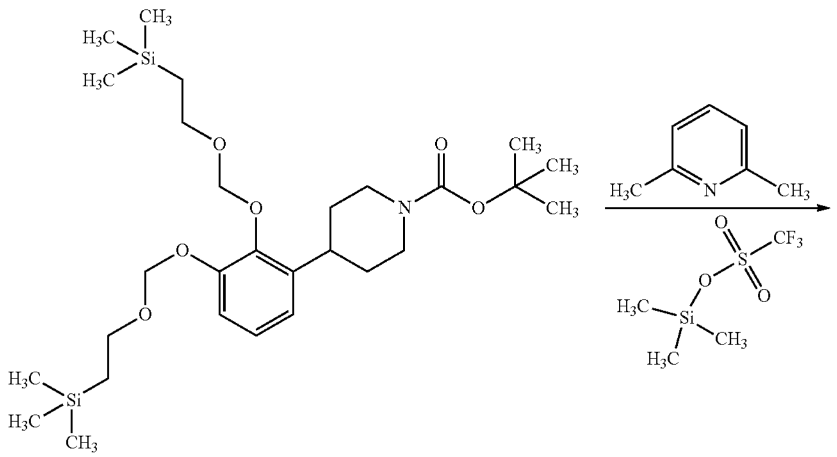
C22
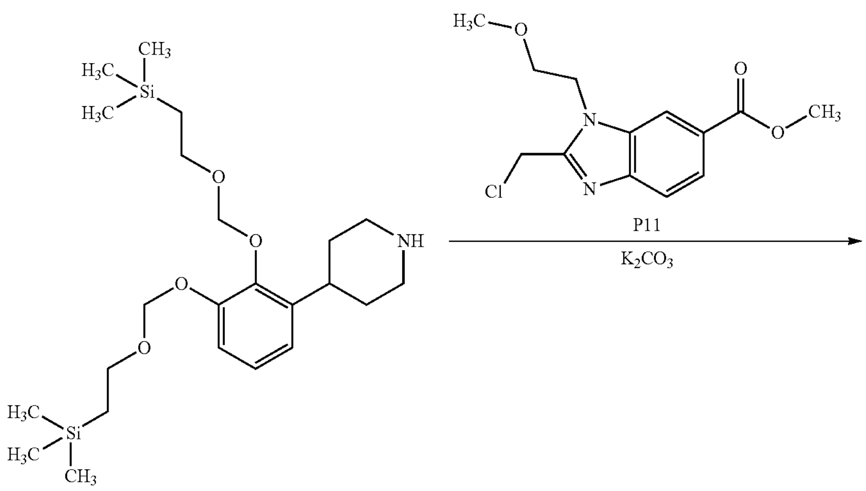
C23

-continued

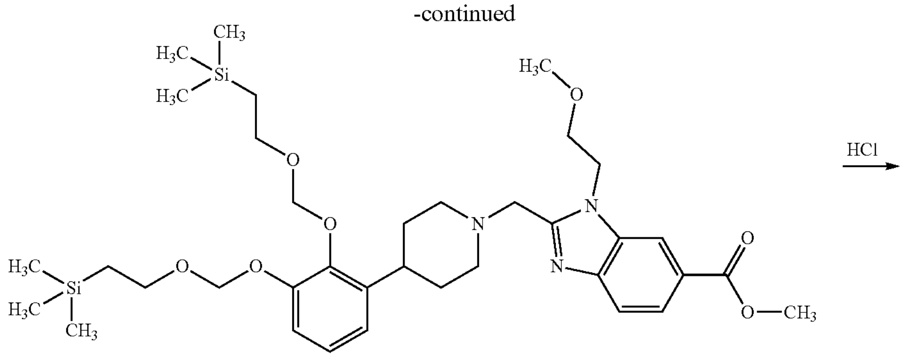

C24

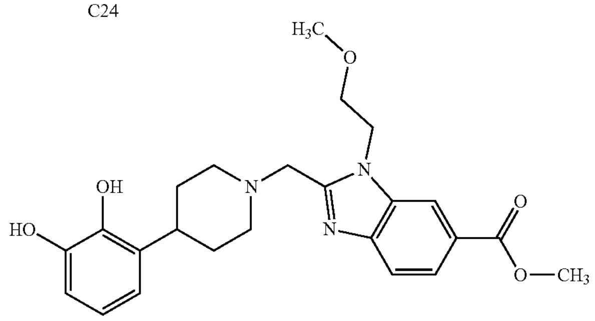

P14

Step 1. Synthesis of [(3-bromobenzene-1,2-diyl)bis(oxymethanediyloxyethane-2,1-diyl)]bis(trimethylsilane) (C20)

This reaction was carried out in two batches of identical scale. N,N-Diisopropylethylamine (37.8 mL, 217 mmol) was added drop-wise to a solution of 3-bromobenzene-1,2-diol (10.0 g, 52.9 mmol) in tetrahydrofuran (300 mL). After the mixture had been stirred for 10 minutes at 20° C., [2-(chloromethoxy)ethyl](trimethyl)silane (19.2 mL, 108 mmol) was added drop-wise over 5 minutes, and stirring was continued for 16 hours at room temperature (18° C.). N,N-Diisopropylethylamine (27.6 mL, 158 mmol) was again added, followed by drop-wise addition of [2-(chloromethoxy)ethyl](trimethyl)silane (14.0 mL, 79.1 mmol) at room temperature (18° C.). After another 2.5 hours at room temperature, the reaction mixture was filtered, and the filtrate was concentrated in vacuo. At this point, the crude products from the two batches were combined and purified using silica gel chromatography (Gradient: 0% to 7% ethyl acetate in petroleum ether), to afford C20 as a colorless oil. By $^{1}H$ NMR analysis, this material was not entirely pure. Combined yield: 22.9 g, 50.9 mmol, 48%. $^{1}H$ NMR (400 MHz, chloroform-d), C20 peaks only: δ 7.19 (dd, J=8.1, 1.5 Hz, 1H), 7.12 (dd, J=8.3, 1.4 Hz, 1H), 6.90 (dd, J=8.2. 8.2 Hz, 1H), 5.26-5.19 (m, 4H), 4.00-3.92 (m, 2H), 3.80-3.73 (m, 2H), 1.00-0.91 (m, 4H), 0.03 (s, 9H), 0.00 (s, 9H).

Step 2. Synthesis of tert-butyl 4-(2,3-bis{[2-(trimethylsilyl)ethoxy]methoxy}phenyl)-3,6-dihydropyridine-1(2H)-carboxylate (C21)

A reaction vessel containing a suspension of C20 (6.11 g, 13.6 mmol), tert-butyl 4-(4,4,5,5-tetramethyl-1,3,2-dioxaborolan-2-yl)-3,6-dihydropyridine-1(2H)-carboxylate (5.04 g, 16.3 mmol), aqueous sodium carbonate solution (1 M; 40.8 mL, 40.8 mmol), and [1,1'-bis(diphenylphosphino)ferrocene]dichloropalladium(II) (497 mg, 0.679 mmol) in 1,4-dioxane (100 mL) was evacuated and charged with nitrogen. This evacuation cycle was repeated twice, and then the reaction mixture was stirred at 85° C. for 16 hours, whereupon the reaction mixture was diluted with water (40 mL) and extracted with ethyl acetate (3×150 mL). The combined organic layers were dried over sodium sulfate, filtered, and concentrated in vacuo. Purification via silica gel chromatography (Gradient: 0% to 8% methanol in dichloromethane) provided C21 as a yellow oil. Yield: 5.47 g, 9.91 mmol, 73%. $^{1}H$ NMR (600 MHz, chloroform-d) δ 7.10 (br d, J=8.2 Hz, 1H), 6.98 (dd, J=7.9, 7.9 Hz, 1H), 6.81 (br d, J=7.7 Hz, 1H), 5.79 (br s, 1H), 5.23 (s, 2H), 5.07 (s, 2H), 4.03 (br s, 2H), 3.83-3.74 (m, 4H), 3.59 (br s, 2H), 2.52 (br s, 2H), 1.49 (s, 9H), 1.01-0.89 (m, 4H), 0.01 (s, 9H), 0.01 (s, 9H).

Step 3. Synthesis of tert-butyl 4-(2,3-bis{[2-(trimethylsilyl)ethoxy]methoxy}phenyl)piperidine-1-carboxylate (C22)

A solution of C21 (12.5 g, 22.6 mmol) in methanol (300 mL) was treated with 10% palladium on carbon (2.94 g, 2.76 mmol) and hydrogenated for 16 hours at 40 psi and 25° C. LCMS analysis at this point indicated conversion to the product: LCMS m/z 576.0 [M+Na$^{+}$]. After the reaction mixture had been filtered, and the filter cake had been washed with methanol (2×100 mL), the combined filtrates were concentrated in vacuo to afford C22 as a colorless oil. Yield: 11.2 g, 20.1 mmol, 89%. $^{1}H$ NMR (400 MHz, chloroform-d) δ 7.05-6.97 (m, 2H), 6.83 (dd, J=6.9, 2.5 Hz, 1H), 5.22 (s, 2H), 5.13 (s, 2H), 4.38-4.10 (br m, 2H), 3.90-3.82 (m, 2H), 3.81-3.73 (m, 2H), 3.22 (tt, J=12.2, 3.5 Hz, 1H), 2.79 (br dd, J=12.8, 12.8 Hz, 2H), 1.78 (br d, J=13 Hz, 2H), 1.65-1.52 (m, 2H), 1.48 (s, 9H), 1.04-0.91 (m, 4H), 0.03 (s, 9H), 0.00 (s, 9H).

Step 4. Synthesis of 4-(2,3-bis{[2-(trimethylsilyl)ethoxy]methoxy}phenyl)piperidine (C23)

To a room temperature (15° C.) solution of C22 (7.23 g, 13.0 mmol) in dichloromethane (90 mL) was added 2,6-dimethylpyridine (2.39 g, 22.3 mmol), followed by drop-wise addition of trimethylsilyl trifluoromethanesulfonate (3.80 g, 17.1 mmol). The reaction mixture was stirred at 15° C. for 16 hours, whereupon additional 2,6-dimethylpyridine (909 mg, 8.48 mmol) and trimethylsilyl trifluoromethane-sulfonate (1.45 g, 6.52 mmol) were added. After stirring at room temperature (15° C.) for another 5 hours, LCMS analysis of the reaction mixture indicated the presence of product: LCMS m/z 454.1 $[M+H]^+$. The reaction mixture was concentrated in vacuo, and the residue was washed sequentially with aqueous ammonium chloride solution (3×100 mL) and saturated aqueous sodium chloride solution (100 mL), dried over sodium sulfate, filtered, and concentrated under reduced pressure to afford C23 as a brown oil (6.6 g). This material was taken directly to the following step.

Step 5. Synthesis of methyl 2-{[4-(2,3-bis{[2-(trimethylsilyl)ethoxy]methoxy}phenyl)piperidin-1-yl]methyl}-1-(2-methoxyethyl)-1H-benzimidazole-6-carboxylate (C24)

To a solution of C23 (from the previous step; 6.6 g, mmol) in acetonitrile (150 mL) was added P11 (3.08 g, 10.9 mmol), followed by potassium carbonate (10.1 g, 73.1 mmol), and the reaction mixture was stirred at room temperature (15° C.) for 16 hours. LCMS analysis at this point indicated the presence of the product: LCMS m/z 700.2 $[M+H]^+$. The reaction mixture was filtered, and the filtrate was concentrated in vacuo; purification via silica gel chromatography (Gradient: 34% to 56% ethyl acetate in petroleum ether) afforded C24 as a yellow oil. Yield: 5.4 g, 7.7 mmol, 59% over 2 steps. $^1H$ NMR (400 MHz, chloroform-d) δ 8.16-8.12 (m, 1H), 7.96 (dd, J=8.5, 1.5 Hz, 1H), 7.73 (d, J=8.5 Hz, 1H), 7.04-6.96 (m, 2H), 6.86 (dd, J=6.7, 2.6 Hz, 1H), 5.21 (s, 2H), 5.12 (s, 2H), 4.63 (t, J=5.5 Hz, 2H), 3.95 (s, 3H), 3.93-3.83 (m, 4H), 3.80-3.72 (m, 4H), 3.31 (s, 3H), 3.17-3.06 (m, 1H), 2.99 (br d, J=11.2 Hz, 2H), 2.35-2.22 (m, 2H), 1.81 (br d, half of AB quartet, J=12.6 Hz, 2H), 1.75-1.61 (m, 2H), 1.04-0.91 (m, 4H), 0.05 (s, 9H), −0.01 (s, 9H).

Step 6. Synthesis of methyl 2-{[4-(2,3-dihydroxyphenyl)piperidin-1-yl]methyl}-1-(2-methoxyethyl)-1H-benzimidazole-6-carboxylate (P14)

A solution of hydrogen chloride in 1,4-dioxane (4 M; 96 mL, 384 mmol) was added to a room temperature (18° C.) solution of C24 (6.40 g, 9.14 mmol) in 1,4-dioxane (120 mL). After completion of the addition, the reaction mixture was stirred at room temperature (18° C.) for 16 hours, combined with a similar reaction carried out using C24 (1.00 g, 1.43 mmol), and concentrated in vacuo. The residue was treated with a mixture of dichloromethane and methanol (20:1, 150 mL) and stirred at room temperature (18° C.) for 1 hour, whereupon the solid (4.85 g) was collected via filtration. This material was treated with water (100 mL), and the mixture was adjusted to a pH of 7 to 8 by addition of aqueous sodium bicarbonate solution, stirred at room temperature (18° C.) for 30 minutes, and filtered. The filter cake was washed with water (2×20 mL), then mixed with methanol (100 mL) and concentrated in vacuo. The resulting material was treated with petroleum ether (100 mL) and stirred at room temperature (18° C.) for 30 minutes. After filtration, the filter cake was mixed with toluene (30 mL) and concentrated in vacuo to provide P14 as a gray solid. Combined yield: 2.92 g, 6.64 mmol, 63%. LCMS m/z 440.1 $[M+H]^+$. $^1H$ NMR (400 MHz, DMSO-$d_6$) δ 8.21 (d, J=1.6 Hz, 1H), 7.81 (dd, J=8.5, 1.6 Hz, 1H), 7.66 (d, J=8.5 Hz, 1H), 6.64-6.51 (m, 3H), 4.63 (t, J=5.3 Hz, 2H), 3.88 (s, 3H), 3.84 (s, 2H), 3.75 (t, J=5.3 Hz, 2H), 3.22 (s, 3H), 2.97-2.78 (m, 3H), 2.18 (br dd, J=11, 11 Hz, 2H), 1.75-1.64 (m, 2H), 1.64-1.49 (m, 2H).

Preparation P15

Methyl 2-(chloromethyl)-1-[(2S)-oxetan-2-ylmethyl]-1H-benzimidazole-6-carboxylate (P15)

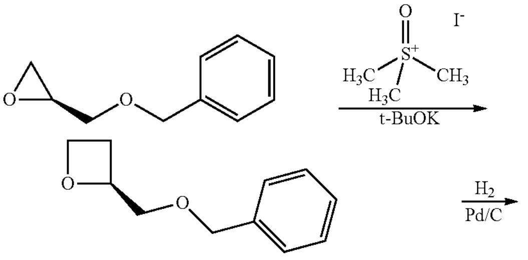

C25

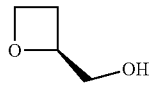
C26

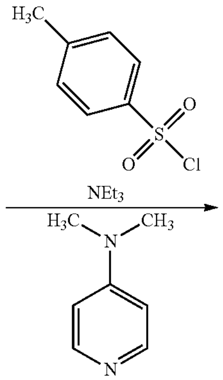

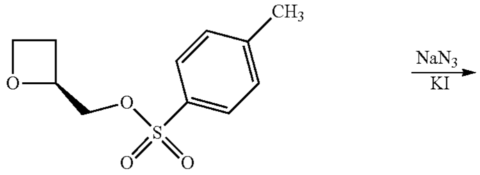

C27

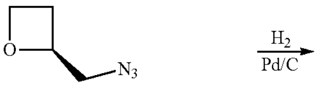

C28

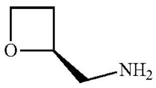
C29

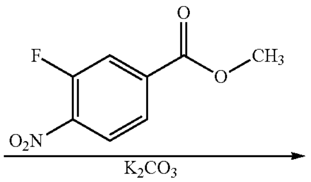

-continued

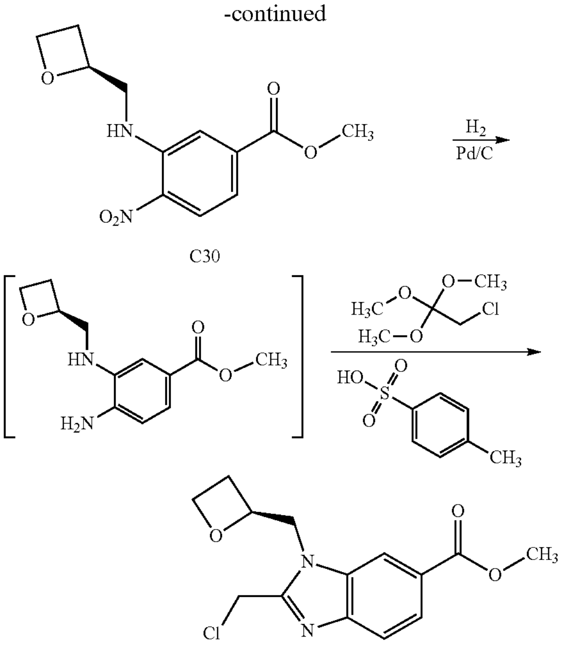

C30

P15

This entire sequence was carried out on large scale. In general, before reactions, as well as after addition of reagents, reactors were evacuated to −0.08 to −0.05 MPa and then filled with nitrogen to normal pressure. This process was generally repeated 3 times, and then oxygen content was assessed to ensure that it was ≤1.0%. For the processes of extraction and washing of organic layers, mixtures were generally stirred for 15 to 60 minutes and then allowed to settle for 15 to 60 minutes before separation of layers.

Step 1. Synthesis of (2S)-2-[(benzyloxy)methyl]oxetane (C25)

This reaction was carried out in three batches of approximately the same scale. A 2000 L glass-lined reactor was charged with 2-methylpropan-2-ol (774.7 kg). Potassium tert-butoxide (157.3 kg, 1402 mol) was added via a solid addition funnel, and the mixture was stirred for 30 minutes. Trimethylsulfoxonium iodide (308.2 kg, 1400 mol) was then added in the same manner, and the reaction mixture was heated at 55° C. to 65° C. for 2 to 3 hours, whereupon (2S)-2-[(benzyloxy)methyl]oxirane (92.1 kg, 561 mol) was added at a rate of 5 to 20 kg/hour. After the reaction mixture had been maintained at 55° C. to 65° C. for 25 hours, it was cooled to 25° C. to 35° C., and filtered through diatomaceous earth (18.4 kg). The filter cake was rinsed with tert-butyl methyl ether (3×340 kg), and the combined filtrates were transferred to a 5000 L reactor, treated with purified water (921 kg), and stirred for 15 to 30 minutes at 15° C. to 30° C. The organic layer was then washed twice using a solution of sodium chloride (230.4 kg) in purified water (920.5 kg), and concentrated under reduced pressure (≤−0.08 MPa) at ≤45° C. n-Heptane (187 kg) was added, and the resulting mixture was concentrated under reduced pressure (≤−0.08 MPa) at ≤45° C.; the organic phase was purified using silica gel chromatography (280 kg), with sodium chloride (18.5 kg) on top of the column. The crude material was loaded onto the column using n-heptane (513 kg), and then eluted with a mixture of n-heptane (688.7 kg) and ethyl acetate (64.4 kg). The three batches were combined, providing C25 as an 85% pure light yellow oil (189.7 kg, 906 mmol, 54%). $^1H$ NMR (400 MHz, chloroform-d), C25 peaks only: δ 7.40-7.32 (m, 4H), 7.32-7.27 (m, 1H), 4.98 (dddd, J=8.1, 6.7, 4.9, 3.7 Hz, 1H), 4.72-4.55 (m, 4H), 3.67 (dd, component of ABX pattern, J=11.0, 4.9 Hz, 1H), 3.62 (dd, component of ABX pattern, J=11.0, 3.7 Hz, 1H), 2.72-2.53 (m, 2H).

Step 2. Synthesis of (2S)-oxetan-2-ylmethanol (C26)

10% Palladium on carbon (30.7 kg) was added through an addition funnel to a 10° C. to 30° C. solution of 85% pure C25 (from previous step; 185.3 kg, 884.8 mol) in tetrahydrofuran (1270 kg) in a 3000 L stainless steel autoclave reactor. The addition funnel was rinsed with purified water and tetrahydrofuran (143 kg), and the rinses were added to the reaction mixture. After the reactor contents had been purged with nitrogen, they were similarly purged with hydrogen, increasing the pressure to 0.3 to 0.5 MPa and then venting to 0.05 MPa. This hydrogen purge was repeated 5 times, whereupon the hydrogen pressure was increased to 0.3 to 0.4 MPa. The reaction mixture was then heated to 35° C. to 45° C. After 13 hours, during which the hydrogen pressure was maintained at 0.3 to 0.5 MPa, the mixture was vented to 0.05 MPa, and purged five times with nitrogen, via increasing the pressure to 0.15 to 0.2 MPa and then venting to 0.05 MPa. After the mixture had been cooled to 10° C. to 25° C., it was filtered, and the reactor was rinsed with tetrahydrofuran (2×321 kg). The filter cake was soaked twice with this rinsing liquor and then filtered; concentration at reduced pressure (≤−0.06 MPa) was carried out at ≤40° C., affording C26 (62.2 kg, 706 mol, 80%) in tetrahydrofuran (251 kg)

Step 3. Synthesis of (2S)-oxetan-2-ylmethyl 4-methylbenzenesulfonate (C27)

4-(Dimethylamino)pyridine (17.5 kg, 143 mol) was added to a 10° C. to 25° C. solution of C26 (from the previous step; 62.2 kg, 706 mol) in tetrahydrofuran (251 kg) and triethylamine (92.7 kg, 916 mol) in dichloromethane (1240 kg). After 30 minutes, p-toluenesulfonyl chloride (174.8 kg, 916.9 mol) was added in portions at intervals of 20 to 40 minutes, and the reaction mixture was stirred at 15° C. to 25° C. for 16 hours and 20 minutes. Purified water (190 kg) was added; after stirring, the organic layer was washed with aqueous sodium bicarbonate solution (prepared using 53.8 kg of sodium bicarbonate and 622 kg of purified water), and then washed with aqueous ammonium chloride solution (prepared using 230 kg of ammonium chloride and 624 kg of purified water). After a final wash with purified water (311 kg), the organic layer was filtered through a stainless steel Nutsche filter that had been preloaded with silica gel (60.2 kg). The filter cake was soaked with dichloromethane (311 kg) for 20 minutes, and then filtered; the combined filtrates were concentrated at reduced pressure (≤−0.05 MPa) and ≤40° C. until 330 to 400 L remained. Tetrahydrofuran (311 kg) was then added, at 15° C. to 30° C., and the mixture was concentrated in the same manner, to a final volume of 330 to 400 L. The tetrahydrofuran addition and concentration was repeated, again to a volume of 330 to 400 L, affording a light yellow solution of C27 (167.6 kg, 692 mmol, 98%) in tetrahydrofuran (251.8 kg). $^1H$ NMR (400 MHz, chloroform-d), C27 peaks only: δ 7.81 (d, J=8.4 Hz, 2H), 7.34 (d, J=8.1 Hz, 2H), 4.91 (ddt, J=8.0, 6.7, 3.9 Hz, 1H), 4.62-4.55

(m, 1H), 4.53-4.45 (m, 1H), 4.14 (d, J=3.9 Hz, 2H), 2.75-2.63 (m, 1H), 2.60-2.49 (m, 1H), 2.44 (s, 3H).

Step 4. Synthesis of (2S)-2-(azidomethyl)oxetane (C28)

N,N-Dimethylformamide (473 kg), sodium azide (34.7 kg, 534 mol), and potassium iodide (5.2 kg, 31 mol) were combined in a 3000 L glass-lined reactor at 10° C. to 25° C. After addition of C27 (83.5 kg, 344.6 mol) in tetrahydrofuran (125.4 kg), the reaction mixture was heated to 55° C. to 65° C. for 17 hours and 40 minutes, whereupon it was cooled to 25° C. to 35° C., and nitrogen was bubbled from the bottom valve for 15 minutes. tert-Butyl methyl ether (623 kg) and purified water (840 kg) were then added, and the resulting aqueous layer was extracted twice with tert-butyl methyl ether (312 kg and 294 kg). The combined organic layers were washed with purified water (2×419 kg) while maintaining the temperature at 10° C. to 25° C., affording C28 (31.2 kg, 276 mol, 80%) in a solution of the above organic layer (1236.8 kg).

Step 5. Synthesis of 1-[(2S)-oxetan-2-yl]methanamine (C29)

10% Palladium on carbon (3.7 kg) was added through an addition funnel to a 10° C. to 30° C. solution of C28 [from the previous step; 1264 kg (31.1 kg of C28, 275 mol)] in tetrahydrofuran (328 kg) in a 3000 L stainless steel autoclave reactor. The addition funnel was rinsed with tetrahydrofuran (32 kg), and the rinse was added to the reaction mixture. After the reactor contents had been purged with nitrogen, they were similarly purged with hydrogen, increasing the pressure to 0.05 to 0.15 MPa and then venting to 0.03 to 0.04 MPa. This hydrogen purge was repeated 5 times, whereupon the hydrogen pressure was increased to 0.05 to 0.07 MPa. The reaction temperature was increased to 25° C. to 33° C., and the hydrogen pressure was maintained at 0.05 to 0.15 MPa for 22 hours, while exchanging the hydrogen every 3 to 5 hours. The mixture was then purged five times with nitrogen, via increasing the pressure to 0.15 to 0.2 MPa and then venting to 0.05 MPa. After filtration, tetrahydrofuran (92 kg and 93 kg) was used to wash the reactor and then soak the filter cake. The combined filtrates were concentrated at reduced pressure (≤−0.07 MPa) and ≤45° C., affording C29 (18.0 kg, 207 mol, 75%) in tetrahydrofuran (57.8 kg). $^1$H NMR (400 MHz, DMSO-$d_6$), C29 peaks only: δ 4.62 (ddt, J=7.6, 6.6, 5.1 Hz, 1H), 4.49 (ddd, J=8.6, 7.3, 5.6 Hz, 1H), 4.37 (dt, J=9.1, 5.9 Hz, 1H), 2.69 (d, J=5.1 Hz, 2H), 2.55-2.49 (m, 1H), 2.39 (m, 1H).

Step 6. Synthesis of methyl 4-nitro-3-{[(2S)-oxetan-2-ylmethyl]amino}benzoate (C30)

Potassium carbonate (58.1 kg, 420 mol) was added to a solution of methyl 3-fluoro-4-nitrobenzoate (54.8 kg, 275 mol) in tetrahydrofuran (148 kg) in a 100 L glass-lined reactor, and the mixture was stirred for 10 minutes. A solution of C29 (29.3 kg, 336 mol) in tetrahydrofuran (212.9 kg) was added, and the reaction mixture was stirred at 20° C. to 30° C. for 12 hours, whereupon ethyl acetate (151 kg) was added, and the mixture was filtered through silica gel (29 kg). The filter cake was rinsed with ethyl acetate (150 kg and 151 kg), and the combined filtrates were concentrated at reduced pressure (≤−0.08 MPa) and ≤45° C. to a volume of 222 to 281 L. After the mixture had been cooled to 10° C. to 30° C., n-heptane (189 kg) was added, stirring was carried out for 20 minutes, and the mixture was concentrated at reduced pressure (≤−0.08 MPa) and ≤45° C. to a volume of 222 L. n-Heptane (181 kg) was again added into the mixture at a reference rate of 100 to 300 kg/hour, and stirring was continued for 20 minutes. The mixture was sampled until residual tetrahydrofuran was ≤5%, and residual ethyl acetate was 10% to 13%. The mixture was heated to 40° C. to 45° C. and stirred for 1 hour, whereupon it was cooled to 15° C. to 25° C. at a rate of 5° C. to 10° C. per hour, and then stirred at 15° C. to 25° C. for 1 hour. Filtration using a stainless steel centrifuge provided a filter cake, which was rinsed with a mixture of ethyl acetate (5.0 kg) and n-heptane (34 kg), and then stirred with tetrahydrofuran (724 kg) at 10° C. to 30° C. for 15 minutes; filtration provided a yellow solid largely composed of C30 (57.3 kg, 210 mol, 76%). $^1$H NMR (400 MHz, DMSO-$d_6$) 8.34 (t, J=5.8 Hz, 1H), 8.14 (d, J=8.9 Hz, 1H), 7.63 (d, J=1.7 Hz, 1H), 7.13 (dd, J=8.9, 1.8 Hz, 1H), 4.99 (dddd, J=7.7, 6.7, 5.3, 4.1 Hz, 1H), 4.55 (ddd, J=8.6, 7.3, 5.8 Hz, 1H), 4.43 (dt, J=9.1, 6.0 Hz, 1H), 3.87 (s, 3H), 3.67-3.61 (m, 2H), 2.67 (dddd, J=11.1, 8.6, 7.7, 6.2 Hz, 1H), 2.57-2.47 (m, 1H).

Step 7. Synthesis of methyl 2-(chloromethyl)-1-[(2S)-oxetan-2-ylmethyl]-1H-benzimidazole-6-carboxylate (P15)

A solution of C30 (from the previous step; 51.8 kg, 190 mol) in tetrahydrofuran (678 kg), in a 3000 L autoclave reactor, was treated with 10% palladium on carbon (5.2 kg) at 10° C. to 30° C. The addition pipe was rinsed with tetrahydrofuran (46 kg) and the rinse was added to the reaction mixture. After the reactor contents had been purged with nitrogen, they were similarly purged with hydrogen, increasing the pressure to 0.1 to 0.2 MPa and then venting to 0.02 to 0.05 MPa. This hydrogen purge was repeated 5 times, whereupon the hydrogen pressure was increased to 0.1 to 0.25 MPa. The reaction mixture was stirred at 20° C. to 30° C., and every 2 to 3 hours, the mixture was purged with nitrogen three times, and then purged with hydrogen five times; after each final hydrogen exchange, the hydrogen pressure was increased to 0.1 to 0.25 MPa. After 11.25 hours total reaction time, the reaction mixture was vented to normal pressure, and purged five times with nitrogen, via increasing the pressure to 0.15 to 0.2 MPa and then venting to 0.05 MPa. It was then filtered, and the filter cake was rinsed twice with tetrahydrofuran (64 kg and 63 kg); the combined rinse and filtrate were concentrated under reduced pressure (≤−0.08 MPa) and ≤40° C. to a volume of 128 to 160 L. Tetrahydrofuran (169 kg) was added, and the mixture was again concentrated to a volume of 128 to 160 L; this process was repeated a total of 4 times, affording a solution of the intermediate methyl 4-amino-3-{[(2S)-oxetan-2-ylmethyl]amino}benzoate.

Tetrahydrofuran (150 kg) was added to this solution, followed by 2-chloro-1,1,1-trimethoxyethane (35.1 kg, 227 mol) and p-toluenesulfonic acid monohydrate (1.8 kg, 9.5 mol). After the reaction mixture had been stirred for 25 minutes, it was heated at 40° C. to 45° C. for 5 hours, whereupon it was concentrated under reduced pressure to a volume of 135 to 181 L. 2-Propanol (142 kg) was added, and the mixture was again concentrated to a volume of 135 to 181 L, whereupon 2-propanol (36.5 kg) and purified water (90 kg) were added, and stirring was continued until a solution was obtained. This was filtered with an in-line liquid filter, and then treated with purified water (447 kg) at a reference rate of 150 to 400 kg/hour at 20° C. to 40° C. After the mixture had been cooled to 20° C. to 30° C., it was stirred for 2 hours, and the solid was collected via filtration with a centrifuge. The filter cake was rinsed with a solution of 2-propanol (20.5 kg) and purified water (154 kg); after drying, P15 was obtained as a white solid (32.1 kg, 109 mol, 57%). $^{1}$H NMR (400 MHz, chloroform-d) δ 8.14-8.11 (m, 1H), 8.01 (dd, J=8.5, 1.1 Hz, 1H), 7.79 (br d, J=8.6 Hz, 1H), 5.26-5.18 (m, 1H), 5.04 (s, 2H), 4.66-4.58 (m, 2H), 4.53 (dd, component of ABX pattern, J=15.7, 2.7 Hz, 1H), 4.34 (dt, J=9.1, 6.0 Hz, 1H), 3.96 (s, 3H), 2.82-2.71 (m, 1H), 2.48-2.37 (m, 1H).

Preparation P16

Methyl 2-(chloromethyl)-1-methyl-1H-benzimidazole-6-carboxylate (P16)

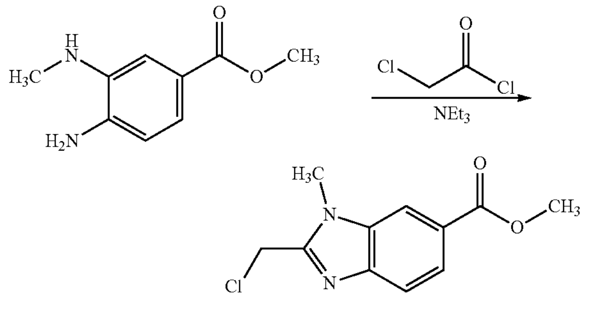

P16

Methyl 4-amino-3-(methylamino)benzoate (206 mg, 1.14 mmol) was dissolved in 1,4-dioxane (11.5 mL) and treated with chloroacetyl chloride (109 μL, 1.37 mmol). The mixture was stirred at 100° C. for 3 hours and cooled to room temperature. Triethylamine (0.8 mL, 7 mmol) and heptane (10 mL) were added and filtered. The filtrate was concentrated under reduced pressure and the crude material was purified by chromatography on silica gel (Eluent: 40% ethyl acetate in heptane) to afford 120 mg of P16 (44%). $^{1}$H NMR (400 MHz, chloroform-d) δ 8.14 (s, 1H), 8.01 (d, 1H), 7.78 (d, 1H), 4.87 (s, 2H), 3.97 (s, 3H), 3.94 (s, 3H); LCMS m/z 239.1 $[M+H]^{+}$.

Preparations P17 and P18

Methyl 2-(6-azaspiro[2.5]oct-1-yl)-1-(2-methoxyethyl)-1H-benzimidazole-6-carboxylate, ENT-1 (P17) and Methyl 2-(6-azaspiro[2.5]oct-1-yl)-1-(2-methoxyethyl)-1H-benzimidazole-6-carboxylate, ENT-2 (P18)

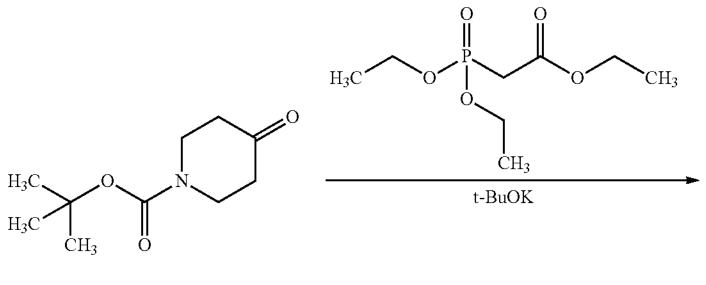

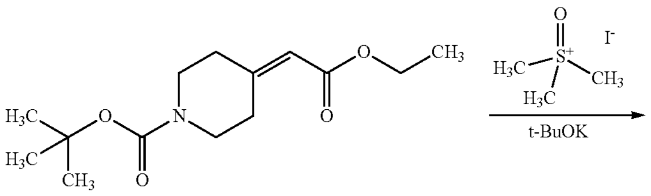

C31

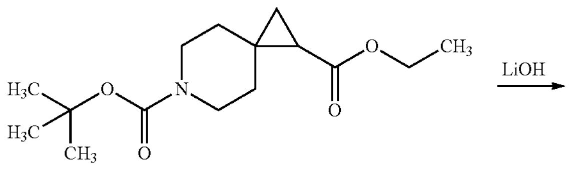

C32

-continued
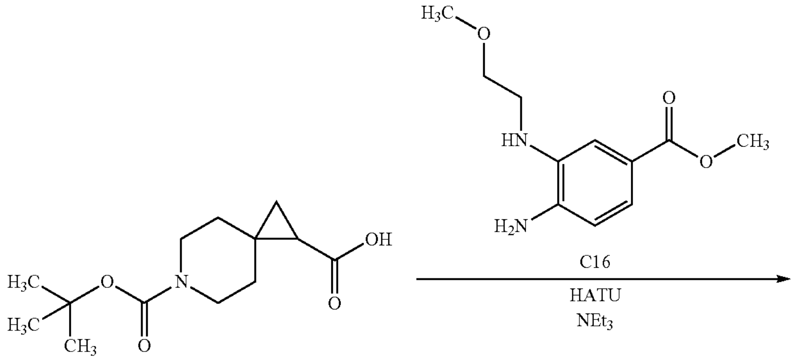
C16
C33
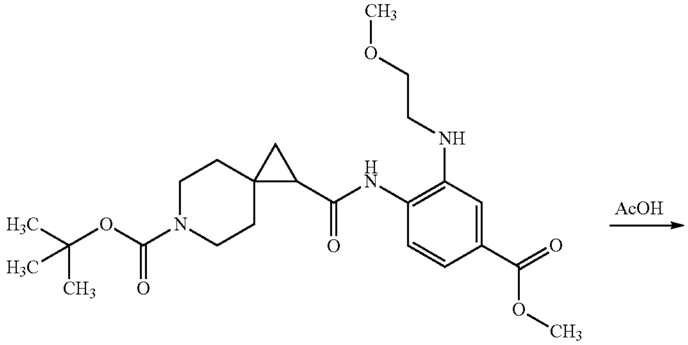
C34
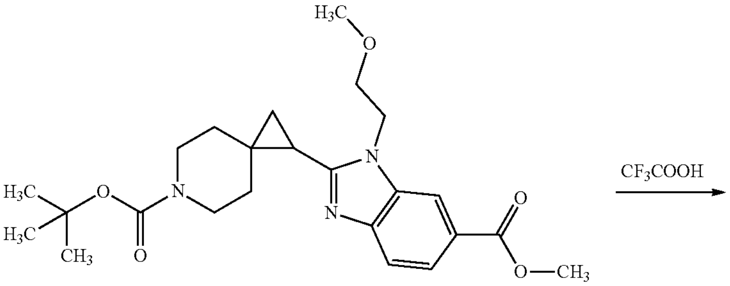
C35
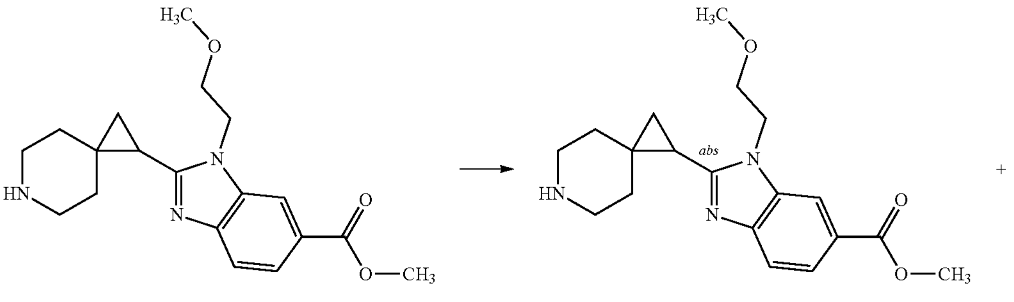
C36
ENT-1
P17

-continued

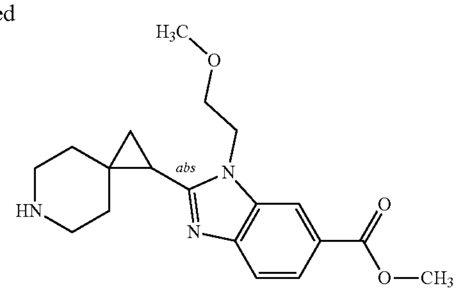

ENT-2
P18

Step 1. Synthesis of tert-butyl 4-(2-ethoxy-2-oxo-ethylidene)piperidine-1-carboxylate (C31)

A solution of potassium tert-butoxide (65.9 g, 587 mmol) in tetrahydrofuran (500 mL) was added to a 0° C. solution of ethyl (diethoxyphosphoryl)acetate (132 g, 589 mmol) in tetrahydrofuran (500 mL), and the resulting suspension was stirred at 0° C. for 1 hour, whereupon it was cooled to −50° C. A solution of tert-butyl 4-oxopiperidine-1-carboxylate (90.0 g, 452 mmol) in tetrahydrofuran (1.5 L) was added drop-wise at −50° C., and the reaction mixture was subsequently allowed to slowly warm to 20° C., and then to stir for 16 hours at 20° C. After addition of water (1 L), the mixture was concentrated in vacuo to remove tetrahydrofuran. The aqueous residue was extracted with ethyl acetate (2×800 mL), and the combined organic layers were washed with saturated aqueous sodium chloride solution (500 mL), dried over sodium sulfate, filtered, and concentrated under reduced pressure. The resulting material was washed several times with petroleum ether (200 mL) to provide C31 as a white solid. Yield: 95.0 g, 353 mmol, 78%. $^1$H NMR (400 MHz, chloroform-d) δ 5.71 (s, 1H), 4.16 (q, J=7.2 Hz, 2H), 3.55-3.43 (m, 4H), 2.94 (br t, J=5.5 Hz, 2H), 2.28 (br t, J=5.5 Hz, 2H), 1.47 (s, 9H), 1.28 (t, J=7.0 Hz, 3H).

Step 2. Synthesis of 6-tert-butyl 1-ethyl 6-azaspiro[2.5]octane-1,6-dicarboxylate (C32)

To a solution of trimethylsulfoxonium iodide (140 g, 636 mmol) in dimethyl sulfoxide (800 mL) was added potassium tert-butoxide (71.2 g, 634 mmol) in one portion at 20° C. After the reaction mixture had been stirred at 20° C. for 1.5 hours, a solution of C31 (95.0 g, 353 mmol) in dimethyl sulfoxide (800 mL) was added drop-wise, and stirring was continued at 20° C. for 16 hours. Saturated aqueous sodium chloride solution (2.0 L) was then added; the resulting mixture was neutralized by addition of ammonium chloride, and extracted with ethyl acetate (3.0 L). The combined organic layers were washed sequentially with water (2×1.0 L) and with saturated aqueous sodium chloride solution (2.0 L), dried over sodium sulfate, filtered, and concentrated in vacuo. Purification via silica gel chromatography (Eluent: 10:1 petroleum ether/ethyl acetate) afforded C32 as a yellow oil. $^1$H NMR analysis indicated that extraneous aliphatic material was present. Yield: 80 g, 280 mmol, 79%. $^1$H NMR (400 MHz, chloroform-d), C32 peaks only: δ 4.19-4.09 (m, 2H), 3.55-3.39 (m, 3H), 3.27 (ddd, J=13.0, 7.0, 4.5 Hz, 1H), 1.76-1.64 (m, 2H), 1.56 (dd, J=8.0, 5.5 Hz, 1H, assumed; partially obscured by water peak), 1.47 (s, 9H), 1.47-1.37 (m, 2H), 1.27 (t, J=7.0 Hz, 3H), 1.17 (dd, J=5.0, 5.0 Hz, 1H), 0.93 (dd, J=8.0, 4.5 Hz, 1H).

Step 3. Synthesis of 6-(tert-butoxycarbonyl)-6-azaspiro[2.5]octane-1-carboxylic acid (C33)

To a mixture of C32 (80 g, 280 mmol) in tetrahydrofuran (500 mL) and water (500 mL) was added lithium hydroxide monohydrate (37.4 g, 891 mmol) in one portion. The reaction mixture was stirred at 25° C. for 16 hours, whereupon it was diluted with water (600 mL) and washed with ethyl acetate (3×300 mL). The organic layers were discarded, and the aqueous layer was acidified to pH 3 to 4 by addition of 6 M hydrochloric acid. The resulting mixture was extracted with ethyl acetate (3×600 mL), and the combined organic layers were dried over sodium sulfate, filtered, and concentrated in vacuo. Trituration of the residue with petroleum ether (300 mL) provided C33 as a white solid. Yield: 42.0 g, 164 mmol, 59%. LCMS m/z 278.2 [M+Na$^+$]. $^1$H NMR (400 MHz, DMSO-$d_6$) δ 12.15-12.03 (br s, 1H), 3.43-3.25 (m, 3H, assumed; partially obscured by water peak), 3.23-3.12 (m, 1H), 1.64-1.50 (m, 2H), 1.52 (dd, J=7.5, 5.5 Hz, 1H), 1.39 (s, 9H), 1.39-1.28 (m, 2H), 0.96-0.88 (m, 2H).

Step 4. Synthesis of tert-butyl 1-({4-(methoxycarbonyl)-2-[(2-methoxyethyl)amino]phenyl}carbamoyl)-6-azaspiro[2.5]octane-6-carboxylate (C34)

A solution of C33 (570 mg, 2.23 mmol), C16 (500 mg, 2.23 mmol), and O-(7-azabenzotriazol-1-yl)-N,N,N',N'-tetramethyluronium hexafluorophosphate (HATU; 1.27 g, 3.34 mmol) in N,N-dimethylformamide (10 mL) was stirred at 30° C. for 30 minutes, whereupon triethylamine (902 mg, 8.91 mmol) was added, and stirring was continued at 30° C. for 16 hours. The reaction mixture was then poured into water (60 mL) and extracted with ethyl acetate (3×50 mL). The combined organic layers were washed with saturated aqueous sodium chloride solution (3×50 mL), dried over sodium sulfate, filtered, and concentrated in vacuo. Silica gel chromatography (Eluent: 1:1 petroleum ether/ethyl acetate) afforded C34 as a brown oil, which was taken directly into the following step.

Step 5. Synthesis of methyl 2-[6-(tert-butoxycarbonyl)-6-azaspiro[2.5]oct-1-yl]-1-(2-methoxyethyl)-1H-benzimidazole-6-carboxylate (C35)

A solution of C34 (from the previous step, ≤2.23 mmol) in acetic acid (15 mL) was stirred at 50° C. for 16 hours, whereupon it was concentrated in vacuo to provide C35 as a brown oil. This material was used directly in the next step. LCMS m/z 444.1 [M+H]$^+$.

Step 6. Synthesis of methyl 2-(6-azaspiro[2.5]oct-1-yl)-1-(2-methoxyethyl)-1H-benzimidazole-6-carboxylate (C36)

Trifluoroacetic acid (5 mL) was added to a solution of C35 (from the previous step; 2.23 mmol) in dichloromethane (10 mL), and the reaction mixture was stirred at 25° C. for 2 hours. After removal of solvents in vacuo, the residue was basified via addition of saturated aqueous potassium carbonate solution (40 mL), and extracted with a mixture of dichloromethane and methanol (10:1, 3×40 mL). The combined organic layers were dried over magnesium sulfate, filtered, concentrated in vacuo, and subjected to silica gel chromatography (Eluent: 10:1:0.1 dichloromethane/methanol/concentrated ammonium hydroxide) to afford C36 as a yellow solid. Yield: 640 mg, 1.86 mmol, 83% over three steps. LCMS m/z 344.1 $[M+H]^+$.

Step 7. Isolation of methyl 2-(6-azaspiro[2.5]oct-1-yl)-1-(2-methoxyethyl)-1H-benzimidazole-6-carboxylate, ENT-1 (P17) and methyl 2-(6-azaspiro[2.5]oct-1-yl)-1-(2-methoxyethyl)-1H-benzimidazole-6-carboxylate, ENT-2 (P18)

Separation of C36 (630 mg, 1.83 mmol) into its component enantiomers was carried out using SFC [Column: Chiral Technologies Chiralpak AD, 10 μm; Mobile phase: 55:45 carbon dioxide/(ethanol containing 0.1% ammonium hydroxide)]. The first-eluting peak was designated as ENT-1 (P17), and the second-eluting enantiomer as ENT-2 (P18); both were isolated as pale yellow solids.

P17 Yield: 300 mg, 0.874 mmol, 48%. LCMS m/z 344.1 $[M+H]^+$. Retention time: 5.10 minutes (Column: Chiral Technologies Chiralpak AD-3, 4.6×150 mm, 3 μm; Mobile phase A: carbon dioxide; Mobile phase B: ethanol containing 0.05% diethylamine; Gradient: 5% to 40% B over 5.5 minutes, then held at 40% B for 3.0 minutes; Flow rate: 2.5 mL/minute).

P18 Yield: 240 mg, 0.699 mmol, 38%. LCMS m/z 344.1 $[M+H]^+$. Retention time: 7.35 minutes (Analytical conditions identical to those used for P17).

Preparation P19

Methyl 4-amino-3-{[(1-ethyl-1H-imidazol-5-yl)methyl]amino}benzoate (P19)

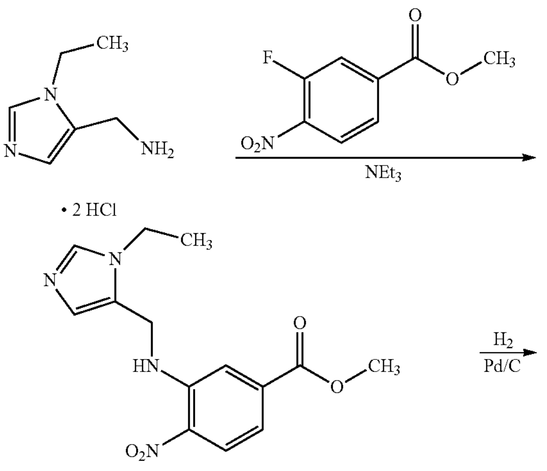

C37

-continued

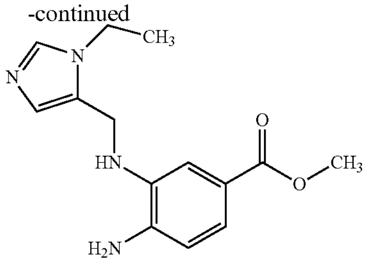

P19

Step 1. Synthesis of methyl 3-{[(1-ethyl-1H-imidazol-5-yl)methyl]amino}-4-nitrobenzoate (C37)

Triethylamine (3.65 mL, 26.2 mmol) was added to a solution of methyl 3-fluoro-4-nitrobenzoate (1.00 g, 5.02 mmol) and 1-(1-ethyl-1H-imidazol-5-yl)methanamine, dihydrochloride salt (1.00 g, 5.05 mmol) in a mixture of tetrahydrofuran (12 mL) and methanol (8 mL). The reaction mixture was stirred at 60° C. for 40 hours, whereupon it was concentrated in vacuo and purified using silica gel chromatography (Gradient: 0% to 2% methanol in dichloromethane) to afford C37 as an orange solid. Yield: 1.27 g, 4.17 mmol, 83%. $^1H$ NMR (400 MHz, chloroform-d) δ 8.24 (d, J=8.8 Hz, 1H), 7.98-7.91 (m, 1H), 7.68 (d, J=1.7 Hz, 1H), 7.57 (br s, 1H), 7.33 (dd, J=8.8, 1.7 Hz, 1H), 7.11 (br s, 1H), 4.53 (d, J=4.9 Hz, 2H), 3.99 (q, J=7.3 Hz, 2H), 3.95 (s, 3H), 1.47 (t, J=7.3 Hz, 3H).

Step 2. Synthesis of methyl 4-amino-3-{[(1-ethyl-1H-imidazol-5-yl)methyl]amino}benzoate (P19)

A mixture of wet palladium on carbon (144 mg) and C37 (412 mg, 1.35 mmol) in methanol (13 mL) was stirred under a balloon of hydrogen for 16 hours at 25° C. The reaction mixture was then filtered through a pad of diatomaceous earth and the filtrate was concentrated in vacuo to afford P19 as a gray solid. Yield: 340 mg, 1.24 mmol, 92%. $^1H$ NMR (400 MHz, methanol-$d_4$) δ 7.66 (br s, 1H), 7.38-7.29 (m, 2H), 6.97 (br s, 1H), 6.67 (d, J=7.9 Hz, 1H), 4.35 (s, 2H), 4.11 (q, J=7.3 Hz, 2H), 3.81 (s, 3H), 1.44 (t, J=7.3 Hz, 3H).

Preparation P20

Methyl 4-amino-3-(methylamino)benzoate (P20)

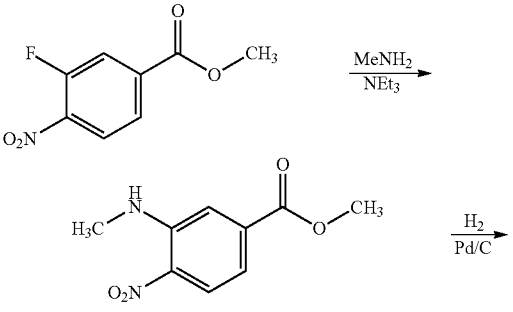

D1

-continued

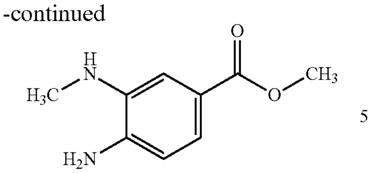

P20

Step 1. Synthesis of methyl 3-(methylamino)-4-nitrobenzoate (D1)

To a solution of methyl 3-fluoro-4-nitrobenzoate (5.10 g, 25.6 mmol) in tetrahydrofuran (60 mL) was added methylamine (38.4 mL, 76.8 mmol, 2 M in tetrahydrofuran), drop-wise, over 10 minutes. The pale yellow solution turned deep orange immediately upon addition and was stirred for 2 hours at room temperature. The reaction mixture was then diluted with diethyl ether (100 mL) and the organic layer was washed sequentially with water (50 mL) and saturated aqueous sodium chloride solution (50 mL). The organic layer was dried over sodium sulfate, filtered, and concentrated under reduced pressure to yield 5.26 g of methyl 3-(methylamino)-4-nitrobenzoate (98%) as a deep orange solid. LCMS m/z 211.1 $[M+H]^+$. $^1H$ NMR (400 MHz, chloroform-d) δ 8.22 (d, J=8.9 Hz, 1H), 8.00 (br s, 1H), 7.56 (d, J=1.7 Hz, 1H), 7.25 (dd, J=8.9, 1.7 Hz, 1H, assumed; partially obscured by solvent peak), 3.95 (s, 3H), 3.09 (d, J=5.1 Hz, 3H).

Step 2. Synthesis of methyl 4-amino-3-(methylamino)benzoate (P20)

A solution of D1 (5.26 g, 25.0 mmol) in ethanol (150 mL) was added to a 500 mL Parr® bottle previously charged with 10% palladium on carbon (50% water; 1 g). The mixture was shaken under 50 psi hydrogen atmosphere for 1 hour at room temperature, whereupon it was filtered and the filter cake was rinsed with ethanol (100 mL). The filtrate was concentrated under reduced pressure to yield 4.38 g of P20 (97%) as an off-white solid. LCMS m/z 181.1 $[M+H]^+$. $^1H$ NMR (400 MHz, chloroform-d) δ 7.46 (dd, J=8.0, 1.9 Hz, 1H), 7.34 (d, J=1.8 Hz, 1H), 6.68 (d, J=8.0 Hz, 1H), 3.87 (s, 3H), 3.72 (br s, 2H), 3.21 (br s, 1H), 2.91 (s, 3H).

Preparations P21 and P22

5-Bromo-$N^3$-methylpyridine-2, 3-diamine (P21) and

5-Bromo-$N^3$,6-dimethylpyridine-2,3-diamine (P22)

P21

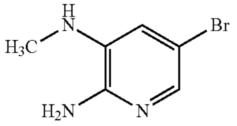

P22

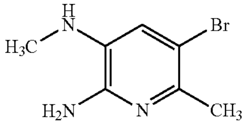

Intermediate P21 was synthesized according to the literature procedure (Choi, J. Y. et al. *J. Med. Chem.* 2012, 55, 852-870). Intermediate P22 was synthesized using the same method.

Preparation P23

Methyl 2-(chloromethyl)-1-[(1-methyl-1H-imidazol-5-yl)methyl]-1H-benzimidazole-6-carboxylate (P23)

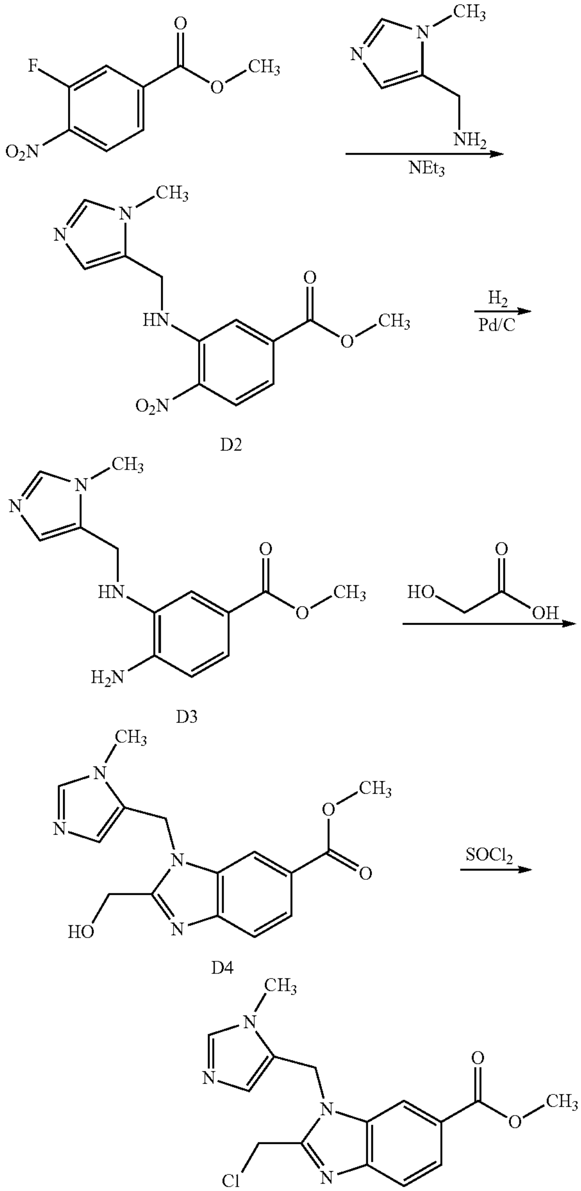

D2

D3

D4

P23

Step 1. Synthesis of methyl 3-{[(1-methyl-1H-imidazol-5-yl)methyl]amino}-4-nitrobenzoate (D2)

To a colorless solution of methyl 3-fluoro-4-nitrobenzoate (1.0 g, 5.0 mmol) in N,N-dimethylformamide (10 mL) was slowly added 1-(1-methyl-1H-imidazol-5-yl)methanamine (670 mg, 6.0 mmol) and triethylamine (762 mg, 7.53 mmol). The reaction mixture was stirred at 60° C. for 16 hours, whereupon it was poured into water (30 mL) and extracted with dichloromethane (3×30 mL). The combined organic layers were dried over sodium sulfate, filtered, and concentrated under reduced pressure. The crude material was purified by silica gel chromatography (Eluent: 20% methanol in dichloromethane). The obtained yellow solid was triturated with 30:1 petroleum ether/ethyl acetate to deliver D2 (1.2 g, 82%) as a yellow solid. LCMS m/z 290.9 $[M+H]^+$. $^1H$ NMR (400 MHz, chloroform-d) δ 8.25 (d, J=8.9 Hz, 1H), 7.98-7.92 (m, 1H), 7.70 (d, J=1.7 Hz, 1H), 7.49 (s, 1H), 7.34 (dd, J=8.9, 1.7 Hz, 1H), 7.12 (s, 1H), 4.54 (d, J=5.0 Hz, 2H), 3.96 (s, 3H), 3.67 (s, 3H).

Step 2. Synthesis of methyl 4-amino-3-{[(1-methyl-1H-imidazol-5-yl)methyl]amino}benzoate (D3)

To a suspension of D2 (5.46 g, 18.8 mmol) in methanol (160 mL) was added wet 10% palladium on carbon (1 g). The mixture was stirred under 1 atmosphere of hydrogen for 36 hours at 20° C. The reaction mixture was filtered and the filter cake was rinsed with methanol (200 mL). The filtrate was concentrated under reduced pressure to deliver D3 (4.8 g, 98%) as a brown solid. LCMS m/z 260.9 $[M+H]^+$. $^1H$ NMR (400 MHz, DMSO-$d_6$) δ 7.56 (s, 1H), 7.18 (br d, J=8.1 Hz, 1H), 7.12 (br s, 1H), 6.87 (s, 1H), 6.55 (d, J=8.2 Hz, 1H), 5.50 (s, 2H), 4.84 (t, J=5.2 Hz, 1H), 4.23 (d, J=5.0 Hz, 2H), 3.73 (s, 3H), 3.63 (s, 3H).

Step 3. Synthesis of methyl 2-(hydroxymethyl)-1-[(1-methyl-1H-imidazol-5-yl)methyl]-1H-benzimidazole-6-carboxylate (D4)

A mixture of D3 (780 mg, 3.00 mmol) and 2-hydroxyacetic acid (342 mg, 4.49 mmol) in 1,3,5-trimethylbenzene (8 mL) was stirred at 140° C. for 14 hours and at 25° C. for 48 hours. The clear yellow solution was decanted off to give a brown residue that was dissolved in methanol (50 mL) and concentrated under reduced pressure. The crude material was purified by silica gel chromatography (Eluent: 20% methanol in dichloromethane) to provide D4 (318 mg, 35%) as a yellow foam. LCMS m/z 300.9 $[M+H]^+$. $^1H$ NMR (400 MHz, DMSO-$d_6$) δ 8.13-8.11 (m, 1H), 7.83 (dd, J=8.4, 1.6 Hz, 1H), 7.71 (d, J=8.5 Hz, 1H), 7.59 (s, 1H), 6.58 (s, 1H), 5.69 (s, 2H), 4.75 (s, 2H), 3.84 (s, 3H), 3.53 (s, 3H).

Step 4. Synthesis of methyl 2-(chloromethyl)-1-[(1-methyl-1H-imidazol-5-yl)methyl]-1H-benzimidazole-6-carboxylate (P23)

To a suspension of D4 (500 mg, 1.66 mmol) in dichloromethane (10 mL) and N,N-dimethylformamide (3 mL) was added thionyl chloride (990 mg, 0.60 mL, 8.32 mmol), drop-wise, at room temperature. The reaction mixture was stirred at room temperature for 1 hour, then concentrated under reduced pressure. The resultant brown residue was triturated with dichloromethane (10 mL). The solids were collected by filtration and rinsed with dichloromethane (5 mL) to provide P23 (431 mg, 73%) as an off-white solid. LCMS m/z 318.9♦ $[M+H]^+$. $^1H$ NMR (400 MHz, DMSO-$d_6$) δ 9.17 (s, 1H), 8.31 (s, 1H), 7.93 (br d, J=8.5 Hz, 1H), 7.82 (d, J=8.5 Hz, 1H), 7.11 (s, 1H), 5.92 (s, 2H), 5.13 (s, 2H), 3.87 (s, 3H), 3.87 (s, 3H).

Preparation P24

5-Chloro-2-(chloromethyl)-3-methyl-3H-imidazo[4,5-b]pyridine (P24)

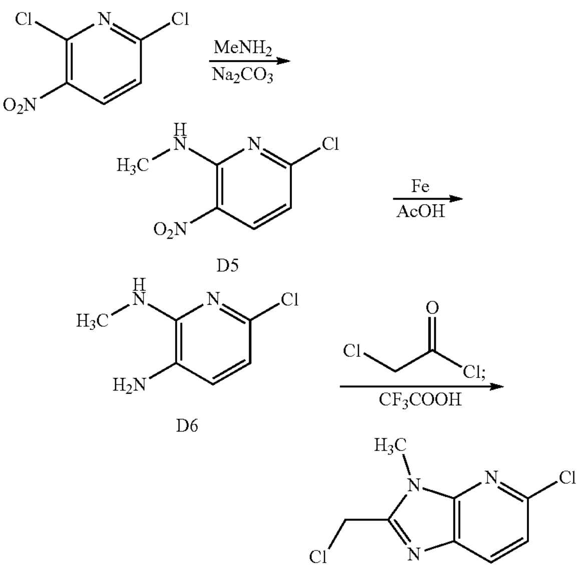

D5

D6

P24

Step 1. Synthesis of 6-chloro-N-methyl-3-nitropyridin-2-amine (D5)

To a suspension of 2,6-dichloro-3-nitropyridine (200 g, 1.04 mol) and $Na_2CO_3$ (132 g, 1.24 mol) in ethanol (1 L) was added a solution of methylamine in tetrahydrofuran (2.0 M; 622 mL, 1.24 mol), drop-wise, at 0° C. via syringe. After completion of the addition, the reaction mixture was stirred at 18° C. for 6 hours. The mixture was filtered and the filtrate was concentrated under reduced pressure to give a yellow solid. The crude material was purified by silica gel chromatography (Gradient: 0% to 5% ethyl acetate in petroleum ether) to afford D5 (158 g, 81% yield) as a yellow solid. $^1H$ NMR (400 MHz, DMSO-$d_6$) δ 8.72 (br s, 1H), 8.41 (d, J=8.6 Hz, 1H), 6.76 (d, J=8.6 Hz, 1H), 3.00 (d, J=4.8 Hz, 3H).

Step 2. Synthesis of 6-chloro-$N^2$-methylpyridine-2,3-diamine (D6)

To a mixture of D5 (15.8 g, 84.2 mmol) in acetic acid (100 mL) was added iron powder (15.4 g, 276 mmol). The reaction mixture was stirred at 80° C. for 3 hours, whereupon it was cooled to room temperature and filtered. The filter cake was washed with ethyl acetate (2×100). The combined organic layers were concentrated under reduced pressure and the crude material was purified by silica gel chromatography (Eluent: 1:1 ethyl acetate/petroleum ether) to afford D6 (8.40 g, 63% yield) as a brown solid. $^1H$ NMR (400 MHz, chloroform-d) δ 6.79 (d, J=7.7 Hz, 1H), 6.49 (d, J=7.7 Hz, 1H), 3.00 (s, 3H).

Step 3. Synthesis of 5-chloro-2-(chloromethyl)-3-methyl-3H-imidazo[4,5-b]pyridine (P24)

To a solution of D6 (50.0 g, 317 mmol) in 1,4-dioxane (1.2 L) was added chloroacetyl chloride (55.5 mL, 698 mmol) and the reaction mixture was stirred at 15° C. for 50 minutes. It was then concentrated under reduced pressure to give a brown solid, which was taken up in trifluoroacetic acid (1.2 L) and stirred at 80° C. for 60 hours. The mixture was concentrated under reduced pressure to give a brown oil, which was diluted with ethyl acetate (1 L) and neutralized by addition of saturated aqueous sodium bicarbonate solution. When carbon dioxide evolution subsided, the layers were separated, and the aqueous layer was extracted with ethyl acetate (200 mL). The organic extracts were combined, dried over sodium sulfate, filtered, and concentrated under reduced pressure. The crude material was purified by silica gel chromatography (Gradient: 10% to 25% ethyl acetate in petroleum ether) to afford P24 (61.0 g, 79% yield) as a yellow solid. LCMS m/z 215.7 (dichloro isotope pattern observed) $[M+H]^+$. $^1H$ NMR (400 MHz, DMSO-$d_6$) δ 8.13 (d, J=8.3 Hz, 1H), 7.37 (d, J=8.4 Hz, 1H), 5.11 (s, 2H), 3.84 (s, 3H).

Examples 1 and 2

2-({4-[2-(4-Chloro-2-fluorophenyl)-1,3-benzodioxol-4-yl]piperazin-1-yl}methyl)-1-(2-methoxyethyl)-1H-benzimidazole-6-carboxylic acid, ENT-X1, trifluoroacetate Salt (1) [from C39]; and 2-({4-[2-(4-Chloro-2-fluorophenyl)-1,3-benzodioxol-4-yl]piperazin-1-yl}methyl)-1-(2-methoxyethyl)-1H-benzimidazole-6-carboxylic acid, ENT-X2, trifluoroacetate Salt (2) [from C40]

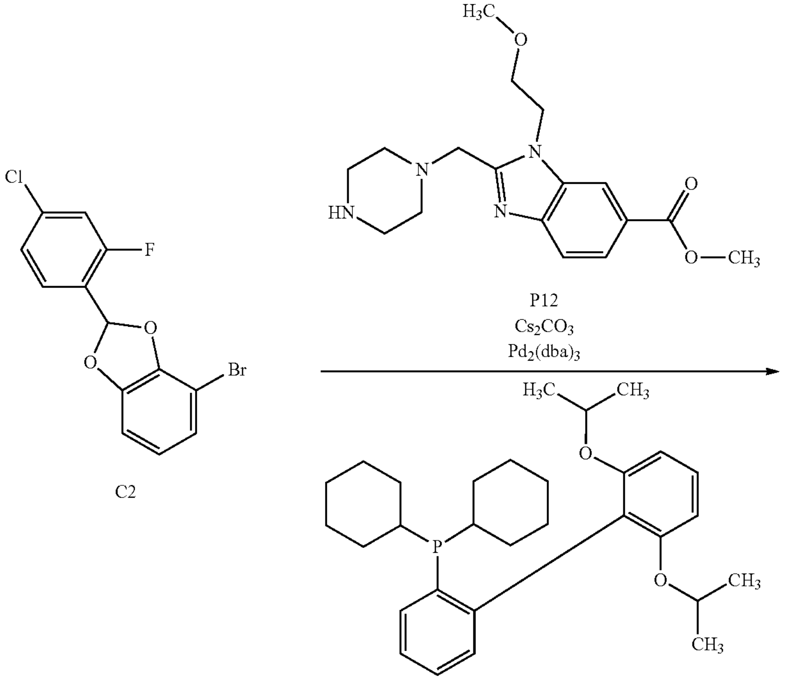

C2

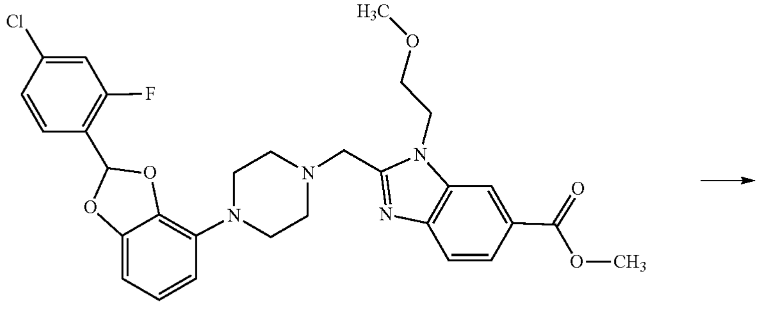

C38

-continued
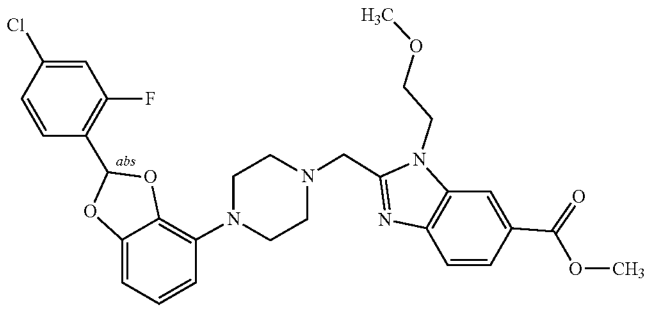
ENT-1
C39
+
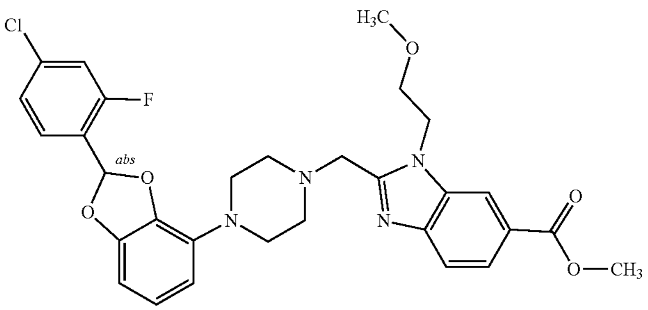
ENT-2
C40
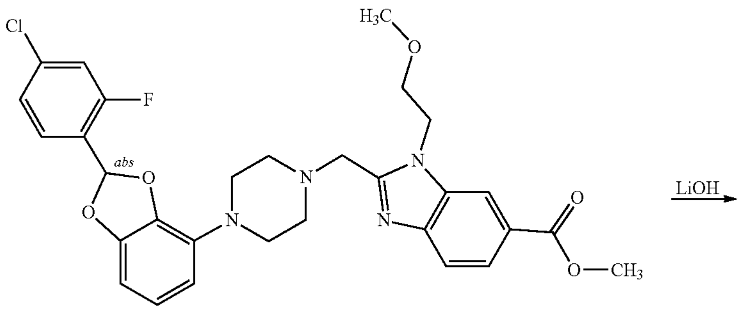
ENT-1
C39
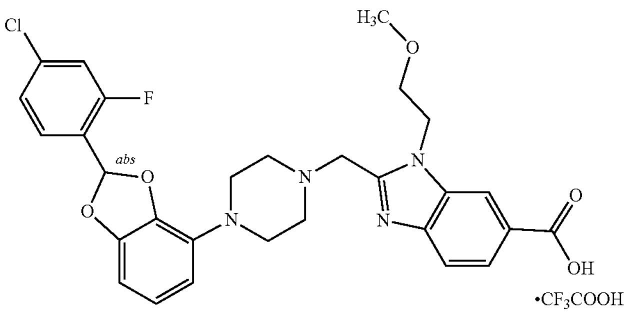
ENT-X1
1

-continued

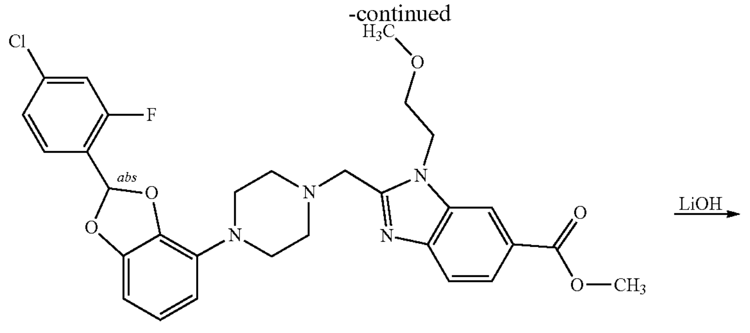

ENT-2
C40

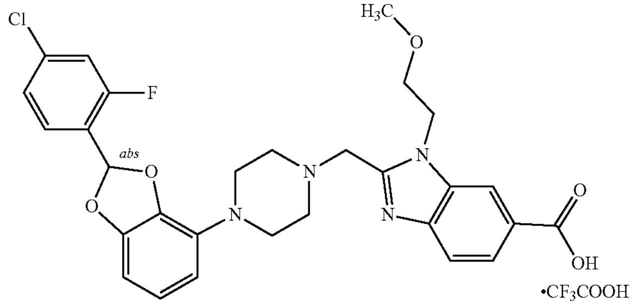

ENT-X2
2

Step 1. Synthesis of methyl 2-({4-[2-(4-chloro-2-fluorophenyl)-1,3-benzodioxol-4-yl]piperazin-1-yl}methyl)-1-(2-methoxyethyl)-1H-benzimidazole-6-carboxylate (C38)

This experiment was carried out in two batches of identical scale. A reaction vessel containing a mixture of C2 (500 mg, 1.52 mmol), P12 (530 mg, 1.59 mmol), [2',6'-bis(propan-2-yloxy)biphenyl-2-yl](dicyclohexyl)phosphane (Ruphos; 142 mg, 0.304 mmol), tris(dibenzylideneacetone)dipalladium(0) (139 mg, 0.152 mmol), and cesium carbonate (1.48 g, 4.54 mmol) in toluene (15 mL) was evacuated and charged with nitrogen. This evacuation cycle was repeated twice, whereupon the reaction mixture was stirred at 100° C. for 16 hours, combined with the second batch, and filtered. The filtrate was concentrated, and the residue was subjected to silica gel chromatography (Gradient: 0% to 60% ethyl acetate in petroleum ether) followed by preparative thin-layer chromatography (Eluent: 1:1 petroleum ether/ethyl acetate) to afford C38 as a pale yellow solid. Combined yield: 600 mg, 1.03 mmol, 34%. LCMS m/z 581.0♦ $[M+H]^+$.

Step 2. Isolation of methyl 2-({4-[2-(4-chloro-2-fluorophenyl)-1,3-benzodioxol-4-yl]piperazin-1-yl}methyl)-1-(2-methoxyethyl)-1H-benzimidazole-6-carboxylate, ENT-1 (C39) and methyl 2-({4-[2-(4-chloro-2-fluorophenyl)-1,3-benzodioxol-4-yl]piperazin-1-yl}methyl)-1-(2-methoxyethyl)-1H-benzimidazole-6-carboxylate, ENT-2 (C40)

Separation of C38 (780 mg, 1.34 mmol) into its component enantiomers was effected using SFC [Column: Chiral Technologies Chiralpak AD, 10 μm; Mobile phase: 3:2 carbon dioxide/(ethanol containing 0.1% ammonium hydroxide)]. The first-eluting enantiomer, designated as ENT-1 (C39), was obtained as a white solid. Yield: 282 mg, 0.485 mmol, 36%. LCMS m/z 581.0♦ $[M+H]^+$. Retention time 1.90 minutes (Column: Chiral Technologies Chiralpak AD-3, 4.6×50 mm, 3 μm; Mobile phase A: carbon dioxide; Mobile phase B: ethanol containing 0.05% diethylamine; Gradient: 5% B for 0.20 minutes, then 5% to 40% B over 1.4 minutes, then held at 40% B for 1.05 minutes; Flow rate: 4.0 mL/minute).

The second-eluting enantiomer, designated as ENT-2, (C40), was subjected to a second purification using SFC [Column: Chiral Technologies Chiralpak AD, 10 μm; Mobile phase: 3:2 carbon dioxide/(ethanol containing 0.1% ammonium hydroxide)]. This provided C40 as a pale brown solid. Yield: 280 mg, 0.482 mmol, 36%. LCMS m/z 581.0♦ $[M+H]^+$. Retention time 2.18 minutes (Analytical conditions identical to those used for C39).

Step 3. Synthesis of 2-({4-[2-(4-chloro-2-fluorophenyl)-1,3-benzodioxol-4-yl]piperazin-1-yl}methyl)-1-(2-methoxyethyl)-1H-benzimidazole-6-carboxylic acid, ENT-X1, trifluoroacetate Salt (1) [from C39]

Aqueous lithium hydroxide solution (2 M; 0.30 mL, 0.60 mmol) was added to a solution of C39 (70 mg, 0.12 mmol) in a mixture of methanol (3 mL) and tetrahydrofuran (3 mL). After the reaction mixture had been stirred at 25° C. for 16 hours, aqueous lithium hydroxide solution (2 M; 0.30 mL, 0.60 mmol) was again added, and stirring was continued for an additional 20 hours. The reaction mixture was then adjusted to pH 7 via addition of 1 M hydrochloric acid, and subsequently concentrated in vacuo to remove methanol and tetrahydrofuran. The residue was adjusted to a pH of 5 to 6 by addition of trifluoroacetic acid and then purified via reversed-phase HPLC (Column: Agela Durashell C18, 5 μm;

Mobile phase A: 0.1% trifluoroacetic acid in water; Mobile phase B: acetonitrile; Gradient: 30% to 60% B) to afford 1 as a white solid. Yield: 40.5 mg, 59.5 μmol, 50%. LCMS m/z 567.0♦ $[M+H]^+$. $^1$H NMR (400 MHz, methanol-$d_4$) δ 8.37 (br s, 1H), 8.07 (dd, J=8.5, 1.5 Hz, 1H), 7.79 (d, J=8.6 Hz, 1H), 7.59 (dd, J=8.0, 8.0 Hz, 1H), 7.34 (dd, J=10.2, 2.0 Hz, 1H), 7.30 (br dd, J=8.3, 2.0 Hz, 1H), 7.22 (s, 1H), 6.87 (dd, J=8.1, 8.1 Hz, 1H), 6.63 (br d, J=8 Hz, 1H), 6.60 (br d, J=8 Hz, 1H), 4.70 (s, 2H), 4.65 (t, J=4.8 Hz, 2H), 3.75 (t, J=4.8 Hz, 2H), 3.59-3.42 (m, 8H), 3.29 (s, 3H).

Step 4. Synthesis of 2-({4-[2-(4-chloro-2-fluorophenyl)-1,3-benzodioxol-4-yl]piperazin-1-yl}methyl)-1-(2-methoxyethyl)-1H-benzimidazole-6-carboxylic acid, ENT-X2, trifluoroacetate Salt (2) [from C40]

Aqueous lithium hydroxide solution (2 M; 0.30 mL, 0.60 mmol) was added to a solution of C40 (69 mg, 0.12 mmol) in a mixture of methanol (3 mL) and tetrahydrofuran (3 mL). After the reaction mixture had been stirred at 25° C. for 16 hours, aqueous lithium hydroxide solution (2 M; 0.30 mL, 0.60 mmol) was again added, and stirring was continued for an additional 20 hours. The reaction mixture was adjusted to pH 7 via addition of 1 M hydrochloric acid, and then concentrated in vacuo to remove methanol and tetrahydrofuran. The residue was adjusted to a pH of 5 to 6 by addition of trifluoroacetic acid and subsequently purified via reversed-phase HPLC (Column: Agela Durashell C18, 5 μm; Mobile phase A: 0.1% trifluoroacetic acid in water; Mobile phase B: acetonitrile; Gradient: 30% to 60% B) to afford 2 as a white solid. Yield: 22.9 mg, 33.6 μmol, 28%. LCMS m/z 567.0♦ $[M+H]^+$. $^1$H NMR (400 MHz, methanol-$d_4$) δ 8.40-8.35 (m, 1H), 8.07 (dd, J=8.6, 1.5 Hz, 1H), 7.79 (d, J=8.6 Hz, 1H), 7.59 (dd, J=8.0, 8.0 Hz, 1H), 7.35 (dd, J=10.2, 2.0 Hz, 1H), 7.31 (br dd, J=8, 2 Hz, 1H), 7.22 (s, 1H), 6.87 (dd, J=8.3, 8.0 Hz, 1H), 6.63 (br d, J=8 Hz, 1H), 6.60 (br d, J=8 Hz, 1H), 4.68 (s, 2H), 4.65 (t, J=4.9 Hz, 2H), 3.76 (t, J=4.8 Hz, 2H), 3.57-3.40 (m, 8H), 3.29 (s, 3H).

Example 3

2-({4-[2-(4-Chloro-2-fluorophenyl)-2-methyl-1,3-benzodioxol-4-yl]piperidin-1-yl}methyl)-1-(2-methoxyethyl)-1H-imidazo[4,5-b]pyridine-6-carboxylic acid, trifluoroacetate Salt (3)

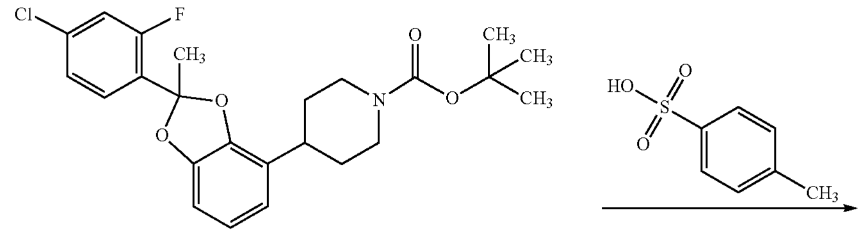

P2

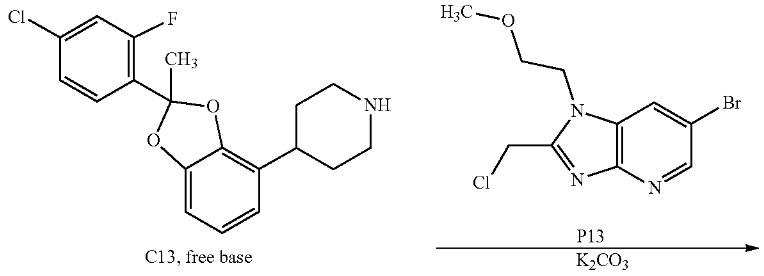

C13, free base

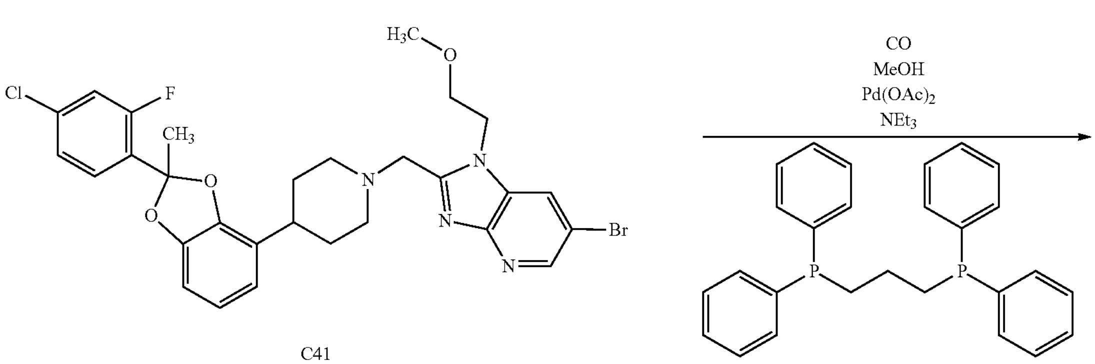

C41

-continued

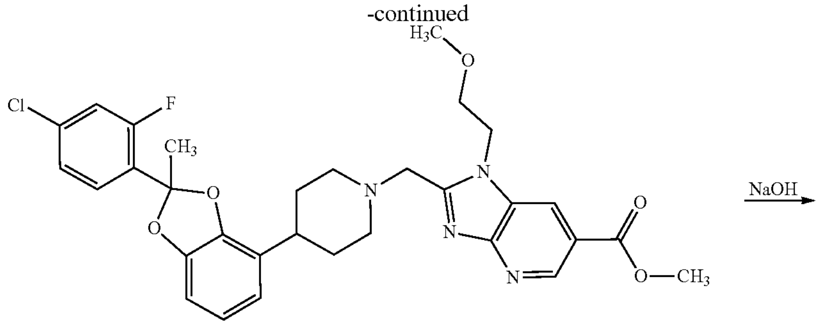

C42

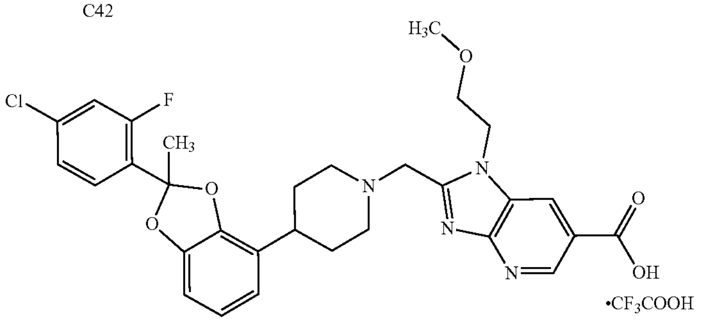

3

Step 1. Synthesis of 4-[2-(4-chloro-2-fluorophenyl)-2-methyl-1,3-benzodioxol-4-yl]piperidine (C13, Free Base)

To a solution of P2 (300 mg, 0.670 mmol) in ethyl acetate (3.5 mL) was added p-toluenesulfonic acid monohydrate (318 mg, 1.67 mmol). The reaction mixture was stirred at 60° C. for 1 hour, whereupon it was basified by addition of saturated aqueous potassium carbonate solution (20 mL) and extracted with a mixture of dichloromethane and methanol (10:1, 3×50 mL). The combined organic layers were dried over magnesium sulfate, filtered, and concentrated in vacuo to provide C13, free base, as a brown solid. Yield: 230 mg, 0.661 mmol, 99%.

Step 2. Synthesis of 6-bromo-2-({4-[2-(4-chloro-2-fluorophenyl)-2-methyl-1,3-benzodioxol-4-yl]piperidin-1-yl}methyl)-1-(2-methoxyethyl)-1H-imidazo[4,5-b]pyridine (C41)

A suspension of C13, free base (130 mg, 0.374 mmol), P13 (130 mg, 0.427 mmol), and potassium carbonate (172 mg, 1.24 mmol) in acetonitrile (2 mL) was stirred at 50° C. for 16 hours. The reaction mixture was then purified using preparative thin-layer chromatography (Eluent: ethyl acetate) to afford C41 as a brown oil. Yield: 114 mg, 0.185 mmol, 49%. LCMS m/z 617.1 (bromine-chlorine isotope pattern observed) $[M+H]^+$.

Step 3. Synthesis of methyl 2-({4-[2-(4-chloro-2-fluorophenyl)-2-methyl-1,3-benzodioxol-4-yl]piperidin-1-yl}methyl)-1-(2-methoxyethyl)-1H-imidazo[4,5-b]pyridine-6-carboxylate (C42)

A solution of C41 (114 mg, 0.185 mmol), 1,3-bis(diphenylphosphino)propane (15.3 mg, 37.1 μmol), palladium(II) acetate (8.3 mg, 37 μmol), and triethylamine (187 mg, 1.85 mmol) in a mixture of methanol (5 mL) and N,N-dimethylformamide (1 mL) was stirred at 80° C. under carbon monoxide (50 psi) for 16 hours. After the reaction mixture had been diluted with ethyl acetate (50 mL), it was washed with saturated aqueous sodium chloride solution (2×50 mL), dried over magnesium sulfate, filtered, and concentrated under reduced pressure. Purification using preparative thin-layer chromatography (Eluent: ethyl acetate) provided C42 as a colorless oil. Yield: 60.0 mg, 0.101 mmol, 55%. LCMS m/z 617.2 (chlorine isotope pattern observed $[M+Na^+]$.

Step 4. Synthesis of 2-({4-[2-(4-chloro-2-fluorophenyl)-2-methyl-1,3-benzodioxol-4-yl]piperidin-1-yl}methyl)-1-(2-methoxyethyl)-1H-imidazo[4,5-b]pyridine-6-carboxylic acid, trifluoroacetate Salt (3)

To a solution of C42 (60.0 mg, 0.101 mmol) in methanol (2.0 mL) was added aqueous sodium hydroxide solution (3 M; 1.0 mL, 3.0 mmol), and the reaction mixture was stirred at 20° C. for 2 hours. It was then adjusted to pH 7 by addition of 1 M hydrochloric acid, and extracted with a mixture of dichloromethane and methanol (10:1, 3×30 mL). The combined organic layers were dried over magnesium sulfate, filtered, concentrated in vacuo, and purified using reversed-phase HPLC (Column: Boston Green ODS, 5 μm; Mobile phase A: 0.1% trifluoroacetic acid in water; Mobile phase B: acetonitrile; Gradient: 10% to 95% B) to afford 3 as a white solid. Yield: 29.6 mg, 42.6 μmol, 42%. LCMS m/z 581.0♦ $[M-H]^+$. $^1H$ NMR (400 MHz, methanol-$d_4$) δ 9.13 (d, J=1.9 Hz, 1H), 8.74 (d, J=1.9 Hz, 1H), 7.63 (dd, J=8.3, 8.3 Hz, 1H), 7.30 (dd, J=10.9, 2.0 Hz, 1H), 7.24 (ddd, J=8.4, 2.0, 0.7 Hz, 1H), 6.89-6.84 (m, 1H), 6.82-6.77 (m, 2H), 4.98-4.89 (m, 2H, assumed; largely obscured by water peak), 4.64 (t, J=4.8 Hz, 2H), 4.04-3.92 (br m, 2H), 3.75 (dd, J=5.4, 4.2 Hz, 2H), 3.51-3.39 (m, 2H), 3.31 (s, 3H), 3.19-3.06 (m, 1H), 2.41-2.24 (m, 2H), 2.24-2.12 (m, 2H), 2.06 (d, J=1.0 Hz, 3H).

Examples 4 and 5
Ammonium 2-({4-[(2R)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylate (4) and Ammonium 2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylate (5)
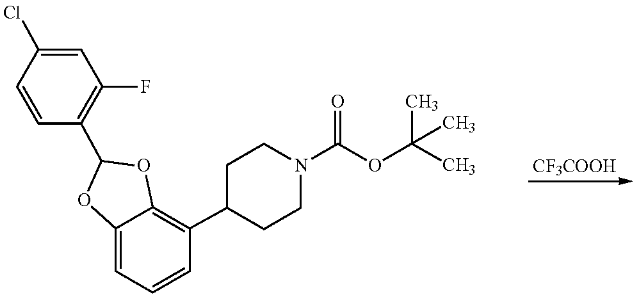
P1
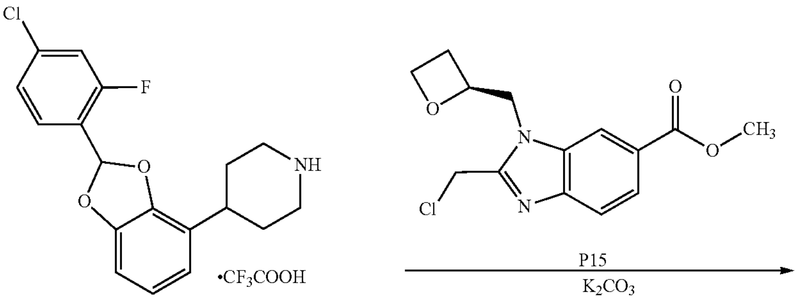
C43
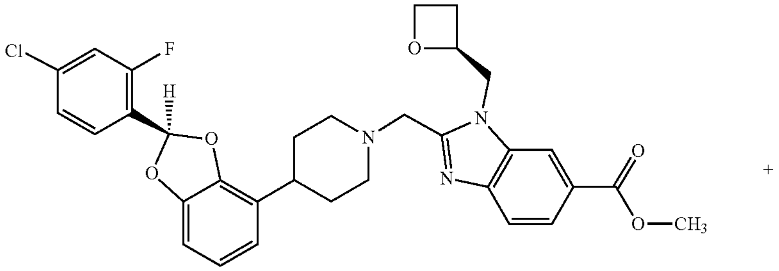
C44
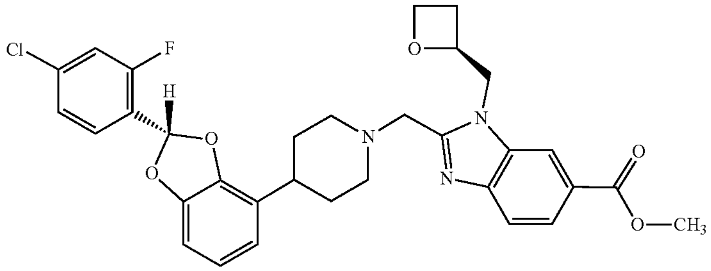
C45

-continued
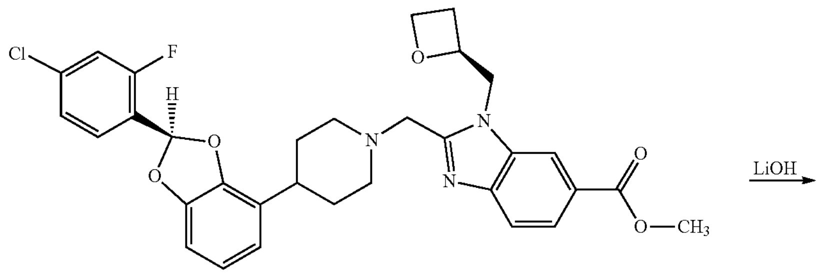
C44
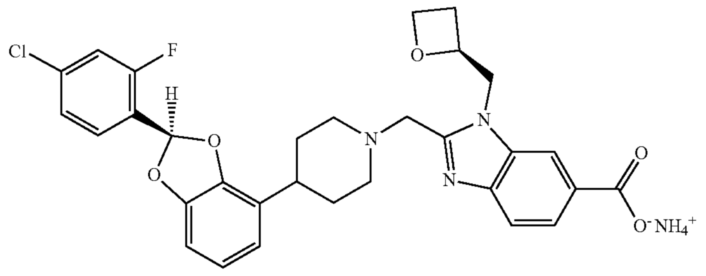
4
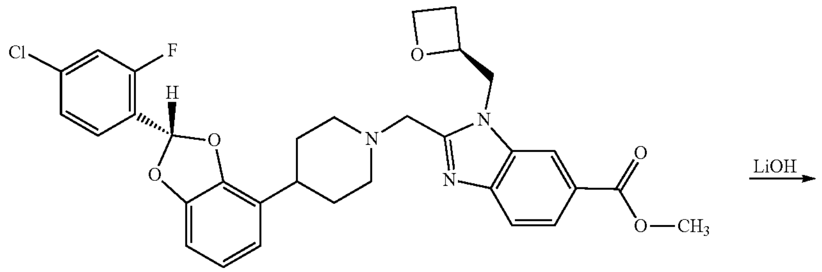
C45
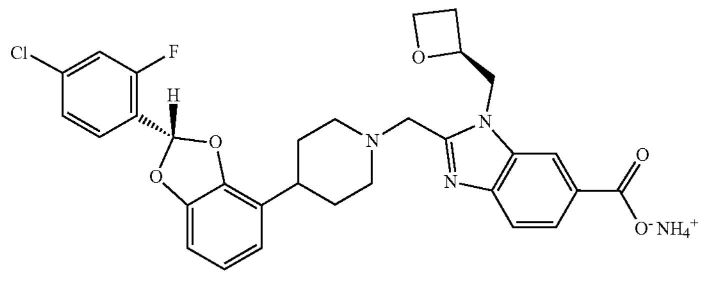
5

Step 1. Synthesis of 4-[2-(4-chloro-2-fluorophenyl)-1,3-benzodioxol-4-yl]piperidine, trifluoroacetate Salt (C43)

To a solution of P1 (300 mg, 0.691 mmol) in dichloromethane (5 mL) was added trifluoroacetic acid (1.3 mL). The reaction mixture was stirred at 29° C. for 2 hours, whereupon it was concentrated in vacuo to afford C43 as a brown oil, which was used directly in the following step.

Step 2. Synthesis of methyl 2-({4-[(2R)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylate (C44) and methyl 2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylate (C45)

To a solution of C43 (from the previous step, ≤0.691 mmol) in acetonitrile (10 mL) was added P15 (204 mg, 0.692 mmol), followed by potassium carbonate (956 mg, 6.92 mmol). The reaction mixture was stirred at 29° C. for 16 hours, whereupon it was filtered; the filtrate was concentrated in vacuo to give a residue, which was purified by preparative thin-layer chromatography (Eluent: 2:1 petroleum ether/ethyl acetate) to provide a mixture of the diastereomeric products as a yellow gum (178 mg). Separation into the two products was carried out via SFC [Column: Chiral Technologies ChiralCel OD, 5 μm; Mobile phase: 55:45 carbon dioxide/(methanol containing 0.1% ammonium hydroxide)]. The first-eluting diastereomer, obtained as a yellow oil, was designated as C44. Yield: 44.3 mg, 74.8 μmol, 11% over 2 steps. LCMS m/z 592.1♦ $[M+H]^+$. Retention time 4.26 minutes (Column: Chiral Technologies ChiralCel OD-3, 4.6×100 mm, 3 μm; Mobile phase A: carbon dioxide; Mobile phase B: methanol containing 0.05% diethylamine; Gradient: 5% to 40% B over 4.5 minutes, then held at 40% B for 2.5 minutes; Flow rate: 2.8 mL/minute).

The second-eluting diastereomer was subjected to a second purification via SFC [Column: Chiral Technologies ChiralCel OD, 5 μm; Mobile phase: 3:2 carbon dioxide/(methanol containing 0.1% ammonium hydroxide)], providing the second-eluting diastereomer as a colorless oil, which was designated as C45. Yield: 38 mg, 64 μmol, 9% over 2 steps. LCMS m/z 592.1♦ $[M+H]^+$. Retention time 4.41 minutes (Analytical conditions identical to those used for C44).

The indicated absolute stereochemistries at the dioxolane were assigned via potency correlation of 5 with a sample of 5, free acid synthesized from intermediate C48; the absolute stereochemistry of that intermediate was determined via single-crystal X-ray structure determination (see below) of C49, a hemisulfate salt of C48.

Step 3. Synthesis of ammonium 2-({4-[(2R)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylate (4)

Aqueous lithium hydroxide solution (2 M; 0.80 mL, 1.6 mmol) was added to a solution of C44 (44.3 mg, 74.8 μmol) in a mixture of methanol (1 mL) and tetrahydrofuran (1 mL), and the reaction mixture was stirred at 26° C. for 3 hours. It was then adjusted to pH 7 by addition of trifluoroacetic acid, and the resulting mixture was concentrated in vacuo and purified using reversed-phase HPLC (Column: Agela Durashell C18, 5 μm; Mobile phase A: 0.05% ammonium hydroxide in water; Mobile phase B: acetonitrile; Gradient: 30% to 50% B) to afford 4 as a white solid. Yield: 26.6 mg, 44.7 μmol, 60%. LCMS m/z 578.0♦ $[M+H]^+$. $^1H$ NMR (400 MHz, methanol-$d_4$)=δ 8.31 (d, J=1.4 Hz, 1H), 7.96 (dd, J=8.5, 1.6 Hz, 1H), 7.66 (d, J=8.5 Hz, 1H), 7.57 (dd, J=8.0, 8.0 Hz, 1H), 7.34 (dd, J=10.1, 2.0 Hz, 1H), 7.29 (br dd, J=8.3, 2.0 Hz, 1H), 7.20 (s, 1H), 6.86-6.79 (m, 1H), 6.77 (br dd, component of ABC pattern, J=7.9, 1.3 Hz, 1H), 6.73 (dd, component of ABC pattern, J=7.5, 1.4 Hz, 1H), 5.29-5.18 (m, 1H), 4.9-4.78 (m, 1H, assumed; partially obscured by water peak), 4.68 (dd, J=15.3, 2.7 Hz, 1H), 4.54 (td, J=8.0, 5.9 Hz, 1H), 4.44 (dt, J=9.2, 5.9 Hz, 1H), 4.02 (AB quartet, $J_{AB}$=13.9 Hz, $\Delta\nu_{AB}$=49.0 Hz, 2H), 3.18-3.08 (m, 1H), 3.05-2.96 (m, 1H), 2.81-2.68 (m, 2H), 2.56-2.45 (m, 1H), 2.45-2.30 (m, 2H), 2.03-1.88 (m, 2H), 1.88-1.79 (m, 2H).

Step 4. Synthesis of ammonium 2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylate (5)

Aqueous lithium hydroxide solution (2 M; 0.80 mL, 1.6 mmol) was added to a solution of C45 (38 mg, 64 μmol) in a mixture of methanol (1 mL) and tetrahydrofuran (1 mL), and the reaction mixture was stirred at 24° C. for 2.5 hours. It was then adjusted to pH 7 by addition of 1 M hydrochloric acid, and the resulting mixture was concentrated in vacuo and purified using reversed-phase HPLC (Column: Agela Durashell C18, 5 μm; Mobile phase A: 0.05% ammonium hydroxide in water; Mobile phase B: acetonitrile; Gradient: 29% to 49% B), providing 5 as a white solid. Yield: 27.9 mg, 46.9 μmol, 73%. LCMS m/z 577.9♦ $[M+H]^+$. $^1H$ NMR (400 MHz, methanol-$d_4$) δ 8.32 (d, J=1.4 Hz, 1H), 7.96 (dd, J=8.5, 1.5 Hz, 1H), 7.66 (d, J=8.5 Hz, 1H), 7.56 (dd, J=8.0, 8.0 Hz, 1H), 7.34 (dd, J=10.2, 2.0 Hz, 1H), 7.29 (br dd, J=8.3, 2.0 Hz, 1H), 7.20 (s, 1H), 6.85-6.80 (m, 1H), 6.77 (dd, component of ABC pattern, J=8.0, 1.3 Hz, 1H), 6.73 (dd, component of ABC pattern, J=7.5, 1.4 Hz, 1H), 5.30-5.20 (m, 1H), 4.9-4.79 (m, 1H, assumed; partially obscured by water peak), 4.68 (dd, J=15.4, 2.7 Hz, 1H), 4.62-4.54 (m, 1H), 4.44 (dt, J=9.2, 5.9 Hz, 1H), 4.02 (AB quartet, $J_{AB}$=13.9 Hz, $\Delta\nu_{AB}$=44.6 Hz, 2H), 3.18-3.09 (m, 1H), 3.06-2.97 (m, 1H), 2.80-2.67 (m, 2H), 2.55-2.30 (m, 3H), 2.02-1.78 (m, 4H).

Alternate Synthesis of Example 5, Free Acid
2-({4-[(2S)-2-(4-Chloro-2-fluorophenyl)-1,3-benzodioxol-4-yl]piperidin-1-yl}methyl)-1-[(2S)-oxetan-2-ylmethyl]-1H-benzimidazole-6-carboxylic acid (5, Free Acid)
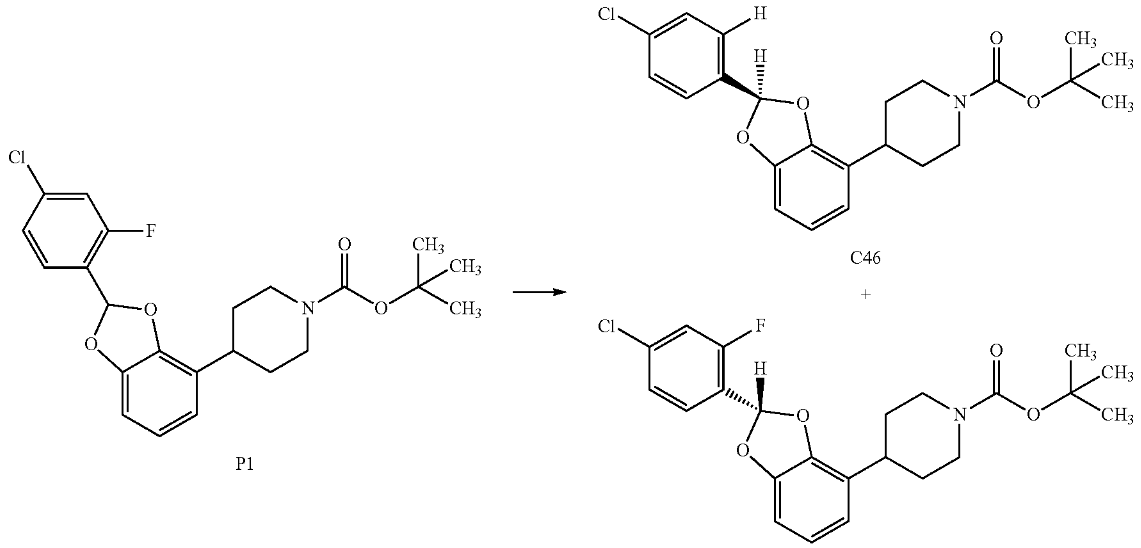
P1
C46
+
C47
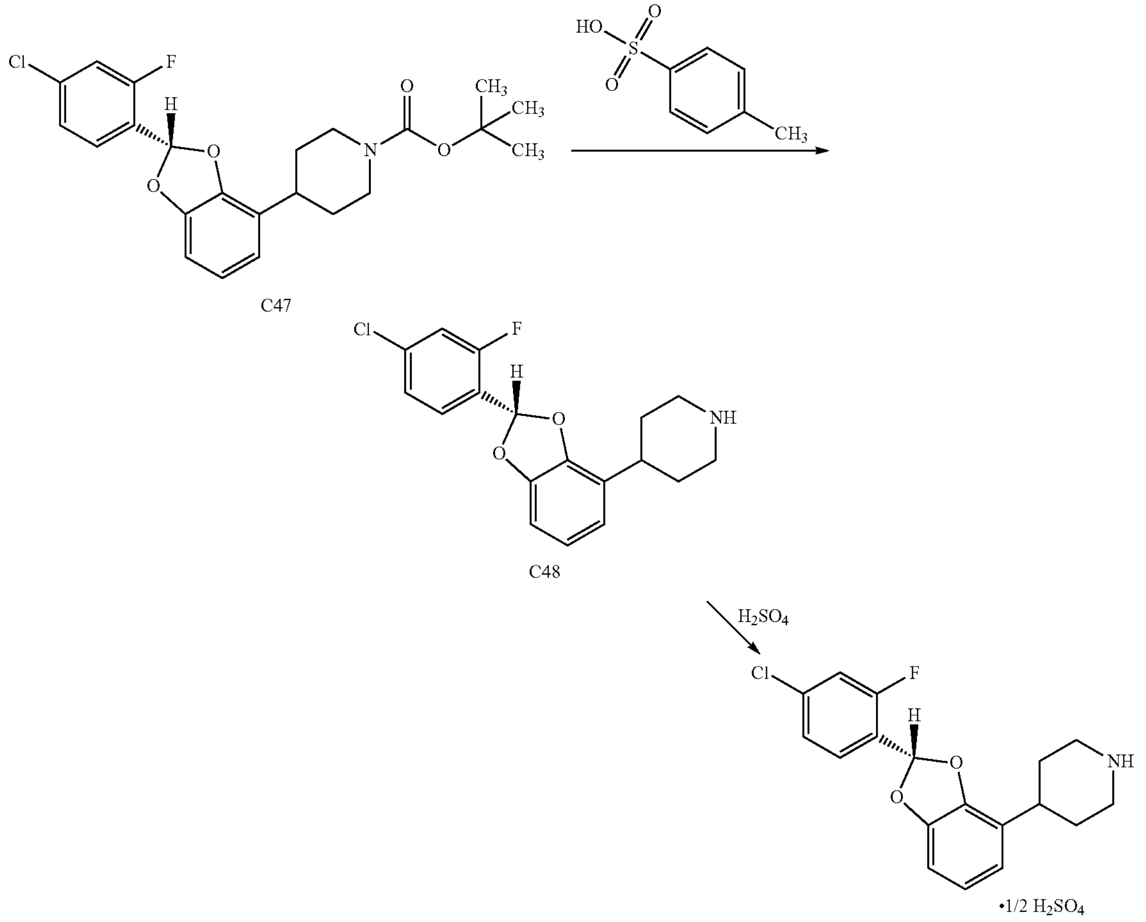
C47
C48
C49

-continued

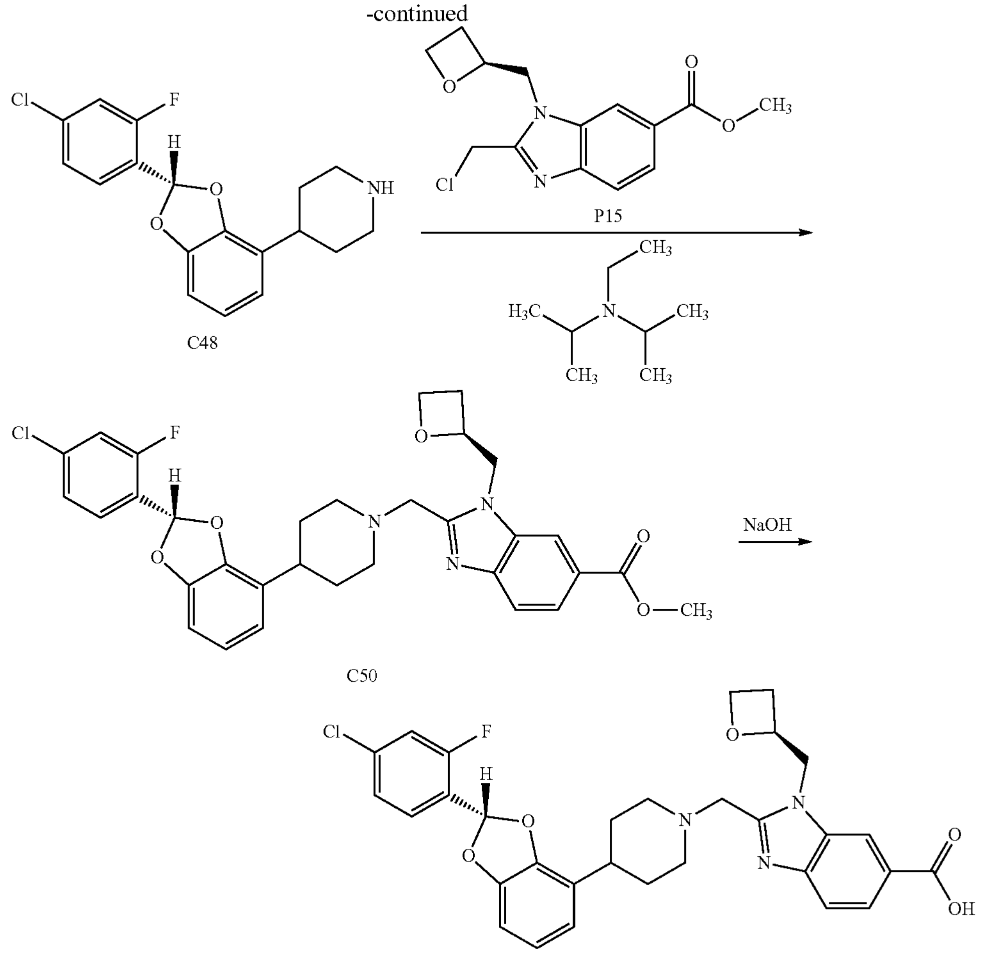

C48

C50

5, free acid

Step 1. Isolation of tert-butyl 4-[(2R)-2-(4-chloro-2-fluorophenyl)-1,3-benzodioxol-4-yl]piperidine-1-carboxylate (C46) and tert-butyl 4-[(2S)-2-(4-chloro-2-fluorophenyl)-1,3-benzodioxol-4-yl]piperidine-1-carboxylate (C47)

Separation of P1 (10 g, 23 mmol) into its component enantiomers was carried out using reversed-phase HPLC [Column: Phenomenex Lux Amylose-1, 5 μm; Mobile phase: 9:1 carbon dioxide/(2-propanol containing 0.2% 1-aminopropan-2-ol)]. The first-eluting enantiomer was designated as C46, and the second-eluting enantiomer as C47; both were obtained as colorless oils. The absolute stereochemistries indicated for C46 and C47 were assigned based on a single-crystal X-ray structure determination carried out on C49, which was synthesized from C47 (see below).

C46 Yield: 4.47 g, 10.3 mmol, 45%. Retention time: 3.98 minutes [Column: Phenomenex Lux Amylose-1, 4.6×250 mm, 5 μm; Mobile phase A: carbon dioxide; Mobile phase B: 2-propanol containing 0.2% 1-aminopropan-2-ol; Gradient: 5% B for 1.00 minute, then 5% to 60% B over 8.00 minutes; Flow rate: 3.0 mL/minute; Back pressure: 120 bar].

C47 Yield: 4.49 g, 10.3 mmol, 45%. Retention time: 4.32 minutes (Analytical SFC conditions identical to those used for C46).

Step 2. Synthesis of 4-[(2S)-2-(4-chloro-2-fluorophenyl)-1,3-benzodioxol-4-yl]piperidine (C48)

p-Toluenesulfonic acid monohydrate (566 mg, 2.98 mmol) was added to a solution of C47 (1.12 g, 2.58 mmol) in ethyl acetate (26 mL). After the reaction mixture had been heated at 45° C. for 16 hours, it was concentrated in vacuo, dissolved in ethyl acetate, and washed with saturated aqueous sodium bicarbonate solution. The aqueous layers were extracted with ethyl acetate, and the combined organic layers were washed with saturated aqueous sodium chloride solution, dried over sodium sulfate, filtered, and concentrated under reduced pressure, affording C48 as a foamy white solid (947 mg), LCMS m/z 334.0♦ $[M+H]^+$. A portion of this material, which still contained some p-toluenesulfonic acid, was used in the synthesis of C50 below.

A second portion of the foamy white solid (440 mg) was dissolved in ethyl acetate (25 mL) and washed with saturated aqueous sodium bicarbonate solution (2×15 mL); the organic layer was dried over magnesium sulfate, filtered, and concentrated in vacuo to afford C48 (350 mg) as a colorless oil that no longer contained p-toluenesulfonic acid. Adjusted yield: 350 mg, 1.05 mmol, 88%. $^1H$ NMR (400 MHz, chloroform-d) δ 7.53 (dd, J=8.4, 7.8 Hz, 1H), 7.22-7.13 (m, 3H), 6.87-6.80 (m, 1H), 6.79-6.71 (m, 2H), 3.23-3.14 (m, 2H), 2.86-2.69 (m, 3H), 1.90-1.68 (m, 4H).

Step 3. Synthesis of 4-[(2S)-2-(4-chloro-2-fluorophenyl)-1,3-benzodioxol-4-yl]piperidine, hemisulfate Salt (C49)

A 0.1 M solution of C48 (the colorless oil from above) in ethyl acetate was prepared and subjected to a salt screen. Only the sulfate salt formation is described here. A mixture of sulfuric acid (25 μmol) and the solution of substrate (0.1 M, 250 μL, 25 μmol) was heated to 45° C. for 1 hour, allowed to cool to room temperature, and stirred for 15 hours. The resulting suspension was treated with methanol (approximately 150 μL) until a solution formed; this was allowed to slowly evaporate overnight, until approximately 50 μL of solvent remained. One of the resulting crystals was analyzed by single-crystal X-ray structure determination, establishing the absolute stereochemistry as that shown.

Single-Crystal X-Ray Structural Determination of C49

Single Crystal X-Ray Analysis

Data collection was performed on a Bruker D8 Venture diffractometer at room temperature.

Data collection consisted of omega and phi scans.

The structure was solved by intrinsic phasing using SHELX software suite in the triclinic class space group P1. The structure was subsequently refined by the full-matrix least squares method. All non-hydrogen atoms were found and refined using anisotropic displacement parameters.

The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms.

The asymmetric unit is comprised of two molecules of protonated C48, one molecule of doubly deprotonated sulfuric acid, and one molecule full occupancy water. Thus, the structure is a hemisulfate salt and hemihydrate. The chlorofluorophenyl ring is disordered and modeled with occupancy of 60/40, with the ring flipped over two positions.

Analysis of the absolute structure using likelihood methods (Hooft, 2008) was performed using PLATON (Spek). The results indicate that the absolute structure has been correctly assigned; the method calculates that the probability that the structure is correct is 100.0. The Hooft parameter is reported as 0.061 with an esd of 0.004 and the Parson's parameter is reported as 0.063 with an esd of 0.005.

The final R-index was 3.1%. A final difference Fourier revealed no missing or misplaced electron density.

Pertinent crystal, data collection, and refinement information is summarized in Table E. Atomic coordinates, bond lengths, bond angles, and displacement parameters are listed in Tables F-H.

SOFTWARE AND REFERENCES

SHELXTL, Version 5.1, Bruker AXS, 1997.

PLATON, A. L. Spek, *J. Appl. Cryst* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Strayer, and A. L. Spek, *J. Appl. Cryst.* 2008, 41, 96-103.

H. D. Flack, *Acta Cryst.* 1983, A39, 867-881.

TABLE E

Crystal data and structure refinement for C49.

| | |
|---|---|
| Empirical formula | $C_{36}H_{38}Cl_2F_2N_2O_9S$ |
| Formula weight | 783.64 |
| Temperature | 296(2) K |
| Wavelength | 1.54178 Å |
| Crystal system | Triclinic |
| Space group | P1 |
| Unit cell dimensions | a = 5.9095(2) Å α = 86.5910(10)°<br>b = 6.1712(2) Å β = 89.3680(10)°<br>c = 25.6096(8) Å γ = 75.7680(10)° |
| Volume | 903.68(5) $Å^3$ |
| Z | 1 |
| Density (calculated) | 1.440 $Mg/m^3$ |
| Absorption coefficient | 2.743 $mm^{-1}$ |
| F(000) | 408 |
| Crystal size | 0.380 × 0.120 × 0.080 $mm^3$ |
| Theta range for data collection | 3.458 to 72.096° |
| Index ranges | −7 <= h <= 7,<br>−7 <= k <= 7,<br>−31<=/<=31 |
| Reflections collected | 24619 |
| Independent reflections | 6399 [$R_{int}$ = 0.0323]] |
| Completeness to theta = 67.679° | 96.6% |
| Absorption correction | Empirical |
| Refinement method | Full-matrix least-squares on $F^2$ |
| Data/restraints/parameters | 6399/9/495 |
| Goodness-of-fit on $F^2$ | 1.014 |
| Final R indices [I > 2σ(I)] | R1 = 0.0305, wR2 = 0.0805 |
| R indices (all data) | R1 = 0.0310, wR2 = 0.0810 |
| Absolute structure parameter | 0.058(4) |
| Extinction coefficient | n/a |
| Largest diff, peak and hole | 0.167 and -0.184 e · $Å^{-3}$ |

TABLE F

Atomic coordinates (×$10^4$) and equivalent isotropic displacement parameters ($Å^2$ × $10^3$) for C49. U(eq) is defined as one-third of the trace of the orthogonalized $U^{ij}$ tensor.

| | x | y | z | U(eq) |
|---|---|---|---|---|
| S(1) | 8968(1) | 2512(1) | 4774(1) | 33(1) |
| Cl(1) | 2534(3) | 7001(5) | 9863(1) | 161(1) |
| F(1) | 9192(9) | 7761(7) | 8721(2) | 95(1) |
| C(1) | 7533(7) | 6719(7) | 8821(1) | 72(1) |
| C(2) | 6041(9) | 7355(8) | 9230(2) | 92(1) |
| C(3) | 4428(8) | 6206(10) | 9350(2) | 93(2) |
| C(4) | 4276(8) | 4392(9) | 9082(2) | 86(1) |
| C(5) | 5801(7) | 3784(7) | 8678(1) | 69(1) |
| C(6) | 7444(6) | 4930(5) | 8533(1) | 56(1) |
| Cl(1') | 2534(3) | 7001(5) | 9863(1) | 161(1) |

TABLE F-continued

Atomic coordinates (×$10^4$) and equivalent isotropic displacement parameters ($Å^2$ × $10^3$) for C49. U(eq) is defined as one-third of the trace of the orthogonalized $U^{ij}$ tensor.

| | x | y | z | U(eq) |
|---|---|---|---|---|
| F(1') | 6045(13) | 1811(12) | 8450(3) | 95(1) |
| C(1') | 5801(7) | 3784(7) | 8678(1) | 69(1) |
| C(2') | 4276(8) | 4392(9) | 9082(2) | 86(1) |
| C(3') | 4428(8) | 6206(10) | 9350(2) | 93(2) |
| C(4') | 6041(9) | 7355(8) | 9230(2) | 92(1) |
| C(5') | 7533(7) | 6719(7) | 8821(1) | 72(1) |
| C(6') | 7444(6) | 4930(5) | 8533(1) | 56(1) |
| Cl(2) | −2047(5) | 12265(3) | 154(1) | 157(1) |
| F(2) | −2662(7) | 5436(7) | 1220(2) | 92(1) |
| C(19) | −1591(6) | 7059(7) | 1154(1) | 68(1) |
| C(20) | −2327(8) | 8653(9) | 752(2) | 88(1) |
| C(21) | −1157(9) | 10260(8) | 665(2) | 88(1) |
| C(22) | 728(9) | 10361(7) | 964(2) | 80(1) |
| C(23) | 1431(6) | 8731(6) | 1364(1) | 65(1) |
| C(24) | 274(5) | 7058(5) | 1472(1) | 54(1) |
| Cl(2') | −2047(5) | 12265(3) | 154(1) | 157(1) |
| F(2') | 3433(15) | 8441(16) | 1630(4) | 92(1) |
| C(19') | 1431(6) | 8731(6) | 1364(1) | 65(1) |
| C(20') | 728(9) | 10361(7) | 964(2) | 80(1) |
| C(21') | −1157(9) | 10260(8) | 665(2) | 88(1) |
| C(22') | −2327(8) | 8653(9) | 752(2) | 88(1) |
| C(23') | −1591(6) | 7059(7) | 1154(1) | 68(1) |
| C(24') | 274(5) | 7058(5) | 1472(1) | 54(1) |
| N(1) | 4370(3) | 2950(4) | 5713(1) | 41(1) |
| N(2) | 4133(4) | 8236(3) | 4386(1) | 42(1) |
| O(1) | 10923(4) | 2331(5) | 8233(1) | 77(1) |
| O(2) | 7874(4) | 3730(4) | 7651(1) | 64(1) |
| O(3) | 1766(4) | 6201(4) | 2352(1) | 64(1) |
| O(4) | 2966(5) | 3591(4) | 1729(1) | 75(1) |
| O(5) | 9024(3) | 2305(3) | 4214(1) | 50(1) |
| O(6) | 7650(4) | 989(3) | 5024(1) | 63(1) |
| O(7) | 11358(3) | 1934(4) | 4982(1) | 64(1) |
| O(8) | 7789(3) | 4827(3) | 4909(1) | 46(1) |
| O(1W) | 10276(4) | 6879(4) | 5537(1) | 54(1) |
| C(7) | 9086(6) | 4293(6) | 8090(1) | 63(1) |
| C(8) | 9234(4) | 1745(5) | 7490(1) | 44(1) |
| C(9) | 11056(5) | 930(6) | 7834(1) | 54(1) |
| C(10) | 12654(5) | −1059(6) | 7768(1) | 62(1) |
| C(11) | 12316(5) | −2213(6) | 7338(1) | 58(1) |
| C(12) | 10459(4) | −1405(5) | 6994(1) | 47(1) |
| C(13) | 8826(4) | 623(4) | 7066(1) | 38(1) |
| C(14) | 6762(4) | 1637(4) | 6711(1) | 37(1) |
| C(15) | 7243(4) | 3516(4) | 6343(1) | 42(1) |
| C(16) | 5126(4) | 4639(4) | 6009(1) | 44(1) |
| C(17) | 3883(5) | 1105(5) | 6056(1) | 50(1) |
| C(18) | 5997(4) | −38(4) | 6386(1) | 41(1) |
| C(25) | 996(6) | 5296(6) | 1900(1) | 60(1) |
| C(26) | 3848(5) | 4738(4) | 2505(1) | 45(1) |
| C(27) | 4542(6) | 3183(5) | 2133(1) | 52(1) |
| C(28) | 6579(6) | 1567(5) | 2178(1) | 56(1) |
| C(29) | 7932(6) | 1577(5) | 2620(1) | 56(1) |
| C(30) | 7236(5) | 3123(5) | 2992(1) | 51(1) |
| C(31) | 5126(5) | 4786(4) | 2944(1) | 42(1) |
| C(32) | 4261(4) | 6474(4) | 3352(1) | 39(1) |
| C(33) | 6145(5) | 7543(5) | 3544(1) | 51(1) |
| C(34) | 5139(5) | 9272(4) | 3932(1) | 50(1) |
| C(35) | 2313(5) | 7116(5) | 4227(1) | 49(1) |
| C(36) | 3263(4) | 5420(4) | 3826(1) | 42(1) |

TABLE G

Bond lengths [Å] and angles [°] for C49.

| | |
|---|---|
| S(1)—O(5) | 1.4463(18) |
| S(1)—O(7) | 1.4668(19) |
| S(1)—O(6) | 1.475(2) |
| S(1)—O(8) | 1.4863(18) |
| Cl(1)—C(3) | 1.731(4) |
| F(1)—C(1) | 1.314(6) |
| C(1)—C(6) | 1.375(5) |
| C(1)—C(2) | 1.374(6) |
| C(2)—C(3) | 1.343(8) |

TABLE G-continued

Bond lengths [Å] and angles [°] for C49.

| | |
|---|---|
| C(2)—H(2) | 0.9300 |
| C(3)—C(4) | 1.369(8) |
| C(4)—C(5) | 1.373(6) |
| C(4)—H(4) | 0.9300 |
| C(5)—C(6) | 1.370(5) |
| C(5)—H(5) | 0.9300 |
| C(6)—C(7) | 1.493(5) |
| Cl(1')—C(3') | 1.731(4) |
| F(1')—C(1') | 1.357(8) |

TABLE G-continued

| Bond lengths [Å] and angles [°] for C49. | |
|---|---|
| C(1')—C(6') | 1.370(5) |
| C(1')—C(2) | 1.373(6) |
| C(2')—C(3') | 1.369(8) |
| C(2')—H(2') | 0.9300 |
| C(3')—C(4') | 1.343(8) |
| C(4')—C(5') | 1.374(6) |
| C(4')—H(4') | 0.9300 |
| C(5')—C(6') | 1.375(5) |
| C(5')—H(5') | 0.9300 |
| C(6')—C(7) | 1.493(5) |
| Cl(2)—C(21) | 1.739(4) |
| F(2)—C(19) | 1.312(5) |
| C(19)—C(24) | 1.378(5) |
| C(19)—C(20) | 1.378(6) |
| C(20)—C(21) | 1.348(7) |
| C(20)—H(20) | 0.9300 |
| C(21)—C(22) | 1.375(7) |
| C(22)—C(23) | 1.384(6) |
| C(22)—H(22) | 0.9300 |
| C(23)—C(24) | 1.385(5) |
| C(23)—H(23) | 0.9300 |
| C(24)—C(25) | 1.485(5) |
| Cl(2')—C(21') | 1.739(4) |
| F(2')—C(19') | 1.340(9) |
| C(19')—C(20') | 1.384(6) |
| C(19')—C(24') | 1.385(5) |
| C(20')—C(21') | 1.375(7) |
| C(20')—H(20') | 0.9300 |
| C(21')—C(22') | 1.348(7) |
| C(22')—C(23') | 1.378(6) |
| C(22')—H(22') | 0.9300 |
| C(23')—C(24') | 1.378(5) |
| C(23')—H(23') | 0.9300 |
| C(24')—C(25) | 1.485(5) |
| N(1)—C(17) | 1.480(4) |
| N(1)—C(16) | 1.480(3) |
| N(1)—H(1X) | 0.95(2) |
| N(1)—H(1Y) | 0.97(2) |
| N(2)—C(34) | 1.483(4) |
| N(2)—C(35) | 1.487(4) |
| N(2)—H(2X) | 0.96(2) |
| N(2)—H(2Y) | 0.99(2) |
| O(1)—C(9) | 1.368(4) |
| O(1)—C(7) | 1.445(4) |
| O(2)—C(8) | 1.373(3) |
| O(2)—C(7) | 1.443(3) |
| O(3)—C(26) | 1.380(3) |
| O(3)—C(25) | 1.440(3) |
| O(4)—C(27) | 1.369(4) |
| O(4)—C(25) | 1.447(4) |
| O(1W)—H(1WX) | 0.93(2) |
| O(1W)—H(1WY) | 0.94(2) |
| C(7)—H(7) | 0.9800 |
| C(8)—C(9) | 1.374(4) |
| C(8)—C(13) | 1.376(4) |
| C(9)—C(10) | 1.370(5) |
| C(10)—C(11) | 1.387(5) |
| C(10)—H(10) | 0.9300 |
| C(11)—C(12) | 1.390(4) |
| C(11)—H(11) | 0.9300 |
| C(12)—C(13) | 1.400(4) |
| C(12)—H(12) | 0.9300 |
| C(13)—C(14) | 1.514(3) |
| C(14)—C(18) | 1.518(3) |
| C(14)—C(15) | 1.528(3) |
| C(14)—H(14) | 0.9800 |
| C(15)—C(16) | 1.518(3) |
| C(15)—H(15A) | 0.9700 |
| C(15)—H(15B) | 0.9700 |
| C(16)—H(16A) | 0.9700 |
| C(16)—H(16B) | 0.9700 |
| C(17)—C(18) | 1.513(4) |
| C(17)—H(17A) | 0.9700 |
| C(17)—H(17B) | 0.9700 |
| C(18)—H(18A) | 0.9700 |
| C(18)—H(18B) | 0.9700 |
| C(25)—H(25) | 0.9800 |
| C(26)—C(31) | 1.367(4) |

TABLE G-continued

| Bond lengths [Å] and angles [°] for C49. | |
|---|---|
| C(26)—C(27) | 1.379(3) |
| C(27)—C(28) | 1.363(4) |
| C(28)—C(29) | 1.394(5) |
| C(28)—H(28) | 0.9300 |
| C(29)—C(30) | 1.376(4) |
| C(29)—H(29) | 0.9300 |
| C(30)—C(31) | 1.408(4) |
| C(30)—H(30) | 0.9300 |
| C(31)—C(32) | 1.514(3) |
| C(32)—C(33) | 1.527(4) |
| C(32)—C(36) | 1.524(3) |
| C(32)—H(32) | 0.9800 |
| C(33)—C(34) | 1.510(4) |
| C(33)—H(33A) | 0.9700 |
| C(33)—H(33B) | 0.9700 |
| C(34)—H(34A) | 0.9700 |
| C(34)—H(34B) | 0.9700 |
| C(35)—C(36) | 1.515(3) |
| C(35)—H(35A) | 0.9700 |
| C(35)—H(35B) | 0.9700 |
| C(36)—H(36A) | 0.9700 |
| C(36)—H(36B) | 0.9700 |
| O(5)—S(1)—O(7) | 109.68(13) |
| O(5)—S(1)—O(6) | 109.65(13) |
| O(7)—S(1)—O(6) | 109.45(15) |
| O(5)—S(1)—O(8) | 111.22(11) |
| O(7)—S(1)—O(8) | 109.11(11) |
| O(6)—S(1)—O(8) | 107.69(11) |
| F(1)—C(1)—C(6) | 118.6(4) |
| F(1)—C(1)—C(2) | 119.1(4) |
| C(6)—C(1)—C(2) | 122.1(4) |
| C(3)—C(2)—C(1) | 118.9(4) |
| C(3)—C(2)—H(2) | 120.5 |
| C(1)—C(2)—H(2) | 120.5 |
| C(2)—C(3)—C(4) | 121.6(4) |
| C(2)—C(3)—Cl(1) | 119.3(4) |
| C(4)—C(3)—Cl(1) | 119.1(5) |
| C(3)—C(4)—C(5) | 118.2(5) |
| C(3)—C(4)—H(4) | 120.9 |
| C(5)—C(4)—H(4) | 120.9 |
| C(6)—C(5)—C(4) | 122.4(4) |
| C(6)—C(5)—H(5) | 118.8 |
| C(4)—C(5)—H(5) | 118.8 |
| C(5)—C(6)—C(1) | 116.7(3) |
| C(5)—C(6)—C(7) | 122.7(3) |
| C(1)—C(6)—C(7) | 120.6(3) |
| F(1')—C(1')—C(6') | 114.7(4) |
| F(1')—C(1')—C(2') | 122.1(5) |
| C(6')—C(1')—C(2') | 122.4(4) |
| C(3')—C(2')—C(1') | 118.2(5) |
| C(3')—C(2')—H(2') | 120.9 |
| C(1')—C(2')—H(2') | 120.9 |
| C(4')—C(3')—C(2') | 121.6(4) |
| C(4')—C(3')—Cl(1') | 119.3(4) |
| C(2')—C(3')—Cl(1') | 119.1(5) |
| C(3')—C(4')—C(5') | 118.9(4) |
| C(3')—C(4')—H(4') | 120.5 |
| C(5')—C(4')—H(4') | 120.5 |
| C(6')—C(5')—C(4') | 122.1(4) |
| C(6')—C(5')—H(5') | 118.9 |
| C(4')—C(5')—H(5') | 118.9 |
| C(1')—C(6')—C(5') | 116.7(3) |
| C(1')—C(6')—C(7) | 122.7(3) |
| C(5')—C(6')—C(7) | 120.6(3) |
| F(2)—C(19)—C(24) | 119.3(4) |
| F(2)—C(19)—C(20) | 118.1(4) |
| C(24)—C(19)—C(20) | 122.5(4) |
| C(21)—C(20)—C(19) | 118.4(4) |
| C(21)—C(20)—H(20) | 120.8 |
| C(19)—C(20)—H(20) | 120.8 |
| C(20)—C(21)—C(22) | 122.4(4) |
| C(20)—C(21)—Cl(2) | 118.9(4) |
| C(22)—C(21)—Cl(2) | 118.7(4) |
| C(21)—C(22)—C(23) | 117.8(4) |
| C(21)—C(22)—H(22) | 121.1 |
| C(23)—C(22)—H(22) | 121.1 |
| C(22)—C(23)—C(24) | 122.0(4) |
| C(22)—C(23)—H(23) | 119.0 |

TABLE G-continued

| Bond lengths [Å] and angles [°] for C49. | |
|---|---|
| C(24)—C(23)—H(23) | 119.0 |
| C(19)—C(24)—C(23) | 116.8(3) |
| C(19)—C(24)—C(25) | 120.3(3) |
| C(23)—C(24)—C(25) | 122.9(3) |
| F(2')—C(19')—C(20') | 123.5(5) |
| F(2')—C(19')—C(24') | 113.9(5) |
| C(20')—C(19')—C(24') | 122.0(4) |
| C(21')—C(20')—C(19') | 117.8(4) |
| C(21')—C(20')—H(20') | 121.1 |
| C(19')—C(20')—H(20') | 121.1 |
| C(22')—C(21')—C(20') | 122.4(4) |
| C(22')—C(21')—Cl(2') | 118.9(4) |
| C(20')—C(21')—Cl(2') | 118.7(4) |
| C(21')—C(22')—C(23') | 118.4(4) |
| C(21')—C(22')—H(22') | 120.8 |
| C(23')—C(22')—H(22') | 120.8 |
| C(24')—C(23')—C(22') | 122.5(4) |
| C(24')—C(23')—H(23') | 118.7 |
| C(22')—C(23')—H(23') | 118.7 |
| C(23')—C(24')—C(19') | 116.8(3) |
| C(23')—C(24')—C(25) | 120.3(3) |
| C(19')—C(24')—C(25) | 122.9(3) |
| C(17)—N(1)—C(16) | 112.6(2) |
| C(17)—N(1)—H(1X) | 110.7(19) |
| C(16)—N(1)—H(1X) | 108(2) |
| C(17)—N(1)—H(1Y) | 108(2) |
| C(16)—N(1)—H(1Y) | 112.4(19) |
| H(1X)—N(1)—H(1Y) | 105(3) |
| C(34)—N(2)—C(35) | 112.2(2) |
| C(34)—N(2)—H(2X) | 109.7(19) |
| C(35)—N(2)—H(2X) | 109.7(19) |
| C(34)—N(2)—H(2Y) | 107.7(19) |
| C(35)—N(2)—H(2Y) | 110.8(19) |
| H(2X)—N(2)—H(2Y) | 107(3) |
| C(9)—O(1)—C(7) | 106.0(2) |
| C(8)—O(2)—C(7) | 105.9(2) |
| C(26)—O(3)—C(25) | 105.9(2) |
| C(27)—O(4)—C(25) | 105.7(2) |
| H(1WX)—O(1W)—H(1WY) | 105(4) |
| O(2)—C(7)—O(1) | 106.5(3) |
| O(2)—C(7)—C(6) | 110.4(3) |
| O(1)—C(7)—C(6) | 111.2(3) |
| O(2)—C(7)—C(6') | 110.4(3) |
| O(1)—C(7)—C(6') | 111.2(3) |
| O(2)—C(7)—H(7) | 109.6 |
| O(1)—C(7)—H(7) | 109.6 |
| C(6)—C(7)—H(7) | 109.6 |
| C(9)—C(8)—O(2) | 110.0(2) |
| C(9)—C(8)—C(13) | 123.4(2) |
| O(2)—C(8)—C(13) | 126.6(2) |
| O(1)—C(9)—C(10) | 128.1(3) |
| O(1)—C(9)—C(8) | 110.1(3) |
| C(10)—C(9)—C(8) | 121.7(3) |
| C(9)—C(10)—C(11) | 116.3(3) |
| C(9)—C(10)—H(10) | 121.8 |
| C(11)—C(10)—H(10) | 121.8 |
| C(10)—C(11)—C(12) | 122.0(3) |
| C(10)—C(11)—H(11) | 119.0 |
| C(12)—C(11)—H(11) | 119.0 |
| C(11)—C(12)—C(13) | 121.3(3) |
| C(11)—C(12)—H(12) | 119.4 |
| C(13)—C(12)—H(12) | 119.4 |
| C(8)—C(13)—C(12) | 115.3(2) |
| C(8)—C(13)—C(14) | 119.8(2) |
| C(12)—C(13)—C(14) | 124.9(2) |
| C(13)—C(14)—C(18) | 114.2(2) |
| C(13)—C(14)—C(15) | 111.38(19) |
| C(18)—C(14)—C(15) | 108.70(19) |
| C(13)—C(14)—H(14) | 107.4 |
| C(18)—C(14)—H(14) | 107.4 |
| C(15)—C(14)—H(14) | 107.4 |
| C(16)—C(15)—C(14) | 111.7(2) |
| C(16)—C(15)—H(15A) | 109.3 |
| C(14)—C(15)—H(15A) | 109.3 |
| C(16)—C(15)—H(15B) | 109.3 |
| C(14)—C(15)—H(15B) | 109.3 |
| H(15A)—C(15)—H(15B) | 107.9 |
| N(1)—C(16)—C(15) | 109.9(2) |

TABLE G-continued

| Bond lengths [Å] and angles [°] for C49. | |
|---|---|
| N(1)—C(16)—H(16A) | 109.7 |
| C(15)—C(16)—H(16A) | 109.7 |
| N(1)—C(16)—H(16B) | 109.7 |
| C(15)—C(16)—H(16B) | 109.7 |
| H(16A)—C(16)—H(16B) | 108.2 |
| N(1)—C(17)—C(18) | 110.94(19) |
| N(1)—C(17)—H(17A) | 109.5 |
| C(18)—C(17)—H(17A) | 109.5 |
| N(1)—C(17)—H(17B) | 109.5 |
| C(18)—C(17)—H(17B) | 109.5 |
| H(17A)—C(17)—H(17B) | 108.0 |
| C(17)—C(18)—C(14) | 110.6(2) |
| C(17)—C(18)—H(18A) | 109.5 |
| C(14)—C(18)—H(18A) | 109.5 |
| C(17)—C(18)—H(18B) | 109.5 |
| C(14)—C(18)—H(18B) | 109.5 |
| H(18A)—C(18)—H(18B) | 108.1 |
| O(3)—C(25)—O(4) | 106.6(2) |
| O(3)—C(25)—C(24') | 111.0(3) |
| O(4)—C(25)—C(24') | 109.4(3) |
| O(3)—C(25)—C(24) | 111.0(3) |
| O(4)—C(25)—C(24) | 109.4(3) |
| O(3)—C(25)—H(25) | 109.9 |
| O(4)—C(25)—H(25) | 109.9 |
| C(24)—C(25)—H(25) | 109.9 |
| C(31)—C(26)—C(27) | 123.2(3) |
| C(31)—C(26)—O(3) | 127.3(2) |
| C(27)—C(26)—O(3) | 109.5(2) |
| C(28)—C(27)—O(4) | 127.7(2) |
| C(28)—C(27)—C(26) | 121.9(3) |
| O(4)—C(27)—C(26) | 110.3(2) |
| C(27)—C(28)—C(29) | 116.3(2) |
| C(27)—C(28)—H(28) | 121.9 |
| C(29)—C(28)—H(28) | 121.9 |
| C(30)—C(29)—C(28) | 121.8(3) |
| C(30)—C(29)—H(29) | 119.1 |
| C(28)—C(29)—H(29) | 119.1 |
| C(29)—C(30)—C(31) | 121.7(3) |
| C(29)—C(30)—H(30) | 119.2 |
| C(31)—C(30)—H(30) | 119.2 |
| C(26)—C(31)—C(30) | 115.1(2) |
| C(26)—C(31)—C(32) | 121.5(2) |
| C(30)—C(31)—C(32) | 123.4(2) |
| C(31)—C(32)—C(33) | 113.3(2) |
| C(31)—C(32)—C(36) | 111.48(19) |
| C(33)—C(32)—C(36) | 108.02(19) |
| C(31)—C(32)—H(32) | 107.9 |
| C(33)—C(32)—H(32) | 107.9 |
| C(36)—C(32)—H(32) | 107.9 |
| C(34)—C(33)—C(32) | 110.5(2) |
| C(34)—C(33)—H(33A) | 109.6 |
| C(32)—C(33)—H(33A) | 109.6 |
| C(34)—C(33)—H(33B) | 109.6 |
| C(32)—C(33)—H(33B) | 109.6 |
| H(33A)—C(33)—H(33B) | 108.1 |
| N(2)—C(34)—C(33) | 110.6(2) |
| N(2)—C(34)—H(34A) | 109.5 |
| C(33)—C(34)—H(34A) | 109.5 |
| N(2)—C(34)—H(34B) | 109.5 |
| C(33)—C(34)—H(34B) | 109.5 |
| H(34A)—C(34)—H(34B) | 108.1 |
| N(2)—C(35)—C(36) | 110.71(19) |
| N(2)—C(35)—H(35A) | 109.5 |
| C(36)—C(35)—H(35A) | 109.5 |
| N(2)—C(35)—H(35B) | 109.5 |
| C(36)—C(35)—H(35B) | 109.5 |
| H(35A)—C(35)—H(35B) | 108.1 |
| C(35)—C(36)—C(32) | 111.9(2) |
| C(35)—C(36)—H(36A) | 109.2 |
| C(32)—C(36)—H(36A) | 109.2 |
| C(35)—C(36)—H(36B) | 109.2 |
| C(32)—C(36)—H(36B) | 109.2 |
| H(36A)—C(36)—H(36B) | 107.9 |

Symmetry Transformations Used to Generate Equivalent Atoms.

TABLE H

Anisotropic displacement parameters ($Å^2 \times 10^3$) for C49. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| S(1) | 32(1) | 32(1) | 32(1) | −3(1) | −2(1) | −1(1) |
| Cl(1) | 107(1) | 258(2) | 90(1) | −63(1) | 19(1) | 19(1) |
| F(1) | 111(2) | 91(2) | 98(2) | −30(2) | 6(2) | −46(2) |
| C(1) | 81(2) | 71(2) | 60(2) | −20(2) | −16(2) | −6(2) |
| C(2) | 100(3) | 92(3) | 74(3) | −42(2) | −16(2) | 7(2) |
| C(3) | 70(2) | 134(4) | 53(2) | −27(2) | −7(2) | 19(3) |
| C(4) | 71(2) | 116(3) | 67(2) | 0(2) | −1(2) | −16(2) |
| C(5) | 75(2) | 70(2) | 59(2) | −11(2) | −7(2) | −10(2) |
| C(6) | 65(2) | 54(2) | 42(1) | −8(1) | −18(1) | −1(1) |
| Cl(1') | 107(1) | 258(2) | 90(1) | −63(1) | 19(1) | 19(1) |
| F(1') | 111(2) | 91(2) | 98(2) | −30(2) | 6(2) | −46(2) |
| C(1') | 75(2) | 70(2) | 59(2) | −11(2) | −7(2) | −10(2) |
| C(2') | 71(2) | 116(3) | 67(2) | 0(2) | −1(2) | −16(2) |
| C(3') | 70(2) | 134(4) | 53(2) | −27(2) | −7(2) | 19(3) |
| C(4') | 100(3) | 92(3) | 74(3) | −42(2) | −16(2) | 7(2) |
| C(5') | 81(2) | 71(2) | 60(2) | −20(2) | −16(2) | −6(2) |
| C(6') | 65(2) | 54(2) | 42(1) | −8(1) | −18(1) | −1(1) |
| Cl(2) | 243(2) | 110(1) | 80(1) | 12(1) | −39(1) | 26(1) |
| F(2) | 88(2) | 106(2) | 93(2) | −12(2) | −22(2) | −44(2) |
| C(19) | 62(2) | 77(2) | 62(2) | −26(2) | −12(2) | −5(2) |
| C(20) | 85(3) | 98(3) | 66(2) | −20(2) | −31(2) | 10(2) |
| C(21) | 117(3) | 74(3) | 51(2) | −11(2) | −10(2) | 18(2) |
| C(22) | 104(3) | 70(2) | 60(2) | −9(2) | 8(2) | −8(2) |
| C(23) | 58(2) | 73(2) | 60(2) | −13(2) | −3(1) | −6(2) |
| C(24) | 50(2) | 60(2) | 47(2) | −23(1) | −4(1) | −2(1) |
| Cl(2') | 243(2) | 110(1) | 80(1) | 12(1) | −39(1) | 26(1) |
| F(2') | 88(2) | 106(2) | 93(2) | −12(2) | −22(2) | −44(2) |
| C(19') | 58(2) | 73(2) | 60(2) | −13(2) | −3(1) | −6(2) |
| C(20') | 104(3) | 70(2) | 60(2) | −9(2) | 8(2) | −8(2) |
| C(21') | 117(3) | 74(3) | 51(2) | −11(2) | −10(2) | 18(2) |
| C(22') | 85(3) | 98(3) | 66(2) | −20(2) | −31(2) | 10(2) |
| C(23') | 62(2) | 77(2) | 62(2) | −26(2) | −12(2) | −5(2) |
| C(24') | 50(2) | 60(2) | 47(2) | −23(1) | −4(1) | −2(1) |
| N(1) | 30(1) | 59(1) | 32(1) | −3(1) | −4(1) | −7(1) |
| N(2) | 49(1) | 38(1) | 37(1) | −11(1) | −5(1) | 0(1) |
| O(1) | 58(1) | 107(2) | 55(1) | −23(1) | −26(1) | 6(1) |
| O(2) | 64(1) | 66(1) | 50(1) | −21(1) | −23(1) | 12(1) |
| O(3) | 66(1) | 62(1) | 52(1) | −27(1) | −19(1) | 11(1) |
| O(4) | 92(2) | 64(1) | 56(1) | −32(1) | −20(1) | 10(1) |
| O(5) | 62(1) | 51(1) | 34(1) | −5(1) | −2(1) | −9(1) |
| O(6) | 76(1) | 43(1) | 70(1) | −4(1) | 32(1) | −14(1) |
| O(7) | 45(1) | 68(1) | 69(1) | −29(1) | −22(1) | 13(1) |
| O(8) | 45(1) | 35(1) | 53(1) | −9(1) | −4(1) | 2(1) |
| O(1W) | 56(1) | 50(1) | 51(1) | −3(1) | −12(1) | 1(1) |
| C(7) | 68(2) | 73(2) | 45(2) | −12(1) | −14(1) | −12(2) |
| C(8) | 38(1) | 51(1) | 36(1) | −4(1) | −3(1) | 0(1) |
| C(9) | 42(1) | 76(2) | 39(1) | −1(1) | −9(1) | −4(1) |
| C(10) | 38(1) | 87(2) | 48(2) | 10(1) | −8(1) | 6(1) |
| C(11) | 45(1) | 60(2) | 55(2) | 9(1) | 2(1) | 13(1) |
| C(12) | 41(1) | 46(1) | 47(1) | 0(1) | 3(1) | 0(1) |
| C(13) | 34(1) | 43(1) | 34(1) | 2(1) | −1(1) | −4(1) |
| C(14) | 30(1) | 44(1) | 31(1) | −4(1) | −1(1) | 0(1) |
| C(15) | 41(1) | 38(1) | 45(1) | 0(1) | −12(1) | −7(1) |
| C(16) | 44(1) | 43(1) | 39(1) | −3(1) | −6(1) | 4(1) |
| C(17) | 39(1) | 73(2) | 42(1) | −1(1) | −3(1) | −23(1) |
| C(18) | 41(1) | 46(1) | 39(1) | −4(1) | 2(1) | −14(1) |
| C(25) | 65(2) | 62(2) | 51(2) | −22(1) | −9(1) | −8(1) |
| C(26) | 55(1) | 37(1) | 37(1) | −8(1) | 1(1) | −2(1) |
| C(27) | 72(2) | 41(1) | 39(1) | −9(1) | −2(1) | −6(1) |
| C(28) | 79(2) | 39(1) | 43(1) | −10(1) | 11(1) | 1(1) |
| C(29) | 62(2) | 45(2) | 48(2) | −2(1) | 7(1) | 8(1) |
| C(30) | 58(2) | 45(2) | 42(1) | −1(1) | −1(1) | 1(1) |
| C(31) | 54(1) | 34(1) | 34(1) | −4(1) | 2(1) | −4(1) |
| C(32) | 50(1) | 30(1) | 33(1) | −4(1) | −6(1) | 0(1) |
| C(33) | 63(2) | 45(1) | 54(2) | −9(1) | 17(1) | −28(1) |
| C(34) | 59(2) | 38(1) | 58(2) | −9(1) | −1(1) | −22(1) |
| C(35) | 46(1) | 46(1) | 56(2) | −17(1) | 16(1) | −11(1) |
| C(36) | 39(1) | 36(1) | 53(1) | −15(1) | 12(1) | −13(1) |

Step 4. Synthesis of methyl 2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylate (C50)

A solution of C48 (500 mg of the foamy white solid from above, corrected for p-toluenesulfonic acid: 1.25 mmol) in acetonitrile (6 mL) was treated with N,N-diisopropylethylamine (0.68 mL, 3.9 mmol) and allowed to stir for 5 minutes at 45° C. After addition of P15 (319 mg, 1.08 mmol), stirring at 45° C. was continued for 7.25 hours, whereupon the reaction mixture was diluted with water (6 mL) and acetonitrile (2 mL) at 45° C. The resulting heterogeneous mixture was allowed to cool to room temperature and stir for 72 hours. More water (5 mL) was added, and after a further 30 minutes of stirring, the solid was collected via filtration and washed with a mixture of acetonitrile and water (15:85, 3×5 mL), to afford C50 as a white solid with a slight pink cast. Yield: 605 mg, 1.02 mmol, 82%. LCMS m/z 592.0♦ $[M+H]^+$. $^1$H NMR (400 MHz, chloroform-d) δ 8.17 (d, J=1.6 Hz, 1H), 7.96 (dd, J=8.5, 1.5 Hz, 1H), 7.73 (d, J=8.4 Hz, 1H), 7.51 (dd, J=8.0, 8.0 Hz, 1H), 7.19 (br s, 1H), 7.18-7.14 (m, 2H), 6.85-6.79 (m, 1H), 6.76-6.71 (m, 2H), 5.26-5.18 (m, 1H), 4.73 (dd, component of ABX pattern, J=15.3, 5.9 Hz, 1H), 4.67 (dd, component of ABX pattern, J=15.3, 3.5 Hz, 1H), 4.63-4.55 (m, 1H), 4.38 (ddd, J=9.1, 6.0, 5.9 Hz, 1H), 3.94 (s, 5H), 3.03-2.89 (m, 2H), 2.77-2.65 (m, 2H), 2.51-2.39 (m, 1H), 2.34-2.20 (m, 2H), 1.91-1.76 (m, 4H).

Step 5. Synthesis of 2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid (5, Free Acid)

A suspension of C50 (595 mg, 1.00 mmol) in methanol (10 mL) was heated to 45° C. and treated with aqueous sodium hydroxide solution (1 M; 2.01 mL, 2.01 mmol). After 21 hours at 45° C., the reaction mixture was allowed to cool to room temperature; it was then treated with aqueous citric acid solution (1 M, 1 mL), which brought the pH to 5 to 6. Water (10 mL) was added, and the mixture was stirred for 1 hour, whereupon the solid was collected by filtration. It was washed with a mixture of methanol and water (1:10, 3×5 mL), to afford a solid (433 mg). A portion of this material (300 mg) was stirred with a mixture of heptane and ethyl acetate (1:3, 5 mL) at 40° C. for 1 hour; after cooling to room temperature with continued stirring, the solid was collected via filtration, and washed with a mixture of heptane and ethyl acetate (3:1, 3×3 mL) to afford 5, free acid, as a white solid. Yield: 260 mg, 0.450 mmol, corresponding to 65% for the entire reaction. LCMS m/z 578.0♦ $[M+H]^+$. $^1$H NMR (400 MHz, DMSO-$d_6$) δ 12.75 (v br s, 1H), 8.26 (br s, 1H), 7.79 (dd, J=8.4, 1.6 Hz, 1H), 7.66-7.56 (m, 3H), 7.40 (dd, J=8.3, 2.0 Hz, 1H), 7.35 (s, 1H), 6.87-6.75 (m, 3H), 5.13-5.03 (m, 1H), 4.76 (dd, component of ABX pattern, J=15.3, 7.2 Hz, 1H), 4.62 (dd, component of ABX pattern, J=15.2, 2.8 Hz, 1H), 4.46-4.38 (m, 1H), 4.34 (ddd, J=9.0, 5.9, 5.8 Hz, 1H), 3.84 (AB quartet, $J_{AB}$=13.5 Hz, $\Delta\nu_{AB}$=67.7 Hz, 2H), 3.00 (br d, J=11.2 Hz, 1H), 2.84 br (d, J=11.3 Hz, 1H), 2.71-2.56 (m, 2H), 2.45-2.34 (m, 1H), 2.28-2.08 (m, 2H), 1.84-1.65 (m, 4H).

This material was determined to be of the same absolute configuration as Example 5 above by comparison of its biological activity with that of both 4 and 5: in Assay 2, this sample of 5, free acid exhibited an $EC_{50}$ of 25 nM (geometric mean of 3 replicates). The activity in Assay 2 for the ammonium salts of Example 4 and Example 5 were >20000 nM (2 replicates) and 20 nM (geometric mean of 3 replicates), respectively.

Synthesis of Example 5, 1,3-dihydroxy-2-(hydroxymethyl)propan-2-aminium Salt 1,3-Dihydroxy-2-(hydroxymethyl)propan-2-aminium 2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylate (5, 1,3-dihydroxy-2-(hydroxymethyl)propan-2-aminium Salt)

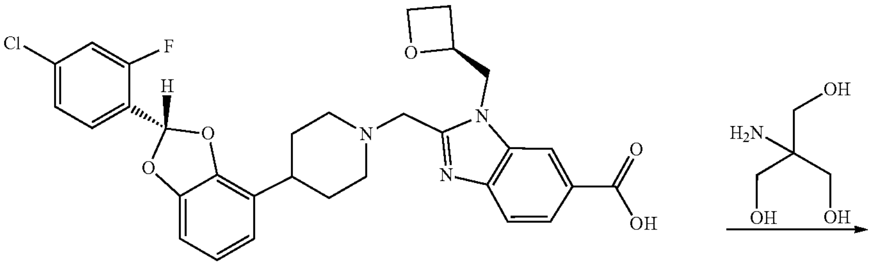

5, free acid

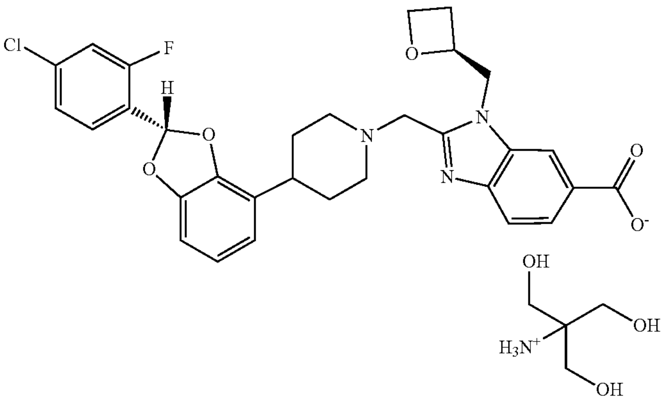

5, 1,3-dihydroxy-2-(hydroxymethyl)propan-2-aminium salt

A mixture of 5, free acid (0.50 g, 0.86 mmol) in tetrahydrofuran (4 mL) was treated with an aqueous solution of 2-amino-2-(hydroxymethyl)propane-1,3-diol (Tris, 1.0 M; 0.5 mL, 1.0 mmol). After 20 hours, the mixture was concentrated in vacuo with ethanol (2×6 mL). The mixture was treated with ethanol (4 mL). After stirring for 48 hours, the solid was collected via filtration, washed with ethanol (2×10 mL) and dried under vacuum to afford 5, 1,3-dihydroxy-2-(hydroxymethyl)propan-2-aminium salt, as a white solid. Yield: 410 mg, 0.586 mmol, 68%. $^{1}H$ NMR (600 MHz, DMSO-$d_6$), characteristic peaks: δ 8.19 (s, 1H), 7.78 (br d, J=8.4 Hz, 1H), 7.62-7.58 (m, 2H), 7.55 (d, J=8.3 Hz, 1H), 7.40 (dd, J=8.4, 2.0 Hz, 1H), 7.35 (s, 1H), 6.85-6.80 (m, 2H), 6.79 (dd, J=6.9, 2.4 Hz, 1H), 5.11-5.05 (m, 1H), 4.73 (dd, J=15.2, 7.2 Hz, 1H), 4.60 (dd, J=15.3, 2.9 Hz, 1H), 4.45-4.39 (m, 1H), 4.34 (ddd, J=9.0, 6.0, 5.8 Hz, 1H), 3.91 (d, J=13.5 Hz, 1H), 3.74 (d, J=13.5 Hz, 1H), 2.99 (br d, J=11.1 Hz, 1H), 2.85 (br d, J=11.3 Hz, 1H), 2.68-2.59 (m, 2H), 2.44-2.37 (m, 1H), 2.25-2.18 (m, 1H), 2.17-2.10 (m, 1H), 1.80-1.69 (m, 4H). mp=168° C. to 178° C.

Examples 6 and 7
Ammonium 2-({4-[(2R)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (6) and Ammonium 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (7)
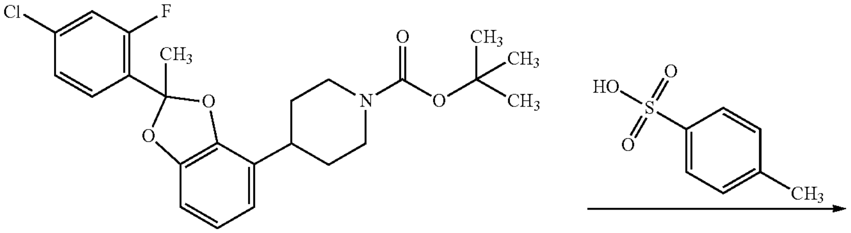
P2
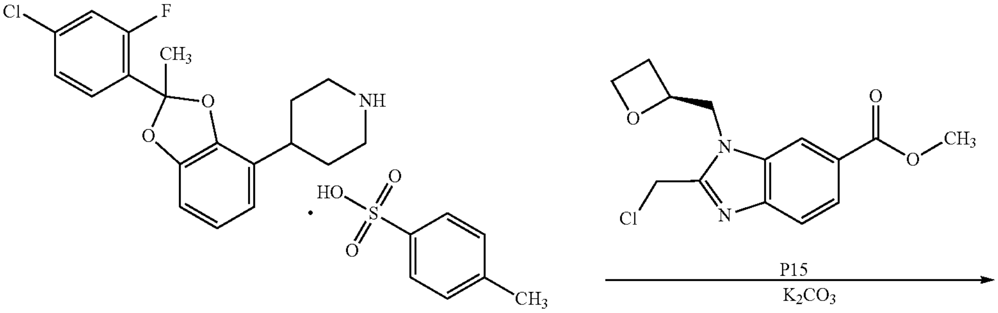
C13
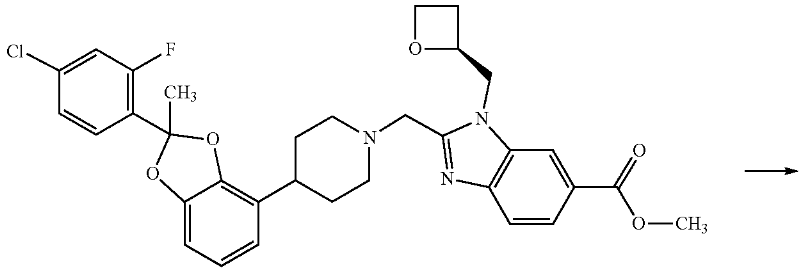
C51
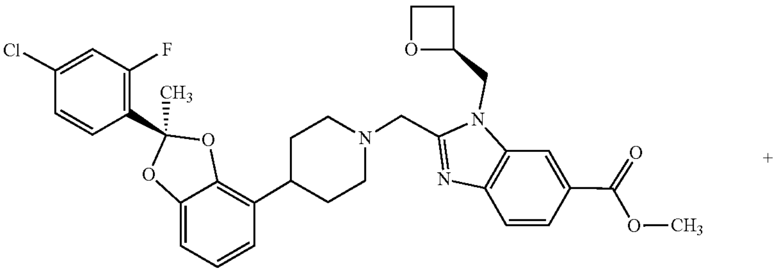
C52

-continued
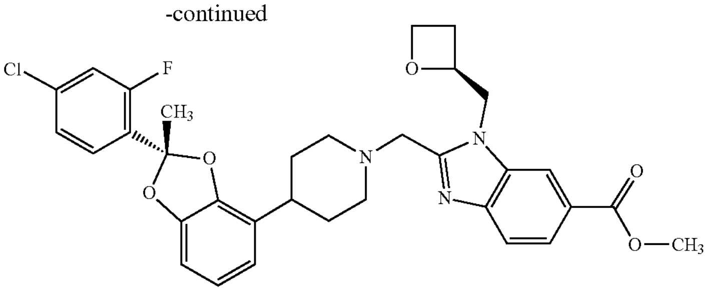
C53
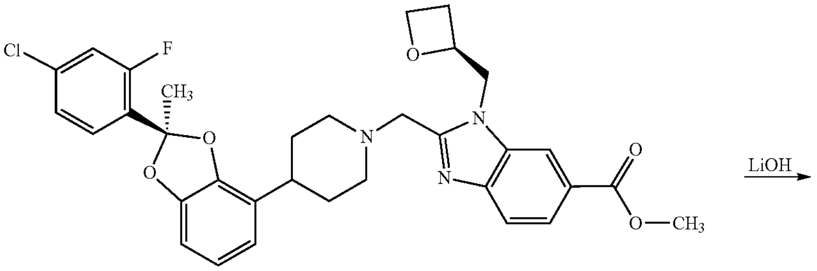
C52
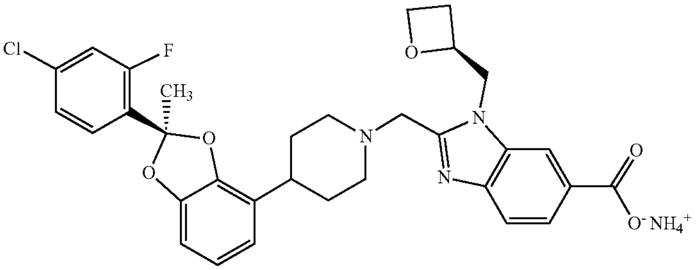
6
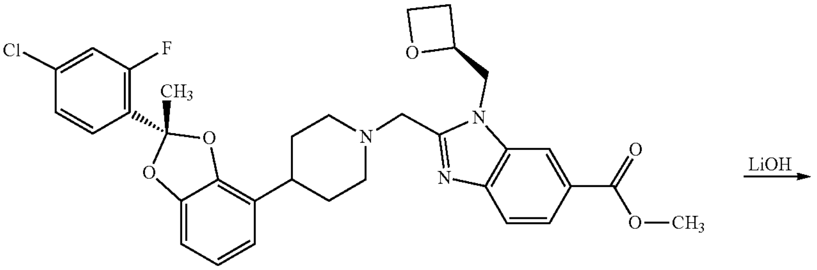
C53
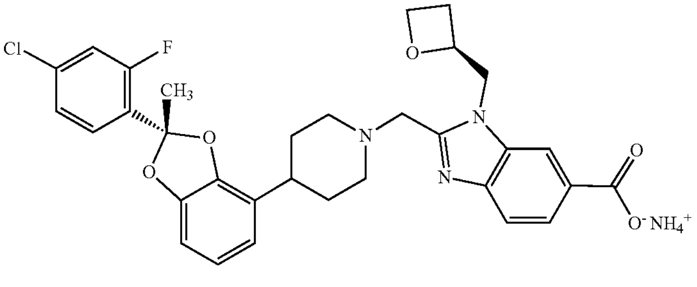
7

Step 1. Synthesis of 4-[2-(4-chloro-2-fluorophenyl)-2-methyl-1,3-benzodioxol-4-yl]piperidine, p-toluenesulfonate Salt (C13)

A solution of P2 (150 mg, 0.335 mmol) and p-toluenesulfonic acid monohydrate (159 mg, 0.836 mmol) in ethyl acetate (2.0 mL) was stirred at 60° C. for 3.5 hours. The reaction mixture was concentrated in vacuo to afford C13 as a brown oil, which was used directly in the following step. LCMS m/z 348.1♦ $[M+H]^+$.

Step 2. Synthesis of methyl 2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (C51)

To a suspension of C13 (from the previous step; ≤0.335 mmol) and potassium carbonate (232 mg, 1.68 mmol) in acetonitrile (5.0 mL) was added P15 (99.1 mg, 0.336 mmol). The reaction mixture was stirred at 60° C. for 10 hours, whereupon it was filtered, and the filtrate was concentrated in vacuo. After the residue (390 mg) had been combined with the material from a similar reaction carried out using C13 (≤0.11 mmol), it was diluted with water (20 mL) and extracted with a mixture of dichloromethane and methanol (10:1, 3×30 mL). The combined organic layers were dried over sodium sulfate, filtered, concentrated in vacuo, and subjected to preparative thin-layer chromatography (Eluent: 1:1 dichloromethane/methanol), providing C51, a mixture of diastereomers, as a colorless oil. Combined yield: 80.6 mg, 0.133 mmol, 30% over 2 steps. LCMS m/z 606.2♦ $[M+H]^+$.

Step 3. Isolation of methyl 2-({4-[(2R)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (C52) and methyl 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (C53)

Separation of C51 (180 mg, 0.297 mmol) into its component diastereomers was carried out via repeated SFC [Column: Chiral Technologies Chiralpak AD, 10 μm; Mobile phase: 65:35 carbon dioxide/(ethanol containing 0.1% ammonium hydroxide)]. The first-eluting diastereomer was designated as C52. Yield: 61.2 mg, 0.101 mmol, 34%. LCMS m/z 627.9♦ $[M+Na^+]$. Retention time: 5.03 minutes (Column: Chiral Technologies Chiralpak AD-3, 4.6×150 mm, 3 μm; Mobile phase A: carbon dioxide; Mobile phase B: ethanol containing 0.05% diethylamine; Gradient: 5% to 40% B over 5.5 minutes, then held at 40% B for 3.0 minutes; Flow rate: 2.5 mL/minute).

The second-eluting diastereomer was designated as C53. Upon analysis, this material proved to be contaminated with the corresponding ethyl ester; it was taken into the hydrolysis step (to generate 7) as this mixture. Yield: 40.0 mg, 66.0 μmol, 22%. LCMS m/z 606.0♦ $[M+H]^+$. Retention time: 5.19 minutes (Analytical conditions identical to those used for C52).

The indicated absolute stereochemistries at the dioxolane were assigned via potency correlation of 7 with a sample of 7, free acid synthesized from intermediate P3 (see below, Alternate Synthesis of Example 7, free acid); the absolute stereochemistry of P3 was established via single-crystal X-ray structure determination of C8 (see above).

Step 4. Synthesis of ammonium 2-({4-[(2R)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (6)

Aqueous lithium hydroxide solution (2 M; 0.990 mL, 1.98 mmol) was added to a solution of C52 (60 mg, 99 μmol) in a mixture of methanol (1.0 mL) and tetrahydrofuran (1.0 mL), and the reaction mixture was stirred at 20° C. for 16 hours. Trifluoroacetic acid was added until the pH of the reaction mixture reached 7, whereupon it was concentrated in vacuo, and the residue was purified using reversed-phase HPLC (Column: Agela Durashell C18, 5 μm; Mobile phase A: 0.05% ammonium hydroxide in water; Mobile phase B: acetonitrile; Gradient: 29% to 49% B), affording 6 as a white solid. Yield: 14.4 mg. 23.6 μmol, 24%. LCMS m/z 592.0♦ $[M-H]^+$. $^1$H NMR (400 MHz, methanol-$d_4$), characteristic peaks: δ 8.35 (d, J=1.3 Hz, 1H), 7.97 (dd, J=8.5, 1.5 Hz, 1H), 7.67 (d, J=8.5 Hz, 1H), 7.58 (dd, J=8.3, 8.3 Hz, 1H), 7.28 (dd, J=10.9, 2.0 Hz, 1H), 7.21 (br dd, J=8.4, 1.9 Hz, 1H), 6.81-6.75 (m, 1H), 6.74-6.68 (m, 2H), 5.33-5.25 (m, 1H), 4.72 (dd, J=15.4, 2.7 Hz, 1H), 4.49 (dt, J=9.1, 6.0 Hz, 1H), 4.03 (AB quartet, $J_{AB}$=13.9 Hz, $\Delta\nu_{AB}$=47.8 Hz, 2H), 3.14 (br d, J=11 Hz, 1H), 3.02 (br d, J=11.5 Hz, 1H), 2.88-2.78 (m, 1H), 2.77-2.68 (m, 1H), 2.60-2.50 (m, 1H), 2.47-2.32 (m, 2H), 2.03 (d, J=1.1 Hz, 3H), 2.01-1.87 (m, 2H), 1.87-1.78 (br m, 2H).

Step 5. Synthesis of ammonium 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (7)

Aqueous lithium hydroxide solution (2 M; 0.642 mL, 1.28 mmol) was added to a solution of C53 (38.9 mg, 64.2 μmol) in a mixture of methanol (1.0 mL) and tetrahydrofuran (1.0 mL). After the reaction mixture had been stirred at 20° C. for 16 hours, it was adjusted to pH 7 by addition of trifluoroacetic acid, concentrated in vacuo, and purified using reversed-phase HPLC (Column: Agela Durashell C18, 5 μm; Mobile phase A: 0.05% ammonium hydroxide in water; Mobile phase B: acetonitrile; Gradient: 0% to 80% B), affording 7 as a white solid. Yield: 25.1 mg, 41.2 μmol, 64%. LCMS m/z 591.9♦ $[M+H]^+$. $^1$H NMR (400 MHz, methanol-$d_4$), characteristic peaks: δ 8.34 (d, J=1.5 Hz, 1H), 7.98 (dd, J=8.5, 1.6 Hz, 1H), 7.68 (d, J=8.5 Hz, 1H), 7.58 (dd, J=8.3, 8.3 Hz, 1H), 7.28 (dd, J=10.9, 2.0 Hz, 1H), 7.20 (br dd, J=8.4, 1.9 Hz, 1H), 6.81-6.74 (m, 1H), 6.74-6.67 (m, 2H), 5.33-5.23 (m, 1H), 4.73 (dd, J=15.4, 2.7 Hz, 1H), 4.68-4.61 (m, 1H), 4.48 (dt, J=9.1, 5.9 Hz, 1H), 4.05 (AB quartet, $J_{AB}$=13.9 Hz, $\Delta\nu_{AB}$=44.1 Hz, 2H), 3.15 (br d, J=11.7 Hz, 1H), 3.03 (br d, J=11.6 Hz, 1H), 2.87-2.69 (m, 2H), 2.60-2.49 (m, 1H), 2.48-2.33 (m, 2H), 2.03 (br s, 3H), 2.01-1.77 (m, 4H).

Alternate Synthesis of Example 7, Free Acid 2-({4-[(2S)-2-(4-Chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid (7, Free Acid)

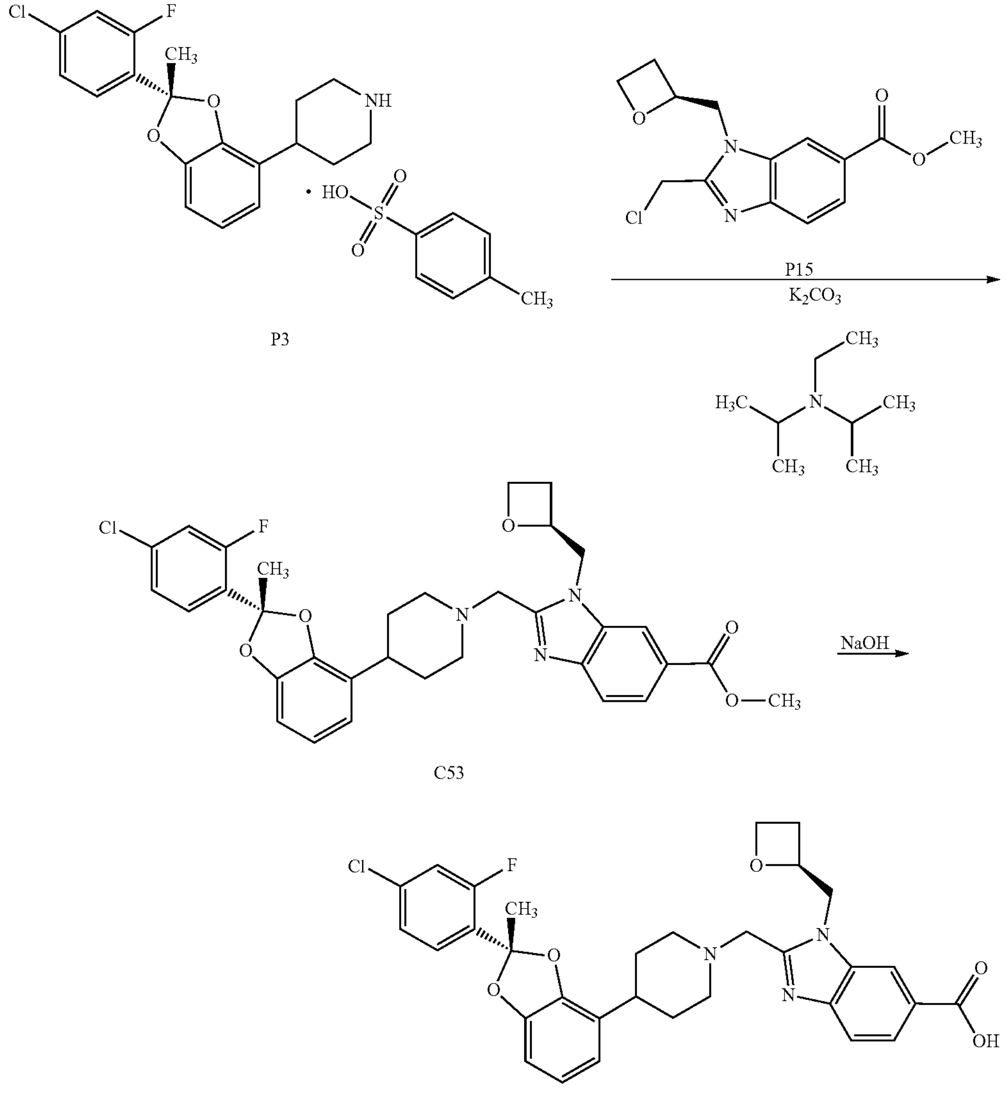

P3

C53

7, free acid

Step 1. Synthesis of methyl 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (C53)

N,N-Diisopropylethylamine (15.1 mL, 86.9 mmol) was added to a mixture of P3 (8.22 g, 15.8 mmol) in acetonitrile (185 mL); after stirring for 5 minutes, P15 (4.57 g, 15.5 mmol) was added, and the reaction mixture was heated at 45° C. After 4 hours, the reaction mixture was concentrated in vacuo to half of its original volume, and the resulting mixture was diluted with water (100 mL) and extracted with ethyl acetate (2×100 mL). The combined organic layers were washed with water (50 mL), dried over magnesium sulfate, filtered, and concentrated in vacuo. Silica gel chromatography (Gradient: 50% to 100% ethyl acetate in heptane) afforded C53 as a white solid. Yield: 8.4 g, 13.9 mmol, 88%. LCMS m/z 606.1♦ $[M+H]^+$. $^1$H NMR (600 MHz, DMSO-$d_6$) δ 8.30 (s, 1H), 7.82 (br d, J=8.4 Hz, 1H), 7.67 (d, J=8.4 Hz, 1H), 7.58-7.53 (m, 2H), 7.33 (dd, J=8.4, 2.1 Hz, 1H), 6.80-6.76 (m, 2H), 6.76-6.72 (m, 1H), 5.14-5.07 (m, 1H), 4.81 (dd, J=15.2, 7.2 Hz, 1H), 4.67 (dd, J=15.3, 2.8 Hz, 1H), 4.51-4.44 (m, 1H), 4.37 (ddd, J=8.9, 5.9, 5.9 Hz, 1H), 3.97 (d, J=13.6 Hz, 1H), 3.87 (s, 3H), 3.78 (d, J=13.5 Hz, 1H), 3.02 (br d, J=11.1 Hz, 1H), 2.86 (br d, J=11.3 Hz, 1H), 2.74-2.60 (m, 2H), 2.48-2.41 (m, 1H), 2.29-2.22 (m, 1H), 2.21-2.14 (m, 1H), 2.02 (s, 3H), 1.83-1.73 (m, 2H), 1.73-1.64 (m, 2H).

Step 2. Synthesis of 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid (7, Free acid)

A mixture of C53 (8.40 g, 14.0 mmol) in methanol (135 mL) was heated to 45° C., and treated with aqueous sodium hydroxide solution (1 M; 27.7 mL, 27.7 mmol). After 20 hours, the reaction mixture was concentrated in vacuo to half its original volume. The resulting mixture was diluted with water (100 mL), and aqueous citric acid solution (1 M, 15 mL) was used to adjust the pH to 5 to 6. The resultant solid was filtered, washed with water (2x15 mL), and transferred to a separatory funnel as a solution in ethyl acetate (50 mL); residual water was removed in this way. The organic layer was dried over magnesium sulfate, filtered, combined with four previously prepared batches from a similar procedure (amount of C53 used in these reactions was 987 mg, 1.63 mmol; 1.15 g, 1.90 mmol; 8.57 g, 14.1 mmol; and 12.6 g, 20.8 mmol) and concentrated in vacuo. The resulting sticky solid was treated with 10% ethyl acetate in heptane (500 mL). After 4 hours, the solid was collected via filtration and washed with 10% ethyl acetate in heptane (2x25 mL) to afford 7, free acid, as a white solid. Yield 29.4 g, 0.527 mmol, 74% for combined reactions. LCMS 592.2♦ [M+H]+. $^{1}H$ NMR (600 MHz, DMSO-$d_6$): δ 12.74 (br s, 1H), 8.28 (s, 1H), 7.80 (br d, J=8.4 Hz, 1H), 7.64 (d, J=8.4 Hz, 1H), 7.59-7.52 (m, 2H), 7.33 (dd, J=8.4, 2.1 Hz, 1H), 6.81-6.76 (m, 2H), 6.76-6.72 (m, 1H), 5.14-5.07 (m, 1H), 4.79 (dd, J=15.3, 7.3 Hz, 1H), 4.65 (dd, J=15.2, 2.8 Hz, 1H), 4.51-4.45 (m, 1H), 4.38 (ddd, J=9.0, 5.9, 5.9 Hz, 1H), 3.96 (br d, J=13.6 Hz, 1H), 3.78 (br d, J=13.5 Hz, 1H), 3.02 (br d, J=11.1 Hz, 1H), 2.86 (br d, J=11.1 Hz, 1H), 2.74-2.60 (m, 2H), 2.48-2.41 (m, 1H), 2.29-2.21 (m, 1H), 2.21-2.14 (m, 1H), 2.02 (s, 3H), 1.83-1.74 (m, 2H), 1.74-1.64 (m, 2H). This material was determined to be of the same absolute configuration as Example 7 above by comparison of its biological activity with that of both 6 and 7: in Assay 2, this sample of 7, free acid exhibited an $EC_{50}$ of 4.3 nM (geometric mean of 3 replicates). The activity in Assay 2 for the ammonium salts of Example 6 and Example 7 were 2400 nM (geometric mean of 5 replicates) and 2.9 nM (geometric mean of 8 replicates), respectively.

Synthesis of Example 7, 1,3-dihydroxy-2-(hydroxymethyl)propan-2-aminium Salt 1,3-Dihydroxy-2-(hydroxymethyl)propan-2-aminium 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (7, 1,3-dihydroxy-2-(hydroxymethyl)propan-2-aminium Salt)

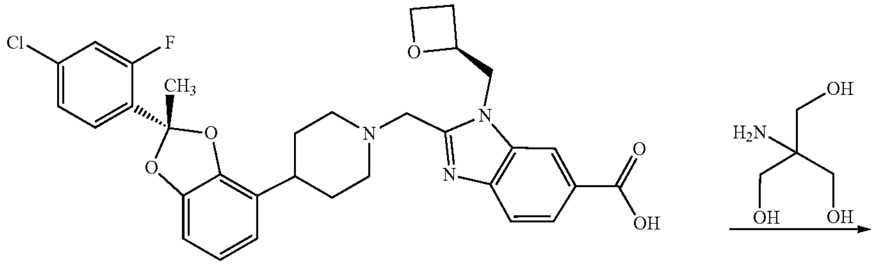

7, free acid

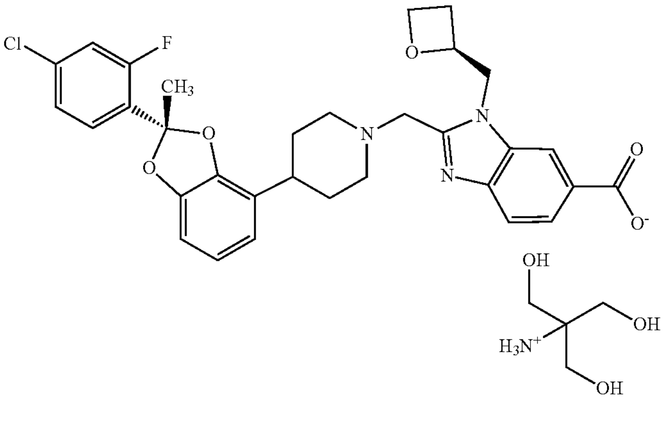

7, 1,3-dihydroxy-2-(hydroxymethyl)propan-2-aminium salt

A mixture of 7, free acid (2.00 g, 3.38 mmol) in tetrahydrofuran (16 mL) was treated with an aqueous solution of 2-amino-2-(hydroxymethyl)propane-1,3-diol (Tris, 1.0 M; 3.55 mL, 3.55 mmol). After 18 hours, the reaction mixture was concentrated in vacuo and treated with ethanol (30 mL). After this mixture had been stirred for 23 hours, the solid was collected via filtration and washed with ethyl acetate (2×10 mL) to afford 7, 1,3-dihydroxy-2-(hydroxymethyl) propan-2-aminium salt as a white solid. Yield: 1.41 g, 1.98 mmol, 59%. LCMS m/z 592.3♦ $[M+H]^+$. $^1H$ NMR (600 MHz, DMSO-$d_6$), characteristic peaks: δ 8.20 (s, 1H), 7.79 (d, J=8.4 Hz, 1H), 7.59-7.52 (m, 3H), 7.33 (br d, J=8.5 Hz, 1H), 6.81-6.72 (m, 3H), 5.14-5.07 (m, 1H), 4.76 (dd, J=15.2, 7.2 Hz, 1H), 4.63 (br d, J=15.4 Hz, 1H), 4.50-4.44 (m, 1H), 4.37 (ddd, J=8.9, 5.9, 5.9 Hz, 1H), 3.94 (d, J=13.4 Hz, 1H), 3.76 (d, J=13.4 Hz, 1H), 3.01 (br d, J=11.1 Hz, 1H), 2.86 (br d, J=11.2 Hz, 1H), 2.73-2.60 (m, 2H), 2.5-2.41 (m, 1H), 2.27-2.20 (m, 1H), 2.20-2.13 (m, 1H), 2.02 (s, 3H), 1.83-1.64 (m, 4H). mp=175° C. to 180° C.

Acquisition of Powder X-Ray Diffraction (PXRD) Data for Form I of Example 7, 1,3-Dihydroxy-2-(Hydroxymethyl) Propan-2-Aminium Salt The white solid of the tris salt of Example 7 was submitted for PXRD analysis and found to be a crystalline material (which is designated as Form I of this anhydrous crystal form). Powder X-ray diffraction analysis was conducted using a Bruker AXS D8 Endeavor diffractometer equipped with a Cu radiation source. The divergence slit was set at 15 mm continuous illumination. Diffracted radiation was detected by a PSD-Lynx Eye detector, with the detector PSD opening set at 2.99 degrees. The X-ray tube voltage and amperage were set to 40 kV and 40 mA respectively. Data was collected at the Cu wavelength ($CuK_{\bar{\alpha}}$=1.5418λ) in the Theta-Theta goniometer from 3.0 to 40.0 degrees 2-Theta using a step size of 0.01 degrees and a step time of 1.0 second. The antiscatter screen was set to a fixed distance of 1.5 mm. Samples were rotated during data collection. Samples were prepared by placing them in a silicon low background sample holder and rotated during collection. Data were collected using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of ≥3% were generally chosen. Typically, the peaks which were not resolved or were consistent with noise were not selected. A typical error associated with the peak position from PXRD stated in USP up to +/−0.2° 2-Theta (USP-941). One diffraction pattern was consistently observed and is provided in FIG. 24. A list of diffraction peaks expressed in terms of the degree 2θ and relative intensities with a relative intensity of ≥3.0% is provided above in Table X1.

TABLE X1

| Angle (2theta) | Relative Intensity (%) |
|---|---|
| 3.7 | 74.3 |
| 7.3 | 83.3 |
| 8.1 | 12.5 |
| 8.5 | 6.5 |
| 10.1 | 6.6 |
| 13.6 | 3.5 |
| 14.7 | 49.8 |
| 15.2 | 7.9 |
| 15.5 | 28.7 |
| 15.9 | 18.3 |
| 16.9 | 60.8 |
| 17.4 | 26.3 |
| 17.7 | 11.4 |
| 17.9 | 13.5 |
| 18.9 | 75.4 |
| 19.7 | 18.7 |
| 20.2 | 100.0 |
| 20.9 | 24.8 |
| 21.5 | 14.8 |
| 22.2 | 31.7 |
| 22.9 | 10.1 |
| 23.5 | 34.6 |
| 23.7 | 8.2 |
| 24.4 | 6.5 |
| 24.9 | 8.7 |
| 25.2 | 6.4 |
| 25.9 | 14.7 |
| 26.4 | 48.6 |
| 26.7 | 12.5 |
| 27.5 | 15.8 |
| 27.9 | 6.1 |
| 28.3 | 10.5 |
| 29.5 | 15.5 |
| 29.8 | 12.6 |
| 30.2 | 12.1 |
| 30.9 | 3.4 |
| 31.7 | 16.4 |
| 33.3 | 17.2 |
| 34.0 | 14.9 |
| 35.8 | 4.8 |
| 37.5 | 3.2 |
| 38.6 | 5.3 |

One embodiment provides a crystal form of anhydrous tris salt of 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid. In some further embodiments, the crystal form of anhydrous (anhydrate) tris salt of 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid is designated as "Form I" that is characterized according to its unique solid state signatures with respect to, for example, powder X-ray diffraction (PXRD), described herein (such as substantially as depicted in FIG. 24). In some embodiments, Form I exhibits a powder X-ray diffraction pattern comprising at least two characteristic peaks, in terms of 2θ, selected from at 3.7±0.2°; 7.3±0.2°; 8.5±0.2°; 10.1±0.2°; 14.7±0.2°; and 16.9±0.2°. In some embodiments, Form I exhibits a powder X-ray diffraction pattern comprising at least three characteristic peaks, in terms of 2θ, selected from at 3.7±0.2°; 7.3±0.2°; 8.5±0.2°; 10.1±0.2°; 14.7±0.2°; and 16.9±0.2°. In some embodiments, Form I exhibits a powder X-ray diffraction pattern comprising at least four characteristic peaks, in terms of 2θ, selected from at 3.7±0.2'; 7.3±0.2'; 8.5±0.2'; 10.1±0.2°; 14.7±0.2°; and 16.9±0.2°. In some embodiments, Form I exhibits a powder X-ray diffraction pattern comprising at least five characteristic peaks, in terms of 2θ, selected from at 3.7±0.2°; 7.3±0.2°; 8.5±0.2°; 10.1±0.2°; 14.7±0.2°; and 16.9±0.2°.

In some embodiments, Form I exhibits a powder X-ray diffraction pattern comprising characteristic peaks, in terms of 2θ, at 3.7±0.2° and 7.3±0.2°.

In some embodiments, Form I exhibits a powder X-ray diffraction pattern comprising peaks, in terms of 2θ, at 3.7±0.2°; 7.3±0.2°; and 14.7±0.2°. In some further embodiments, Form I exhibits the X-ray powder diffraction pattern further comprises at least one peak, in terms of 2θ, selected from at 8.5±0.2°; 10.1±0.2°; and 16.9±0.2°.

In some embodiments, Form I exhibits a powder X-ray diffraction pattern comprising peaks, in terms of 2θ, at 3.7±0.2°; 7.3±0.2°; 14.7±0.2°; and 16.9±0.2°.

In some embodiments, Form I exhibits a powder X-ray diffraction pattern comprising peaks, in terms of 2θ, at 3.7±0.2'; 7.3±0.2'; 8.5±0.2'; 10.1±0.2°; 14.7±0.2°; and 16.9±0.2°.

In some embodiments, Form I exhibits a powder X-ray diffraction pattern substantially as shown in FIG. 24. A list of diffraction peaks expressed in terms of the degree 2θ and relative intensities with a relative intensity of ≥3.0% is provided above in Table X1.

Examples 8 and 9

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid, DIAST-X1 (8) [from C56]; and 2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2 (9) [from C57]

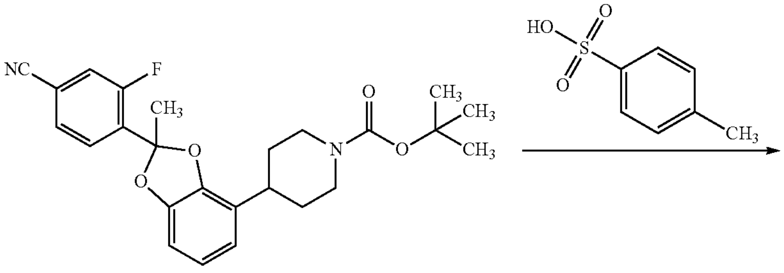

P4

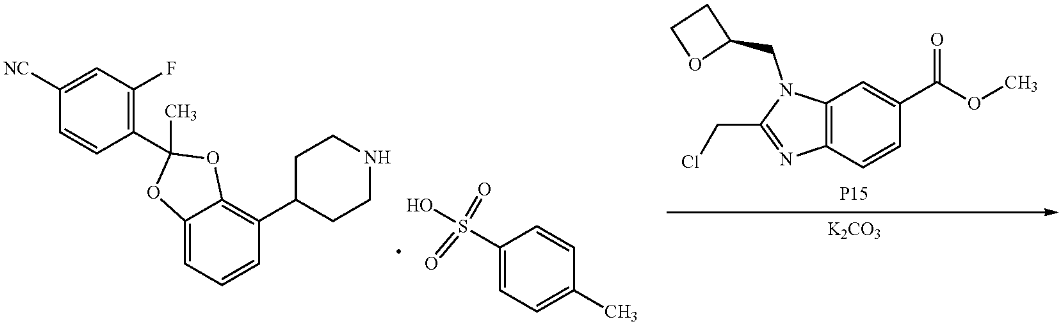

C54

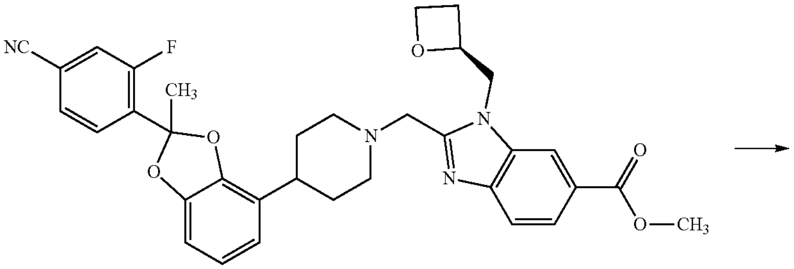

C55

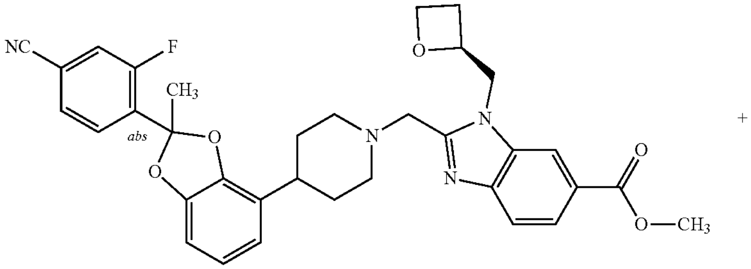

ENT-1
C56

-continued
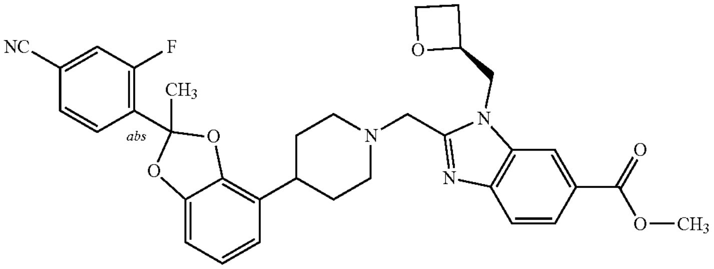
ENT-2
C57
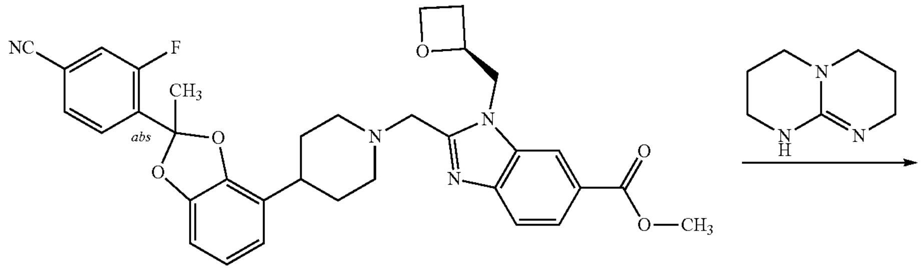
ENT-1
C56
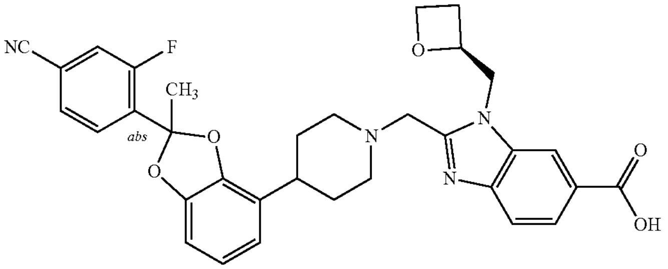
DIAST-X1
8
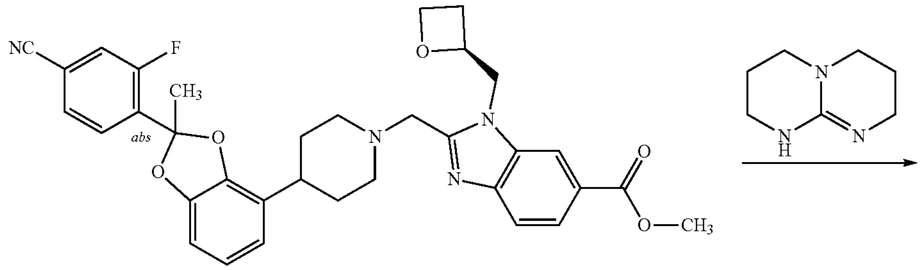
ENT-2
C57
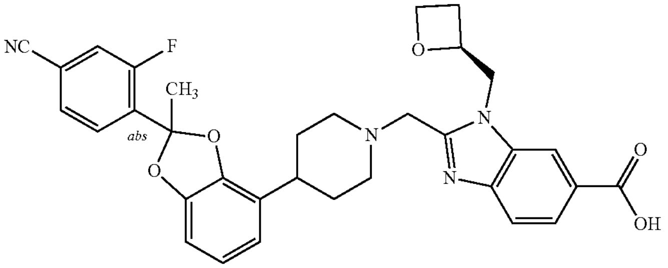
DIAST-X2
9

Step 1. Synthesis of 3-fluoro-4-[2-methyl-4-(piperidin-4-yl)-1,3-benzodioxol-2-yl]benzonitrile, p-toluenesulfonate Salt (C54)

To a solution of P4 (161 mg, 0.367 mmol) in ethyl acetate (8 mL) was added p-toluenesulfonic acid (158 mg, 0.919 mmol), and the reaction mixture was stirred at 65° C. for 16 hours. Removal of solvent in vacuo provided C54 as a dark yellow gum; this material was taken directly into the next step.

Step 2. Synthesis of methyl 2-({4-[2-(4-cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylate (C55)

To a solution of C54 (from the previous step; ≤0.367 mmol) in acetonitrile (3.7 mL) was added potassium carbonate (219 mg, 1.58 mmol), followed by P15 (115 mg, 0.390 mmol). The reaction mixture was stirred at 50° C. for 20 hours, whereupon it was diluted with ethyl acetate (10 mL) and filtered. The filter cake was washed with ethyl acetate (3×10 mL), and the combined filtrates were concentrated in vacuo. Silica gel chromatography (Gradient: 0% to 100% ethyl acetate in petroleum ether) afforded C55 as a dark yellow oil. Yield: 191.0 mg, 0.320 mmol, 87% over 2 steps. LCMS m/z 619.1 [M+Na$^+$].

Step 3. Isolation of methyl 2-({4-[2-(4-cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylate, ENT-1 (C56) and methyl 2-({4-[2-(4-cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylate, ENT-2 (C57)

Separation of C55 (191 mg, 0.320 mmol) into its component stereoisomers at the dioxolane was carried out via SFC [Column: Chiral Technologies ChiralCel OD, 5 μm; Mobile phase: 3:2 carbon dioxide/2-propanol]. The first-eluting isomer, obtained as a white gum, was designated as ENT-1 (C56). Yield: 114 mg; this material contained residual ethanol. LCMS m/z 597.1 [M+H]$^+$. Retention time 4.40 minutes (Column: Chiral Technologies ChiralCel OD-3, 4.6×100 mm, 3 μm; Mobile phase A: carbon dioxide; Mobile phase B: 2-propanol containing 0.05% diethylamine; Gradient: 5% to 40% B over 4.5 minutes, then held at 40% B for 2.5 minutes; Flow rate: 2.8 mL/minute).

The second-eluting isomer was repurified using SFC [Column: Chiral Technologies ChiralCel OD, 5 μm; Mobile phase: 55:45 carbon dioxide/(2-propanol containing 0.1% ammonium hydroxide)], to afford a colorless gum that was designated as ENT-2 (C57). Yield: 50 mg, 83.8 μmol, 26%. LCMS m/z 597.1 [M+H]$^+$. Retention time 4.74 minutes (Analytical conditions identical to those used for C56).

Step 4. Synthesis of 2-({4-[2-(4-cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid, DIAST-X1 (8) [from C56]

A solution of C56 (114 mg, 0.191 mmol) in acetonitrile (10 mL) was treated with an aqueous solution of 1,3,4,6,7,8-hexahydro-2H-pyrimido[1,2-a]pyrimidine (0.97 M, 394 μL, 0.382 mmol), and the reaction mixture was stirred at room temperature for 23 hours. More of the aqueous solution of 1,3,4,6,7,8-hexahydro-2H-pyrimido[1,2-a]pyrimidine (0.97 M, 394 μL, 0.382 mmol) was added, and stirring was continued for 6 hours, whereupon the pH was carefully adjusted to 7 to 8 by addition of 1 M hydrochloric acid. After removal of volatiles in vacuo, purification was carried out using reversed-phase HPLC (Column: Agela Durashell C18, 5 μm; Mobile phase A: 0.05% ammonium hydroxide in water; Mobile phase B: acetonitrile; Gradient: 30% to 50% B) to provide 8 as a white solid. Yield: 22.2 mg, 38.1 μmol, 20%. LCMS m/z 583.3 [M+H]$^+$. $^1$H NMR (400 MHz, methanol-$d_4$): δ 8.19 (d, J=1.4 Hz, 1H), 7.94 (dd, J=8.4, 1.5 Hz, 1H), 7.77 (dd, J=7.7, 7.7 Hz, 1H), 7.64 (dd, J=10.6, 1.6 Hz, 1H), 7.58 (d, J=8.4 Hz, 1H), 7.57 (dd, J=8.0, 1.5 Hz, 1H), 6.81-6.75 (m, 1H), 6.75-6.68 (m, 2H), 5.34-5.25 (m, 1H), 4.73 (dd, J=15.3, 3.0 Hz, 1H), 4.67-4.59 (m, 1H), 4.49 (dt, J=9.2, 6.0 Hz, 1H), 3.96 (AB quartet, $J_{AB}$=13.7 Hz, $\Delta\nu_{AB}$=41.2 Hz, 2H), 3.06 (br d, J=11 Hz, 1H), 2.95 (br d, J=11 Hz, 1H), 2.87-2.76 (m, 1H), 2.71 (tt, J=12.0, 3.9 Hz, 1H), 2.61-2.50 (m, 1H), 2.36-2.21 (m, 2H), 2.06 (s, 3H), 1.95-1.72 (m, 4H).

Step 5. Synthesis of 2-({4-[2-(4-cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2 (9) [from C57]

A solution of C57 (50 mg, 84 μmol) in acetonitrile (10 mL) was treated with an aqueous solution of 1,3,4,6,7,8-hexahydro-2H-pyrimido[1,2-a]pyrimidine (0.97 M; 173 μL, 0.168 mmol). The reaction was stirred at room temperature (about 25° C.) for 16 hours, whereupon an additional quantity of an aqueous solution of 1,3,4,6,7,8-hexahydro-2H-pyrimido[1,2-a]pyrimidine (0.97 M; 173 μL, 0.168 mmol) was added, and stirring was continued at 25° C. for 29 hours. The reaction mixture was then carefully adjusted to pH 7 to 8 by addition of 1 M hydrochloric acid; the resulting mixture was concentrated in vacuo and subjected to reversed-phase HPLC (Column: Xtimate™ C18, 5 μm; Mobile phase A: 0.05% ammonium hydroxide in water; Mobile phase B: acetonitrile; Gradient: 27% to 67% B), affording 9 as a white solid. Yield: 18.0 mg, 30.9 μmol, 37%. LCMS m/z 583.3 [M+H]$^+$. $^1$H NMR (400 MHz, methanol-$d_4$) δ 8.36-8.33 (m, 1H), 7.97 (dd, J=8.5, 1.5 Hz, 1H), 7.78 (dd, J=7.7, 7.7 Hz, 1H), 7.70-7.63 (m, 2H), 7.57 (dd, J=8.0, 1.5 Hz, 1H), 6.83-6.76 (m, 1H), 6.76-6.71 (m, 2H), 5.34-5.25 (m, 1H), 4.95-4.85 (m, 1H, assumed; partially obscured by water peak), 4.73 (dd, component of ABX pattern, J=15.3, 2.7 Hz, 1H), 4.68-4.60 (m, 1H), 4.50 (dt, J=9.2, 6.0 Hz, 1H), 4.02 (AB quartet, $J_{AB}$=13.8 Hz, $\Delta\nu_{AB}$=48.2 Hz, 2H), 3.13 (br d, J=11 Hz, 1H), 3.01 (br d, J=11.5 Hz, 1H), 2.89-2.78 (m, 1H), 2.78-2.68 (m, 1H), 2.60-2.50 (m, 1H), 2.45-2.30 (m, 2H), 2.07 (br s, 3H), 2.00-1.86 (m, 2H), 1.83 (m, 2H).

Example 10

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2 (10) [from P9]

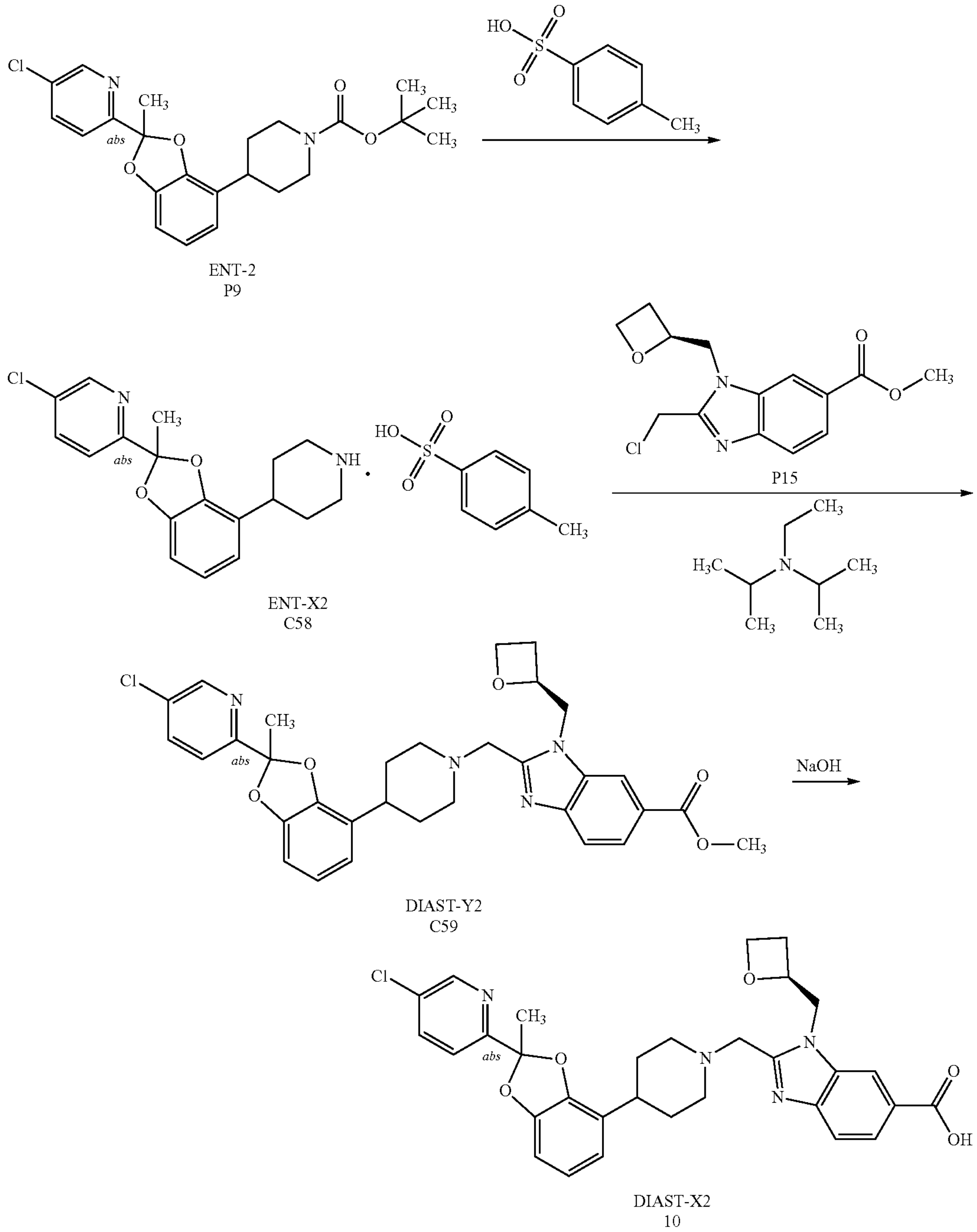

Step 1. Synthesis of 5-chloro-2-[2-methyl-4-(piperidin-4-yl)-1,3-benzodioxol-2-yl]pyridine, ENT-X2, p-toluenesulfonate Salt (C58) [from P9]

A solution of P9 (228 mg, 0.529 mmol) in ethyl acetate (2.7 mL) was treated with p-toluenesulfonic acid monohydrate (116 mg, 0.610 mmol), and the reaction mixture was heated at 50° C. for 16 hours. It was then allowed to stir at room temperature overnight, whereupon the precipitate was collected via filtration and rinsed with a mixture of ethyl acetate and heptane (1:1, 2×20 mL) to provide C58 as a white solid. Yield: 227 mg, 0.451 mmol, 85%. LCMS m/z 331.0♦ $[M+H]^+$. $^1H$ NMR (400 MHz, DMSO-$d_6$): δ 8.73 (d, J=2.4 Hz, 1H), 8.61-8.46 (br m, 1H), 8.35-8.18 (br m, 1H), 8.02 (dd, J=8.5, 2.5 Hz, 1H), 7.64 (d, J=8.5 Hz, 1H), 7.47 (d, J=7.8, 2H), 7.11 (d, J=7.8 Hz, 2H), 6.89-6.81 (m, 2H), 6.72 (pentet, J=4.0 Hz, 1H), 3.45-3.27 (m, 2H, assumed; partially obscured by water peak), 3.10-2.91 (m, 3H), 2.28 (s, 3H), 2.02 (s, 3H), 1.97-1.80 (m, 4H).

Step 2. Synthesis of methyl 2-({4-[2-(5-chloropyridin-2-yl)-2-methyl-1,3-benzodioxol-4-yl]piperidin-1-yl}methyl)-1-[(2S)-oxetan-2-ylmethyl]-1H-benzimidazole-6-carboxylate, DIAST-Y2 (C59) [from P9]

N,N-Diisopropylethylamine (0.234 mL, 1.34 mmol) was added to a solution of C58 (225 mg, 0.447 mmol) in acetonitrile (2.2 mL). After this mixture had been stirred for 5 minutes at 45° C., P15 (120 mg, 0.407 mmol) was added, and stirring was continued at 45° C. for 16 hours, whereupon P15 (11 mg, 37 μmol) was again added. After an additional 3 hours of stirring, the reaction mixture was treated with water (2.5 mL) and allowed to cool to room temperature. More water (5 mL) was added, and the resulting slurry was stirred for 2 hours, whereupon the solid was collected via filtration and washed with a mixture of acetonitrile and water (15:85, 3×5 mL) to afford C59 as an off-white solid (252 mg). This material contained some N,N-diisopropylethylamine by $^1H$ NMR analysis, and was taken directly to the following step. LCMS m/z 589.1♦ $[M+H]^+$. $^1H$ NMR (400 MHz, chloroform-d) 8.61 (d, J=2.3 Hz, 1H), 8.18 (d, J=1.5 Hz, 1H), 7.96 (dd, J=8.5, 1.5 Hz, 1H), 7.74 (d, J=8.5 Hz, 1H), 7.67 (dd, component of ABX pattern, J=8.4, 2.4 Hz, 1H), 7.59-7.51 (m, 1H), 6.82-6.75 (m, 1H), 6.74-6.66 (m, 2H), 5.28-5.19 (m, 1H), 4.75 (dd, component of ABX pattern, J=15.3, 6.0 Hz, 1H), 4.68 (dd, component of ABX pattern, J=15.3, 3.4 Hz, 1H), 4.67-4.58 (m, 1H), 4.41 (ddd, J=9.1, 5.9, 5.9 Hz, 1H), 3.95 (s, 2H), 3.95 (s, 3H), 3.07-2.89 (m, 2H), 2.81-2.69 (m, 2H), 2.53-2.41 (m, 1H), 2.37-2.22 (m, 2H), 2.05 (s, 3H), 1.93-1.74 (m, 4H).

Step 3. Synthesis of 2-({4-[2-(5-chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2 (10) [from P9]

A suspension of C59 (from the previous step; 250 mg, ≤0.407 mmol) in methanol (2 mL) was heated to 40° C., whereupon aqueous sodium hydroxide solution (1 M; 0.81 mL, 0.81 mmol) was added. After 17 hours, the reaction mixture was allowed to cool to room temperature, and the pH was adjusted to 5 to 6 with 1 M aqueous citric acid solution. The resulting mixture was diluted with water (2 mL), stirred for 2 hours, and extracted with ethyl acetate (3×5 mL); the combined organic layers were washed with saturated aqueous sodium chloride solution (5 mL), dried over sodium sulfate, filtered, and concentrated in vacuo to provide a foamy solid. This material was taken up in a mixture of ethyl acetate and heptane (1:1, 4 mL), heated to 50° C., and then allowed to cool and stir overnight. Filtration afforded 10 as a white solid. Yield: 179 mg, 0.311 mmol, 76% over 2 steps. LCMS m/z 575.1♦ $[M+H]^+$. $^1H$ NMR (400 MHz, DMSO-$d_6$) δ 12.73 (br s, 1H), 8.71 (d, J=2.5 Hz, 1H), 8.27 (d, J=1.5 Hz, 1H), 8.00 (dd, J=8.5, 2.5 Hz, 1H), 7.80 (dd, J=8.4, 1.6 Hz, 1H), 7.64 (d, J=8.4 Hz, 1H), 7.60 (d, J=8.5 Hz, 1H), 6.83-6.72 (m, 3H), 5.14-5.06 (m, 1H), 4.77 (dd, component of ABX pattern, J=15.2, 7.2 Hz, 1H), 4.63 (dd, component of ABX pattern, J=15.2, 2.8 Hz, 1H), 4.50-4.42 (m, 1H), 4.37 (ddd, J=9.0, 5.9, 5.9 Hz, 1H), 3.85 (AB quartet, $J_{AB}$=13.6 Hz, $\Delta\nu_{AB}$=71.5 Hz, 2H), 3.01 (br d, J=11.2 Hz, 1H), 2.85 (br d, J=11.2 Hz, 1H), 2.74-2.57 (m, 2H), 2.47-2.38 (m, 1H), 2.29-2.10 (m, 2H), 2.01 (s, 3H), 1.81-1.64 (m, 4H).

Synthesis of Example 10, 1,3-dihydroxy-2-(hydroxymethyl)propan-2-aminium Salt

Synthesis of 1,3-dihydroxy-2-(hydroxymethyl)propan-2-aminium 2-({4-[2-(5-chloropyridin-2-yl)-2-methyl-1,3-benzodioxol-4-yl]piperidin-1-yl}methyl)-1-[(2S)-oxetan-2-ylmethyl]-1H-benzimidazole-6-carboxylate, DIAST-X2 (10, 1,3-dihydroxy-2-(hydroxymethyl)propan-2-aminium Salt) [from P9]

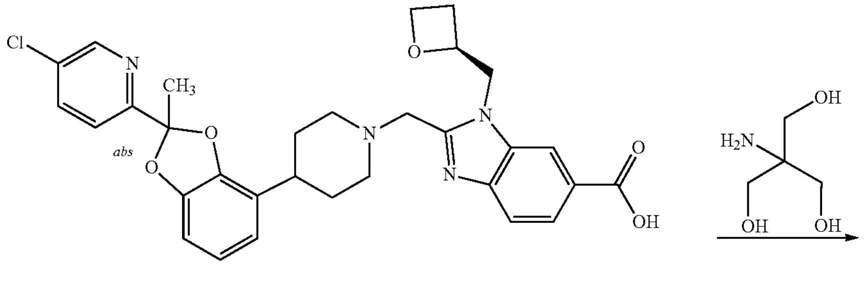

DIAST-X2
10

-continued

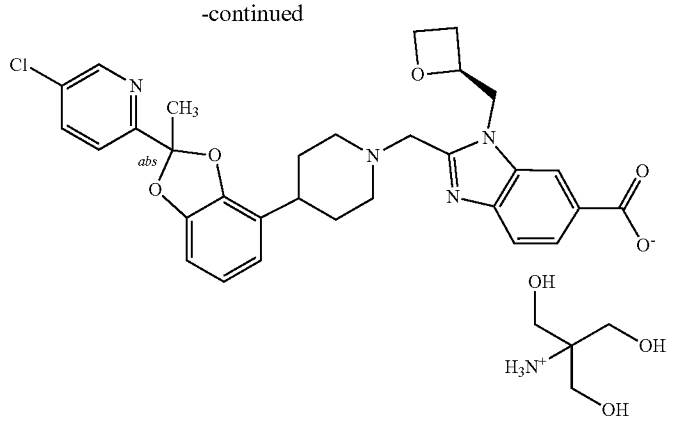

DIAST-X2
10, 1,3-dihydroxy-2-(hydroxymethyl)propan-2-aminium salt

A mixture of 10 (1.54 g, 2.68 mmol) in tetrahydrofuran (10 mL) was treated with an aqueous solution of 2-amino-2-(hydroxymethyl)propane-1,3-diol (Tris, 1.0 M; 2.81 mL, 2.81 mmol). After 24 hours, the reaction mixture was concentrated in vacuo with ethanol (2×50 mL). The residue was treated with ethanol (15 mL). After stirring for 20 hours, the solid was collected via filtration and washed with cold ethanol (5 mL) to afford 10, 1,3-dihydroxy-2-(hydroxymethyl)propan-2-aminium salt as a white solid. Yield: 1.41 g, 2.03 mmol, 76%. LCMS m/z 575.3♦ $[M+H]^+$. $^1H$ NMR (600 MHz, DMSO-$d_6$) δ 8.71 (d, J=2.5 Hz, 1H), 8.21 (br s, 1H), 8.00 (dd, J=8.5, 2.5 Hz, 1H), 7.79 (br d, J=8.4 Hz, 1H), 7.60 (d, J=8.5 Hz, 1H), 7.57 (d, J=8.4 Hz, 1H), 6.82-6.73 (m, 3H), 5.13-5.07 (m, 1H), 4.74 (dd, J=15.3, 7.2 Hz, 1H), 4.61 (dd, J=15.3, 2.9 Hz, 1H), 4.49-4.43 (m, 1H), 4.37 (ddd, J=9.0, 5.9, 5.9 Hz, 1H), 3.93 (d, J=13.6 Hz, 1H), 3.75 (d, J=13.5 Hz, 1H), 3.01 (br d, J=11.3 Hz, 1H), 2.86 (br d, J=11.4 Hz, 1H), 2.73-2.59 (m, 2H), 2.48-2.37 (m, 1H), 2.27-2.20 (m, 1H), 2.19-2.12 (m, 1H), 2.01 (s, 3H), 1.82-1.66 (m, 4H). mp=184° C. to 190° C.

Acquisition of Powder X-Ray Diffraction (PXRD) Data for Form a of Example 10, 1,3-Dihydroxy-2-(Hydroxymethyl) Propan-2-Aminium Salt (Also Known as Form a of Anhydrous Tris Salt of Compound Example 10)

The white solid of the tris salt of Example 10 was submitted for PXRD analysis and found to be a crystalline material (which is designated as Form A). Powder X-ray diffraction analysis was conducted using a Bruker AXS D8 Endeavor diffractometer equipped with a Cu radiation source. The divergence slit was set at 15 mm continuous illumination. Diffracted radiation was detected by a PSD-Lynx Eye detector, with the detector PSD opening set at 2.99 degrees. The X-ray tube voltage and amperage were set to 40 kV and 40 mA respectively. Data was collected at the Cu wavelength ($CuK_{\bar{\alpha}}$=1.5418λ) in the Theta-Theta goniometer from 3.0 to 40.0 degrees 2-Theta using a step size of 0.01 degrees and a step time of 1.0 second. The antiscatter screen was set to a fixed distance of 1.5 mm. Samples were rotated during data collection. Samples were prepared by placing them in a silicon low background sample holder and rotated during collection. Data were collected using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of ≥3% were generally chosen. Typically, the peaks which were not resolved or were consistent with noise were not selected. A typical error associated with the peak position from PXRD stated in USP up to +/−0.2° 2-Theta (USP-941). One diffraction pattern was consistently observed and is provided in FIG. 25. A list of diffraction peaks expressed in terms of the degree 2θ and relative intensities with a relative intensity of ≥3.0% is provided above in Table X2.

TABLE X2

| Angle (2 theta) | Relative Intensity (%) |
|---|---|
| 3.9 | 18.4 |
| 7.7 | 36.3 |
| 8.1 | 10.4 |
| 8.7 | 3.4 |
| 10.2 | 4.1 |
| 14.6 | 5.8 |
| 15.2 | 30.1 |
| 15.7 | 45.5 |
| 16.0 | 31.3 |
| 16.8 | 8.7 |
| 17.6 | 86.0 |
| 19.2 | 46.6 |
| 19.5 | 25.4 |
| 19.8 | 31.4 |
| 20.2 | 25.0 |
| 21.1 | 100.0 |
| 21.4 | 40.2 |
| 22.2 | 37.0 |
| 23.0 | 19.8 |
| 24.3 | 43.0 |
| 25.0 | 9.9 |
| 26.0 | 15.8 |
| 27.3 | 35.3 |
| 28.2 | 14.1 |
| 29.3 | 19.7 |
| 29.8 | 11.7 |
| 31.6 | 9.3 |
| 32.8 | 6.0 |
| 34.0 | 14.4 |
| 34.5 | 12.1 |
| 35.4 | 3.0 |
| 36.5 | 4.1 |

One embodiment provides a crystal form of anhydrous tris salt of 2-({4-[2-(5-Chloropyridin-2-yl)-2-methyl-1,3-benzodioxol-4-yl]piperidin-1-yl}methyl)-1-[(2S)-oxetan-2- ylmethyl]-1H-benzimidazole-6-carboxylic acid, DIAST-X2. In some further embodiments, the crystal form of anhydrous (anhydrate) tris salt of 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, is designated as "Form A" that is characterized according to its unique solid state signatures with respect to, for example, powder X-ray diffraction (PXRD), described herein (such as substantially as depicted in FIG. 25). In some embodiments, Form A exhibits a powder X-ray diffraction pattern comprising at least two characteristic peaks, in terms of 2θ, selected from at 7.7±0.2°; 15.2±0.2°; 15.7±0.2°; and 17.6±0.2°. In some embodiments, Form A exhibits a powder X-ray diffraction pattern comprising at least three characteristic peaks, in terms of 2θ, selected from at 7.7±0.2°; 15.2±0.2°; 15.7±0.2°; and 17.6±0.2°. In some embodiments, Form A exhibits a powder X-ray diffraction pattern comprising characteristic peaks, in terms of 2θ, selected from at 7.7±0.2°; 15.2±0.2°; 15.7±0.2°; and 17.6±0.2°.

In some embodiments, Form I exhibits a powder X-ray diffraction pattern comprising characteristic peaks, in terms of 2θ, at 7.7±0.2° and 17.6±0.2°.

In some embodiments, Form A exhibits a powder X-ray diffraction pattern comprising peaks, in terms of 2θ, at 7.7±0.2°; 15.2±0.2°; and 17.6±0.2°.

In some embodiments, Form I exhibits a powder X-ray diffraction pattern comprising peaks, in terms of 2θ, at 7.7±0.2°; 15.2±0.2°; and 15.7±0.2°.

In some embodiments, Form I exhibits a powder X-ray diffraction pattern comprising peaks, in terms of 2θ, at 7.7±0.2°; 15.2±0.2°; 15.7±0.2°; and 17.6±0.2°.

In some embodiments, Form A exhibits a powder X-ray diffraction pattern substantially as shown in FIG. 25. A list of diffraction peaks expressed in terms of the degree 20 and relative intensities with a relative intensity of ≥3.0% is provided above in Table X2.

As is well known in the art of powder diffraction, the relative intensities of the peaks (reflections) can vary, depending upon the sample preparation technique, the sample mounting procedure and the particular instrument employed. Moreover, instrument variation and other factors can affect the 2-theta values. Therefore, the XRPD peak assignments can vary by plus or minus about 0.2°.

Example 11

1-(2-Methoxyethyl)-2-({4-[2-methyl-2-(pyridin-3-yl)-1,3-benzodioxol-4-yl]piperidin-1-yl}methyl)-1H-benzimidazole-6-carboxylic acid, formate Salt (11)

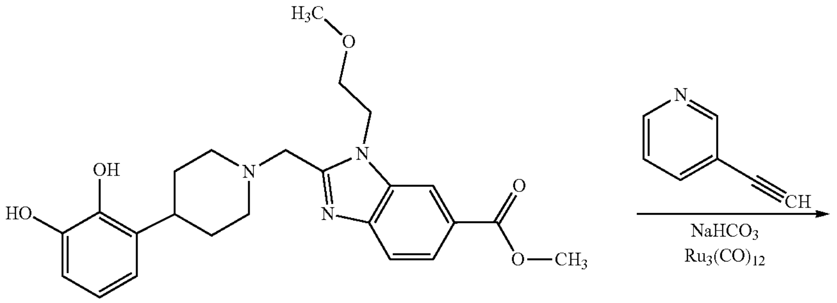

P14

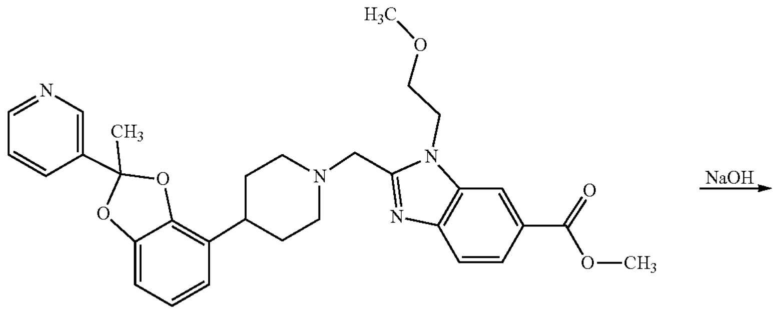

C60

-continued

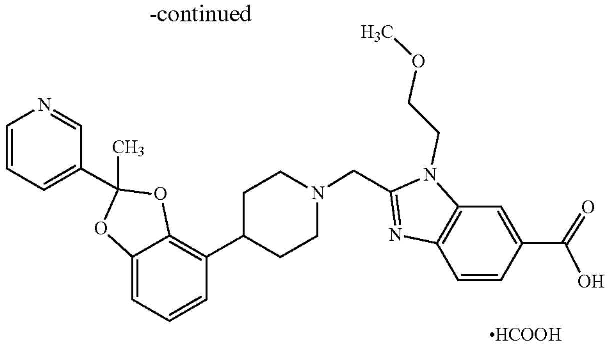

•HCOOH

11

This entire synthetic sequence was carried out in library format.

Step 1. Synthesis of methyl 1-(2-methoxyethyl)-2-({4-[2-methyl-2-(pyridin-3-yl)-1,3-benzodioxol-4-yl]piperidin-1-yl}methyl)-1H-benzimidazole-6-carboxylate (C60)

A mixture of P14 (44 mg, 100 μmol) and 3-ethynylpyridine (21 mg, 200 μmol) in toluene (800 μL) was treated with sodium bicarbonate (100 μmol), followed by triruthenium dodecacarbonyl (6 mg, 9 μmol). The reaction vial was then capped and shaken at 120° C. for 16 hours. Removal of solvent using a Speedvac® concentrator provided C60, which was taken directly into the following step.

Step 2. Synthesis of 1-(2-methoxyethyl)-2-({4-[2-methyl-2-(pyridin-3-yl)-1,3-benzodioxol-4-yl]piperidin-1-yl}methyl)-1H-benzimidazole-6-carboxylic acid, formate Salt (11)

An aqueous solution of sodium hydroxide (1.0 M; 200 μL, 200 μmol) was added to a solution of C60 (from the previous step, 100 μmol) in a mixture of methanol (400 μL) and tetrahydrofuran (400 μL). The reaction vial was capped and shaken at 80° C. for 16 hours, whereupon the reaction mixture was evaporated using a Speedvac® concentrator, and purified using reversed-phase HPLC (Column: Agela Durashell C18, 5 μm; Mobile phase A: 0.225% formic acid in water; Mobile phase B: acetonitrile; Gradient: 12% to 52% B) to afford 11. Yield: 2.2 mg, 4.2 μmol, 4% over 2 steps. LCMS m/z 529 $[M+H]^+$. Retention time: 2.47 minutes (Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute).

Example 12

2-({4-[2-(4-Chloro-2-fluorophenyl)-2-methyl-1,3-benzodioxol-4-yl]piperidin-1-yl}methyl)-1-[2-(dimethylamino)ethyl]-1H-benzimidazole-6-carboxylic acid (12)

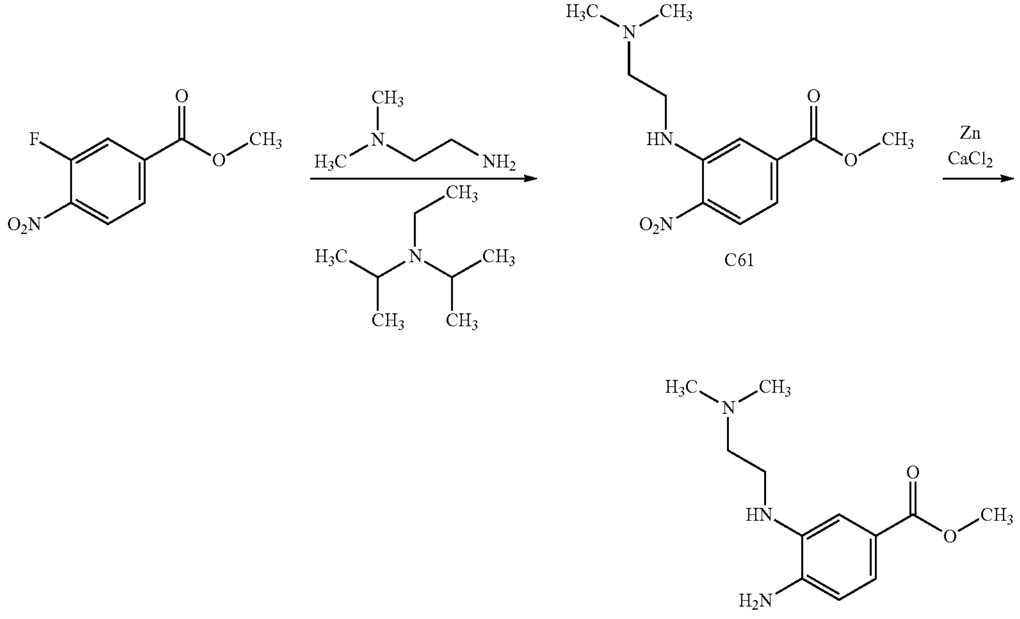

C61

C62

-continued
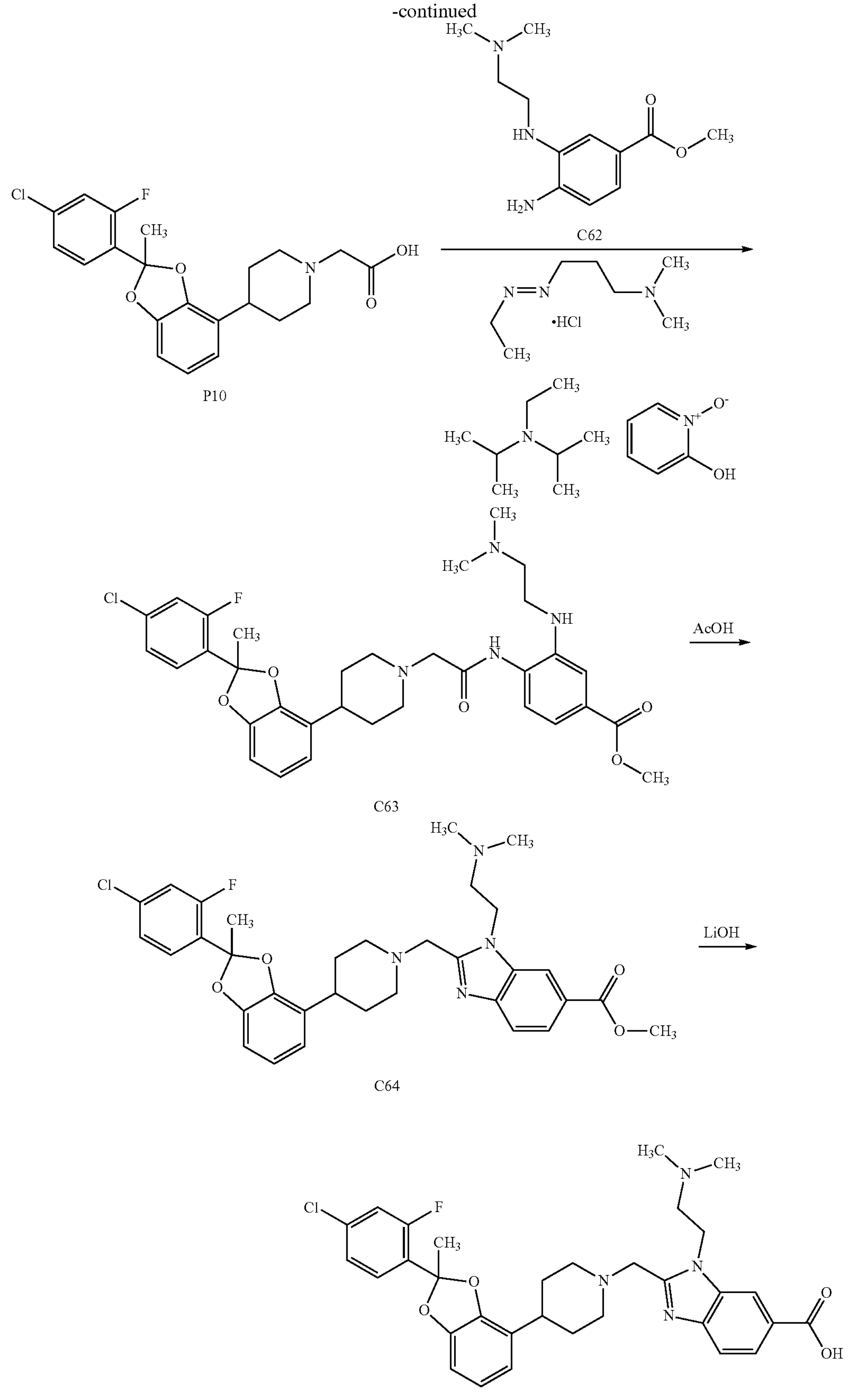
12

This entire synthetic sequence was carried out in library format.

Step 1. Synthesis of methyl 3-{[2-(dimethylamino) ethyl]amino}-4-nitrobenzoate (C61)

Methyl 3-fluoro-4-nitrobenzoate (0.2 M solution in N,N-dimethylformamide; 1 mL, 200 μmol) was treated with N,N-dimethylethane-1,2-diamine (18 mg, 200 μmol) and N,N-diisopropylethylamine (78 mg, 600 μmol). The reaction vial was then capped and shaken at 50° C. for 16 hours, whereupon the reaction mixture was evaporated using a Speedvac® concentrator to afford C61. This material was taken directly to the following step.

Step 2. Synthesis of methyl 4-amino-3-{[2-(dimethylamino)ethyl]amino}benzoate (C62)

Zinc dust was activated using dilute hydrochloric acid. Methanol (2 mL) was added to C61 (from the previous step, 200 μmol), followed by an aqueous solution of calcium chloride (1.0 M; 200 μL, 200 μmol) and the activated zinc dust (130 mg, 2.0 mmol). The reaction vial was capped and shaken at 70° C. for 16 hours, whereupon the reaction mixture was filtered. The filtrate was concentrated using a Speedvac® concentrator, and the residue was taken up in water (2 mL) and then extracted with ethyl acetate (2×3 mL). The combined organic layers were evaporated using a Speedvac® concentrator to afford C62 (estimated to be 150 μmol), which was used directly in the next step.

Step 3. Synthesis of methyl 4-[({4-[2-(4-chloro-2-fluorophenyl)-2-methyl-1,3-benzodioxol-4-yl]piperidin-1-yl}acetyl)amino]-3-{[2-(dimethylamino)ethyl]amino}benzoate (C63)

Compound P10 (41 mg, 100 μmol) was added to C62 (from the previous step, approximately 150 μmol), and the mixture was treated with an N,N-dimethylacetamide solution of 2-hydroxypyridine 1-oxide and 1-[3-(dimethylamino)propyl]-3-ethylcarbodiimide hydrochloride (0.1 M in each; 1 mL, 100 μmol of each). N,N-Diisopropylethylamine (39 mg, 300 μmol) was then added, and the reaction vial was capped and shaken at 50° C. for 16 hours. The reaction mixture was then concentrated using a Speedvac® concentrator and purified using preparative thin-layer chromatography to provide C63, which was advanced directly to the following step.

Step 4. Synthesis of methyl 2-({4-[2-(4-chloro-2-fluorophenyl)-2-methyl-1,3-benzodioxol-4-yl]piperidin-1-yl}methyl)-1-[2-(dimethylamino)ethyl]-1H-benzimidazole-6-carboxylate (C64)

A mixture of acetic acid (500 μL) and C63 (from the previous step, ≤100 μmol) was shaken in a capped vial at 150° C. for 2 hours, whereupon the reaction mixture was evaporated using a Speedvac® concentrator. The resulting C64 was advanced directly to the following step.

Step 5. Synthesis of 2-({4-[2-(4-chloro-2-fluorophenyl)-2-methyl-1,3-benzodioxol-4-yl]piperidin-1-yl}methyl)-1-[2-(dimethylamino)ethyl]-1H-benzimidazole-6-carboxylic acid (12)

A solution of C64 (from the previous step, 100 μmol) in ethanol (500 μL) was treated with an aqueous solution of lithium hydroxide (2.0 M; 500 μL, 1 mmol), and the reaction mixture was shaken at 50° C. for 2 hours in a sealed vial. After the pH of the mixture had been adjusted to 7 by addition of 1.0 M hydrochloric acid, the resulting mixture was concentrated using a Speedvac® concentrator, and then purified via reversed-phase HPLC [Column: Agela Durashell C18, 5 μm; Mobile phase A: ammonium hydroxide in water (pH 10); Mobile phase B: acetonitrile; Gradient: 25% to 65% B] to afford 12. Yield: 7.0 mg, 12 μmol, 12% over 3 steps. LCMS m/z 593 $[M+H]^+$. Retention time: 2.45 minutes (Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 10% to 100% B over 4.0 minutes; Flow rate: 0.8 mL/minute).

Example 13

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid (13)

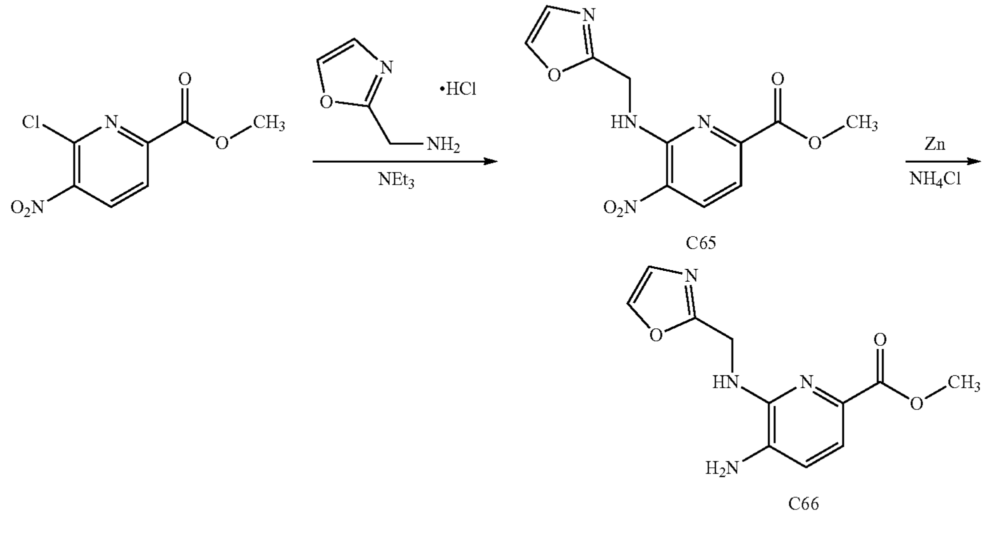

C65

C66

-continued

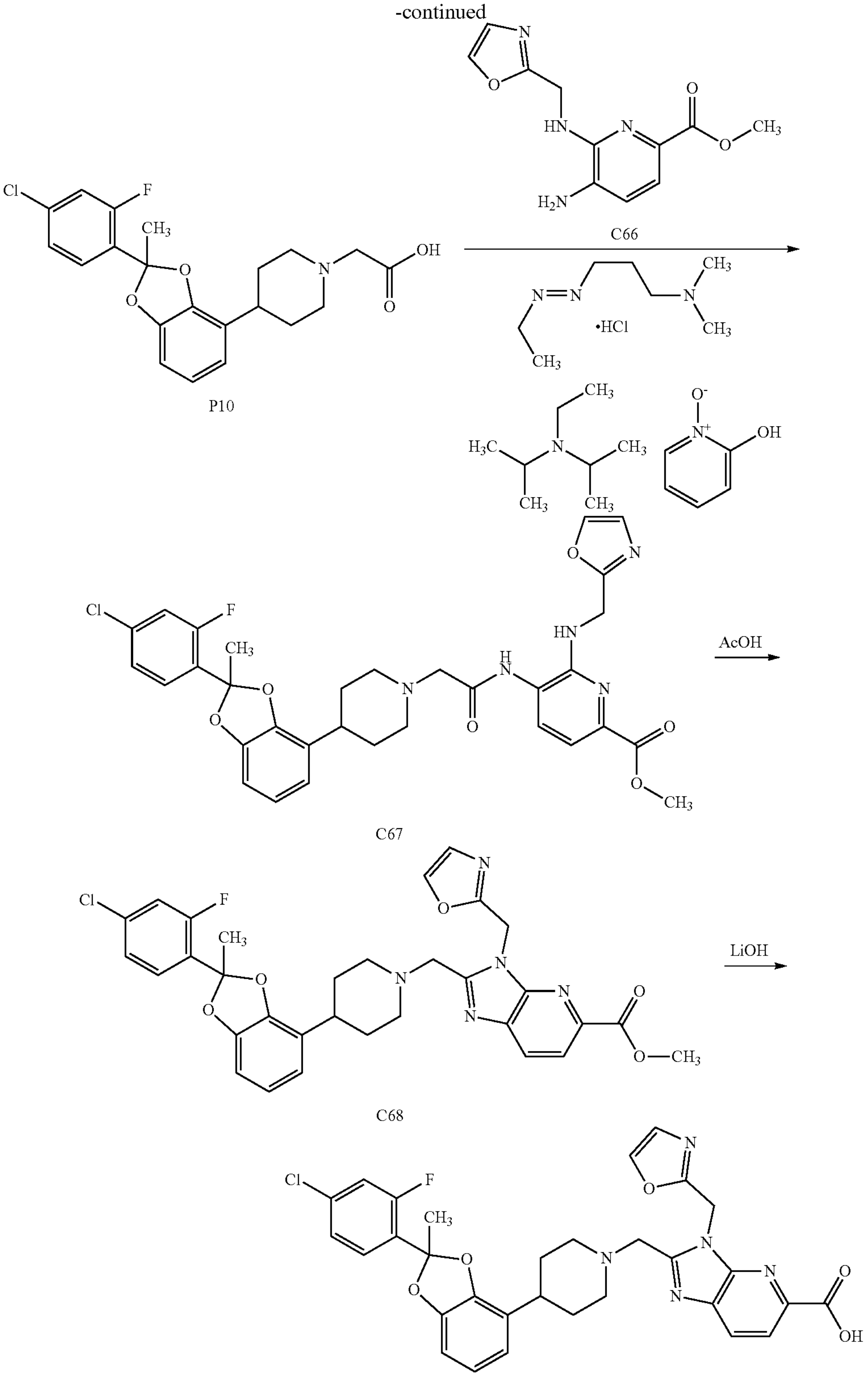

P10 C66 C67 C68 13

Step 1. Synthesis of methyl 6-[(1,3-oxazol-2-ylmethyl)amino]-5-nitropyridine-2-carboxylate (C65)

Triethylamine (532 mg, 5.26 mmol) was added to a suspension of 1-(1,3-oxazol-2-yl)methanamine, hydrochloride salt (236 mg, 1.75 mmol) and methyl 6-chloro-5-nitropyridine-2-carboxylate (386 mg, 1.78 mmol) in tetrahydrofuran (5 mL). After the reaction mixture had been stirred at 25° C. for 14 hours, it was poured into water (30 mL) and extracted with dichloromethane (2×50 mL). The combined organic layers were dried over magnesium sulfate, filtered, and concentrated in vacuo; silica gel chromatography (Gradient: 0% to 5% methanol in dichloromethane) afforded C65 as a yellow solid. Yield: 310 mg, 1.11 mmol, 63%. LCMS m/z 278.7 $[M+H]^+$. $^1H$ NMR (400 MHz, chloroform-d) δ 8.69-8.61 (br m, 1H), 8.58 (d, J=8.4 Hz, 1H), 7.65 (d, J=0.8 Hz, 1H), 7.46 (d, J=8.4 Hz, 1H), 7.11 (d, J=1.0 Hz, 1H), 5.07 (d, J=5.3 Hz, 2H), 3.97 (s, 3H).

The remainder of this synthetic sequence was carried out in library format.

Step 2. Synthesis of methyl 5-amino-6-[(1,3-oxazol-2-ylmethyl)amino]pyridine-2-carboxylate (C66)

Aqueous ammonium chloride solution (5.0 M; 400 μL, 2.0 mmol), followed by activated zinc (131 mg, 2.0 mmol), was added to a solution of C65 (56 mg, 200 μmol) in methanol (2.0 mL). The reaction vial was then capped and shaken at 30° C. for 16 hours, whereupon the reaction mixture was filtered. The filtrate was concentrated using a Speedvac® concentrator, then mixed with water (1.0 mL) and extracted with dichloromethane (3×1.0 mL); the combined organic layers were evaporated using a Speedvac® concentrator to provide C66, which was taken directly into the following step.

Step 3. Synthesis of methyl 5-[({4-[2-(4-chloro-2-fluorophenyl)-2-methyl-1,3-benzodioxol-4-yl]piperidin-1-yl}acetyl)amino]-6-[(1,3-oxazol-2-ylmethyl)amino]pyridine-2-carboxylate (C67)

A mixture of P10 (81 mg, 200 μmol) and C66 (from the previous step, 200 μmol) was mixed with N,N-dimethylacetamide and then treated with N,N-diisopropylethylamine (100 μL, 600 μmol). A solution containing 1-[3-(dimethylamino)propyl]-3-ethylcarbodiimide hydrochloride (0.24 M) and 2-hydroxypyridine 1-oxide (0.1 M) in N,N-dimethylacetamide (1.0 mL, containing 240 μmol 1-[3-(dimethylamino)propyl]-3-ethylcarbodiimide hydrochloride and 100 μmol 2-hydroxypyridine 1-oxide) was added, and the reaction vial was capped and shaken at 50° C. for 16 hours. Volatiles were then removed using a Speedvac® concentrator, and the residue was subjected to preparative thin-layer chromatography to afford C67, which was advanced directly to the next step.

Step 4. Synthesis of methyl 2-({4-[2-(4-chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylate (C68)

A mixture of acetic acid (1.0 mL) and C67 (from the previous step, 200 μmol) was shaken at 150° C. for 2 hours, whereupon the reaction mixture was evaporated using a Speedvac® concentrator. The resulting C68 was used directly in the following step.

Step 5. Synthesis of 2-({4-[2-(4-chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid (13)

Aqueous lithium hydroxide solution (2.0 M; 1.0 mL, 2.0 mmol) was added to a mixture of C68 (from the previous step, ≤200 μmol) in tetrahydrofuran (1.0 mL). After addition of methanol (500 μL), the reaction vial was capped and shaken at 50° C. for 16 hours. After removal of volatiles using a Speedvac® concentrator, dimethyl sulfoxide (1.0 mL) was added, and the pH was adjusted to 7 to 8 with concentrated hydrochloric acid. The resulting mixture was purified using reversed-phase HPLC [Column: Agela Durashell C18, 5 μm; Mobile phase A: ammonium hydroxide in water (pH 10); Mobile phase B: acetonitrile; Gradient: 24% to 64% 13] to afford 13. Yield: 3.9 mg, 6.5 μmol, 3% over 4 steps. LCMS m/z 604 $[M+H]^+$. Retention time: 3.14 minutes (Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute).

Example 14

2-({4-[(2S)-2-(4-Chloro-2-fluorophenyl)-2-methyl-1,3-benzodioxol-4-yl]piperidin-1-yl}methyl)-1-methyl-1H-benzimidazole-6-carboxylic acid (14)

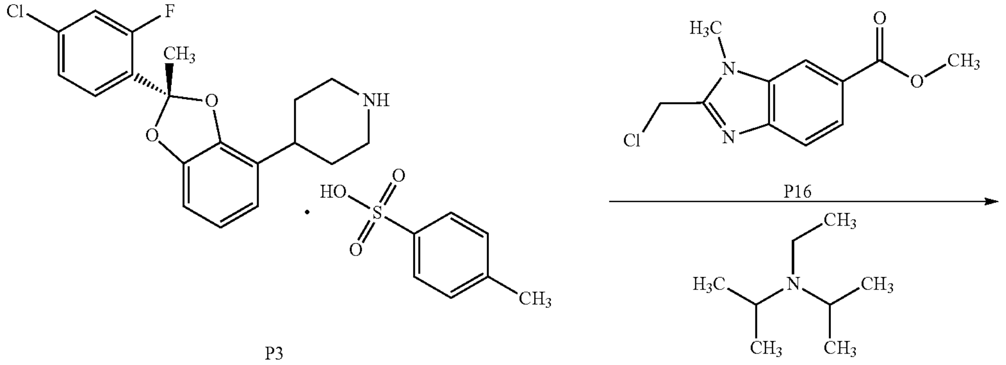

P3

-continued

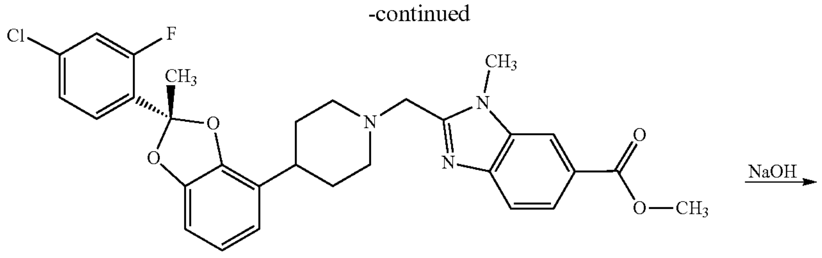

C69

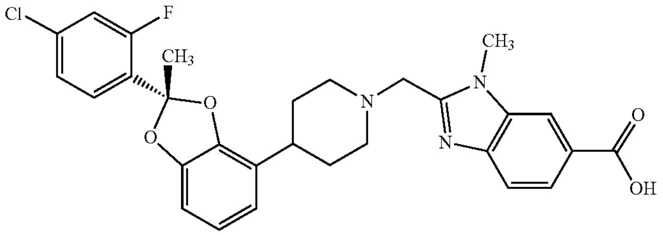

14

Step 1. Synthesis of methyl 2-({4-[(2S)-2-(4-chloro-2-fluorophenyl)-2-methyl-1,3-benzodioxol-4-yl]piperidin-1-yl}methyl)-1-methyl-1H-benzimidazole-6-carboxylate (C69)

N,N-Diisopropylethylamine (683 μL, 3.92 mmol), was added to a mixture of P3 (680 mg, 1.31 mmol) in acetonitrile (5.2 mL); this was allowed to stir for 5 minutes at 45° C., whereupon P16 (319 mg, 1.34 mmol) was added. Stirring was continued at 45° C. for 2.75 hours, and then water (6 mL) was added before allowing the reaction mixture to cool to room temperature and stir for 30 minutes. Solids were collected via filtration and washed with a mixture of acetonitrile and water (1:4, 3×5 mL) to afford C69 as a white solid. Yield: 635 mg, 1.15 mmol, 88%. LCMS m/z 550.1♦ $[M+H]^+$. $^1H$ NMR (400 MHz, chloroform-d) δ 8.15-8.12 (m, 1H), 7.97 (dd, J=8.5, 1.6 Hz, 1H), 7.74 (d, J=8.5 Hz, 1H), 7.50 (dd, J=8.2, 8.2 Hz, 1H), 7.16-7.07 (m, 2H), 6.79-6.73 (m, 1H), 6.72-6.65 (m, 2H), 3.98 (s, 3H), 3.96 (s, 3H), 3.88 (s, 2H), 3.04-2.93 (m, 2H), 2.76-2.66 (m, 1H), 2.37-2.25 (m, 2H), 2.04 (br s, 3H), 1.89-1.78 (m, 4H).

Step 2. Synthesis of 2-({4-[(2S)-2-(4-chloro-2-fluorophenyl)-2-methyl-1,3-benzodioxol-4-yl]piperidin-1-yl}methyl)-1-methyl-1H-benzimidazole-6-carboxylic acid (14)

A mixture of C69 (600 mg, 1.09 mmol) in methanol (11 mL) was heated to 45° C., and then treated with aqueous sodium hydroxide solution (1 M; 2.2 mL, 2.2 mmol). After 24 hours, the reaction mixture was adjusted to pH 5 to 6 via addition of aqueous citric acid (1 M; 1.1 mL), and then diluted with water (10 mL). The resulting mixture was allowed to cool to room temperature and stir for 1 hour, whereupon the precipitated solid was collected via filtration and washed with a mixture of methanol and water (1:4; 3×5 mL). This afforded 14 as a white solid. Yield: 535 mg, 0.998 mmol, 92%. LCMS m/z 536.1♦ $[M+H]^+$. $^1H$ NMR (400 MHz, DMSO-$d_6$) δ 8.16 (d, J=1.5 Hz, 1H), 7.81 (dd, J=8.4, 1.6 Hz, 1H), 7.64 (d, J=8.4 Hz, 1H), 7.59-7.52 (m, 2H), 7.33 (dd, J=8.3, 2.1 Hz, 1H), 6.81-6.70 (m, 3H), 3.94 (s, 3H), 3.84 (s, 2H), 3.01-2.91 (m, 2H), 2.70-2.59 (m, 1H), 2.28-2.16 (m, 2H), 2.02 (s, 3H), 1.73 (m, 4H).

Examples 15 and 16
2-{6-[2-(4-Chloro-2-fluorophenyl)-2-methyl-1,3-benzodioxol-4-yl]-6-azaspiro[2.5]oct-1-yl}-1-(2-methoxyethyl)-1H-benzimidazole-6-carboxylic acid, DIAST-X1, trifluoroacetate Salt (15) [from P18 via C71]; and 2-{6-[2-(4-Chloro-2-fluorophenyl)-2-methyl-1,3-benzodioxol-4-yl]-6-azaspiro[2.5]oct-1-yl}-1-(2-methoxyethyl)-1H-benzimidazole-6-carboxylic acid, DIAST-X2, trifluoroacetate Salt (16) [from P18 via C72]
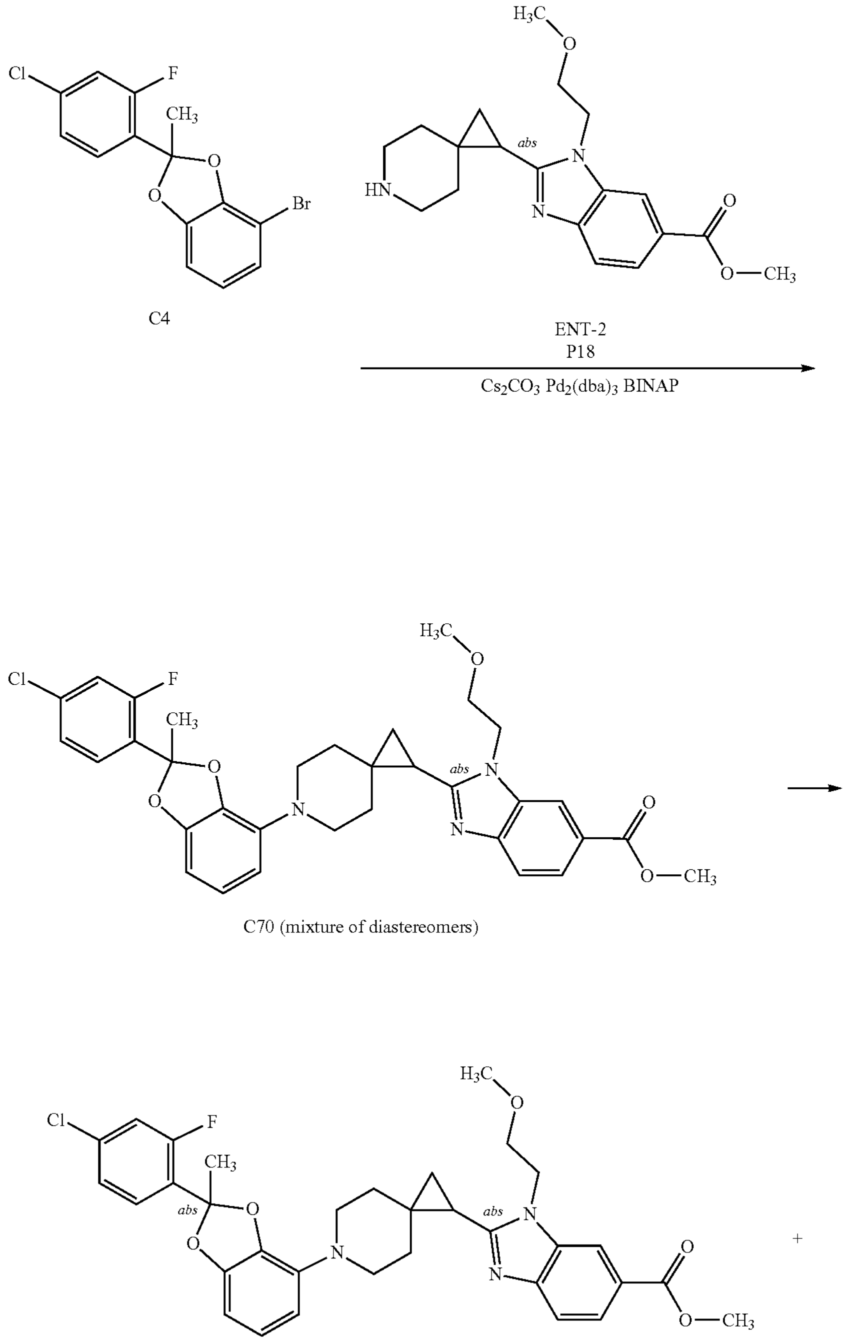
DIAST-Y1
C71 (from P18)

-continued
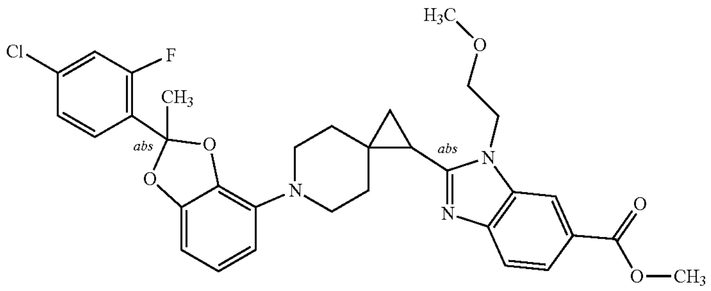
DIAST-Y2
C72 (from P18)
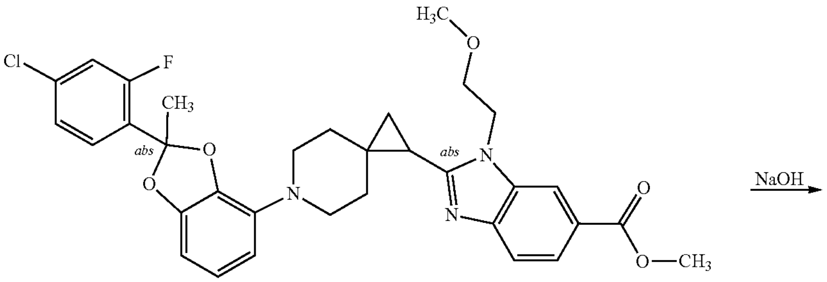
DIAST-Y1
C71 (from P18)
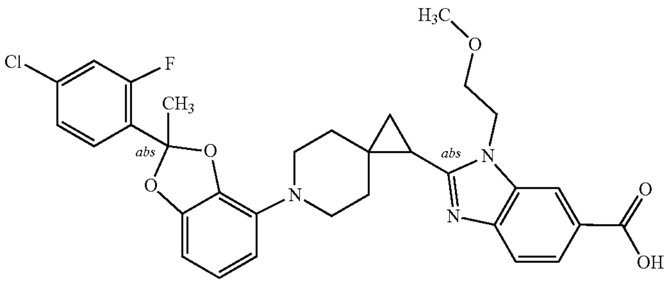
$\cdot CF_3COOH$
DIAST-X1
15
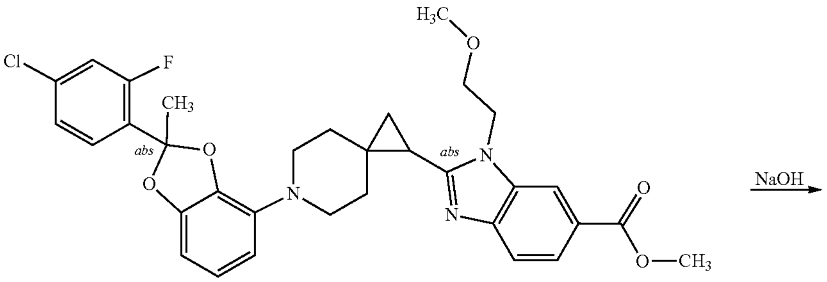
DIAST-Y2
C72 (from P18)

-continued

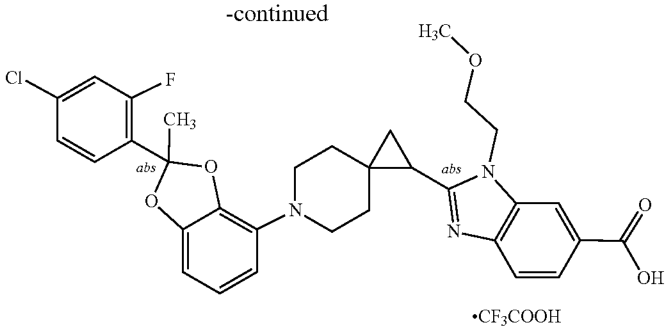

DIAST-X2
16

Step 1. Synthesis of methyl 2-{6-[2-(4-chloro-2-fluorophenyl)-2-methyl-1,3-benzodioxol-4-yl]-6-azaspiro[2.5]oct-1-yl}-1-(2-methoxyethyl)-1H-benzimidazole-6-carboxylate (C70) [from P18]

A mixture of P18 (240 mg, 0.699 mmol), C4 (275 mg, 0.800 mmol), cesium carbonate (455 mg, 1.40 mmol), tris(dibenzylideneacetone)dipalladium(0) (40.0 mg, 43.7 μmol), and 1,1'-binaphthalene-2,2'-diylbis(diphenylphosphane) (BINAP; 52.2 mg, 83.8 μmol) in toluene (5 mL) was degassed with nitrogen for 5 minutes and then stirred at 90° C. for 16 hours. The reaction mixture was filtered, and the filtrate was concentrated in vacuo; preparative thin-layer chromatography (Eluent: 1:1 petroleum ether/ethyl acetate) afforded C70, a mixture of diastereomers, as a yellow oil. Yield: 165 mg, 0.272 mmol, 39%. LCMS m/z 628.1♦ [M+Na$^+$].

Step 2. Isolation of methyl 2-{6-[2-(4-chloro-2-fluorophenyl)-2-methyl-1,3-benzodioxol-4-yl]-6-azaspiro[2.5]oct-1-yl}-1-(2-methoxyethyl)-1H-benzimidazole-6-carboxylate, DIAST-Y1 (C71) [from P18]; and methyl 2-{6-[2-(4-chloro-2-fluorophenyl)-2-methyl-1,3-benzodioxol-4-yl]-6-azaspiro[2.5]oct-1-yl}-1-(2-methoxyethyl)-1H-benzimidazole-6-carboxylate, DIAST-Y2 (C72) [from P18]

Separation of the stereoisomers at the dioxolane in C70 (165 mg, 0.272 mmol) was carried out using SFC [Column: Chiral Technologies Chiralpak AD, 10 μm; Mobile phase: 65:35 carbon dioxide/(ethanol containing 0.1% ammonium hydroxide)]. The first-eluting isomer was designated as DIAST-Y1 (C71), and the second-eluting isomer as DIAST-Y2 (C72); both were isolated as white solids.

C71 Yield: 55.0 mg, 90.7 μmol, 33%. LCMS m/z 605.9♦ [M+H]$^+$. Retention time 4.47 minutes (Column: Chiral Technologies Chiralpak AD-3, 4.6×100 mm, 3 μm; Mobile phase A: carbon dioxide; Mobile phase B: ethanol containing 0.05% diethylamine; Gradient: 5% to 40% B over 4.5 minutes, then held at 40% B for 2.5 minutes; Flow rate: 2.8 mL/minute).

C72 Yield: 58.0 mg, 95.7 μmol, 35%. LCMS m/z 628.0♦ [M+Na$^+$]. Retention time 4.88 minutes (Analytical conditions identical to those used for C71).

Step 3. Synthesis of 2-{6-[2-(4-chloro-2-fluorophenyl)-2-methyl-1,3-benzodioxol-4-yl]-6-azaspiro[2.5]oct-1-yl}-1-(2-methoxyethyl)-1H-benzimidazole-6-carboxylic acid, DIAST-X1, trifluoroacetate Salt (15) [from P18 via C71]

To a solution of C71 (55.0 mg, 90.7 μmol) in a mixture of methanol (2.0 mL) and tetrahydrofuran (1.0 mL) was added an aqueous solution of sodium hydroxide (3 M; 1.0 mL, 3.0 mmol). After the reaction mixture had been stirred at 20° C. for 2 hours, the pH was adjusted to 7 by addition of 1 M hydrochloric acid, and the resulting mixture was extracted with a mixture of dichloromethane and methanol (10:1, 3×30 mL). The combined organic layers were dried over magnesium sulfate, filtered, and concentrated in vacuo. Reversed-phase HPLC (Column: Boston Green ODS, 5 μm; Mobile phase A: 0.1% trifluoroacetic acid in water; Mobile phase B: acetonitrile; Gradient: 10% to 95% B) provided 15 as a white solid. Yield: 35.8 mg, 50.7 μmol, 56%. LCMS m/z 592.3♦ [M+H]$^+$. $^1$H NMR (400 MHz, methanol-$d_4$) δ 8.46 (s, 1H), 8.21 (d, J=8.6 Hz, 1H), 7.78 (d, J=8.6 Hz, 1H), 7.54 (dd, J=8.3, 8.3 Hz, 1H), 7.16-7.08 (m, 2H), 6.76 (dd, J=8.2, 8.1 Hz, 1H), 6.55-6.47 (m, 2H), 4.9-4.70 (m, 2H, assumed; partially obscured by water peak), 3.82 (t, J=4.9 Hz, 2H), 3.66-3.56 (m, 1H), 3.50-3.41 (m, 1H), 3.19-3.09 (m, 1H), 3.15 (s, 3H), 3.08-2.99 (m, 1H), 2.63-2.57 (m, 1H), 2.27-2.17 (m, 1H), 2.01 (s, 3H), 1.76-1.66 (m, 2H), 1.62-1.50 (m, 2H), 1.35-1.26 (m, 1H).

Step 4. Synthesis of 2-{6-[2-(4-chloro-2-fluorophenyl)-2-methyl-1,3-benzodioxol-4-yl]-6-azaspiro[2.5]oct-1-yl}-1-(2-methoxyethyl)-1H-benzimidazole-6-carboxylic acid, DIAST-X2, trifluoroacetate Salt (16) [from P18 via C72]

To a solution of C72 (58.0 mg, 95.7 μmol) in a mixture of methanol (2.0 mL) and tetrahydrofuran (1.0 mL) was added an aqueous solution of sodium hydroxide (3 M; 1.0 mL, 3.0 mmol). After the reaction mixture had been stirred at 20° C. for 2 hours, the pH was adjusted to 7 by addition of 1 M hydrochloric acid, and the resulting mixture was extracted with a mixture of dichloromethane and methanol (10:1, 3×30 mL). The combined organic layers were dried over magnesium sulfate, filtered, and concentrated in vacuo. Reversed-phase HPLC (Column: Boston Green ODS, 5 μm; Mobile phase A: 0.1% trifluoroacetic acid in water; Mobile phase B: acetonitrile; Gradient: 35% to 95% B) provided 16 as a white solid. Yield: 33.4 mg, 47.3 μmol, 49%. LCMS m/z 592.2♦ $[M+H]^+$. $^1H$ NMR (400 MHz, methanol-$d_4$) δ 8.53-8.50 (m, 1H), 8.25 (dd, J=8.6, 1.4 Hz, 1H), 7.80 (br d, J=8.6 Hz, 1H), 7.57 (dd, J=8.4, 8.2 Hz, 1H), 7.25 (dd, J=10.8, 2.0 Hz, 1H), 7.19 (br dd, J=8.4, 2.1 Hz, 1H), 6.77 (dd, J=8.2, 8.1 Hz, 1H), 6.55-6.50 (m, 2H), 4.9-4.72 (m, 2H, assumed; partially obscured by water peak), 3.93-3.80 (m, 2H), 3.68-3.58 (m, 1H), 3.41-3.3 (m, 1H, assumed; partially obscured by solvent peak), 3.25 (s, 3H), 3.22-3.12 (m, 1H), 3.07-2.97 (m, 1H), 2.67 (dd, J=8.3, 5.8 Hz, 1H), 2.28-2.17 (m, 1H), 2.01 (d, J=1.0 Hz, 3H), 1.86-1.71 (m, 2H), 1.69-1.56 (m, 2H), 1.36-1.26 (m, 1H).

Examples 17 and 18

Ammonium 2-({4-[2-(4-chloro-2-fluorophenyl)-2-methyl-1,3-benzodioxol-4-yl]piperidin-1-yl}methyl)-1-[(1-ethyl-1H-imidazol-5-yl)methy]-1H-benzimidazole-6-carboxylate, ENT-1 (17) and Ammonium 2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylate, ENT-2 (18)

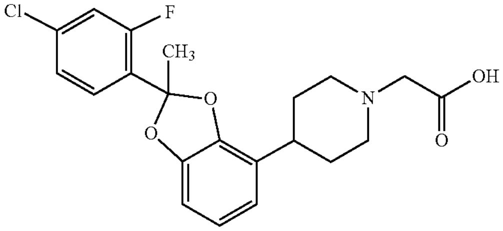

P10

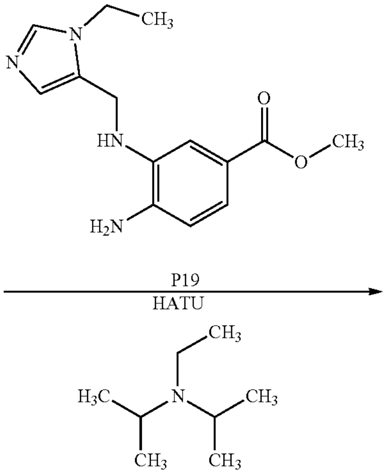

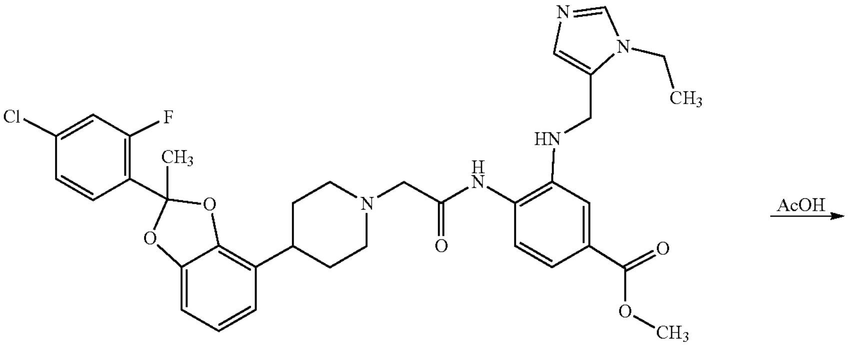

C73

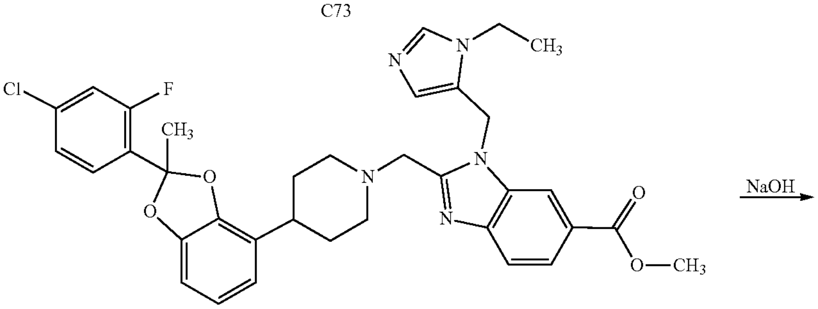

C74

-continued

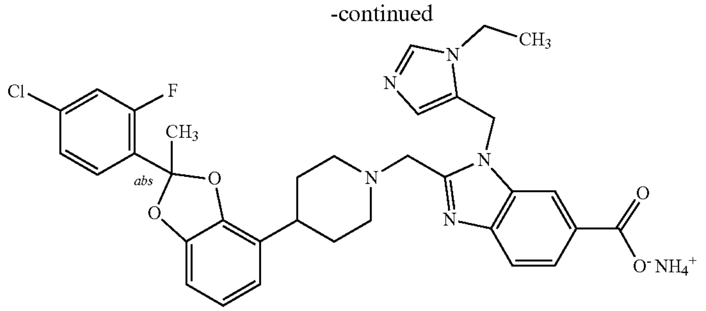

+

ENT-1
17

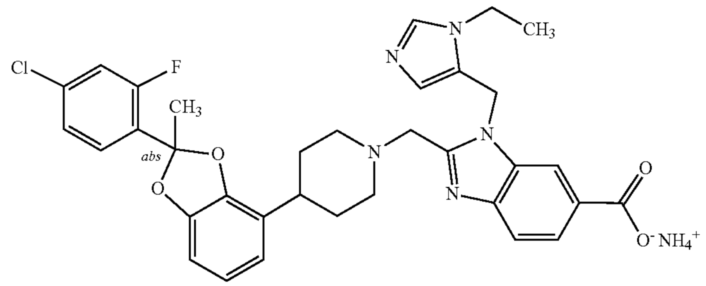

ENT-2
18

Step 1. Synthesis of methyl 4-[({4-[2-(4-chloro-2-fluorophenyl)-2-methyl-1,3-benzodioxol-4-yl]piperidin-1-yl}acetyl)amino]-3-{[(1-ethyl-1H-imidazol-5-yl)methyl]amino}benzoate (C73)

O-(7-Azabenzotriazol-1-yl)-N,N,N',N'-tetramethyluronium hexafluorophosphate (566 mg, 1.49 mmol) was added to a mixture of P19 (340 mg, 1.24 mmol) in N,N-dimethylformamide (10 mL), and the mixture was stirred at 25° C. for 10 minutes. A solution of P10 (503 mg, 1.24 mmol) and N,N-diisopropylethylamine (615 μL, 3.53 mmol) in N,N-dimethylformamide (7.7 mL) was then added, and the reaction mixture was stirred at 25° C. for 16 hours, whereupon it was poured into water (10 mL) and extracted with ethyl acetate (3×50 mL). The combined organic layers were washed sequentially with aqueous ammonium chloride solution (3×20 mL) and saturated aqueous sodium chloride solution (2×20 mL), dried over sodium sulfate, filtered, and concentrated in vacuo. Upon purification using silica gel chromatography (Gradient: 0% to 5% methanol in ethyl acetate), C73 was obtained as a pale brown gum. Yield: 316 mg, 0.477 mmol, 38%. LCMS m/z 662.2♦ $[M+H]^+$.

Step 2. Synthesis of methyl 2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylate (C74)

A solution of C73 (316 mg, 0.477 mmol) in acetic acid (14 mL) was stirred at 55° C. for 16 hours. Solvent was removed under high vacuum, and the residue was purified using preparative thin-layer chromatography (Eluent: 10:1 dichloromethane/methanol) to afford C74 as a colorless oil. Yield: 200 mg, 0.310 mmol, 65%. LCMS m/z 644.3♦ $[M+H]^+$.

Step 3. Synthesis of ammonium 2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylate, ENT-1 (17) and ammonium 2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylate, ENT-2 (18)

A mixture of C74 (150 mg, 0.233 mmol) and aqueous sodium hydroxide solution (2 M; 233 μL, 0.466 mmol) in a mixture of methanol (3 mL) and tetrahydrofuran (3 mL) was stirred at 45° C. for 16 hours. After the reaction mixture had been adjusted to pH 7 by addition of 1 M hydrochloric acid, it was concentrated in vacuo to afford a mixture of 17 and 18. These enantiomers were separated via SFC [Column: Chiral Technologies ChiralCel OD, 10 μm; Mobile phase: 1:1 carbon dioxide/(ethanol containing 0.1% ammonium hydroxide)]. The first-eluting enantiomer was designated as ENT-1 (17), and the second-eluting enantiomer as ENT-2 (18); both were isolated as white solids.

17 Yield: 45.0 mg, 69.5 μmol, 30%. LCMS m/z 630.3♦ $[M-H]^+$. $^1H$ NMR (400 MHz, methanol-$d_4$) δ 8.15 (br s, 1H), 8.00 (br d, J=8.4 Hz, 1H), 7.81 (s, 1H), 7.72 (d, J=8.2 Hz, 1H), 7.56 (dd, J=8.3, 8.3 Hz, 1H), 7.28 (dd, J=10.9, 2.0 Hz, 1H), 7.21 (dd, J=8.3, 2.1 Hz, 1H), 6.77 (dd, component of ABC pattern, J=8.0, 7.7 Hz, 1H), 6.69 (dd, component of ABC pattern, J=7.8, 1.2 Hz, 1H), 6.67-6.60 (m, 2H), 5.82 (s, 2H), 4.12 (q, J=7.2 Hz, 2H), 3.89 (AB quartet, $J_{AB}$=14.3 Hz, $\Delta\nu_{AB}$=6.9 Hz, 2H), 3.00-2.90 (m, 2H), 2.74-2.64 (m, 1H), 2.32-2.21 (m, 2H), 2.02 (s, 3H), 1.82-1.61 (m, 4H), 1.29 (t, J=7.3 Hz, 3H). Retention time 5.66 minutes (Column: Chiral Technologies Chiralpak AD-3, 4.6×150 mm, 3 μm; Mobile phase A: carbon dioxide; Mobile phase B: methanol containing 0.05% diethylamine; Gradient: 5% to 40% B over 5.5 minutes, then held at 40% B for 3.0 minutes; Flow rate: 2.5 mL/minute).

18 Yield: 32.8 mg, 50.7 μmol, 22%. LCMS m/z 630.3♦ $[M+H]^+$. $^1$H NMR (400 MHz, methanol-$d_4$) δ 8.15 (s, 1H), 8.00 (d, J=8.5 Hz, 1H), 7.81 (s, 1H), 7.72 (d, J=8.5 Hz, 1H), 7.56 (dd, J=8.3, 8.3 Hz, 1H), 7.28 (dd, J=10.9, 2.0 Hz, 1H), 7.21 (dd, J=8.3, 2.0 Hz, 1H), 6.77 (dd, component of ABC pattern, J=7.8, 7.8 Hz, 1H), 6.69 (dd, component of ABC pattern, J=7.9, 1.2 Hz, 1H), 6.67-6.60 (m, 2H), 5.82 (s, 2H), 4.12 (q, J=7.3 Hz, 2H), 3.89 (AB quartet, $J_{AB}$=14.1 Hz, $\Delta\nu_{AB}$=7.4 Hz, 2H), 3.01-2.90 (m, 2H), 2.74-2.63 (m, 1H), 2.31-2.21 (m, 2H), 2.02 (s, 3H), 1.82-1.60 (m, 4H), 1.29 (t, J=7.3 Hz, 3H). Retention time 5.34 minutes (Analytical SFC conditions identical to those used for 17).

The compounds listed in Table 1 were prepared using procedures analogous to the examples identified in Table 2 using the appropriate intermediate(s) identified in Table 2. The compounds were purified using methods discussed herein. The final compounds may have been isolated as neutrals or acid or base salts.

TABLE 1

Structure and IUPAC name for Examples 19-102

| Ex. No. | Structure | IUPAC Name |
|---|---|---|
| 19 | 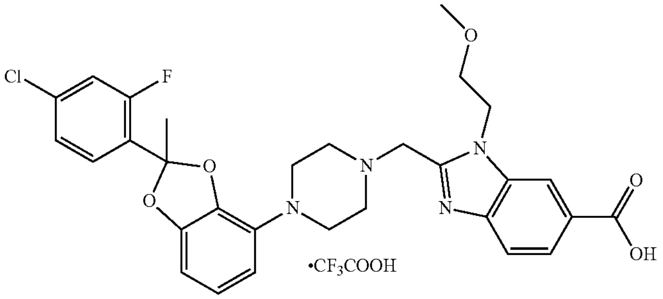 [SMILES: COCCn1c(CN2CCN(c3cccc4c3OC(C)(c3ccc(Cl)cc3F)O4)CC2)nc2ccc(C(=O)O)cc21 ; "·CF3COOH"] | 2-({4-[2-(4-chloro-2-fluorophenyl)-2-methyl-1,3-benzodioxol-4-yl]piperazin-1-yl}methyl)-1-(2-methoxyethyl)-1H-benzimidazole-6-carboxylic acid, trifluoroacetate salt |
| 20 | 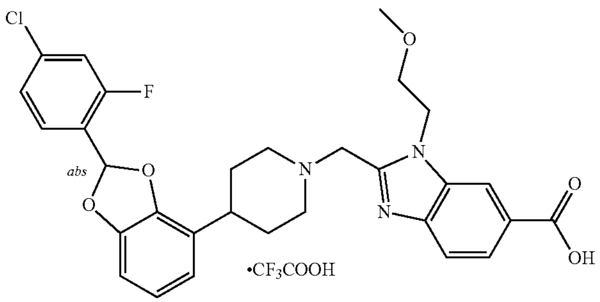 ENT-X2 | 2-({4-[2-(4-chloro-2-fluorophenyl)-1,3-benzodioxol-4-yl]piperidin-1-yl}methyl)-1-(2-methoxyethyl)-1H-benzimidazole-6-carboxylic acid, ENT-X2, trifluoroacetate salt, [from C77; footnote 1 in Table 2] |
| 21 | 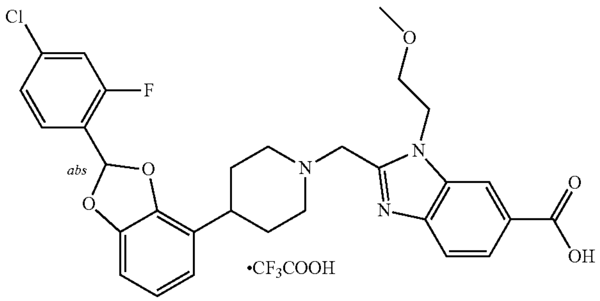 ENT-X1 | 2-({4-[2-(4-chloro-2-fluorophenyl)-1,3-benzodioxol-4-yl]piperidin-1-yl}methyl)-1-(2-methoxyethyl)-1H-benzimidazole-6-carboxylic acid, ENT-X1, trifluoroacetate salt, [from C76; footnote 1 in Table 2] |

TABLE 1-continued

| Structure and IUPAC name for Examples 19-102 | | |
|---|---|---|
| Ex. No. | Structure | IUPAC Name |
| 22 | 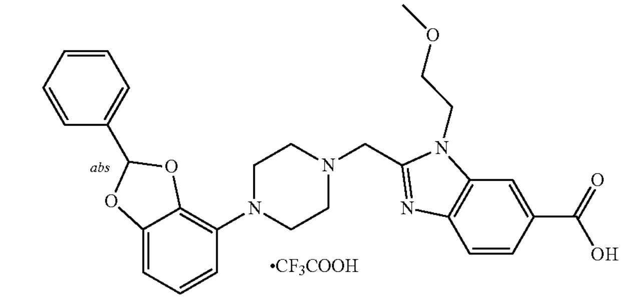 •$CF_3COOH$ ENT-X1 | 1-(2-methoxyethyl)-2-{[4-(2-phenyl-1,3-benzodioxol-4-yl)piperazin-1-yl]methyl}-1H-benzimidazole-6-carboxylic acid, ENT-X1, trifluoroacetate salt, [from P5] |
| 23 | 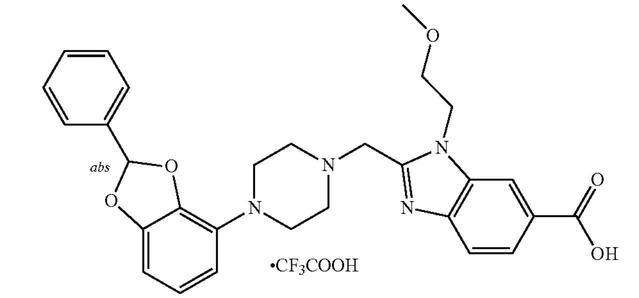 •$CF_3COOH$ ENT-X2 | 1-(2-methoxyethyl)-2-{[4-(2-phenyl-1,3-benzodioxol-4-yl)piperazin-1-yl]methyl}-1H-benzimidazole-6-carboxylic acid, ENT-X2, trifluoroacetate salt, [from P6] |
| 24 | 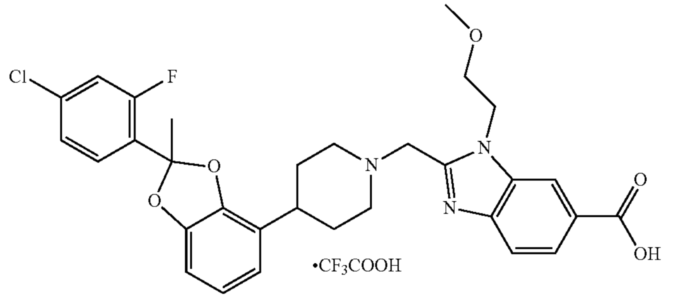 [SMILES: COCCn1c(CN2CCC(c3cccc4c3OC(C)(c3ccc(Cl)cc3F)O4)CC2)nc2ccc(C(=O)O)cc21 ; "·CF3COOH"] •$CF_3COOH$ | 2-({4-[2-(4-chloro-2-fluorophenyl)-2-methyl-1,3-benzodioxol-4-yl]piperidin-1-yl}methyl)-1-(2-methoxyethyl)-1H-benzimidazole-6-carboxylic acid, trifluoroacetate salt |
| 25 | 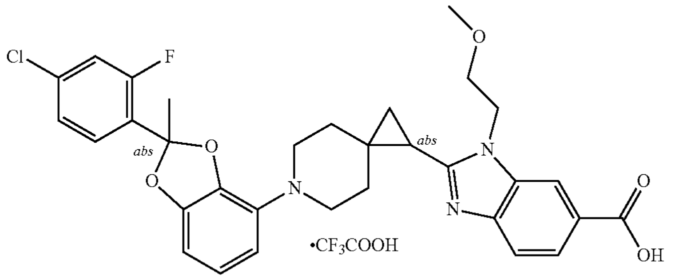 •$CF_3COOH$ DIAST-Z2 | 2-{6-[2-(4-chloro-2-fluorophenyl)-2-methyl-1,3-benzodioxol-4-yl]-6-azaspiro[2.5]oct-1-yl}-1-(2-methoxyethyl)-1H-benzimidazole-6-carboxylic acid, DIAST-Z2, trifluoroacetate salt, [from P17 via C79; footnote 2 in Table 2] |

TABLE 1-continued

Structure and IUPAC name for Examples 19-102

| Ex. No. | Structure | IUPAC Name |
|---|---|---|
| 26 | 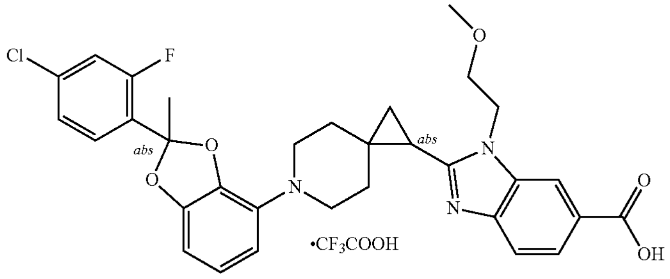<br>DIAST-Z1 | 2-{6-[2-(4-chloro-2-fluorophenyl)-2-methyl-1,3-benzodioxol-4-yl]-6-azaspiro[2.5]oct-1-yl}-1-(2-methoxyethyl)-1H-benzimidazole-6-carboxylic acid, DIAST-Z1, trifluoroacetate salt, [from P17 via C78; footnote 2 in Table 2] |
| 27 | 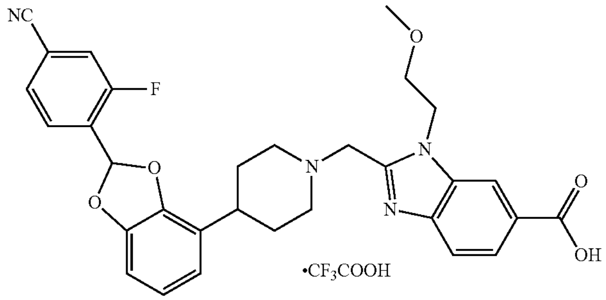 [SMILES: COCCn1c(CN2CCC(c3cccc4c3OC(c3ccc(C#N)cc3F)O4)CC2)nc2ccc(C(=O)O)cc21 ; "·CF3COOH"] | 2-({4-[2-(4-cyano-2-fluorophenyl)-1,3-benzodioxol-4-yl]piperidin-1-yl}methyl)-1-(2-methoxyethyl)-1H-benzimidazole-6-carboxylic acid, trifluoroacetate salt |
| 28 | 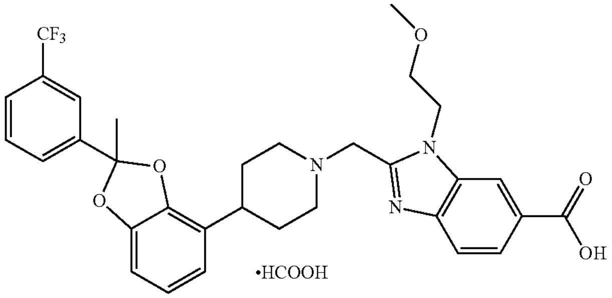 [SMILES: COCCn1c(CN2CCC(c3cccc4c3OC(C)(c3cccc(C(F)(F)F)c3)O4)CC2)nc2ccc(C(=O)O)cc21 ; "·HCOOH"] | 1-(2-methoxyethyl)-2-[(4-{2-methyl-2-[3-(trifluoromethyl)phenyl]-1,3-benzodioxol-4-yl}piperidin-1-yl)methyl]-1H-benzimidazole-6-carboxylic acid, formate salt |
| 29 | 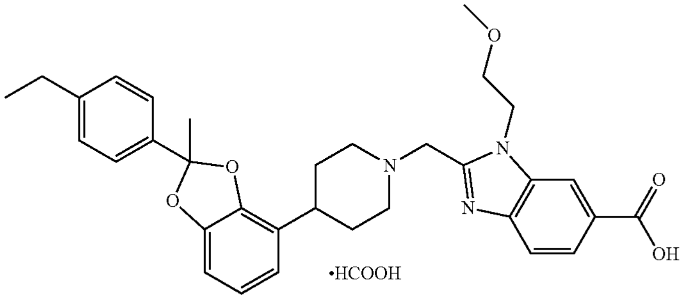 [SMILES: CCc1ccc(C2(C)Oc3cccc(C4CCN(Cc5nc6ccc(C(=O)O)cc6n5CCOC)CC4)c3O2)cc1 ; "·HCOOH"] | 2-({4-[2-(4-ethylphenyl)-2-methyl-1,3-benzodioxol-4-yl]piperidin-1-yl}methyl)-1-(2-methoxyethyl)-1H-benzimidazole-6-carboxylic acid, formate salt |
| 30 | 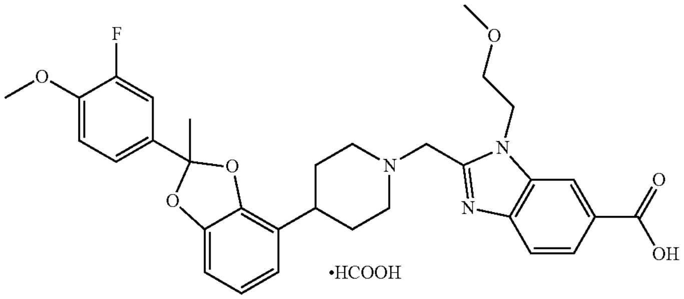 [SMILES: COCCn1c(CN2CCC(c3cccc4c3OC(C)(c3ccc(OC)c(F)c3)O4)CC2)nc2ccc(C(=O)O)cc21 ; "·HCOOH"] | 2-({4-[2-(3-fluoro-4-methoxyphenyl)-2-methyl-1,3-benzodioxol-4-yl]piperidin-1-yl}methyl)-1-(2-methoxyethyl)-1H-benzimidazole-6-carboxylic acid, formate salt |

TABLE 1-continued

| Ex. No. | Structure | IUPAC Name |
| --- | --- | --- |
| Structure and IUPAC name for Examples 19-102 | | |
| 31 | 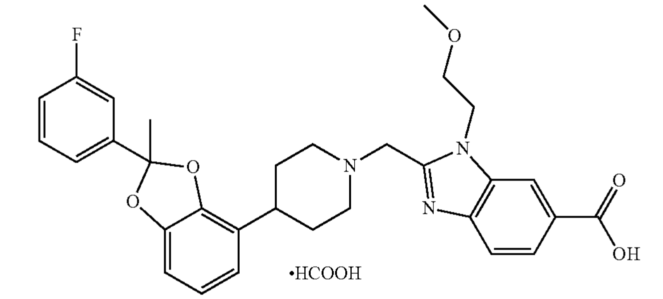 [SMILES: COCCn1c(CN2CCC(c3cccc4c3OC(C)(c3cccc(F)c3)O4)CC2)nc2ccc(C(=O)O)cc21 ; "·HCOOH"] | 2-({4-[2-(3-fluorophenyl)-2-methyl-1,3-benzodioxol-4-yl]piperidin-1-yl}methyl)-1-(2-methoxyethyl)-1H-benzimidazole-6-carboxylic acid, formate salt |
| 32 | 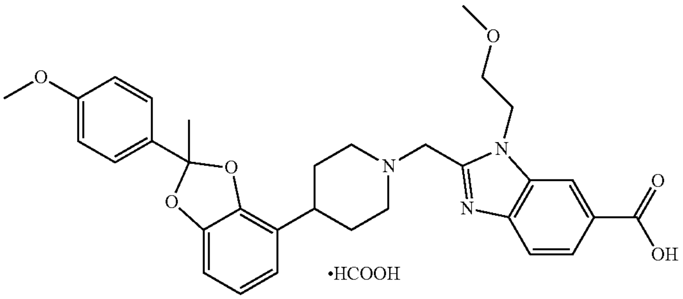 [SMILES: COCCn1c(CN2CCC(c3cccc4c3OC(C)(c3ccc(OC)cc3)O4)CC2)nc2ccc(C(=O)O)cc21 ; "·HCOOH"] | 1-(2-methoxyethyl)-2-({4-[2-(4-methoxyphenyl)-2-methyl-1,3-benzodioxol-4-yl]piperidin-1-yl}methyl)-1H-benzimidazole-6-carboxylic acid, formate salt |
| 33 | 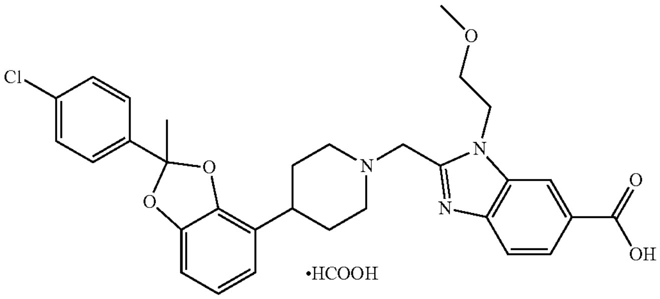 [SMILES: COCCn1c(CN2CCC(c3cccc4c3OC(C)(c3ccc(Cl)cc3)O4)CC2)nc2ccc(C(=O)O)cc21 ; "·HCOOH"] | 2-({4-[2-(4-chlorophenyl)-2-methyl-1,3-benzodioxol-4-yl]piperidin-1-yl}methyl)-1-(2-methoxyethyl)-1H-benzimidazole-6-carboxylic acid, formate salt |
| 34 | 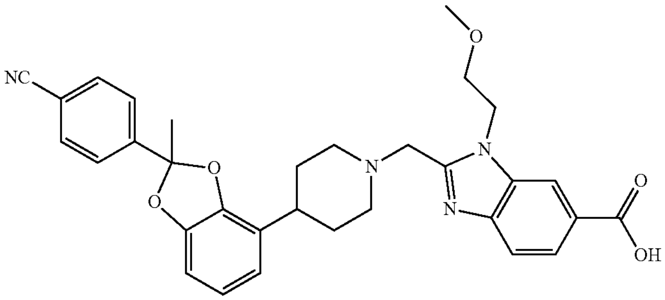 [SMILES: COCCn1c(CN2CCC(c3cccc4c3OC(C)(c3ccc(C#N)cc3)O4)CC2)nc2ccc(C(=O)O)cc21] | 2-({4-[2-(4-cyanophenyl)-2-methyl-1,3-benzodioxol-4-yl]piperidin-1-yl}methyl)-1-(2-methoxyethyl)-1H-benzimidazole-6-carboxylic acid |
| 35 | 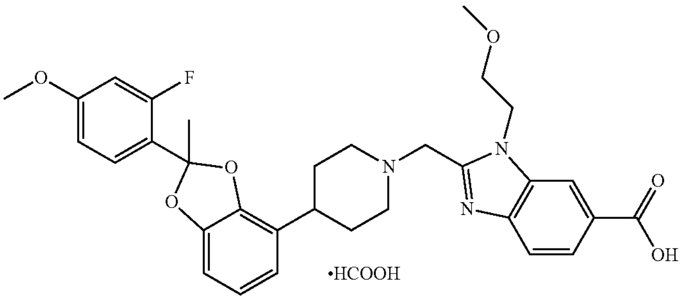 [SMILES: COCCn1c(CN2CCC(c3cccc4c3OC(C)(c3ccc(OC)cc3F)O4)CC2)nc2ccc(C(=O)O)cc21 ; "·HCOOH"] | 2-({4-[2-(2-fluoro-4-methoxyphenyl)-2-methyl-1,3-benzodioxol-4-yl]piperidin-1-yl}methyl)-1-(2-methoxyethyl)-1H-benzimidazole-6-carboxylic acid, formate salt |

TABLE 1-continued

| Ex. No. | Structure | IUPAC Name |
|---|---|---|
| Structure and IUPAC name for Examples 19-102 | | |
| 36 | 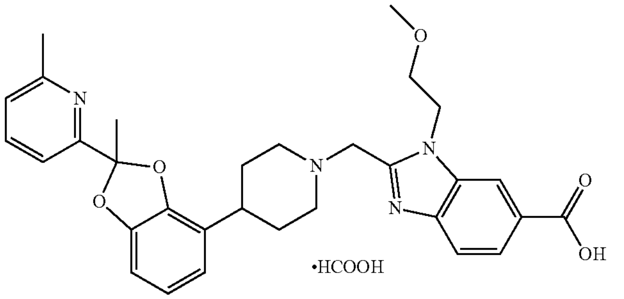 [SMILES: COCCn1c(CN2CCC(c3cccc4c3OC(C)(c3cccc(C)n3)O4)CC2)nc2ccc(C(=O)O)cc21 ; "·HCOOH"] | 1-(2-methoxyethyl)-2-({4-[2-methyl-2-(6-methylpyridin-2-yl)-1,3-benzodioxol-4-yl]piperidin-1-yl}methyl)-1H-benzimidazole-6-carboxylic acid, formate salt |
| 37 | 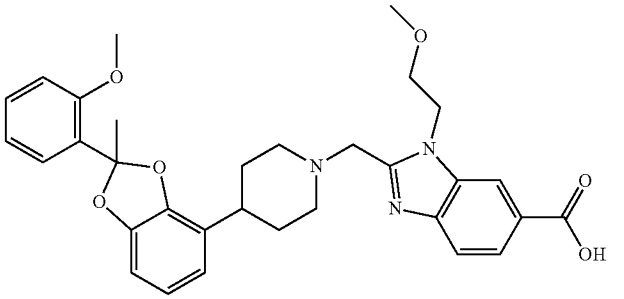 [SMILES: COCCn1c(CN2CCC(c3cccc4c3OC(C)(c3ccccc3OC)O4)CC2)nc2ccc(C(=O)O)cc21] | 1-(2-methoxyethyl)-2-({4-[2-(2-methoxyphenyl)-2-methyl-1,3-benzodioxol-4-yl]piperidin-1-yl}methyl)-1H-benzimidazole-6-carboxylic acid |
| 38 | 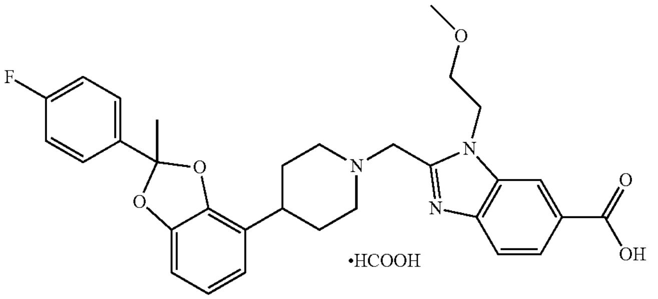 [SMILES: COCCn1c(CN2CCC(c3cccc4c3OC(C)(c3ccc(F)cc3)O4)CC2)nc2ccc(C(=O)O)cc21 ; "·HCOOH"] | 2-({4-[2-(4-fluorophenyl)-2-methyl-1,3-benzodioxol-4-yl]piperidin-1-yl}methyl)-1-(2-methoxyethyl)-1H-benzimidazole-6-carboxylic acid, formate salt |
| 39 | 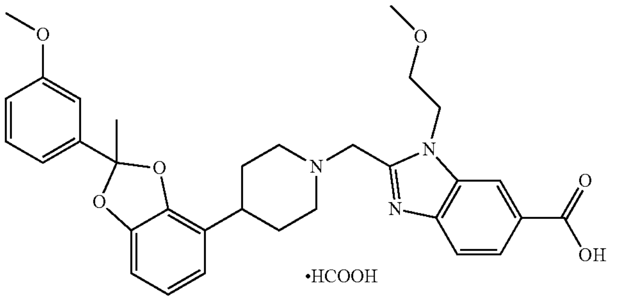 [SMILES: COCCn1c(CN2CCC(c3cccc4c3OC(C)(c3cccc(OC)c3)O4)CC2)nc2ccc(C(=O)O)cc21 ; "·HCOOH"] | 1-(2-methoxyethyl)-2-({4-[2-(3-methoxyphenyl)-2-methyl-1,3-benzodioxol-4-yl]piperidin-1-yl}methyl)-1H-benzimidazole-6-carboxylic acid, formate salt |
| 40 | 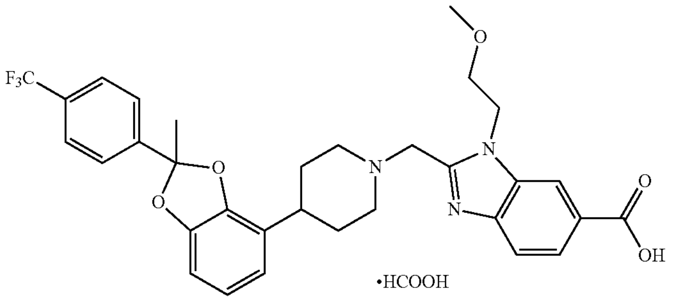 [SMILES: COCCn1c(CN2CCC(c3cccc4c3OC(C)(c3ccc(C(F)(F)F)cc3)O4)CC2)nc2ccc(C(=O)O)cc21 ; "·HCOOH"] | 1-(2-methoxyethyl)-2-[(4-{2-methyl-2-[4-(trifluoromethyl)phenyl]-1,3-benzodioxol-4-yl}piperidin-1-yl)methyl]-1H-benzimidazole-6-carboxylic acid, formate salt |

TABLE 1-continued

| Ex. No. | Structure | IUPAC Name |
| --- | --- | --- |
| | Structure and IUPAC name for Examples 19-102 | |
| 41 | 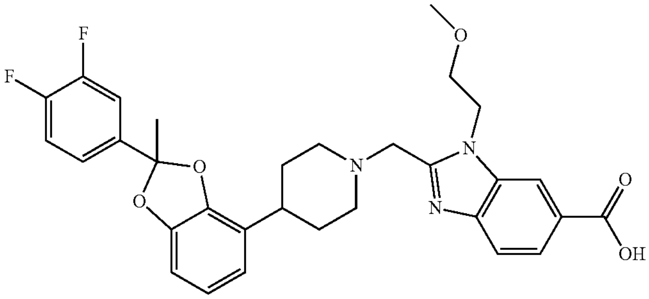 [SMILES: COCCn1c(CN2CCC(c3cccc4c3OC(C)(c3ccc(F)c(F)c3)O4)CC2)nc2ccc(C(=O)O)cc21] | 2-({4-[2-(3,4-difluorophenyl)-2-methyl-1,3-benzodioxol-4-yl]piperidin-1-yl}methyl)-1-(2-methoxyethyl)-1H-benzimidazole-6-carboxylic acid |
| 42 | 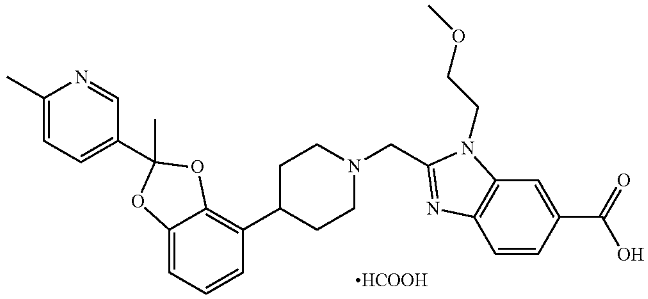 [SMILES: COCCn1c(CN2CCC(c3cccc4c3OC(C)(c3ccc(C)nc3)O4)CC2)nc2ccc(C(=O)O)cc21 ; "·HCOOH"] •HCOOH | 1-(2-methoxyethyl)-2-({4-[2-methyl-2-(6-methylpyridin-3-yl)-1,3-benzodioxol-4-yl]piperidin-1-yl}methyl)-1H-benzimidazole-6-carboxylic acid, formate salt |
| 43 | 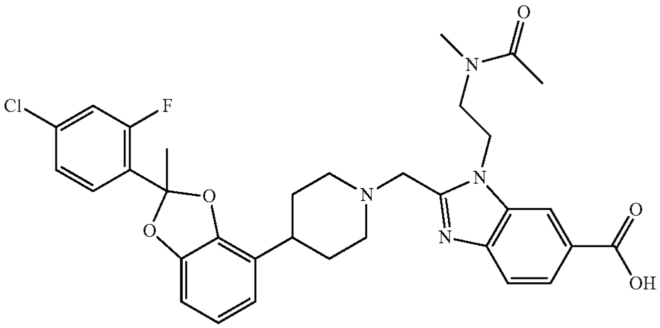 [SMILES: CC(=O)N(C)CCn1c(CN2CCC(c3cccc4c3OC(C)(c3ccc(Cl)cc3F)O4)CC2)nc2ccc(C(=O)O)cc21] | 1-{2-[acetyl(methyl)amino]ethyl}-2-({4-[2-(4-chloro-2-fluorophenyl)-2-methyl-1,3-benzodioxol-4-yl]piperidin-1-yl}methyl)-1H-benzimidazole-6-carboxylic acid |
| 44 | 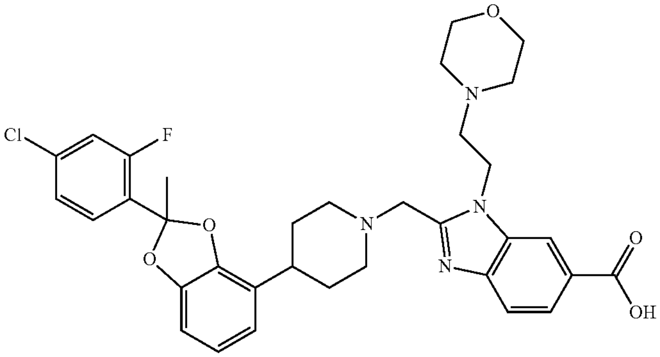 [SMILES: CC1(c2ccc(Cl)cc2F)Oc2cccc(C3CCN(Cc4nc5ccc(C(=O)O)cc5n4CCN4CCOCC4)CC3)c2O1] | 2-({4-[2-(4-chloro-2-fluorophenyl)-2-methyl-1,3-benzodioxol-4-yl]piperidin-1-yl}methyl)-1-[2-(morpholin-4-yl)ethyl]-1H-benzimidazole-6-carboxylic acid |

TABLE 1-continued

| Structure and IUPAC name for Examples 19-102 | | |
|---|---|---|
| Ex. No. | Structure | IUPAC Name |
| 45 | 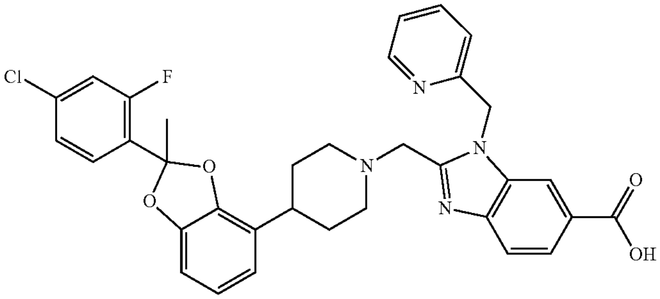 [SMILES: CC1(c2ccc(Cl)cc2F)Oc2cccc(C3CCN(Cc4nc5ccc(C(=O)O)cc5n4Cc4ccccn4)CC3)c2O1] | 2-({4-[2-(4-chloro-2-fluorophenyl)-2-methyl-1,3-benzodioxol-4-yl]piperidin-1-yl}methyl)-1-(pyridin-2-ylmethyl)-1H-benzimidazole-6-carboxylic acid |
| 46 | 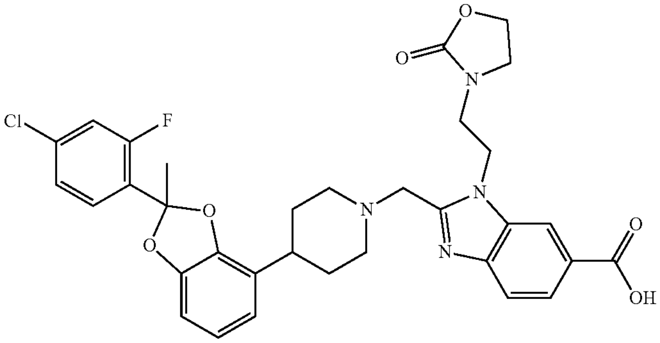 [SMILES: CC1(c2ccc(Cl)cc2F)Oc2cccc(C3CCN(Cc4nc5ccc(C(=O)O)cc5n4CCN4CCOC4=O)CC3)c2O1] | 2-({4-[2-(4-chloro-2-fluorophenyl)-2-methyl-1,3-benzodioxol-4-yl]piperidin-1-yl}methyl)-1-[2-(2-oxo-1,3-oxazolidin-3-yl)ethyl]-1H-benzimidazole-6-carboxylic acid |
| 47 | 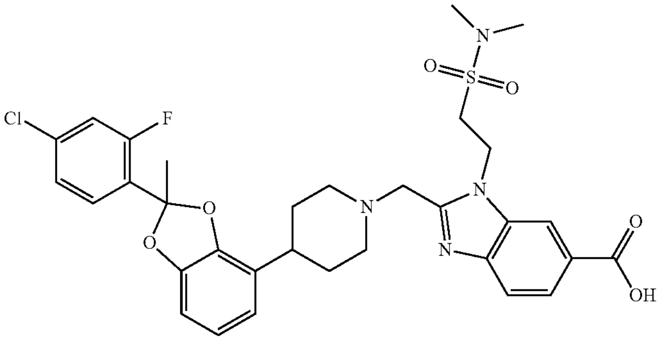 [SMILES: CN(C)S(=O)(=O)CCn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[2-(dimethylsulfamoyl)ethyl]-1H-benzimidazole-6-carboxylic acid |
| 48 | 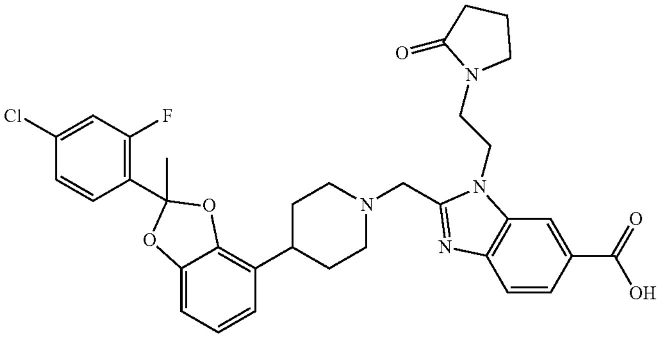 [SMILES: CC1(c2ccc(Cl)cc2F)Oc2cccc(C3CCN(Cc4nc5ccc(C(=O)O)cc5n4CCN4CCCC4=O)CC3)c2O1] | 2-({4-[2-(4-chloro-2-fluorophenyl)-2-methyl-1,3-benzodioxol-4-yl]piperidin-1-yl}methyl)-1-[2-(2-oxopyrrolidin-1-yl)ethyl]-1H-benzimidazole-6-carboxylic acid |

TABLE 1-continued

| Structure and IUPAC name for Examples 19-102 | | |
|---|---|---|
| Ex. No. | Structure | IUPAC Name |
| 49 | 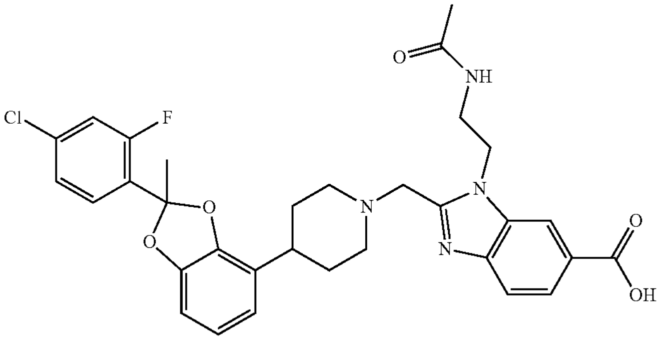 [SMILES: CC(=O)NCCn1c(CN2CCC(c3cccc4c3OC(C)(c3ccc(Cl)cc3F)O4)CC2)nc2ccc(C(=O)O)cc21] | 1-[2-(acetylamino)ethyl]-2-({4-[2-(4-chloro-2-fluorophenyl)-2-methyl-1,3-benzodioxol-4-yl]piperidin-1-yl}methyl)-1H-benzimidazole-6-carboxylic acid |
| 50 | 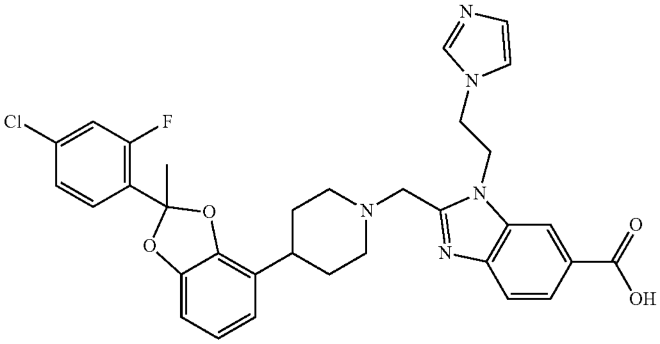 [SMILES: CC1(c2ccc(Cl)cc2F)Oc2cccc(C3CCN(Cc4nc5ccc(C(=O)O)cc5n4CCn4ccnc4)CC3)c2O1] | 2-({4-[2-(4-chloro-2-fluorophenyl)-2-methyl-1,3-benzodioxol-4-yl]piperidin-1-yl}methyl)-1-[2-(1H-imidazol-1-yl)ethyl]-1H-benzimidazole-6-carboxylic acid |
| 51 | 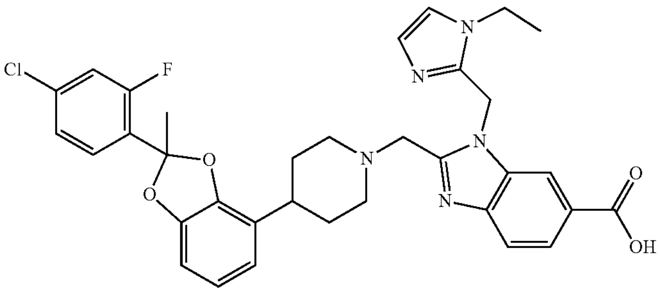 [SMILES: CCn1ccnc1Cn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[(1-ethyl-1H-imidazol-2-yl)methyl]-1H-benzimidazole-6-carboxylic acid |
| 52 | 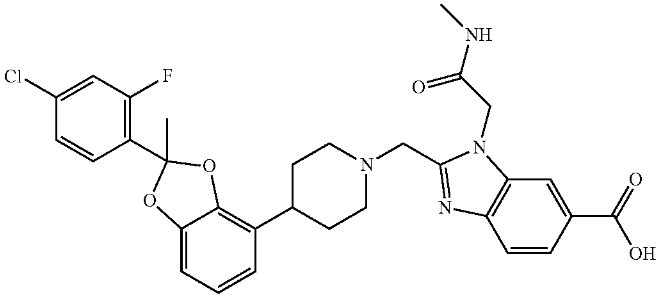 [SMILES: CNC(=O)Cn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[2-(methylamino)-2-oxoethyl]-1H-benzimidazole-6-carboxylic acid |

TABLE 1-continued

| Structure and IUPAC name for Examples 19-102 | | |
|---|---|---|
| Ex. No. | Structure | IUPAC Name |
| 53 | 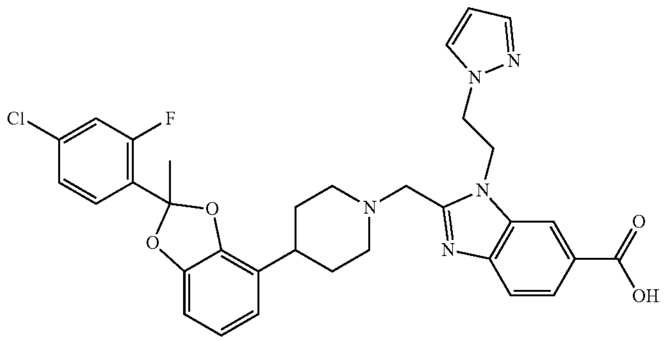 [SMILES: CC1(c2ccc(Cl)cc2F)Oc2cccc(C3CCN(Cc4nc5ccc(C(=O)O)cc5n4CCn4cccn4)CC3)c2O1] | 2-({4-[2-(4-chloro-2-fluorophenyl)-2-methyl-1,3-benzodioxol-4-yl]piperidin-1-yl}methyl)-1-[2-(1H-pyrazol-1-yl)ethyl]-1H-benzimidazole-6-carboxylic acid |
| 54 | 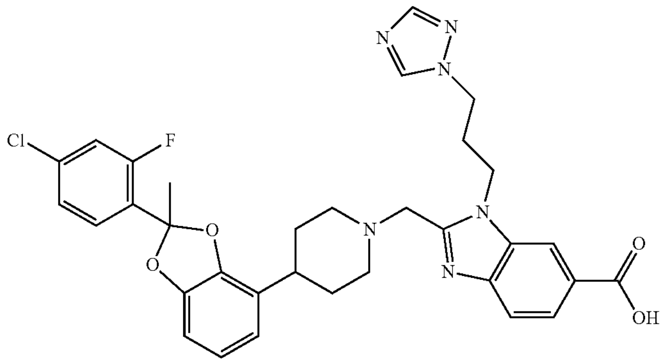 [SMILES: CC1(c2ccc(Cl)cc2F)Oc2cccc(C3CCN(Cc4nc5ccc(C(=O)O)cc5n4CCCn4cncn4)CC3)c2O1] | 2-({4-[2-(4-chloro-2-fluorophenyl)-2-methyl-1,3-benzodioxol-4-yl]piperidin-1-yl}methyl)-1-[3-(1H-1,2,4-triazol-1-yl)propyl]-1H-benzimidazole-6-carboxylic acid |
| 55 | 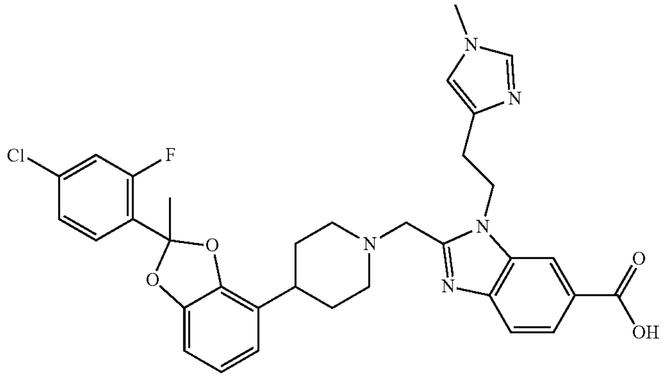 [SMILES: Cn1cnc(CCn2c(CN3CCC(c4cccc5c4OC(C)(c4ccc(Cl)cc4F)O5)CC3)nc3ccc(C(=O)O)cc32)c1] | 2-({4-[2-(4-chloro-2-fluorophenyl)-2-methyl-1,3-benzodioxol-4-yl]piperidin-1-yl}methyl)-1-[2-(1-methyl-1H-imidazol-4-yl)ethyl]-1H-benzimidazole-6-carboxylic acid |
| 56 | 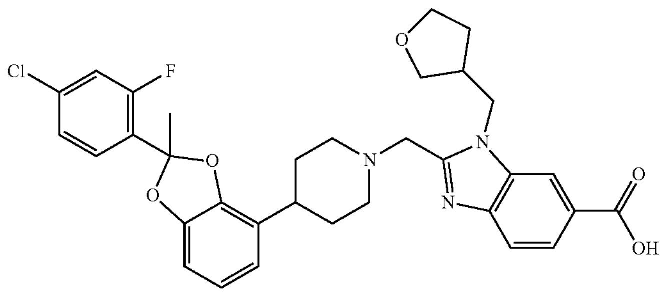 [SMILES: CC1(c2ccc(Cl)cc2F)Oc2cccc(C3CCN(Cc4nc5ccc(C(=O)O)cc5n4CC4CCOC4)CC3)c2O1] | 2-({4-[2-(4-chloro-2-fluorophenyl)-2-methyl-1,3-benzodioxol-4-yl]piperidin-1-yl}methyl)-1-(tetrahydrofuran-3-ylmethyl)-1H-benzimidazole-6-carboxylic acid |

TABLE 1-continued

| Ex. No. | Structure | IUPAC Name |
|---|---|---|
| | Structure and IUPAC name for Examples 19-102 | |
| 57 | 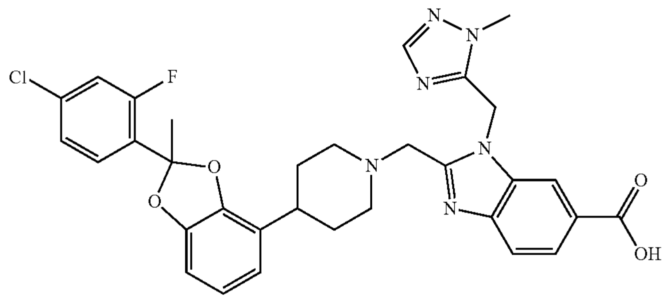 [SMILES: Cn1ncnc1Cn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[(1-methyl-1H-1,2,4-triazol-5-yl)methyl]-1H-benzimidazole-6-carboxylic acid |
| 58 | 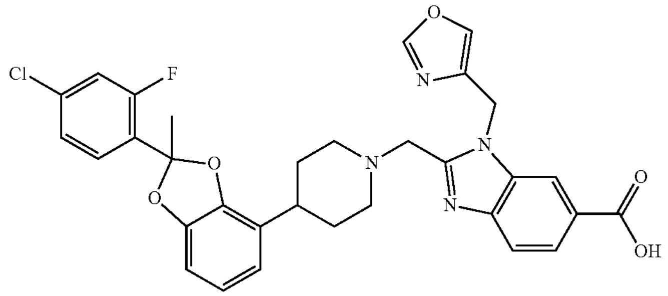 [SMILES: CC1(c2ccc(Cl)cc2F)Oc2cccc(C3CCN(Cc4nc5ccc(C(=O)O)cc5n4Cc4cocn4)CC3)c2O1] | 2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid |
| 59 | 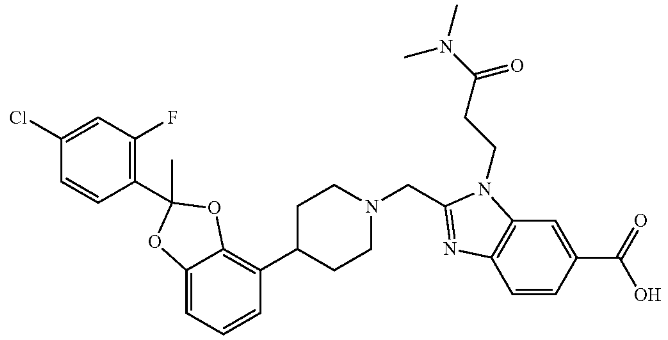 [SMILES: CN(C)C(=O)CCn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[3-(dimethylamino)-3-oxopropyl]-1H-benzimidazole-6-carboxylic acid |
| 60 | 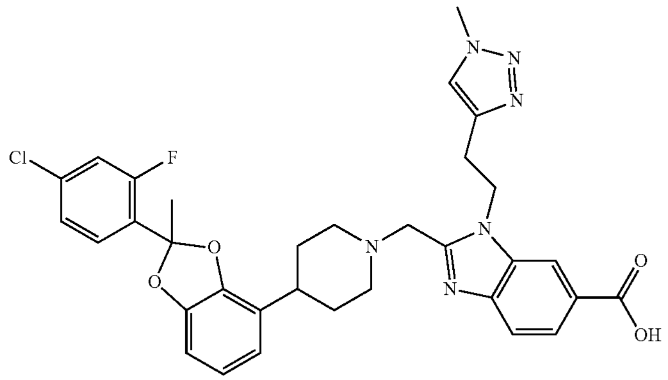 [SMILES: Cn1cc(CCn2c(CN3CCC(c4cccc5c4OC(C)(c4ccc(Cl)cc4F)O5)CC3)nc3ccc(C(=O)O)cc32)nn1] | 2-({4-[2-(4-chloro-2-fluorophenyl)-2-methyl-1,3-benzodioxol-4-yl]piperidin-1-yl}methyl)-1-[2-(1-methyl-1H-1,2,3-triazol-4-yl)ethyl]-1H-benzimidazole-6-carboxylic acid |

TABLE 1-continued

| Ex. No. | Structure | IUPAC Name |
| --- | --- | --- |
| | Structure and IUPAC name for Examples 19-102 | |
| 61 | 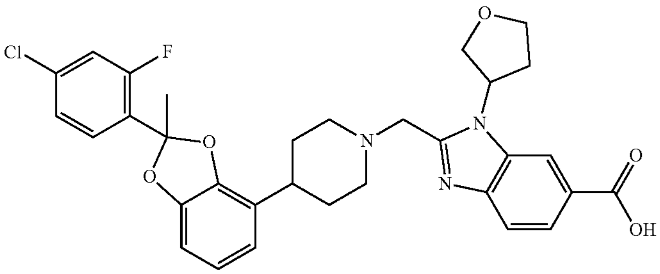 [SMILES: CC1(c2ccc(Cl)cc2F)Oc2cccc(C3CCN(Cc4nc5ccc(C(=O)O)cc5n4C4CCOC4)CC3)c2O1] | 2-({4-[2-(4-chloro-2-fluorophenyl)-2-methyl-1,3-benzodioxol-4-yl]piperidin-1-yl}methyl)-1-(tetrahydrofuran-3-yl)-1H-benzimidazole-6-carboxylic acid |
| 62 | 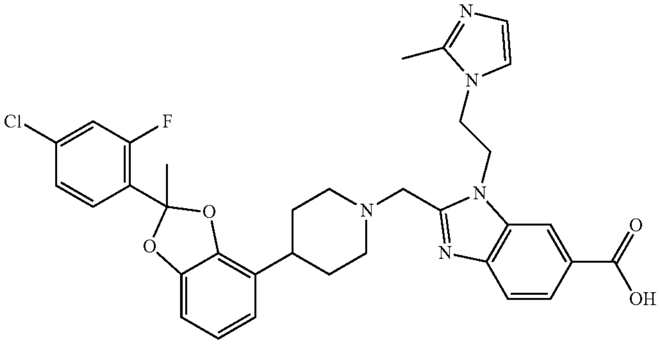 [SMILES: Cc1nccn1CCn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[2-(2-methyl-1H-imidazol-1-yl)ethyl]-1H-benzimidazole-6-carboxylic acid |
| 63 | 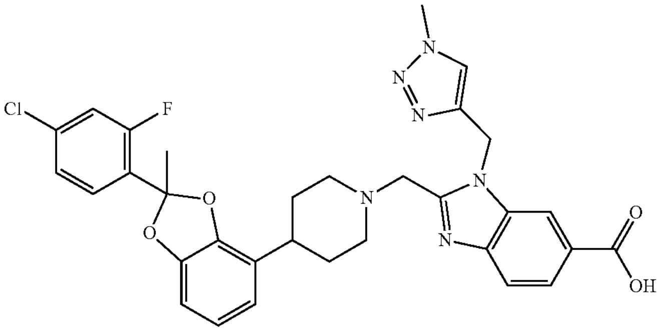 [SMILES: Cn1cc(Cn2c(CN3CCC(c4cccc5c4OC(C)(c4ccc(Cl)cc4F)O5)CC3)nc3ccc(C(=O)O)cc32)nn1] | 2-({4-[2-(4-chloro-2-fluorophenyl)-2-methyl-1,3-benzodioxol-4-yl]piperidin-1-yl}methyl)-1-[(1-methyl-1H-1,2,3-triazol-4-yl)methyl]-1H-benzimidazole-6-carboxylic acid |
| 64 | 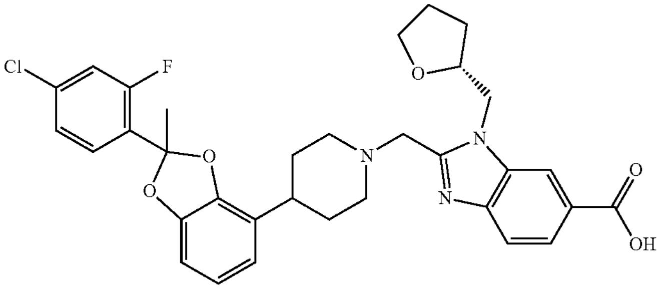 [SMILES: CC1(c2ccc(Cl)cc2F)Oc2cccc(C3CCN(Cc4nc5ccc(C(=O)O)cc5n4C[C@H]4CCCO4)CC3)c2O1] | 2-({4-[2-(4-chloro-2-fluorophenyl)-2-methyl-1,3-benzodioxol-4-yl]piperidin-1-yl}methyl)-1-[(2R)-tetrahydrofuran-2-ylmethyl]-1H-benzimidazole-6-carboxylic acid |

TABLE 1-continued

| Ex. No. | Structure | IUPAC Name |
| --- | --- | --- |
| | Structure and IUPAC name for Examples 19-102 | |
| 65 | 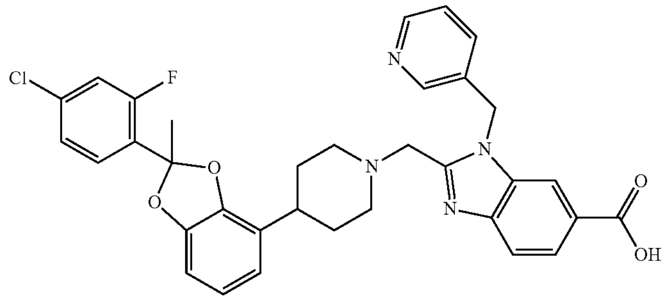 [SMILES: CC1(c2ccc(Cl)cc2F)Oc2cccc(C3CCN(Cc4nc5ccc(C(=O)O)cc5n4Cc4cccnc4)CC3)c2O1] | 2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid |
| 66 | 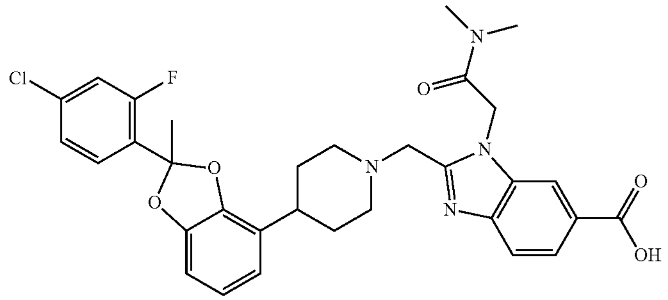 [SMILES: CN(C)C(=O)Cn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[2-(dimethylamino)-2-oxoethyl]-1H-benzimidazole-6-carboxylic acid |
| 67 | 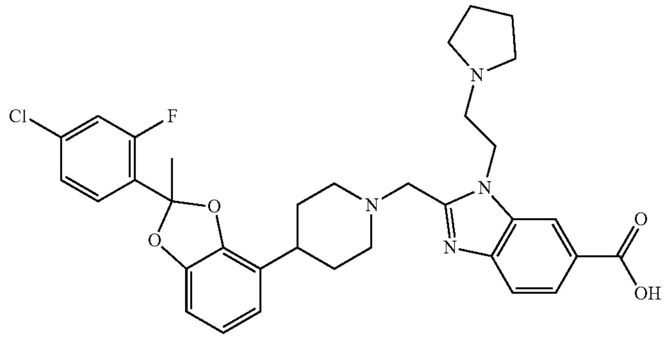 [SMILES: CC1(c2ccc(Cl)cc2F)Oc2cccc(C3CCN(Cc4nc5ccc(C(=O)O)cc5n4CCN4CCCC4)CC3)c2O1] | 2-({4-[2-(4-chloro-2-fluorophenyl)-2-methyl-1,3-benzodioxol-4-yl]piperidin-1-yl}methyl)-1-[2-(pyrrolidin-1-yl)ethyl]-1H-benzimidazole-6-carboxylic acid |
| 68 | 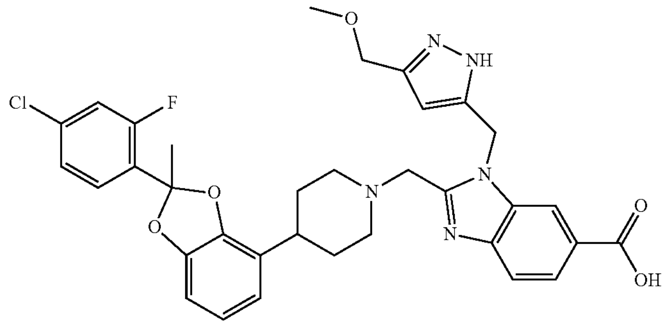 [SMILES: COCc1cc(Cn2c(CN3CCC(c4cccc5c4OC(C)(c4ccc(Cl)cc4F)O5)CC3)nc3ccc(C(=O)O)cc32)[nH]n1] | 2-({4-[2-(4-chloro-2-fluorophenyl)-2-methyl-1,3-benzodioxol-4-yl]piperidin-1-yl}methyl)-1-{[3-(methoxymethyl)-1H-pyrazol-5-yl]methyl}-1H-benzimidazole-6-carboxylic acid |

TABLE 1-continued

Structure and IUPAC name for Examples 19-102

| Ex. No. | Structure | IUPAC Name |
|---|---|---|
| 69 | 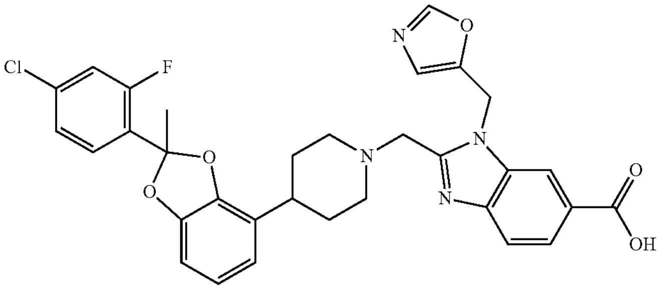 [SMILES: CC1(c2ccc(Cl)cc2F)Oc2cccc(C3CCN(Cc4nc5ccc(C(=O)O)cc5n4Cc4cnco4)CC3)c2O1] | 2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid |
| 70 | 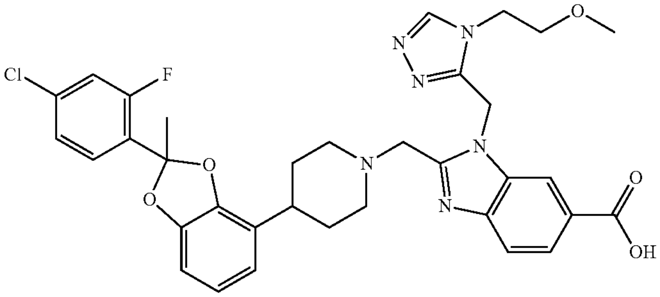 [SMILES: COCCn1cnnc1Cn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-{[4-(2-methoxyethyl)-4H-1,2,4-triazol-3-yl]methyl}-1H-benzimidazole-6-carboxylic acid |
| 71 | 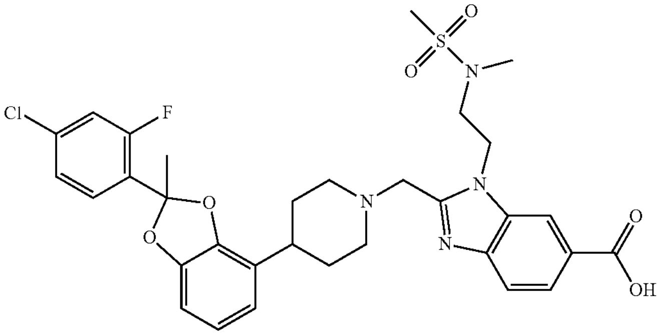 [SMILES: CN(CCn1c(CN2CCC(c3cccc4c3OC(C)(c3ccc(Cl)cc3F)O4)CC2)nc2ccc(C(=O)O)cc21)S(C)(=O)=O] | 2-({4-[2-(4-chloro-2-fluorophenyl)-2-methyl-1,3-benzodioxol-4-yl]piperidin-1-yl}methyl)-1-{2-[methyl(methylsulfonyl)amino]ethyl}-1H-benzimidazole-6-carboxylic acid |
| 72 | 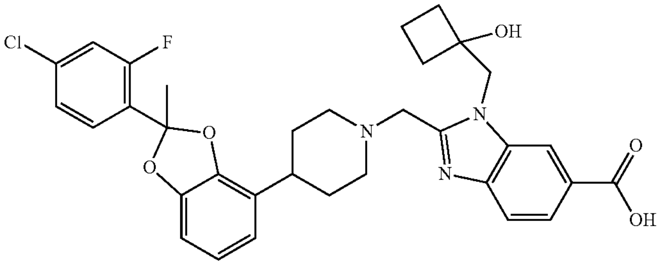 [SMILES: CC1(c2ccc(Cl)cc2F)Oc2cccc(C3CCN(Cc4nc5ccc(C(=O)O)cc5n4CC4(O)CCC4)CC3)c2O1] | 2-({4-[2-(4-chloro-2-fluorophenyl)-2-methyl-1,3-benzodioxol-4-yl]piperidin-1-yl}methyl)-1-[(1-hydroxycyclobutyl)methyl]-1H-benzimidazole-6-carboxylic acid |
| 73 | 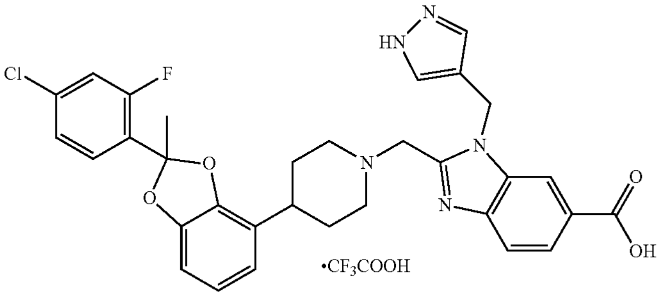 [SMILES: CC1(c2ccc(Cl)cc2F)Oc2cccc(C3CCN(Cc4nc5ccc(C(=O)O)cc5n4Cc4cn[nH]c4)CC3)c2O1 ; "·CF3COOH"] | 2-({4-[2-(4-chloro-2-fluorophenyl)-2-methyl-1,3-benzodioxol-4-yl]piperidin-1-yl}methyl)-1-(1H-pyrazol-4-ylmethyl)-1H-benzimidazole-6-carboxylic acid, trifluoroacetate salt |

TABLE 1-continued

| Ex. No. | Structure | IUPAC Name |
|---|---|---|
| 74 | 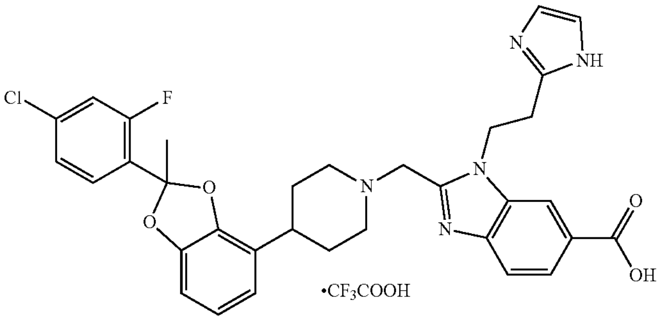 [SMILES: CC1(c2ccc(Cl)cc2F)Oc2cccc(C3CCN(Cc4nc5ccc(C(=O)O)cc5n4CCc4ncc[nH]4)CC3)c2O1 ; "·CF3COOH"] •$CF_3COOH$ | 2-({4-[2-(4-chloro-2-fluorophenyl)-2-methyl-1,3-benzodioxol-4-yl]piperidin-1-yl}methyl)-1-[2-(1H-imidazol-2-yl)ethyl]-1H-benzimidazole-6-carboxylic acid, trifluoroacetate salt |
| 75 | 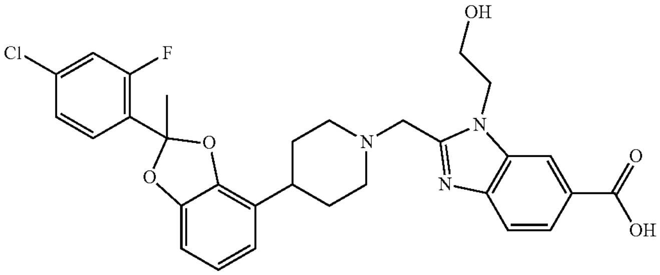 [SMILES: CC1(c2ccc(Cl)cc2F)Oc2cccc(C3CCN(Cc4nc5ccc(C(=O)O)cc5n4CCO)CC3)c2O1] | 2-({4-[2-(4-chloro-2-fluorophenyl)-2-methyl-1,3-benzodioxol-4-yl]piperidin-1-yl}methyl)-1-(2-hydroxyethyl)-1H-benzimidazole-6-carboxylic acid |
| 76 | 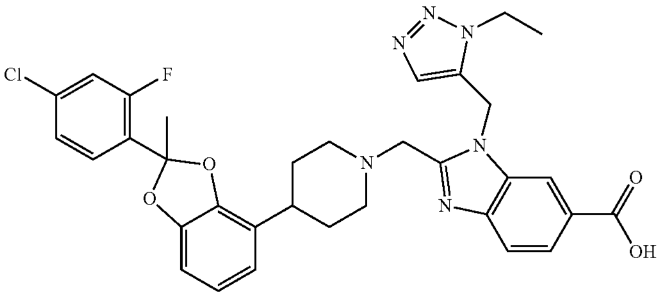 [SMILES: CCn1nncc1Cn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid |
| 77 | 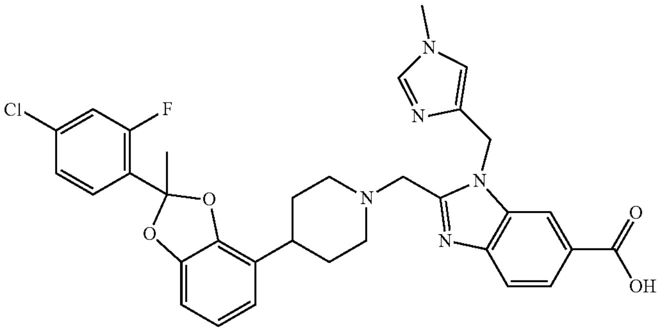 | 2-({4-[2-(4-chloro-2-fluorophenyl)-2-methyl-1,3-benzodioxol-4-yl]piperidin-1-yl}methyl)-1-[(1-methyl-1H-imidazol-4-yl)methyl]-1H-benzimidazole-6-carboxylic acid |
| 78 | 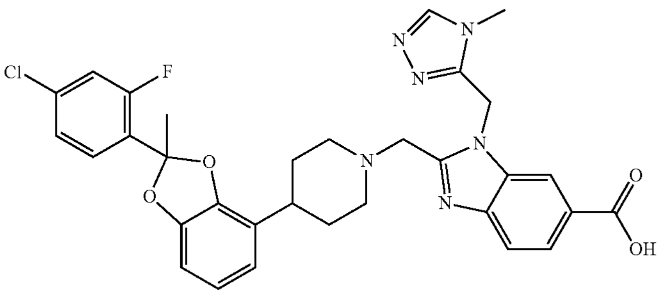 [SMILES: Cn1cnnc1Cn1c(CN2CCC(c3cccc4c3OC(C)(c3ccc(Cl)cc3F)O4)CC2)nc2ccc(C(=O)O)cc21] | 2-({4-[2-(4-chloro-2-fluorophenyl)-2-methyl-1,3-benzodioxol-4-yl]piperidin-1-yl}methyl)-1-[(4-methyl-4H-1,2,4-triazol-3-yl)methyl]-1H-benzimidazole-6-carboxylic acid |

Structure and IUPAC name for Examples 19-102

TABLE 1-continued

| Ex. No. | Structure | IUPAC Name |
|---|---|---|
| | Structure and IUPAC name for Examples 19-102 | |
| 79 | 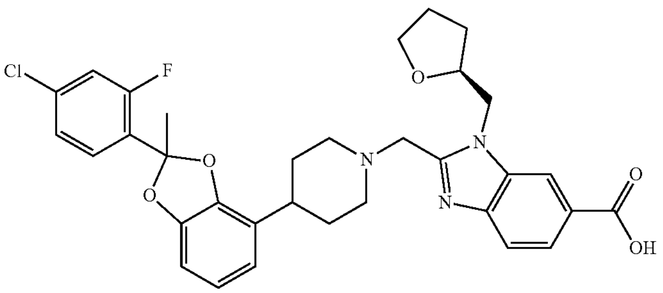 [SMILES: CC1(c2ccc(Cl)cc2F)Oc2cccc(C3CCN(Cc4nc5ccc(C(=O)O)cc5n4C[C@@H]4CCCO4)CC3)c2O1] | 2-({4-[2-(4-chloro-2-fluorophenyl)-2-methyl-1,3-benzodioxol-4-yl]piperidin-1-yl}methyl)-1-[(2S)-tetrahydrofuran-2-ylmethyl]-1H-benzimidazole-6-carboxylic acid |
| 80 | 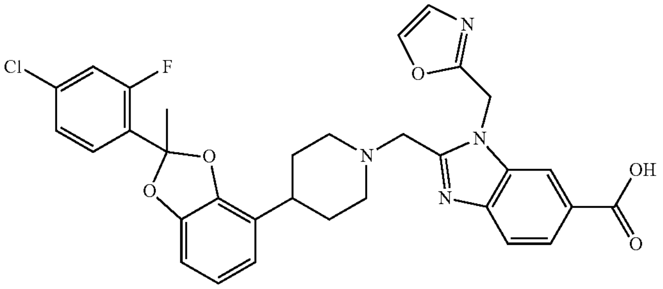 [SMILES: CC1(c2ccc(Cl)cc2F)Oc2cccc(C3CCN(Cc4nc5ccc(C(=O)O)cc5n4Cc4ncco4)CC3)c2O1] | 2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid |
| 81 | 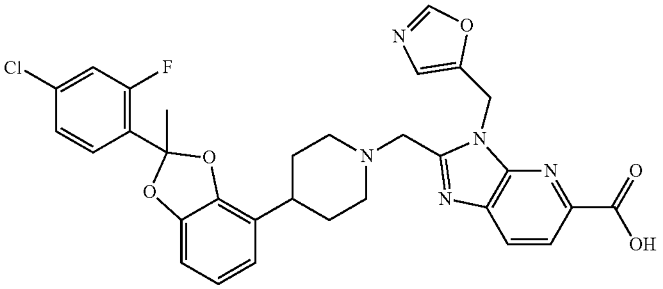 [SMILES: CC1(c2ccc(Cl)cc2F)Oc2cccc(C3CCN(Cc4nc5ccc(C(=O)O)nc5n4Cc4cnco4)CC3)c2O1] | 2-({4-[2-(4-chloro-2-fluorophenyl)-2-methyl-1,3-benzodioxol-4-yl]piperidin-1-yl}methyl)-3-(1,3-oxazol-5-ylmethyl)-3H-imidazo[4,5-b]pyridine-5-carboxylic acid |
| 82 | 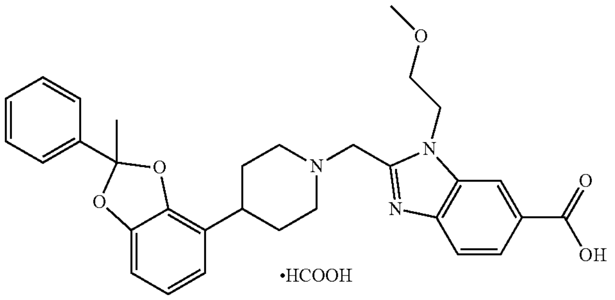 [SMILES: COCCn1c(CN2CCC(c3cccc4c3OC(C)(c3ccccc3)O4)CC2)nc2ccc(C(=O)O)cc21 ; "·HCOOH"] | 1-(2-methoxyethyl)-2-{[4-(2-methyl-2-phenyl-1,3-benzodioxol-4-yl)piperidin-1-yl]methyl}-1H-benzimidazole-6-carboxylic acid, formate salt |
| 83 | 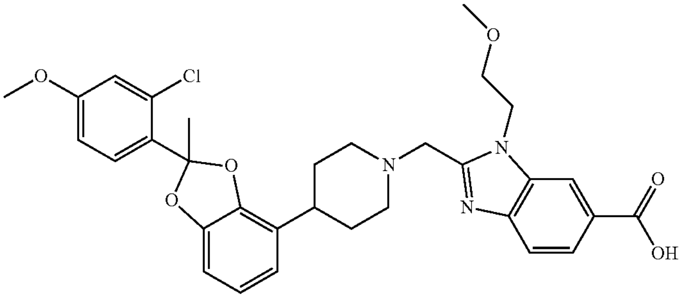 [SMILES: COCCn1c(CN2CCC(c3cccc4c3OC(C)(c3ccc(OC)cc3Cl)O4)CC2)nc2ccc(C(=O)O)cc21] | 2-({4-[2-(2-chloro-4-methoxyphenyl)-2-methyl-1,3-benzodioxol-4-yl]piperidin-1-yl}methyl)-1-(2-methoxyethyl)-1H-benzimidazole-6-carboxylic acid, formate salt |

TABLE 1-continued

| Ex. No. | Structure | IUPAC Name |
|---|---|---|
| Structure and IUPAC name for Examples 19-102 | | |
| 84 | 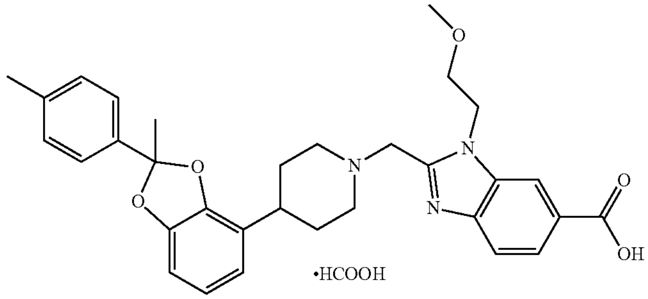 [SMILES: COCCn1c(CN2CCC(c3cccc4c3OC(C)(c3ccc(C)cc3)O4)CC2)nc2ccc(C(=O)O)cc21 ; "·HCOOH"] | 1-(2-methoxyethyl)-2-({4-[2-methyl-2-(4-methylphenyl)-1,3-benzodioxol-4-yl]piperidin-1-yl}methyl)-1H-benzimidazole-6-carboxylic acid, formate salt |
| 85 | 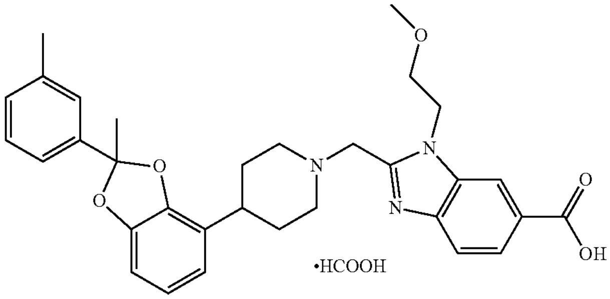 [SMILES: COCCn1c(CN2CCC(c3cccc4c3OC(C)(c3cccc(C)c3)O4)CC2)nc2ccc(C(=O)O)cc21 ; "·HCOOH"] | 1-(2-methoxyethyl)-2-({4-[2-methyl-2-(3-methylphenyl)-1,3-benzodioxol-4-yl]piperidin-1-yl}methyl)-1H-benzimidazole-6-carboxylic acid, formate salt |
| 86 | 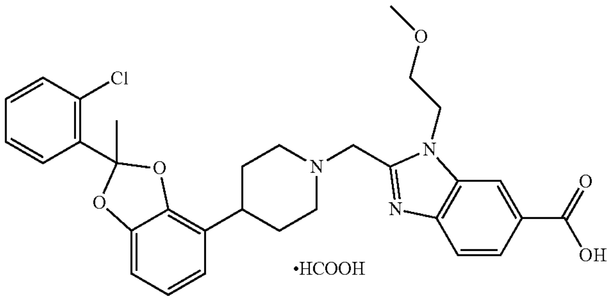 [SMILES: COCCn1c(CN2CCC(c3cccc4c3OC(C)(c3ccccc3Cl)O4)CC2)nc2ccc(C(=O)O)cc21 ; "·HCOOH"] | 2-({4-[2-(2-chlorophenyl)-2-methyl-1,3-benzodioxol-4-yl]piperidin-1-yl}methyl)-1-(2-methoxyethyl)-1H-benzimidazole-6-carboxylic acid, formate salt |
| 87 | 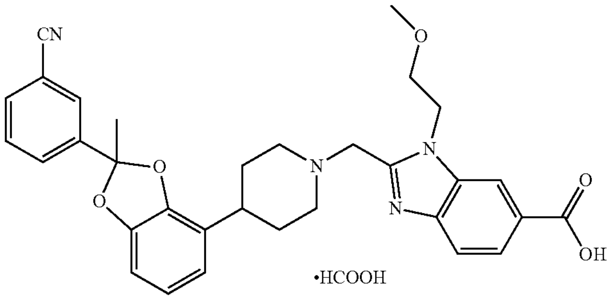 [SMILES: COCCn1c(CN2CCC(c3cccc4c3OC(C)(c3cccc(C#N)c3)O4)CC2)nc2ccc(C(=O)O)cc21 ; "·HCOOH"] | 2-({4-[2-(3-cyanophenyl)-2-methyl-1,3-benzodioxol-4-yl]piperidin-1-yl}methyl)-1-(2-methoxyethyl)-1H-benzimidazole-6-carboxylic acid, formate salt |
| 88 | 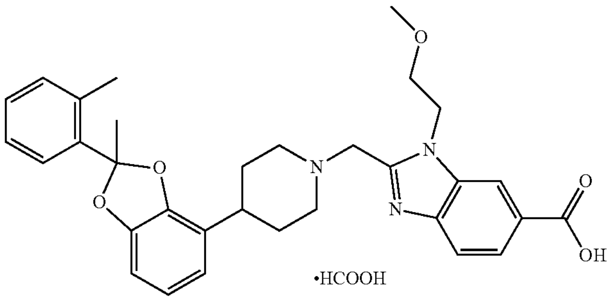 [SMILES: COCCn1c(CN2CCC(c3cccc4c3OC(C)(c3ccccc3C)O4)CC2)nc2ccc(C(=O)O)cc21 ; "·HCOOH"] | 1-(2-methoxyethyl)-2-({4-[2-methyl-2-(2-methylphenyl)-1,3-benzodioxol-4-yl]piperidin-1-yl}methyl)-1H-benzimidazole-6-carboxylic acid, formate salt |

TABLE 1-continued

Structure and IUPAC name for Examples 19-102

| Ex. No. | Structure | IUPAC Name |
|---|---|---|
| 89 | 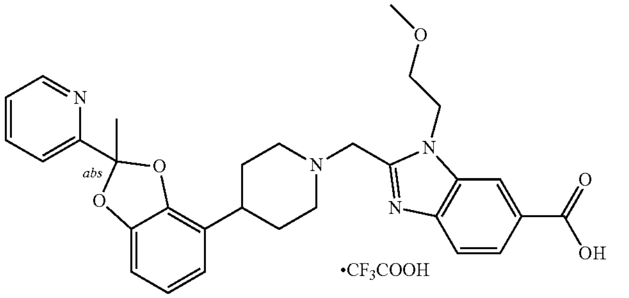 •$CF_3COOH$ ENT-X2 | 1-(2-methoxyethyl)-2-({4-[2-methyl-2-(pyridin-2-yl)-1,3-benzodioxol-4-yl]piperidin-1-yl}methyl)-1H-benzimidazole-6-carboxylic acid, ENT-X2, trifluoroacetate salt [from C81; footnote 7 in Table 2] |
| 90 | 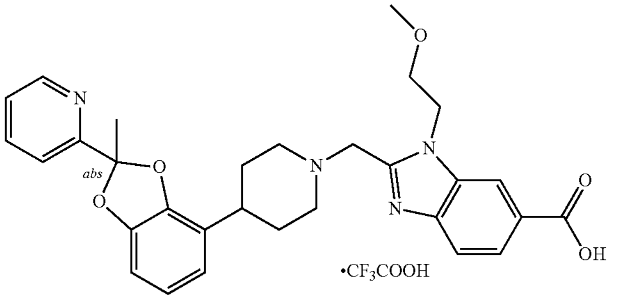 •$CF_3COOH$ ENT-X1 | 1-(2-methoxyethyl)-2-({4-[2-methyl-2-(pyridin-2-yl)-1,3-benzodioxol-4-yl]piperidin-1-yl}methyl)-1H-benzimidazole-6-carboxylic acid, ENT-X1, trifluoroacetate salt [from C80; footnote 7 in Table 2] |
| 91 | 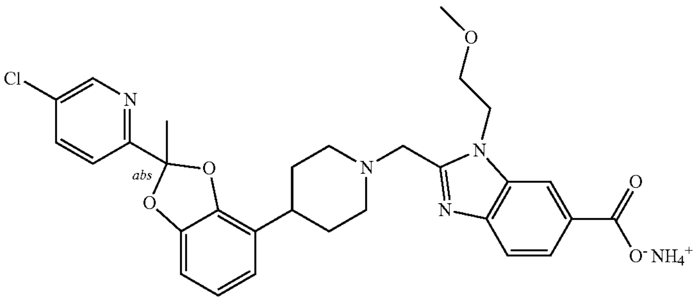 ENT-X1 | ammonium 2-({4-[2-(5-chloropyridin-2-yl)-2-methyl-1,3-benzodioxol-4-yl]piperidin-1-yl}methyl)-1-(2-methoxyethyl)-1H-benzimidazole-6-carboxylate, ENT-X1 [from P8] |
| 92 | 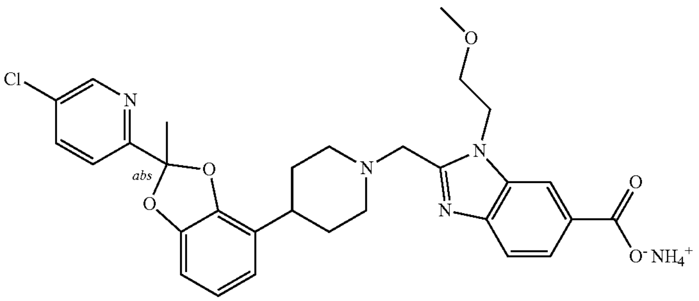 ENT-X2 | ammonium 2-({4-[2-(5-chloropyridin-2-yl)-2-methyl-1,3-benzodioxol-4-yl]piperidin-1-yl}methyl)-1-(2-methoxyethyl)-1H-benzimidazole-6-carboxylate, ENT-X2 [from P9] |

TABLE 1-continued

Structure and IUPAC name for Examples 19-102

| Ex. No. | Structure | IUPAC Name |
|---|---|---|
| 93 | 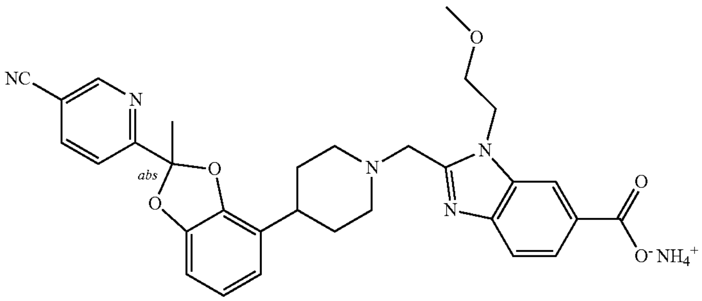 ENT-X1 | ammonium 2-({4-[2-(5-cyanopyridin-2-yl)-2-methyl-1,3-benzodioxol-4-yl]piperidin-1-yl}methyl)-1-(2-methoxyethyl)-1H-benzimidazole-6-carboxylate, ENT-X1 [from P8] |
| 94 | 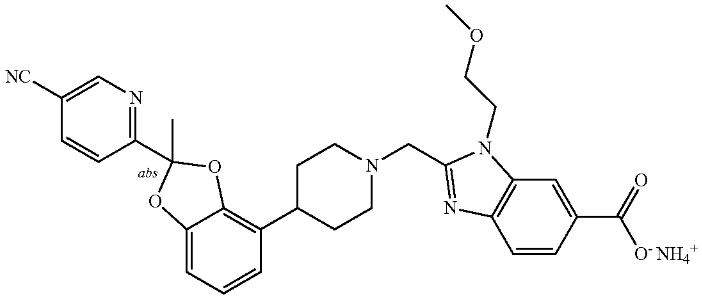 ENT-X2 | ammonium 2-({4-[2-(5-cyanopyridin-2-yl)-2-methyl-1,3-benzodioxol-4-yl]piperidin-1-yl}methyl)-1-(2-methoxyethyl)-1H-benzimidazole-6-carboxylate, ENT-X2 [from P9] |
| 95 | 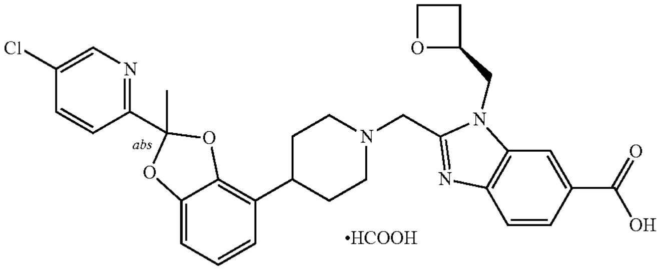 •HCOOH DIAST-X1 | 2-({4-[2-(5-chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X1 [from P8] |
| 96 | 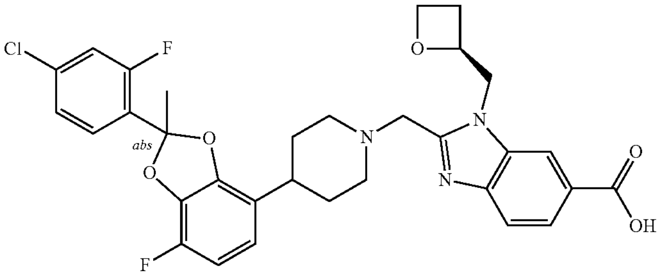 DIAST-1 | 2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid, DIAST-1 [footnote 10 in Table 2] |

TABLE 1-continued

| Structure and IUPAC name for Examples 19-102 | | |
|---|---|---|
| Ex. No. | Structure | IUPAC Name |
| 97 | 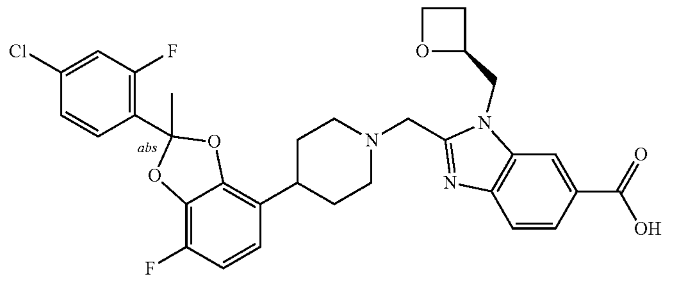 DIAST-2 | 2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid, DIAST-2 [footnote 10 in Table 2] |
| 98 | 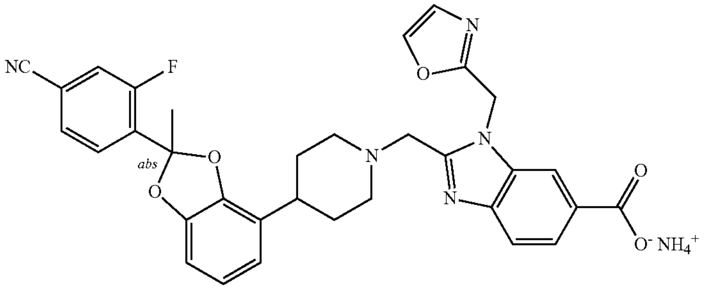 ENT-X2 | ammonium 2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylate, ENT-X2 [from C83; footnote 12 in Table 2] |
| 99 | 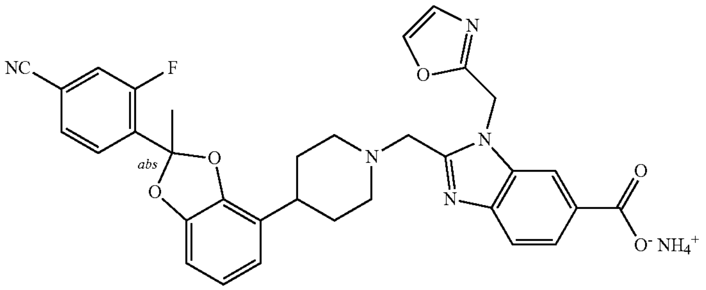 ENT-X1 | ammonium 2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylate, ENT-X1 [from C82; footnote 12 in Table 2] |
| 100 | 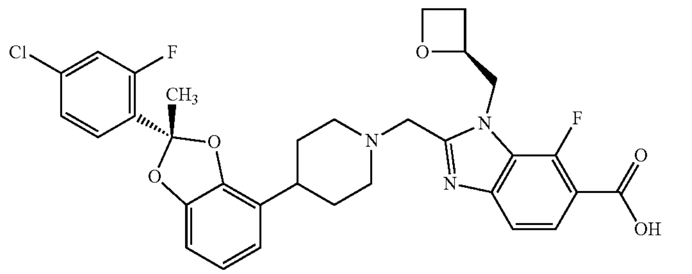 •1/2 citric acid | 2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid, hemicitrate salt [from P3] |

TABLE 1-continued

| Structure and IUPAC name for Examples 19-102 | | |
|---|---|---|
| Ex. No. | Structure | IUPAC Name |
| 101 | 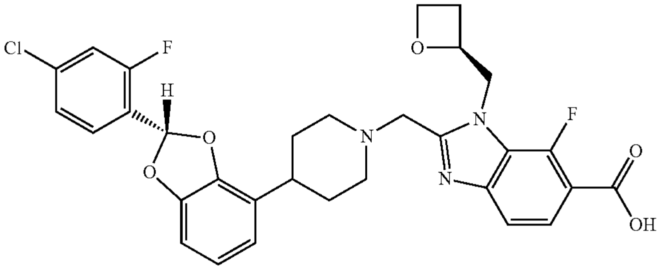 •1/2 citric acid | 2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid, hemicitrate salt [from C48] |
| 102 | 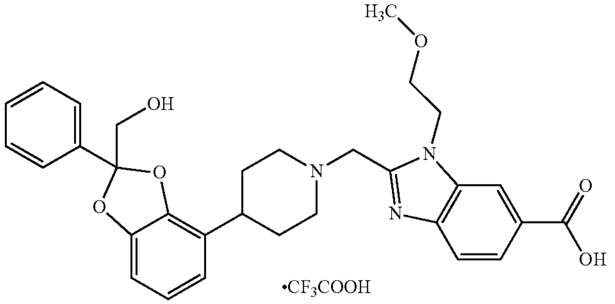 [SMILES: COCCn1c(CN2CCC(c3cccc4c3OC(CO)(c3ccccc3)O4)CC2)nc2ccc(C(=O)O)cc21 ; "·CF3COOH"] •$CF_3COOH$ | 2-({4-[2-(hydroxymethyl)-2-phenyl-1,3-benzodioxol-4-yl]piperidin-1-yl}methyl)-1-(2-methoxyethyl)-1H-benzimidazole-6-carboxylic acid, trifluoroacetate salt |

TABLE 2

| Method of preparation and physicochemical data for Examples 19-102. | | |
|---|---|---|
| Ex. No. | Method | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
| 19 | Examples 15 and 16; C4, P12 | 8.39 (br s, 1H), 8.08 (d, J = 8.5 Hz, 1H), 7.81 (d, J = 8.6 Hz, 1H), 7.60 (dd, J = 8.3, 8.3 Hz, 1H), 7.28 (dd, J = 10.9, 2.1 Hz, 1H), 7.22 (dd, J = 8.4, 2.0 Hz, 1H), 6.83 (dd, J = 8.1, 8.1 Hz, 1H), 6.60 (d, J = 7.8 Hz, 1H), 6.55 (d, J = 8.4 Hz, 1H), 4.73 (s, 2H), 4.66 (t, J = 4.9 Hz, 2H), 3.77 (t, J = 4.8 Hz, 2H), 3.59-3.43 (m, 8H), 3.30 (s, 3H^^), 2.05 (s, 3H); 581.0 |
| 20 | Examples 4 and 5[1]; C43, P11 | 8.34-8.31 (m, 1H), 8.03 (dd, J = 8.5, 1.5 Hz, 1H), 7.78 (d, J = 8.6 Hz, 1H), 7.60 (dd, J = 8.0, 8.0 Hz, 1H), 7.36 (dd, J = 10.2, 1.9 Hz, 1H), 7.31 (dd, J = 8.4, 1.8 Hz, 1H), 7.25 (s, 1H), 6.90 (dd, component of ABC pattern, J = 8.9, 6.6 Hz, 1H), 6.86-6.80 (m, 2H), 4.79 (s, 2H), 4.60 (br t, J = 4.8 Hz, 2H), 3.95-3.85 (m, 2H), 3.74 (dd, J = 5.3, 4.2 Hz, 2H), 3.44-3.33 (m, 2H), 3.28 (s, 3H), 3.15-3.05 (m, 1H), 2.37-2.12 (m, 4H); 566.0♦ |
| 21 | Examples 4 and 5[1]; C43, P11 | 8.32 (dd, J = 1.6, 0.7 Hz, 1H), 8.03 (dd, J = 8.5, 1.5 Hz, 1H), 7.78 (dd, J = 8.5, 0.7 Hz, 1H), 7.60 (dd, J = 8.1, 7.9 Hz, 1H), 7.36 (dd, J = 10.2, 2.0 Hz, 1H), 7.31 (br dd, J = 8.3, 1.8 Hz, 1H), 7.25 (s, 1H), 6.90 (dd, component of ABC pattern, J = 8.8, 6.7 Hz, 1H), 6.87-6.80 (m, 2H), 4.79 (s, 2H), 4.60 (t, J = 4.8 Hz, 2H), 3.90 (br d, J = 12.3 Hz, 2H), 3.74 (dd, J = 5.3, 4.2 Hz, 2H), 3.38 (br dd, J = 12.6, 12.5 Hz, 2H), 3.28 (s, 3H), 3.10 (tt, J = 11.9, 4.0 Hz, 1H), 2.37-2.11 (m, 4H); 566.0♦ |
| 22 | Examples 1 and 2; P12, P5 | 8.37 (d, J = 1.5 Hz, 1H), 8.07 (dd, J = 8.5, 1.5 Hz, 1H), 7.79 (d, J = 8.6 Hz, 1H), 7.60-7.54 (m, 2H), 7.50-7.42 (m, 3H), 6.98 (s, 1H), 6.86 (dd, J = 8.1, 8.1 Hz, 1H), 6.61 (dd, J = 7.9, 0.9 Hz, 1H), 6.59 (dd, J = 8.4, 0.9 Hz, 1H), 4.73 (s, 2H), 4.64 (t, J = 4.8 Hz, 2H), 3.75 (dd, J = 5.4, 4.3 Hz, 2H), 3.61-3.44 (m, 8H), 3.28 (s, 3H); 515.1 |

TABLE 2-continued

Method of preparation and physicochemical data for Examples 19-102.

| Ex. No. | Method | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|
| 23 | Examples 1 and 2; P12, P6 | 8.37 (br s, 1H), 8.07 (dd, J = 8.6, 1.5 Hz, 1H), 7.79 (d, J = 8.5 Hz, 1H), 7.61-7.54 (m, 2H), 7.51-7.42 (m, 3H), 6.98 (s, 1H), 6.86 (dd, J = 8.2, 8.1 Hz, 1H), 6.61 (br d, J = 8 Hz, 1H), 6.59 (br d, J = 8.5 Hz, 1H), 4.69 (s, 2H), 4.64 (t, J = 4.9 Hz, 2H), 3.75 (t, J = 4.9 Hz, 2H), 3.59-3.43 (m, 8H), 3.29 (s, 3H); 515.1 |
| 24 | Examples 4 and 5; C13, P11 | 8.33 (dd, J = 1.5, 0.6 Hz, 1H), 8.03 (dd, J = 8.5, 1.5 Hz, 1H), 7.79 (dd, J = 8.5, 0.5 Hz, 1H), 7.62 (dd, J = 8.4, 8.3 Hz, 1H), 7.29 (dd, J = 10.9, 2.0 Hz, 1H), 7.22 (ddd, J = 8.4, 2.0, 0.7 Hz, 1H), 6.88-6.82 (m, 1H), 6.82-6.76 (m, 2H), 4.83 (s, 2H), 4.63 (t, J = 4.8 Hz, 2H), 3.98-3.88 (m, 2H), 3.75 (dd, J = 5.3, 4.2 Hz, 2H), 3.47-3.36 (m, 2H), 3.31 (s, 3H^^), 3.10 (tt, J = 12.0, 4.1 Hz, 1H), 2.36-2.10 (m, 4H), 2.05 (d, J = 1.0 Hz, 3H); 580.1◆ |
| 25 | Examples 15 and 16[2]; C4, P17 | 8.51 (dd, J = 1.5, 0.7 Hz, 1H), 8.25 (dd, J = 8.6, 1.4 Hz, 1H), 7.79 (dd, J = 8.6, 0.7 Hz, 1H), 7.57 (dd, J = 8.3, 8.3 Hz, 1H), 7.25 (dd, J = 10.8, 2.0 Hz, 1H), 7.19 (ddd, J = 8.4, 2.0, 0.7 Hz, 1H), 6.80-6.73 (m, 1H), 6.55-6.50 (m, 2H), 4.9-4.73 (m, 2H^), 3.92-3.81 (m, 2H), 3.66-3.58 (m, 1H), 3.41-3.3 (m, 1H^^), 3.25 (s, 3H), 3.20-3.12 (m, 1H), 3.05-2.97 (m, 1H), 2.70-2.63 (m, 1H), 2.27-2.17 (m, 1H), 2.01 (d, J = 1.0 Hz, 3H), 1.84-1.71 (m, 2H), 1.67-1.58 (m, 2H), 1.31 (br d, J = 13 Hz, 1H); 592.3◆ |
| 26 | Examples 15 and 16[2]; C4, P17 | 8.53-8.50 (m, 1H), 8.26 (dd, J = 8.6, 1.4 Hz, 1H), 7.81 (d, J = 8.6 Hz, 1H), 7.55 (dd, J = 8.3, 8.2 Hz, 1H), 7.16-7.08 (m, 2H), 6.77 (dd, J = 8.3, 7.9 Hz, 1H), 6.52 (br d, J = 8.3 Hz, 1H), 6.51 (br d, J = 7.7 Hz, 1H), 4.9-4.74 (m, 2H^), 3.83 (t, J = 4.8 Hz, 2H), 3.68-3.60 (m, 1H), 3.54-3.46 (m, 1H), 3.18-3.09 (m, 1H), 3.14 (s, 3H), 3.09-3.01 (m, 1H), 2.69-2.62 (m, 1H), 2.31-2.21 (m, 1H), 2.01 (br s, 3H), 1.78-1.69 (m, 2H), 1.63-1.52 (m, 2H), 1.33-1.25 (m, 1H); 592.3◆ |
| 27 | Examples 4 and 5[3]; P11 | 8.32 (br s, 1H), 8.02 (dd, J = 8.5, 1.5 Hz, 1H), 7.82-7.76 (m, 2H), 7.73 (br d, J = 10.0 Hz, 1H), 7.67 (br d, J = 8.0 Hz, 1H), 7.35 (s, 1H), 6.96-6.89 (m, 1H), 6.88-6.83 (m, 2H), 4.76 (s, 2H), 4.61 (t, J = 4.8 Hz, 2H), 3.87 (br d, J = 12.3 Hz, 2H), 3.74 (t, J = 4.8 Hz, 2H), 3.39-3.3 (m, 2H^^), 3.29 (s, 3H), 3.15-3.05 (m, 1H), 2.35-2.10 (m, 4H); 557.1 |
| 28 | Example 11; P14 | 3.08 minutes[4]; 596 |
| 29 | Example 11; P14 | 3.12 minutes[4]; 556 |
| 30 | Example 11; P14 | 2.90 minutes[4]; 576 |
| 31 | Example 11; P14 | 2.92 minutes[4]; 546 |
| 32 | Example 11; P14 | 2.88 minutes[4]; 558 |
| 33 | Example 11; P14 | 3.04 minutes[4]; 562 |
| 34 | Example 11; P14 | 2.99 minutes[5]; 553 |
| 35 | Example 11; P14 | 2.92 minutes[4]; 576 |
| 36 | Example 11; P14 | 2.81 minutes[5]; 543 |
| 37 | Example 11; P14 | 2.90 minutes[4]; 558 |
| 38 | Example 11; P14 | 2.91 minutes[4]; 546 |
| 39 | Example 11; P14 | 2.89 minutes[4]; 558 |
| 40 | Example 11; P14 | 3.11 minutes[4]; 596 |
| 41 | Example 11; P14 | 2.97 minutes[4]; 564 |
| 42 | Example 11; P14 | 2.40 minutes[5]; 543 |
| 43 | Example 12; P10 | 2.70 minutes[4]; 621 |

TABLE 2-continued

Method of preparation and physicochemical data for Examples 19-102.

| Ex. No. | Method | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|
| 44 | Example 12; P10 | 2.49 minutes[4]; 635 |
| 45 | Example 12; P10 | 2.79 minutes[4]; 613 |
| 46 | Example 12; P10 | 2.71 minutes[4]; 635 |
| 47 | Example 12; P10 | 2.85 minutes[4]; 657 |
| 48 | Example 12; P10 | 2.71 minutes[4]; 633 |
| 49 | Example 12; P10 | 2.66 minutes[4]; 607 |
| 50 | Example 12; P10 | 2.43 minutes[4]; 616 |
| 51 | Example 12; P10 | 2.74 minutes[4]; 630 |
| 52 | Example 12; P10 | 2.73 minutes[4]; 593 |
| 53 | Example 12; P10 | 2.79 minutes[4]; 616 |
| 54 | Example 12; P10 | 2.67 minutes[4]; 631 |
| 55 | Example 12; P10 | 2.44 minutes[4]; 630 |
| 56 | Example 12; P10 | 2.77 minutes[4]; 606 |
| 57 | Example 12; P10 | 2.72 minutes[4]; 617 |
| 58 | Example 12; P10 | 2.78 minutes[4]; 603 |
| 59 | Example 12; P10 | 2.82 minutes[4]; 621 |
| 60 | Example 12; P10 | 2.74 minutes[4]; 631 |
| 61 | Example 12; P10 | 2.76 minutes[4]; 592 |
| 62 | Example 12; P10 | 2.45 minutes[4]; 630 |
| 63 | Example 12; P10 | 2.78 minutes[4]; 617 |
| 64 | Example 12; P10 | 2.84 minutes[4]; 606 |
| 65 | Example 12; P10 | 2.56 minutes[4]; 613 |
| 66 | Example 12; P10 | 2.75 minutes[4]; 607 |
| 67 | Example 12; P10 | 2.48 minutes[4]; 619 |
| 68 | Example 12; P10 | 2.75 minutes[4]; 646 |
| 69 | Example 12; P10 | 2.73 minutes[4]; 603 |
| 70 | Example 12; P10 | 2.86 minutes[5]; 661 |
| 71 | Example 12; P10 | 2.77 minutes[4]; 657 |
| 72 | Example 12; P10 | 2.79 minutes[4]; 606 |
| 73 | Example 12; P10 | 2.70 minutes[4]; 602 |
| 74 | Example 12; P10 | 2.45 minutes[4]; 616 |
| 75 | Example 13; P10 | 2.92 minutes[4]; 566 |
| 76 | Example 13; P10 | 2.99 minutes[4]; 631 |
| 77 | Example 13; P10 | 2.94 minutes[4]; 616 |
| 78 | Example 13; P10 | 3.08 minutes[5]; 617 |
| 79 | Example 13; P10 | 3.09 minutes[4]; 606 |
| 80 | Example 13; P10 | 3.02 minutes[4]; 603 |

TABLE 2-continued

| Ex. No. | Method | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|
| | Method of preparation and physicochemical data for Examples 19-102. | |
| 81 | Example 13; P10 | 3.10 minutes[5]; 604 |
| 82 | Example 11; P14 | 2.87 minutes[4]; 528 |
| 83 | Example 11; P14 | 3.00 minutes[4]; 592 |
| 84 | Example 11; P14 | 2.99 minutes[4]; 542 |
| 85 | Example 11; P14 | 2.98 minutes[4]; 542 |
| 86 | Example 11; P14 | 2.97 minutes[4]; 562 |
| 87 | Example 11; P14 | 2.97 minutes[5]; 553 |
| 88 | Example 11; P14 | 2.90 minutes[4]; 542 |
| 89 | Examples 4 and 5[6,7]; P11 | 8.63 (ddd, J = 4.9, 1.8, 0.9 Hz, 1H), 8.34 (dd, J = 1.6, 0.7 Hz, 1H), 8.03 (dd, J = 8.5, 1.5 Hz, 1H), 7.90 (ddd, J = 7.8, 7.8, 1.7 Hz, 1H), 7.80 (dd, J = 8.5, 0.7 Hz, 1H), 7.74 (ddd, J = 7.9, 1.1, 1.0 Hz, 1H), 7.45 (ddd, J = 7.6, 4.9, 1.2 Hz, 1H), 6.88-6.83 (m, 1H), 6.83-6.76 (m, 2H), 4.83 (s, 2H), 4.63 (t, J = 4.8 Hz, 2H), 3.99-3.88 (m, 2H), 3.75 (dd, J = 5.3, 4.2 Hz, 2H), 3.45-3.34 (m, 2H), 3.31 (s, 3H), 3.15-3.03 (m, 1H), 2.41-2.20 (m, 2H), 2.19-2.08 (m, 2H), 2.05 (s, 3H); 529.3 |
| 90 | Examples 4 and 5[6,7]; P11 | 8.63 (ddd, J = 4.9, 1.8, 0.9 Hz, 1H), 8.34 (dd, J = 1.6, 0.7 Hz, 1H), 8.04 (dd, J= 8.5, 1.5 Hz, 1H), 7.90 (ddd, J = 7.8, 7.8, 1.7 Hz, 1H), 7.80 (dd, J = 8.5, 0.7 Hz, 1H), 7.73 (ddd, J = 8.0, 1.1, 1.0 Hz, 1H), 7.45 (ddd, J = 7.6, 4.9, 1.2 Hz, 1H), 6.88-6.83 (m, 1H), 6.83-6.75 (m, 2H), 4.83 (s, 2H), 4.63 (t, J = 4.9 Hz, 2H), 3.98-3.88 (m, 2H), 3.75 (t, J = 4.8 Hz, 2H), 3.44-3.34 (m, 2H), 3.32 (s, 3H^^), 3.15-3.03 (m, 1H), 2.40-2.19 (m, 2H), 2.18-2.08 (m, 2H), 2.05 (s, 3H); 529.3 |
| 91 | Examples 6 and 7; P8, P11 | 8.59 (d, J = 2.4 Hz, 1H), 8.26 (d, J = 1.4 Hz, 1H), 7.96 (dd, J = 8.5, 1.5 Hz, 1H), 7.87 (dd, J = 8.5, 2.5 Hz, 1H), 7.68-7.61 (m, 2H), 6.83-6.75 (m, 1H), 6.75-6.67 (m, 2H), 4.67 (t, J = 5.2 Hz, 2H), 4.00 (s, 2H), 3.82 (t, J = 5.1 Hz, 2H), 3.29 (s, 3H), 3.13-3.05 (m, 2H), 2.81-2.70 (m, 1H), 2.45-2.34 (m, 2H), 2.01 (s, 3H), 1.98-1.77 (m, 4H); 563.3♦ |
| 92 | Examples 6 and 7; P9, P11 | 8.59 (d, J = 2.3 Hz, 1H), 8.26 (d, J = 1.4 Hz, 1H), 7.96 (dd, J = 8.5, 1.5 Hz, 1H), 7.87 (dd, J = 8.5, 2.5 Hz, 1H), 7.68-7.62 (m, 2H), 6.82-6.76 (m, 1H), 6.74-6.68 (m, 2H), 4.67 (t, J = 5.2 Hz, 2H), 4.00 (s, 2H), 3.82 (t, J = 5.1 Hz, 2H), 3.29 (s, 3H), 3.13-3.04 (m, 2H), 2.76 (tt, J = 11.8, 4 Hz, 1H), 2.45-2.34 (m, 2H), 2.01 (s, 3H), 1.97-1.78 (m, 4H); 563.3♦ |
| 93 | Examples 8 and 9[8]; P8, P11 | 8.97 (dd, J = 2.1, 0.9 Hz, 1H), 8.27-8.25 (m, 1H), 8.21 (dd, J = 8.2, 2.1 Hz, 1H), 7.96 (dd, J = 8.5, 1.5 Hz, 1H), 7.81 (dd, J = 8.3, 0.9 Hz, 1H), 7.64 (d, J = 8.6 Hz, 1H), 6.83-6.77 (m, 1H), 6.76-6.68 (m, 2H), 4.68 (t, J = 5.2 Hz, 2H), 3.95 (s, 2H), 3.83 (t, J = 5.2 Hz, 2H), 3.30 (s, 3H), 3.08-2.99 (m, 2H), 2.79-2.69 (m, 1H), 2.39-2.28 (m, 2H), 2.04 (s, 3H), 1.96-1.76 (m, 4H); 554.4 |
| 94 | Examples 8 and 9[8]; P9, P11 | 8.97 (dd, J = 2.2, 0.9 Hz, 1H), 8.26 (br s, 1H), 8.21 (dd, J = 8.2, 2.1 Hz, 1H), 7.96 (dd, J = 8.4, 1.4 Hz, 1H), 7.81 (dd, J = 8.2, 0.9 Hz, 1H), 7.64 (br d, J = 8.5 Hz, 1H), 6.83-6.77 (m, 1H), 6.76-6.69 (m, 2H), 4.68 (t, J = 5.3 Hz, 2H), 3.95 (s, 2H), 3.83 (t, J = 5.2 Hz, 2H), 3.30 (s, 3H), 3.08-2.99 (m, 2H), 2.79-2.69 (m, 1H), 2.39-2.28 (m, 2H), 2.04 (s, 3H), 1.96-1.76 (m, 4H); 554.4 |
| 95 | Example 10; P8, P15 | 8.61 (dd, J = 2.5, 0.7 Hz, 1H), 8.41 (s, 1H), 8.33 (dd, J = 1.6, 0.7 Hz, 1H), 7.97 (dd, J = 8.5, 1.5 Hz, 1H), 7.88 (dd, J = 8.5, 2.5 Hz, 1H), 7.66 (dd, J = 8.5, 0.6 Hz, 1H), 7.65 (dd, J = 8.5, 0.7 Hz, 1H), 6.82-6.77 (m, 1H), 6.76-6.69 (m, 2H), 5.32-5.24 (m, 1H), 4.9-4.83 (m, 1H^), 4.71 (dd, J = 15.4, 2.6 Hz, 1H), 4.65-4.58 |

TABLE 2-continued

Method of preparation and physicochemical data for Examples 19-102.

| Ex. No. | Method | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|
| | | (m, 1H), 4.48 (ddd, J = 9.2, 6.0, 5.9 Hz, 1H), 4.03 (AB quartet, $J_{AB}$ = 13.9 Hz, $\Delta\nu_{AB}$ = 49.7 Hz, 2H), 3.18-3.11 (m, 1H), 3.06-2.98 (m, 1H), 2.87-2.69 (m, 2H), 2.60-2.49 (m, 1H), 2.46-2.31 (m, 2H), 2.02 (s, 3H), 1.98-1.79 (m, 4H); 574.9◆ |
| 96 | Examples 6 and 7[9,10]; P15 | 7.01 minutes[11]; 610.5◆ |
| 97 | Examples 6 and 7[9,10]; P15 | 7.89 minutes[11]; 610.5◆ |
| 98 | C54[12] | 8.25-8.23 (m, 1H), 8.00 (dd, J = 8.5, 1.5 Hz, 1H), 7.89 (d, J = 0.9 Hz, 1H), 7.76 (dd, J = 7.9, 7.6 Hz, 1H), 7.70 (d, J = 8.5 Hz, 1H), 7.64 (dd, J = 10.6, 1.5 Hz, 1H), 7.57 (dd, J = 8.0, 1.5 Hz, 1H), 7.14 (d, J = 0.9 Hz, 1H), 6.78 (dd, component of ABC pattern, J = 7.9, 7.8 Hz, 1H), 6.70 (dd, component of ABC pattern, J = 7.8, 1.2 Hz, 1H), 6.66 (br d, component of ABC pattern, J = 7.9 Hz, 1H), 5.94 (AB quartet, $J_{AB}$ = 17.2 Hz, $\Delta\nu_{AB}$ = 6.5 Hz, 2H), 3.96 (s, 2H), 3.02-2.92 (m, 2H), 2.74-2.63 (m, 1H), 2.31-2.21 (m, 2H), 2.05 (br s, 3H), 1.80-1.58 (m, 4H); 594.3 |
| 99 | C54[12] | 8.23 (d, J = 1.4 Hz, 1H), 8.00 (dd, J = 8.5, 1.5 Hz, 1H), 7.89 (d, J = 0.9 Hz, 1H), 7.76 (dd, J = 7.9, 7.6 Hz, 1H), 7.69 (d, J = 8.5 Hz, 1H), 7.64 (dd, J = 10.6, 1.5 Hz, 1H), 7.57 (dd, J = 8.1, 1.5 Hz, 1H), 7.14 (d, J = 0.9 Hz, 1H), 6.78 (dd, component of ABC pattern, J = 7.8, 7.8 Hz, 1H), 6.70 (dd, component of ABC pattern, J = 7.8, 1.2 Hz, 1H), 6.66 (br d, component of ABC pattern, J = 7.9 Hz, 1H), 5.94 (AB quartet, $J_{AB}$ = 17.1 Hz, $\Delta\nu_{AB}$ = 6.6 Hz, 2H), 3.96 (s, 2H), 3.01-2.92 (m, 2H), 2.74-2.63 (m, 1H), 2.30-2.20 (m, 2H), 2.05 (br s, 3H), 1.80-1.58 (m, 4H); 594.3 |
| 100 | Example 7, free acid[13]; P3, C29 | characteristic peaks: 7.80 (dd, J = 8.5, 6.6 Hz, 1H), 7.59 (dd, J = 8.3, 8.3 Hz, 1H), 7.51 (d, J = 8.6 Hz, 1H), 7.28 (dd, J = 10.9, 2.0 Hz, 1H), 7.21 (br dd, J = 8.4, 2.0 Hz, 1H), 6.83-6.77 (m, 1H), 6.76-6.71 (m, 2H), 5.32-5.23 (m, 1H), 4.99 (dd, J = 15.5, 7.1 Hz, 1H), 4.79 (dd, J = 15.6, 2.8 Hz, 1H), 4.72-4.63 (m, 1H), 4.47 (ddd, J = 9.1, 6.0, 6.0 Hz, 1H), 4.31 (AB quartet, $J_{AB}$ = 14.4 Hz, $\Delta\nu_{AB}$ = 33.3 Hz, 2H), 3.40 (br d, J = 11.9 Hz, 1H), 2.92-2.65 (m, 4H), 2.82 (AB quartet, $J_{AB}$ = 15.5 Hz, $\Delta\nu_{AB}$ = 37.5 Hz, 2H), 2.61-2.49 (m, 1H), 2.13-1.87 (m, 4H), 2.04 (s, 3H); 610.0◆ |
| 101 | Example 5, free acid[13]; C48, C29 | characteristic peaks: 7.79 (dd, J = 8.5, 6.6 Hz, 1H), 7.57 (dd, J = 8.0, 8.0 Hz, 1H), 7.49 (d, J = 8.5 Hz, 1H), 7.35 (dd, J = 10.2, 1.9 Hz, 1H), 7.30 (br d, J = 8.4 Hz, 1H), 7.22 (s, 1H), 6.88-6.82 (m, 1H), 6.82-6.74 (m, 2H), 5.30-5.21 (m, 1H), 4.95 (dd, J = 15.4, 7.1 Hz, 1H), 4.77 (br d, J = 15.1 Hz, 1H), 4.67-4.59 (m, 1H), 4.44 (ddd, J = 9.1, 5.9, 5.9 Hz, 1H), 4.28 (AB quartet, $J_{AB}$ = 14.4 Hz, $\Delta\nu_{AB}$ = 31.7 Hz, 2H), 3.37 (br d, J = 12.3 Hz, 1H^^), 2.92-2.61 (m, 4H), 2.82 (AB quartet, $J_{AB}$ = 15.6 Hz, $\Delta\nu_{AB}$ = 37.1 Hz, 2H), 2.58-2.47 (m, 1H), 2.12-1.89 (m, 4H); 596.1◆ |
| 102 | Examples 4 and 5[14]; P11 | 8.34 (dd, J = 1.6, 0.7 Hz, 1H), 8.04 (dd, J = 8.5, 1.5 Hz, 1H), 7.80 (dd, J = 8.5, 0.7 Hz, 1H), 7.66-7.60 (m, 2H), 7.46-7.36 (m, 3H), 6.84-6.76 (m, 2H), 6.74 (dd, J = 7.2, 2.0 Hz, 1H), 4.84 (s, 2H), 4.63 (t, J = 4.7 Hz, 2H), 4.01-3.91 (m, 4H), 3.76 (dd, J = 5.3, 4.2 Hz, 2H), 3.47-3.37 (m, 2H), 3.32 (s, 3H), 3.19-3.08 (m, 1H), 2.41-2.26 (m, 2H), 2.26-2.13 (m, 2H); 544.2 |

^area is assumed, peak is partially obscured by water peak

^^area is assumed, peak is partially obscured by solvent peak

◆chlorine isotope pattern observed

1. The racemic methyl ester [methyl 2-({4-[2-(4-chloro-2-fluorophenyl)-1,3-benzodioxol-4-yl]piperidin-1-yl}methyl)-1-(2-methoxyethyl)-1H-benzimidazole-6-carboxylate] was separated into its component enantiomers via SFC [Column: Chiral Technologies ChiralCel OD-H, 5 μm; Mobile phase: 7:3 carbon dioxide/(2-propanol containing 0.1% ammonium hydroxide)]. The first-eluting enantiomer, ENT-1 (C76), was used in the synthesis of Example 21, and the second-eluting enantiomer, ENT-2 (C77), was converted to Example 20. C76 retention time: 5.72 minutes (Column: Chiral Technologies Chiralpak OD-3, 4.6×150 mm, 3 μm; Mobile phase A: carbon dioxide; Mobile phase B: 2-propanol containing 0.05% diethylamine; Gradient: 5% to 40% B over 5.5 minutes, then held at 40% B for 3.0 minutes; Flow rate: 2.5 mL/minute). C77 retention time: 6.01 minutes (Analytical SFC conditions identical to those used for C76).

2. The methyl ester (methyl 2-{6-[2-(4-chloro-2-fluorophenyl)-2-methyl-1,3-benzodioxol-4-yl]-6-azaspiro[2.5]oct-1-yl}-1-(2-methoxyethyl)-1H-benzimidazole-6-carboxylate) derived from coupling of C4 and P17 was separated into its component stereoisomers at the dioxolane via SFC [Column: Chiral Technologies Chiralpak AD, 10 μm; Mobile phase: 65:35 carbon dioxide/(ethanol containing 0.1% ammonium hydroxide)]. The first-eluting isomer, DIAST-1 (C78), was converted to Example 26; by examination of $^1$H NMR data, this material was the enantiomer of Example 15. The second-eluting isomer, DIAST-2 (C79), was used in the synthesis of Example 25; by examination of $^1$H NMR data, this material was the enantiomer of Example 16. C78 retention time: 3.60 minutes (Column: Chiral Technologies Chiralpak AD-3, 4.6×100 mm, 3 μm; Mobile phase A: carbon dioxide; Mobile phase B: ethanol containing 0.05% diethylamine; Gradient: 5% to 40% B over 4.5 minutes, then held at 40% B for 2.5 minutes; Flow rate: 2.8 mL/minute). C79 retention time: 3.82 minutes (Analytical SFC conditions identical to those used for C78).

3. 4-(4-Bromo-1,3-benzodioxol-2-yl)-3-fluorobenzonitrile was prepared via treatment of 3-fluoro-4-formylbenzonitrile and 3-bromobenzene-1,2-diol with p-toluenesulfonic acid in toluene, with removal of water using a Dean-Stark apparatus. This material was then reacted with [1-(tert-butoxycarbonyl)piperidin-4-yl](iodo)zinc in the presence of [1,1'-bis(diphenylphosphino)ferrocene]dichloropalladium(II) and copper(i) iodide, followed by ester cleavage using p-toluenesulfonic acid, to afford the requisite 3-fluoro-4-[4-(piperidin-4-yl)-1,3-benzodioxol-2-yl]benzonitrile.

4. Conditions for analytical HPLC. Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 10% to 100% B over 4.0 minutes; Flow rate: 0.8 mL/minute.

5. Conditions for analytical HPLC. Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute.

6. tert-Butyl 4-[2-methyl-2-(pyridin-2-yl)-1,3-benzodioxol-4-yl]-3,6-dihydropyridine-1(2H)-carboxylate was synthesized from 3-bromobenzene-1,2-diol and 2-ethynylpyridine using the procedure described for synthesis of C12 in Preparation P7. Subsequent hydrogenation over palladium on carbon, followed by treatment with hydrogen chloride in ethyl acetate, afforded the requisite 2-[2-methyl-4-(piperidin-4-yl)-1,3-benzodioxol-2-yl]pyridine, hydrochloride salt.

7. The racemic methyl ester [methyl 1-(2-methoxyethyl)-2-({4-[2-methyl-2-(pyridin-2-yl)-1,3-benzodioxol-4-yl]piperidin-1-yl}methyl)-1H-benzimidazole-6-carboxylate] was separated into its component enantiomers via SFC [Column: Chiral Technologies Chiralpak AD, 10 μm; Mobile phase: 65:35 carbon dioxide/(ethanol containing 0.1% ammonium hydroxide)]. The first-eluting enantiomer ENT-1 (C80) was used in the synthesis of Example 90, and the second-eluting enantiomer ENT-2 (C81) was converted to Example 89. C80 retention time: 4.11 minutes (Column: Chiral Technologies Chiralpak AD-3, 4.6×100 mm, 3 μm; Mobile phase A: carbon dioxide; Mobile phase B: ethanol containing 0.05% diethylamine; Gradient: 5% to 40% B over 4.5 minutes, then held at 40% B for 2.5 minutes; Flow rate: 2.8 mL/minute). C81 retention time: 4.62 minutes (Analytical SFC conditions identical to those used for C80).

8. Conversion of P8 and P9 to the corresponding cyano-substituted derivatives was carried out using the method described for synthesis of P4 from P2 in Preparation P4.

9. Treatment of 1-(4-chloro-2-fluorophenyl)ethanone with trimethyl orthoformate and p-toluene-sulfonic acid provided 4-chloro-1-(1,1-dimethoxyethyl)-2-fluorobenzene, which was reacted with 3-bromo-6-fluorobenzene-1,2-diol in the presence of p-toluenesulfonic acid to afford 4-bromo-2-(4-chloro-2-fluorophenyl)-7-fluoro-2-methyl-1,3-benzodioxole. This material was converted to the requisite tert-butyl 4-[2-(4-chloro-2-fluorophenyl)-7-fluoro-2-methyl-1,3-benzodioxol-4-yl]piperidine-1-carboxylate using the method described in Preparation P1 for synthesis of P1 from C2.

10. Separation of the stereoisomers at the dioxolane in 96 and 97 was carried out using SFC [Column: Chiral Technologies Chiralpak IG, 5 μm; Mobile phase: 3:1 carbon dioxide/(2-propanol containing 0.2% ammonium hydroxide)]. The first-eluting isomer was designated as DIAST-1 (96) and the second-eluting isomer as DIAST-2 (97).

11. Conditions for analytical SFC. Column: Chiral Technologies Chiralpak IG, 4.6×100 mm, 5 μm; Mobile phase: 7:3 carbon dioxide/(2-propanol containing 0.2% ammonium hydroxide); Flow rate: 1.5 mL/minute; Back pressure: 150 bar.

12. tert-Butyl 2-(chloromethyl)-1-(1,3-oxazol-2-ylmethyl)-1H-benzimidazole-6-carboxylate was synthesized from tert-butyl 3-fluoro-4-nitrobenzoate and 1-(1,3-oxazol-2-yl)methanamine, using the method described for synthesis of P11. Subsequent reaction with C54 was carried out using triethylamine to afford tert-butyl 2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylate, which was separated into its component enantiomers using SFC [Column: Chiral Technologies ChiralCel OD-H, 5 μm; Mobile phase: 55:45 carbon dioxide/(ethanol containing 0.1% ammonium hydroxide)]. The first-eluting enantiomer ENT-1 (C82) was used in the synthesis of 99, and the second-eluting enantiomer ENT-2 (C83) was converted to 98. C82 retention time: 1.47 minutes (Column: Chiral Technologies Chiralpak OD-3, 4.6×50 mm, 3 μm; Mobile phase A: carbon dioxide; Mobile phase B: methanol containing 0.05% diethylamine; Gradient: 5% B for 0.2 minutes, then 5% to 40% B over 1.4 minutes, then held at 40% B for 1.05 minutes; Flow rate: 4 mL/minute). C83 retention time: 1.85 minutes (Analytical SFC conditions identical to those used for C82).

13. Reaction of 1-bromo-2,3-difluoro-4-nitrobenzene with copper(I) cyanide in 1-methylpyrrolidin-2-one at elevated temperature provided 2,3-difluoro-4-nitrobenzonitrile, which was subjected to thionyl chloride and methanol to afford methyl 2,3-difluoro-4-nitrobenzoate. This material was converted, through use of C29, to the requisite methyl 2-(chloromethyl)-7-fluoro-1-[(2S)-oxetan-2-ylmethyl]-1H-benzimidazole-6-carboxylate, via the method described in Preparation P11 for synthesis of P11 from methyl 3-fluoro-4-nitrobenzoate.

14. The requisite [2-phenyl-4-(piperidin-4-yl)-1,3-benzodioxol-2-yl]methanol was synthesized from 2-oxo-2-phenylethyl acetate, by analogy to the method described for synthesis of C13.

Example 103

2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid

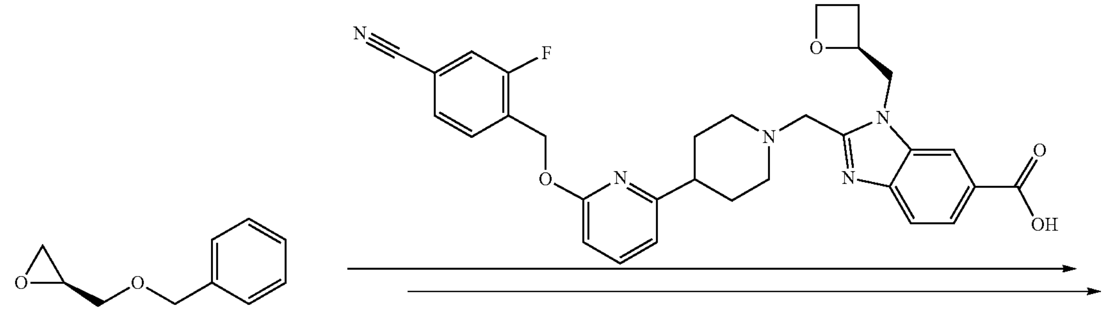

(S)-2-((benzyloxy)methyl)oxirane

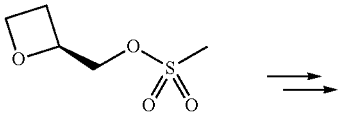

Intermediate 103-1

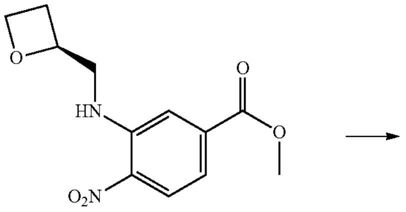

Intermediate 103-2

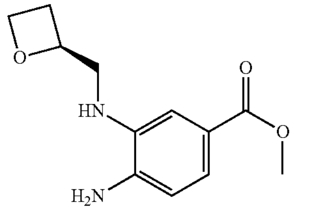

Intermediate 103-3

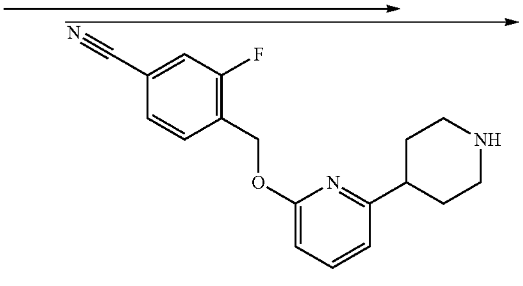

Intermediate 103-0

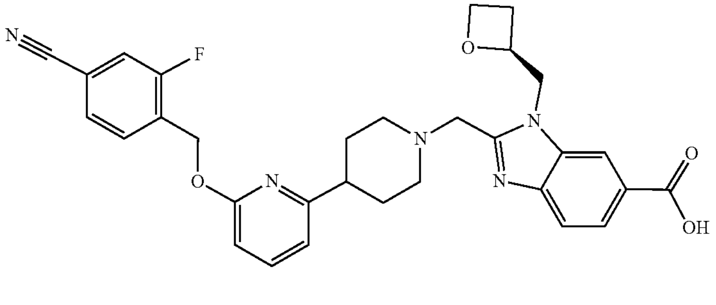

Example 103

Intermediate 103-0: 3-Fluoro-4-(((6-(piperidin-4-yl)pyridin-2-yl)oxy)methyl)benzonitrile bis(4-methylbenzenesulfonate)

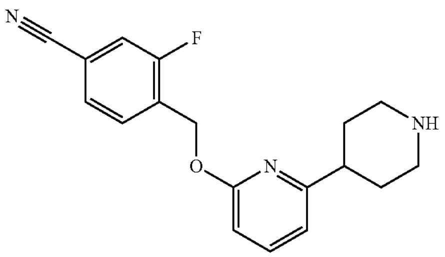 [SMILES: N#Cc1ccc(COc2cccc(C3CCNCC3)n2)c(F)c1]

Step 1

To a solution of diisopropylamine (92 mL, 656 mmol) in THF (350 mL) at −26° C. was added n-butyllithium in heptanes (2.6 M, 250 mL, 650 mmol) over 15 min. The mixture was cooled to −30° C. and a solution of 1-(tert-butyl) 4-methyl piperidine-1,4-dicarboxylate (156 g, 641 mmol) in THF (150 mL) added over 25 min. After 10 min, a solution of 2,6-dichloropyridine (94 g, 635 mmol) in THF (150 mL) was added over 2 min. The mixture was warmed to 25° C. for 2.5 h and then cooled to 8° C. and treated with 6 M HCl (125 mL) over 20 min to bring the pH of the mixture to ~7-8. The mixture was diluted with water (100 mL) and MTBE (150 mL) and the layers separated. The aq. layer was extracted with MTBE (150 mL) and the combined organic layers washed with brine (150 mL), dried over $MgSO_4$. The solvent was removed under reduced pressure to provide crude 1-(tert-butyl) 4-methyl 4-(6-chloropyridin-2-yl)piperidine-1,4-dicarboxylate (241 g) as a yellow oil, which was used in the next step without purification. $^1H$ NMR of a purified sample (400 MHz, $CDCl_3$) δ: 7.62 (t, 1H), 7.21 (d, 2H), 3.83 (br s, 2H), 3.71 (s, 3H), 3.14 (br s, 2H), 2.41 (d, 2H), 2.08 (ddd, 2H), 1.45 (s, 9H).

Step 2

The crude 1-(tert-butyl) 4-methyl 4-(6-chloropyridin-2-yl)piperidine-1,4-dicarboxylate (241 g, assumed 635 mmol) was dissolved in MeOH (400 mL) at 43° C. and treated with 4 M aq. NaOH (300 mL) over 20 min. The mixture was warmed to 50° C. and stirred for 35 min. The mixture was then cooled to 11° C. and the pH adjusted to ~2 by addition of 6 M HCl (200 mL) over 25 min while continuing to cool to 5° C., after which a solid precipitate formed. The slurry was diluted with water (300 mL) and stirred for 40 min, after which the solid was collected by filtration, washed with water and then dried under vacuum at 50° C. to provide a white solid (224 g). The solid was triturated in heptane (750 mL) at 45° C. for 45 min. The mixture was cooled to 16° C. and the solid collected by filtration, washed with heptane and dried to provide 1-(tert-butoxycarbonyl)-4-(6-chloropyridin-2-yl)piperidine-4-carboxylic acid (187 g, 549 mmol, 86% for two steps) as a white solid.

Step 3

A solution of 1-(tert-butoxycarbonyl)-4-(6-chloropyridin-2-yl)piperidine-4-carboxylic acid (187 g, 549 mmol) in DCE (900 mL) was heated at 82° C. overnight and then cooled to 20° C. The mixture was treated with Magnesol® (30 g) for 40 min. The slurry was filtered through a pad of Magnesol® (30 g) and the solids washed with 1:1 MTBE:heptane (300 mL). The filtrate was concentrated under reduced pressure to give a pale yellow solid, which was triturated in heptane (250 mL) at 50° C. The mixture was cooled to 12° C. and the solid collected by filtration, washed with heptane and dried under vacuum at 45° C. to provide tert-butyl 4-(6-chloropyridin-2-yl)piperidine-1-carboxylate (143 g, 481 mmol, 88%) as a solid. $^1H$ NMR (600 MHz, $CDCl_3$) δ: 7.58 (t, 1H), 7.17 (d, 1H), 7.06 (d, 1H), 4.25 (br s, 2H), 2.66-2.93 (m, 3H), 1.91 (d, 2H), 1.69 (qd, 2H), 1.47 (s, 9H).

Step 4

A mixture of tert-butyl 4-(6-chloropyridin-2-yl)piperidine-1-carboxylate (100 g, 337 mmol), 3-fluoro-4-(hydroxymethyl)benzonitrile (53.9 g, 357 mmol) and $Cs_2CO_3$ (170 g, 522 mmol) in dioxane (900 mL) was deoxygenated with 5 vacuum/nitrogen fill cycles. JohnPhos ([1,1'-biphenyl]-2-yl-di-tert-butylphosphine, 2.02 g, 6.77 mmol) and $Pd_2(dba)_3$ (3.10 g, 3.39 mmol) were added and 2 further vacuum/nitrogen fill cycles applied. The mixture was then heated at 95° C. for 3 h. Additional JohnPhos (660 mg, 2.21 mmol) and $Pd_2(dba)_3$ (990 mg, 1.08 mmol) were added and heating continued overnight. The mixture was cooled to 20° C. and filtered through a pad of Celite®, washing with MTBE (250 mL). The filtrate was concentrated under reduced pressure to give a red-orange oil (174 g). This material was dissolved in 30% MTBE/hexane (600 mL), stirred with Magnesol® (20 g) and Darco® G-60 (10 g) for 70 min and then filtered through a pad of silica (100 g), washing with 50% MTBE/hexane (600 mL). The filtrate was concentrated under reduced pressure and azeotroped with EtOAc (100 mL) to provide tert-butyl 4-(6-((4-cyano-2-fluorobenzyl)oxy)pyridin-2-yl)piperidine-1-carboxylate as an oil (147 g), which was used without further purification. $^1H$ NMR of a purified sample (600 MHz, $CDCl_3$) δ: 7.62 (t, 1H), 7.53 (t, 1H), 7.44 (d, 1H), 7.37 (d, 1H), 6.75 (d, 1H), 6.65 (d, 1H), 5.49 (s, 2H), 4.20 (br s, 2H), 2.81 (br s, 2H), 2.70 (tt, 1H), 1.82 (d, 2H), 1.67 (d, 2H), 1.49 (s, 9H).

Step 5

To a stirred solution of tert-butyl 4-(6-((4-cyano-2-fluorobenzyl)oxy)pyridin-2-yl)piperidine-1-carboxylate (147 g, assumed 337 mmol) in EtOAc (1.8 L) at RT was added pTSA·$H_2O$ (161 g, 846 mmol). The mixture was heated to 60° C., which resulted in gas evolution and solid formation. The mixture was stirred for 1.5 h, after which additional pTSA·$H_2O$ (12 g, 63 mmol) added, and stirring continued for 45 min. The slurry was cooled to 17° C. and the solids collected by filtration, washed with EtOAc (200 mL), and dried to provide 205 g of solid. This material was dissolved in MeOH (500 mL) at 55° C. and diluted with EtOAc (1 L). The resulting slurry was cooled to 20° C. and the solids collected by filtration, washed with 9:1 EtOAc:MeOH (100 mL) and EtOAc (250 mL) and dried to provide Intermediate 103-0 (176.6 g, 269 mmol, 80% for two steps) as a white solid. $^1H$ NMR (600 MHz, DMSO-d6) δ: 8.53 (br s, 1H), 8.26 (br s, 1H), 7.89 (d, 1H), 7.67-7.78 (m, 3H), 7.48 (d, 4H), 7.11 (d, 4H), 6.90 (d, 1H), 6.79 (d, 1H), 5.48 (s, 2H), 3.35 (d, 2H), 2.96-3.09 (m, 2H), 2.79-2.96 (m, 1H), 2.29 (s, 6H), 1.93-2.03 (m, 2H), 1.77-1.90 (m, 2H).

Intermediate 103-1: (S)-Oxetan-2-ylmethyl methanesulfonate

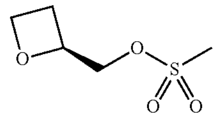

Step 1

To a solution of potassium t-butoxide (670 g, 5.98 mol) in t-BuOH (5 L) was added trimethylsulfoxonium iodide (1.32 kg, 5.98 mol) at 25° C. The mixture was heated to 60° C. and stirred for 30 min, then (S)-2-((benzyloxy)methyl)oxirane (500 g, 2.99 mol) was added. The mixture was heated to 80° C. for 2 h. The mixture was cooled to 25° C. and filtered through Celite®. The solids were washed with PE (3×2 L). The filtrate was treated with water (10 L) and extracted with PE (2×5 L). The organic layer was washed with brine, dried, filtered and concentrated in vacuo. The crude product was purified by column chromatography (PE/EtOAc gradient from 15:1 to 10:1) to deliver (S)-2-((benzyloxy)methyl) oxetane (280 g, 52.6%) as a clear oil. $^1H$ NMR (400 MHz, $CDCl_3$) δ 7.15-7.34 (m, 5H), 4.90 (tdd, 1H), 4.44-4.67 (m, 4H), 3.49-3.63 (m, 2H), 2.44-2.66 (m, 2H).

Step 2

The reaction was carried out in two parallel batches; an example batch follows: To a solution of (S)-2-((benzyloxy) methyl)oxetane (140 g, 780 mmol) in THF (1.4 L) was added $Pd(OH)_2$ (14 g) under a blanket of nitrogen. The mixture was heated to 45° C. and stirred under $H_2$ (50 psi) for 16 h. The mixture was cooled to 25° C. and filtered through Celite® to deliver the desired compound (S)-oxetan-2-ylmethanol as a solution in THF. A small aliquot was checked by $^1H$ NMR and the remaining solution used directly in the next step. $^1H$ NMR (400 MHz, DMSO-d6) δ 4.76-4.90 (m, 1H), 4.66 (tdd, 1H), 4.46 (ddd, 1H), 4.37 (td, 1H), 3.47 (dd, 2H), 2.32-2.58 (m, 2H).

Step 3

The reaction was carried out in two parallel batches; an example batch follows: To a solution of (S)-oxetan-2-yl-methanol (from Step 2, assumed 69 g, 780 mmol) in THF (1.4 L) was added $Et_3N$ (197 g, 1.95 mol) at 0° C. Methanesulfonic anhydride (204 g, 1.17 mol) was added, dropwise, keeping the internal temperature below 10° C. The mixture was stirred at 25° C. for 2 h. The two batches were combined and the mixture was treated with water (1 L) and the layers separated. The aq. phase was extracted with DCM (3×2 L). The combined organic solution was dried, filtered and concentrated under reduced pressure. The crude product was purified by column chromatography (EtOAc/PE 50-100% gradient) to yield Intermediate 20 (250 g, 96% for two steps) as a yellow oil. $^1H$ NMR (400 MHz, $CDCl_3$) δ 4.98-5.09 (m, 1H), 4.69 (ddd, 1H), 4.59 (td, 1H), 4.37 (d, 2H), 3.11 (s, 3H), 2.72-2.82 (m, 1H), 2.64 (tdd, 1H).

Intermediate 103-2: Methyl (S)-4-nitro-3-((oxetan-2-ylmethyl)amino)benzoate

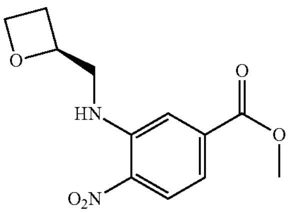 [SMILES: COC(=O)c1ccc([N+](=O)[O-])c(NC[C@@H]2CCO2)c1]

Step 1

To a solution of (S)-oxetan-2-ylmethyl methanesulfonate (180 g, 1.08 mol) in DMF (1.2 L) was added sodium azide (105 g, 1.62 mol). The mixture was heated to 80° C. and stirred for 16 h. The mixture was cooled to 0° C. and treated with diethyl ether (1.5 L) and the resultant suspension was stirred for 30 min. The solids were removed by filtration and the filter cake was washed with diethyl ether (2×200 mL). The diethyl ether was removed under vacuum at 25° C. to deliver a solution of (S)-2-(azidomethyl)oxetane in DMF (~1.2 L), which was used directly in the next step.

Step 2

The reaction was carried out in three parallel batches; an example batch follows: To a solution of (S)-2-(azidomethyl) oxetane (assumed 41 g, 360 mmol) in DMF (~400 mL) and THF (1 L) was added 10% Pd/C (50 wt % wet, 13 g) under a blanket of nitrogen. The mixture was stirred at 25° C. under $H_2$ (50 psi) for 16 h. The solution was filtered through Celite®, 10% Pd/C (dry, 4.0 g) added and the mixture stirred at 40° C. under $H_2$ (50 psi) for 3 h, after which TLC analysis indicated complete reaction. The mixture was cooled to 0° C. and all three batches were combined. The mixture was filtered through Celite® to obtain a solution of (S)-2-(aminomethyl)oxetane in DMF (~1.4 L) and THF (~2.6 L), which was used directly in the next step.

Step 3

To a solution of (S)-2-(aminomethyl)oxetane (assumed 94 g, 1.08 mol) in DMF (~1.4 L) and THF (~2.6 L) were added $Et_3N$ (327 g, 3.24 mol) and methyl 3-fluoro-4-nitrobenzoate (200 g, 1.0 mol) at 25° C. The mixture was stirred at 25° C. for 16 h. The mixture was concentrated under reduced pressure to remove THF and the remaining solution was diluted with water (1 L). The mixture was extracted with EtOAc (2×1.5 L). The combined organic extracts were washed with brine (2×), dried and concentrated under reduced pressure. The crude product was purified by column chromatography (EtOAc/PE=10-50% gradient) to deliver Intermediate 3-2 (158 g, 55%) as a yellow solid. $^1H$ NMR (600 MHz, $CDCl_3$) δ 8.38 (br s, 1H), 8.25 (d, 1H), 7.64 (s, 1H), 7.27 (d, 1H), 5.13-5.20 (m, 1H), 4.70-4.82 (m, 1H), 4.64 (td, 1H), 3.95 (s, 3H), 3.57-3.71 (m, 2H), 2.71-2.86 (m, 1H), 2.55-2.70 (m, 1H); MS (ES+)=266.7.

Intermediate 103-3: Methyl (S)-4-amino-3-((oxetan-2-ylmethyl)amino)benzoate

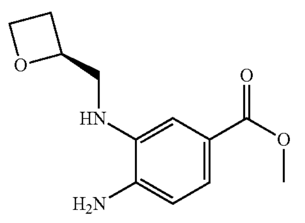 [SMILES: COC(=O)c1ccc(N)c(NC[C@@H]2CCO2)c1]

Intermediate 103-2 (15 g, 56 mmol) was dissolved in THF (100 mL) in a Parr® reactor. Pd/C (10% w/w, 1.5 g) was added to the reactor and the mixture was shaken at RT under 50 psi $H_2$ for 4 h. The mixture was filtered through Celite® and the filtrate was concentrated under reduced pressure to deliver Intermediate 103-3 (12.3 g, 92%) as a tan solid. $^1$H NMR (600 MHz, $CDCl_3$) δ 7.49 (dd, 1H), 7.39 (d, 1H), 6.70 (d, 1H), 5.05-5.18 (m, 1H), 4.76 (ddd, 1H), 4.62 (dt, 1H), 3.87 (s, 3H), 3.42-3.50 (m, 1H), 3.34-3.40 (m, 1H), 2.71-2.82 (m, 1H), 2.60 (ddt, 1H).

Preparation of 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid (Example 103)

Step 1

To a stirred solution of Intermediate 103-3 (33.6 g, 142 mmol) in MeCN (285 mL) was added 2-chloro-1,1,1-trimethoxyethane (20.1 mL, 149 mmol) followed by pTSA·$H_2O$ (1.35 g, 7.1 mmol). After 2 h at 50° C., MeCN (280 mL), $K_2CO_3$ (79 g, 570 mmol) and Intermediate 103-0 (93.2 g, 142 mmol) were added. After 2 h, the solution was treated with water (800 mL), allowed to cool to RT and stirred for 2 h. The resulting precipitate was collected by filtration, washed with 10% MeCN in water (150 mL), water (2×200 mL) and then dried under reduced pressure to provide methyl (S)-2-((4-(6-((4-cyano-2-fluorobenzyl)oxy)pyridin-2-yl)piperidin-1-yl)methyl)-1-(oxetan-2-ylmethyl)-1H-benzo[d]imidazole-6-carboxylate as a colorless solid (77 g, 95%). $^1$H NMR (600 MHz, DMSO-d6) δ 8.28 (s, 1H), 7.87 (d, 1H), 7.80 (d, 1H), 7.55-7.73 (m, 4H), 6.87 (d, 1H), 6.70 (d, 1H), 5.45 (s, 2H), 5.04-5.19 (m, 1H), 4.81 (dd, 1H), 4.66 (dd, 1H), 4.41-4.54 (m, 1H), 4.36 (dt, 1H), 3.94 (d, 1H), 3.86 (s, 3H), 3.76 (d, 1H), 2.97 (d, 1H), 2.82 (d, 1H), 2.63-2.77 (m, 1H), 2.49-2.63 (m, 1H), 2.37-2.46 (m, 1H), 2.18-2.29 (m, 1H), 2.05-2.18 (m, 1H), 1.47-1.82 (m, 4H).

Step 2

To a stirred solution of methyl (S)-2-((4-(6-((4-cyano-2-fluorobenzyl)oxy)pyridin-2-yl)piperidin-1-yl)methyl)-1-(oxetan-2-ylmethyl)-1H-benzo[d]imidazole-6-carboxylate (4 g, 7 mmol) in MeCN (70 mL) was added a solution of 1,5,7-triazabicyclo[4.4.0]dec-5-ene in water (0.97 M, 14.7 mL). After 20 h, the solution was acidified to pH ~6 with citric acid in water (2 M, 7 mL) and diluted with water (50 mL). The aq. phase was extracted with EtOAc (2×75 mL), the combined organic layers were dried over anhydrous $Na_2SO_4$, filtered, and the solvent removed under reduced pressure to give an off-white solid. The crude material was purified using column chromatography eluting with MeOH/DCM (0:100 to 8:92) to obtain Example 103 as a solid (3.65 g, 90%). $^1$H NMR (400 MHz, DMSO-d6) δ 12.75 (br s, 1H), 8.27 (s, 1H), 7.89 (d, 1H), 7.80 (d, 1H), 7.68-7.72 (m, 2H), 7.60-7.67 (m, 2H), 6.89 (d, 1H), 6.72 (d, 1H), 5.47 (s, 2H), 5.11 (d, 1H), 4.74-4.86 (m, 1H), 4.62-4.72 (m, 1H), 4.43-4.53 (m, 1H), 4.35-4.42 (m, 1H), 3.95 (d, 1H), 3.77 (d, 1H), 2.98 (d, 1H), 2.84 (d, 1H), 2.65-2.77 (m, 1H), 2.53-2.64 (m, 1H), 2.37-2.45 (m, 1H), 2.10-2.28 (m, 2H), 1.57-1.84 (m, 4H). LC-MS (ES+): 556.6 (M+H).

Tris Salt of Example 103

2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid tris Salt To a stirred solution of Example 103 (6.5 g, 11.7 mmol) in 1-propanol (275 mL) at 70° C. was added an aq. solution of tris (2.0 M, 6.1 mL, 12.2 mmol), dropwise, during which the solution remained homogeneous. After stirring for 5 min, seed crystals were added and the mixture was allowed to cool to RT over 2 h. After stirring overnight at RT, a solid had formed. The solid was collected by filtration, washed with 1-propanol (2×30 mL) and dried, first under a nitrogen stream and then in a vacuum oven at 45° C. for 15 h, to give the tris salt of Example 3 (6.95 g, 88%) as a crystalline solid. $^1$H NMR (600 MHz, DMSO-d6) δ: 8.20 (s, 1H), 7.89 (d, 1H), 7.79 (d, 1H), 7.70 (br s, 2H), 7.64 (t, 1H), 7.56 (d, 1H), 6.89 (d, 1H), 6.72 (d, 1H), 5.47 (s, 2H), 5.11 (qd, 1H), 4.77 (dd, 1H), 4.64 (dd, 1H), 4.44-4.53 (m, 1H), 4.38 (dt, 1H), 3.93 (d, 1H), 3.76 (d, 1H), 3.35 (br s, 9H), 2.98 (d, 1H), 2.85 (d, 1H), 2.64-2.75 (m, 1H), 2.54-2.64 (m, 1H), 2.40-2.49 (m, 1H), 2.08-2.26 (m, 2H), 1.56-1.83 (m, 4H). mp=194° C.

CHO GLP-1R Clone H6—Assay 1

GLP-1R-mediated agonist activity was determined with a cell-based functional assay utilizing an HTRF (Homogeneous Time-Resolved Fluorescence) cAMP detection kit (cAMP HI Range Assay Kit; CisBio cat #62AM6PEJ) that measures cAMP levels in the cell. The method is a competitive immunoassay between native cAMP produced by the cells and exogenous cAMP labeled with the dye d2. The tracer binding is visualized by a mAb anti-cAMP labeled with Cryptate. The specific signal (i.e. energy transfer) is inversely proportional to the concentration of cAMP in either standard or experimental sample.

The human GLP-1R coding sequence (NCBI Reference Sequence NP_002053.3, including naturally-occurring variant Glyl68Ser) was subcloned into pcDNA3 (Invitrogen) and a cell line stably expressing the receptor was isolated (designated Clone H6). Saturation binding analyses (filtration assay procedure) using $^{125}$I-GLP-$1_{7-36}$ (Perkin Elmer) showed that plasma membranes derived from this cell line express a high GLP-1R density ($K_d$: 0.4 nM, $B_{max}$: 1900 fmol/mg protein).

Cells were removed from cryopreservation, re-suspended in 40 mL of Dulbecco's Phosphate Buffered Saline (DPBS—Lonza Cat #17-512Q) and centrifuged at 800×g for 5 minutes at 22° C. The cell pellet was then re-suspended in 10 mL of growth medium [DMEM/F12 1:1 Mixture with HEPES, L-Gln, 500 mL (DMEM/F12 Lonza Cat #12-719F), 10% heat inactivated fetal bovine serum (Gibco Cat #16140-071), 5 mL of 100× Pen-Strep (Gibco Cat #15140-122), 5 mL of 100× L-Glutamine (Gibco Cat #25030-081) and 500 μg/mL Geneticin (G418) (Invitrogen #10131035)]. A 1 mL sample of the cell suspension in growth media was counted on a Becton Dickinson ViCell to determine cell viability and cell count per mL. The remaining cell suspension was then adjusted with growth media to deliver 2000 viable cells per well using a Matrix Combi Multidrop reagent dispenser, and the cells were dispensed into a white 384 well tissue culture treated assay plate (Corning 3570). The assay plate was then incubated for 48 hours at 37° C. in a humidified environment in 5% carbon dioxide.

Varying concentrations of each compound to be tested (in DMSO) were diluted in assay buffer (HBSS with Calcium/Magnesium (Lonza/BioWhittaker cat #10-527F)/0.1% BSA (Sigma Aldrich cat #A7409-1L)/20 mM HEPES (Lonza/BioWhittaker cat #17-737E) containing 100 μM 3-isobutyl-1-methylxanthin (IBMX; Sigma cat #I5879). The final DMSO concentration is 1%.

After 48 hours, the growth media was removed from the assay plate wells, and the cells were treated with 20 μL of the serially diluted compound in assay buffer for 30 minutes at 37° C. in a humidified environment in 5% carbon dioxide. Following the 30 minute incubation, 10 μL of labeled d2 cAMP and 10 μL of anti-cAMP antibody (both diluted 1:20 in cell lysis buffer; as described in the manufacturer's assay protocol) were added to each well of the assay plate. The plates were then incubated at room temperature and after 60 minutes, changes in the HTRF signal were read with an Envision 2104 multi-label plate reader using excitation of 330 nm and emissions of 615 and 665 nm. Raw data were converted to nM cAMP by interpolation from a cAMP standard curve (as described in the manufacturers assay protocol) and the percent effect was determined relative to a saturating concentration of the full agonist GLP-$1_{7-36}$ (1 μM) included on each plate. $EC_{50}$ determinations were made from agonist dose-response curves analyzed with a curve fitting program using a 4-parameter logistic dose response equation.

CHO GLP-1R Clone C6—Assay 2

GLP-1R-mediated agonist activity was determined with a cell-based functional assay utilizing an HTRF (Homogeneous Time-Resolved Fluorescence) cAMP detection kit (cAMP HI Range Assay Kit; Cis Bio cat #62AM6PEJ) that measures cAMP levels in the cell. The method is a competitive immunoassay between native cAMP produced by the cells and exogenous cAMP labeled with the dye d2. The tracer binding is visualized by a mAb anti-cAMP labeled with Cryptate. The specific signal (i.e. energy transfer) is inversely proportional to the concentration of cAMP in either a standard or an experimental sample.

The human GLP-1R coding sequence (NCBI Reference Sequence NP_002053.3, including naturally-occurring variant Leu260Phe) was subcloned into pcDNA5-FRT-TO and a clonal CHO cell line stably expressing a low receptor density was isolated using the Flp-In™ T-Rex™ System, as described by the manufacturer (ThermoFisher). Saturation binding analyses (filtration assay procedure) using $^{125}$I-GLP-1 (Perkin Elmer) showed that plasma membranes derived from this cell line (designated clone C6) express a low GLP-1R density ($K_d$: 0.3 nM, $B_{max}$: 240 fmol/mg protein), relative to the clone H6 cell line.

Cells were removed from cryopreservation, re-suspended in 40 mL of Dulbecco's Phosphate Buffered Saline (DPBS—Lonza Cat #17-512Q) and centrifuged at 800×g for 5 minutes at 22° C. The DPBS was aspirated, and the cell pellet was re-suspended in 10 mL of complete growth medium (DMEM:F12 1:1 Mixture with HEPES, L-Gln, 500 mL (DMEM/F12 Lonza Cat #12-719F), 10% heat inactivated fetal bovine serum (Gibco Cat #16140-071), 5 mL of 100× Pen-Strep (Gibco Cat #15140-122), 5 mL of 100× L-Glutamine (Gibco Cat #25030-081), 700 μg/mL Hygromycin (Invitrogen Cat #10687010) and 15 μg/mL Blasticidin (Gibco Cat #R21001). A 1 mL sample of the cell suspension in growth media was counted on a Becton Dickinson ViCell to determine cell viability and cell count per mL. The remaining cell suspension was then adjusted with growth media to deliver 1600 viable cells per well using a Matrix Combi Multidrop reagent dispenser, and the cells were dispensed into a white 384 well tissue culture treated assay plate (Corning 3570). The assay plate was then incubated for 48 hours at 37° C. in a humidified environment (95% $O_2$, 5% $CO_2$)

Varying concentrations of each compound to be tested (in DMSO) were diluted in assay buffer [HBSS with Calcium/Magnesium (Lonza/BioWhittaker cat #10-527F)/0.1% BSA (Sigma Aldrich cat #A7409-1L)/20 mM HEPES (Lonza/BioWhittaker cat #17-737E)] containing 100 μM 3-isobutyl-1-methylxanthin (IBMX; Sigma cat #I5879). The final DMSO concentration in the compound/assay buffer mixture is 1%.

After 48 hours, the growth media was removed from the assay plate wells, and the cells were treated with 20 μL of the serially diluted compound in assay buffer for 30 minutes at 37° C. in a humidified environment (95% $O_2$, 5% $CO_2$). Following the 30 minute incubation, 10 μL of labeled d2 cAMP and 10 μL of anti-cAMP antibody (both diluted 1:20 in cell lysis buffer; as described in the manufacturer's assay protocol) were added to each well of the assay plate. The plates were then incubated at room temperature and after 60 minutes, changes in the HTRF signal were read with an Envision 2104 multi-label plate reader using excitation of 330 nm and emissions of 615 and 665 nm. Raw data were converted to nM cAMP by interpolation from a cAMP standard curve (as described in the manufacturers assay protocol) and the percent effect was determined relative to a saturating concentration of the full agonist GLP-1 (1 μM) included on each plate. $EC_{50}$ determinations were made from agonist dose response curves analyzed with a curve fitting program using a 4-parameter logistic dose response equation.

In Table 3, assay data are presented to two (2) significant figures as the geometric mean ($EC_{50}$s) and arithmetic mean (Emax) based on the number of replicates listed (Number). A blank cell means there was no data for that Example or the Emax was not calculated.

TABLE 3

Biological activity for Examples 1-102.

| Ex. No. | Assay 1 $EC_{50}$ (nM) | Assay 1 Emax (%) | Assay 1 Number | Assay 2 $EC_{50}$ (nM) | Assay 2 Emax (%) | Assay 2 Number |
|---|---|---|---|---|---|---|
| 1 | 880 | 99 | 3 | >20000 | | 1 |
| 2* | 6.6 | 81 | 5 | 260 | 100 | 4 |

TABLE 3-continued

Biological activity for Examples 1-102.

| Ex. No. | Assay 1 $EC_{50}$ (nM) | Assay 1 Emax (%) | Assay 1 Number | Assay 2 $EC_{50}$ (nM) | Assay 2 Emax (%) | Assay 2 Number |
|---|---|---|---|---|---|---|
| 3 | 1.3 | 94 | 3 | 45 | 120 | 3 |
| 4 | 1600 | 87 | 3 | >20000 | | 1 |
| 5** | 1.3 | 89 | 6 | 23 | 97 | 7 |
| 6 | 140 | 89 | 7 | 2400 | 89 | 5 |
| 7** | 0.26 | 98 | 3 | 3.1 | 93 | 12 |
| 8*** | 0.30 | 92 | 6 | 3.6 | 91 | 6 |
| 9*** | 73 | 88 | 9 | 1600 | 90 | 4 |
| 10**** | 0.96 | 99 | 5 | 17 | 96 | 8 |
| 11 | 290 | 78 | 3 | | | |
| 12 | 29 | 83 | 3 | 690 | 92 | 3 |
| 13 | 4.5 | 95 | 3 | 38 | 110 | 3 |
| 14 | 7 | 95 | 6 | 79 | 85 | 5 |
| 15 | >18000 | 100 | 3 | >20000 | | 1 |
| 16 | 7.7 | 90 | 3 | 120 | 64 | 3 |
| 17 | 0.079 | 97 | 3 | 1.1 | 96 | 4 |
| 18 | 210 | 97 | 3 | 1000 | 87 | 3 |
| 19 | 1.2 | 87 | 3 | 25 | 100 | 3 |
| 20 | 17 | 85 | 3 | 270 | 100 | 3 |
| 21 | >20000 | | 1 | >20000 | | 1 |
| 22 | >20000 | | 1 | | | |
| 23 | 680 | 76 | 3 | | | |
| 24 | 1.4 | 82 | 3 | 49 | 110 | 3 |
| 25 | >20000 | | 1 | >20000 | | 1 |
| 26 | >20000 | | 1 | >20000 | | 1 |
| 27 | 61 | 98 | 3 | 1000 | 100 | 3 |
| 28 | 480 | 87 | 3 | | | |
| 29 | 5.3 | 87 | 4 | 150 | 93 | 3 |
| 30 | 45 | 86 | 4 | 1100 | 77 | 4 |
| 31 | 190 | 88 | 3 | 1900 | 65 | 3 |
| 32 | 18 | 86 | 3 | 450 | 87 | 3 |
| 33 | 2.6 | 85 | 3 | 100 | 86 | 3 |
| 34 | 7.8 | 98 | 3 | 110 | 88 | 3 |
| 35 | 6.6 | 86 | 3 | 170 | 89 | 3 |
| 36 | 760 | 85 | 3 | | | |
| 37 | 81 | 100 | 3 | 1000 | 83 | 3 |
| 38 | 10 | 87 | 3 | 240 | 73 | 3 |
| 39 | 200 | 83 | 3 | | | |
| 40 | 14 | 88 | 3 | 130 | 73 | 3 |
| 41 | 91 | 78 | 3 | 2000 | 74 | 2 |
| 42 | 120 | 93 | 3 | 1700 | 83 | 3 |
| 43 | 3.5 | 88 | 4 | 65 | 86 | 3 |
| 44 | 160 | 78 | 4 | | | |
| 45 | 9.9 | 81 | 3 | 220 | 79 | 3 |
| 46 | 5.2 | 95 | 4 | 57 | 96 | 3 |
| 47 | 42 | 75 | 3 | 1400 | 76 | 4 |
| 48 | 14 | 81 | 3 | 280 | 73 | 3 |
| 49 | 230 | 93 | 3 | | | |
| 50 | 12 | 87 | 4 | 140 | 92 | 4 |
| 51 | 19 | 80 | 3 | 280 | 81 | 3 |
| 52 | 32 | 85 | 3 | 570 | 80 | 3 |
| 53 | 3.1 | 87 | 3 | 52 | 84 | 4 |
| 54 | 18 | 82 | 3 | 160 | 64 | 3 |
| 55 | 74 | 81 | 3 | 1100 | 50 | 3 |
| 56 | 1.2 | 87 | 4 | 11 | 81 | 3 |
| 57 | 15 | 86 | 3 | 500 | 98 | 3 |
| 58 | 4 | 98 | 3 | 23 | 88 | 4 |
| 59 | 74 | 85 | 3 | 680 | 53 | 3 |
| 60 | 15 | 82 | 3 | 240 | 60 | 3 |
| 61 | 10 | 79 | 3 | 240 | 85 | 3 |
| 62 | 2.2 | 94 | 3 | 82 | 95 | 3 |
| 63 | 5.2 | 91 | 3 | 66 | 96 | 3 |
| 64 | 9.2 | 94 | 3 | 91 | 80 | 3 |
| 65 | 1.2 | 99 | 3 | 11 | 99 | 6 |
| 66 | 51 | 82 | 3 | 850 | 74 | 3 |
| 67 | 710 | 83 | 3 | | | |
| 68 | 73 | 89 | 3 | 1200 | 94 | 3 |
| 69 | 10 | 100 | 3 | 8.3 | 98 | 3 |
| 70 | 2.8 | 100 | 4 | 97 | 100 | 4 |
| 71 | 6.8 | 80 | 4 | 74 | 80 | 3 |
| 72 | 14 | 76 | 3 | 310 | 80 | 3 |
| 73 | 1.7 | 98 | 3 | 10 | 100 | 3 |
| 74 | 460 | 90 | 3 | | | |
| 75 | 65 | 82 | 3 | 1000 | 71 | 3 |
| 76 | 0.77 | 93 | 3 | 7.6 | 100 | 3 |
| 77 | 53 | 89 | 3 | 1700 | 92 | 3 |

TABLE 3-continued

| Biological activity for Examples 1-102. | | | | | | |
|---|---|---|---|---|---|---|
| Ex. No. | Assay 1 $EC_{50}$ (nM) | Assay 1 Emax (%) | Assay 1 Number | Assay 2 $EC_{50}$ (nM) | Assay 2 Emax (%) | Assay 2 Number |
| 78 | 4.5 | 89 | 4 | 78 | 100 | 3 |
| 79 | 1.4 | 85 | 3 | 21 | 85 | 3 |
| 80 | 1.1 | 87 | 3 | 6.9 | 96 | 4 |
| 81 | 29 | 110 | 3 | 54 | 110 | 3 |
| 82 | 47 | 83 | 3 | 1000 | 83 | 3 |
| 83 | 3.4 | 85 | 4 | 44 | 88 | 4 |
| 84 | 9.1 | 93 | 3 | 100 | 86 | 3 |
| 85 | 230 | 80 | 3 | | | |
| 86 | 24 | 91 | 3 | 410 | 100 | 3 |
| 87 | 570 | 89 | 3 | | | |
| 88 | 17 | 86 | 3 | 360 | 91 | 3 |
| 89 | 130 | 85 | 3 | 2900 | 87 | 3 |
| 90 | >20000 | | 1 | | | |
| 91 | 14000 | 100 | 3 | >20000 | | 1 |
| 92 | 4.2 | 90 | 5 | 72 | 83 | 3 |
| 93 | >6500 | 84 | 5 | >20000 | | 1 |
| 94 | 12 | 89 | 5 | 360 | 87 | 3 |
| 95**** | 220 | 77 | 3 | >13000 | | 5 |
| 96 | 1.1 | 85 | 3 | 11 | 93 | 4 |
| 97 | 14 | 86 | 3 | 140 | 93 | 4 |
| 98 | 50 | 97 | 3 | 440 | 95 | 3 |
| 99 | 2.8 | 99 | 4 | 5.4 | 91 | 2 |
| 100 | | | | 7.6 | 99 | 1 |
| 101 | | | | 19 | 74 | 1 |
| 102 | 600 | 86 | 4 | | | |
| 103 | 1.1 | 79 | 5 | 13 | 100 | 18 |

*Tested as ammonium and trifluoroacetate salts
**Tested as ammonium and 1,3-dihydroxy-2-(hydroxymethyl)propan-2-aminium (Tris) salts, and free acid
***Tested as ammonium salt and free acid
****Tested as formate salt and free acid

Example ACCi: Preparation of 4-(4-(1-isopropyl-7-oxo-1,4,6,7-tetrahydrospiro[indazole-5,4'-piperidine]-1'-carbonyl)-6-methoxypyridin-2-yl)benzoic acid, (ACCi Compound)

In the preparation of the compound of Example ACCi, it is noted that some of the preparation methods described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, Protective Groups in Organic Synthesis, John Wiley & Sons, New York, 1991. Furthermore, this invention is not limited to specific synthetic methods provided herein that may vary.

Intermediate A1: 1-Isopropyl-4,6-dihydrospiro[indazole-5,4'-piperidin]-7(1H)-one, hydrochloride Salt

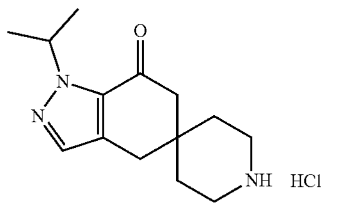 [SMILES: CC(C)n1ncc2c1C(=O)CC1(CCNCC1)C2 ; Cl]

Step 1. tert-Butyl 9-oxo-3-azaspiro[5.5]undec-7-ene-3-carboxylate

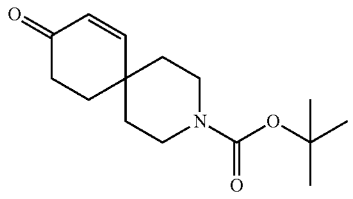 [SMILES: CC(C)(C)OC(=O)N1CCC2(C=CC(=O)CC2)CC1]

A dry reactor was charged with tert-butyl 4-formylpiperidine-1-carboxylate (108 Kg), cyclohexane (1080 L) and pyrrolidine (64.8 Kg) at 25-30° C. The mixture was stirred 5-10 min, and was then heated to reflux for 12-16h, while collecting water using a Dean-Stark trap. The reaction mixture was then cooled to 50-60° C., at which temperature vacuum was applied to distill excess pyrrolidine and cyclohexane. The reaction mixture was then cooled to 25-30° C., and cyclohexane (648 L) was charged, followed by methyl vinyl ketone (49.63 Kg). The mixture was stirred for 12-16 h, then filtered and the filtrate was charged into a clean and dry reactor. The solution was cooled to 10-15° C., then a solution of acetic acid (54.75 Kg) in water (54 L) was slowly added, maintaining the temperature below 15° C. At the end of the addition, the mixture was warmed up to 25-30° C. and stirred for 12-16 h. The layers were separated and the aqueous was extracted with ethyl acetate (324 L). Combined organic layers were washed with a solution of sodium bicarbonate (32.34 Kg) in water (324 L), then dried over sodium sulfate. The solids were washed with ethyl acetate (54 L), and combined filtrates were concentrated under reduced pressure at below 40° C. n-Heptane (216 L) was charged into the reactor and distillation was pursued under reduced pressure and at below 40° C. until dryness. The mixture was cooled to 25-30° C. and n-heptane (216 L) was charged in the reactor. The mixture was stirred for 1-2 h after formation of solids. The solids were then filtered, washed with n-heptane (54 L) and dried at 40-50° C. for 10-12 h to generate the desired material (90.1 Kg, 67% yield). Step 2. (E)-tert-Butyl 10-((dimethylamino)methylene)-9-oxo-3-azaspiro[5.5]undec-7-ene-3-carboxylate.

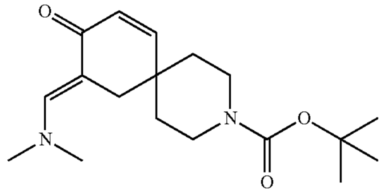 [SMILES: CN(C)/C=C1\CC2(C=CC1=O)CCN(C(=O)OC(C)(C)C)CC2]

A clean and dry reactor was charged with tert-butyl 9-oxo-3-azaspiro[5.5]undec-7-ene-3-carboxylate (50 Kg), N,N-dimethylformamide (500 L) and N,N-dimethylformamide dimethyl acetal (135 Kg) at 25-30° C. under nitrogen atmosphere. The reaction mixture was stirred 5-10 min then heated to 120-130° C. for 20 h. the mixture was then cooled to 50-60° C., and the solvent was distilled under high vacuum at below 60° C. Mix-xylenes (200 L) was charged at below 45° C. and the solvent was distilled under high vacuum at below 60° C. This operation was repeated with another lot of mix-xylenes (200 L). Toluene (200 L) was then charged into the reactor and the solvent was distilled under high vacuum at below 60° C. This operation was repeated with a second lot of toluene (200 L). Methyl tert-butyl ether (100 L) was then charged at below 30° C. and the solvent was distill under high vacuum at below 40° C. The mixture was cooled down to 15-20° C. and methyl tert-butyl ether (100 L) was charged at below 20° C. The mixture was stirred for 20-30 min and the solids were filtered, washed with methyl tert-butyl ether (50 L) and dried without vacuum at 50-55° C. for 10 h to provide the desired compound (52.1 Kg, 87% yield). $^1$H NMR (400 MHz, $CDCl_3$) δ ppm 7.48 (s, 1H), 6.57 (d, J=9.97 Hz, 1H), 5.99 (d, J=10.16 Hz, 1H), 3.32-3.51 (m, 4H), 3.06 (s, 6H), 2.72 (s, 2H), 1.57-1.66 (m, 2H), 1.41-1.53 (m, 11H).

Step 3. tert-Butyl 1-isopropyl-1,4-dihydrospiro[indazole-5,4'-piperidine]-1'-carboxylate

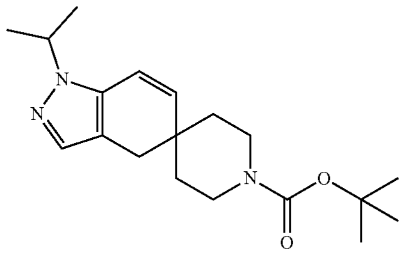 [SMILES: CC(C)n1ncc2c1C=CC1(CCN(C(=O)OC(C)(C)C)CC1)C2]

A clean and dry reactor was charged with (E)-tert-butyl 10-((dimethylamino)methylene)-9-oxo-3-azaspiro[5.5]undec-7-ene-3-carboxylate (80 Kg), toluene (704 L) and trimethylamine (16 L) at 25-30° C. The reaction mixture was warmed up to 70-80° C., and a solution of isopropyl hydrazine hydrochloride salt in methanol (1.25 equiv., 141 Kg total) was added over 4-5 h. The reaction mixture was then stirred for 8-10 h at 70-80° C., prior cooling to 15-25° C. A solution of citric acid (48 Kg) in water (480 L) was then slowly added, maintaining internal temperature below 25° C. Ethyl acetate (208 L) was added and the mixture was stirred for 10 min. Layers were separated and the organic layer was successively washed with a solution of citric acid (48 Kg) in water (480 L), then with only water (320 L). Combined aqueous layers were extracted with ethyl acetate (320 L). Combined organic layers were then dried over sodium sulfate (8 Kg) and the solvents were evaporated to dryness under reduce pressure and at below 40° C. Dichloromethane (240 L) was charged into the reactor and the mixture was stirred at 25-30° C. until clear. Activated carbon (1.84 Kg), magnesium silicate (1.84 Kg) and silica gel (32 Kg, 100-200 mesh) were successively charged at 25-30° C. and the heterogeneous mixture was stirred for 1 h. The slurry was then filter on a Hyflow bed, prepared by mixing Hyflow supercell (8 Kg) and dichloromethane (40 L). The cake was washed with dichloromethane (three times 120 L). The combined filtrates were charged back in the reactor and the solvent was evaporated under reduced pressure at below 40° C. n-Heptane (160 L) was then charged and distilled under reduced pressure at below 40° C. n-Heptane (200 L) was charged in the reactor and the mixture was cooled down to 0-5° C. After stirring for 12-15 h, the solids were filtered at 0° C., washed with chilled (0-5° C.) n-heptane (160 L) and dried under vacuum at 40-50° C. to provide the title compound (82.4 Kg, 75%). $^1$H NMR (400 MHz, $CDCl_3$) δ ppm 7.25 (s, 1H), 6.42 (dd, J=10.05, 0.49 Hz, 1H) 5.84 (d, J=9.95 Hz, 1H), 4.42-4.52 (m, 1H), 3.36-3.53 (m, 4H), 2.62 (s, 2H) 1.56-1.68 (m, 2H) 1.45-1.55 (m, 17H).

Step 4. 1-Isopropyl-4,6-dihydrospiro[indazole-5,4'-piperidin]-7(1H)-one, hydrochloride Salt

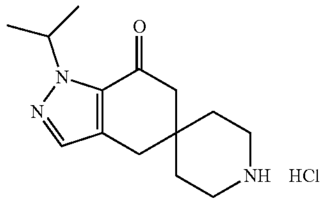 [SMILES: CC(C)n1ncc2c1C(=O)CC1(CCNCC1)C2 ; Cl]

A clean and dry reactor was charged with tert-butyl 1-isopropyl-1,4-dihydrospiro[indazole-5,4'-piperidine]-1'-carboxylate (60 Kg) and methanol (600 L) at 25-30° C. N-Bromosuccinimide (32.4 Kg) was added in 5 portions over 30-40 min at 25-30° C. and stirring was continued for 30-60 min. A solution of sodium thiosulfate pentahydrate (5.4 Kg) in water (102 L) was slowly added, maintaining internal temperature below 30° C. The mixture was stirred for 20-30 min then the solvent was evaporated under reduced pressure at below 45° C. The residue was cooled down to 25-30° C. and 2-methyltetrahydrofuan (420 L) was charged in the reactor, along with water (90 L). The mixture was stirred for 15-20 min, then the layers were separated, the aqueous layer was further extracted with 2-methyltetrahydrofuran (120 L). Combined organic extracts were treated for 15-20 min at 25-30° C. with a solution of sodium hydroxide (4.8 Kg) in water (120 L). Layers were separated and the organic layer was washed with water (120 L), followed by a solution of sodium chloride (12 Kg) in water (120 L) and then dried over sodium sulfate (6 Kg). After filtration, the cake was washed with 2-methyltetrahydrofuran (30 L) and combined filtrate were charged back into the reactor. The solvent was completely distilled at below 45° C. under reduced pressure and the residue was solubilized in tetrahydrofuran (201 L). In another clean and dry reactor was charged potassium tert-butoxide (60.6 Kg) and tetrahydrofuran (360 L) at 25-30° C. To that mixture was slowly added the solution of the residue in tetrahydrofuran maintaining a temperature below 30° C. The reaction mixture was then warmed up to 60-65° C. and kept at this temperature for 1-2 h. Upon completion, the mixture was cooled to 0-10° C., and slowly quenched with a solution of hydrochloric acid (1 N, 196 L), maintaining internal temperature below 10° C. The reaction mixture was allowed to warm up to 25-30° C., and ethyl acetate (798 L) was charged. After stirring for 15-20 min, the layers were separated, and the aqueous layer was further extracted with ethyl acetate (160 L). Combined organic layers were washed with water (160 L), dried over sodium sulfate (8 Kg), filtered, and the cake was washed with ethyl acetate (300 L). The solvents were entirely distilled under reduced pressure at below 45° C., and ethyl acetate (540 L) was charged into the reactor at 25-30° C., followed by methanol (156 L). The mixture was cooled to 0-5° C., at which point acetyl chloride (79.8 Kg) was slowly added, maintaining the temperature in the specified range. The mixture was then allowed to warm up to 20-25° C. and was kept at this temperature for 4-5 h with stirring. The resulting slurry was filtered and the solids were washed with ethyl acetate (120 L), then dried at 40-45° C. for 8-10 h to furnish the desired crude product (33.5 Kg, 65%).

A final purification step was performed by solubilizing this crude solid (56.8 Kg) in methanol (454.4 L) in a clean a dried reactor at 25-30° C. The solution was stirred for 30-45 min, then passed through a 0.2 micron cartridge filter into a clean and dry reactor at 25-30° C. Methanol was distilled under reduced pressure at below 50° C. until ~1 vol solvent remains. The reaction mixture was cooled to 25-30° C. and fresh acetonitrile (113.6 L) was charged through a 0.2 micron cartridge filter. The solvents were distilled under reduced pressure at below 50° C. until ~1 vol solvent remains. The reaction mixture was cooled to 25-30° C. and fresh acetonitrile (190 L) was charged into the reactor through a 0.2 micron cartridge filter. The mixture was warmed up to 65-70° C. and stirred for 45 min, then cooled down to 25-30° C. and stirred for 1 h. the resulting slurry was filtered, and the cake was washed with chilled (15° C.) acetonitrile (56.8 L). The solids were dried under reduced pressure at 40-50° C. for 8 h to afford Intermediate A1 (36.4 Kg, 64%). $^1$H NMR (400 MHz, $CD_3OD$) δ ppm 7.43 (s, 1H), 5.32-5.42 (m, 1H), 3.15-3.25 (m, 4H), 2.89 (s, 2H), 2.64 (s, 2H), 1.69-1.90 (m, 4H), 1.37-1.45 (m, 6H); ESI $[M+H]^+$=248.

Intermediate A2: 2-(4-(tert-Butoxycarbonyl)phenyl)-6-methoxyisonicotinic acid

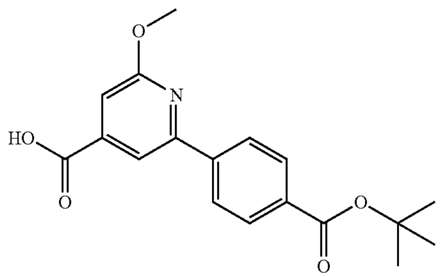 [SMILES: COc1cc(C(=O)O)cc(-c2ccc(C(=O)OC(C)(C)C)cc2)n1]

A clean and dried reactor was charged with 2,6-dichloroisonicotinic acid (30 Kg) and methanol (120 L) at 20-25° C. The slurry was stirred for 5 min then heated up to 65° C. (reflux). A solution of sodium methoxide in methanol (30%, 87.2 Kg) was then slowly charged over at least 4 h via addition funnel. The funnel was rinsed with methanol (15 L), and stirring was pursued at 65° C. for at least 15 h. the mixture was then cooled down to 45° C. and distilled under reduced pressure until a residual volume of ~90 L. A solution of potassium bicarbonate (28.2 Kg) and potassium carbonate (21.6 Kg) in water (180 L) was then charged into the reactor at 40-45° C. The reactor containing the aqueous solution was rinsed with water (21 L) and the wash was charged into the reaction mixture. The mixture was distilled under reduced pressure at below 80° C. until a residual volume of ~240 L, then cooled down to 20-25° C.

Another clean and dry reactor was charged with tert-butyl 4-(4,4,5,5-tetramethyl-1,3,2-dioxoborolan-2-yl) benzoate (52.3 Kg) and dioxane (340 Kg), and stirred at 2-25° C. until complete dissolution. The content of the former reactor was then heated at 40° C. to ensure complete solubility and transferred into this new reactor. The reaction mixture was cooled down to 20-25° C., and a deoxygenation step was performed via vacuum/nitrogen cycles. The mixture was further cooled down to 0-10° C. and palladium acetate (0.65 Kg) was charged into the reactor followed by triphenylphosphine (2.46 Kg) under nitrogen flow. The mixture was warmed up to 20-25° C. and another deoxygenation step was performed via vacuum/nitrogen cycles. The mixture was then heated to 80° C. and maintained at this temperature for at least 18 h. the mixture was cooled down to 20-25° C., then methyl tert-butyl ether (133.2 Kg) and water (30 L) were successively charged into the reactor. The layers were separated, and the aqueous was diluted with water (110 L), then extracted with methyl tert-butyl ether (110 L). Combined organic extracts were washed with a solution of citric acid (52 Kg) in water (84 L), and the layers were separated. The aqueous layer was further extracted with methyl tert-butyl ether (88.8 Kg) and organic layers were combined, then washed three times with a third of a solution of sodium chloride (43 Kg) in water (80 L). After final layer separation, the organic layer was filtered through pall filter containing a charcoal cartridge, and the cake was washed with methyl tert-butyl ether (11.2 Kg). The filtrate was distilled under reduced pressure at below 50° C. down to ~90 L, and was then successively co-distilled with heptane (120 L), at below 50° C. and down to ~120 L. the mixture was then cooled down to 20-25° C. over 1 h, then stirred at this temperature for another 1 h. The slurry was filtered and the cake was washed three times with heptane (3×18 L), then three times with acetonitrile (3×18 L). The resulting wet solid was dried under vacuum and nitrogen flow at below 45° C. for at least 15 h to afford Intermediate A2 (44.6 Kg, 87% yield). $^1$H NMR (400 MHz, $CDCl_3$) δ ppm 8.13 (s, 2H), 8.09 (s, 2H), 7.97 (d, J=1.17 Hz, 1H), 7.34 (d, J=0.98 Hz, 1H), 4.08 (s, 3H), 1.61 (s, 9H); ESI $[M+H]^+$=330.

Intermediate A3: tert-Butyl 4-(4-(1-isopropyl-7-oxo-1,4,6,7-tetrahydrospiro[indazole-5,4'-piperidine]-1'-carbonyl)-6-methoxypyridin-2-yl)benzoate

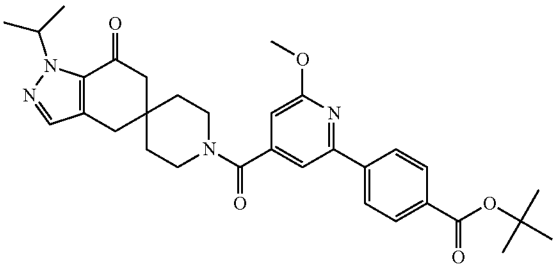 [SMILES: COc1cc(C(=O)N2CCC3(CC2)CC(=O)c2c(cnn2C(C)C)C3)cc(-c2ccc(C(=O)OC(C)(C)C)cc2)n1]

A round bottomed flask was charged with 2-(4-(tert-butoxycarbonyl)phenyl)-6-methoxyisonicotinic acid (Intermediate A2, 15.2 g, 46.2 mmol) and ethyl acetate (140 mL). 1,1'-Carbonyldiimidazole (8.98 g, 55.4 mmol) was added in one portion and stirred for 1 h at rt. 1-isopropyl-4,6-dihydrospiro[indazole-5,4'-piperidin]-7(1H)-one hydrochloride (Intermediate A1, 14.8 g, 52.2 mmol) was added followed by N,N-diisopropylethylamine (9.1 mL, 52.2 mL) and the reaction stirred for 18 h at rt. Aqueous 2 M HCl (40 mL) was added, followed by 1 M potassium hydrogensulfate (40 mL) and 50 mL of heptane. The obtained mixture was stirred for 1 h at rt. The mixture was transferred to separation funnel. The organic phase was separated, washed successively with water (20 mL), saturated sodium bicarbonate (30 mL), water (20 mL), brine (20 mL), dried over 20 g of magnesium sulfate and 10 g of silica gel, filtered, and concentrated in vacuo. Solid began to form towards the end of concentration. The residue was stirred in 40 mL of ethyl acetate at 80° C. and heptane (120 mL) was added slowly dropwise. The mixture was stirred at 80° C. for 1 h, then slowly cooled to room temperature with stirring over 1 h and stirred for 18 h at rt. The solid was collected via filtration, washed with water and ethyl acetate-heptane (1:3), and dried under vacuum at 50° C. for 18 h to obtain Intermediate A3 (19.64 g, 76% yield).

Alternative Preparation of Intermediate A3:

A clean and dry reactor was charged with acetonitrile (219 Kg) and 2-(4-(tert-butoxycarbonyl)phenyl)-6-methoxyisonicotinic acid (Intermediate A2, 34.8 Kg) at 20-25° C. The mixture was stirred for 5 min, then 1,1-carbodiimidazole (18.9 Kg) was charged in three successive portions. The slurry was further stirred at 20-25° C. for at least 1 h, then 1-isopropyl-4,6-dihydrospiro[indazole-5,4'-piperidin]-7(1H)-one hydrochloride salt (Intermediate A1, 33.0 Kg) was charged into the reactor, followed by N,N-diisopropylethylamine (20.5 Kg) via pump. The reagent pump as well as the walls of the reactor were washed with acetonitrile (13.7 Kg), and stirring was pursued at 20-25° C. for at least 2 h. Upon completion, the mixture was seeded with tert-butyl 4-(4-(1-isopropyl-7-oxo-1,4,6,7-tetrahydrospiro[indazole-5,4'-piperidine]-1'-carbonyl)-6-methoxypyridin-2-yl)benzoate (Intermediate A3, 209 g) and stirred for at least 30 min. After confirmation of crystallization start, a solution of citric acid monohydrate (58.5 Kg) in water (257 L) was charged over 1 h. The resulting slurry was further stirred at 20-25° C. for at least 2 h, then filtered and the cake was washed with a mixture of acetonitrile (68.4 Kg) and water (87 L). This wash was used to rinse the reactor as well. The solids were dried under reduced pressure at below 55° C., affording Intermediate A3 (43.44 Kg, 73% yield).

Compound of Example ACCi (as the Free Acid): 4-(4-(1-isopropyl-7-oxo-1,4,6,7-tetrahydrospiro[indazole-5,4'-piperidine]-1'-carbonyl)-6-methoxypyridin-2-yl)benzoic acid

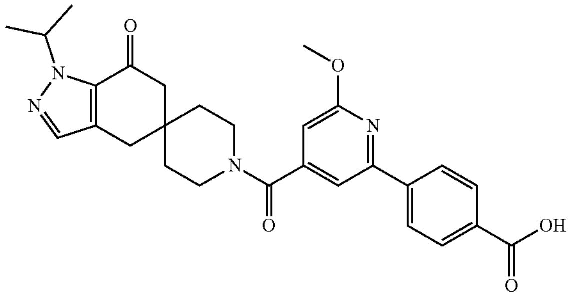 [SMILES: COc1cc(C(=O)N2CCC3(CC2)CC(=O)c2c(cnn2C(C)C)C3)cc(-c2ccc(C(=O)O)cc2)n1]

A round bottomed flask was charged with tert-butyl 4-(4-(1-isopropyl-7-oxo-1,4,6,7-tetrahydrospiro[indazole-5,4'-piperidine]-1'-carbonyl)-6-methoxypyridin-2-yl)benzoate (3.7 g, 6.6 mmol) and toluene (25 mL). 85% Phosphoric acid (3.0 mL) was added dropwise with stirring and the reaction was heated to 60° C. for 4 hours. A colorless thick gum formed. The reaction was cooled to rt and water was added. White solids were observed. The toluene organic layer was discarded, reserving the aqueous layer and solids. Ethyl acetate was added (60 mL) and 4N NaOH solution was added to adjust pH to ~7. The layers were separated and the aqueous was extracted with ethyl acetate (50 mL). The combined ethyl acetate organic layers were dried over sodium sulfate, filtered, and concentrated in vacuo to provide white solids. These were dissolved in ethyl acetate (80 mL) at 50° C. and heptane (90 mL) was added slowly. The heat was removed and the mixture was cooled to rt and stirred for 16 h. The resultant solids were collected via filtration, rinsed with the mother liquor, and dried to provide the title compound (4-(4-(1-Isopropyl-7-oxo-1,4,6,7-tetrahydrospiro[indazole-5,4'-piperidine]-1'-carbonyl)-6-methoxypyridin-2-yl)benzoic acid free form, 2.15 g, 65% yield) as a white solid.

Alternative Preparation of Compound of Example ACCi (as the Free Acid):

A clean a dry reactor was charged with acetonitrile (130.4 Kg) and tert-butyl 4-(4-(1-isopropyl-7-oxo-1,4,6,7-tetrahydrospiro[indazole-5,4'-piperidine]-1'-carbonyl)-6-methoxypyridin-2-yl)benzoate (Intermediate A3, 20.72 Kg) at 20-25° C. The mixture was stirred for 5 min, then p-toluenesulfonic acid (8.5 Kg) was charged under a gentle nitrogen sweep. The reaction mixture was warmed up to 70° C. and maintained at this temperature for at least 6.5 h. Upon completion, the mixture was cooled down to 40° C., seeded with Compound of Example ACCi (104 g) and water (83 L) was slowly charged over at least 1 h. the mixture was further stirred at 40° C. fora minimum of 4 h, then cooled down to 20-25° C. over 2 h. Further stirring for at least 2 h was followed by filtration, and the cake was rinsed with a solution of acetonitrile (33 Kg) and water (41 L). This wash was used to rinse the reactor as well. The resulting solids were dried under reduced pressure at below 55° C. to afford 4-(4-(1-Isopropyl-7-oxo-1,4,6,7-tetrahydrospiro[indazole-5,4'-piperidine]-1'-carbonyl)-6-methoxypyridin-2-yl)benzoic acid (16.5 Kg, 89% yield).

Preparation of Form 1 of Compound of Example ACCi—Anhydrous Mono-Tris of Example ACCi:

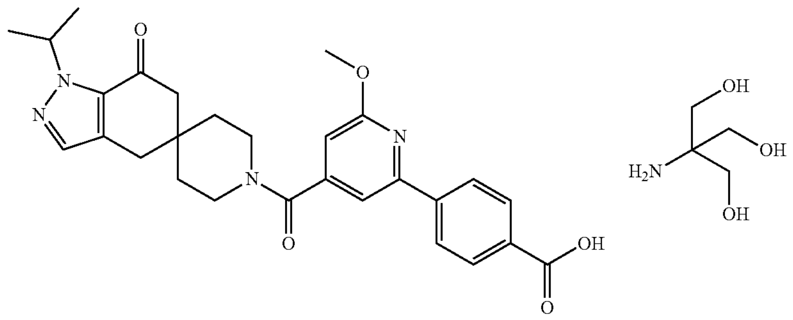 [SMILES: COc1cc(C(=O)N2CCC3(CC2)CC(=O)c2c(cnn2C(C)C)C3)cc(-c2ccc(C(=O)O)cc2)n1 ; NC(CO)(CO)CO]

A vial was charged with 4-(4-(1-isopropyl-7-oxo-1,4,6,7-tetrahydrospiro[indazole-5,4'-piperidine]-t-carbonyl)-6-methoxypyridin-2-yl)benzoic acid (151 mg, 0.300 mmol) and 3 mL of ethanol. The mixture was heated to 80° C. for 5 minutes to dissolve the solid and then cooled to rt. Tris(hydroxymethyl)aminomethane (39 mg, 0.32 mmol) was added, and the mixture was stirred overnight at rt. Heptane (2.25 mL) was added dropwise to produce a slurry that was heated to 50° C. to produce a clear solution. The mixture was cooled to rt overnight with stirring. White solids were observed, and the mixture was stirred for an additional 3 days. The material was filtered and dried in a vacuum oven at 50° C. overnight to produce Form 1 (151 mg, 0.242 mmol, 81% yield).

Alternative Preparation of Form 1 of Example ACCi: Anhydrous Mono-Tris of Example ACCi:

To a clean and dry reactor was charged ethanol (83 L), followed by the addition of Compound Example ACCi (9.43 Kg) and tris (2.55 kg) while the mixture was maintained at a temperature of 20-25° C. The tank walls were rinsed with ethanol (2 L), and the resulting mixture was heated at 65-70° C., maintained at this temperature for at least 30 min until all solids dissolved, then cooled down to 45-50° C. A warm filtration through a 10 μm in-line polypropylene filter was performed, and the reactor as well as the filter were washed with ethanol (9 L). n-Heptane (24 L) was charged into the warm solution through the same in-line filter, and the mixture was seeded with 4-(4-(1-isopropyl-7-oxo-1,4,6,7-tetrahydrospiro[indazole-5,4'-piperidine]-1'-carbonyl)-6-methoxypyridin-2-yl)benzoic acid anhydrous tris salt (100 g) in ethanol (0.5 L) at 45-50° C. The temperature was held for at least 2 h before cooling down to 20-25° C. over at least 2 h. Stirring was pursued for at least 5 days. The slurry was then filtered, and the cake was washed with a mixture of ethanol (13 L) and n-heptane (6 L). The solids were dried under reduced pressure at below 45° C. for at least 12 h, affording Example ACCi (11.7 Kg, 77%).

Preparation of Form 2 of Example ACCi—Trihydrate of the Mono-Tris Salt of Example ACCi:

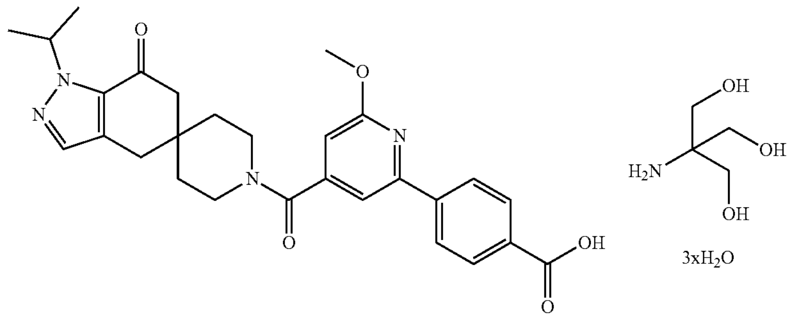 [SMILES: COc1cc(C(=O)N2CCC3(CC2)CC(=O)c2c(cnn2C(C)C)C3)cc(-c2ccc(C(=O)O)cc2)n1 ; NC(CO)(CO)CO]

Form 2 of the compound of Example ACCi was obtained from conversion from Form 1 of the compound of Example ACCi. Into a 50 mL EasyMax reactor was added Form 1 (1.7214 g, 2.760 mmol), Isopropanol (16.50 mL, 215.8 mmol), and Water (688 μL, 38.190 mmol). The mixture was stirred (300 rpm) for about 72 hr with a reactor jacket temperature of 25° C. The reaction mixture was then warmed to 40° C. over 15 min and held at 40° C. for about 24 hours, cooling once to 20° C. to remove a sample for testing. A mixture of forms was seen by PXRD; therefore, additional water Water (688 μL, 38.190 mmol) was added. The stir rate was increased to 400 rpm and the slurry was allowed to stir for 6 hours and was then cooled to 15° C. The solids were isolated on a 60 mL/40 M filter and washed with 96/4 isopropanol/water. The resulting material was consistent with Form 2 of the compound of Example ACCi by PXRD.

Alternative Preparation of Form 2 of the Compound of Example ACCi—Trihydrate of the Mono-Tris Salt of Example ACCi:

A clean and dry reactor was charged with isopropanol (60.4 Kg), and Compound of Example ACCi (16.68 Kg) and tris (4.42 kg) were added while the mixture was maintained at a temperature of 20-25° C. The mixture was stirred for 5 min, then water (6.7 Kg) was charged and the slurry was warmed up to 55° C. The now clear solution was filtered into a pre-warmed clean and dry reactor (50-55° C.) through an in-line 10 μm polypropylene filter. The solution was then seeded with the mono-tris salt of the compound of Example ACCi as a trihydrate (167 g). After verification that the seed persisted, the mixture was cooled down to 15° C. over at least 2 h, then maintained at 15° C. for a minimum of 16 h. The slurry was filtered and the cake washed with chilled isopropanol (13.1 Kg). The solids were then dried under reduced pressure at below 25° C. to afford only Form 2 of Example ACCi (22.1 Kg, 98% yield).

Figure 3:
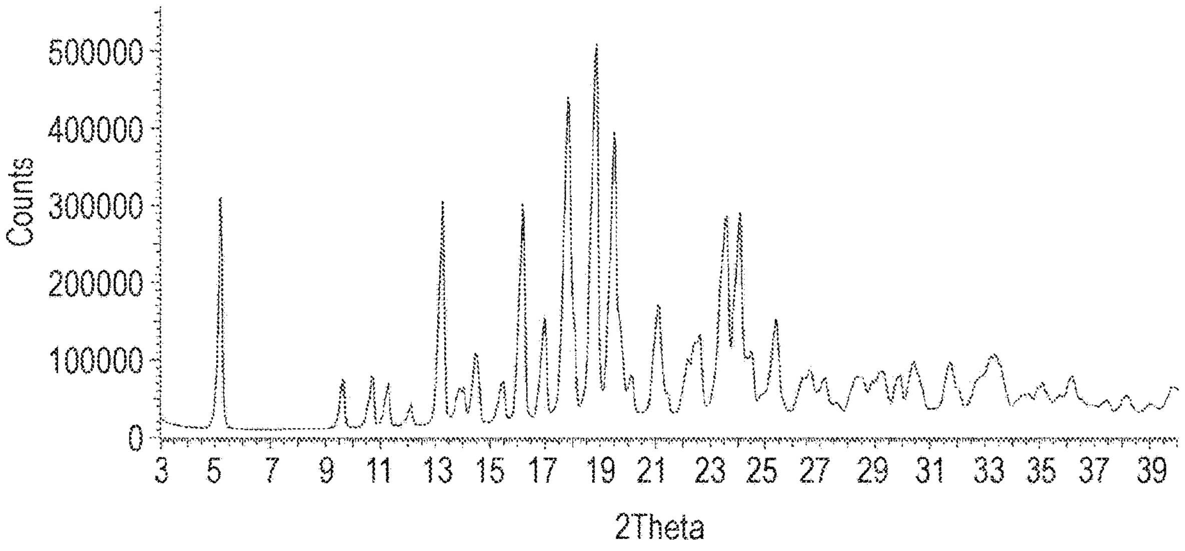
FIG. 3 shows an illustrative PXRD pattern of Form 1 of 4-(4-(1-Isopropyl-7-oxo-1,4,6,7-tetrahydrospiro[indazole-5,4'-piperidine]-1'-carbonyl)-6-methoxypyridin-2-yl)benzoic acid (Example ACCi compound) carried out on a Bruker AXS D4 Endeavor diffractometer equipped with a Cu radiation source.

Form 1 of Example ACCi is anhydrous and is thermodynamically stable below a water activity of about 0.2 (20% RH) at ambient temperature. Form 1 of Example ACCi has a PXRD pattern substantially the same as that shown in FIG. 3 of Example ACCi. Characteristic PXRD peaks of Form 1 of Example ACCi, expressed as 2Θ±0.2° 2Θ are at 9.6, 10.7, and 11.3. Peak locations and intensities for the PXRD pattern in FIG. 3 are provided in Table 1.

TABLE 1

PXRD Peaks and Relative Intensities of Form 1 of Example ACCi

| Degrees 2Θ + 0.2° 2Θ | Relative Intensity (%) |
|---|---|
| 5.2 | 62 |
| 9.6 | 13 |
| 10.7 | 14 |
| 11.3 | 11 |
| 12.1 | 6 |
| 13.3 | 60 |
| 13.9 | 9 |
| 14.0 | 10 |
| 15.5 | 11 |
| 16.2 | 58 |
| 17.0 | 27 |
| 17.8 | 86 |
| 18.9 | 100 |
| 19.5 | 77 |
| 20.1 | 11 |
| 21.1 | 29 |
| 22.2 | 15 |
| 22.4 | 19 |
| 22.6 | 21 |

TABLE 1-continued

PXRD Peaks and Relative Intensities of Form 1 of Example ACCi

| Degrees 2Θ + 0.2° 2Θ | Relative Intensity (%) |
|---|---|
| 23.6 | 53 |
| 24.1 | 54 |
| 24.5 | 16 |
| 25.4 | 25 |
| 26.4 | 9 |
| 26.6 | 11 |
| 27.2 | 9 |
| 28.3 | 9 |
| 29.3 | 10 |
| 29.9 | 9 |
| 30.4 | 13 |
| 31.7 | 13 |
| 33.4 | 15 |

Figure 4:
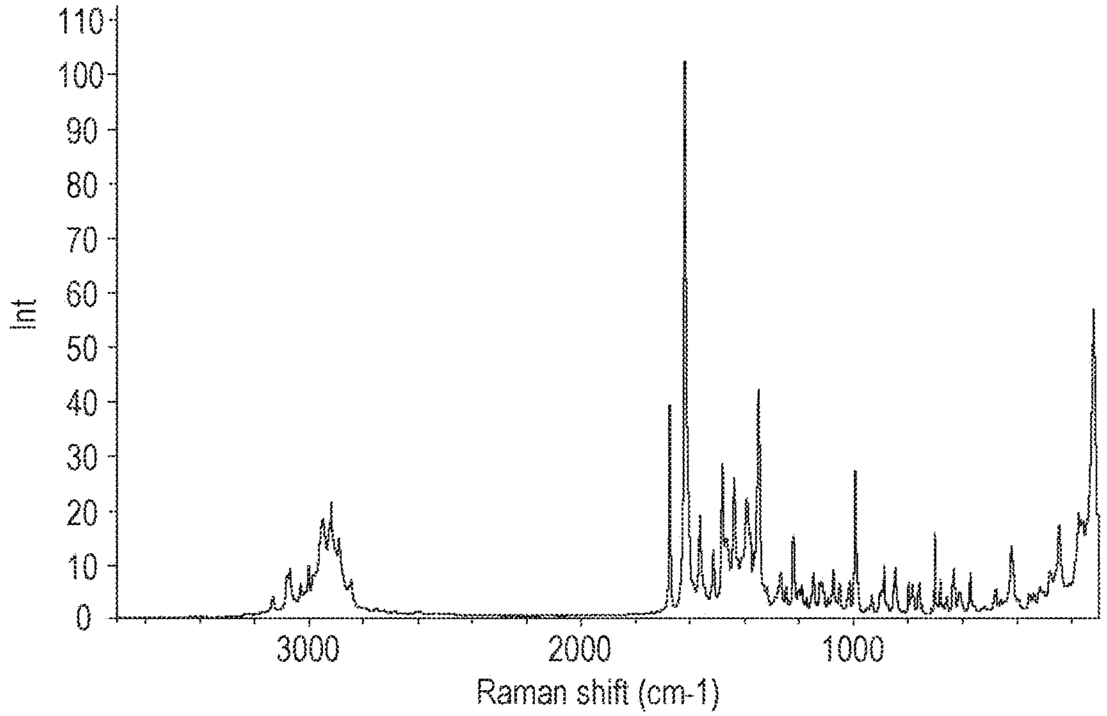
FIG. 4 shows an illustrative Raman spectra of Form 1 of 4-(4-(1-Isopropyl-7-oxo-1,4,6,7-tetrahydrospiro[indazole-5,4'-piperidine]-1'-carbonyl)-6-methoxypyridin-2-yl)benzoic acid (Example ACCi compound) collected using a Nicolet NXR FT-Raman accessory attached to the FT-IR bench.

Form 1 of Example ACCi has a Raman spectrum substantially the same as that shown in FIG. 4. Form 1 of Example ACCi has characteristic Raman peak shifts, expressed as $cm^{-1}$, at 568, 698, 989, 1218, 1511, 1561, and 1615, +2 $cm^{-1}$. Peak positions (+2 $cm^{-1}$) and normalized intensity (W=weak, M=medium, S=strong) of Form 1 of Example ACCi in FIG. 4 are listed in Table 2.

TABLE 2

Raman Peaks and Normalized Intensity of Form 1 of Example ACCi

| Raman Peak Position ($cm^{-1}$) | Normalized Intensity |
|---|---|
| 115 | M |
| 156 | W |
| 170 | W |
| 241 | W |
| 274 | W |
| 311 | W |
| 334 | W |
| 350 | W |
| 417 | W |
| 456 | W |
| 476 | W |
| 568 | W |
| 608 | W |
| 628 | W |
| 653 | W |
| 678 | W |
| 698 | W |
| 755 | W |
| 779 | W |
| 794 | W |
| 842 | W |
| 885 | W |
| 929 | W |
| 989 | W |
| 1011 | W |
| 1047 | W |
| 1071 | W |
| 1090 | W |
| 1119 | W |
| 1143 | W |
| 1169 | W |
| 1187 | W |
| 1196 | W |
| 1218 | W |
| 1244 | W |
| 1265 | W |
| 1315 | W |
| 1345 | M |
| 1363 | W |
| 1388 | W |
| 1435 | W |
| 1466 | W |

TABLE 2-continued

| Raman Peaks and Normalized Intensity of Form 1 of Example ACCi | |
|---|---|
| Raman Peak Position ($cm^{-1}$) | Normalized Intensity |
| 1478 | W |
| 1511 | W |
| 1561 | W |
| 1615 | S |
| 1671 | M |
| 2840 | W |
| 2885 | W |
| 2914 | W |
| 2945 | W |
| 2998 | W |
| 3027 | W |
| 3066 | W |
| 3129 | W |

Figure 5:
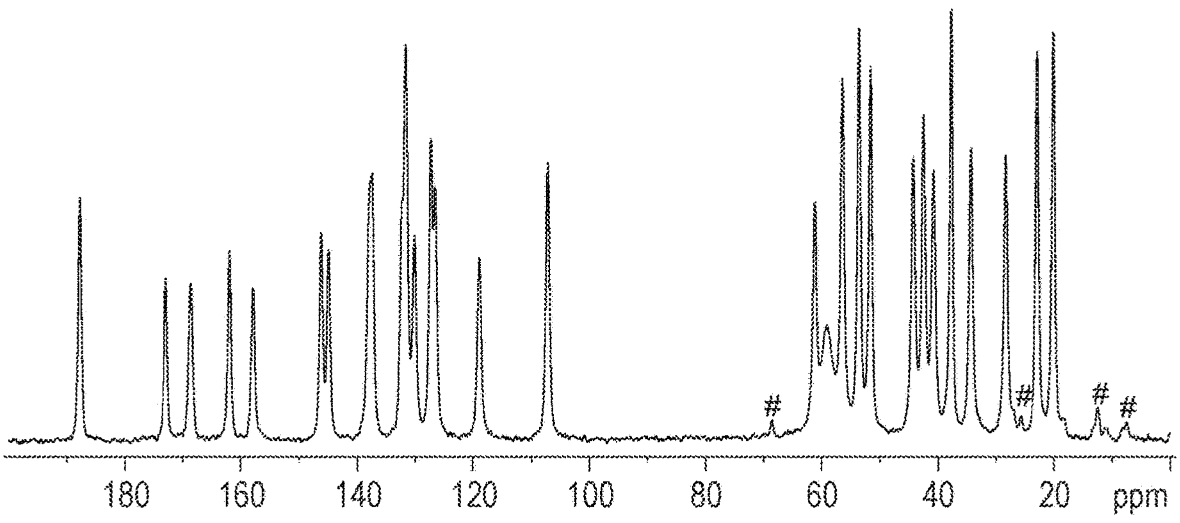
FIG. 5 shows an illustrative $^{13}C$ ssNMR pattern of Form 1 of 4-(4-(1-Isopropyl-7-oxo-1,4,6,7-tetrahydrospiro[indazole-5,4'-piperidine]-1'-carbonyl)-6-methoxypyridin-2-yl) benzoic acid (Example ACCi compound) conducted on a Bruker-BioSpin CPMAS probe positioned into a Bruker-BioSpin Avance III 500 MHz ($^1H$ frequency) NMR spectrometer.

Form 1 of Example ACCi has a $^{13}C$ ssNMR spectrum substantially the same as that shown in FIG. 5. Form 1 of Example ACCi has characteristic $^{13}C$ ssNMR chemical shifts, expressed as ppm, at 22.9, 146.2, 157.9, 161.9, and 172.9, +0.2 ppm. $^{13}C$ chemical shifts (+0.2 ppm) of Form 1 of Example ACCi as shown in FIG. 5 are listed in Table 3.

TABLE 3

| $^{13}C$ chemical shifts and Intensity of Form 1 of Example ACCi | |
|---|---|
| $^{13}C$ chemical shifts (ppm) | Intensity |
| 20.1 | 95 |
| 22.9 | 90 |
| 28.4 | 66 |
| 34.3 | 68 |
| 37.7 | 100 |
| 40.8 | 63 |
| 42.5 | 76 |
| 44.3 | 66 |
| 51.6 | 87 |
| 53.6 | 96 |
| 56.4 | 84 |
| 59.1 | 27 |
| 61.2 | 55 |
| 107.1 | 65 |
| 118.9 | 42 |
| 126.6 | 59 |
| 127.3 | 70 |
| 130.2 | 47 |
| 131.7 | 92 |
| 132.3 | 56 |
| 137.5 | 62 |
| 137.9 | 59 |
| 144.9 | 44 |
| 146.2 | 48 |
| 157.9 | 36 |
| 161.9 | 44 |
| 168.6 | 36 |
| 172.9 | 38 |
| 187.7 | 56 |

Figure 6:
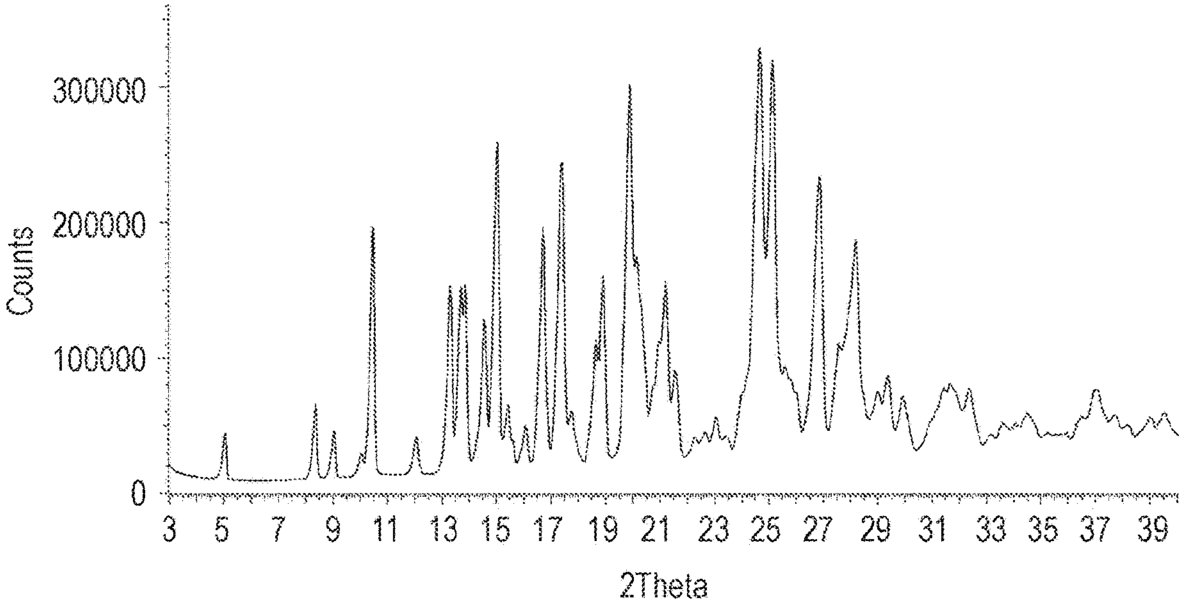
FIG. 6 shows an illustrative PXRD pattern of Form 2 of 4-(4-(1-Isopropyl-7-oxo-1,4,6,7-tetrahydrospiro[indazole-5,4'-piperidine]-1'-carbonyl)-6-methoxypyridin-2-yl)benzoic acid (Example ACCi compound) carried out on a Bruker AXS D4 Endeavor diffractometer equipped with a Cu radiation source.

Form 2 of Example ACCi is a trihydrate and is thermodynamically stable above a water activity of about 0.2 at ambient temperature and 20% RH. Form 2 of Example ACCi has a PXRD pattern substantially the same as that shown in FIG. 6. Characteristic PXRD peaks of Form 2 of Example ACCi, expressed as 2Θ+0.2° 2Θ are at 8.4, 9.0, 10.5, 15.0, and 24.7. Peak locations and intensities for the PXRD pattern in FIG. 6 are provided in Table 4.

TABLE 4

| PXRD Peaks and Relative Intensities of Form 2 of Example ACCi | |
|---|---|
| Degrees 2Θ + 0.2° 2Θ | Relative Intensity (%) |
| 5.0 | 11 |
| 8.4 | 18 |
| 9.0 | 12 |
| 10.0 | 6 |
| 10.5 | 62 |
| 12.1 | 9 |
| 13.3 | 46 |
| 13.7 | 45 |
| 13.9 | 46 |
| 14.6 | 37 |
| 15.0 | 80 |
| 15.4 | 15 |
| 16.1 | 10 |
| 16.7 | 59 |
| 17.4 | 74 |
| 17.8 | 13 |
| 18.6 | 30 |
| 18.9 | 45 |
| 19.9 | 93 |
| 20.1 | 50 |
| 21.2 | 46 |
| 21.5 | 21 |
| 24.7 | 100 |
| 25.2 | 97 |
| 26.9 | 71 |
| 28.2 | 52 |
| 29.0 | 15 |
| 29.4 | 18 |
| 29.9 | 13 |
| 31.4 | 15 |
| 31.7 | 16 |
| 32.4 | 14 |
| 33.6 | 5 |
| 34.5 | 7 |
| 37.0 | 12 |

Figure 7:
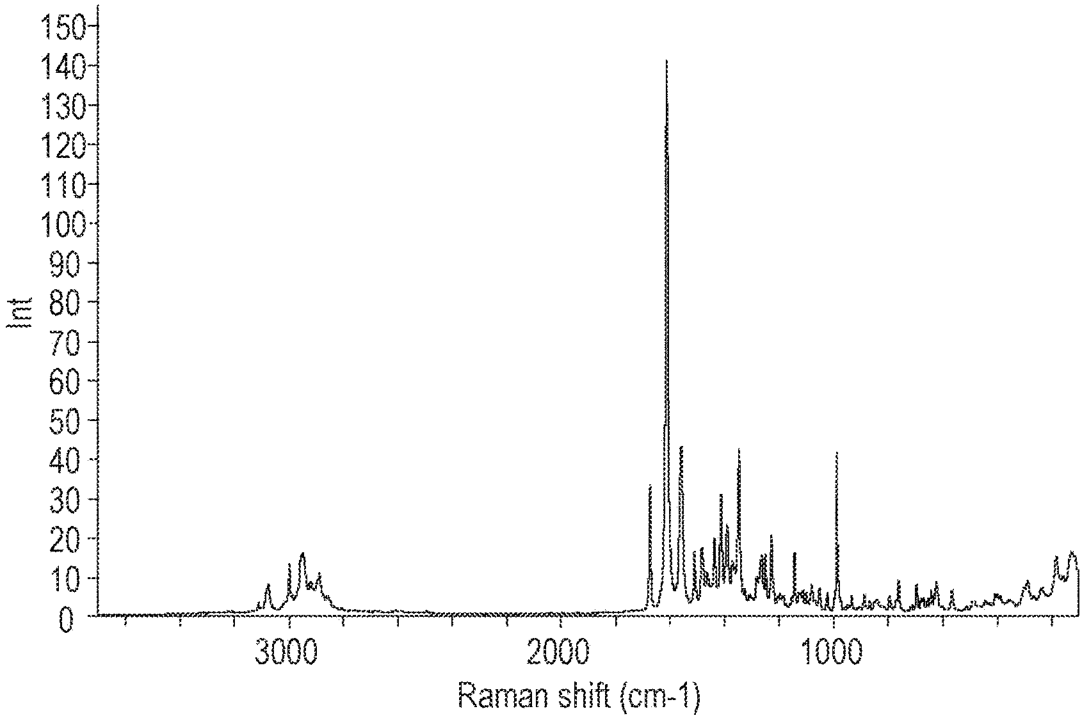
FIG. 7 shows an illustrative Raman spectra of Form 2 of 4-(4-(1-Isopropyl-7-oxo-1,4,6,7-tetrahydrospiro[indazole-5,4'-piperidine]-1'-carbonyl)-6-methoxypyridin-2-yl)benzoic acid (Example ACCi compound) collected using a Nicolet NXR FT-Raman accessory attached to the FT-IR bench.

Form 2 of Example ACCi has a Raman spectrum substantially the same as that shown in FIG. 7. Form 2 of Example ACCi has characteristic Raman peak shift, expressed as $cm^{-1}$, at 562, 692, 984, 1225, 1507, 1557, and 1610+2 $cm^{-1}$. Peak positions (+2 $cm^{-1}$) and normalized intensity (W=weak, M=medium, S=strong) of Form 2 of the compound of Example ACCi in FIG. 7 are listed in Table 5.

TABLE 5

| Raman Peaks and Normalized Intensity of Form 2 of Example ACCi | |
|---|---|
| Raman Peak Position ($cm^{-1}$) | Normalized Intensity |
| 123 | W |
| 179 | W |
| 232 | W |
| 284 | W |
| 405 | W |
| 441 | W |
| 481 | W |
| 562 | W |
| 620 | W |
| 628 | W |
| 639 | W |
| 650 | W |
| 667 | W |
| 692 | W |
| 710 | W |
| 758 | W |
| 790 | W |
| 839 | W |
| 864 | W |
| 884 | W |

TABLE 5-continued

| Raman Peaks and Normalized Intensity of Form 2 of Example ACCi | |
|---|---|
| Raman Peak Position ($cm^{-1}$) | Normalized Intensity |
| 931 | W |
| 984 | W |
| 1019 | W |
| 1048 | W |
| 1077 | W |
| 1097 | W |
| 1109 | W |
| 1118 | W |
| 1140 | W |
| 1194 | W |
| 1225 | W |
| 1246 | W |
| 1261 | W |
| 1277 | W |
| 1305 | W |
| 1321 | W |
| 1344 | W |
| 1369 | W |
| 1387 | W |
| 1410 | W |
| 1433 | W |
| 1460 | W |
| 1480 | W |
| 1507 | W |
| 1557 | M |
| 1610 | S |
| 1670 | W |
| 2884 | W |
| 2916 | W |
| 2946 | W |
| 2995 | W |
| 3073 | W |
| 3108 | W |

Figure 8:
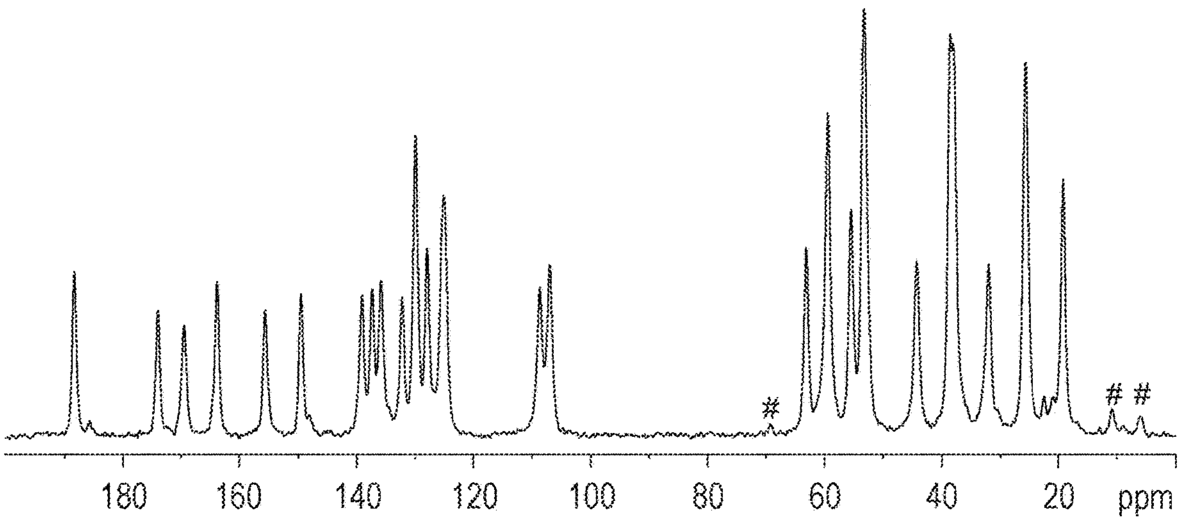
FIG. 8 shows an illustrative $^{13}C$ ssNMR pattern of Form 2 of 4-(4-(1-Isopropyl-7-oxo-1,4,6,7-tetrahydrospiro[indazole-5,4'-piperidine]-1'-carbonyl)-6-methoxypyridin-2-yl) benzoic acid (Example ACCi compound) conducted on a Bruker-BioSpin CPMAS probe positioned into a Bruker-BioSpin Avance III 500 MHz ($^1H$ frequency) NMR spectrometer.

Form 2 of Example ACCi has a $^{13}C$ ssNMR spectrum substantially the same as that shown in FIG. 8. Form 2 of Example ACCi has characteristic $^{13}C$ ssNMR chemical shifts, expressed as ppm, at 19.2, 149.5, 155.6, 163.8, and 188.3, +0.2 ppm. $^{13}C$ chemical shifts (+0.2 ppm) of Form 2 of Example ACCi as shown in FIG. 8 are listed in Table 6.

TABLE 6

| $^{13}C$ chemical shifts and Intensity of Form 2 of Example ACCi | |
|---|---|
| $^{13}C$ chemical shifts (ppm) | Intensity |
| 19.2 | 60 |
| 25.7 | 87 |
| 32.0 | 40 |
| 38.0 | 92 |
| 38.5 | 94 |
| 44.2 | 41 |
| 53.2 | 100 |
| 55.5 | 53 |
| 59.4 | 76 |
| 63.1 | 44 |
| 107.0 | 40 |
| 108.7 | 35 |
| 125.1 | 56 |
| 128.0 | 44 |
| 130.0 | 70 |
| 132.3 | 33 |
| 135.9 | 37 |
| 137.4 | 35 |
| 139.1 | 33 |
| 149.5 | 33 |

TABLE 6-continued

| $^{13}C$ chemical shifts and Intensity of Form 2 of Example ACCi | |
|---|---|
| $^{13}C$ chemical shifts (ppm) | Intensity |
| 155.6 | 30 |
| 163.8 | 36 |
| 169.5 | 26 |
| 174.0 | 29 |
| 188.3 | 39 |

Based on the disclosure provided herein, one of ordinary skill in the art would appreciate that each Form 1 and Form 2 of Example ACCi can be uniquely identified by several different spectral peaks or patterns in varying combinations. Described below are exemplary combinations of characteristic peak values that can be used to separately identify Form 1 and Form 2 of the compound of Example ACCi but in no way should these exemplary combinations be viewed as limiting other peak value combinations disclosed herein.

Figure 9:
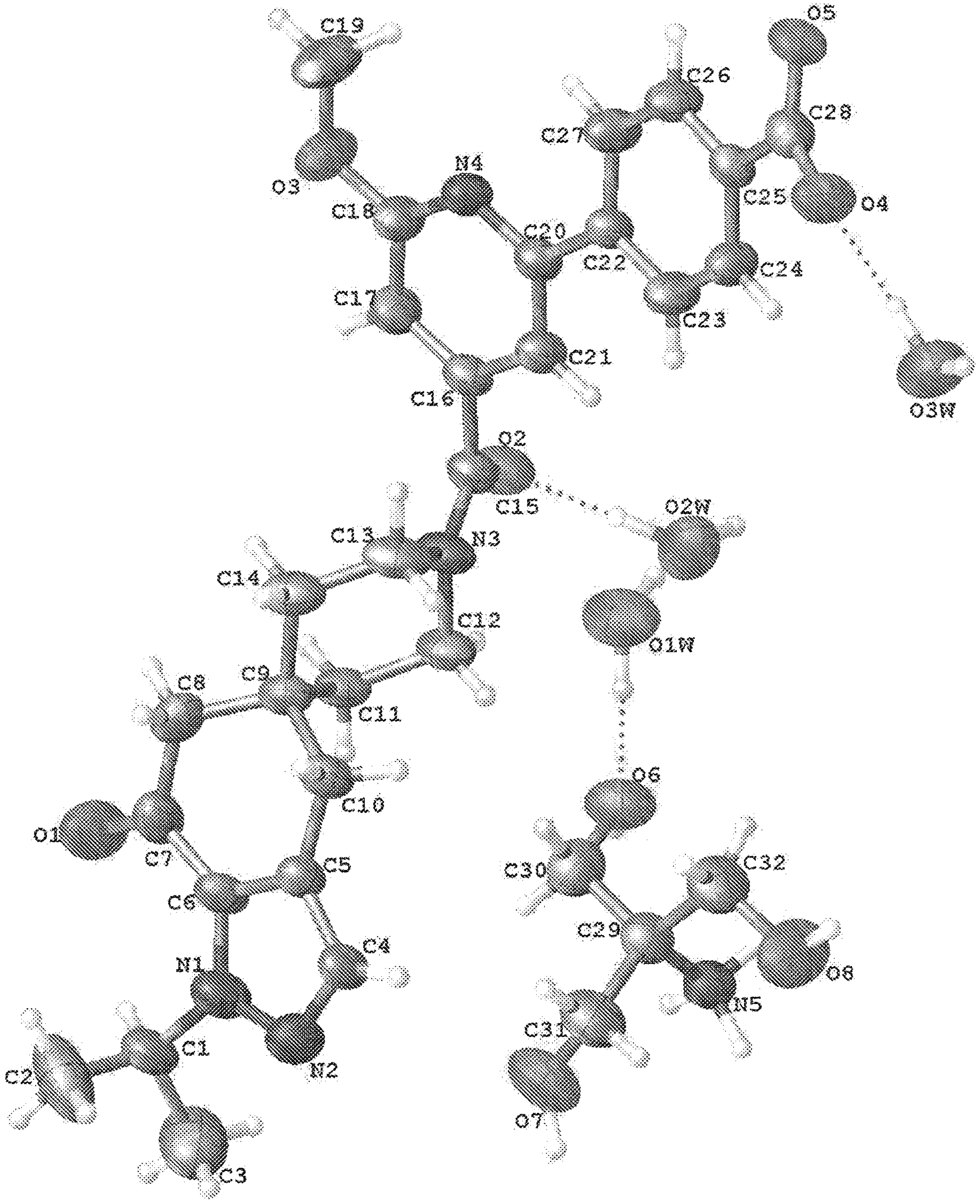
FIG. 9 shows an illustrative single crystal structure of Form 2 of 4-(4-(1-Isopropyl-7-oxo-1,4,6,7-tetrahydrospiro[indazole-5,4'-piperidine]-1'-carbonyl)-6-methoxypyridin-2-yl)benzoic acid (Example ACCi compound).
Figure 10:
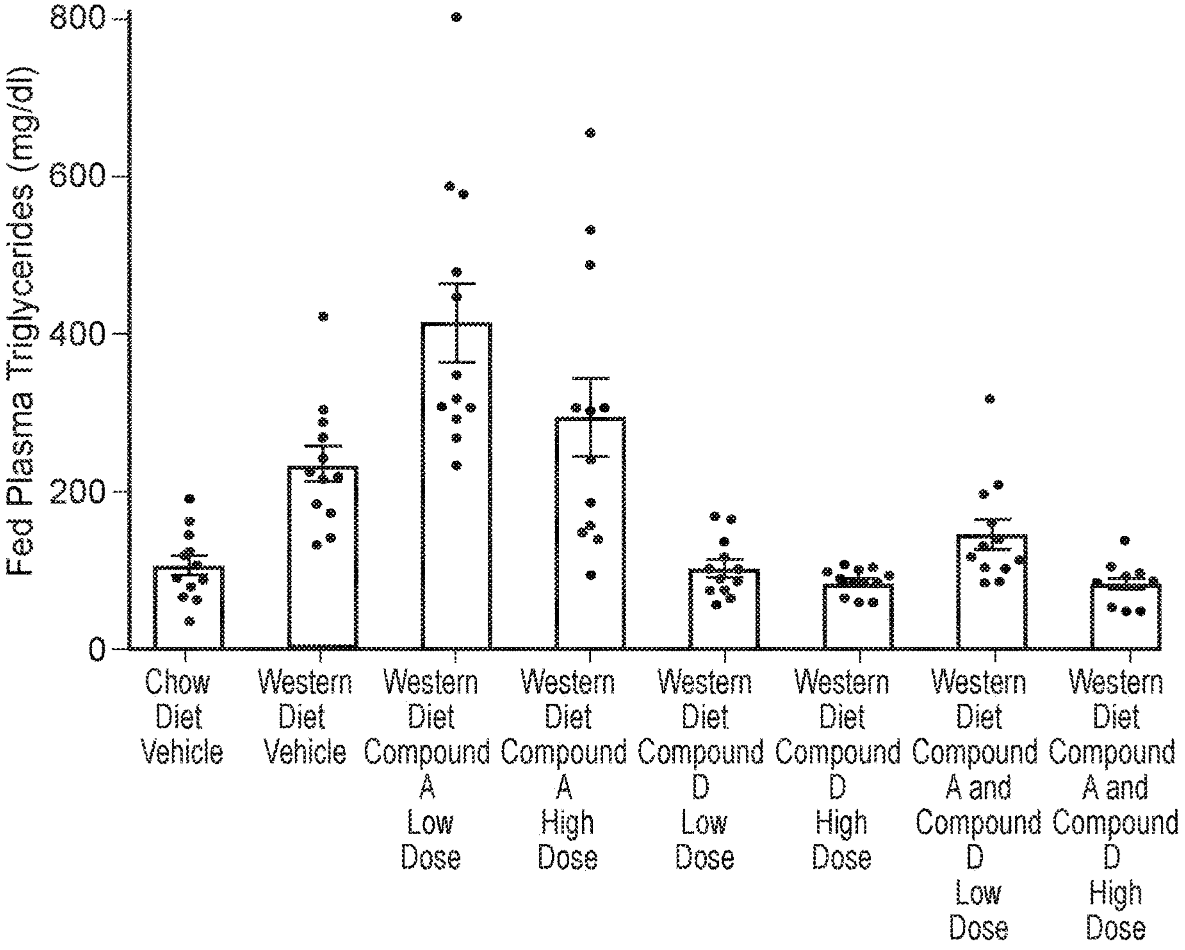
FIG. 10 summarizes the effects of oral administration as monotherapy and in combination of 4-(4-(1-Isopropyl-7-oxo-1,4,6,7-tetrahydrospiro[indazole-5,4'-piperidine]-1'-carbonyl)-6-methoxypyridin-2-yl)benzoic acid and (S)-2-(5-((3-ethoxypyridin-2-yl)oxy)pyridin-3-yl)-N-(tetrahydrofuran-3-yl)pyrimidine-5-carboxamide on plasma triglyceride levels in Western diet fed Sprague Dawley rats, measured at the fed state.
Figure 11:
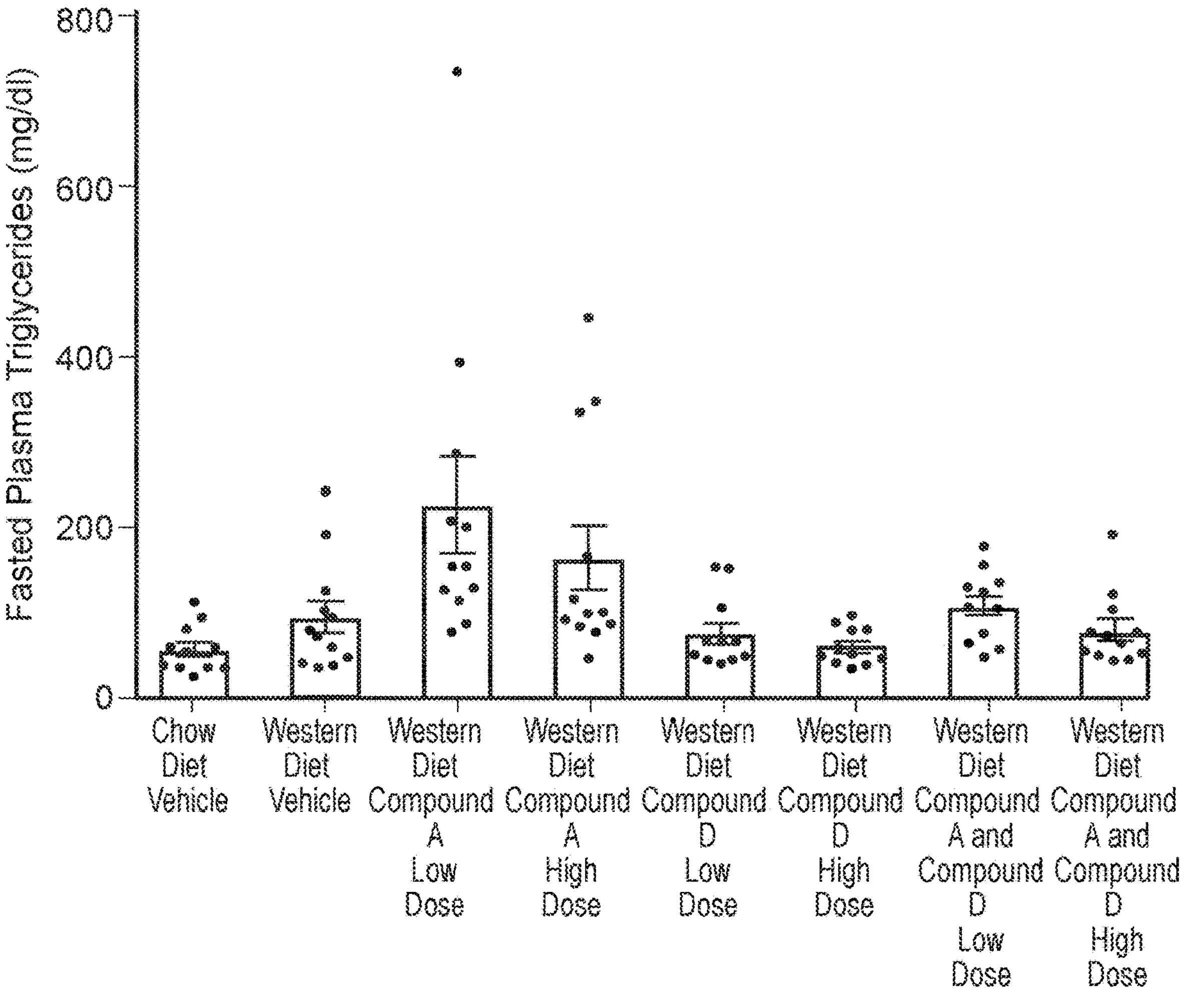
FIG. 11 summarizes the effects of oral administration as monotherapy and in combination 4-(4-(1-Isopropyl-7-oxo-1,4,6,7-tetrahydrospiro[indazole-5,4'-piperidine]-1'-carbonyl)-6-methoxypyridin-2-yl)benzoic acid and (S)-2-(5-((3-ethoxypyridin-2-yl)oxy)pyridin-3-yl)-N-(tetrahydrofuran-3-yl)pyrimidine-5-carboxamide on plasma triglyceride levels in Western diet fed Sprague Dawley rats measured at the fasted state.
Figure 12:
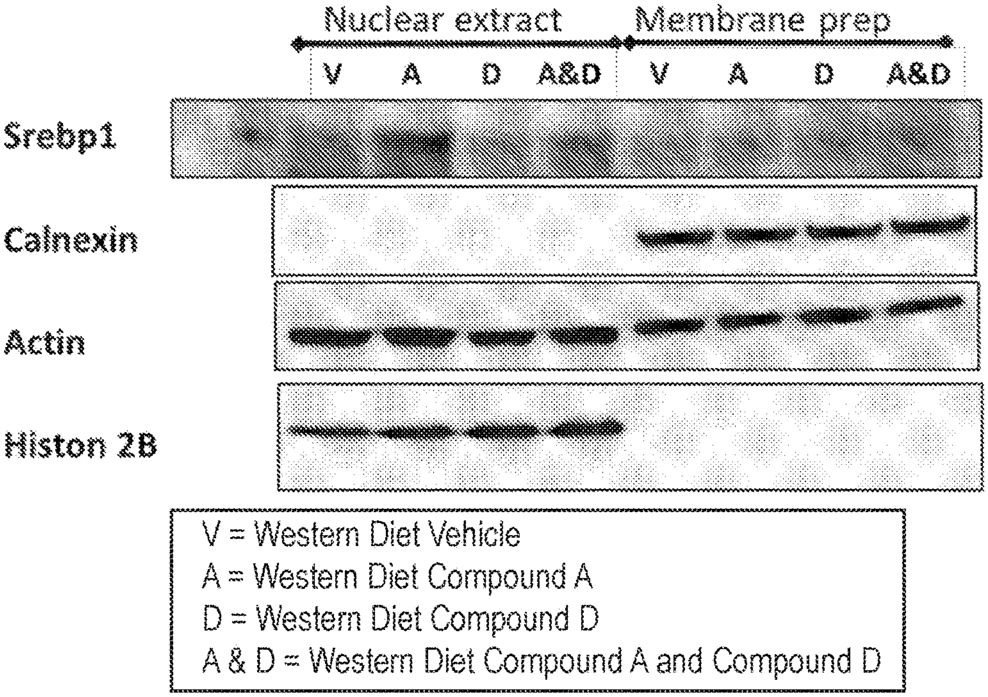
FIG. 12 summarizes the effect of administration of 4-(4-(1-Isopropyl-7-oxo-1,4,6,7-tetrahydrospiro[indazole-5,4'-piperidine]-1'-carbonyl)-6-methoxypyridin-2-yl)benzoic acid and (S)-2-(5-((3-ethoxypyridin-2-yl)oxy)pyridin-3-yl)-N-(tetrahydrofuran-3-yl)pyrimidine-5-carboxamide as monotherapy and in combination on SREBP-1 nuclear localization in Western diet fed rats.
Figure 12:
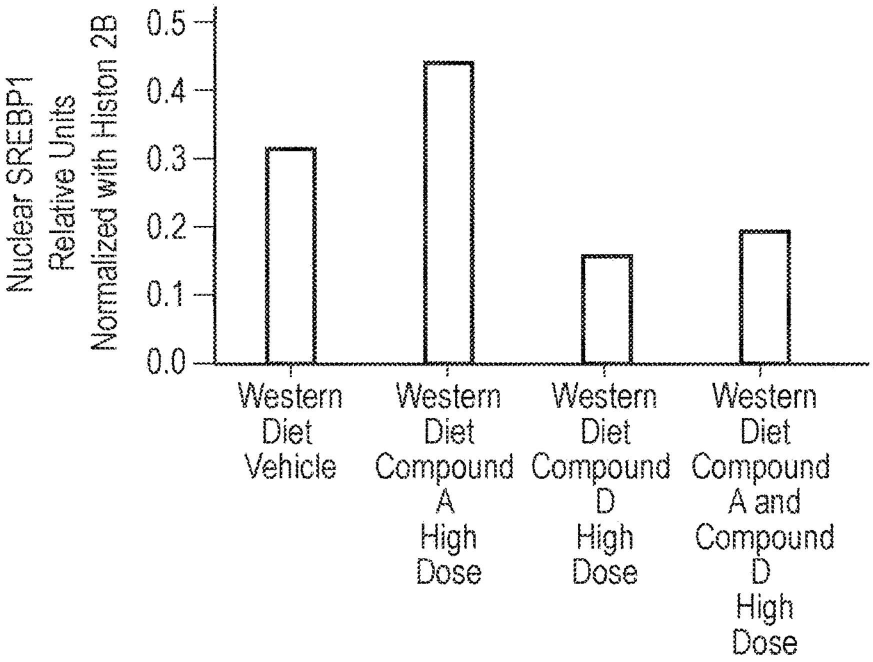
Figure 13:
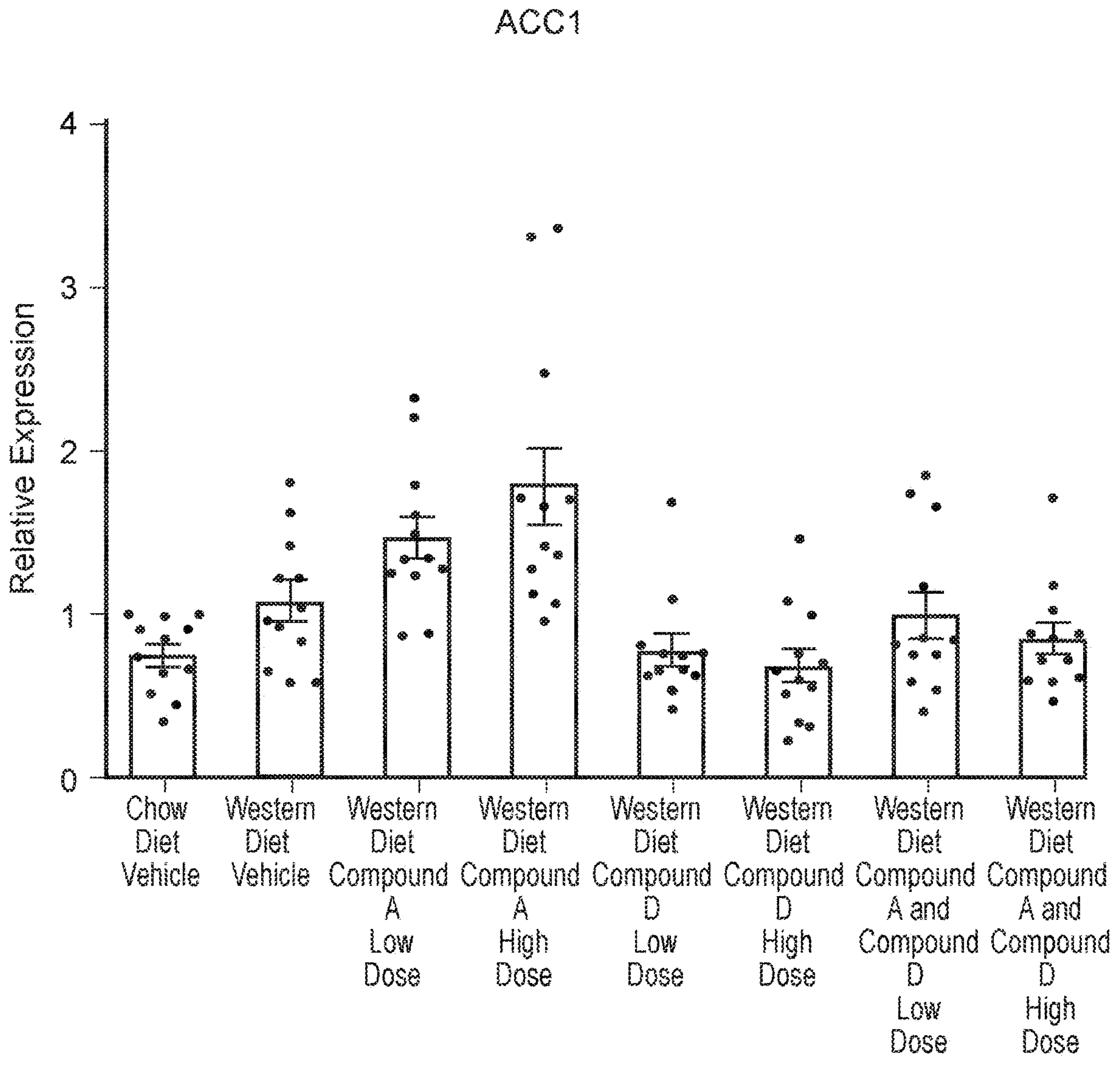
FIG. 13 summarizes the effect of administration of 4-(4-(1-Isopropyl-7-oxo-1,4,6,7-tetrahydrospiro[indazole-5,4'-piperidine]-1'-carbonyl)-6-methoxypyridin-2-yl)benzoic acid and (S)-2-(5-((3-ethoxypyridin-2-yl)oxy)pyridin-3-yl)-N-(tetrahydrofuran-3-yl)pyrimidine-5-carboxamide as monotherapy and in combination on hepatic lipogenic gene expression in Western diet fed rats, specifically acetyl-CoA carboxylase (ACC1).
Figure 14:
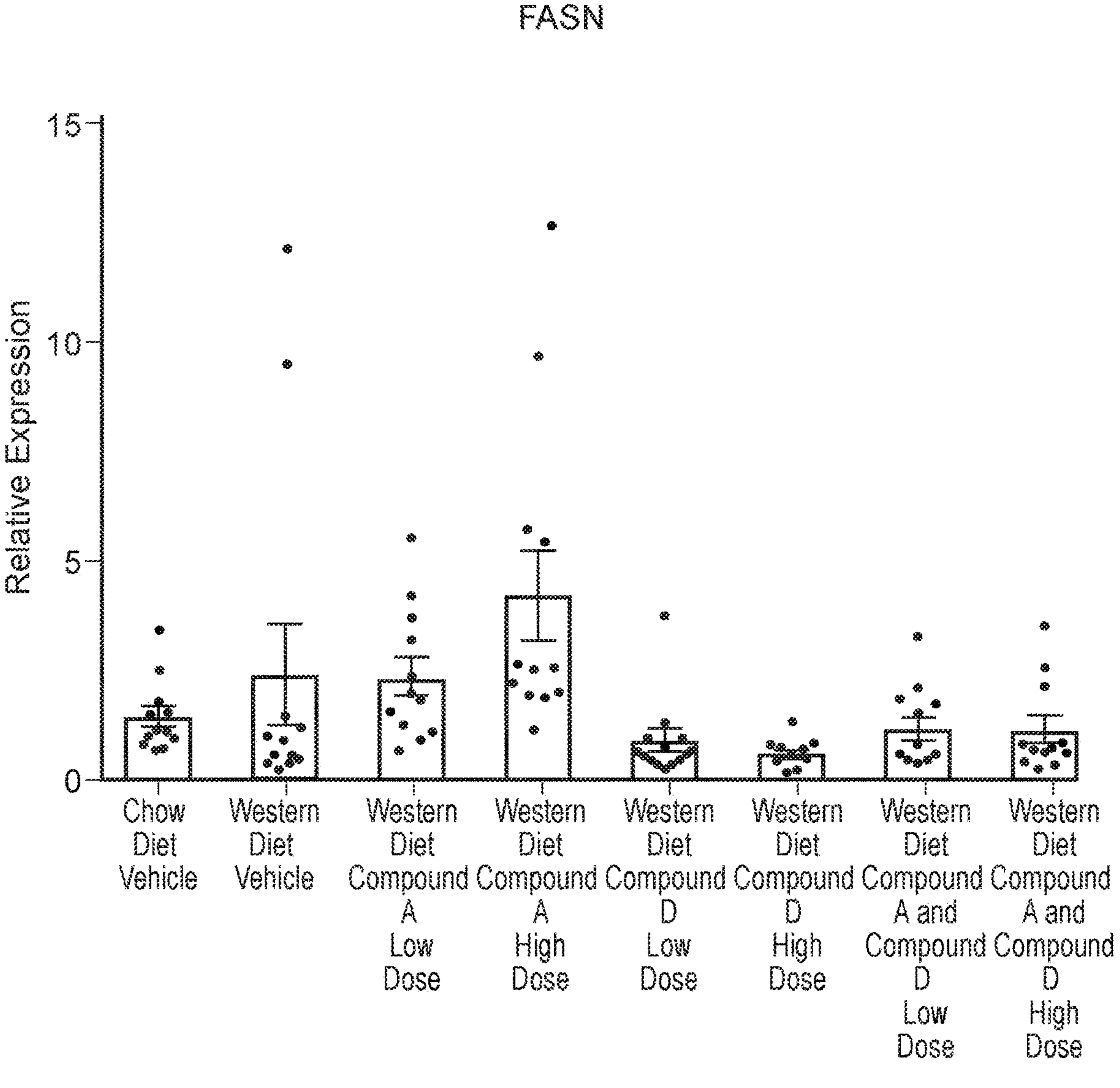
FIG. 14 summarizes the effect of administration of 4-(4-(1-Isopropyl-7-oxo-1,4,6,7-tetrahydrospiro[indazole-5,4'-piperidine]-1'-carbonyl)-6-methoxypyridin-2-yl)benzoic acid and (S)-2-(5-((3-ethoxypyridin-2-yl)oxy)pyridin-3-yl)-N-(tetrahydrofuran-3-yl)pyrimidine-5-carboxamide as monotherapy and in combination on hepatic lipogenic gene expression in Western diet fed rats, specifically fatty acid synthase (FASN).
Figure 15:
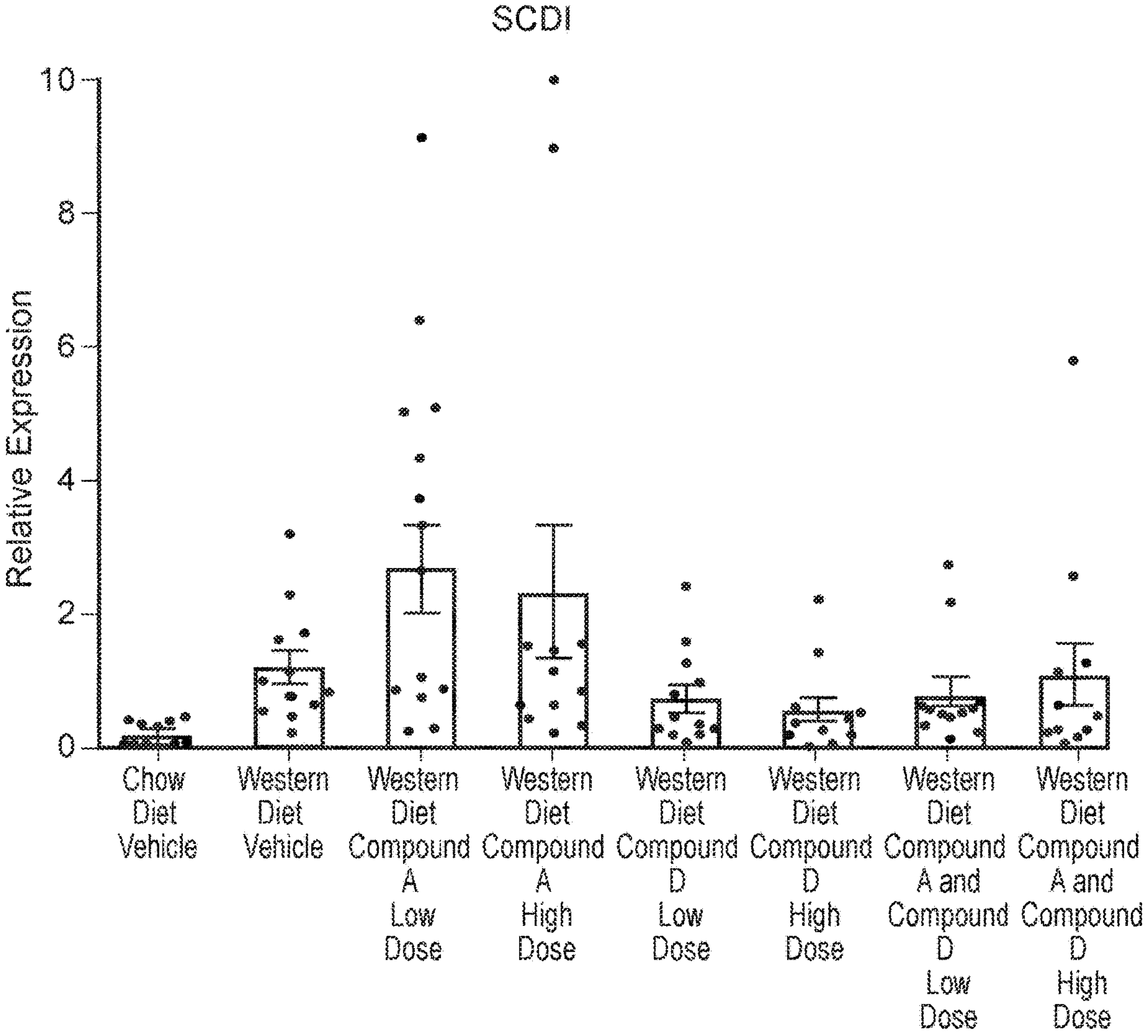

To confirm the presence of three water molecules in Form 2 of Example ACCi, data was collected using a Bruker D8 Venture diffractometer at room temperature. See FIG. 9. The structure was solved by intrinsic phasing using SHELX software suite in the Monoclinic class space group $P2_1/c$ (Version 5.1, Bruker AXS, 1997). The structure was subsequently refined by the full-matrix least squares method. All non-hydrogen atoms were found and refined using anisotropic displacement parameters.

The hydrogen atoms located on nitrogen and oxygen were found from the Fourier difference map and refined with distances restrained. The remaining hydrogen atoms were placed in calculated positions and were allowed to ride on their carrier atoms.

The final R-index was 7.2%. A final difference Fourier revealed no missing or misplaced electron density.

Table 7 provides data collected with regard to Form 2 of Example ACCi:

TABLE 7

| | |
|---|---|
| Empirical formula | $C_{28}H_{30}N_4O_5$•$C_4H_{11}NO_3$•$3H_2O$ |
| Formula weight | 677.74 |
| Temperature | RT |
| Wavelength | 1.54178 Å |
| Crystal system | Monoclinic |
| Space group | $P2_1/c$ |
| Unit cell dimensions | a = 17.6927(9) Å α = 90°. |
| | b = 13.2753(7) Å β = 92.451(3)°. |
| | c = 14.6480(8) Å γ = 90°. |
| Volume | 3437.3(3) $Å^3$ |
| Z | 4 |
| Density (calculated) | 1.310 $Mg/m^3$ |
| Goodness-of-fit on $F^2$ | 1.053 |
| Final R indices [I > 2sigma(I)] | R1 = 0.0723, wR2 = 0.1835 |
| R indices (all data) | R1 = 0.1244, wR2 = 0.2110 |

A crystalline 2-amino-2-(hydroxymethyl)propane-1,3-diol salt of is 4-(4-(1-isopropyl-7-oxo-1,4,6,7-tetrahydrospiro[indazole-5,4'-piperidine]-1'-carbonyl)-6-methoxypyridin-2-yl)benzoic acid. This crystalline salt is generally referred to as the tris salt.

The crystalline tris salt of Example ACCi, wherein the ratio of 4-(4-(1-isopropyl-7-oxo-1,4,6,7-tetrahydrospiro[indazole-5,4'-piperidine]-1'-carbonyl)-6-methoxypyridin-2-yl)benzoic acid and the salt is 1:1.

The crystalline tris salt of Example ACCi, wherein the crystalline salt is an anhydrous crystalline salt.

The anhydrous crystalline tris salt of Example ACCi, wherein said anhydrous crystalline salt has a PXRD pattern comprising peaks at diffraction angles of 9.6, 10.7, and 11.3 2Θ, +0.2° 2Θ.

The anhydrous crystalline tris salt of Example ACCi, wherein said anhydrous crystalline salt has a Raman spectrum comprising peak shifts at 1511, 1561, and 1615 $cm^{-1}$, +2 $cm^{-1}$.

The anhydrous crystalline tris salt of Example ACCi, wherein said anhydrous crystalline salt has a $^{13}C$ ssNMR spectrum comprising chemical shifts at 22.9, 146.2, and 161.9 ppm, +0.2 ppm.

The anhydrous crystalline tris salt of Example ACCi, wherein said anhydrous crystalline salt has an analytical parameter selected from the group consisting of a Raman spectrum comprising peak shifts at 1511 and 1615 $cm^{-1}$, +2 $cm^{-1}$, and a $^{13}C$ ssNMR spectrum comprising at least one chemical shift at 22.9, 146.2, or 161.9 ppm, +0.2 ppm.

The anhydrous crystalline tris salt of Example, where said anhydrous crystalline salt is substantially pure.

The crystalline tris salt of Example ACCi, wherein the crystalline salt is a trihydrate crystalline salt.

The trihydrate crystalline tris salt of Example ACCi, wherein said trihydrate crystalline salt has a PXRD pattern comprising peaks at diffraction angles of 8.4, 9.0, and 10.5 2Θ, +0.2° 2Θ.

The trihydrate crystalline tris salt of Example ACCi, wherein said trihydrate crystalline salt has a Raman spectrum comprising peak shifts at 1507, 1557, and 1610 $cm^{-1}$, +2 $cm^{-1}$.

The trihydrate crystalline tris salt of Example ACCi, wherein said trihydrate crystalline salt has a $^{13}C$ ssNMR spectrum comprising chemical shifts at 19.2, 149.5, and 163.8 ppm, +0.2 ppm.

The trihydrate crystalline tris salt of Example ACCi, wherein said trihydrate crystalline salt has an analytical parameter selected from the group consisting of

- a PXRD pattern comprising peaks at diffraction angles of 8.4 and 9.0 2Θ, +0.2° 2Θ,
- a Raman spectrum comprising peak shifts at 1557 and 1610 $cm^{-1}$, +2 $cm^{-1}$, and
- a $^{13}C$ ssNMR spectrum comprising at least one chemical shift at 19.2, 149.5, or 163.8 ppm, +0.2 ppm.

The trihydrate crystalline tris salt of Example ACCi, wherein said trihydrate crystalline salt has an analytical parameter selected from the group consisting of a PXRD pattern comprising peaks at diffraction angles of 8.4 and 9.0 2Θ, +0.2° 2Θ, and a Raman spectrum comprising at least one peak shift at 1507, 1557, or 1610 $cm^{-1}$, +2 $cm^{-1}$.

The trihydrate crystalline tris salt of Example ACCi, wherein said trihydrate crystalline salt has an analytical parameter selected from the group consisting of a PXRD pattern comprising peaks at diffraction angles of 8.4 and 9.0 2Θ, +0.2° 2Θ, and a $^{13}C$ ssNMR spectrum comprising at least one chemical shift at 19.2, 149.5, or 163.8 ppm, +0.2 ppm.

Example DGAT2i (DGAT2i Compound): (S)-2-(5-((3-ethoxypyridin-2-yl)oxy)pyridin-3-yl)-N-(tetrahydrofuran-3-yl)pyrimidine-5-carboxamide

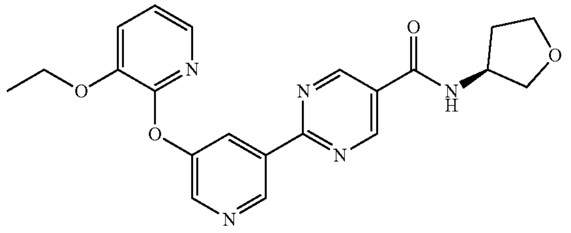 [SMILES: CCOc1cccnc1Oc1cncc(-c2ncc(C(=O)N[C@H]3CCOC3)cn2)c1]

Step 1: 3-Ethoxypyridine

Cesium carbonate (12 mol, 1.5 equiv) and ethyl iodide (9.7 mol, 1.2 equiv) were added to a solution of 3-hydroxypyridine (8.10 mol, 1.0 equiv) in acetone (12 L) at 15° C. The reaction mixture was stirred at room temperature for 24 hours. The reaction mixture was filtered and the organic layer was concentrated to give crude product. Ethyl acetate (20 L) was added and washed with water (3×5 L). The organic layer was dried over sodium sulfate, filtered and concentrated to give 3-ethoxypyridine (620 g, 62%) as an oil. $^1H$ NMR (400 MHz, $CDCl_3$) δ 1.44 (t, 3H), 4.07 (q, 2H), 7.15-7.23 (m, 2H), 8.20 (dd, 1H), 8.30 (d, 1H).

Step 2: 3-Ethoxypyridine-1-oxide m-Chloroperoxybenzoic acid (6.5 mol, 1.3 equiv) was added to a solution of 3-ethoxypyridine (5.0 mol, 1.0 equiv) in dichloromethane (12 L) at 10° C. The reaction mixture was stirred at room temperature for 24 hours. Sodium thiosulfate (4 kg, in 5 L of water) was added. The reaction mixture was stirred at 15° C. for 2 hours. Another portion of sodium thiosulfate (1.5 kg, in 5 L of water) was added. The reaction mixture was stirred at 15° C. for 1 hour. The mixture was extracted with dichloromethane (16×10 L). The combined organic layers were concentrated to give crude product. The crude product was purified by silica gel column chromatography (dichloromethane:methanol; 100:1-10:1) to give the title compound (680 g, 97%) as brown oil. This was further purified by trituration with petroleum ether (4 L) at room temperature for 24 hours to give 3-ethoxypyridine-1-oxide (580 g, 83%) as yellow solid. $^1H$ NMR (400 MHz, $CDCl_3$) δ 1.41 (t, 3H), 4.02 (q, 2H), 6.84 (dd, 1H), 7.12 (dd, 1H), 7.85 (d, 1H), 7.91-7.95 (m, 1H).

Step 3: 2-((5-Bromopyridin-3-yl)oxy)-3-ethoxypyridine

This reaction was carried out in five parallel batches.

Diisopropylethylamine (2.69 mol, 3.7 equiv) and bromotripyrrolidinophosphonium hexafluorophosphate (0.93 mol, 1.3 equiv) were added to a stirred solution of 3-ethoxypyridine-1-oxide (0.72 mol, 1.0 equiv) and 3-bromo-5-hydroxypyridine (0.72 mol, 1.0 equiv) in tetrahydrofuran (2500 mL) at room temperature. The reaction mixture was stirred at room temperature for 2 days then the separate batches were combined to a single batch. The resulting suspension was concentrated to dryness and dissolved in dichloromethane (25 L). The organic layer was washed with 1N sodium hydroxide (15 L), water (3×20 L), and brine (20

L). The organic layer was dried over sodium sulfate, filtered and concentrated to give an oil. The crude oil was purified by silica gel column chromatography (petroleum ether:ethyl acetate; 10:1-1:1) to give crude product as brown solid. This solid was triturated with methyl tert-butyl ether: petroleum ether (1:10; 11 L) to afford 2-((5-bromopyridin-3-yl)oxy)-3-ethoxypyridine (730 g, 69%) as off yellow solid. $^1$H NMR (400 MHz, $CDCl_3$) δ 1.49 (t, 3H), 4.16 (q, 2H), 7.04 (dd, 1H), 7.25 (dd, 1H), 7.68-7.73 (m, 2H), 8.44 (d, 1H), 8.49 (d, 1H). MS (ES+) 297.1 (M+H).

Step 4: Ethyl 2-(5-((3-ethoxypyridin-2-yl)oxy)pyridin-3-yl)pyrimidine-5-carboxylate A solution of 2-((5-bromopyridin-3-yl)oxy)-3-ethoxypyridine (300 mmol, 1.0 equiv) in tetrahydrofuran (1.3 L) was degassed with nitrogen for 30 minutes. Turbo Grignard (390 mmol, 1.3 equiv, 1.3 M in tetrahydrofuran) was added at room temperature at a rate to maintain the internal temperature below 30° C. The reaction mixture was allowed to cool to room temperature and stirred for 3 hours. The reaction was cooled to 10° C. and zinc chloride (390 mmol, 1.3 equiv, 1.9 M in 2-methyltetrahydrofuran) was added at a rate to maintain the temperature below 15° C. The resulting suspension was warmed to room temperature until all the precipitate was dissolved and then cooled back to 10° C. Ethyl 2-chloropyrimidine-5-carboxylate (360 mmol, 1.2 equiv) and dichloro[bis(2-(diphenylphosphino)phenyl) ether]palladium(II) (6.00 mmol, 0.02 equiv) were added as solids. The resulting suspension was degassed with nitrogen for 30 minutes then heated to 50° C. for 16 hours. The reaction was worked up under aqueous conditions then treated sequentially with ethylenediaminetetraacetic acid disodium salt, thiosilica, and charcoal to remove metal impurities. The crude compound was recrystallized from methanol (450 mL) to yield ethyl 2-(5-((3-ethoxypyridin-2-yl)oxy)pyridin-3-yl)pyrimidine-5-carboxylate (77 g, 70%) as a pale, yellow solid. $^1$H NMR (400 MHz, $CDCl_3$) δ 1.44 (t, 3H), 1.50 (t, 3H), 4.19 (q, 2H), 4.46 (q, 2H), 7.00-7.04 (m, 1H), 7.25 (s, 1H), 7.71 (d, 1H), 8.59 (s, 1H), 8.66 (d, 1H), 9.32 (s, 2H), 9.55 (s, 1H).

Step 5: 2-(5-((3-ethoxypyridin-2-yl)oxy)pyridin-3-yl)pyrimidine-5-carboxylic acid (Intermediate 1)

Sodium hydroxide (307 mmol, 1.5 equiv, 4M aqueous) and methanol (50 mL) were added to a suspension of 2-(5-((3-ethoxypyridin-2-yl)oxy)pyridin-3-yl)pyrimidine-5-carboxylate (205 mmol, 1.0 equiv) in tetrahydrofuran (300 mL). The resulting solution was stirred at room temperature for 3 hours. The reaction mixture was diluted with water (400 mL) and extracted with 2:1 diethyl ether:heptanes (2×300 mL). The aqueous layer was acidified to pH of 4 with 4M hydrochloric acid. The resulting suspension was stirred at room temperature for 1 hour. The solid was filtered, washed with water, and dried to yield 2-(5-((3-ethoxypyridin-2-yl)oxy)pyridin-3-yl)pyrimidine-5-carboxylic acid (69 g, 100%) as a pale, yellow solid. $^1$H NMR (400 MHz, DMSO-$d_6$) δ1.37 (t, 3H), 4.18 (q, 2H), 7.19 (dd, 1H), 7.58 (dd, 1H), 7.70 (dd, 1H), 8.35-8.40 (m, 1H), 8.66 (d, 1H), 9.33 (s, 2H), 9.41 (d, 1H), 13.9 (br. s, 1H).

Step 6: (S)-2-(5-((3-ethoxypyridin-2-yl)oxy)pyridin-3-yl)-N-(tetrahydrofuran-3-yl)pyrimidine-5-carboxamide [Example DGAT2i (DGAT2i Compound)]

Oxalyl chloride (13.8 mL, 160 mmol, 1.2 equiv) and dimethylformamide (0.510 mL, 6.65 mmol, 0.05 equiv) were added to a suspension of 2-(5-((3-ethoxypyridin-2-yl)oxy)pyridin-3-yl)pyrimidine-5-carboxylic acid (45.0 g, 133 mmol, 1.0 equiv) in dichloromethane (500 mL). The suspension was stirred for 2 hours when a solution was achieved. The reaction mixture was concentrated to yield crude acid chloride as a red solid. A solution of (S)-tetrahydrofuran-3-amine (12.2 g, 140 mmol, 1.05 equiv) and diisopropylethylamine (51.0 mL, 293 mmol, 2.2 equiv) in tetrahydrofuran (100 mL) was added dropwise to a solution of the crude acid chloride in dichloromethane (200 mL) at 0° C. The reaction was allowed to warm to room temperature and stirred for 16 hours. Water (1.0 L) and ethyl acetate (600 mL) were added and the organic layer was separated, washed with saturated sodium bicarbonate, dried over magnesium sulfate, and filtered. The filtrate was treated with activated charcoal (20 g) was stirred at 65° C. for 20 minutes. The suspension was filtered warm and filtrate was concentrated to a pale, yellow solid which was recrystallized from methanol in ethyl acetate (1:4, 1 L) to yield (S)-2-(5-((3-ethoxypyridin-2-yl)oxy)pyridin-3-yl)-N-(tetrahydrofuran-3-yl)pyrimidine-5-carboxamide (43.5 g, 81%) as a colorless solid. The title compound was combined with previous batches (108.7 g, 266.8 mmol) prepared in the same manner and slurried with ethyl acetate (1.0 L) at 80° C. for 4 hours. The suspension was allowed to cool to room temperature and stirred for 4 days. The solid was filtered, washed with ethyl acetate (3×200 mL) and dried under high vacuum at 50° C. for 24 hours to yield (S)-2-(5-((3-ethoxypyridin-2-yl)oxy)pyridin-3-yl)-N-(tetrahydrofuran-3-yl)pyrimidine-5-carboxamide (100.5 g, 92%) as a colorless solid. $^1$H NMR (300 MHz, DMSO-$d_6$) δ 1.38 (t, 3H), 1.89-1.98 (m, 1H), 2.15-2.26 (m, 1H), 3.65 (dd, 1H), 3.70-3.78 (m, 1H), 3.85-3.92 (m, 2H), 4.18 (q, 2H), 4.46-4.55 (m, 1H), 7.18 (dd, 1H), 7.58 (dd, 1H), 7.69 (dd, 1H), 8.37 (dd, 1H), 8.64 (d, 1H), 8.95 (d, 1H), 9.28 (s, 2H), 9.39 (d, 1H). MS (ES+) 408.4 (M+H). Melting point 177.5° C. Elemental analysis for $C_{21}1\text{-}H_{21}N_6O_4$: calculated C, 61.91; H, 5.20; N, 17.19; found C, 61.86; H, 5.18; N, 17.30.

The solid form from this procedure was characterized by Powder X-ray diffraction (PXRD) analysis and assigned as Form 1 of Example DGAT2i.

Alternative Step 6 for preparation of (S)-2-(5-((3-ethoxypyridin-2-yl)oxy)pyridin-3-yl)-N-(tetrahydrofuran-3-yl)pyrimidine-5-carboxamide (Example DGAT2i)

A 100 mL reactor was charged with acetonitrile (35 mL), 2-(5-((3-ethoxypyridin-2-yl)oxy)pyridin-3-yl)pyrimidine-5-carboxylic acid (5.0 g, 15 mmol) and (S)-tetrahydrofuran-3-amine hydrochloride (2.2 g, 18 mmol, 1.2 equiv). Diisopropylethylamine (18 mL, 103 mmol, 7.0 equiv) was charged while maintaining the temperature at 20° C. to 30° C. A solution of propane phosphonic acid anhydride (T3P) in acetonitrile (21 mL, 30 mmol, 2.0 equiv) was charged at a rate that maintained the temperature below 45° C. The reactor was heated to 40±5° C. for 1 hour then sampled for reaction completion. The reaction was cooled to 20° C. to 25° C. and tetrahydrofuran (25 mL) was added. A solution of sodium bicarbonate (0.5M, 40 mL) was charged and the mixture was stirred for 1 hour. The pH was checked and measured at 8.5. Ethyl acetate (40 mL) was added and the mixture stirred for 15 minutes. The mixture was settled and the phases split. The aqueous layer was transferred to a separatory funnel and back extracted with ethyl acetate (100 mL). The organic phases were combined and washed with water (40 mL). The organic layer was transferred to a 100 mL reactor in portions and concentrated under vacuum to a low volume. Methyl ethyl ketone (100 mL) was added and the mixture was concentrated to a final volume of approximately 60 mL. Vacuum was removed and the slurry was heated to reflux and held until the solids were washed down the reactor walls. The slurry was cooled to 15° C. over 2 hours and granulated overnight. The solids were isolated by filtration, washing the reactor and cake twice with methyl ethyl ketone (10 mL each). The solids were dried in a vacuum oven at 50° C. to yield 4.86 g (81%) of the desired product. The solid form from this procedure was characterized by PXRD analysis and assigned as Form 2 of Example DGAT2i.

Conversion of the Form 2 to the Form 1 of Example DGAT2i

To a 100 mL reactor was charged Form 2 of (S)-2-(5-((3-ethoxypyridin-2-yl)oxy)pyridin-3-yl)-N-(tetrahydrofuran-3-yl)pyrimidine-5-carboxamide (Example DGAT2i) (10.0 g, 24.6 mmol, 1.00 equiv.), Methyl ethyl ketone (8.8 mL/g), 88.0 mL) and water (1.2 mL/g, 12.0 mL). The reactor was heated to 50° C. over 30 minutes. A complete solution appeared at approximately 44° C. The reactor was cooled to 40° C. over 30 minutes then seed Form 1 of (S)-2-(5-((3-ethoxypyridin-2-yl)oxy)pyridin-3-yl)-N-(tetrahydrofuran-3-yl)pyrimidine-5-carboxamide (Example DGAT2i) (0.050 g, 0.123 mmol, 0.0050 equiv.) was charged. After seeding, the hazy slurry was stirred for 1 hour before cooling to 5° C. over 2 hours and then stirred at 5° C. for 12 hours. An in process control sample was pulled and characterized by PXRD analysis to confirm the solids were Form 1. The slurry was filtered, and the reactor and cake was washed with 0° C. methyl ethyl ketone (2.5 mL/g, 25 mL). The solids were dried in a vacuum oven at 50° C. to yield 8.15 g (81.5%) of the desired product. PXRD patterns of the desired product were consistent with Form 1 of Example DGAT2i.

Powder X-Ray Diffraction:

Powder X-ray diffraction analysis was conducted using a Bruker AXS D8 Advance diffractometer equipped with a Cu radiation source (Kα-average wavelength of 1.54056 Å), equipped with a twin primary utilizing a gobel mirror. Diffracted radiation was detected by a PSD-Lynx Eye detector. Both primary and secondary equipped with 2.5 soller slits. The X-ray tube voltage and amperage were set at 40 kV and 40 mA respectively. Data was collected in the Theta-Theta goniometer in a locked couple scan from 3.0 to 40.0 degrees 2-Theta with 1000 steps using a scan speed of 6 seconds per step. Samples were prepared by placement in a silicon low background sample holder (C79298A3244B261). Data were collected using Bruker DIFFRAC Plus software. Analysis performed by EVA diffract plus software.

The PXRD data file was not processed prior to peak searching. Using the peak search algorithm in the EVA software, peaks were selected with a threshold value of 5 and a width value of 0.2. The output of automated assignments was visually checked to ensure validity and adjustments manually made if necessary. Peaks with relative intensity of ≥3% were generally chosen. The peaks which were not resolved or were consistent with noise were also discarded. A typical error associated with the peak position from PXRD stated in USP is within +/−0.2° (USP-941).

TABLE 9

| Key PXRD peaks to characterize crystalline material Example DGAT2i | |
|---|---|
| Form 1 of Example DGAT2i | Form 2 of Example DGAT2i |
| Angle 2Θ (°) | Angle 2Θ (°) |
| 5.3, 7.7, 15.4 | 6.5, 9.3, 13.6 |

Figure 1:
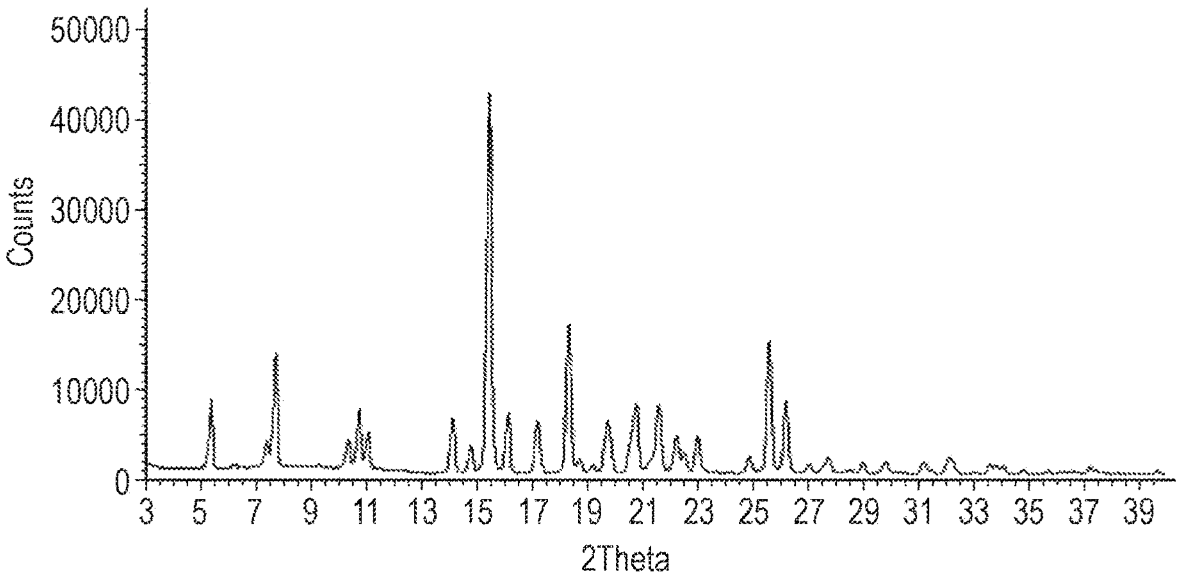
FIG. 1 is a characteristic x-ray powder diffraction pattern showing crystalline Form 1 of Example DGAT2i Compound (Vertical Axis: Intensity (CPS); Horizontal Axis: Two theta (degrees)).

FIG. 1 is a characteristic x-ray powder diffraction pattern showing crystalline form 1 of the compound of Example DGAT2i (Vertical Axis: Intensity (CPS); Horizontal Axis: Two theta (degrees)).

Figure 2:
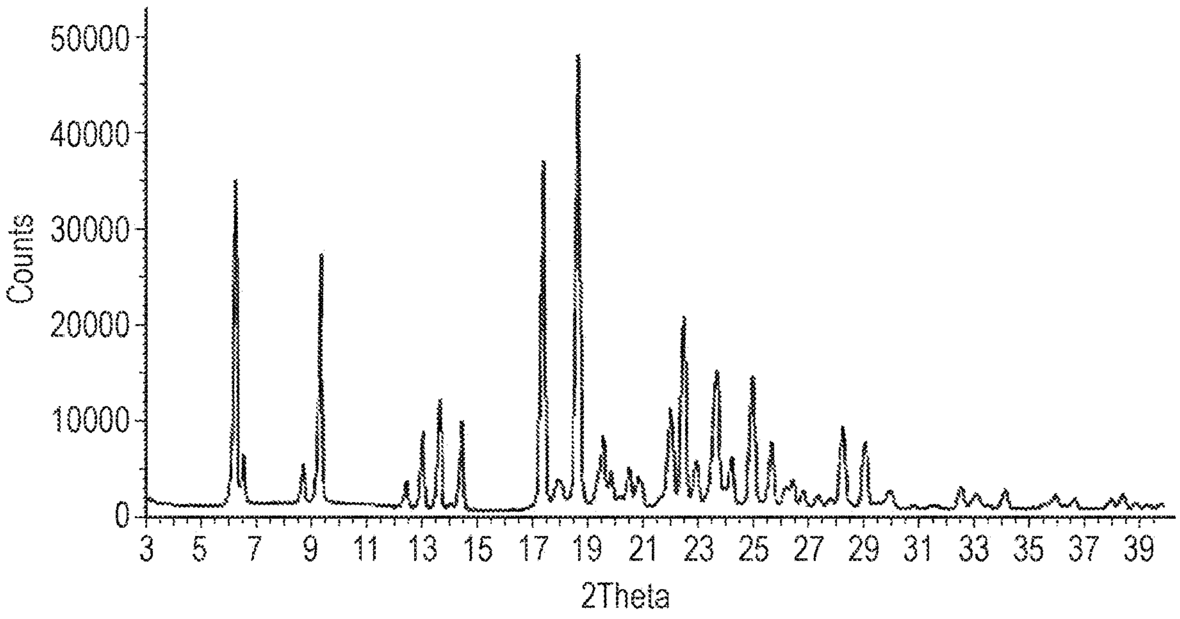
FIG. 2 is a characteristic x-ray powder diffraction pattern showing crystalline Form 2 of Example DGAT2i Compound (Vertical Axis: Intensity (CPS); Horizontal Axis: Two theta (degrees)).

FIG. 2 is a characteristic x-ray powder diffraction pattern showing crystalline Form 2 of the compound of Example DGAT2i (Vertical Axis: Intensity (CPS); Horizontal Axis: Two theta (degrees)).

Example FXRa ("Tropifexor")

Intermediates

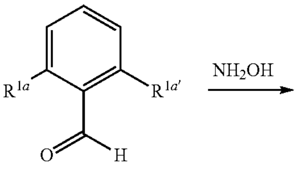

I-1A

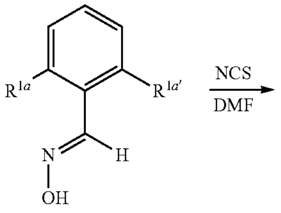

I-1B

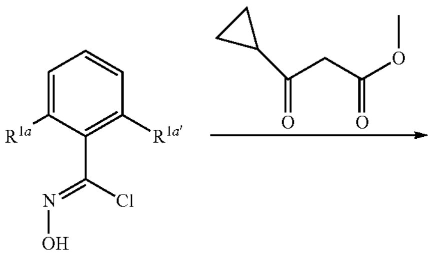

I-1C

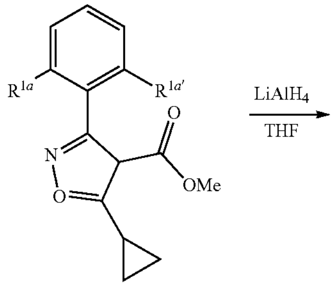

I-1D

-continued

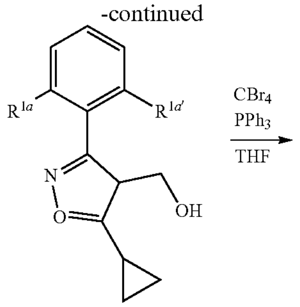

I-1E

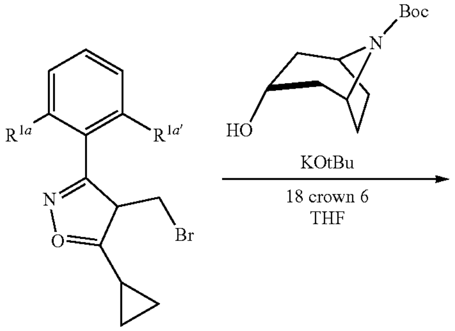

I-1F

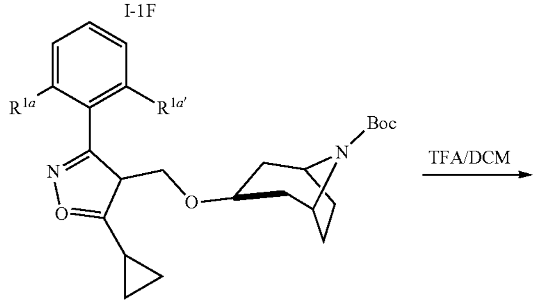

I-1G

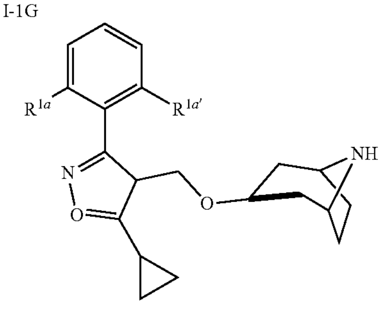

I-1G $R^{1a}$ = —$OCF_3$; $R^{1a'}$ = H (I-1H)
$R^{1a}$ = —$CF_3$; $R^{1a'}$ = H (I-1I)
$R^{1a}$ = —$OCF_2$; $R^{1a'}$ = H (I-1J)
$R^{1a}$, $R^{1a'}$ = fluoro (I-1K)

2-(Trifluoromethoxy)Benzaldehyde oxime (1-1B). To a solution of sodium hydroxide (7 g, 175.00 mmol, 1.19 equiv) in water (120 mL) was added a stirred solution of $NH_2OH \cdot HCl$ (11.8 g, 169.78 mmol, 1.15 equiv) in water (120 mL) at 0° C. The resulting solution was stirred for 10 min at 0° C. Then a solution of 2-(trifluoromethoxy)benzaldehyde (28 g, 147.29 mmol, 1.00 equiv) in ethanol (120 mL) was added. The resulting solution was allowed to stir for an additional 1 h at room temperature. The resulting solution was diluted with 500 ml of $H_2O$, extracted with 2×700 mL of ethyl acetate and the organic layers were combined, washed with 2×300 mL of brine, dried over anhydrous sodium sulfate and concentrated under vacuum to give (E)-2-(trifluoromethoxy)benzaldehyde oxime as an off-white crystalline solid.

N-hydroxy-2-(trifluoromethoxy)benzimidoyl chloride (I-1C). NCS (22 g, 166.04 mmol, 1.12 equiv) was slowly added to a stirred solution of (E)-2-(trifluoromethoxy)benzaldehyde oxime (30 g, 146.27 mmol, 1.00 equiv) in N,N-dimethylformamide (300 mL) keeping the internal temperature below 25° C. The reaction mixture was stirred for 1 h at room temperature. The resulting solution was diluted with water (300 mL) and extracted with ethyl acetate (2×500 mL). The organic layers were combined, washed with brine (5×300 mL), dried over anhydrous sodium sulfate, and concentrated under vacuum to give (Z)-2-(trifluoromethoxy) benzoyl chloride oxime as a light yellow crystalline solid.

Methyl 5-cyclopropyl-3-(2-(trifluoromethoxy)phenyl) isoxazole-4-carboxylat-e (I-1 D). Potassium carbonate (11 g, 79.7 mmol, 1.09 equiv) was suspended in THF (100 mL) and the mixture was stirred. A solution of methyl 3-cyclopropyl-3-oxopropanoate (11 g, 77.5 mmol, 1.06 equiv) in 50 ml THF was added to the above stirred mixture and stirred for 30 min at −10° C. To this reaction mixture was added a solution of (Z)-2-(trifluoromethoxy)benzoyl chloride oxime (17.6 g, 73.3 mmol, 1.00 equiv) in THF (50 mL) at -5° C. and then allowed to stir for 6 h at 35° C. The reaction mixture was diluted with 200 mL of $H_2O$, extracted with ethyl acetate (2×300 mL). The organic layer was washed with brine (2×200 mL), dried over anhydrous sodium sulfate, concentrated under vacuum, and then purified by silica gel column chromatography using ethyl acetate/petroleum ether (1:100-1:20) eluent to afford methyl 5-cyclopropyl-3-(2-(trifluoromethoxy)phenyl)isoxazole-4-carboxylate as a white solid.

(5-Cyclopropyl-3-(2-(trifluoromethoxy)phenyl)isoxazol-4-yl)-methanol (1-1E). A 250-mL round-bottom flask was purged with nitrogen and a suspension of $LiAlH_4$ (2.5 g, 65.8 mmol, 2.87 equiv) in tetrahydrofuran (50 mL) was added. This was followed by the addition of a solution of methyl 5-cyclopropyl-3-(2-(trifluoromethoxy)phenyl)isoxazole-4-carboxylate (7.5 g, 22.9 mmol, 1.00 equiv) in tetrahydrofuran (50 mL) dropwise at −10° C. The resulting reaction mixture was stirred for 30 min at −10° C. When the reaction was complete, it was quenched by the addition of 3 mL of ethyl acetate, followed by 3 mL of water and 01 mL of 15% aqueous NaOH, all whilst maintaining a vigorous stirring. The resulting white precipitate was filtered through Celite®, and the filter cake was washed with 200 mL of ethyl acetate. The filtrate was washed with brine (2×100 mL), dried over anhydrous sodium sulfate, and concentrated under vacuum. This resulted in 7 g of (5-cyclopropyl-3-(2-(trifluoromethoxy)phenyl)isoxazol-4-yl)methanol as yellow oil. ($^1$H-NM (300 MHz, $CDCl_3$) δ7.56 (m, 2H), 7.41 (m, 2H), 4.50 (s, 2H), 2.20 (m, 1H), 1.72 (s, 1H, —OH) 1.11-1.28 (m, 4H).

4-(Bromomethyl)-5-cyclopropyl-3-(2-(trifluoromethoxy)-phenyl)isoxazole (I-1F). Into a 100 mL round bottom flask was placed (5-cyclopropyl-3-(2-(trifluoromethoxy)phenyl)isoxazol-4-yl)-methanol (4 g, 13.3 mmol), triphenylphosphine (5.6 g, 20 mmol, 1.5 equiv) and dichloromethane (40 mL). The mixture was stirred until completely dissolved, and then slowly cannulated dropwise into a stirring solution of carbon tetrabromide (6.6 g, 20 mmol, 1.5 eq) in dichloromethane (20 ml). The mixture was stirred for one hour and the solvent was then evaporated in vacuo. The crude residue was purified by silica gel chromatography using a 0-50% gradient of ethyl acetate/hexane.

The desired product was obtained as a colorless oil. MS m/z 361.9/363.9 (M+1, $Br_{79}/B_{81}$ isotope pattern).

tert-Butyl 34(5-cyclopropyl-3-(2-(trifluoromethoxy)phenyl)isoxazol-4-yl)methoxy)-8-azabicyclo[3.2.1]octane-8-carboxylate (1-1G). A 250-mL flask was purged with nitrogen and then charged with N-Boc-nortropine (2.9 g, 12.8 mmol), 18-Crown-6 (3.4 g, 12.8 mmol), and anhydrous tetrahydrofuran (80 mL). Potassium tert-butoxide (2.9 g, 25.6 mmol) was added in small portions, and the mixture was stirred vigorously under nitrogen for 1 h. 4-(bromomethyl)-5-cyclopropyl-3-(2-(trifluoromethoxy)-phenyl)isoxazole (4.18 g, 11.6 mmol) was dissolved in anhydrous tetrahydrofuran (20 mL) and added dropwise, and the reaction mixture was stirred overnight under a positive nitrogen pressure. The solvent was removed in vacuo and the mixture diluted with water (100 mL) and ethyl acetate (100 mL). The organic layer was separated, dried with anhydrous $MgSO_4$, and evaporated in vacuo. The crude residue was purified by silica gel chromatography using a gradient of 0-100% ethyl acetate/hexanes to yield the desired product as yellow oil. MS m/z 509.2 (M+1).

4-((8-azabicyclo[3.2.1]octan-3-yloxy)methyl)-5-cyclopropyl-3-(2-(trifluoro-methoxy)phenyl)isoxazole (I-1H). tert-butyl-34(5-cyclopropyl-3-(2-(trifluoromethoxy)phenyl)isoxazol-4-yl)-methoxy)-8-azabicyclo[3.2.1]octane-8-carboxylate was dissolved in 30 mL of a 20% solution of trifluoroacetic acid in dichloromethane. The solution was stirred for 1 h at room temperature and the solvent was evaporated. The residue was dissolved in ethyl acetate (125 mL), washed with a saturated solution of sodium bicarbonate (100 mL), the organic layer was dried with anhydrous $MgSO_4$ and evaporated in vacuo. The crude residue was purified by silica gel chromatography using a gradient of 0-20% ethanol/dichloromethane to afford the desired product as a colorless oil. MS m/z 409.2 (M+1).

$^1$H NMR (DMSOd.sub.6, 400 MHz); δ8.51 (br s, 1H, NH), 7.72-7.68 (m, 1H), 7.64 (dd, J=7.6, 1.8 Hz, 1H), 7.58-7.52 (m, 2H), 4.33 (s, 2H), 3.81 (bs, 2H), 3.55 (t, J=4.5 Hz, 1H), 2.36-2.33 (m, 1H), 1.98 (app dt, J=14.8, 4.0 Hz, 2H), 1.91-1.76 (m, 6H), 1.14-1.07 (m, 4H).

4-((8-azabicyclo[3.2.1]octan-3-yloxy)methyl)-5-cyclopropyl-3-(2-(trifluoromethyl)phenyl)isoxazole (I-1I) was prepared following the same procedures. MS m/z 393.2 (M+1); $^1$H NMR (DMSO$d_6$, 400 MHz); δ8.51 (br s, 1H, NH), 7.92 (d, J=8.0, 1.8 Hz, 1H), 7.81 (app t, J=7.1 Hz, 1H), 7.78 (app t, J=7.1 Hz, 1H), 7.58 (d, J=7.3 Hz, 1H), 4.24 (s, 2H), 3.81 (bs, 2H), 3.52 (t, J=3.7 Hz, 1H), 2.36-2.33 (m, 1H), 1.92 (app dt, J=14.8, 4.0 Hz, 2H), 1.81-1.69 (m, 6H), 1.14-1.09 (m, 4H).

4-((8-azabicyclo[3.2.1]octan-3-yloxy)methyl)-5-cyclopropyl-3-(2-(difluoro-methoxy)phenyl)isoxazole (1-1J) was prepared following the same procedures. MS m/z 391.3 (M+1); $^1$H NMR (CDCl.sub.3, 400 MHz); δ9.10 (br s, 1H, NH), 7.32 (app t, J=8.4 Hz, 2H), 7.26 (app d, J=8.4 Hz, 2H), 6.44 (t, J=74 Hz, 1H, $CHF_2$), 4.32 (s, 2H), 3.82 (bs, 2H), 3.56 (t, J=4.0 Hz, 1H), 2.32 (app dt, J=15.2, 4.6 Hz, 2H), 2.08-2.04 (m, 1H), 1.98-1.89 (m, 4H), 1.78 (app br d, J=15.9 Hz, 2H), 1.26-1.20 (m, 2H), 1.14-1.09 (m, 2H).

4-((8-azabicyclo[3.2.1]octan-3-yloxy)methyl)-5-cyclopropyl-3-(2,6-difluorophenyl)isoxazole (I-1K) was prepared following the same procedures. MS m/z 361.2 (M+1); 1H NMR ($CDCl_3$, 400 MHz); δ 9.18 (br s, 1H, NH), 7.48-7.40 (m, 1H), 7.06-6.99 (m, 2H), 4.31 (s, 2H), 3.82 (bs, 2H), 3.59 (t, J=4.7 Hz, 1H), 2.16 (app dt, J=15.9, 4.0 Hz, 2H), 2.09-2.02 (m, 1H), 1.98-1.92 (m, 4H), 1.76 (app br d, J=15.2 Hz, 2H), 1.26-1.19 (m, 2H), 1.15-1.09 (m, 2H).

Example FXRa: Tropifexor

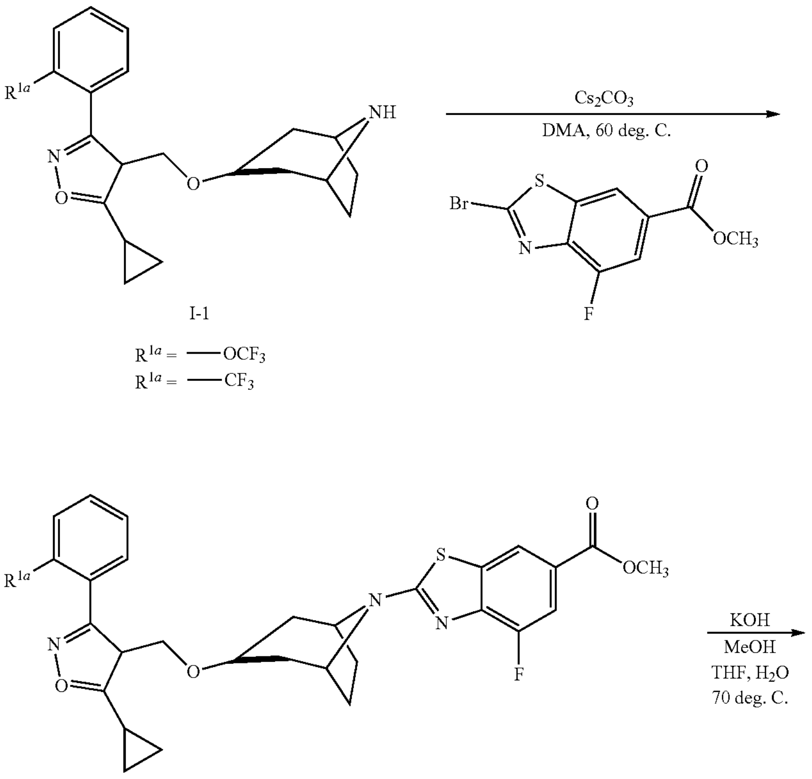

I-1

-continued

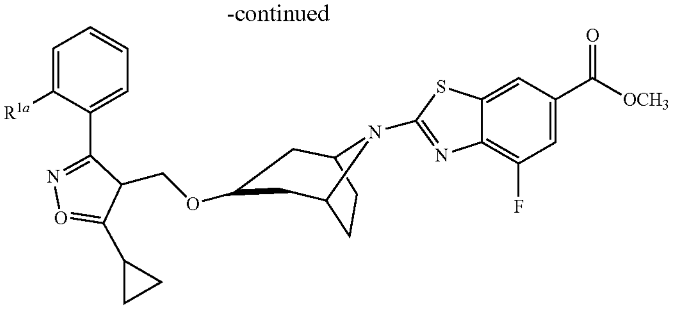

R1a = —OCF3

Tropifexor

Methyl 2-(3-((5-cyclopropyl-3-(2-(trifluoromethoxy)phenyl)isoxazol-4-yl)m-ethoxy)-8-azabicyclo[3.2.1]octan-8-yl)-4-fluorobenzo[d]thiazole-6-carboxyl-ate (I-1A). Into a 25-mL round-bottom flask equipped with a stir bar was added sequentially 4-((8-azabicyclo[3.2.1]octan-3-yloxy)methyl)-5-cyclopropyl-3-(2-(trifluor-omethoxy)phenyl)isoxazole (1-1H) (0.525 g, 1.29 mmol), 3.6 mL of N,N-dimethylacetamide, cesium carbonate (1.08 g, 3.31 mmol), and methyl 2-bromo-4-fluorobenzo[d]thiazole-6-carboxylate (1.12 g, 3.87 mmoles). After stirring the resulting slurry at room temperature for 10 minutes, the mixture was then warmed to 60° C. and stirred for 1 h. The reaction slurry was allowed to cool to RT, and was diluted with 200 mL of ethyl acetate and washed with water (3x30 mL). The organic extracts were concentrated under vacuum and directly purified using normal phase silica gel chromatography (40 g silica column) with a 15 min gradient of 10% to 60% ethyl acetate/hexanes. Desired fractions were concentrated in vacuo, and the resulting residue crystallized upon standing to give the desired product as a white crystalline solid.

2-[3-({5-cyclopropyl]-3-[2-(trifluoromethoxy)phenyl-1,2-oxazol-4-yl}metho-xy)-8-azabicyclo[3.2.1]octan-8-yl]-4-fluoro-1,3-benzothiazole-6-carboxylic acid (I-1B). To a 25-mL round-bottom flask equipped with a stir bar was added sequentially methyl 2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-carboxylate (0.55 g, 0.89 mmol), 4.0 mL of THF, 2.0 mL of MeOH, and 3 N aqueous KOH solution (1 mL, 3 mmol). The resulting homogenous solution was stirred for 1 hour at 70° C., cooled to RT, and then quenched with AcOH (roughly 0.2 mL of glacial acetic, 3 mmoles) until pH=6 was achieved (Whatman class pH strip paper). At this time the reaction was diluted with ethyl acetate (40 mL) and washed with water (3.times.5 mL). The ethyl acetate fraction was concentrated under vacuum to give to an oily residue. To the resulting oil was then added 6 mL of MeOH. The oil quickly dissolved, then immediately began to crystallize. Upon standing for 2.5 hrs the mother liquor was withdrawn and crystals washed (3x2 mL of ice cold MeOH). The crystals were dried via vacuum (10 mm Hg pressure at 45° C. overnight) and then recrystallized from acetonitrile, filtered, and dried under vacuum to give the desired product 2-(34(5-cyclopropyl-3-(2-(trifluoromethoxy)phenyl)isoxazol-4-yl)-methoxy)-8-azabicyclo[3.2.1]octan-8-yl)-4-fluorobenzo[d]thiazole-6-carboxylic acid.

2-[3-({5-cyclopropyl-3-[2-(trifluoromethyl)phenyl]-1,2-oxazol-4-yl}methox-y)-8-azabicyclo[3.2.1]octan-8-yl]-4-fluoro-1,3-benzothiazole-6-carboxylic acid (1-2B). Examples 1-2A and the corresponding acid 1-2B can be prepared following the same procedures, from the reaction of intermediate 4-((8-azabicyclo[3.2.1]octan-3-yloxy)methyl)-5-cyclopropyl-3-(2-(trifluoromethyl)phenyl)isoxazole.

Physical Data Ex MS (m/z), $^1$H NMR

Tropifexor

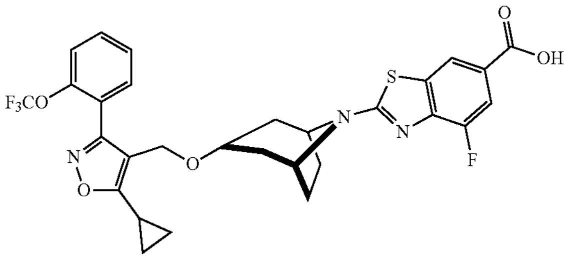

Elemental Analysis ($C_{30}H_{29}F_4N_3O_6S$): C, 56.69, H, 4.60, N, 6.61; Found: C, 56.79, H, 4.61, N, 6.65. MS m/z 604.2 (M+1); $^1$H NMR (MeOD, 400 MHz) δ 8.03 (d, J=1.6 Hz, 1H), 7.57-7.53 (m, 2H), 7.49 (dd, J=8.1, 1.8 Hz, 2H), 7.41 (app t, J=7.6, 1H), 4.31 (s, 2H), 4.22 (broad s, 2H), 3.50 (t, J=4.4 Hz, 1H), 2.22-2.15 (m, 1H), 2.00 (app dt, J=14.8, 4.0 Hz, 2H), 1.91-1.81 (m, 4H), 1.75 (d, J=14.4, 2H), 1.10-1.05 (m, 4H).

Example KHKi (KHKi Compound)

[(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid

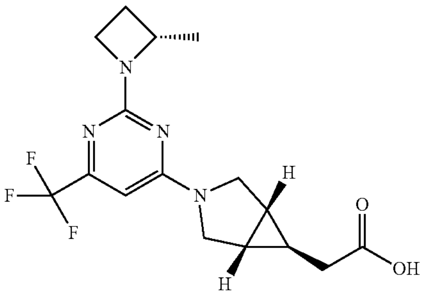 [SMILES: C[C@H]1CCN1c1nc(N2C[C@@H]3[C@@H](CC(=O)O)[C@@H]3C2)cc(C(F)(F)F)n1]

Step 1

Methyl {(1R,5S,6s)-3-[2-chloro-6-(trifluoromethyl) pyrimidin-4-yl]-3-azabicyclo[3.1.0]hex-6-yl}acetate To a solution of methyl (1R,5S,6s)-3-azabicyclo[3.1.0] hex-6-ylacetate hydrochloride (120.2 g, 627.2 mmol) in DCM (1250 mL) 2,4-dichloro-6-(trifluoromethyl)pyrimidine (145.7 g, 671.5 mmol) in DCM (50 ml) was added in drops at −72° C.; the addition funnel was washed with DCM (50 ml) and the wash was added into the reaction flask. DIPEA (273 mL, 1570 mmol) was added over 10 min with the reaction temperature maintained between −70° C. to −60° C. The mixture was stirred at −65° C. to −63° C. for 1 h and then warmed to 25° C. over 3 h. The resulting clear solution was concentrated to ~1/5 of the initial volume. To the obtained heavy slurry, MTBE (700 mL) and heptane (700 mL) were added and the resulting slurry was stirred at 25° C. for 10 min then solids were filtered off and washed with MTBE-heptane (4:1). The combined mother liquor was concentrated in vacuo to an oil, which was combined with heptane (1200 mL). The obtained heterogeneous mixture was stirred at 25° C. for 2.5 days. A white solid formed. The liquid was decanted and the solid was washed with heptane (200 mL) and dried in flow of nitrogen. The obtained title product was used for the next step without additional purification.

$^1$H NMR (400 MHz, $CDCl_3$) δ: 6.47 (s, 1H), 4.07 (d, 1H), 3.71 (s, 3H), 3.53-3.68 (m, 3H), 2.36-2.49 (m, 1H), 2.21-2.34 (m, 1H), 1.60-1.73 (m, 2H), 0.88-0.97 (m, 1H).

Step 2

Methyl {(1R,5S,6S)-3-[2-chloro-6-(trifluoromethyl)pyrimidin-4-yl]-3-azabicyclo[3.1.0]hex-6-yl}acetate from Step 1 was dissolved in acetonitrile (1500 mL) and (2S)-2-methylazetidinium [(1R,4S)-7,7-dimethyl-2-oxobicyclo [2.2.1]hept-1-yl]methanesulfonate (223.0 g, 735 mmol) was added. The mixture was stirred at 60° C. and DIPEA (77.0 mL, 442 mmol) was added during 3 h. The mixture was stirred for 3 h and then DIPEA (180 mL, 1.03 mol) was added over 3 h and the mixture was stirred at 60° C. for 18 h. Additional (2S)-2-methylazetidinium [(1R,4S)-7,7-dimethyl-2-oxobicyclo[2.2.1]hept-1-yl]methanesulfonate (18.0 g, 59 mmol) was added and the mixture was stirred at 60° C. for another 18 h. The mixture was concentrated to ~1/4 of the initial volume and the resultant yellow oil was partitioned between 500 mL of water, 400 mL of heptane, and 400 mL of MTBE. The aqueous phase was separated and extracted again with MTBE-heptane (1:1) mixture (2×150 mL). The combined organic extract was washed with 120 mL of saturated $NaHCO_3$ (120 mL), and then stirred with $SiO_2$ (70 g) and anhydrous $MgSO_4$ (70 g). Solids were filtered off and the clear solution was concentrated to obtain 216.6 g Example FXRa as a colorless oil.

MS (ES+): 371.1 (M+H). $^1$H NMR (400 MHz, $CDCl_3$) δ: 5.91 (s, 1H), 4.37-4.48 (m, 1H), 3.87-4.05 (m, 3H), 3.70 (s, 3H), 3.50-3.64 (m, 1H), 3.41-3.50 (m, 2H), 2.33-2.42 (m, 1H), 2.31 (d, 2H), 1.88-1.99 (m, 1H), 1.52-1.59 (m, 2H), 1.49 (d, 3H), 0.88-0.96 (m, 1H).

Step 3

To a stirred solution of unpurified methyl [(1R,5S,6R)-3-{2-[(2S)-2-methylazetidin-1-yl]-6-(trifluoromethyl)pyrimidin-4-yl}-3-azabicyclo[3.1.0]hex-6-yl]acetate in methanol (650 mL) was added a solution of sodium hydroxide (35.1 g, 877 mmol) in water (70 mL) in small portions under stirring at 5° C. to 15° C. The mixture became clear in 30 min. The clear solution was stirred at RT for 3 h, then concentrated to ~1/3 of the initial volume and the residue was diluted with water (750 mL) and brine (250 mL), then washed with a mixture of MTBE (260 mL) and heptane (130 mL). The organic wash was discarded. The aqueous phase was washed with MTBE-heptane (2:1) mixture (2×300 mL) and the organic layers discarded. The aqueous layer was then combined with MTBE (250 mL) and heptane (250 mL) and cooled to 0° C. Slowly under stirring at 0° C. to 4° C., 6 M aq. HCl (130 mL) was added, followed by 1 M aq. $KHSO_4$ (150 mL), and the obtained mixture was stirred for 15 min. The organic phase was separated and the aqueous phase was additionally extracted with a mixture of MTBE (170 mL) and heptane (170 mL). The combined organic extract was washed with water-brine (1:1) mixture (150 mL), dried over anhydrous $MgSO_4$ (60 g) and $SiO_2$ (60 g), filtered, and concentrated to give a colorless oil. It was combined (as a concentrated solution in MTBE) with another batch, which was prepared using identical conditions on the same scale. The combined MTBE solution was concentrated in vacuo, then heptane (2000 mL) was added and the suspension was concentrated again, with gradual increase of vacuum to obtain the desired product (406.0 g). A portion of this material (196 g) was dissolved in MTBE (220 mL) at 60° C. to 63° C., stirred slowly, and heptane (1500 mL) was added at 55° C. to 60° C. The mixture was seeded with crystalline title compound (50 mg). The mixture was stirred at 60° C. for 30 min, then additional heptane (1700 mL) was added during 20 min. The heterogeneous mixture was stirred at 60° C. for 2 h and then slowly cooled to 25° C. and stirred for 20 h. A small amount of solid was stuck on the flask walls and easily moved into the liquid phase with a spatula and the mixture was further stirred at 25° C. for 24 h. The solids were filtered off, washed with 5% MTBE in heptane, and dried in vacuo at 50° C. for 48 h to obtain Example KHKi as a white crystalline solid (178.2 g, 73% over 3 steps). Crystalline solid of Example KHKi has also been obtained using similar purification conditions without seeding.

MP: 122-123° C., $[\alpha]_D$ +86.3° ($CDCl_3$, c=1.37). MS (ES+): 357.3 (M+H). $^1$H NMR (400 MHz, $CDCl_3$) δ: 10.84 (br. s, 1H), 5.92 (s, 1H), 4.38-4.51 (m, 1H), 3.89-4.10 (m, 3H), 3.53-3.66 (m, 1H), 3.41-3.53 (m, 2H), 2.30-2.46 (m, 3H), 1.94 (ddt, 1H), 1.55-1.63 (m, 2H), 1.50 (d, 3H), 0.94 (m, 1H).

Powder X-ray diffraction analysis was conducted using a Bruker AXS D4 Endeavor diffractometer equipped with a Cu radiation source. The divergence slit was set at 0.6 mm while the secondary optics used variable slits. Diffracted radiation was detected by a PSD-Lynx Eye detector. The X-ray tube voltage and amperage were set to 40 kV and 40 mA respectively. Data was collected in the Theta-2Theta goniometer at the Cu wavelength $K\alpha_1$=1.54056 Å from 3.0 to 40.0 degrees 2-Theta using a step size of 0.020 degrees and a step time of 0.3 second. Samples were prepared by placing them in a silicon low background sample holder and rotated during collection. Data were collected using Bruker DIFFRAC Plus software and analysis was performed by EVA diffract plus software.

PXRD data file was not processed prior to peak searching. Using the peak search algorithm in the EVA software, peaks were selected with a threshold value of 1 and a width value of 0.3 were used to make preliminary peak assignments. The output of automated assignments was visually checked to ensure validity and adjustments manually made if necessary. Peaks with relative intensity of ≥3% were generally chosen.

The peaks which were not resolved or were consistent with noise were also discarded. A typical error associated with the peak position from PXRD stated in USP and JP is up to +/−0.2°.

Characteristic peaks for crystalline free acid of Example KHKi include Angle 2Θ (°) values of about 9.0, 10.4, 15.0, and 21.4+/−0.2°. Yet another embodiment of the crystalline free acid of Example KHKi is where characteristic peaks include Angle 2Θ (°) values of about 9.0, 15.0 19.6, 21.4, and 26.5+/−0.2°. Yet another embodiment of the crystalline free acid of Example KHKi is where characteristic peaks include Angle 2Θ (°) values of about 9.0, 10.4, 11.5, 15.0, 16.5, 19.6, 21.4, and 26.5+/−0.2°. Yet another embodiment of the crystalline free acid of Example KHKi is where characteristic peaks include Angle 2Θ (°) values of about 10.4, 11.5, 15.0, 19.6, and 26.5+/−0.2°. Table 10 provides PXRD peak list for crystalline free acid of Example KHKi, +/−0.2° is to apply to said peaks. FIG. 1 provides the PXRD pattern of crystalline free acid of Example KHKi.

TABLE 10

PXRD peak list for crystalline free acid of Example KHKi

| Angle 2Θ (°)* | Intensity (%) |
|---|---|
| 9.0 | 37 |
| 10.4 | 17 |
| 11.5 | 16 |
| 13.5 | 10 |
| 13.9 | 5 |
| 15.0 | 45 |
| 16.5 | 23 |
| 17.3 | 4 |
| 17.7 | 14 |
| 18.1 | 40 |
| 18.3 | 85 |
| 18.8 | 17 |
| 18.9 | 7 |
| 19.6 | 100 |
| 21.4 | 36 |
| 22.8 | 22 |
| 22.9 | 15 |
| 23.3 | 55 |
| 23.7 | 6 |
| 25.7 | 7 |
| 25.9 | 20 |
| 26.5 | 30 |
| 27.1 | 9 |
| 27.6 | 5 |
| 28.1 | 9 |
| 29.1 | 6 |
| 30.1 | 10 |
| 30.5 | 6 |
| 31.6 | 4 |

Additional Pharmacology and Pharmacological Data

Pharmacology of 4-(4-(1-Isopropyl-7-oxo-1,4,6,7-tetrahydrospiro[indazole-5,4'-piperidine]-1'-carbonyl)-6-methoxypyridin-2-yl)benzoic acid (Example ACCi)

4-(4-(1-Isopropyl-7-oxo-1,4,6,7-tetrahydrospiro[indazole-5,4'-piperidine]-1'-carbonyl)-6-methoxypyridin-2-yl) benzoic acid is a reversible dual ACC1/2 inhibitor that is currently being developed for the treatment of NASH with liver fibrosis. The compound is designed to have asymmetric distribution to the liver, with ≥100-fold asymmetric hepatic distribution demonstrated in both rats and monkeys; as such it is expected to inhibit de novo lipogenesis (DNL) and stimulate fatty acid oxidation in the liver to a greater extent than in peripheral tissues. Dose-response experiments for inhibition of human and rat ACC isozymes were performed at saturating concentrations of adenosine triphosphate (ATP) where the inhibitory concentration (IC50) approximates the equilibrium dissociation constant for an enzyme (Ki) for uncompetitive inhibitors. the compound of Example ACCi inhibited incorporation of [$^{14}$C]-carbonate into [$^{14}$C]-malonyl-CoA in a concentration-dependent manner. In rats, the ACC inhibitor produced dose and free plasma concentration-dependent reductions in liver malonyl-CoA. In humans, administration of 4-(4-(1-Isopropyl-7-oxo-1,4,6,7-tetrahydrospiro[indazole-5,4'-piperidine]-t-carbonyl)-6-methoxypyridin-2-yl)benzoic acid has been shown to suppress hepatic DNL in a Phase 1 study in healthy adult subjects (Bergman et al. 2017); in addition, the drug is expected to stimulate hepatic fatty acid oxidation, and consequently reduce fat accumulation in the liver. This inhibition of hepatic DNL is postulated to result in a decrease and normalization of the excessive DNL observed in nonalcoholic fatty liver disease (NAFLD). In addition, 4-(4-(1-Isopropyl-7-oxo-1,4,6,7-tetrahydrospiro[indazole-5,4'-piperidine]-t-carbonyl)-6-methoxypyridin-2-yl)benzoic acid also has the potential for anti-inflammatory effects in non-alcoholic steatohepatitis (NASH).

Pharmacology (S)-2-(5-((3-ethoxypyridin-2-yl)oxy)pyridin-3-yl)-N-(tetrahydrofuran-3-yl)pyrimidine-5-carboxamide (Example DGAT2i)

(S)-2-(5-((3-ethoxypyridin-2-yl)oxy)pyridin-3-yl)-N-(tetrahydrofuran-3-yl)pyrimidine-5-carboxamide is an oral, small molecule DGAT2 inhibitor that is postulated to decrease hepatic triglyceride (TG) synthesis and hepatic lipid burden in NAFLD and NASH. By in vitro biochemical assessment, the compound inhibited The selectivity of (S)-2-(5-((3-ethoxypyridin-2-yl)oxy)pyridin-3-yl)-N-(tetrahydrofuran-3-yl)pyrimidine-5-carboxamide was supported by in vitro studies demonstrating >2000-fold selectivity by biochemical assessment versus related acyltransferases including recombinant human DGAT1 (hDGAT1), monoacylglycerol acyltransferase 2 (MGAT2) and MGAT3, as well as mouse MGAT1. (S)-2-(5-((3-ethoxypyridin-2-yl)oxy)pyridin-3-yl)-N-(tetrahydrofuran-3-yl)pyrimidine-5-carboxamide demonstrated robust, dose-dependent reduction of plasma triacylglycerol in rats fed a sucrose-diet. In longer-term studies in western diet fed rats, the compound reduced both plasma triacylglycerol and hepatic lipid accumulation.

Pharmacology of Tropifexor (Example FXRa)

Pharmacological activation of tropifexor has been proposed as a target for the treatment of NASH (Cariou 2008, Porez et al 2012). Clinical validation of an FXR agonist for the treatment of NASH was demonstrated with obeticholic acid, a semi-synthetic bile acid (Neuschwander-Tetri et al 2015). The nuclear receptor FXR, also known as the Bile Acid Receptor (BAR; NR1H4), is responsible for modulating bile acid production, conjugation, and elimination. Tropifexor is a potent and selective non-steroidal FXR agonist Both single and multiple doses of tropifexor resulted in robust, dose-dependent increase in circulating FGF19 levels.

Pharmacology [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid (Example KHKi)

[(1R,5S,6R)-3-{2-[(2S)-2-methylazetidin-1-yl]-6-(trifluoromethyl)pyrimidin-4-yl}-3-azabicyclo[3.1.0]hex-6-yl]

acetic acid is a potent reversible inhibitor of human KHK-C The fructose, not glucose, component of dietary sugar is unique in its ability to promote features of metabolic syndrome, including steatosis, insulin resistance, and obesity. In a dietary fructose-feeding model with Sprague Dawley rats, the compound reduced the incidence of fructose-induced steatosis.

Throughout this application, various publications are referenced. The disclosures of these publications in their entireties are hereby incorporated by reference into this application for all purposes.

It will be apparent to those skilled in the art that various modifications and variations can be made in the invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treating a disease or condition in a patient in need thereof, which method comprises administering to the patient a therapeutically effective amount of a combination comprising (1) a GLP-1R agonist and (2) 4-(4-(1-isopropyl-7-oxo-1,4,6,7-tetrahydrospiro[indazole-5,4'-piperidine]-1'-carbonyl)-6-methoxypyridin-2-yl)benzoic acid or a pharmaceutically acceptable salt thereof, wherein:

the disease or condition is selected from fatty liver, nonalcoholic fatty liver disease, nonalcoholic steatohepatitis, nonalcoholic steatohepatitis with liver fibrosis, nonalcoholic steatohepatitis with cirrhosis, and nonalcoholic steatohepatitis with cirrhosis and with hepatocellular carcinoma or with a metabolic-related disease, obesity, and type 2 diabetes; and the GLP-1R agonist selected from:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo [4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid; and 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or pharmaceutically acceptable salt thereof.

2. The method of claim 1, wherein the GLP-1R agonist is 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or a pharmaceutically acceptable salt thereof.

3. The method of claim 1, wherein the 4-(4-(1-isopropyl-7-oxo-1,4,6,7-tetrahydrospiro[indazole-5,4'-piperidine]-1'-carbonyl)-6-methoxypyridin-2-yl)benzoic acid or pharmaceutically acceptable salt thereof is 2-amino-2-(hydroxymethyl)propane-1,3-diol salt of 4-(4-(1-Isopropyl-7-oxo-1,4,6,7-tetrahydrospiro[indazole-5,4'-piperidine]-1'-carbonyl)-6-methoxypyridin-2-yl)benzoic acid.

4. The method of claim 3, wherein the 2-amino-2-(hydroxymethyl)propane-1,3-diol salt of 4-(4-(1-Isopropyl-7-oxo-1,4,6,7-tetrahydrospiro[indazole-5,4'-piperidine]-1'-carbonyl)-6-methoxypyridin-2-yl)benzoic acid is a crystal form.

5. The method of claim 1, wherein the method further comprises administering to the patient at least one other pharmaceutical agent.

6. The method of claim 5, wherein the at least one other pharmaceutical agent is selected from the group consisting of an acetyl-CoA carboxylase-(ACC) inhibitor, a diacylglycerol O-acyltransferase 1 (DGAT-1) inhibitor, monoacylglycerol O-acyltransferase inhibitors, a phosphodiesterase (PDE)-10 inhibitor, an AMPK activator, a sulfonylurea, a meglitinide, an α-amylase inhibitor, an α-glucoside hydrolase inhibitor, an α-glucosidase inhibitor, a PPARγ agonist, a PPAR α/γ agonist, a biguanide, a glucagon-like peptide 1 (GLP-1) modulator, liraglutide, albiglutide, exenatide, albiglutide, lixisenatide, dulaglutide, semaglutide, a protein tyrosine phosphatase-1B (PTP-1B) inhibitor, SIRT-1 activator, a dipeptidyl peptidase IV (DPP-IV) inhibitor, an insulin secretagogue, a fatty acid oxidation inhibitor, an A2 antagonist, a c-jun amino-terminal kinase (JNK) inhibitor, glucokinase activators (GKa), insulin, an insulin mimetic, a glycogen phosphorylase inhibitor, a VPAC2 receptor agonist, SGLT2 inhibitors, a glucagon receptor modulator, GPR119 modulators, FGF21 derivatives or analogs, TGR5 receptor modulators, GPBAR1 receptor modulators, GPR40 agonists, GPR120 modulators, high affinity nicotinic acid receptor (HM74A) activators, SGLT1 inhibitors, inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms, inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors, inhibitors or modulators of PDHK2 or PDHK4, inhibitors of MAP4K4, modulators of IL1 family, HMG-COA reductase inhibitors, squalene synthetase inhibitors, fibrates, bile acid sequestrants, ACAT inhibitors, MTP inhibitors, lipoxygenase inhibitors, cholesterol absorption inhibitors, PCSK9 modulators, cholesteryl ester transfer protein inhibitors and modulators of RXRalpha.

7. The method of claim 1, wherein the GLP-1R agonist is 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid, or a pharmaceutically acceptable salt thereof.

8. The method of claim 1, wherein the 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid or pharmaceutically acceptable salt thereof is tris salt of 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid.

9. The method of claim 8, wherein the tris salt of 2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid is a crystal form.

10. The method of claim 2, wherein the 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2, or pharmaceutically acceptable salt thereof is tris salt of 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2.

11. The method of claim 10, wherein the tris salt of 2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2 is a crystal form.

* * * * *